US012384834B2

(12) United States Patent
Quiroz et al.

(10) Patent No.: US 12,384,834 B2
(45) Date of Patent: Aug. 12, 2025

(54) ANTI-ApoE ANTIBODIES AND POLYNUCLEOTIDES THEREOF

(71) Applicants: The General Hospital Corporation, Boston, MA (US); Banner Health, Phoenix, AZ (US); The Schepens Eye Research Institute, Inc., Boston, MA (US)

(72) Inventors: Yakeel T. Quiroz, Charlestown, MA (US); Joseph F. Arboleda-Velasquez, Newton, MA (US); Eric Reiman, Phoenix, AZ (US); Francisco Lopera, Medellin (CO)

(73) Assignees: The General Hospital Corporation, Boston, MA (US); Banner Health, Phoenix, AZ (US); The Schepens Eye Research Institute, Inc., Boston, MA (US)

( * ) Notice: Subject to any disclaimer, the term of this patent is extended or adjusted under 35 U.S.C. 154(b) by 679 days.

(21) Appl. No.: 17/614,008

(22) PCT Filed: May 28, 2020

(86) PCT No.: PCT/US2020/034978

§ 371 (c)(1),
(2) Date: Nov. 24, 2021

(87) PCT Pub. No.: WO2020/243346

PCT Pub. Date: Dec. 3, 2020

(65) Prior Publication Data

US 2022/0227852 A1 Jul. 21, 2022

Related U.S. Application Data

(60) Provisional application No. 62/873,019, filed on Jul. 11, 2019, provisional application No. 62/853,676, filed on May 28, 2019.

(51) Int. Cl.

| | |
|---|---|
| ***A61K 39/395*** | (2006.01) |
| ***A61K 39/00*** | (2006.01) |
| ***A61K 49/00*** | (2006.01) |
| ***A61K 49/16*** | (2006.01) |
| ***A61P 25/28*** | (2006.01) |
| ***C07K 14/775*** | (2006.01) |
| ***C07K 16/00*** | (2006.01) |
| ***C07K 16/18*** | (2006.01) |

(52) U.S. Cl.

CPC .............. *C07K 16/18* (2013.01); *A61P 25/28* (2018.01); *C07K 14/775* (2013.01); *A61K 2039/505* (2013.01); *C07K 2317/24* (2013.01); *C07K 2317/34* (2013.01); *C07K 2317/92* (2013.01); *C07K 2319/30* (2013.01)

(58) Field of Classification Search

CPC .......... C07K 2317/622; C07K 2317/24; C07K 2317/34; C07K 16/18; C07K 14/775; A61K 2039/505; A61K 39/0012; A61P 25/28; A61P 25/00

See application file for complete search history.

(56) References Cited

U.S. PATENT DOCUMENTS

| | | | |
|---|---|---|---|
| 4,399,216 A | | 8/1983 | Axel et al. |
| 4,522,811 A | | 6/1985 | Eppstein et al. |
| 4,634,665 A | | 1/1987 | Axel et al. |
| 5,057,313 A | | 10/1991 | Shih et al. |
| 5,156,840 A | | 10/1992 | Goers et al. |
| 5,179,017 A | | 1/1993 | Axel et al. |
| 5,508,167 A | | 4/1996 | Roses et al. |
| 5,641,640 A | | 6/1997 | Hanning |
| 5,869,046 A | | 2/1999 | Presta et al. |
| 6,468,798 B1 | | 10/2002 | Debs et al. |
| 6,503,713 B1 | | 1/2003 | Rana |
| 8,058,016 B2 | | 11/2011 | Nordstedt et al. |
| 8,741,298 B2 | * | 6/2014 | Schenk ................... A61P 25/00 536/23.53 |
| 2005/0079574 A1 | | 4/2005 | Bond |
| 2006/0073104 A1 | | 4/2006 | Mahley et al. |
| 2007/0104715 A1 | * | 5/2007 | Nordstedt .......... G01N 33/6893 435/7.2 |
| 2012/0100140 A1 | | 4/2012 | Reyes et al. |
| 2012/0204275 A1 | * | 8/2012 | Schenk ................ C07K 14/775 424/193.1 |

FOREIGN PATENT DOCUMENTS

| | | | | |
|---|---|---|---|---|
| EP | 3309550 A1 | * | 4/2018 | ....... G01N 33/54393 |
| JP | 2008-502311 | | 1/2008 | |
| WO | WO 1988/009344 | | 12/1988 | |
| WO | WO 1989/009622 | | 10/1989 | |
| WO | WO 1990/007861 | | 7/1990 | |
| WO | WO 1991/010741 | | 7/1991 | |
| WO | WO 1994/002602 | | 2/1994 | |

(Continued)

OTHER PUBLICATIONS

MacCallum et al.,J. Mol. Biol., 1996; 262: 732-745.*
Pascalis et al., The Journal of Immunology, 2002; 169: 3076-3084.*
Casset et al., BBRC, 2003; 307: 198-205.*
Vajdos et al.,J. Mol. Biol. 2002; 320: 415-428.*
Holm et al., Mol. Immunol., 2007; 44: 1075-1084.*
Chen et al., J. Mol. Bio., 1999; 293: 865-881.*
Wu et al., J. Mol. Biol., 1999; 294:151-162.*
Burgess et al. J of Cell Bio. 1990, 111:2129-2138.*
Bowie et al. Science, 1990, 247:1306-1310.*
Pawson et al. 2003, Science 300:445-452.*

(Continued)

*Primary Examiner* — Chang-Yu Wang
(74) *Attorney, Agent, or Firm* — Fish & Richardson P.C.

(57) ABSTRACT

Methods and compositions for preventing or treating cognitive decline associated with dementia and/or mild cognitive impairment and/or neurodegeneration using antibodies, peptides, fusion proteins, or genome editing systems that modulate HSPG/heparin binding affinities of ApoE.

22 Claims, 58 Drawing Sheets

Specification includes a Sequence Listing.

(56) References Cited

FOREIGN PATENT DOCUMENTS

| | | | | |
|---|---|---|---|---|
| WO | WO 1996/033735 | | 10/1996 | |
| WO | WO 1996/034096 | | 10/1996 | |
| WO | WO 2007/067809 | | 6/2007 | |
| WO | WO-2012075422 | A2 * | 6/2012 | A61K 39/395 |
| WO | WO-2013181618 | A2 * | 12/2013 | C07K 16/18 |
| WO | WO 2015/054653 | | 4/2015 | |
| WO | WO 2018/026976 | | 2/2018 | |
| WO | WO-2019197676 | A1 * | 10/2019 | A61K 35/17 |

OTHER PUBLICATIONS

Alaoui-Ismaili et al., Cytokine Growth Factor Rev. 2009; 20:501-507.*
Guo et al., PNAS 2004; 101:9205-9210.*
Rudikoff et al., Proc. Natl. Acad. Sci. USA 1982 Vol. 79: p. 1979.*
Kontermann et al., Book: Antibody Engineering vol. 2nd edition, Springer-Verlag Berlin Heidelberg, Germany, 2010.*
Weisgraber et al.,J. Biol. Chem. 1986; 261:2068-2076.*
Burgess et al., "ApoE of the HepG2 Cell Surface Includes a Major Pool Associated with Chondroitin Sulfate Proteoglycans," Biochemistry, Dec. 1998, 38(2):524-531.
Milne et al., "Characterization of monoclonal antibodies against human apolipoprotein E," J Clin Invest., Jul. 1981, 68(1):111-117.
Office Action in Chinese Appln. No. 202080054661.6, dated Aug. 11, 2023, 15 pages (with English translation).
Raffai et al., "Molecular characterization of two monoclonal antibodies specific for the LDL receptor-binding site of human apolipoprotein E," J Lipid Res., Sep. 1995, 36(9):1905-18.
Extended European Search Report in European Appln. No. 20815122.5, dated Oct. 9, 2023, 31 pages.
Jiang et al., "Apolipoprotein E Mediates Attachment of Clinical Hepatitis C Virus to Hepatocytes by Binding to Cell Surface Heparan Sulfate Proteoglycan Receptors," PLoS One, Jul. 2013, 8(7):e67982, 8 pages.
Kanekiyo et al., "ApoE and Aβ in Alzheimer's disease: accidental encounters or partners?," Neuron, Feb. 2014, 81(4):740-54.
Kunik et al., "Structural Consensus among Antibodies Defines the Antigen Binding Site," PLoS Comput Biol., Feb. 2012, 8(2):e1002388, 12 pages.
Ophir et al., "Abstract: Neutralization of apoE4 phenotypes with apoE4 specific antibodies," Neural Plasticity, Jan. 2003, 10(3):222.
Acosta-Baena et al., "Pre-dementia clinical stages in presenilin 1 E280A familial early-onset Alzheimer's disease: a retrospective cohort study," Lancet Neurol, Mar. 2011, 10(3):213-220.
Aguirre-Acevedo et al., "English Abstract: Validity and reliability of the CERAD-Col neuropsychological battery," Rev Neurol, Dec. 2007, 45(11):655-660, 1 page (English Abstract Only).
Alberer et al., "Safety and immunogenicity of a mRNA rabies vaccine in healthy adults: an open-label, non-randomised, prospective, first-in-human phase 1 clinical trial," Lancet, Sep. 2017, 390(10101):1511-1520, 10 pages.
Albert et al., "The diagnosis of mild cognitive impairment due to Alzheimer's disease: recommendations from the National Institute on Aging-Alzheimer's Association workgroups on diagnostic guidelines for Alzheimer's disease," Alzheimers Dement, 2011, 7(3): 270-279.
Allocca et al., "Novel adeno-associated virus serotypes efficiently transduce murine photoreceptors," J. Viral., Oct. 2007, 81(20):11372-11380.
Amariglio et al., "Subjective cognitive concerns, amyloid-β, and neurodegeneration in clinically normal elderly," Neurology, 2015, 85:56-62.
Arboleda-Velasquez et al., "Resistance to autosomal dominant Alzheimer's disease in an APOE3 Christchurch homozygote: a case report," Nature Medicine, Nov. 2019, 25(11):1680-1683.
Asokan et al., "The AAV Vector Toolkit: Poised at the Clinical Crossroads," Mol Ther., Apr. 2012, 20(4):699-708.
Baek et al., "GalaxyHomomer: a web server for protein homo-oligomer structure prediction from a monomer sequence or structure," Nucleic Acids Res, Jul. 2017, 45(W1):W320-W324.
Bateman et al., "Autosomal-dominant Alzheimer's disease: a review and proposal for the prevention of Alzheimer's disease," Alzheimer's Research & Therapy, Jan. 2011, 3(1): 13 pages.
Becker et al., "Amyloid-β associated cortical thinning in clinically normal elderly," Ann Neural., Jun. 2011, 69(6):1032-42.
Beecham et al., "Genome-Wide Association Meta-analysis of Neuropathologic Features of Alzheimer's Disease and Related Dementias," PLoS Genet., Sep. 2014, 10(9):e1004606, 15 pages.
Berlau et al., "Apoe ϵ2 is associated with intact cognition but increased Alzheimer pathology in the oldest old," Neurology, Mar. 2009, 72(9):829-34.
Bettcher et al., "MCP-1 and eotaxin-1 selectively and negatively associate with memory in MCI and Alzheimer's disease dementia phenotypes," Alzheimers Dement (Arnst), Jun. 2016, 3:91-7.
Better et al., "*Escherichia coli* Secretion of an Active Chimeric Antibody Fragment," Science, May 1988, 240(4855):1041-1043.
Better et al., "Expression of engineered antibodies and antibody fragments in microorganisms," Methods in Enzymology, 1989, 178(33):476-496.
Bird et al., "Single chain antibody variable regions," Tibtech, Apr. 1991, 9(1):132-137.
Braak et al., "Diagnostic Criteria for Neuropathologic Assessment of Alzheimer's Disease," Neurobiol Aging, Jul.-Aug. 1997, 18(4 Suppl):S85-88.
Braak et al., "Vulnerability of cortical neurons to Alzheimer's and Parkinson's diseases," J Alzheimers Dis., 2006, 9(3 Suppl):35-44.
Breslow et al., "Studies of familial type III hyperlipoproteinemia using as a genetic marker the apoE phenotype E2/2," J Lipid Res., Nov. 1982, 23(8):1224-35.
Bugiani et al., "Frontotemporal dementia and corticobasal degeneration in a family with a P301S mutation in tau," J Neuripathol Exp Neurol., 1999, 58(6):667-77.
Cacace et al., "Molecular genetics of early-onset Alzheimer's disease revisited," Alzheimers Dement., Jun. 2016, 12(6):733-748.
Candas-Estebanez et al., "APOE Variants E2, E3, and E4 Can Be Miscalled By Classical PCR-RFLP When The Christchurch Variant Is Also Present," J Clin Lab Anal., Mar. 2017, 31(2):e22040, 3 pages.
Carter et al., "High Level *Escherichia coli* Expression and Production of a Bivalent Humanized Antibody Fragment," BioTechnology, Feb. 1992, 10(2):163-167.
Carter et al., "Improved oligonucleotide site-directed mutagenesis using M13 vectors," Nucl. Acids Res., Jun. 1985, 13(12):4431-4443.
Carvajal-Carmona et al., "Strong Amerind/White Sex Bias and a Possible Sephardic Contribution among the Founders of a Population in Northwest Colombia," Am J Hum Genet., Nov. 2000, 67(5):1287-95.
Castellano et al., "Human apoE Isoforms Differentially Regulate Brain Amyloid-β Peptide Clearance," Sci Transl Med., Jun. 2011, 3(89):89ra57, 13 pages.
Chavez-Gutierrez et al., "The mechanism of gamma-Secretase dysfunction in familial Alzheimer disease," EMBO J., May 2012, 31(10):2261-74.
Chen et al., "Topology of human apolipoprotein E3 uniquely regulates its diverse biological functions," PNAS, Sep. 2011, 108(36):14813-14818.
Chien et al., "Early Clinical PET Imaging Results with the Novel PHF-Tau Radioligand [F-18]-T807," J Alzheimers Dis., 2014, 34(1):457-468.
Co et al., "A humanized antibody specific for the platelet integrin gpIIb/IIIa," J. Immunol., Mar. 1994, 152(6):2968-2976.
Cokol et al., "Finding nuclear localization signals," EMBO Rep., Nov. 2000, 1(5):411-415.
Corder et al., "Gene dose of apolipoprotein E type 4 allele and the risk of Alzheimer's disease in late onset families," Science, Aug. 1993, 261(5123):921-923.
Corder et al., "Protective effect of apolipoprotein E type 2 allele for late onset Alzheimer disease," Nat Genet., Jun. 1994, 7(2):180-184.

(56) References Cited

OTHER PUBLICATIONS

Czarnik, "Encoding methods for combinatorial chemistry," Curr. Opin. Chem. Bio., Jun. 1997, 1(1):60-6.
Davies et al., "Single antibody domains as small recognition units: design and in vitro antigen selection of camelized, human VH domains with improved protein stability," Protein Eng., Jun. 1996, 9(6):531-7.
De Strooper et al., "Deficiency of presenilin-1 inhibits the normal cleavage of amyloid precursor protein," Nature, Jan. 1998, 391(6665):387-90.
Deng et al., "The Structure of Dimeric Apolipoprotein A-IV and Its Mechanism of Self-Association," Structure, May 2012, 20(5):767-79.
Deyle et al., "Adeno-associated virus vector integration," Curr Opin Mol Ther., Aug. 2009, 11(4):442-447, 11 pages.
Dominguez et al., "Nanoparticles and blood-brain barrier: the key to central nervous system diseases," J Nanosci nanotechnol., Jan. 2014, 14(1):766-79.
Ebrahimi et al., "Drug Delivery using genetically modified Mesenchymal Stem Cells: A promising targeted-delivery method," J.D.Med., Apr. 2013, 5(1):90-104.
Farrer et al., "Effects of age, sex, and ethnicity on the association between apolipoprotein E genotype and Alzheimer disease. A meta-analysis. APOE and Alzheimer Disease Meta Analysis Consortium," JAMA, Oct. 1997, 278(16):1349-1356.
Fisher et al., "A scalable, fully automated process for construction of sequence-ready human exome targeted capture libraries," Genome Biol., 2011, 12(1):R1, 15 pages.
Fleisher et al., "Associations Between Biomarkers and Age in the Presenilin 1 E280A Autosomal Dominant Alzheimer Disease Kindred: A Cross-sectional Study," JAMA Neurol., Mar. 2015, 72(3):316-324.
Freitas et al., "Mechanisms and Signals for the Nuclear Import of Proteins," Curr Genomics, Dec. 2009,1 0(8):550-557.
Frieden et al., "Structural differences between apoE3 and apoE4 may be useful in developing therapeutic agents for Alzheimer's disease," PNSA, Apr. 2012, 109(23):8913-8918.
Futamura et al., "Two-step Mechanism of Binding of Apolipoprotein E to Heparin," The Journal of Biological Chemistry, Feb. 2005, 280(7):5414-5422.
Garrison et al., "Haplotype-based variant detection from short-read sequencing," arXiv:12073907 [q-bioGN], Jul. 2012, 9 pages.
Gaudelli et al., "Programmable base editing of A•T to G•C in genomic DNA without DNA cleavage," Nature, Nov. 2107, 551(7681), 464-471.
Georgiadou et al., "Biophysical Analysis of Apolipoprotein E3 Variants Linked with Development of Type III Hyperlipoproteinemia," PLoS One, 2011, 6(11):e27037, 11 pages.
Ghiselli et al., "Type III hyperlipoproteinemia associated with apolipoprotein E deficiency," Science, Dec. 1981, 214(4526):1239-1241.
Harmsen et al., "Properties, production, and applications of camelid single-domain antibody fragments," Appl. Microbiol. Biotechnol., Nov. 2007, 77(1):13-22.
Hashimoto et al., "Apolipoprotein E, especially apolipoprotein E4, increases the oligomerization of amyloid beta peptide," J Neurosci., Oct. 2021, 32(43):15181-15192.
Hauser et al., "Impact of apolipoprotein E on Alzheimer's disease," Cure Alzheimer Res, Oct. 2013, 10(8):809-817, 17 pages.
He et al., "Towards improvements for penetrating the blood-brain barrier-recent progress from a material and pharmaceutical perspective," Cells, 2018, 7(4):24, 21 pages.
Hedden et al., "Disruption of functional connectivity in clinically normal older adults harboring amyloid burden," J Neurosci, Oct. 2009, 29(40):12686-12694.
Hofman et al., "Atherosclerosis, apolipoprotein E, and prevalence of dementia and Alzheimer's disease in the Rotterdam Study," Lancet, Jan. 1997, 349(9046):151-4.
Hollingworth et al., "Common variants at ABCA7, MS4A6A/MS4A4E, EPHA1, CD33 and CD2AP are associated with Alzheimer's disease," Nat Genet, Apr. 2011, 43(5):429-35.
Huang and Mahley, "Apolipoprotein E: structure and function in lipid metabolism, neurobiology, and Alzheimer's diseases," Neurobiol Dis, 2014, 72(Pt A):3-12.
Huang et al., "ApoE2, ApoE3, and ApoE4 Differentially Stimulate APP Transcription and Abeta Secretion," Cell, Jan. 2017, 168(3):427-441.e21, 37 pages.
Hudry et al., "Gene transfer of human Apoe isoforms results in differential modulation of amyloid deposition and neurotoxicity in mouse brain," Sci Transl Med, 2013, 5:212ra161, 23 pages.
Huynh et al., "Age-Dependent Effects of apoE Reduction Using Antisense Oligonucleotides in a Model of beta-amyloidosis," Neuron, Dec. 2017, 96(5):1013-1023.e4.
International Preliminary Report on Patentability in International Appln. No. PCT/US2020/034978, mailed on Dec. 9, 2021, 8 pages.
International Search Report and Written Opinion in International Appln. No. PCT/US2020/034978, mailed on Oct. 26, 2021, 13 pages.
Jiang et al., "ApoE promotes the proteolytic degradation of Abeta," Neuron, Jun. 2008, 58(5):681-93.
Johnson et al., "Tau positron emission tomographic imaging in aging and early Alzheimer disease," Ann Neurol, Jan. 2016, 79(1):110-9.
Johnson et al., "The Alzheimer's A beta-peptide is deposited at sites of complement activation in pathologic deposits associated with aging and age-related macular degeneration," PNAS, Sep. 2002, 99(18):11830-11835.
Kaufman and Sharp, "Amplification and expression of sequences cotransfected with a modular dihydrofolate reductase complementary DNA gene," J. Mol. Biol., Aug. 1982, 159(4):601-621.
Khani et al., "AAV-mediated expression targeting of rod and cone photoreceptors with a human rhodopsin kinase promoter," Invest Ophthalmol Vis Sci., Sep. 2007, 48(9):3954-61.
Köhler and Milstein, "Continuous cultures of fused cells secreting antibody of predefined specificit," Nature, Aug. 1975, 256(5517):495-7.
Köhler and Milstein, "Derivation of specific antibody-producing tissue culture and tumor lines by cell fusion," Eur. J. Immunol., Jul. 1976, 6(7):511-9.
Köhler et al., "The Human Phenotype Ontology project: linking molecular biology and disease through phenotype data," Nucleic Acids Res, 2014, 42:D966-974.
Komor et al., "Programmable editing of a target base in genomic DNA without double-stranded DNA cleavage," Nature, May 2016, 533(7603):420-424, 17 pages.
Kunkel, "Rapid and efficient site-specific mutagenesis without phenotypic selection," Proc. Natl. Acad Sci. USA, Jan. 1985, 82:488-492.
Lalazar et al., "Site-specific mutagenesis of human apolipoprotein E. Receptor binding activity of variants with single amino acid substitutions," J Biol Chem, Mar. 1988, 263(8):3542-3545.
Lalli et al., "Whole-genome sequencing suggests a chemokine gene cluster that modifies age at onset in familial Alzheimer's disease," Mol Psychiatry, 2015, 20:1294-1300.
Lamoyi, "[62] Preparation of $F(ab')_2$ fragments from mouse IgG of various subclasses," Methods in Enzymology, 1986, 121:652-663.
Lefevre et al., "Syndecan 4 is involved in mediating HCV entry through interaction with lipoviral particle-associated apolipoprotein E," PLoS One, Apr. 2014, 9(4):e95550, 8 pages.
Lei et al., "Characterization of the Erwinia carotovora pelB gene and its product pectate lyase," J Bacterial., Sep. 1987, 169(9):4379-83.
Lek et al., "Analysis of protein-coding genetic variation in 60,706 humans," Nature, Aug. 2016, 536(7616):285-291, 13 pages.
Lemere et al., "The E280A presenilin 1 Alzheimer mutation produces increased A beta 42 deposition and severe cerebellar pathology," Nature Medicine, Oct. 1996, 2(10):1146-50.
Lendon et al., "E280A PS-1 mutation causes Alzheimer's disease but age of onset is not modified by ApoE alleles," Hum Mutat, 1997, 10(3):186-195.

(56) References Cited

OTHER PUBLICATIONS

Li, "Aligning sequence reads, clone sequences and assembly contigs with BWA-MEM," arXiv, published on Mar. 16, 2013, arXiv:1303.3997 [q-bio.GN], 3 pages.
Libeu et al., "New insights into the heparan sulfate proteoglycan-binding activity of apolipoprotein E," J Biol Chem., Oct. 2001, 276(42):39138-44.
Logan et al., Graphical analysis of reversible radioligand binding from time-activity measurements applied to [N-11 C-methyl ]-(-)-cocaine PET studies in human subjects, J Cereb Blood Flow Metab, Sep. 1990, 10(5):740-747.
Lopera et al., "Clinical features of early-onset Alzheimer disease in a large kindred with an E280A presenilin-1 mutation," JAMA, Mar. 1997, 277(10):793-799.
Mahley et al., "Pathogenesis of type III hyperlipoproteinemia (dysbetalipoproteinemia). Questions, quandaries, and paradoxes," J Lipid Res, Nov. 1999, 40(11):1933-1949.
Mahley, "Apolipoprotein E: from cardiovascular disease to neurodegenerative disorders," J Mol Med (Berl), Jul. 2016, 94(7):739-46, 8 pages.
Malmborg and Borrebaeck, "BIAcore as a tool in antibody engineering," J. Immunol. Methods, Jun. 1995, 183(1):7-13.
McCall et al., "Pathogen-inspired drug delivery to the central nervous system" Tissue Barriers, Aug. 2014, 2(4):e944449, 12 pages.
McKinnon, "Glaucoma: Ocular Alzheimer's disease?," Frontiers in Bioscience, Oct. 2003, 8(1-3):s1140-1156.
Mingozzi and High, "Therapeutic in vivo gene transfer for genetic disease using AAV: progress and challenges," Nature Reviews Genetics, May 2011, 12(5):341-355.
Miyake et al., "Bypassing the blood-brian barrier using established skull base reconstruction techniques," World J Otorhinolaryngol Head Neck Surg., Oct. 2015, 1(1):11-16.
Mizushima et al., "pEF-BOS, a powerful mammalian expression vector," Nucleic Acids Res., Sep. 1990, 18(17):5322.
Möller et al., "Intracellular activation of interferon regulatory factor-1 by nanobodies to the multifunctional (Mf1) domain," J Biol. Chem., Dec. 2010, 285(49):38348-38361.
Mondal et al., "ApoE: In Vitro Studies of a Small Molecule Effector," Biochemistry, May 2016, 55(18):2613-21, 20 pages.
Mulligan et al., "Synthesis of rabbit beta-globin in cultured monkey kidney cells following infection with a SV40 beta-globin recombinant genome," Nature, Jan. 1979, 277(5692):108-14.
Muzyczka, "Use of adeno-associated virus as a general transduction vector for mammalian cells," Curr. Topics in Micro and Immunol., 1992, 158:97-129.
Pandey et al., "Blood brain barrier: An overview on strategies in drug delivery, realistic in vitro modeling and in vivo live tracking," Tissue Barriers, Feb. 2016, 4(1):e1129476, 14 pages.
Pang et al., "Comparative analysis of in vivo and in vitro AAV vector transduction in the neonatal mouse retina: effects of serotype and site of administration," Vision Research, Feb. 2008, 48(3):377-385.
Pardridge, "Drug transport across the blood-brain barrier," J Cereb Blood Flow Metab, Nov. 2012, 32(11):1959-1972.
Partial European Search Report in European Appln. No. 20815122.5, dated Jan. 12, 2023, 28 pages.
PCR Protocols: a Guide to Methods and Applications, 1st ed., Innis et al. (eds.), 1990, Chapter 22, pp. 177-183.
Pérez De La Lastra et al., "Epitope mapping of 10 monoclonal antibodies against the pig analogue of human membrane cofactor protein (MCP)," Immunology, Apr. 1999, 96(4):663-70.
Plückthun and Skerra, "[34] Expression of functional antibody Fv and Fab fragments in *Escherichia coli*," Methods in Enzymology, 1989, 178:497-515.
Powers et al., "Expression of single-chain Fv-Fc fusions in Pichia pastoris," J Immunol Methods, May 2001, 251(1-2):123-35.
Quiroz et al., "Association Between Amyloid and Tau Accumulation in Young Adults With Autosomal Dominant Alzheimer Disease," JAMA Neurol, May 2018, 75(5):548-556.
Rauch et al., "Tau internalization is regulated by 6-O sulfation on heparan sulfate proteoglycans (HSPGs)," Sci Rep., Apr. 2018, 8(1):6382, 10 pages.
Reiman et al., "Exceptionally low likelihood of Alzheimer's dementia in APOE2 homozygotes from a 5,000-person neuropathological study," Nat Commun, 2020, 11:667, 11 pages.
Reisberg, "Functional assessment staging (FAST)," Psychopharmacol Bull, 1988, 24(4):653-659.
Reisberg, "Global measures: utility in defining and measuring treatment response in dementia," Int Psychogeriatr., Jun. 2007, 19(3):421-56.
Roger et al., "Mesenchymal stem cells as cellular vehicles for delivery of nanoparticles to brain tumors," Biomaterials, Nov. 2010, 31(23):8393-8401.
Romeo et al., "Population-based resequencing of ANGPTL4 uncovers variations that reduce triglycerides and increase HDL," Nat Genet, Apr. 2007, 39(4):513-6.
Rose et al., "NGL viewer: web-based molecular graphics for large complexes," Bioinformatics, Nov. 2018, 34(21):3755-3758.
Rosenberg et al., "AAVrh.10-Mediated APOE2 Central Nervous System Gene Therapy for APOE4-Associated Alzheimer's Disease," Hum Gene Ther Clin Dev, Mar. 2018, 29(1):24-47.
Rousseaux et al., "[63] Optimal conditions for the preparation of proteolytic fragments from monoclonal IgG of different rat IgG subclasses," Methods in Enzymology, 1986, 121:663-669.
Saito et al., "Characterization of the heparin binding sites in human apolipoprotein E," J Biol. Chem., Apr. 2003, 278(17):14782-7.
Sanchez-Covarrubias et al., "Transporters at CNS barrier sites: obstacles or opportunities for drug delivery?," Curr Pharm Des., 2014, 20(10):1422-49, 59 pages.
Saura et al., "Loss of presenilin function causes impairments of memory and synaptic plasticity followed by age-dependent neurodegeneration," Neuron, Apr. 2004, 42(1):23-36.
Schier and Marks, "Efficient in vitro affinity maturation of phage antibodies using BIAcore guided selections," Human Antibodies Hybridomas, 1996, 7(3):97-105.
Sherrington et al., "Cloning of a gene bearing missense mutations in early-onset familial Alzheimer's disease," Nature, Jun. 1995, 375(6534):754-60.
Shi and Holtzman, "Interplay between innate immunity and Alzheimer disease: APOE and TREM2 in the spotlight," Nat Rev Immunol., Dec. 2018, 18(12):759-772, 14 pages.
Shi et al., "ApoE4 markedly exacerbates tau-mediated neurodegeneration in a mouse model of tauopathy," Nature, Sep. 2017, 549(7673):523-7, 20 pages.
Sivak, "The aging eye: common degenerative mechanisms between the Alzheimer's brain and retinal disease," Investigative Ophthalmology & Visual Science, 2013, 54(1):871-880.
Smedley et al., "A Whole-Genome Analysis Framework for Effective Identification of Pathogenic Regulatory Variants in Mendelian Disease," Am J Hum Genet, Sep. 2016, 99:595-606.
Sun et al., "Analysis of 138 pathogenic mutations in presenilin-1 on the in vitro production of Abeta42 and Abeta40 peptides by gamma-secretase," Proc Natl Acad Sci U S A, 2017, 114(4):E476-E85.
Tzioras et al., "APOE at the interface of inflammation, neurodegeneration and pathological protein spread in Alzheimer's disease," Neuropathology and Applied Neurobiology, Jun. 2019, 45(4):327-346, 21 pages.
Urlaub and Chasin, "Isolation of Chinese hamster cell mutants deficient in dihydrofolate reductase activity," Proc. Natl. Acad Sci. USA, Jul. 1980, 77(7):4216-4220.
Utermann et al., "Familial hyperlipoproteinemia type III: deficiency of a specific apolipoprotein (apo E-III) in the very-low-density lipoproteins," FEBS Lett, Aug. 1975, 56(2):352-5.
Vafa et al., "An engineered Fc variant of an IgG eliminates all immune effector functions via structural perturbations," Methods, Jan. 2014, 65(1):114-26.
Vallette et al., "Construction of mutant and chimeric genes using the polymerase chain reaction," Nucl. Acids Res., Jan. 1989, 17(2):723-733.
Vélez et al., "APOE*E2 allele delays age of onset in PSEN1 E280A Alzheimer's disease," Mol Psychiatry, 2016, 21:916-24.

(56) References Cited

OTHER PUBLICATIONS

Walsh et al., "Naturally secreted oligomers of amyloid beta protein potently inhibit hippocampal long-term potentiation in vivo," Nature, Apr. 2002, 416(6880):535-539.
Wang et al., "Evaluation of Tau Imaging in Staging Alzheimer Disease and Revealing Interactions Between beta-Amyloid and Tauopathy," JAMA Neurol, Sep. 2016, 73(9):1070-1077.
Wang et al., "IgG Fc engineering to modulate antibody effector functions," Protein Cell, Jan. 2018, 9(1):63-73.
Ward et al., "Binding activities of a repertoire of single immunoglobulin variable domains secreted from *Escherichia coli*, " Nature, Oct. 1989, 341(6242):544-546.
Wardell et al., "Apolipoprotein E2-Christchurch (136 Arg-Ser). New variant of human apolipoprotein E in a patient with type III hyperlipoproteinemia," J Clin Invest, Aug. 1987, 80(2):483-90.
Weisgraber et al., "Human apolipoprotein E. Determination of the heparin binding sites of apolipoprotein E3," J Biol Chem, Feb. 1986, 261(5):2068-76.
Wells et al., "Cassette mutagenesis: an efficient method for generation of multiple mutations at defined sites," Gene, 1985, 34(2-3):315-323.
Yesavage, "Opportunities for and obstacles to treatments for dementias," J Am Geriatr Soc, Jan. 1983, 31(1):59-60.
Yoshiyama et al., "Synapse loss and microglial activation precede tangles in a P301S tauopathy mouse model," Neuron, Feb. 2007, 53(3):337-51, 18 pages.
Zalocusky et al., "An Alzheimer's-disease-protective APOE mutation," Nat Med., Nov. 2019, 25(11):1648-1649.
Zangi et al., "Modified mRNA directs the fate of heart progenitor cells and induces vascular regeneration after myocardial infarction," Nat Biotechnol., Sep. 2013, 31(10):898-907.
Zhong et al., "A rapid and cost-effective method for genotyping apolipoprotein E gene polymorphism," Mol Neurodegener, 2016, 11:2, 8 pages.
Zhou et al., "Dominant negative effect of the loss-of-function gamma-secretase mutants on the wild-type enzyme through heterooligomerization," Proc Natl Acad Sci U S A, Nov. 2017, 114(48):12731-6.
Office Action in Japanese Appln. No. 2021-570726, dated May 7, 2024, 10 pages (with English translation).
Yamada and Itoh, "Epitope Analysis of Anti-Serum Protein Antibodies and its Application for Amyloidosis Research," Jpn J Clin Pathol, May 1998, 46(5):456-460 (with English abstract).
Yamada et al., "Further Characterization of a Monoclonal Antibody Recognizing Apolipoprotein E Peptides in Amyloid Deposits," Annals of Clinical and Laboratory Science, 1997, 27(4):276-281.
Office Action in Chinese Appln. No. 202080054661.6, dated Jun. 19, 2024, 9 pages (with English translation).
Office Action in Japanese Appln. No. 2021-570726, mailed on Nov. 12, 2024, 7 pages (with English translation).

* cited by examiner

23B2

16H8

= PHF tau + Ganglion cell

= PHF tau + Nerve Fiber

SEQUENCE LISTING

<160> NUMBER OF SEQ ID NOS: 115

<210> SEQ ID NO 1
<211> LENGTH: 299
<212> TYPE: PRT
<213> ORGANISM: Homo sapiens

<400> SEQUENCE: 1

Lys Val Glu Gln Ala Val Glu Thr Glu Pro Glu Pro Glu Leu Arg Gln
1 5 10 15

Gln Thr Glu Trp Gln Ser Gly Gln Arg Trp Glu Leu Ala Leu Gly Arg
20 25 30

Phe Trp Asp Tyr Leu Arg Trp Val Gln Thr Leu Ser Glu Gln Val Gln
35 40 45

Glu Glu Leu Leu Ser Ser Gln Val Thr Gln Glu Leu Arg Ala Leu Met
50 55 60

Asp Glu Thr Met Lys Glu Leu Lys Ala Tyr Lys Ser Glu Leu Glu Glu
65 70 75 80

Gln Leu Thr Pro Val Ala Glu Glu Thr Arg Ala Arg Leu Ser Lys Glu
85 90 95

Leu Gln Ala Ala Gln Ala Arg Leu Gly Ala Asp Met Glu Asp Val Cys
100 105 110

Gly Arg Leu Val Gln Tyr Arg Gly Glu Val Gln Ala Met Leu Gly Gln
115 120 125

Ser Thr Glu Glu Leu Arg Val Arg Leu Ala Ser His Leu Arg Lys Leu
130 135 140

Arg Lys Arg Leu Leu Arg Asp Ala Asp Asp Leu Gln Lys Arg Leu Ala
145 150 155 160

Val Tyr Gln Ala Gly Ala Arg Glu Gly Ala Glu Arg Gly Leu Ser Ala
165 170 175

Ile Arg Glu Arg Leu Gly Pro Leu Val Glu Gln Gly Arg Val Arg Ala
180 185 190

Ala Thr Val Gly Ser Leu Ala Gly Gln Pro Leu Gln Glu Arg Ala Gln
195 200 205

Ala Trp Gly Glu Arg Leu Arg Ala Arg Met Glu Glu Met Gly Ser Arg
210 215 220

Thr Arg Asp Arg Leu Asp Glu Val Lys Glu Gln Val Ala Glu Val Arg
225 230 235 240

Ala Lys Leu Glu Glu Gln Ala Gln Gln Ile Arg Leu Gln Ala Glu Ala
245 250 255

Phe Gln Ala Arg Leu Lys Ser Trp Phe Glu Pro Leu Val Glu Asp Met
260 265 270

Gln Arg Gln Trp Ala Gly Leu Val Glu Lys Val Gln Ala Ala Val Gly
275 280 285

Thr Ser Ala Ala Pro Val Pro Ser Asp Asn His
290 295

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2

Thr Glu Glu Leu Arg Val Ser Leu Ala Ser His Leu Arg Lys 1 5 10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 3

Thr Glu Glu Leu Arg Val Arg Leu Ala Ser His Leu Arg Lys
1 5 10

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 4

Lys Ala Ser Gln Ser Val Asp Tyr Asp Gly Asp Ser Tyr Met Asn
1 5 10 15

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 5

Ala Ala Ser Asn Leu Glu Ser
1 5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 6

Gln Gln Ser Asn Glu Asp Pro Trp Thr
1 5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 7

Ser Tyr Thr Met Ser
1 5

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Lys Ile Arg Asn Gly Gly Gly Ile Thr Tyr Tyr Leu Asp Thr Leu Lys
1 5 10 15

Gly

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 9

His Tyr Tyr Gly Ser Glu Asp Tyr Phe Asp Tyr
1 5 10

<210> SEQ ID NO 10
<211> LENGTH: 393
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10
atggagacag acacaatcct gctatgggtg ctgctgctct gggttccagg ctccactggt 60
gacaatgtgc tgacccaatc tccagcttct ttggctgtgt ctctagggca gagggccacc 120
atctcctgca aggccagcca aagtgttgat tatgatggtg atagttatat gaactggtac 180
caacagaaac caggacagcc acccaaagtc ttcatctatg ctgcatccaa tctagaatct 240
gggatcccag ccaggtttag tggcagtggg tctgggacag acttcaccct caacatccat 300
cctgtggagg aggaggatgc tgcaacctat tactgtcagc aaagtaatga ggatccgtgg 360
acgttcggtg gaggcaccaa gctggaaatc aaa 393

<210> SEQ ID NO 11
<211> LENGTH: 417
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 11
atgaatttcg ggctcagctt gattttcctt gtccttgttt taaaaggtgt cctgtgtgaa 60
gtgaagctgg tggaatctgg gggaggtgtg gtgcagcctg gagggtccct gaaactctcc 120
tgtgcagcct ctggattcac tttcagtagc tataccatgt cttgggttcg tcagactcca 180
gagaagaggc tggagtgggt cgcaaaaatt cgtaatggtg gtggtatcac ctactattta 240
gacactttaa agggccgatt caccatctcc agagacaacg ccaagaacac cctatacctg 300
caaatgagca gtctgaagtc tgaagacacg gccatttatt tctgtgcaag acattactac 360
ggtagcgagg actactttga ctactggggc caaggcacca ctctcacagt ctcctca 417

<210> SEQ ID NO 12
<211> LENGTH: 131
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 12

```
Met Glu Thr Asp Thr Ile Leu Leu Trp Val Leu Leu Leu Trp Val Pro
1               5                   10                  15

Gly Ser Thr Gly Asp Asn Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45

Val Asp Tyr Asp Gly Asp Ser Tyr Met Asn Trp Tyr Gln Gln Lys Pro
    50                  55                  60

Gly Gln Pro Pro Lys Val Phe Ile Tyr Ala Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln Gln Ser Asn Glu Asp Pro Trp Thr Phe Gly Gly Gly Thr Lys Leu
        115                 120                 125

Glu Ile Lys
    130
```

<210> SEQ ID NO 13
<211> LENGTH: 139
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 13

```
Met Asn Phe Gly Leu Ser Leu Ile Phe Leu Val Leu Val Leu Lys Gly
1               5                   10                  15

Val Leu Cys Glu Val Lys Leu Val Glu Ser Gly Gly Gly Val Val Gln
            20                  25                  30

Pro Gly Gly Ser Leu Lys Leu Ser Cys Ala Ala Ser Gly Phe Thr Phe
        35                  40                  45

Ser Ser Tyr Thr Met Ser Trp Val Arg Gln Thr Pro Glu Lys Arg Leu
    50                  55                  60

Glu Trp Val Ala Lys Ile Arg Asn Gly Gly Gly Ile Thr Tyr Tyr Leu
65                  70                  75                  80

Asp Thr Leu Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Ile
            100                 105                 110

Tyr Phe Cys Ala Arg His Tyr Tyr Gly Ser Glu Asp Tyr Phe Asp Tyr
        115                 120                 125

Trp Gly Gln Gly Thr Thr Leu Thr Val Ser Ser
    130                 135
```

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Lys Ala Ser Gln Ser Val Asp Tyr Asp Gly Asp Ser Tyr Met Asn
1               5                   10                  15

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Ala Ser Asn Leu Glu Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Gln Ser Asn Glu Asp Pro Trp Thr
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Tyr Thr Met Ser
1               5

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Ile Arg Asn Val Gly Gly Ile Thr Tyr Tyr Pro Asp Thr Val Lys
1               5                   10                  15

Gly

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

His Tyr Tyr Gly Ser Glu Asp Tyr Phe Asp Tyr
1               5                   10

<210> SEQ ID NO 20

<211> LENGTH: 417
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 20
atgaatttcg ggctcagcgt gattttcctt gtccttgttt taaaaggtgt cctgtgtgaa 60
gtgaagctgg tggagtctgg gggaggttta gtgcagcctg gagggtccct gaaactctcc 120
tgtgcagcct ctggattcac tttcagtagg tataccatgt cttgggttcg gcagactcca 180
gagaagaggc tggagtgggt cgcaaaaatt cgtaatgttg gtggtatcac ctactatcca 240
gacactgtaa agggccgatt caccatctcc agagacaacg ccaagaacac cctttacctg 300
caaatgagca gtctgaagtc tgaagacacg gccatgtatt actgtgcaag acattattac 360
ggtagcgagg actactttga ctactggggc caaggcacca ctctcacagt ctcctca 417

<210> SEQ ID NO 21
<211> LENGTH: 393
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 21
atggagacag acacaatcct gctatgggtg ctgctgctct gggttccagg ctccactggt 60
gacaatgtgc tgacccaatc tccagcttct ttggctgtgt ctctagggca gagggccacc 120
atctcctgca aggccagcca aagtgttgat tatgatggtg atagttatat gaactggtac 180
caacagaaac caggacagcc acccaaagtc ttcatctatg ctgcatccaa tctagaatct 240
gggatcccag ccaggtttag tggcagtggg tctgggacaa acttcaccct caacatccat 300
cctgtggagg aggaggatgc tgcaacctat tactgtcagc aaagtaatga ggatccgtgg 360
acgttcggtg gaggcaccaa gctggaaatc aaa 393

<210> SEQ ID NO 22
<211> LENGTH: 139
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 22

Met Asn Phe Gly Leu Ser Val Ile Phe Leu Val Leu Val Leu Lys Gly
1 5 10 15

Val Leu Cys Glu Val Lys Leu Val Glu Ser Gly Gly Gly Leu Val Gln
20 25 30

Pro Gly Gly Ser Leu Lys Leu Ser Cys Ala Ala Ser Gly Phe Thr Phe
35 40 45

Ser Arg Tyr Thr Met Ser Trp Val Arg Gln Thr Pro Glu Lys Arg Leu
50 55 60

Glu Trp Val Ala Lys Ile Arg Asn Val Gly Gly Ile Thr Tyr Tyr Pro
65 70 75 80

Asp Thr Val Lys Gly Arg Phe Thr Ile Ser Arg Asp Asn Ala Lys Asn
85 90 95

Thr Leu Tyr Leu Gln Met Ser Ser Leu Lys Ser Glu Asp Thr Ala Met
100 105 110

```
Tyr Tyr Cys Ala Arg His Tyr Tyr Gly Ser Glu Asp Tyr Phe Asp Tyr
        115                 120                 125

Trp Gly Gln Gly Thr Thr Leu Thr Val Ser Ser
    130                 135


<210> SEQ ID NO 23
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Glu Thr Asp Thr Ile Leu Leu Trp Val Leu Leu Leu Trp Val Pro
1               5                   10                  15

Gly Ser Thr Gly Asp Asn Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45

Val Asp Tyr Asp Gly Asp Ser Tyr Met Asn Trp Tyr Gln Gln Lys Pro
    50                  55                  60

Gly Gln Pro Pro Lys Val Phe Ile Tyr Ala Ala Ser Asn Leu Glu Ser
65                  70                  75                  80

Gly Ile Pro Ala Arg Phe Ser Gly Ser Gly Ser Gly Thr Asn Phe Thr
                85                  90                  95

Leu Asn Ile His Pro Val Glu Glu Glu Asp Ala Ala Thr Tyr Tyr Cys
            100                 105                 110

Gln Gln Ser Asn Glu Asp Pro Trp Thr Phe Gly Gly Gly Thr Lys Leu
        115                 120                 125

Glu Ile Lys
    130


<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Ala Ser Gln Ser Val Asp Tyr Asp Gly Asp Ser Tyr Met Asn
1               5                   10                  15


<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Ala Ser Asn Leu Glu Ser
1               5


<210> SEQ ID NO 26
<211> LENGTH: 9
<212> TYPE: PRT
<213> ORGANISM: Artificial Sequence
<220> FEATURE:
```

<223> OTHER INFORMATION: Description of Artificial Sequence: Synthetic peptide

<400> SEQUENCE: 26

Gln Gln Ser Asn Val Asp Pro Trp Thr
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Asp Tyr His Met His
1               5

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Trp Ile Asp Pro Glu Asn Gly Asn Thr Met Tyr Asp Pro Lys Phe Gln
1               5                   10                  15

Gly

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 29

Gly Thr Ala Arg Ala Ser Phe Asp Tyr
1               5

<210> SEQ ID NO 30
<211> LENGTH: 393
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30
atggagacag acacaatcct gctatgggtg ctgctgctct gggttccagg ctccactggt 60
gacattgtgc tgacccaatc tccagcttct ttggctgtgt ctctagggca gagggccacc 120
atctcctgca aggccagcca aagtgttgat tatgatggtg atagttatat gaattggtac 180
caacagaaat caggacagcc acccaaactc ctcatctatg ctgcatccaa tctagaatct 240
gggatcccag ccaggtttag tggcagtggg tctgggacag acttcaccct caacatccat 300
cctgtggagg aggaggatgc tgcaacctat tactgtcagc aaagtaatgt ggatccgtgg 360
acgttcggtg gaggcaccaa gctggaaatc aaa 393

<210> SEQ ID NO 31

-continued

<211> LENGTH: 411
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 31
atgaaatgca gctgggtcat cttcttcctg atggcagtgg ttacaggggt caattcagag 60
gttcagctgc agcagtctgg ggctgagctt gtgaggccag ggccttagt caagttgtcc 120 tgcaaagctt ctggcttcaa cattaaagac taccatatgc actgggtgaa ggagaggcct 180
gaacagggcc tggagtggat tggatggatt gatcctgaga atggtaatac tatgtatgac 240
ccgaagttcc agggcaaggc cagtataaca gcagacacat cctccaacac agcctacctg 300
cagctcagca gcctgacatc tgaggacact gccgtctatt actgtgttag ggggacagct 360
cgggcttcct ttgactactg gggccaaggc accactctca cagtctcctc a 411

<210> SEQ ID NO 32
<211> LENGTH: 131
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 32

Met Glu Thr Asp Thr Ile Leu Leu Trp Val Leu Leu Leu Trp Val Pro
1 5 10 15

Gly Ser Thr Gly Asp Ile Val Leu Thr Gln Ser Pro Ala Ser Leu Ala
20 25 30

Val Ser Leu Gly Gln Arg Ala Thr Ile Ser Cys Lys Ala Ser Gln Ser
35 40 45

Val Asp Tyr Asp Gly Asp Ser Tyr Met Asn Trp Tyr Gln Gln Lys Ser
50 55 60

Gly Gln Pro Pro Lys Leu Leu Ile Tyr Ala Ala Ser Asn Leu Glu Ser
65 70 75 80

Gly Ile Pro Ala Arg Phe Ser Gly Ser Gly Ser Gly Thr Asp Phe Thr
85 90 95

Leu Asn Ile His Pro Val Glu Glu Glu Asp Ala Ala Thr Tyr Tyr Cys
100 105 110

Gln Gln Ser Asn Val Asp Pro Trp Thr Phe Gly Gly Gly Thr Lys Leu
115 120 125

Glu Ile Lys
130

<210> SEQ ID NO 33
<211> LENGTH: 137
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 33

Met Lys Cys Ser Trp Val Ile Phe Phe Leu Met Ala Val Val Thr Gly
1 5 10 15

Val Asn Ser Glu Val Gln Leu Gln Gln Ser Gly Ala Glu Leu Val Arg
20 25 30

Pro Gly Ala Leu Val Lys Leu Ser Cys Lys Ala Ser Gly Phe Asn Ile

-continued

```
        35                  40                  45

Lys Asp Tyr His Met His Trp Val Lys Glu Arg Pro Glu Gln Gly Leu
    50                  55                  60

Glu Trp Ile Gly Trp Ile Asp Pro Glu Asn Gly Asn Thr Met Tyr Asp
65                  70                  75                  80

Pro Lys Phe Gln Gly Lys Ala Ser Ile Thr Ala Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Val Arg Gly Thr Ala Arg Ala Ser Phe Asp Tyr Trp Gly
        115                 120                 125

Gln Gly Thr Thr Leu Thr Val Ser Ser
    130                 135


<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Ala Ser Gln Ser Val Asp Tyr Asp Gly Asp Thr Tyr Met Asn
1               5                   10                  15


<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Thr Ala Ser Asn Leu Glu Ser
1               5


<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Gln Ser Asn Glu Asp Pro Trp Thr
1               5


<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Tyr His Ile His
1               5


<210> SEQ ID NO 38
<211> LENGTH: 17
```

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 38

Trp Ile Asp Pro Glu Ile Asp Lys Thr Leu Tyr Asp Pro Lys Phe Gln
1 5 10 15

Gly

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 39

Gly Thr Ala Arg Ala Ser Phe Asp Tyr
1 5

<210> SEQ ID NO 40
<211> LENGTH: 393
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 40
atggagacag acacaatcct gctatgggtg ctgctgctct gggttccagg ctccactggt 60
gacattgtgc tgacccaatc tccagcttct ttggctgtgt ctctagggca gagggccacc 120
atctcctgca aggccagcca aagtgttgat tatgatggtg atacttatat gaactggtac 180
caacagaaac caggacagcc acccaaactc ctcatctata ctgcatccaa tctagaatct 240
gggatcccag ccaggtttag tggcagtggg tctgggacag acttcaccct caacatccat 300
cctgtggagg aggtggatgc tgcaacctat tactgtcagc aaagtaatga ggatccatgg 360
acgttcggtg gaggcaccaa gctggaaatc aaa 393

<210> SEQ ID NO 41
<211> LENGTH: 411
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 41
atgaaatgca gctgggtcat cttcttcctg atggcagtgg ttacaggggt caattcagag 60
gttcagctgc agcagtctgg ggctgagctt gtgaggccag gggccttagt caagtggtcc 120
tgcaaagctt ctggcttcaa cattaaagac taccatatac actgggtgaa acagaggcct 180
gaacagggcc tggactggat tggatggatt gatcctgaga ttgataaaac tctatatgac 240
ccgaagtttc agggcaaggc cagaataaca gcagacacat cctccaatac agcctacctg 300
cagctcagca gcctgacatc tgaagacact gccgtctatt actgtgccag ggggacagct 360
cgggcttcct ttgactactg gggccaaggc accactctca cagtctcctc a 411

<210> SEQ ID NO 42

```
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Glu Thr Asp Thr Ile Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45

Val Asp Tyr Asp Gly Asp Thr Tyr Met Asn Trp Tyr Gln Gln Lys Pro
    50                  55                  60

Gly Gln Pro Pro Lys Leu Leu Ile Tyr Thr Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Val Asp Ala Ala Thr Tyr Tyr Cys
            100                 105                 110

Gln Gln Ser Asn Glu Asp Pro Trp Thr Phe Gly Gly Gly Thr Lys Leu
        115                 120                 125

Glu Ile Lys
    130


<210> SEQ ID NO 43
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Arg
            20                  25                  30

Pro Gly Ala Leu Val Lys Trp Ser Cys Lys Ala Ser Gly Phe Asn Ile
        35                  40                  45

Lys Asp Tyr His Ile His Trp Val Lys Gln Arg Pro Glu Gln Gly Leu
    50                  55                  60

Asp Trp Ile Gly Trp Ile Asp Pro Glu Ile Asp Lys Thr Leu Tyr Asp
65                  70                  75                  80

Pro Lys Phe Gln Gly Lys Ala Arg Ile Thr Ala Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Ala Arg Gly Thr Ala Arg Ala Ser Phe Asp Tyr Trp Gly
        115                 120                 125

Gln Gly Thr Thr Leu Thr Val Ser Ser
    130                 135


<210> SEQ ID NO 44
<211> LENGTH: 15
<212> TYPE: PRT
<213> ORGANISM: Artificial Sequence
```

<220> FEATURE:
<223> OTHER INFORMATION: Description of Artificial Sequence: Synthetic
peptide

<400> SEQUENCE: 44

Lys Ala Ser Gln Ser Val Asp Tyr Asp Gly Glu Asn Tyr Met Asn
1 5 10 15

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 45

Val Ala Ser Asn Leu Glu Ser
1 5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 46

Gln Gln Ser Asn Leu Asp Pro Trp Thr
1 5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 47

Gly Phe Asn Ile Lys Asp Tyr
1 5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 48

Asp Pro Glu Asn Gly Asn
1 5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 49

Gly Thr Ala Arg Ala Ser Phe Asp Tyr
1 5

<210> SEQ ID NO 50
<211> LENGTH: 317
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 50

```
Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Ser Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
    210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
        275                 280                 285

Asp Met Gln Arg Gln Trp Ala Gly Leu Val Glu Lys Val Gln Ala Ala
    290                 295                 300

Val Gly Thr Ser Ala Ala Pro Val Pro Ser Asp Asn His
305                 310                 315
```

<210> SEQ ID NO 51

<400> SEQUENCE: 51

000

<210> SEQ ID NO 52
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Glu Asn Tyr Met Asn Trp Tyr Gln Gln Lys Pro Gly Gln Ser Pro
        35                  40                  45

Lys Leu Leu Ile Tyr Val Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Leu Asp Pro Trp Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215
```

<210> SEQ ID NO 53
<211> LENGTH: 442
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

```
Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
            20                  25                  30

His Leu His Trp Val Lys Gln Arg Pro Glu Gln Gly Leu Glu Trp Ile
        35                  40                  45

Gly Trp Ile Asp Pro Glu Asn Gly Asn Val Ile Tyr Asp Pro Lys Phe
    50                  55                  60

Gln Gly Lys Ala Thr Met Thr Val Val Thr Ser Ser Asn Thr Ala Tyr
65                  70                  75                  80

Leu Gln Leu Arg Ser Leu Thr Ser Glu Asp Thr Ala Val Tyr Phe Cys
```

-continued

```
                85                  90                  95

Thr Arg Gly Thr Ala Arg Ala Ser Phe Asp Tyr Trp Gly Gln Gly Thr
            100                 105                 110

Ser Leu Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly Lys
        435                 440
```

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Cys Thr Glu Glu Leu Arg Val Arg Leu Ala Ser His Leu Arg Lys
1 5 10 15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

Cys Thr Glu Glu Leu Arg Val Ser Leu Ala Ser His Leu Arg Lys
1 5 10 15

<210> SEQ ID NO 56
<211> LENGTH: 954
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56
atgaaggttc tgtgggctgc gttgctggtc acattcctgg caggatgcca ggccaaggtg 60
gagcaagcgg tggagacaga gccggagccc gagctgcgcc agcagaccga gtggcagagc 120
ggccagcgct gggaactggc actgggtcgc ttttgggatt acctgcgctg ggtgcagaca 180
ctgtctgagc aggtgcagga ggagctgctc agctcccagg tcacccagga actgagggcg 240
ctgatggacg agaccatgaa ggagttgaag gcctacaaat cggaactgga ggaacaactg 300
accccggtgg cggaggagac gcgggcacgg ctgtccaagg agctgcaggc ggcgcaggcc 360
cggctgggcg cggacatgga ggacgtgtgc ggccgcctgg tgcagtaccg cggcgaggtg 420
caggccatgc tcggccagag caccgaggag ctgcgggtga gcctcgcctc ccacctgcgc 480
aagctgcgta agcggctcct ccgcgatgcc gatgacctgc agaagcgcct ggcagtgtac 540
caggccgggg cccgcgaggg cgccgagcgc ggcctcagcg ccatccgcga gcgcctgggg 600
cccctggtgg aacagggccg cgtgcgggcc gccactgtgg gctccctggc cggccagccg 660
ctacaggagc gggcccaggc ctggggcgag cggctgcgcg cgcggatgga ggagatgggc 720
agccggaccc gcgaccgcct ggacgaggtg aaggagcagg tggcggaggt gcgcgccaag 780
ctggaggagc aggcccagca gatacgcctg caggccgagg ccttccaggc ccgcctcaag 840
agctggttcg agcccctggt ggaagacatg cagcgccagt gggccgggct ggtggagaag 900
gtgcaggctg ccgtgggcac cagcgccgcc cctgtgccca gcgacaatca ctga 954

<210> SEQ ID NO 57
<211> LENGTH: 29
<212> TYPE: PRT
<213> ORGANISM: Homo sapiens

<400> SEQUENCE: 57

Ser Thr Glu Glu Leu Arg Val Arg Leu Ala Ser His Leu Arg Lys Leu
1 5 10 15

Arg Lys Arg Leu Leu Arg Asp Ala Asp Asp Leu Gln Lys
20 25

<210> SEQ ID NO 58
<211> LENGTH: 29
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 58

Ser Thr Glu Glu Leu Arg Val Ser Leu Ala Ser His Leu Arg Lys Leu
1 5 10 15

Arg Lys Arg Leu Leu Arg Asp Ala Asp Asp Leu Gln Lys
20 25

<210> SEQ ID NO 59
<211> LENGTH: 31
<212> TYPE: PRT
<213> ORGANISM: Homo sapiens

<400> SEQUENCE: 59

Arg Leu Val Gln Tyr Arg Gly Glu Val Gln Ala Met Leu Gly Gln Ser
1 5 10 15

Thr Glu Glu Leu Arg Val Arg Leu Ala Ser His Leu Arg Lys Leu
20 25 30

<210> SEQ ID NO 60
<211> LENGTH: 31
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 60

Arg Leu Val Gln Tyr Arg Gly Glu Val Gln Ala Met Leu Gly Gln Ser
1 5 10 15

Thr Glu Glu Leu Arg Val Ser Leu Ala Ser His Leu Arg Lys Leu
20 25 30

<210> SEQ ID NO 61
<211> LENGTH: 7
<212> TYPE: PRT
<213> ORGANISM: Unknown
<220> FEATURE:
<223> OTHER INFORMATION: Description of Unknown:
nuclear localization sequence

<400> SEQUENCE: 61

Pro Lys Lys Lys Arg Lys Val
1 5

<210> SEQ ID NO 62
<211> LENGTH: 7
<212> TYPE: PRT
<213> ORGANISM: Simian virus 40

<400> SEQUENCE: 62

Pro Lys Lys Lys Arg Arg Val
1 5

<210> SEQ ID NO 63
<211> LENGTH: 16
<212> TYPE: PRT
<213> ORGANISM: Unknown
<220> FEATURE:
<223> OTHER INFORMATION: Description of Unknown:
nucleoplasmin NLS sequence

<400> SEQUENCE: 63

```
Lys Arg Pro Ala Ala Thr Lys Lys Ala Gly Gln Ala Lys Lys Lys Lys
1               5                   10                  15
```

<210> SEQ ID NO 64
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
tagcaataaa ggatcgttta ttttcattgg aagcgtgtgt tggttttttg atcaggcgcg    60

<210> SEQ ID NO 65
<211> LENGTH: 127
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
cgcctggtgc agtaccgcgg cgaggtgcag gccatgctcg gccagagcac agaggagctc    60
cgcgtgagtc tcgcaagcca cctgcgcaag ctgcgtaagc ggctcctccg cgatgccgat   120
gacctgc                                                             127

<210> SEQ ID NO 66
<211> LENGTH: 264
<212> TYPE: DNA
<213> ORGANISM: Homo sapiens

<400> SEQUENCE: 66
aaggtcgggc aggaagaggg cctatttccc atgattcctt catatttgca tatacgatac    60
aaggctgtta gagagataat tagaattaat ttgactgtaa acacaaagat attagtacaa   120
aatacgtgac gtagaaagta ataatttctt gggtagtttg cagttttaaa attatgtttt   180
aaaatggact atcatatgct taccgtaact tgaaagtatt tcgatttctt ggctttatat   240
atcttgtgga aaggacgaaa cacc                                          264

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
agcccttctc cccgcctccc actgt                                          25

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ctccgccacc tgctccttca cctcg                                          25

<210> SEQ ID NO 69

-continued

<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
cttacgcagc ttgcgcaggt 20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gcttgcgcag gtgggaggcg 20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
acgcagcttg cgcaggtggg 20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ccagagcacc gaggagctgc 20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gccagagcac cgaggagctg 20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gaggcgcacc cgcagctcct 20

<210> SEQ ID NO 75
<211> LENGTH: 20

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 75
agctgcgcca gcagaccgag 20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 76
ccaggccaag gtggagcaag 20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 77
cacaggatgc caggccaagg 20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 78
acagtgtctg cacccagcgc 20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 79
ggccaaggtg gagcaagcgg 20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 80
gaggcgcacc cgcagctcct 20

<210> SEQ ID NO 81
<211> LENGTH: 4290
<212> TYPE: DNA

-continued

<213> ORGANISM: Artificial Sequence
<220> FEATURE:
<223> OTHER INFORMATION: Description of Artificial Sequence: Synthetic
polynucleotide

<400> SEQUENCE: 81
ggatctgcga tcgctccggt gcccgtcagt gggcagagcg cacatcgccc acagtccccg 60
agaagttggg gggaggggtc ggcaattgaa cgggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctacctgaga tcaccggcga aggagggcca ccatgtacag gatgcaactc ctgtcttgca 600
ttgcactaag tcttgcactt gtcacgaatt cggcacctct cgagcgcaaa tctagtgtcg 660
agtgcccacc gtgcccagca ccacctgtgg caggaccgtc agtcttcctc ttccccccaa 720
aacccaagga caccctcatg atctcccgga cccctgaggt cacgtgcgtg gtggtggacg 780
tgagccacga agaccccgag gtccagttca actggtacgt ggacggcgtg gaggtgcata 840
atgccaagac aaagccacgg gaggagcagt tcaacagcac gttccgtgtg gtcagcgtcc 900
tcaccgttgt gcaccaggac tggctgaacg gcaaggagta caagtgcaag gtctccaaca 960
aaggcctccc agcccccatc gagaaaacca tctccaaaac caaagggcag ccccgagaac 1020
cacaggtgta caccctgccc ccatcccggg aggagatgac caagaaccag gtcagcctga 1080
cctgcctggt caaaggcttc taccccagcg acatcgccgt ggagtgggag agcaatgggc 1140
agccggagaa caactacaag accacgcctc ccatgctgga ctccgacggc tccttcttcc 1200
tctacagcaa gctcaccgtg gacaagagca ggtggcagca ggggaacgtc ttctcatgct 1260
ccgtgatgca tgaggctctg cacaaccact acacgcagaa gagcctctcc ctgtctccgg 1320
gtgcacgtac gcgcctggtg cagtaccgcg gcgaggtgca ggccatgctc ggccagagca 1380
ccgaggagct gcgggtgcgc ctcgcctccc acctgcgcaa gctgtgatat ctcgagctag 1440
ctggccagac atgataagat acattgatga gtttggacaa accacaacta gaatgcagtg 1500
aaaaaaatgc tttatttgtg aaatttgtga tgctattgct ttatttgtaa ccattataag 1560
ctgcaataaa caagttaaca acaacaattg cattcatttt atgtttcagg ttcaggggga 1620
ggtgtgggag gttttttaaa gcaagtaaaa cctctacaaa tgtggtatgg aattaattct 1680
aaaatacagc atagcaaaac tttaacctcc aaatcaagcc tctacttgaa tccttttctg 1740
agggatgaat aaggcatagg catcaggggc tgttgccaat gtgcattagc tgtttgcagc 1800
ctcaccttct ttcatggagt ttaagatata gtgtattttc ccaaggtttg aactagctct 1860
tcatttcttt atgttttaaa tgcactgacc tcccacattc cctttttagt aaaatattca 1920
gaaataattt aaatacatca ttgcaatgaa aataaatgtt ttttattagg cagaatccag 1980
atgctcaagg cccttcataa tatcccccag tttagtagtt ggacttaggg aacaaaggaa 2040
cctttaatag aaattggaca gcaagaaagc gagcttctag cttatcctca gtcctgctcc 2100
tctgccacaa agtgcacgca gttgccggcc gggtcgcgca gggcgaactc ccgcccccac 2160

-continued ggctgctcgc cgatctcggt catggccggc ccggaggcgt cccggaagtt cgtggacacg 2220
acctccgacc actcggcgta cagctcgtcc aggccgcgca cccacaccca ggccagggtg 2280
ttgtccggca ccacctggtc ctggaccgcg ctgatgaaca gggtcacgtc gtcccggacc 2340
acaccggcga agtcgtcctc cacgaagtcc cgggagaacc cgagccggtc ggtccagaac 2400
tcgaccgctc cggcgacgtc gcgcgcggtg agcaccggaa cggcactggt caacttggcc 2460
atgatggctc ctcctgtcag gagaggaaag agaagaaggt tagtacaatt gctatagtga 2520
gttgtattat actatgcaga tatactatgc caatgattaa ttgtcaaact agggctgcag 2580
ggttcatagt gccacttttc ctgcactgcc ccatctcctg cccacccttt cccaggcata 2640
gacagtcagt gacttaccaa actcacagga gggagaaggc agaagcttga gacagacccg 2700
cgggaccgcc gaactgcgag gggacgtggc tagggcggct tcttttatgg tgcgccggcc 2760
ctcggaggca gggcgctcgg ggaggcctag cggccaatct gcggtggcag gaggcggggc 2820
cgaaggccgt gcctgaccaa tccggagcac ataggagtct cagcccccg ccccaaagca 2880 aggggaagtc acgcgcctgt agcgccagcg tgttgtgaaa tgggggcttg ggggggttgg 2940
ggccctgact agtcaaaaca aactcccatt gacgtcaatg gggtggagac ttggaaatcc 3000
ccgtgagtca aaccgctatc cacgcccatt gatgtactgc caaaaccgca tcatcatggt 3060
aatagcgatg actaatacgt agatgtactg ccaagtagga aagtcccata aggtcatgta 3120
ctgggcataa tgccaggcgg gccatttacc gtcattgacg tcaatagggg gcgtacttgg 3180
catatgatac acttgatgta ctgccaagtg ggcagtttac cgtaaatact ccacccattg 3240
acgtcaatgg aaagtcccta ttggcgttac tatgggaaca tacgtcatta ttgacgtcaa 3300
tgggcggggg tcgttgggcg gtcagccagg cgggccattt accgtaagtt atgtaacgcc 3360
tgcaggttaa ttaagaacat gtgagcaaaa ggccagcaaa aggccaggaa ccgtaaaaag 3420
gccgcgttgc tggcgttttt ccataggctc cgcccccctg acgagcatca caaaaatcga 3480
cgctcaagtc agaggtggcg aaacccgaca ggactataaa gataccaggc gtttccccct 3540
ggaagctccc tcgtgcgctc tcctgttccg accctgccgc ttaccggata cctgtccgcc 3600
tttctccctt cgggaagcgt ggcgctttct catagctcac gctgtaggta tctcagttcg 3660
gtgtaggtcg ttcgctccaa gctgggctgt gtgcacgaac cccccgttca gcccgaccgc 3720
tgcgccttat ccggtaacta tcgtcttgag tccaacccgg taagacacga cttatcgcca 3780
ctggcagcag ccactggtaa caggattagc agagcgaggt atgtaggcgg tgctacagag 3840
ttcttgaagt ggtggcctaa ctacggctac actagaagaa cagtatttgg tatctgcgct 3900
ctgctgaagc cagttacctt cggaaaaaga gttggtagct cttgatccgg caaacaaacc 3960
accgctggta gcggtggttt ttttgtttgc aagcagcaga ttacgcgcag aaaaaaagga 4020
tctcaagaag atcctttgat cttttctacg gggtctgacg ctcagtggaa cgaaaactca 4080
cgttaaggga ttttggtcat ggctagttaa ttaacattta aatcagcggc cgcaataaaa 4140
tatctttatt ttcattacat ctgtgtgttg gttttttgtg tgaatcgtaa ctaacatacg 4200
ctctccatca aaacaaaacg aaacaaaaca aactagcaaa ataggctgtc cccagtgcaa 4260
gtgcaggtgc cagaacattt ctctatcgaa 4290

<210> SEQ ID NO 82
<211> LENGTH: 284
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

```
Met Tyr Arg Met Gln Leu Leu Ser Cys Ile Ala Leu Ser Leu Ala Leu
1               5                   10                  15

Val Thr Asn Ser Ala Pro Leu Glu Arg Lys Ser Ser Val Glu Cys Pro
            20                  25                  30

Pro Cys Pro Ala Pro Pro Val Ala Gly Pro Ser Val Phe Leu Phe Pro
        35                  40                  45

Pro Lys Pro Lys Asp Thr Leu Met Ile Ser Arg Thr Pro Glu Val Thr
    50                  55                  60

Cys Val Val Val Asp Val Ser His Glu Asp Pro Glu Val Gln Phe Asn
65                  70                  75                  80

Trp Tyr Val Asp Gly Val Glu Val His Asn Ala Lys Thr Lys Pro Arg
                85                  90                  95

Glu Glu Gln Phe Asn Ser Thr Phe Arg Val Val Ser Val Leu Thr Val
            100                 105                 110

Val His Gln Asp Trp Leu Asn Gly Lys Glu Tyr Lys Cys Lys Val Ser
        115                 120                 125

Asn Lys Gly Leu Pro Ala Pro Ile Glu Lys Thr Ile Ser Lys Thr Lys
    130                 135                 140

Gly Gln Pro Arg Glu Pro Gln Val Tyr Thr Leu Pro Pro Ser Arg Glu
145                 150                 155                 160

Glu Met Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Met Leu Asp Ser Asp Gly Ser Phe
        195                 200                 205

Phe Leu Tyr Ser Lys Leu Thr Val Asp Lys Ser Arg Trp Gln Gln Gly
    210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Ala Arg Thr Arg Leu Val
                245                 250                 255

Gln Tyr Arg Gly Glu Val Gln Ala Met Leu Gly Gln Ser Thr Glu Glu
            260                 265                 270

Leu Arg Val Arg Leu Ala Ser His Leu Arg Lys Leu
        275                 280
```

<210> SEQ ID NO 83
<211> LENGTH: 4290
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 83

```
ggatctgcga tcgctccggt gcccgtcagt gggcagagcg cacatcgccc acagtccccg      60

agaagttggg gggaggggtc ggcaattgaa cgggtgccta gagaaggtgg cgcggggtaa     120

actgggaaag tgatgtcgtg tactggctcc gcctttttcc cgagggtggg ggagaaccgt     180

atataagtgc agtagtcgcc gtgaacgttc tttttcgcaa cgggtttgcc gccagaacac     240

agctgaagct tcgaggggct cgcatctctc cttcacgcgc ccgccgccct acctgaggcc     300
```

-continued

```
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cggcacctct cgagcgcaaa tctagtgtcg    660
agtgcccacc gtgcccagca ccacctgtgg caggaccgtc agtcttcctc ttccccccaa    720
aacccaagga caccctcatg atctcccgga cccctgaggt cacgtgcgtg gtggtggacg    780
tgagccacga agaccccgag gtccagttca actggtacgt ggacggcgtg gaggtgcata    840
atgccaagac aaagccacgg gaggagcagt tcaacagcac gttccgtgtg gtcagcgtcc    900
tcaccgttgt gcaccaggac tggctgaacg gcaaggagta caagtgcaag gtctccaaca    960
aaggcctccc agcccccatc gagaaaacca tctccaaaac caaagggcag ccccgagaac   1020
cacaggtgta caccctgccc ccatcccggg aggagatgac caagaaccag gtcagcctga   1080
cctgcctggt caaaggcttc taccccagcg acatcgccgt ggagtgggag agcaatgggc   1140
agccggagaa caactacaag accacgcctc ccatgctgga ctccgacggc tccttcttcc   1200
tctacagcaa gctcaccgtg gacaagagca ggtggcagca ggggaacgtc ttctcatgct   1260
ccgtgatgca tgaggctctg cacaaccact acacgcagaa gagcctctcc ctgtctccgg   1320
gtgcacgtac gcgcctggtg cagtaccgcg gcgaggtgca ggccatgctc ggccagagca   1380
ccgaggagct gcgggtgagc ctcgcctccc acctgcgcaa gctgtgatat ctcgagctag   1440
ctggccagac atgataagat acattgatga gtttggacaa accacaacta gaatgcagtg   1500
aaaaaaatgc tttatttgtg aaatttgtga tgctattgct ttatttgtaa ccattataag   1560
ctgcaataaa caagttaaca acaacaattg cattcatttt atgtttcagg ttcaggggga   1620
ggtgtgggag gtttttttaaa gcaagtaaaa cctctacaaa tgtggtatgg aattaattct   1680
aaaatacagc atagcaaaac tttaacctcc aaatcaagcc tctacttgaa tccttttctg   1740
agggatgaat aaggcatagg catcaggggc tgttgccaat gtgcattagc tgtttgcagc   1800
ctcaccttct ttcatggagt ttaagatata gtgtattttc ccaaggtttg aactagctct   1860
tcatttcttt atgttttaaa tgcactgacc tcccacattc ccttttttagt aaaatattca   1920
gaaataattt aaatacatca ttgcaatgaa aataaatgtt ttttattagg cagaatccag   1980
atgctcaagg cccttcataa tatcccccag tttagtagtt ggacttaggg aacaaaggaa   2040
cctttaatag aaattggaca gcaagaaagc gagcttctag cttatcctca gtcctgctcc   2100
tctgccacaa agtgcacgca gttgccggcc gggtcgcgca gggcgaactc ccgcccccac   2160
ggctgctcgc cgatctcggt catggccggc ccggaggcgt cccggaagtt cgtggacacg   2220
acctccgacc actcggcgta cagctcgtcc aggccgcgca cccacaccca ggccagggtg   2280
ttgtccggca ccacctggtc ctggaccgcg ctgatgaaca gggtcacgtc gtcccggacc   2340
acaccggcga agtcgtcctc cacgaagtcc cgggagaacc cgagccggtc ggtccagaac   2400
tcgaccgctc cggcgacgtc gcgcgcggtg agcaccggaa cggcactggt caacttggcc   2460
atgatggctc ctcctgtcag gagaggaaag agaagaaggt tagtacaatt gctatagtga   2520
gttgtattat actatgcaga tatactatgc caatgattaa ttgtcaaact agggctgcag   2580
ggttcatagt gccacttttc ctgcactgcc ccatctcctg cccacccttt cccaggcata   2640
gacagtcagt gacttaccaa actcacagga gggagaaggc agaagcttga gacagacccg   2700
```

-continued cgggaccgcc gaactgcgag gggacgtggc tagggcggct tcttttatgg tgcgccggcc 2760
ctcggaggca gggcgctcgg ggaggcctag cggccaatct gcggtggcag gaggcggggc 2820
cgaaggccgt gcctgaccaa tccggagcac ataggagtct cagccccccg ccccaaagca 2880
aggggaagtc acgcgcctgt agcgccagcg tgttgtgaaa tgggggcttg ggggggttgg 2940
ggccctgact agtcaaaaca aactcccatt gacgtcaatg gggtggagac ttggaaatcc 3000
ccgtgagtca aaccgctatc cacgcccatt gatgtactgc caaaaccgca tcatcatggt 3060
aatagcgatg actaatacgt agatgtactg ccaagtagga aagtcccata aggtcatgta 3120
ctgggcataa tgccaggcgg gccatttacc gtcattgacg tcaatagggg gcgtacttgg 3180
catatgatac acttgatgta ctgccaagtg ggcagtttac cgtaaatact ccacccattg 3240
acgtcaatgg aaagtcccta ttggcgttac tatgggaaca tacgtcatta ttgacgtcaa 3300
tgggcggggg tcgttgggcg gtcagccagg cgggccattt accgtaagtt atgtaacgcc 3360
tgcaggttaa ttaagaacat gtgagcaaaa ggccagcaaa aggccaggaa ccgtaaaaag 3420
gccgcgttgc tggcgttttt ccataggctc cgcccccctg acgagcatca caaaaatcga 3480
cgctcaagtc agaggtggcg aaacccgaca ggactataaa gataccaggc gtttccccct 3540
ggaagctccc tcgtgcgctc tcctgttccg accctgccgc ttaccggata cctgtccgcc 3600
tttctccctt cgggaagcgt ggcgctttct catagctcac gctgtaggta tctcagttcg 3660
gtgtaggtcg ttcgctccaa gctgggctgt gtgcacgaac cccccgttca gcccgaccgc 3720
tgcgccttat ccggtaacta tcgtcttgag tccaacccgg taagacacga cttatcgcca 3780
ctggcagcag ccactggtaa caggattagc agagcgaggt atgtaggcgg tgctacagag 3840
ttcttgaagt ggtggcctaa ctacggctac actagaagaa cagtatttgg tatctgcgct 3900
ctgctgaagc cagttacctt cggaaaaaga gttggtagct cttgatccgg caaacaaacc 3960
accgctggta gcggtggttt ttttgtttgc aagcagcaga ttacgcgcag aaaaaaagga 4020
tctcaagaag atcctttgat cttttctacg gggtctgacg ctcagtggaa cgaaaactca 4080
cgttaaggga ttttggtcat ggctagttaa ttaacattta aatcagcggc cgcaataaaa 4140
tatctttatt ttcattacat ctgtgtgttg gttttttgtg tgaatcgtaa ctaacatacg 4200
ctctccatca aaacaaaacg aaacaaaaca aactagcaaa ataggctgtc cccagtgcaa 4260
gtgcaggtgc cagaacattt ctctatcgaa 4290

<210> SEQ ID NO 84
<211> LENGTH: 284
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Met Tyr Arg Met Gln Leu Leu Ser Cys Ile Ala Leu Ser Leu Ala Leu
1               5                   10                  15

Val Thr Asn Ser Ala Pro Leu Glu Arg Lys Ser Ser Val Glu Cys Pro
            20                  25                  30

Pro Cys Pro Ala Pro Pro Val Ala Gly Pro Ser Val Phe Leu Phe Pro
        35                  40                  45

Pro Lys Pro Lys Asp Thr Leu Met Ile Ser Arg Thr Pro Glu Val Thr
    50                  55                  60

Cys Val Val Val Asp Val Ser His Glu Asp Pro Glu Val Gln Phe Asn

```
65                  70                  75                  80

Trp Tyr Val Asp Gly Val Glu Val His Asn Ala Lys Thr Lys Pro Arg
                85                  90                  95

Glu Glu Gln Phe Asn Ser Thr Phe Arg Val Val Ser Val Leu Thr Val
            100                 105                 110

Val His Gln Asp Trp Leu Asn Gly Lys Glu Tyr Lys Cys Lys Val Ser
        115                 120                 125

Asn Lys Gly Leu Pro Ala Pro Ile Glu Lys Thr Ile Ser Lys Thr Lys
    130                 135                 140

Gly Gln Pro Arg Glu Pro Gln Val Tyr Thr Leu Pro Pro Ser Arg Glu
145                 150                 155                 160

Glu Met Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Met Leu Asp Ser Asp Gly Ser Phe
        195                 200                 205

Phe Leu Tyr Ser Lys Leu Thr Val Asp Lys Ser Arg Trp Gln Gln Gly
    210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Ala Arg Thr Arg Leu Val
                245                 250                 255

Gln Tyr Arg Gly Glu Val Gln Ala Met Leu Gly Gln Ser Thr Glu Glu
            260                 265                 270

Leu Arg Val Ser Leu Ala Ser His Leu Arg Lys Leu
        275                 280
```

<210> SEQ ID NO 85
<211> LENGTH: 4284
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 85

```
ggatctgcga tcgctccggt gcccgtcagt gggcagagcg cacatcgccc acagtccccg     60

agaagttggg gggaggggtc ggcaattgaa cgggtgccta gagaaggtgg cgcggggtaa    120

actgggaaag tgatgtcgtg tactggctcc gcctttttcc cgagggtggg ggagaaccgt    180

atataagtgc agtagtcgcc gtgaacgttc tttttcgcaa cgggtttgcc gccagaacac    240

agctgaagct tcgaggggct cgcatctctc cttcacgcgc ccgccgccct acctgaggcc    300

gccatccacg ccggttgagt cgcgttctgc cgcctcccgc ctgtggtgcc tcctgaactg    360

cgtccgccgt ctaggtaagt ttaaagctca ggtcgagacc gggcctttgt ccggcgctcc    420

cttggagcct acctagactc agccggctct ccacgctttg cctgaccctg cttgctcaac    480

tctacgtctt tgtttcgttt tctgttctgc gccgttacag atccaagctg tgaccggcgc    540

ctacctgaga tcaccggcga aggagggcca ccatgtacag gatgcaactc ctgtcttgca    600

ttgcactaag tcttgcactt gtcacgaatt cgatacgcct ggtgcagtac cgcggcgagg    660

tgcaggccat gctcggccag agtactgagg agctgcgggt gcgcctcgcc tcccacctgc    720

gcaagctgat atcggccatg gttagatctg tggagtgccc accttgccca gcaccacctg    780

tggcaggacc ttcagtcttc ctcttccccc caaaacccaa ggacaccctg atgatctcca    840
```

-continued

```
gaacccctga ggtcacgtgc gtggtggtgg acgtgagcca cgaagacccc gaggtccagt    900
tcaactggta cgtggacggc atggaggtgc ataatgccaa gacaaagcca cgggaggagc    960
agttcaacag cacgttccgt gtggtcagcg tcctcaccgt cgtgcaccag gactggctga   1020
acggcaagga gtacaagtgc aaggtctcca acaaaggcct cccagccccc atcgagaaaa   1080
ccatctccaa aaccaaaggg cagccccgag aaccacaggt gtacaccctg cccccatccc   1140
gggaggagat gaccaagaac caggtcagcc tgacctgcct ggtcaaaggc ttctacccca   1200
gcgacatcgc cgtggagtgg gagagcaatg ggcagccgga gaacaactac aagaccacac   1260
ctcccatgct ggactccgac ggctccttct tcctctacag caagctcacc gtggacaaga   1320
gcaggtggca gcaggggaac gtcttctcat gctccgtgat gcatgaggct ctgcacaacc   1380
actacacaca gaagagcctc tccctgtctc cgggtaaatg agtgccacgg ctagctggcc   1440
agacatgata agatacattg atgagtttgg acaaaccaca actagaatgc agtgaaaaaa   1500
atgctttatt tgtgaaattt gtgatgctat tgctttattt gtaaccatta taagctgcaa   1560
taaacaagtt aacaacaaca attgcattca ttttatgttt caggttcagg gggaggtgtg   1620
ggaggttttt taaagcaagt aaaacctcta caaatgtggt atggaattaa ttctaaaata   1680
cagcatagca aaactttaac ctccaaatca agcctctact tgaatccttt tctgagggat   1740
gaataaggca taggcatcag gggctgttgc caatgtgcat tagctgtttg cagcctcacc   1800
ttctttcatg gagtttaaga tatagtgtat tttcccaagg tttgaactag ctcttcattt   1860
ctttatgttt taaatgcact gacctcccac attccctttt tagtaaaata ttcagaaata   1920
atttaaatac atcattgcaa tgaaaataaa tgttttttat taggcagaat ccagatgctc   1980
aaggcccttc ataatatccc ccagtttagt agttggactt agggaacaaa ggaaccttta   2040
atagaaattg gacagcaaga aagcgagctt ctagcttatc ctcagtcctg ctcctctgcc   2100
acaaagtgca cgcagttgcc ggccgggtcg cgcagggcga actcccgccc ccacggctgc   2160
tcgccgatct cggtcatggc cggcccggag gcgtcccgga agttcgtgga cacgacctcc   2220
gaccactcgg cgtacagctc gtccaggccg cgcacccaca cccaggccag ggtgttgtcc   2280
ggcaccacct ggtcctggac cgcgctgatg aacagggtca cgtcgtcccg gaccacaccg   2340
gcgaagtcgt cctccacgaa gtcccgggag aacccgagcc ggtcggtcca gaactcgacc   2400
gctccggcga cgtcgcgcgc ggtgagcacc ggaacggcac tggtcaactt ggccatgatg   2460
gctcctcctg tcaggagagg aaagagaaga aggttagtac aattgctata gtgagttgta   2520
ttatactatg cagatatact atgccaatga ttaattgtca aactagggct gcagggttca   2580
tagtgccact tttcctgcac tgccccatct cctgcccacc ctttcccagg catagacagt   2640
cagtgactta ccaaactcac aggagggaga aggcagaagc ttgagacaga cccgcgggac   2700
cgccgaactg cgaggggacg tggctagggc ggcttctttt atggtgcgcc ggccctcgga   2760
ggcagggcgc tcggggaggc ctagcggcca atctgcggtg gcaggaggcg gggccgaagg   2820
ccgtgcctga ccaatccgga gcacatagga gtctcagccc cccgccccaa agcaagggga   2880
agtcacgcgc ctgtagcgcc agcgtgttgt gaaatggggg cttggggggg ttggggccct   2940
gactagtcaa aacaaactcc cattgacgtc aatggggtgg agacttggaa atccccgtga   3000
gtcaaaccgc tatccacgcc cattgatgta ctgccaaaac cgcatcatca tggtaatagc   3060
gatgactaat acgtagatgt actgccaagt aggaaagtcc cataaggtca tgtactgggc   3120
ataatgccag gcgggccatt taccgtcatt gacgtcaata gggggcgtac ttggcatatg   3180
```

-continued atacacttga tgtactgcca agtgggcagt ttaccgtaaa tactccaccc attgacgtca 3240
atggaaagtc cctattggcg ttactatggg aacatacgtc attattgacg tcaatgggcg 3300
ggggtcgttg ggcggtcagc caggcgggcc atttaccgta agttatgtaa cgcctgcagg 3360
ttaattaaga acatgtgagc aaaaggccag caaaaggcca ggaaccgtaa aaaggccgcg 3420
ttgctggcgt ttttccatag gctccgcccc cctgacgagc atcacaaaaa tcgacgctca 3480
agtcagaggt ggcgaaaccc gacaggacta taaagatacc aggcgtttcc ccctggaagc 3540
tccctcgtgc gctctcctgt tccgaccctg ccgcttaccg gatacctgtc cgcctttctc 3600
ccttcgggaa gcgtggcgct ttctcatagc tcacgctgta ggtatctcag ttcggtgtag 3660
gtcgttcgct ccaagctggg ctgtgtgcac gaaccccccg ttcagcccga ccgctgcgcc 3720
ttatccggta actatcgtct tgagtccaac ccggtaagac acgacttatc gccactggca 3780
gcagccactg gtaacaggat tagcagagcg aggtatgtag gcggtgctac agagttcttg 3840
aagtggtggc ctaactacgg ctacactaga agaacagtat ttggtatctg cgctctgctg 3900
aagccagtta ccttcggaaa aagagttggt agctcttgat ccggcaaaca aaccaccgct 3960
ggtagcggtg gtttttttgt ttgcaagcag cagattacgc gcagaaaaaa aggatctcaa 4020
gaagatcctt tgatcttttc tacggggtct gacgctcagt ggaacgaaaa ctcacgttaa 4080
gggattttgg tcatggctag ttaattaaca tttaaatcag cggccgcaat aaaatatctt 4140
tattttcatt acatctgtgt gttggttttt tgtgtgaatc gtaactaaca tacgctctcc 4200
atcaaaacaa aacgaaacaa aacaaactag caaaataggc tgtccccagt gcaagtgcag 4260
gtgccagaac atttctctat cgaa 4284

<210> SEQ ID NO 86
<211> LENGTH: 282
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 86

Met Tyr Arg Met Gln Leu Leu Ser Cys Ile Ala Leu Ser Leu Ala Leu
1 5 10 15

Val Thr Asn Ser Ile Arg Leu Val Gln Tyr Arg Gly Glu Val Gln Ala
20 25 30

Met Leu Gly Gln Ser Thr Glu Glu Leu Arg Val Arg Leu Ala Ser His
35 40 45

Leu Arg Lys Leu Ile Ser Ala Met Val Arg Ser Val Glu Cys Pro Pro
50 55 60

Cys Pro Ala Pro Pro Val Ala Gly Pro Ser Val Phe Leu Phe Pro Pro
65 70 75 80

Lys Pro Lys Asp Thr Leu Met Ile Ser Arg Thr Pro Glu Val Thr Cys
85 90 95

Val Val Val Asp Val Ser His Glu Asp Pro Glu Val Gln Phe Asn Trp
100 105 110

Tyr Val Asp Gly Met Glu Val His Asn Ala Lys Thr Lys Pro Arg Glu
115 120 125

Glu Gln Phe Asn Ser Thr Phe Arg Val Val Ser Val Leu Thr Val Val
130 135 140

His Gln Asp Trp Leu Asn Gly Lys Glu Tyr Lys Cys Lys Val Ser Asn
145 150 155 160

```
Lys Gly Leu Pro Ala Pro Ile Glu Lys Thr Ile Ser Lys Thr Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Met Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280
```

```
<210> SEQ ID NO 87
<211> LENGTH: 4284
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87

ggatctgcga tcgctccggt gcccgtcagt gggcagagcg cacatcgccc acagtccccg     60

agaagttggg gggaggggtc ggcaattgaa cgggtgccta gagaaggtgg cgcggggtaa    120

actgggaaag tgatgtcgtg tactggctcc gcctttttcc cgagggtggg ggagaaccgt    180

atataagtgc agtagtcgcc gtgaacgttc tttttcgcaa cgggtttgcc gccagaacac    240

agctgaagct tcgaggggct cgcatctctc cttcacgcgc ccgccgccct acctgaggcc    300

gccatccacg ccggttgagt cgcgttctgc cgcctcccgc ctgtggtgcc tcctgaactg    360

cgtccgccgt ctaggtaagt ttaaagctca ggtcgagacc gggcctttgt ccggcgctcc    420

cttggagcct acctagactc agccggctct ccacgctttg cctgaccctg cttgctcaac    480

tctacgtctt tgtttcgttt tctgttctgc gccgttacag atccaagctg tgaccggcgc    540

ctacctgaga tcaccggcga aggagggcca ccatgtacag gatgcaactc ctgtcttgca    600

ttgcactaag tcttgcactt gtcacgaatt cgatacgcct ggtgcagtac cgcggcgagg    660

tgcaggccat gctcggccag agtactgagg agctgcgggt gagcctcgcc tcccacctgc    720

gcaagctgat atcggccatg gttagatctg tggagtgccc accttgccca gcaccacctg    780

tggcaggacc ttcagtcttc ctcttccccc caaaacccaa ggacaccctg atgatctcca    840

gaacccctga ggtcacgtgc gtggtggtgg acgtgagcca cgaagacccc gaggtccagt    900

tcaactggta cgtggacggc atggaggtgc ataatgccaa gacaaagcca cgggaggagc    960

agttcaacag cacgttccgt gtggtcagcg tcctcaccgt cgtgcaccag gactggctga   1020

acggcaagga gtacaagtgc aaggtctcca acaaaggcct cccagccccc atcgagaaaa   1080

ccatctccaa aaccaaaggg cagccccgag aaccacaggt gtacaccctg cccccatccc   1140

gggaggagat gaccaagaac caggtcagcc tgacctgcct ggtcaaaggc ttctacccca   1200

gcgacatcgc cgtggagtgg gagagcaatg ggcagccgga gaacaactac aagaccacac   1260

ctcccatgct ggactccgac ggctccttct tcctctacag caagctcacc gtggacaaga   1320
```

-continued

```
gcaggtggca gcaggggaac gtcttctcat gctccgtgat gcatgaggct ctgcacaacc   1380
actacacaca gaagagcctc tccctgtctc cgggtaaatg agtgccacgg ctagctggcc   1440
agacatgata agatacattg atgagtttgg acaaaccaca actagaatgc agtgaaaaaa   1500
atgctttatt tgtgaaattt gtgatgctat tgctttattt gtaaccatta taagctgcaa   1560
taaacaagtt aacaacaaca attgcattca ttttatgttt caggttcagg gggaggtgtg   1620
ggaggttttt taaagcaagt aaaacctcta caaatgtggt atggaattaa ttctaaaata   1680
cagcatagca aaactttaac ctccaaatca agcctctact tgaatccttt tctgagggat   1740
gaataaggca taggcatcag gggctgttgc caatgtgcat tagctgtttg cagcctcacc   1800
ttctttcatg gagtttaaga tatagtgtat tttcccaagg tttgaactag ctcttcattt   1860
ctttatgttt taaatgcact gacctcccac attccctttt tagtaaaata ttcagaaata   1920
atttaaatac atcattgcaa tgaaaataaa tgttttttat taggcagaat ccagatgctc   1980
aaggcccttc ataatatccc ccagtttagt agttggactt agggaacaaa ggaaccttta   2040
atagaaattg gacagcaaga aagcgagctt ctagcttatc ctcagtcctg ctcctctgcc   2100
acaaagtgca cgcagttgcc ggccgggtcg cgcagggcga actcccgccc ccacggctgc   2160
tcgccgatct cggtcatggc cggcccggag gcgtcccgga agttcgtgga cacgacctcc   2220
gaccactcgg cgtacagctc gtccaggccg cgcacccaca cccaggccag ggtgttgtcc   2280
ggcaccacct ggtcctggac cgcgctgatg aacagggtca cgtcgtcccg gaccacaccg   2340
gcgaagtcgt cctccacgaa gtcccgggag aacccgagcc ggtcggtcca gaactcgacc   2400
gctccggcga cgtcgcgcgc ggtgagcacc ggaacggcac tggtcaactt ggccatgatg   2460
gctcctcctg tcaggagagg aaagagaaga aggttagtac aattgctata gtgagttgta   2520
ttatactatg cagatatact atgccaatga ttaattgtca aactagggct gcagggttca   2580
tagtgccact tttcctgcac tgccccatct cctgcccacc ctttcccagg catagacagt   2640
cagtgactta ccaaactcac aggagggaga aggcagaagc ttgagacaga cccgcgggac   2700
cgccgaactg cgaggggacg tggctagggc ggcttctttt atggtgcgcc ggccctcgga   2760
ggcagggcgc tcggggaggc ctagcggcca atctgcggtg gcaggaggcg gggccgaagg   2820
ccgtgcctga ccaatccgga gcacatagga gtctcagccc cccgccccaa agcaagggga   2880
agtcacgcgc ctgtagcgcc agcgtgttgt gaaatggggg cttgggggg ttggggccct   2940
gactagtcaa aacaaactcc cattgacgtc aatggggtgg agacttggaa atccccgtga   3000
gtcaaaccgc tatccacgcc cattgatgta ctgccaaaac cgcatcatca tggtaatagc   3060
gatgactaat acgtagatgt actgccaagt aggaaagtcc cataaggtca tgtactgggc   3120
ataatgccag gcgggccatt taccgtcatt gacgtcaata gggggcgtac ttggcatatg   3180
atacacttga tgtactgcca agtgggcagt ttaccgtaaa tactccaccc attgacgtca   3240
atggaaagtc cctattggcg ttactatggg aacatacgtc attattgacg tcaatgggcg   3300
ggggtcgttg ggcggtcagc caggcgggcc atttaccgta agttatgtaa cgcctgcagg   3360
ttaattaaga acatgtgagc aaaaggccag caaaaggcca ggaaccgtaa aaaggccgcg   3420
ttgctggcgt ttttccatag gctccgcccc cctgacgagc atcacaaaaa tcgacgctca   3480
agtcagaggt ggcgaaaccc gacaggacta taaagatacc aggcgtttcc ccctggaagc   3540
tccctcgtgc gctctcctgt tccgaccctg ccgcttaccg gatacctgtc cgcctttctc   3600
ccttcgggaa gcgtggcgct ttctcatagc tcacgctgta ggtatctcag ttcggtgtag   3660
gtcgttcgct ccaagctggg ctgtgtgcac gaaccccccg ttcagcccga ccgctgcgcc   3720
```

-continued

```
ttatccggta actatcgtct tgagtccaac ccggtaagac acgacttatc gccactggca   3780

gcagccactg gtaacaggat tagcagagcg aggtatgtag gcggtgctac agagttcttg   3840

aagtggtggc ctaactacgg ctacactaga agaacagtat ttggtatctg cgctctgctg   3900

aagccagtta ccttcggaaa aagagttggt agctcttgat ccggcaaaca aaccaccgct   3960

ggtagcggtg gtttttttgt ttgcaagcag cagattacgc gcagaaaaaa aggatctcaa   4020

gaagatcctt tgatcttttc tacggggtct gacgctcagt ggaacgaaaa ctcacgttaa   4080

gggattttgg tcatggctag ttaattaaca tttaaatcag cggccgcaat aaaatatctt   4140

tattttcatt acatctgtgt gttggttttt tgtgtgaatc gtaactaaca tacgctctcc   4200

atcaaaacaa aacgaaacaa aacaaactag caaaataggc tgtccccagt gcaagtgcag   4260

gtgccagaac atttctctat cgaa                                          4284
```

```
<210> SEQ ID NO 88
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Tyr Arg Met Gln Leu Leu Ser Cys Ile Ala Leu Ser Leu Ala Leu
1               5                   10                  15

Val Thr Asn Ser Ile Arg Leu Val Gln Tyr Arg Gly Glu Val Gln Ala
            20                  25                  30

Met Leu Gly Gln Ser Thr Glu Glu Leu Arg Val Ser Leu Ala Ser His
        35                  40                  45

Leu Arg Lys Leu Ile Ser Ala Met Val Arg Ser Val Glu Cys Pro Pro
    50                  55                  60

Cys Pro Ala Pro Pro Val Ala Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Gln Phe Asn Trp
            100                 105                 110

Tyr Val Asp Gly Met Glu Val His Asn Ala Lys Thr Lys Pro Arg Glu
        115                 120                 125

Glu Gln Phe Asn Ser Thr Phe Arg Val Val Ser Val Leu Thr Val Val
    130                 135                 140

His Gln Asp Trp Leu Asn Gly Lys Glu Tyr Lys Cys Lys Val Ser Asn
145                 150                 155                 160

Lys Gly Leu Pro Ala Pro Ile Glu Lys Thr Ile Ser Lys Thr Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Met Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255
```

Val Phe Ser Cys Ser Val Met His Glu Ala Leu His Asn His Tyr Thr
260 265 270

Gln Lys Ser Leu Ser Leu Ser Pro Gly Lys
275 280

<210> SEQ ID NO 89
<211> LENGTH: 4284
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89
ggatctgcga tcgctccggt gcccgtcagt gggcagagcg cacatcgccc acagtccccg 60
agaagttggg gggaggggtc ggcaattgaa cgggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctacctgaga tcaccggcga aggagggcca ccatgtacag gatgcaactc ctgtcttgca 600
ttgcactaag tcttgcactt gtcacgaatt cggcacctct cgagcgcaaa tctagtgtcg 660
agtgcccacc gtgcccagca ccacctgtgg caggaccgtc agtcttcctc ttccccccaa 720
aacccaagga caccctcatg atctcccgga cccctgaggt cacgtgcgtg gtggtggacg 780
tgagccacga agaccccgag gtccagttca actggtacgt ggacggcgtg gaggtgcata 840
atgccaagac aaagccacgg gaggagcagt tcaacagcac gttccgtgtg gtcagcgtcc 900
tcaccgttgt gcaccaggac tggctgaacg gcaaggagta caagtgcaag gtctccaaca 960
aaggcctccc agcccccatc gagaaaacca tctccaaaac caaagggcag ccccgagaac 1020
cacaggtgta caccctgccc ccatcccggg aggagatgac caagaaccag gtcagcctga 1080
cctgcctggt caaaggcttc taccccagcg acatcgccgt ggagtgggag agcaatgggc 1140
agccggagaa caactacaag accacgcctc ccatgctgga ctccgacggc tccttcttcc 1200
tctacagcaa gctcaccgtg gacaagagca ggtggcagca ggggaacgtc ttctcatgct 1260
ccgtgatgca tgaggctctg cacaaccact acacgcagaa gagcctctcc ctgtctccgg 1320
gtgcacgtac gagcaccgag gagctgcggg tgcgcctcgc ctcccacctg cgcaagctgc 1380
gtaagcggct cctccgcgat gccgatgacc tgcagaagtg atatctcgag ctagctggcc 1440
agacatgata agatacattg atgagtttgg acaaaccaca actagaatgc agtgaaaaaa 1500
atgctttatt tgtgaaattt gtgatgctat tgctttattt gtaaccatta taagctgcaa 1560
taaacaagtt aacaacaaca attgcattca ttttatgttt caggttcagg gggaggtgtg 1620
ggaggttttt taaagcaagt aaaacctcta caaatgtggt atggaattaa ttctaaaata 1680
cagcatagca aaactttaac ctccaaatca agcctctact tgaatccttt tctgagggat 1740
gaataaggca taggcatcag ggctgttgc caatgtgcat tagctgtttg cagcctcacc 1800
ttctttcatg gagtttaaga tatagtgtat tttcccaagg tttgaactag ctcttcattt 1860
ctttatgttt taaatgcact gacctcccac attccctttt tagtaaaata ttcagaaata 1920
atttaaatac atcattgcaa tgaaaataaa tgttttttat taggcagaat ccagatgctc 1980
aaggcccttc ataatatccc ccagtttagt agttggactt agggaacaaa ggaaccttta 2040
atagaaattg gacagcaaga aagcgagctt ctagcttatc ctcagtcctg ctcctctgcc 2100
acaaagtgca cgcagttgcc ggccgggtcg cgcagggcga actcccgccc ccacggctgc 2160
tcgccgatct cggtcatggc cggcccggag gcgtcccgga agttcgtgga cacgacctcc 2220
gaccactcgg cgtacagctc gtccaggccg cgcacccaca cccaggccag ggtgttgtcc 2280
ggcaccacct ggtcctggac cgcgctgatg aacagggtca cgtcgtcccg gaccacaccg 2340
gcgaagtcgt cctccacgaa gtcccgggag aacccgagcc ggtcggtcca gaactcgacc 2400
gctccggcga cgtcgcgcgc ggtgagcacc ggaacggcac tggtcaactt ggccatgatg 2460
gctcctcctg tcaggagagg aaagagaaga aggttagtac aattgctata gtgagttgta 2520
ttatactatg cagatatact atgccaatga ttaattgtca aactagggct gcagggttca 2580
tagtgccact tttcctgcac tgccccatct cctgcccacc ctttcccagg catagacagt 2640
cagtgactta ccaaactcac aggagggaga aggcagaagc ttgagacaga cccgcgggac 2700
cgccgaactg cgaggggacg tggctagggc ggcttctttt atggtgcgcc ggccctcgga 2760
ggcagggcgc tcggggaggc ctagcggcca atctgcggtg gcaggaggcg gggccgaagg 2820
ccgtgcctga ccaatccgga gcacatagga gtctcagccc cccgccccaa agcaagggga 2880
agtcacgcgc ctgtagcgcc agcgtgttgt gaaatggggg cttgggggg ttggggccct 2940
gactagtcaa aacaaactcc cattgacgtc aatggggtgg agacttggaa atccccgtga 3000
gtcaaaccgc tatccacgcc cattgatgta ctgccaaaac cgcatcatca tggtaatagc 3060
gatgactaat acgtagatgt actgccaagt aggaaagtcc cataaggtca tgtactgggc 3120
ataatgccag gcgggccatt taccgtcatt gacgtcaata gggggcgtac ttggcatatg 3180
atacacttga tgtactgcca agtgggcagt ttaccgtaaa tactccaccc attgacgtca 3240
atggaaagtc cctattggcg ttactatggg aacatacgtc attattgacg tcaatgggcg 3300
ggggtcgttg ggcggtcagc caggcgggcc atttaccgta agttatgtaa cgcctgcagg 3360
ttaattaaga acatgtgagc aaaaggccag caaaaggcca ggaaccgtaa aaaggccgcg 3420
ttgctggcgt ttttccatag gctccgcccc cctgacgagc atcacaaaaa tcgacgctca 3480
agtcagaggt ggcgaaaccc gacaggacta taaagatacc aggcgtttcc ccctggaagc 3540
tccctcgtgc gctctcctgt tccgaccctg ccgcttaccg gatacctgtc cgcctttctc 3600
ccttcgggaa gcgtggcgct ttctcatagc tcacgctgta ggtatctcag ttcggtgtag 3660
gtcgttcgct ccaagctggg ctgtgtgcac gaaccccccg ttcagcccga ccgctgcgcc 3720
ttatccggta actatcgtct tgagtccaac ccggtaagac acgacttatc gccactggca 3780
gcagccactg gtaacaggat tagcagagcg aggtatgtag gcggtgctac agagttcttg 3840
aagtggtggc ctaactacgg ctacactaga agaacagtat ttggtatctg cgctctgctg 3900
aagccagtta ccttcggaaa aagagttggt agctcttgat ccggcaaaca aaccaccgct 3960
ggtagcggtg gtttttttgt ttgcaagcag cagattacgc gcagaaaaaa aggatctcaa 4020
gaagatcctt tgatcttttc tacggggtct gacgctcagt ggaacgaaaa ctcacgttaa 4080
gggattttgg tcatggctag ttaattaaca tttaaatcag cggccgcaat aaaatatctt 4140
tattttcatt acatctgtgt gttggttttt tgtgtgaatc gtaactaaca tacgctctcc 4200

```
atcaaaacaa aacgaaacaa aacaaactag caaaataggc tgtccccagt gcaagtgcag   4260

gtgccagaac atttctctat cgaa                                          4284


<210> SEQ ID NO 90
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Met Tyr Arg Met Gln Leu Leu Ser Cys Ile Ala Leu Ser Leu Ala Leu
1               5                   10                  15

Val Thr Asn Ser Ala Pro Leu Glu Arg Lys Ser Ser Val Glu Cys Pro
            20                  25                  30

Pro Cys Pro Ala Pro Pro Val Ala Gly Pro Ser Val Phe Leu Phe Pro
        35                  40                  45

Pro Lys Pro Lys Asp Thr Leu Met Ile Ser Arg Thr Pro Glu Val Thr
    50                  55                  60

Cys Val Val Val Asp Val Ser His Glu Asp Pro Glu Val Gln Phe Asn
65                  70                  75                  80

Trp Tyr Val Asp Gly Val Glu Val His Asn Ala Lys Thr Lys Pro Arg
                85                  90                  95

Glu Glu Gln Phe Asn Ser Thr Phe Arg Val Val Ser Val Leu Thr Val
            100                 105                 110

Val His Gln Asp Trp Leu Asn Gly Lys Glu Tyr Lys Cys Lys Val Ser
        115                 120                 125

Asn Lys Gly Leu Pro Ala Pro Ile Glu Lys Thr Ile Ser Lys Thr Lys
    130                 135                 140

Gly Gln Pro Arg Glu Pro Gln Val Tyr Thr Leu Pro Pro Ser Arg Glu
145                 150                 155                 160

Glu Met Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Met Leu Asp Ser Asp Gly Ser Phe
        195                 200                 205

Phe Leu Tyr Ser Lys Leu Thr Val Asp Lys Ser Arg Trp Gln Gln Gly
    210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Ala Arg Thr Ser Thr Glu
                245                 250                 255

Glu Leu Arg Val Arg Leu Ala Ser His Leu Arg Lys Leu Arg Lys Arg
            260                 265                 270

Leu Leu Arg Asp Ala Asp Asp Leu Gln Lys
        275                 280


<210> SEQ ID NO 91
<211> LENGTH: 4284
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
```

-continued

```
ggatctgcga tcgctccggt gcccgtcagt gggcagagcg cacatcgccc acagtccccg     60
agaagttggg gggaggggtc ggcaattgaa cgggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cggcacctct cgagcgcaaa tctagtgtcg    660
agtgcccacc gtgcccagca ccacctgtgg caggaccgtc agtcttcctc ttcccccaa     720
aacccaagga caccctcatg atctcccgga cccctgaggt cacgtgcgtg gtggtggacg    780
tgagccacga agaccccgag gtccagttca actggtacgt ggacggcgtg gaggtgcata    840
atgccaagac aaagccacgg gaggagcagt tcaacagcac gttccgtgtg gtcagcgtcc    900
tcaccgttgt gcaccaggac tggctgaacg gcaaggagta caagtgcaag gtctccaaca    960
aaggcctccc agcccccatc gagaaaacca tctccaaaac caaagggcag ccccgagaac   1020
cacaggtgta caccctgccc ccatcccggg aggagatgac caagaaccag gtcagcctga   1080
cctgcctggt caaaggcttc taccccagcg acatcgccgt ggagtgggag agcaatgggc   1140
agccggagaa caactacaag accacgcctc ccatgctgga ctccgacggc tccttcttcc   1200
tctacagcaa gctcaccgtg gacaagagca ggtggcagca ggggaacgtc ttctcatgct   1260
ccgtgatgca tgaggctctg cacaaccact acacgcagaa gagcctctcc ctgtctccgg   1320
gtgcacgtac gagcaccgag gagctgcggg tgagcctcgc ctcccacctg cgcaagctgc   1380
gtaagcggct cctccgcgat gccgatgacc tgcagaagtg atatctcgag ctagctggcc   1440
agacatgata agatacattg atgagtttgg acaaaccaca actagaatgc agtgaaaaaa   1500
atgctttatt tgtgaaattt gtgatgctat tgctttattt gtaaccatta taagctgcaa   1560
taaacaagtt aacaacaaca attgcattca ttttatgttt caggttcagg gggaggtgtg   1620
ggaggttttt taaagcaagt aaaacctcta caaatgtggt atggaattaa ttctaaaata   1680
cagcatagca aaactttaac ctccaaatca agcctctact tgaatccttt tctgagggat   1740
gaataaggca taggcatcag gggctgttgc caatgtgcat tagctgtttg cagcctcacc   1800
ttctttcatg gagtttaaga tatagtgtat tttcccaagg tttgaactag ctcttcattt   1860
ctttatgttt taaatgcact gacctcccac attccctttt tagtaaaata ttcagaaata   1920
atttaaatac atcattgcaa tgaaaataaa tgttttttat taggcagaat ccagatgctc   1980
aaggcccttc ataatatccc ccagtttagt agttggactt agggaacaaa ggaaccttta   2040
atagaaattg gacagcaaga aagcgagctt ctagcttatc ctcagtcctg ctcctctgcc   2100
acaaagtgca cgcagttgcc ggccgggtcg cgcagggcga actcccgccc ccacggctgc   2160
tcgccgatct cggtcatggc cggcccggag gcgtcccgga agttcgtgga cacgacctcc   2220
gaccactcgg cgtacagctc gtccaggccg cgcacccaca cccaggccag ggtgttgtcc   2280
ggcaccacct ggtcctggac cgcgctgatg aacagggtca cgtcgtcccg gaccacaccg   2340
```

-continued

```
gcgaagtcgt cctccacgaa gtcccgggag aacccgagcc ggtcggtcca gaactcgacc   2400
gctccggcga cgtcgcgcgc ggtgagcacc ggaacggcac tggtcaactt ggccatgatg   2460
gctcctcctg tcaggagagg aaagagaaga aggttagtac aattgctata gtgagttgta   2520
ttatactatg cagatatact atgccaatga ttaattgtca aactagggct gcagggttca   2580
tagtgccact tttcctgcac tgccccatct cctgcccacc ctttcccagg catagacagt   2640
cagtgactta ccaaactcac aggagggaga aggcagaagc ttgagacaga cccgcgggac   2700
cgccgaactg cgaggggacg tggctagggc ggcttctttt atggtgcgcc ggccctcgga   2760
ggcagggcgc tcggggaggc ctagcggcca atctgcggtg gcaggaggcg gggccgaagg   2820
ccgtgcctga ccaatccgga gcacatagga gtctcagccc cccgccccaa agcaagggga   2880
agtcacgcgc ctgtagcgcc agcgtgttgt gaaatggggg cttgggggg ttggggccct   2940
gactagtcaa aacaaactcc cattgacgtc aatggggtgg agacttggaa atccccgtga   3000
gtcaaaccgc tatccacgcc cattgatgta ctgccaaaac cgcatcatca tggtaatagc   3060
gatgactaat acgtagatgt actgccaagt aggaaagtcc cataaggtca tgtactgggc   3120
ataatgccag gcgggccatt taccgtcatt gacgtcaata gggggcgtac ttggcatatg   3180
atacacttga tgtactgcca agtgggcagt ttaccgtaaa tactccaccc attgacgtca   3240
atggaaagtc cctattggcg ttactatggg aacatacgtc attattgacg tcaatgggcg   3300
ggggtcgttg ggcggtcagc caggcgggcc atttaccgta agttatgtaa cgcctgcagg   3360
ttaattaaga acatgtgagc aaaaggccag caaaaggcca ggaaccgtaa aaaggccgcg   3420
ttgctggcgt ttttccatag gctccgcccc cctgacgagc atcacaaaaa tcgacgctca   3480
agtcagaggt ggcgaaaccc gacaggacta taaagatacc aggcgtttcc ccctggaagc   3540
tccctcgtgc gctctcctgt tccgaccctg ccgcttaccg gatacctgtc cgcctttctc   3600
ccttcgggaa gcgtggcgct ttctcatagc tcacgctgta ggtatctcag ttcggtgtag   3660
gtcgttcgct ccaagctggg ctgtgtgcac gaaccccccg ttcagcccga ccgctgcgcc   3720
ttatccggta actatcgtct tgagtccaac ccggtaagac acgacttatc gccactggca   3780
gcagccactg gtaacaggat tagcagagcg aggtatgtag gcggtgctac agagttcttg   3840
aagtggtggc ctaactacgg ctacactaga agaacagtat ttggtatctg cgctctgctg   3900
aagccagtta ccttcggaaa aagagttggt agctcttgat ccggcaaaca aaccaccgct   3960
ggtagcggtg gtttttttgt ttgcaagcag cagattacgc gcagaaaaaa aggatctcaa   4020
gaagatcctt tgatcttttc tacggggtct gacgctcagt ggaacgaaaa ctcacgttaa   4080
gggattttgg tcatggctag ttaattaaca tttaaatcag cggccgcaat aaaatatctt   4140
tattttcatt acatctgtgt gttggttttt tgtgtgaatc gtaactaaca tacgctctcc   4200
atcaaaacaa aacgaaacaa aacaaactag caaaataggc tgtccccagt gcaagtgcag   4260
gtgccagaac atttctctat cgaa                                          4284
```

<210> SEQ ID NO 92
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

```
Met Tyr Arg Met Gln Leu Leu Ser Cys Ile Ala Leu Ser Leu Ala Leu
1               5                   10                  15
```

```
Val Thr Asn Ser Ala Pro Leu Glu Arg Lys Ser Ser Val Glu Cys Pro
            20                  25                  30

Pro Cys Pro Ala Pro Pro Val Ala Gly Pro Ser Val Phe Leu Phe Pro
        35                  40                  45

Pro Lys Pro Lys Asp Thr Leu Met Ile Ser Arg Thr Pro Glu Val Thr
    50                  55                  60

Cys Val Val Val Asp Val Ser His Glu Asp Pro Glu Val Gln Phe Asn
65                  70                  75                  80

Trp Tyr Val Asp Gly Val Glu Val His Asn Ala Lys Thr Lys Pro Arg
                85                  90                  95

Glu Glu Gln Phe Asn Ser Thr Phe Arg Val Val Ser Val Leu Thr Val
            100                 105                 110

Val His Gln Asp Trp Leu Asn Gly Lys Glu Tyr Lys Cys Lys Val Ser
        115                 120                 125

Asn Lys Gly Leu Pro Ala Pro Ile Glu Lys Thr Ile Ser Lys Thr Lys
    130                 135                 140

Gly Gln Pro Arg Glu Pro Gln Val Tyr Thr Leu Pro Pro Ser Arg Glu
145                 150                 155                 160

Glu Met Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Met Leu Asp Ser Asp Gly Ser Phe
        195                 200                 205

Phe Leu Tyr Ser Lys Leu Thr Val Asp Lys Ser Arg Trp Gln Gln Gly
    210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Ala Arg Thr Ser Thr Glu
                245                 250                 255

Glu Leu Arg Val Ser Leu Ala Ser His Leu Arg Lys Leu Arg Lys Arg
            260                 265                 270

Leu Leu Arg Asp Ala Asp Asp Leu Gln Lys
        275                 280
```

<210> SEQ ID NO 93
<211> LENGTH: 4278
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 93

```
ggatctgcga tcgctccggt gcccgtcagt gggcagagcg cacatcgccc acagtccccg      60

agaagttggg gggaggggtc ggcaattgaa cgggtgccta gagaaggtgg cgcggggtaa     120

actgggaaag tgatgtcgtg tactggctcc gcctttttcc cgagggtggg ggagaaccgt     180

atataagtgc agtagtcgcc gtgaacgttc tttttcgcaa cgggtttgcc gccagaacac     240

agctgaagct tcgaggggct cgcatctctc cttcacgcgc ccgccgccct acctgaggcc     300

gccatccacg ccggttgagt cgcgttctgc cgcctcccgc ctgtggtgcc tcctgaactg     360

cgtccgccgt ctaggtaagt ttaaagctca ggtcgagacc gggcctttgt ccggcgctcc     420

cttggagcct acctagactc agccggctct ccacgctttg cctgaccctg cttgctcaac     480
```

-continued

```
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cgataagcac cgaggagctg cgggtgcgcc    660
tcgcctccca cctgcgcaag ctgcgtaagc ggctcctccg cgatgccgat gacctgcaga    720
agatatcggc catggttaga tctgtggagt gcccaccttg cccagcacca cctgtggcag    780
gaccttcagt cttcctcttc cccccaaaac ccaaggacac cctgatgatc tccagaaccc    840
ctgaggtcac gtgcgtggtg gtggacgtga gccacgaaga ccccgaggtc cagttcaact    900
ggtacgtgga cggcatggag gtgcataatg ccaagacaaa gccacgggag gagcagttca    960
acagcacgtt ccgtgtggtc agcgtcctca ccgtcgtgca ccaggactgg ctgaacggca   1020
aggagtacaa gtgcaaggtc tccaacaaag gcctcccagc ccccatcgag aaaaccatct   1080
ccaaaaccaa agggcagccc cgagaaccac aggtgtacac cctgccccca tcccgggagg   1140
agatgaccaa gaaccaggtc agcctgacct gcctggtcaa aggcttctac cccagcgaca   1200
tcgccgtgga gtgggagagc aatgggcagc cggagaacaa ctacaagacc acacctccca   1260
tgctggactc cgacggctcc ttcttcctct acagcaagct caccgtggac aagagcaggt   1320
ggcagcaggg gaacgtcttc tcatgctccg tgatgcatga ggctctgcac aaccactaca   1380
cacagaagag cctctccctg tctccgggta aatgagtgcc acggctagct ggccagacat   1440
gataagatac attgatgagt ttggacaaac cacaactaga atgcagtgaa aaaaatgctt   1500
tatttgtgaa atttgtgatg ctattgcttt atttgtaacc attataagct gcaataaaca   1560
agttaacaac aacaattgca ttcattttat gtttcaggtt cagggggagg tgtgggaggt   1620
tttttaaagc aagtaaaacc tctacaaatg tggtatggaa ttaattctaa aatacagcat   1680
agcaaaactt taacctccaa atcaagcctc tacttgaatc cttttctgag ggatgaataa   1740
ggcataggca tcaggggctg ttgccaatgt gcattagctg tttgcagcct caccttcttt   1800
catggagttt aagatatagt gtattttccc aaggtttgaa ctagctcttc atttctttat   1860
gttttaaatg cactgacctc ccacattccc tttttagtaa aatattcaga aataatttaa   1920
atacatcatt gcaatgaaaa taaatgtttt ttattaggca gaatccagat gctcaaggcc   1980
cttcataata tcccccagtt tagtagttgg acttagggaa caaaggaacc tttaatagaa   2040
attggacagc aagaaagcga gcttctagct tatcctcagt cctgctcctc tgccacaaag   2100
tgcacgcagt tgccggccgg gtcgcgcagg gcgaactccc gcccccacgg ctgctcgccg   2160
atctcggtca tggccggccc ggaggcgtcc cggaagttcg tggacacgac ctccgaccac   2220
tcggcgtaca gctcgtccag gccgcgcacc cacacccagg ccagggtgtt gtccggcacc   2280
acctggtcct ggaccgcgct gatgaacagg gtcacgtcgt cccggaccac accggcgaag   2340
tcgtcctcca cgaagtcccg ggagaacccg agccggtcgg tccagaactc gaccgctccg   2400
gcgacgtcgc gcgcggtgag caccggaacg gcactggtca acttggccat gatggctcct   2460
cctgtcagga gaggaaagag aagaaggtta gtacaattgc tatagtgagt tgtattatac   2520
tatgcagata tactatgcca atgattaatt gtcaaactag ggctgcaggg ttcatagtgc   2580
cacttttcct gcactgcccc atctcctgcc caccctttcc caggcataga cagtcagtga   2640
cttaccaaac tcacaggagg gagaaggcag aagcttgaga cagacccgcg ggaccgccga   2700
actgcgaggg gacgtggcta gggcggcttc ttttatggtg cgccggccct cggaggcagg   2760
gcgctcgggg aggcctagcg gccaatctgc ggtggcagga ggcggggccg aaggccgtgc   2820
ctgaccaatc cggagcacat aggagtctca gccccccgcc ccaaagcaag ggaagtcac    2880
```

-continued

```
gcgcctgtag cgccagcgtg ttgtgaaatg ggggcttggg ggggttgggg ccctgactag   2940

tcaaaacaaa ctcccattga cgtcaatggg gtggagactt ggaaatcccc gtgagtcaaa   3000

ccgctatcca cgcccattga tgtactgcca aaaccgcatc atcatggtaa tagcgatgac   3060

taatacgtag atgtactgcc aagtaggaaa gtcccataag gtcatgtact gggcataatg   3120

ccaggcgggc catttaccgt cattgacgtc aatagggggc gtacttggca tatgatacac   3180

ttgatgtact gccaagtggg cagtttaccg taaatactcc acccattgac gtcaatggaa   3240

agtccctatt ggcgttacta tgggaacata cgtcattatt gacgtcaatg ggcgggggtc   3300

gttgggcggt cagccaggcg ggccatttac cgtaagttat gtaacgcctg caggttaatt   3360

aagaacatgt gagcaaaagg ccagcaaaag gccaggaacc gtaaaaaggc cgcgttgctg   3420

gcgtttttcc ataggctccg cccccctgac gagcatcaca aaaatcgacg ctcaagtcag   3480

aggtggcgaa acccgacagg actataaaga taccaggcgt ttccccctgg aagctccctc   3540

gtgcgctctc ctgttccgac cctgccgctt accggatacc tgtccgcctt tctcccttcg   3600

ggaagcgtgg cgctttctca tagctcacgc tgtaggtatc tcagttcggt gtaggtcgtt   3660

cgctccaagc tgggctgtgt gcacgaaccc cccgttcagc ccgaccgctg cgccttatcc   3720

ggtaactatc gtcttgagtc caacccggta agacacgact tatcgccact ggcagcagcc   3780

actggtaaca ggattagcag agcgaggtat gtaggcggtg ctacagagtt cttgaagtgg   3840

tggcctaact acggctacac tagaagaaca gtatttggta tctgcgctct gctgaagcca   3900

gttaccttcg gaaaaagagt tggtagctct tgatccggca aacaaaccac cgctggtagc   3960

ggtggttttt ttgtttgcaa gcagcagatt acgcgcagaa aaaaaggatc tcaagaagat   4020

cctttgatct tttctacggg gtctgacgct cagtggaacg aaaactcacg ttaagggatt   4080

ttggtcatgg ctagttaatt aacatttaaa tcagcggccg caataaaata tctttatttt   4140

cattacatct gtgtgttggt tttttgtgtg aatcgtaact aacatacgct ctccatcaaa   4200

acaaaacgaa acaaaacaaa ctagcaaaat aggctgtccc cagtgcaagt gcaggtgcca   4260

gaacatttct ctatcgaa                                                 4278
```

```
<210> SEQ ID NO 94
<211> LENGTH: 280
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Met Tyr Arg Met Gln Leu Leu Ser Cys Ile Ala Leu Ser Leu Ala Leu
1               5                   10                  15

Val Thr Asn Ser Ile Ser Thr Glu Glu Leu Arg Val Arg Leu Ala Ser
            20                  25                  30

His Leu Arg Lys Leu Arg Lys Arg Leu Leu Arg Asp Ala Asp Asp Leu
        35                  40                  45

Gln Lys Ile Ser Ala Met Val Arg Ser Val Glu Cys Pro Pro Cys Pro
    50                  55                  60

Ala Pro Pro Val Ala Gly Pro Ser Val Phe Leu Phe Pro Pro Lys Pro
65                  70                  75                  80

Lys Asp Thr Leu Met Ile Ser Arg Thr Pro Glu Val Thr Cys Val Val
                85                  90                  95

Val Asp Val Ser His Glu Asp Pro Glu Val Gln Phe Asn Trp Tyr Val
```

```
            100                 105                 110

Asp Gly Met Glu Val His Asn Ala Lys Thr Lys Pro Arg Glu Glu Gln
        115                 120                 125

Phe Asn Ser Thr Phe Arg Val Val Ser Val Leu Thr Val Val His Gln
    130                 135                 140

Asp Trp Leu Asn Gly Lys Glu Tyr Lys Cys Lys Val Ser Asn Lys Gly
145                 150                 155                 160

Leu Pro Ala Pro Ile Glu Lys Thr Ile Ser Lys Thr Lys Gly Gln Pro
                165                 170                 175

Arg Glu Pro Gln Val Tyr Thr Leu Pro Pro Ser Arg Glu Glu Met Thr
            180                 185                 190

Lys Asn Gln Val Ser Leu Thr Cys Leu Val Lys Gly Phe Tyr Pro Ser
        195                 200                 205

Asp Ile Ala Val Glu Trp Glu Ser Asn Gly Gln Pro Glu Asn Asn Tyr
    210                 215                 220

Lys Thr Thr Pro Pro Met Leu Asp Ser Asp Gly Ser Phe Phe Leu Tyr
225                 230                 235                 240

Ser Lys Leu Thr Val Asp Lys Ser Arg Trp Gln Gln Gly Asn Val Phe
                245                 250                 255

Ser Cys Ser Val Met His Glu Ala Leu His Asn His Tyr Thr Gln Lys
            260                 265                 270

Ser Leu Ser Leu Ser Pro Gly Lys
        275                 280
```

<210> SEQ ID NO 95
<211> LENGTH: 4278
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95

```
ggatctgcga tcgctccggt gcccgtcagt gggcagagcg cacatcgccc acagtccccg     60

agaagttggg gggaggggtc ggcaattgaa cgggtgccta gagaaggtgg cgcggggtaa    120

actgggaaag tgatgtcgtg tactggctcc gcctttttcc cgagggtggg ggagaaccgt    180

atataagtgc agtagtcgcc gtgaacgttc tttttcgcaa cgggtttgcc gccagaacac    240

agctgaagct tcgaggggct cgcatctctc cttcacgcgc ccgccgccct acctgaggcc    300

gccatccacg ccggttgagt cgcgttctgc cgcctcccgc ctgtggtgcc tcctgaactg    360

cgtccgccgt ctaggtaagt ttaaagctca ggtcgagacc gggcctttgt ccggcgctcc    420

cttggagcct acctagactc agccggctct ccacgctttg cctgaccctg cttgctcaac    480

tctacgtctt tgtttcgttt tctgttctgc gccgttacag atccaagctg tgaccggcgc    540

ctacctgaga tcaccggcga aggagggcca ccatgtacag gatgcaactc ctgtcttgca    600

ttgcactaag tcttgcactt gtcacgaatt cgataagcac cgaggagctg cgggtgagcc    660

tcgcctccca cctgcgcaag ctgcgtaagc ggctcctccg cgatgccgat gacctgcaga    720

agatatcggc catggttaga tctgtggagt gcccaccttg cccagcacca cctgtggcag    780

gaccttcagt cttcctcttc cccccaaaac ccaaggacac cctgatgatc tccagaaccc    840

ctgaggtcac gtgcgtggtg gtggacgtga gccacgaaga ccccgaggtc cagttcaact    900

ggtacgtgga cggcatggag gtgcataatg ccaagacaaa gccacgggag gagcagttca    960

acagcacgtt ccgtgtggtc agcgtcctca ccgtcgtgca ccaggactgg ctgaacggca   1020
```

-continued

```
aggagtacaa gtgcaaggtc tccaacaaag gcctcccagc ccccatcgag aaaaccatct   1080
ccaaaaccaa agggcagccc cgagaaccac aggtgtacac cctgccccca tcccgggagg   1140
agatgaccaa gaaccaggtc agcctgacct gcctggtcaa aggcttctac cccagcgaca   1200
tcgccgtgga gtgggagagc aatgggcagc cggagaacaa ctacaagacc acacctccca   1260
tgctggactc cgacggctcc ttcttcctct acagcaagct caccgtggac aagagcaggt   1320
ggcagcaggg gaacgtcttc tcatgctccg tgatgcatga ggctctgcac aaccactaca   1380
cacagaagag cctctccctg tctccgggta aatgagtgcc acggctagct ggccagacat   1440
gataagatac attgatgagt ttggacaaac cacaactaga atgcagtgaa aaaaatgctt   1500
tatttgtgaa atttgtgatg ctattgcttt atttgtaacc attataagct gcaataaaca   1560
agttaacaac aacaattgca ttcattttat gtttcaggtt cagggggagg tgtgggaggt   1620
tttttaaagc aagtaaaacc tctacaaatg tggtatggaa ttaattctaa aatacagcat   1680
agcaaaactt taacctccaa atcaagcctc tacttgaatc cttttctgag ggatgaataa   1740
ggcataggca tcaggggctg ttgccaatgt gcattagctg tttgcagcct caccttcttt   1800
catggagttt aagatatagt gtattttccc aaggtttgaa ctagctcttc atttctttat   1860
gttttaaatg cactgacctc ccacattccc tttttagtaa aatattcaga aataatttaa   1920
atacatcatt gcaatgaaaa taaatgtttt ttattaggca gaatccagat gctcaaggcc   1980
cttcataata tcccccagtt tagtagttgg acttagggaa caaaggaacc tttaatagaa   2040
attggacagc aagaaagcga gcttctagct tatcctcagt cctgctcctc tgccacaaag   2100
tgcacgcagt tgccggccgg gtcgcgcagg gcgaactccc gcccccacgg ctgctcgccg   2160
atctcggtca tggccggccc ggaggcgtcc cggaagttcg tggacacgac ctccgaccac   2220
tcggcgtaca gctcgtccag gccgcgcacc cacacccagg ccagggtgtt gtccggcacc   2280
acctggtcct ggaccgcgct gatgaacagg gtcacgtcgt cccggaccac accggcgaag   2340
tcgtcctcca cgaagtcccg ggagaacccg agccggtcgg tccagaactc gaccgctccg   2400
gcgacgtcgc gcgcggtgag caccggaacg gcactggtca acttggccat gatggctcct   2460
cctgtcagga gaggaaagag aagaaggtta gtacaattgc tatagtgagt tgtattatac   2520
tatgcagata tactatgcca atgattaatt gtcaaactag ggctgcaggg ttcatagtgc   2580
cacttttcct gcactgcccc atctcctgcc cacccttccc caggcataga cagtcagtga   2640
cttaccaaac tcacaggagg gagaaggcag aagcttgaga cagacccgcg ggaccgccga   2700
actgcgaggg gacgtggcta gggcggcttc ttttatggtg cgccggccct cggaggcagg   2760
gcgctcgggg aggcctagcg gccaatctgc ggtggcagga ggcggggccg aaggccgtgc   2820
ctgaccaatc cggagcacat aggagtctca gccccccgcc ccaaagcaag gggaagtcac   2880
gcgcctgtag cgccagcgtg ttgtgaaatg gggggcttggg ggggttgggg ccctgactag   2940
tcaaaacaaa ctcccattga cgtcaatggg gtggagactt ggaaatcccc gtgagtcaaa   3000
ccgctatcca cgcccattga tgtactgcca aaaccgcatc atcatggtaa tagcgatgac   3060
taatacgtag atgtactgcc aagtaggaaa gtcccataag gtcatgtact gggcataatg   3120
ccaggcgggc catttaccgt cattgacgtc aatagggggc gtacttggca tatgatacac   3180
ttgatgtact gccaagtggg cagtttaccg taaatactcc acccattgac gtcaatggaa   3240
agtccctatt ggcgttacta tgggaacata cgtcattatt gacgtcaatg ggcgggggtc   3300
gttgggcggt cagccaggcg ggccatttac cgtaagttat gtaacgcctg caggttaatt   3360
```

-continued

```
aagaacatgt gagcaaaagg ccagcaaaag gccaggaacc gtaaaaaggc cgcgttgctg   3420

gcgtttttcc ataggctccg cccccctgac gagcatcaca aaaatcgacg ctcaagtcag   3480

aggtggcgaa acccgacagg actataaaga taccaggcgt ttccccctgg aagctccctc   3540

gtgcgctctc ctgttccgac cctgccgctt accggatacc tgtccgcctt tctcccttcg   3600

ggaagcgtgg cgctttctca tagctcacgc tgtaggtatc tcagttcggt gtaggtcgtt   3660

cgctccaagc tgggctgtgt gcacgaaccc cccgttcagc ccgaccgctg cgccttatcc   3720

ggtaactatc gtcttgagtc caacccggta agacacgact tatcgccact ggcagcagcc   3780

actggtaaca ggattagcag agcgaggtat gtaggcggtg ctacagagtt cttgaagtgg   3840

tggcctaact acggctacac tagaagaaca gtatttggta tctgcgctct gctgaagcca   3900

gttaccttcg gaaaaagagt tggtagctct tgatccggca aacaaaccac cgctggtagc   3960

ggtggttttt ttgtttgcaa gcagcagatt acgcgcagaa aaaaaggatc tcaagaagat   4020

cctttgatct tttctacggg gtctgacgct cagtggaacg aaaactcacg ttaagggatt   4080

ttggtcatgg ctagttaatt aacatttaaa tcagcggccg caataaaata tctttatttt   4140

cattacatct gtgtgttggt tttttgtgtg aatcgtaact aacatacgct ctccatcaaa   4200

acaaaacgaa acaaaacaaa ctagcaaaat aggctgtccc cagtgcaagt gcaggtgcca   4260

gaacatttct ctatcgaa                                                 4278


<210> SEQ ID NO 96
<211> LENGTH: 280
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Met Tyr Arg Met Gln Leu Leu Ser Cys Ile Ala Leu Ser Leu Ala Leu
1               5                   10                  15

Val Thr Asn Ser Ile Ser Thr Glu Glu Leu Arg Val Ser Leu Ala Ser
            20                  25                  30

His Leu Arg Lys Leu Arg Lys Arg Leu Leu Arg Asp Ala Asp Asp Leu
        35                  40                  45

Gln Lys Ile Ser Ala Met Val Arg Ser Val Glu Cys Pro Pro Cys Pro
    50                  55                  60

Ala Pro Pro Val Ala Gly Pro Ser Val Phe Leu Phe Pro Pro Lys Pro
65                  70                  75                  80

Lys Asp Thr Leu Met Ile Ser Arg Thr Pro Glu Val Thr Cys Val Val
                85                  90                  95

Val Asp Val Ser His Glu Asp Pro Glu Val Gln Phe Asn Trp Tyr Val
            100                 105                 110

Asp Gly Met Glu Val His Asn Ala Lys Thr Lys Pro Arg Glu Glu Gln
        115                 120                 125

Phe Asn Ser Thr Phe Arg Val Val Ser Val Leu Thr Val Val His Gln
    130                 135                 140

Asp Trp Leu Asn Gly Lys Glu Tyr Lys Cys Lys Val Ser Asn Lys Gly
145                 150                 155                 160

Leu Pro Ala Pro Ile Glu Lys Thr Ile Ser Lys Thr Lys Gly Gln Pro
                165                 170                 175

Arg Glu Pro Gln Val Tyr Thr Leu Pro Pro Ser Arg Glu Glu Met Thr
            180                 185                 190
```

-continued

```
Lys Asn Gln Val Ser Leu Thr Cys Leu Val Lys Gly Phe Tyr Pro Ser
        195                 200                 205

Asp Ile Ala Val Glu Trp Glu Ser Asn Gly Gln Pro Glu Asn Asn Tyr
    210                 215                 220

Lys Thr Thr Pro Pro Met Leu Asp Ser Asp Gly Ser Phe Phe Leu Tyr
225                 230                 235                 240

Ser Lys Leu Thr Val Asp Lys Ser Arg Trp Gln Gln Gly Asn Val Phe
                245                 250                 255

Ser Cys Ser Val Met His Glu Ala Leu His Asn His Tyr Thr Gln Lys
            260                 265                 270

Ser Leu Ser Leu Ser Pro Gly Lys
        275                 280
```

<210> SEQ ID NO 97
<211> LENGTH: 6773
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97

```
gttaggcgtt ttgcgctgct tcgcgatgta cgggccagat atacgcgttg acattgatta     60

ttgactagtt attaatagta atcaattacg gggtcattag ttcatagccc atatatggag    120

ttccgcgtta cataacttac ggtaaatggc ccgcctggct gaccgcccaa cgacccccgc    180

ccattgacgt caataatgac gtatgttccc atagtaacgc caatagggac tttccattga    240

cgtcaatggg tggagtattt acggtaaact gcccacttgg cagtacatca agtgtatcat    300

atgccaagta cgccccctat tgacgtcaat gacggtaaat ggcccgcctg gcattatgcc    360

cagtacatga ccttatggga ctttcctact tggcagtaca tctacgtatt agtcatcgct    420

attaccatgg tgatgcggtt ttggcagtac atcaatgggc gtggatagcg gtttgactca    480

cggggatttc caagtctcca ccccattgac gtcaatggga gtttgttttg gcaccaaaat    540

caacgggact ttccaaaatg tcgtaacaac tccgccccat tgacgcaaat gggcggtagg    600

cgtgtacggt gggaggtcta tataagcaga gctcgtttag tgaaccgtca gatcgcctgg    660

agacgccatc cacgctgttt tgacctccat agaagacacc gggaccgatc cagcctccgg    720

actctagagg atcgaaccct taagcttgcc accatgtaca ggatgcaact cctgtcttgc    780

attgcactaa gtcttgcact tgtcacgaat tcagacaacg tgctgacaca gagccctgcc    840

agcctggctg tttctctggg acagagagcc accatcagct gcaaggccag ccagagcgtt    900

gactacgacg gcgacagcta catgaactgg tatcagcaga agcccggcca gccacctaag    960

gtgttcatct acgccgccag caacctggaa agcggcatcc ctgccagatt ttctggctct   1020

ggcagcggca ccgacttcac cctgaatatc catcctgtgg aagaagagga cgccgccacc   1080

tactactgcc agcagagcaa tgaggacccc tggacatttg gcggaggcac caagctggaa   1140

atcaagcgta cggtggctgc accatctgtc ttcatcttcc cgccatctga tgagcagttg   1200

aaatctggaa ctgcctctgt tgtgtgcctg ctgaataact tctatcccag agaggccaaa   1260

gtacagtgga aggtggataa cgccctccaa tcgggtaact cccaggagag tgtcacagag   1320

caggacagca aggacagcac ctacagcctc agcagcaccc tgacgctgag caaagcagac   1380

tacgagaaac acaaagtcta cgcctgcgaa gtcacccatc agggcctgag ctcgcccgtc   1440

acaaagagct tcaacagggg agagtgttag agggagctag cgtggcatct agacactctc   1500
```

-continued

```
gagaagggtt cgatccctac cggttagtaa tgagtttgat atctcgacaa tcaacctctg   1560
gattacaaaa tttgtgaaag attgactggt attcttaact atgttgctcc ttttacgcta   1620
tgtggatacg ctgctttaat gcctttgtat catgctattg cttcccgtat ggctttcatt   1680
ttctcctcct tgtataaatc ctggttgctg tctctttatg aggagttgtg gcccgttgtc   1740
aggcaacgtg gcgtggtgtg cactgtgttt gctgacgcaa cccccactgg ttggggcatt   1800
gccaccacct gtcagctcct ttccgggact ttcgctttcc ccctccctat tgccacggcg   1860
gaactcatcg ccgcctgcct tgcccgctgc tggacagggg ctcggctgtt gggcactgac   1920
aattccgtgg tgttgtcggg gaagctgacg tcctttccat ggctgctcgc ctgtgttgcc   1980
acctggattc tgcgcgggac gtccttctgc tacgtccctt cggccctcaa tccagcggac   2040
cttccttccc gcggcctgct gccggctctg cggcctcttc cgcgtcttcg ccttcgccct   2100
cagacgagtc ggatctccct ttgggccgcc tccccgcctg gaaacggggg aggctaactg   2160
aaacacggaa ggagacaata ccggaaggaa cccgcgctat gacggcaata aaaagacaga   2220
ataaaacgca cgggtgttgg gtcgtttgtt cataaacgcg gggttcggtc ccagggctgg   2280
cactctgtcg ataccccacc gagaccccat tggggccaat acgcccgcgt ttcttccttt   2340
tccccacccc accccccaag ttcgggtgaa ggcccagggc tcgcagccaa cgtcggggcg   2400
gcaggccctg ccatagcaga tctgcgcagc tggggctcta gggggtatcc ccacgcgccc   2460
tgtagcggcg cattaagcgc ggcgggtgtg gtggttacgc gcagcgtgac cgctacactt   2520
gccagcgccc tagcgcccgc tcctttcgct ttcttccctt cctttctcgc cacgttcgcc   2580
ggctttcccc gtcaagctct aaatcggggc atccctttag ggttccgatt tagtgcttta   2640
cggcacctcg accccaaaaa acttgattag ggtgatggtt cacgtagtgg gccatcgccc   2700
tgatagacgg tttttcgccc tttgacgttg gagtccacgt tctttaatag tggactcttg   2760
ttccaaactg gaacaacact caaccctatc tcggtctatt cttttgattt ataagggatt   2820
ttggggattt cggcctattg gttaaaaaat gagctgattt aacaaaaatt taacgcgaat   2880
taattctgtg gaatgtgtgt cagttagggt gtggaaagtc cccaggctcc ccagcaggca   2940
gaagtatgca aagcatgcat ctcaattagt cagcaaccag gtgtggaaag tccccaggct   3000
ccccagcagg cagaagtatg caaagcatgc atctcaatta gtcagcaacc atagtcccgc   3060
ccctaactcc gcccatcccg cccctaactc cgcccagttc cgcccattct ccgccccatg   3120
gctgactaat tttttttatt tatgcagagg ccgaggccgc ctctgcctct gagctattcc   3180
agaagtagtg aggaggcttt tttggaggcc taggcttttg caaaaagctc ccgggagctt   3240
gtatatccat tttcggatct gatcaagaga caggatgagg atcgtttcgc atgattgaac   3300
aagatggatt gcacgcaggt tctccggccg cttgggtgga gaggctattc ggctatgact   3360
gggcacaaca gacaatcggc tgctctgatg ccgccgtgtt ccggctgtca gcgcaggggc   3420
gcccggttct ttttgtcaag accgacctgt ccggtgccct gaatgaactg caggacgagg   3480
cagcgcggct atcgtggctg gccacgacgg gcgttccttg cgcagctgtg ctcgacgttg   3540
tcactgaagc gggaagggac tggctgctat tgggcgaagt gccggggcag gatctcctgt   3600
catctcacct tgctcctgcc gagaaagtat ccatcatggc tgatgcaatg cggcggctgc   3660
atacgcttga tccggctacc tgcccattcg accaccaagc gaaacatcgc atcgagcgag   3720
cacgtactcg gatggaagcc ggtcttgtcg atcaggatga tctggacgaa gagcatcagg   3780
ggctcgcgcc agccgaactg ttcgccaggc tcaaggcgcg catgcccgac ggcgaggatc   3840
tcgtcgtgac ccatggcgat gcctgcttgc cgaatatcat ggtggaaaat ggccgctttt   3900
```

-continued

```
ctggattcat cgactgtggc cggctgggtg tggcggaccg ctatcaggac atagcgttgg   3960
ctacccgtga tattgctgaa gagcttggcg gcgaatgggc tgaccgcttc ctcgtgcttt   4020
acggtatcgc cgctcccgat tcgcagcgca tcgccttcta tcgccttctt gacgagttct   4080
tctgagcggg actctggggt tcgcgaaatg accgaccaag cgacgcccaa cctgccatca   4140
cgagatttcg attccaccgc cgccttctat gaaaggttgg gcttcggaat cgttttccgg   4200
gacgccggct ggatgatcct ccagcgcggg gatctcatgc tggagttctt cgcccacccc   4260
aacttgttta ttgcagctta taatggttac aaataaagca atagcatcac aaatttcaca   4320
aataaagcat ttttttcact gcattctagt tgtggtttgt ccaaactcat caatgtatct   4380
tatcatgtct gtataccgtc gacctctagc tagagcttgg cgtaatcatg gtcatagctg   4440
tttcctgtgt gaaattgtta tccgctcaca attccacaca acatacgagc cggaagcata   4500
aagtgtaaag cctggggtgc ctaatgagtg agctaactca cattaattgc gttgcgctca   4560
ctgcccgctt tccagtcggg aaacctgtcg tgccagctgc attaatgaat cggccaacgc   4620
gcggggagag gcggtttgcg tattgggcgc tcttccgctt cctcgctcac tgactcgctg   4680
cgctcggtcg ttcggctgcg gcgagcggta tcagctcact caaaggcggt aatacggtta   4740
tccacagaat caggggataa cgcaggaaag aacatgtgag caaaaggcca gcaaaaggcc   4800
aggaaccgta aaaaggccgc gttgctggcg tttttccata ggctccgccc ccctgacgag   4860
catcacaaaa atcgacgctc aagtcagagg tggcgaaacc cgacaggact ataaagatac   4920
caggcgtttc cccctggaag ctccctcgtg cgctctcctg ttccgaccct gccgcttacc   4980
ggatacctgt ccgcctttct cccttcggga agcgtggcgc tttctcaatg ctcacgctgt   5040
aggtatctca gttcggtgta ggtcgttcgc tccaagctgg gctgtgtgca cgaacccccc   5100
gttcagcccg accgctgcgc cttatccggt aactatcgtc ttgagtccaa cccggtaaga   5160
cacgacttat cgccactggc agcagccact ggtaacagga ttagcagagc gaggtatgta   5220
ggcggtgcta cagagttctt gaagtggtgg cctaactacg gctacactag aaggacagta   5280
tttggtatct gcgctctgct gaagccagtt accttcggaa aaagagttgg tagctcttga   5340
tccggcaaac aaaccaccgc tggtagcggt ggtttttttg tttgcaagca gcagattacg   5400
cgcagaaaaa aaggatctca agaagatcct ttgatctttt ctacggggtc tgacgctcag   5460
tggaacgaaa actcacgtta agggattttg gtcatgagat tatcaaaaag gatcttcacc   5520
tagatccttt taaattaaaa atgaagtttt aaatcaatct aaagtatata tgagtaaact   5580
tggtctgaca gttaccaatg cttaatcagt gaggcaccta tctcagcgat ctgtctattt   5640
cgttcatcca tagttgcctg actccccgtc gtgtagataa ctacgatacg ggagggctta   5700
ccatctggcc ccagtgctgc aatgataccg cgagacccac gctcaccggc tccagattta   5760
tcagcaataa accagccagc cggaagggcc gagcgcagaa gtggtcctgc aactttatcc   5820
gcctccatcc agtctattaa ttgttgccgg gaagctagag taagtagttc gccagttaat   5880
agtttgcgca acgttgttgc cattgctaca ggcatcgtgg tgtcacgctc gtcgtttggt   5940
atggcttcat tcagctccgg ttcccaacga tcaaggcgag ttacatgatc ccccatgttg   6000
tgcaaaaaag cggttagctc cttcggtcct ccgatcgttg tcagaagtaa gttggccgca   6060
gtgttatcac tcatggttat ggcagcactg cataattctc ttactgtcat gccatccgta   6120
agatgctttt ctgtgactgg tgagtactca accaagtcat tctgagaata gtgtatgcgg   6180
cgaccgagtt gctcttgccc ggcgtcaata cgggataata ccgcgccaca tagcagaact   6240
```

-continued ttaaaagtgc tcatcattgg aaaacgttct tcggggcgaa aactctcaag gatcttaccg 6300
ctgttgagat ccagttcgat gtaacccact cgtgcaccca actgatcttc agcatctttt 6360
actttcacca gcgtttctgg gtgagcaaaa acaggaaggc aaaatgccgc aaaaaaggga 6420
ataagggcga cacggaaatg ttgaatactc atactcttcc tttttcaata ttattgaagc 6480
atttatcagg gttattgtct catgagcgga tacatatttg aatgtattta gaaaaataaa 6540
caaatagggg ttccgcgcac atttccccga aaagtgccac ctgacgtcga cggatcggga 6600
gatctcccga tcccctatgg tcgactctca gtacaatctg ctctgatgcc gcatagttaa 6660
gccagtatct gctccctgct tgtgtgttgg aggtcgctga gtagtgcgcg agcaaaattt 6720
aagctacaac aaggcaaggc ttgaccgaca attgcatgaa gaatctgctt agg 6773

<210> SEQ ID NO 98
<211> LENGTH: 7452
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 98
gttaggcgtt ttgcgctgct tcgcgatgta cgggccagat atacgcgttg acattgatta 60
ttgactagtt attaatagta atcaattacg gggtcattag ttcatagccc atatatggag 120
ttccgcgtta cataacttac ggtaaatggc ccgcctggct gaccgcccaa cgacccccgc 180
ccattgacgt caataatgac gtatgttccc atagtaacgc caatagggac tttccattga 240
cgtcaatggg tggagtattt acggtaaact gcccacttgg cagtacatca agtgtatcat 300
atgccaagta cgccccctat tgacgtcaat gacggtaaat ggcccgcctg gcattatgcc 360
cagtacatga ccttatggga ctttcctact tggcagtaca tctacgtatt agtcatcgct 420
attaccatgg tgatgcggtt ttggcagtac atcaatgggc gtggatagcg gtttgactca 480
cggggatttc caagtctcca ccccattgac gtcaatggga gtttgttttg gcaccaaaat 540
caacgggact ttccaaaatg tcgtaacaac tccgccccat tgacgcaaat gggcggtagg 600
cgtgtacggt gggaggtcta tataagcaga gctcgtttag tgaaccgtca gatcgcctgg 660
agacgccatc cacgctgttt tgacctccat agaagacacc gggaccgatc cagcctccgg 720
actctagagg atcgaaccct taagcttgcc accatgtaca ggatgcaact cctgtcttgc 780
attgcactaa gtcttgcact tgtcacgaat tcggaagtga agctggtgga aagcggcgga 840
ggtgttgttc agcctggcgg atctctgaag ctgagctgtg ccgccagcgg cttcaccttt 900
agcagctaca caatgagctg ggtccgacag acccctgaga agagactgga atgggtcgcc 960
aagatccgga acggcggagg catcacctac tacctggata ccctgaaggg cagattcacc 1020
atcagccggg acaacgccaa gaacaccctg tacctgcaga tgagcagcct gaagtccgag 1080
gacaccgcca tctacttttg cgccagacac tactacggca gcgaggacta cttcgactat 1140
tggggccagg gcaccacact gaccgttagc tctgctagca ccaagggccc atcggtcttc 1200
cccctggcgc cctgctccag gagcacctcc gagagcacag cggccctggg ctgcctggtc 1260
aaggactact tccccgaacc ggtgacggtg tcgtggaact caggcgctct gaccagcggc 1320
gtgcacacct tcccagctgt cctacagtcc tcaggactct actccctcag cagcgtggtg 1380
accgtgccct ccagcaactt cggcacccag acctacacct gcaacgtaga tcacaagccc 1440
agcaacacca aggtggacaa gacagttgag cgcaaatgtt gtgtcgagtg cccaccgtgc 1500

-continued

```
ccagcaccac ctgtggcagg accgtcagtc ttcctcttcc ccccaaaacc caaggacacc   1560
ctcatgatct cccggacccc tgaggtcacg tgcgtggtgg tggacgtgag ccacgaagac   1620
cccgaggtcc agttcaactg gtacgtggac ggcgtggagg tgcataatgc caagacaaag   1680
ccacgggagg agcagttcaa cagcacgttc cgtgtggtca gcgtcctcac cgttgtgcac   1740
caggactggc tgaacggcaa ggagtacaag tgcaaggtct ccaacaaagg cctcccagcc   1800
cccatcgaga aaaccatctc caaaaccaaa gggcagcccc gagaaccaca ggtgtacacc   1860
ctgcccccat cccgggagga gatgaccaag aaccaggtca gcctgacctg cctggtcaaa   1920
ggcttctacc ccagcgacat cgccgtggag tgggagagca atgggcagcc ggagaacaac   1980
tacaagacca cgcctcccat gctggactcc gacggctcct tcttcctcta cagcaagctc   2040
accgtggaca agagcaggtg gcagcagggg aacgtcttct catgctccgt gatgcatgag   2100
gctctgcaca accactacac gcagaagagc ctctccctgt ctccgggtaa atgacctagc   2160
gtggcatcta gacactctcg agaagggttc gatccctacc ggttagtaat gagtttgata   2220
tctcgacaat caacctctgg attacaaaat ttgtgaaaga ttgactggta ttcttaacta   2280
tgttgctcct tttacgctat gtggatacgc tgctttaatg cctttgtatc atgctattgc   2340
ttcccgtatg gctttcattt tctcctcctt gtataaatcc tggttgctgt ctctttatga   2400
ggagttgtgg cccgttgtca ggcaacgtgg cgtggtgtgc actgtgtttg ctgacgcaac   2460
ccccactggt tggggcattg ccaccacctg tcagctcctt tccgggactt tcgctttccc   2520
cctccctatt gccacggcgg aactcatcgc cgcctgcctt gcccgctgct ggacaggggc   2580
tcggctgttg ggcactgaca attccgtggt gttgtcgggg aagctgacgt cctttccatg   2640
gctgctcgcc tgtgttgcca cctggattct gcgcgggacg tccttctgct acgtcccttc   2700
ggccctcaat ccagcggacc ttccttcccg cggcctgctg ccggctctgc ggcctcttcc   2760
gcgtcttcgc cttcgccctc agacgagtcg gatctccctt tgggccgcct ccccgcctgg   2820
aaacggggga ggctaactga aacacggaag gagacaatac cggaaggaac ccgcgctatg   2880
acggcaataa aaagacagaa taaaacgcac gggtgttggg tcgtttgttc ataaacgcgg   2940
ggttcggtcc cagggctggc actctgtcga taccccaccg agaccccatt ggggccaata   3000
cgcccgcgtt tcttcctttt ccccacccca ccccccaagt tcgggtgaag gcccagggct   3060
cgcagccaac gtcggggcgg caggccctgc catagcagat ctgcgcagct ggggctctag   3120
ggggtatccc cacgcgccct gtagcggcgc attaagcgcg gcgggtgtgg tggttacgcg   3180
cagcgtgacc gctacacttg ccagcgccct agcgcccgct cctttcgctt tcttcccttc   3240
ctttctcgcc acgttcgccg gctttccccg tcaagctcta aatcggggca tccctttagg   3300
gttccgattt agtgctttac ggcacctcga ccccaaaaaa cttgattagg gtgatggttc   3360
acgtagtggg ccatcgccct gatagacggt ttttcgccct ttgacgttgg agtccacgtt   3420
ctttaatagt ggactcttgt tccaaactgg aacaacactc aaccctatct cggtctattc   3480
ttttgattta taagggattt tggggatttc ggcctattgg ttaaaaaatg agctgattta   3540
acaaaaattt aacgcgaatt aattctgtgg aatgtgtgtc agttagggtg tggaaagtcc   3600
ccaggctccc cagcaggcag aagtatgcaa agcatgcatc tcaattagtc agcaaccagg   3660
tgtggaaagt ccccaggctc cccagcaggc agaagtatgc aaagcatgca tctcaattag   3720
tcagcaacca tagtcccgcc cctaactccg cccatcccgc ccctaactcc gcccagttcc   3780
gcccattctc cgccccatgg ctgactaatt ttttttattt atgcagaggc cgaggccgcc   3840
tctgcctctg agctattcca gaagtagtga ggaggctttt ttggaggcct aggcttttgc   3900
```

-continued

```
aaaaagctcc cgggagcttg tatatccatt ttcggatctg atcaagagac aggatgagga   3960
tcgtttcgca tgattgaaca agatggattg cacgcaggtt ctccggccgc ttgggtggag   4020
aggctattcg gctatgactg ggcacaacag acaatcggct gctctgatgc cgccgtgttc   4080
cggctgtcag cgcaggggcg cccggttctt tttgtcaaga ccgacctgtc cggtgccctg   4140
aatgaactgc aggacgaggc agcgcggcta tcgtggctgg ccacgacggg cgttccttgc   4200
gcagctgtgc tcgacgttgt cactgaagcg ggaagggact ggctgctatt gggcgaagtg   4260
ccggggcagg atctcctgtc atctcacctt gctcctgccg agaaagtatc catcatggct   4320
gatgcaatgc ggcggctgca tacgcttgat ccggctacct gcccattcga ccaccaagcg   4380
aaacatcgca tcgagcgagc acgtactcgg atggaagccg gtcttgtcga tcaggatgat   4440
ctggacgaag agcatcaggg gctcgcgcca gccgaactgt tcgccaggct caaggcgcgc   4500
atgcccgacg gcgaggatct cgtcgtgacc catggcgatg cctgcttgcc gaatatcatg   4560
gtggaaaatg gccgcttttc tggattcatc gactgtggcc ggctgggtgt ggcggaccgc   4620
tatcaggaca tagcgttggc tacccgtgat attgctgaag agcttggcgg cgaatgggct   4680
gaccgcttcc tcgtgcttta cggtatcgcc gctcccgatt cgcagcgcat cgccttctat   4740
cgccttcttg acgagttctt ctgagcggga ctctggggtt cgcgaaatga ccgaccaagc   4800
gacgcccaac ctgccatcac gagatttcga ttccaccgcc gccttctatg aaaggttggg   4860
cttcggaatc gttttccggg acgccggctg gatgatcctc cagcgcgggg atctcatgct   4920
ggagttcttc gcccacccca acttgtttat tgcagcttat aatggttaca aataaagcaa   4980
tagcatcaca aatttcacaa ataaagcatt tttttcactg cattctagtt gtggtttgtc   5040
caaactcatc aatgtatctt atcatgtctg tataccgtcg acctctagct agagcttggc   5100
gtaatcatgg tcatagctgt ttcctgtgtg aaattgttat ccgctcacaa ttccacacaa   5160
catacgagcc ggaagcataa agtgtaaagc ctggggtgcc taatgagtga gctaactcac   5220
attaattgcg ttgcgctcac tgcccgcttt ccagtcggga aacctgtcgt gccagctgca   5280
ttaatgaatc ggccaacgcg cggggagagg cggtttgcgt attgggcgct cttccgcttc   5340
ctcgctcact gactcgctgc gctcggtcgt tcggctgcgg cgagcggtat cagctcactc   5400
aaaggcggta atacggttat ccacagaatc aggggataac gcaggaaaga acatgtgagc   5460
aaaaggccag caaaaggcca ggaaccgtaa aaaggccgcg ttgctggcgt ttttccatag   5520
gctccgcccc cctgacgagc atcacaaaaa tcgacgctca agtcagaggt ggcgaaaccc   5580
gacaggacta taaagatacc aggcgtttcc ccctggaagc tccctcgtgc gctctcctgt   5640
tccgaccctg ccgcttaccg gatacctgtc cgcctttctc ccttcgggaa gcgtggcgct   5700
ttctcaatgc tcacgctgta ggtatctcag ttcggtgtag gtcgttcgct ccaagctggg   5760
ctgtgtgcac gaaccccccg ttcagcccga ccgctgcgcc ttatccggta actatcgtct   5820
tgagtccaac ccggtaagac acgacttatc gccactggca gcagccactg gtaacaggat   5880
tagcagagcg aggtatgtag gcggtgctac agagttcttg aagtggtggc ctaactacgg   5940
ctacactaga aggacagtat ttggtatctg cgctctgctg aagccagtta ccttcggaaa   6000
aagagttggt agctcttgat ccggcaaaca aaccaccgct ggtagcggtg gtttttttgt   6060
ttgcaagcag cagattacgc gcagaaaaaa aggatctcaa gaagatcctt tgatcttttc   6120
tacggggtct gacgctcagt ggaacgaaaa ctcacgttaa gggattttgg tcatgagatt   6180
atcaaaaagg atcttcacct agatcctttt aaattaaaaa tgaagtttta aatcaatcta   6240
```

aagtatatat gagtaaactt ggtctgacag ttaccaatgc ttaatcagtg aggcacctat 6300
ctcagcgatc tgtctatttc gttcatccat agttgcctga ctccccgtcg tgtagataac 6360
tacgatacgg gagggcttac catctggccc cagtgctgca atgataccgc gagacccacg 6420
ctcaccggct ccagatttat cagcaataaa ccagccagcc ggaagggccg agcgcagaag 6480
tggtcctgca actttatccg cctccatcca gtctattaat tgttgccggg aagctagagt 6540
aagtagttcg ccagttaata gtttgcgcaa cgttgttgcc attgctacag gcatcgtggt 6600
gtcacgctcg tcgtttggta tggcttcatt cagctccggt tcccaacgat caaggcgagt 6660
tacatgatcc cccatgttgt gcaaaaaagc ggttagctcc ttcggtcctc cgatcgttgt 6720
cagaagtaag ttggccgcag tgttatcact catggttatg gcagcactgc ataattctct 6780
tactgtcatg ccatccgtaa gatgcttttc tgtgactggt gagtactcaa ccaagtcatt 6840
ctgagaatag tgtatgcggc gaccgagttg ctcttgcccg gcgtcaatac gggataatac 6900
cgcgccacat agcagaactt taaaagtgct catcattgga aaacgttctt cggggcgaaa 6960
actctcaagg atcttaccgc tgttgagatc cagttcgatg taacccactc gtgcacccaa 7020
ctgatcttca gcatctttta ctttcaccag cgtttctggg tgagcaaaaa caggaaggca 7080
aaatgccgca aaaaagggaa taagggcgac acggaaatgt tgaatactca tactcttcct 7140
ttttcaatat tattgaagca tttatcaggg ttattgtctc atgagcggat acatatttga 7200
atgtatttag aaaaataaac aaataggggt tccgcgcaca tttccccgaa aagtgccacc 7260
tgacgtcgac ggatcgggag atctcccgat cccctatggt cgactctcag tacaatctgc 7320
tctgatgccg catagttaag ccagtatctg ctccctgctt gtgtgttgga ggtcgctgag 7380
tagtgcgcga gcaaaattta agctacaaca aggcaaggct tgaccgacaa ttgcatgaag 7440
aatctgctta gg 7452

<210> SEQ ID NO 99
<211> LENGTH: 6773
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 99
gttaggcgtt ttgcgctgct tcgcgatgta cgggccagat atacgcgttg acattgatta 60
ttgactagtt attaatagta atcaattacg gggtcattag ttcatagccc atatatggag 120
ttccgcgtta cataacttac ggtaaatggc ccgcctggct gaccgcccaa cgacccccgc 180
ccattgacgt caataatgac gtatgttccc atagtaacgc caatagggac tttccattga 240
cgtcaatggg tggagtattt acggtaaact gcccacttgg cagtacatca agtgtatcat 300
atgccaagta cgccccctat tgacgtcaat gacggtaaat ggcccgcctg gcattatgcc 360
cagtacatga ccttatggga ctttcctact tggcagtaca tctacgtatt agtcatcgct 420
attaccatgg tgatgcggtt ttggcagtac atcaatgggc gtggatagcg gtttgactca 480
cggggatttc caagtctcca ccccattgac gtcaatggga gtttgttttg gcaccaaaat 540
caacgggact ttccaaaatg tcgtaacaac tccgccccat tgacgcaaat gggcggtagg 600
cgtgtacggt gggaggtcta tataagcaga gctcgtttag tgaaccgtca gatcgcctgg 660
agacgccatc cacgctgttt tgacctccat agaagacacc gggaccgatc cagcctccgg 720
actctagagg atcgaaccct taagcttgcc accatgtaca ggatgcaact cctgtcttgc 780

-continued

```
attgcactaa gtcttgcact tgtcacgaat tcagacatcg tgctgacaca gagccctgcc    840
agcctggctg tttctctggg acagagagcc accatcagct gcaaggccag ccagagcgtt    900
gactacgacg gcgagaacta catgaactgg tatcagcaga agcccggaca gagccccaag    960
ctgctgatct acgtggccag caatctggaa agcggcatcc ccgccagatt ttctggcagc   1020
ggaagcggca ccgacttcac cctgaatatc catcctgtgg aagaagagga cgccgccacc   1080
tactactgcc agcagtccaa tctggacccc tggacatttg gcggaggcac caagctggaa   1140
atcaagcgta cggtggctgc accatctgtc ttcatcttcc cgccatctga tgagcagttg   1200
aaatctggaa ctgcctctgt tgtgtgcctg ctgaataact tctatcccag agaggccaaa   1260
gtacagtgga aggtggataa cgccctccaa tcgggtaact cccaggagag tgtcacagag   1320
caggacagca aggacagcac ctacagcctc agcagcaccc tgacgctgag caaagcagac   1380
tacgagaaac acaaagtcta cgcctgcgaa gtcacccatc agggcctgag ctcgcccgtc   1440
acaaagagct tcaacagggg agagtgttag agggagctag cgtggcatct agacactctc   1500
gagaagggtt cgatccctac cggttagtaa tgagtttgat atctcgacaa tcaacctctg   1560
gattacaaaa tttgtgaaag attgactggt attcttaact atgttgctcc ttttacgcta   1620
tgtggatacg ctgctttaat gcctttgtat catgctattg cttcccgtat ggctttcatt   1680
ttctcctcct tgtataaatc ctggttgctg tctctttatg aggagttgtg gcccgttgtc   1740
aggcaacgtg gcgtggtgtg cactgtgttt gctgacgcaa cccccactgg ttggggcatt   1800
gccaccacct gtcagctcct ttccgggact ttcgctttcc ccctccctat tgccacggcg   1860
gaactcatcg ccgcctgcct tgcccgctgc tggacagggg ctcggctgtt gggcactgac   1920
aattccgtgg tgttgtcggg gaagctgacg tcctttccat ggctgctcgc ctgtgttgcc   1980
acctggattc tgcgcgggac gtccttctgc tacgtccctt cggccctcaa tccagcggac   2040
cttccttccc gcggcctgct gccggctctg cggcctcttc cgcgtcttcg ccttcgccct   2100
cagacgagtc ggatctccct ttgggccgcc tccccgcctg gaaacggggg aggctaactg   2160
aaacacggaa ggagacaata ccggaaggaa cccgcgctat gacggcaata aaaagacaga   2220
ataaaacgca cgggtgttgg gtcgtttgtt cataaacgcg gggttcggtc ccagggctgg   2280
cactctgtcg ataccccacc gagaccccat tggggccaat acgcccgcgt ttcttccttt   2340
tccccacccc accccccaag ttcgggtgaa ggcccagggc tcgcagccaa cgtcggggcg   2400
gcaggccctg ccatagcaga tctgcgcagc tggggctcta gggggtatcc ccacgcgccc   2460
tgtagcggcg cattaagcgc ggcgggtgtg gtggttacgc gcagcgtgac cgctacactt   2520
gccagcgccc tagcgcccgc tcctttcgct ttcttccctt cctttctcgc cacgttcgcc   2580
ggctttcccc gtcaagctct aaatcggggc atccctttag ggttccgatt tagtgcttta   2640
cggcacctcg accccaaaaa acttgattag ggtgatggtt cacgtagtgg gccatcgccc   2700
tgatagacgg tttttcgccc tttgacgttg gagtccacgt tctttaatag tggactcttg   2760
ttccaaactg gaacaacact caaccctatc tcggtctatt cttttgattt ataagggatt   2820
ttggggattt cggcctattg gttaaaaaat gagctgattt aacaaaaatt taacgcgaat   2880
taattctgtg gaatgtgtgt cagttagggt gtggaaagtc cccaggctcc ccagcaggca   2940
gaagtatgca aagcatgcat ctcaattagt cagcaaccag gtgtggaaag tccccaggct   3000
ccccagcagg cagaagtatg caaagcatgc atctcaatta gtcagcaacc atagtcccgc   3060
ccctaactcc gcccatcccg cccctaactc cgcccagttc cgcccattct ccgccccatg   3120
gctgactaat tttttttatt tatgcagagg ccgaggccgc ctctgcctct gagctattcc   3180
```

-continued

```
agaagtagtg aggaggcttt tttggaggcc taggcttttg caaaaagctc ccgggagctt   3240
gtatatccat tttcggatct gatcaagaga caggatgagg atcgtttcgc atgattgaac   3300
aagatggatt gcacgcaggt tctccggccg cttgggtgga gaggctattc ggctatgact   3360
gggcacaaca gacaatcggc tgctctgatg ccgccgtgtt ccggctgtca gcgcaggggc   3420
gcccggttct ttttgtcaag accgacctgt ccggtgccct gaatgaactg caggacgagg   3480
cagcgcggct atcgtggctg gccacgacgg gcgttccttg cgcagctgtg ctcgacgttg   3540
tcactgaagc gggaagggac tggctgctat tgggcgaagt gccggggcag gatctcctgt   3600
catctcacct tgctcctgcc gagaaagtat ccatcatggc tgatgcaatg cggcggctgc   3660
atacgcttga tccggctacc tgcccattcg accaccaagc gaaacatcgc atcgagcgag   3720
cacgtactcg gatggaagcc ggtcttgtcg atcaggatga tctggacgaa gagcatcagg   3780
ggctcgcgcc agccgaactg ttcgccaggc tcaaggcgcg catgcccgac ggcgaggatc   3840
tcgtcgtgac ccatggcgat gcctgcttgc cgaatatcat ggtggaaaat ggccgctttt   3900
ctggattcat cgactgtggc cggctgggtg tggcggaccg ctatcaggac atagcgttgg   3960
ctacccgtga tattgctgaa gagcttggcg gcgaatgggc tgaccgcttc ctcgtgcttt   4020
acggtatcgc cgctcccgat tcgcagcgca tcgccttcta tcgccttctt gacgagttct   4080
tctgagcggg actctggggt tcgcgaaatg accgaccaag cgacgcccaa cctgccatca   4140
cgagatttcg attccaccgc cgccttctat gaaaggttgg gcttcggaat cgttttccgg   4200
gacgccggct ggatgatcct ccagcgcggg gatctcatgc tggagttctt cgcccacccc   4260
aacttgttta ttgcagctta taatggttac aaataaagca atagcatcac aaatttcaca   4320
aataaagcat ttttttcact gcattctagt tgtggtttgt ccaaactcat caatgtatct   4380
tatcatgtct gtataccgtc gacctctagc tagagcttgg cgtaatcatg gtcatagctg   4440
tttcctgtgt gaaattgtta tccgctcaca attccacaca acatacgagc cggaagcata   4500
aagtgtaaag cctggggtgc ctaatgagtg agctaactca cattaattgc gttgcgctca   4560
ctgcccgctt tccagtcggg aaacctgtcg tgccagctgc attaatgaat cggccaacgc   4620
gcggggagag gcggtttgcg tattgggcgc tcttccgctt cctcgctcac tgactcgctg   4680
cgctcggtcg ttcggctgcg gcgagcggta tcagctcact caaaggcggt aatacggtta   4740
tccacagaat caggggataa cgcaggaaag aacatgtgag caaaaggcca gcaaaaggcc   4800
aggaaccgta aaaaggccgc gttgctggcg tttttccata ggctccgccc ccctgacgag   4860
catcacaaaa atcgacgctc aagtcagagg tggcgaaacc cgacaggact ataaagatac   4920
caggcgtttc cccctggaag ctccctcgtg cgctctcctg ttccgaccct gccgcttacc   4980
ggatacctgt ccgcctttct cccttcggga agcgtggcgc tttctcaatg ctcacgctgt   5040
aggtatctca gttcggtgta ggtcgttcgc tccaagctgg gctgtgtgca cgaacccccc   5100
gttcagcccg accgctgcgc cttatccggt aactatcgtc ttgagtccaa cccggtaaga   5160
cacgacttat cgccactggc agcagccact ggtaacagga ttagcagagc gaggtatgta   5220
ggcggtgcta cagagttctt gaagtggtgg cctaactacg gctacactag aaggacagta   5280
tttggtatct gcgctctgct gaagccagtt accttcggaa aaagagttgg tagctcttga   5340
tccggcaaac aaaccaccgc tggtagcggt ggtttttttg tttgcaagca gcagattacg   5400
cgcagaaaaa aaggatctca agaagatcct ttgatctttt ctacggggtc tgacgctcag   5460
tggaacgaaa actcacgtta agggattttg gtcatgagat tatcaaaaag gatcttcacc   5520
```

```
tagatccttt taaattaaaa atgaagtttt aaatcaatct aaagtatata tgagtaaact   5580

tggtctgaca gttaccaatg cttaatcagt gaggcaccta tctcagcgat ctgtctattt   5640

cgttcatcca tagttgcctg actccccgtc gtgtagataa ctacgatacg ggagggctta   5700

ccatctggcc ccagtgctgc aatgataccg cgagacccac gctcaccggc tccagattta   5760

tcagcaataa accagccagc cggaagggcc gagcgcagaa gtggtcctgc aactttatcc   5820

gcctccatcc agtctattaa ttgttgccgg gaagctagag taagtagttc gccagttaat   5880

agtttgcgca acgttgttgc cattgctaca ggcatcgtgg tgtcacgctc gtcgtttggt   5940

atggcttcat tcagctccgg ttcccaacga tcaaggcgag ttacatgatc ccccatgttg   6000

tgcaaaaaag cggttagctc cttcggtcct ccgatcgttg tcagaagtaa gttggccgca   6060

gtgttatcac tcatggttat ggcagcactg cataattctc ttactgtcat gccatccgta   6120

agatgctttt ctgtgactgg tgagtactca accaagtcat tctgagaata gtgtatgcgg   6180

cgaccgagtt gctcttgccc ggcgtcaata cgggataata ccgcgccaca tagcagaact   6240

ttaaaagtgc tcatcattgg aaaacgttct tcggggcgaa aactctcaag gatcttaccg   6300

ctgttgagat ccagttcgat gtaacccact cgtgcaccca actgatcttc agcatctttt   6360

actttcacca gcgtttctgg gtgagcaaaa acaggaaggc aaaatgccgc aaaaaaggga   6420

ataagggcga cacggaaatg ttgaatactc atactcttcc tttttcaata ttattgaagc   6480

atttatcagg gttattgtct catgagcgga tacatatttg aatgtattta gaaaaataaa   6540

caaatagggg ttccgcgcac atttccccga aaagtgccac ctgacgtcga cggatcggga   6600

gatctcccga tcccctatgg tcgactctca gtacaatctg ctctgatgcc gcatagttaa   6660

gccagtatct gctccctgct tgtgtgttgg aggtcgctga gtagtgcgcg agcaaaattt   6720

aagctacaac aaggcaaggc ttgaccgaca attgcatgaa gaatctgctt agg          6773
```

<210> SEQ ID NO 100
<211> LENGTH: 7446
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 100

```
gttaggcgtt ttgcgctgct tcgcgatgta cgggccagat atacgcgttg acattgatta     60

ttgactagtt attaatagta atcaattacg gggtcattag ttcatagccc atatatggag    120

ttccgcgtta cataacttac ggtaaatggc ccgcctggct gaccgcccaa cgacccccgc    180

ccattgacgt caataatgac gtatgttccc atagtaacgc caatagggac tttccattga    240

cgtcaatggg tggagtattt acggtaaact gcccacttgg cagtacatca agtgtatcat    300

atgccaagta cgccccctat tgacgtcaat gacggtaaat ggcccgcctg gcattatgcc    360

cagtacatga ccttatggga ctttcctact tggcagtaca tctacgtatt agtcatcgct    420

attaccatgg tgatgcggtt ttggcagtac atcaatgggc gtggatagcg gtttgactca    480

cggggatttc caagtctcca ccccattgac gtcaatggga gtttgttttg gcaccaaaat    540

caacgggact ttccaaaatg tcgtaacaac tccgccccat tgacgcaaat gggcggtagg    600

cgtgtacggt gggaggtcta tataagcaga gctcgtttag tgaaccgtca gatcgcctgg    660

agacgccatc cacgctgttt tgacctccat agaagacacc gggaccgatc cagcctccgg    720

actctagagg atcgaaccct taagcttgcc accatgtaca ggatgcaact cctgtcttgc    780
```

-continued

```
attgcactaa gtcttgcact tgtcacgaat tcggaggtcc agctgcagca gtctggcgcc    840
gaacttgtta gacctggcgc tctggtcaag ctgagctgta aagccagcgg cttcaacatc    900
aaggactacc atctgcactg ggtcaagcag aggcctgagc agggactcga gtggatcggc    960
tggatcgacc ccgagaacgg caacgtgatc tacgacccca agttccaggg caaagccacc   1020
atgaccgtgg tcaccagcag caacacagcc tacctgcagc tgagaagcct gaccagcgaa   1080
gataccgccg tgtacttctg caccagaggc acagccagag ccagcttcga ttattggggc   1140
cagggcacca gcctgaccgt ttcttctgct agcaccaagg gcccatcggt cttccccctg   1200
gcgccctgct ccaggagcac ctccgagagc acagcggccc tgggctgcct ggtcaaggac   1260
tacttccccg aaccggtgac ggtgtcgtgg aactcaggcg ctctgaccag cggcgtgcac   1320
accttcccag ctgtcctaca gtcctcagga ctctactccc tcagcagcgt ggtgaccgtg   1380
ccctccagca acttcggcac ccagacctac acctgcaacg tagatcacaa gcccagcaac   1440
accaaggtgg acaagacagt tgagcgcaaa tgttgtgtcg agtgcccacc gtgcccagca   1500
ccacctgtgg caggaccgtc agtcttcctc ttccccccaa aacccaagga caccctcatg   1560
atctcccgga cccctgaggt cacgtgcgtg gtggtggacg tgagccacga agaccccgag   1620
gtccagttca actggtacgt ggacggcgtg gaggtgcata atgccaagac aaagccacgg   1680
gaggagcagt tcaacagcac gttccgtgtg gtcagcgtcc tcaccgttgt gcaccaggac   1740
tggctgaacg gcaaggagta caagtgcaag gtctccaaca aaggcctccc agcccccatc   1800
gagaaaacca tctccaaaac caaagggcag ccccgagaac cacaggtgta caccctgccc   1860
ccatcccggg aggagatgac caagaaccag gtcagcctga cctgcctggt caaaggcttc   1920
taccccagcg acatcgccgt ggagtgggag agcaatgggc agccggagaa caactacaag   1980
accacgcctc ccatgctgga ctccgacggc tccttcttcc tctacagcaa gctcaccgtg   2040
gacaagagca ggtggcagca ggggaacgtc ttctcatgct ccgtgatgca tgaggctctg   2100
cacaaccact acacgcagaa gagcctctcc ctgtctccgg gtaaatgacc tagcgtggca   2160
tctagacact ctcgagaagg gttcgatccc taccggttag taatgagttt gatatctcga   2220
caatcaacct ctggattaca aaatttgtga aagattgact ggtattctta actatgttgc   2280
tccttttacg ctatgtggat acgctgcttt aatgcctttg tatcatgcta ttgcttcccg   2340
tatggctttc attttctcct ccttgtataa atcctggttg ctgtctcttt atgaggagtt   2400
gtggcccgtt gtcaggcaac gtggcgtggt gtgcactgtg tttgctgacg caacccccac   2460
tggttggggc attgccacca cctgtcagct cctttccggg actttcgctt tccccctccc   2520
tattgccacg gcggaactca tcgccgcctg ccttgcccgc tgctggacag gggctcggct   2580
gttgggcact gacaattccg tggtgttgtc ggggaagctg acgtcctttc catggctgct   2640
cgcctgtgtt gccacctgga ttctgcgcgg gacgtccttc tgctacgtcc cttcggccct   2700
caatccagcg gaccttcctt cccgcggcct gctgccggct ctgcggcctc ttccgcgtct   2760
tcgccttcgc cctcagacga gtcggatctc cctttgggcc gcctccccgc ctggaaacgg   2820
gggaggctaa ctgaaacacg gaaggagaca ataccggaag gaacccgcgc tatgacggca   2880
ataaaaagac agaataaaac gcacgggtgt tgggtcgttt gttcataaac gcggggttcg   2940
gtcccagggc tggcactctg tcgatacccc accgagaccc cattggggcc aatacgcccg   3000
cgtttcttcc ttttccccac cccacccccc aagttcgggt gaaggcccag ggctcgcagc   3060
caacgtcggg gcggcaggcc ctgccatagc agatctgcgc agctggggct ctagggggta   3120
tccccacgcg ccctgtagcg gcgcattaag cgcggcgggt gtggtggtta cgcgcagcgt   3180
```

```
gaccgctaca cttgccagcg ccctagcgcc cgctcctttc gctttcttcc cttcctttct   3240
cgccacgttc gccggctttc cccgtcaagc tctaaatcgg ggcatccctt tagggttccg   3300
atttagtgct ttacggcacc tcgaccccaa aaaacttgat tagggtgatg gttcacgtag   3360
tgggccatcg ccctgataga cggtttttcg ccctttgacg ttggagtcca cgttctttaa   3420
tagtggactc ttgttccaaa ctggaacaac actcaaccct atctcggtct attcttttga   3480
tttataaggg attttgggga tttcggccta ttggttaaaa aatgagctga tttaacaaaa   3540
atttaacgcg aattaattct gtggaatgtg tgtcagttag ggtgtggaaa gtccccaggc   3600
tccccagcag gcagaagtat gcaaagcatg catctcaatt agtcagcaac caggtgtgga   3660
aagtccccag gctccccagc aggcagaagt atgcaaagca tgcatctcaa ttagtcagca   3720
accatagtcc cgcccctaac tccgcccatc ccgcccctaa ctccgcccag ttccgcccat   3780
tctccgcccc atggctgact aatttttttt atttatgcag aggccgaggc cgcctctgcc   3840
tctgagctat tccagaagta gtgaggaggc ttttttggag gcctaggctt ttgcaaaaag   3900
ctcccgggag cttgtatatc cattttcgga tctgatcaag agacaggatg aggatcgttt   3960
cgcatgattg aacaagatgg attgcacgca ggttctccgg ccgcttgggt ggagaggcta   4020
ttcggctatg actgggcaca acagacaatc ggctgctctg atgccgccgt gttccggctg   4080
tcagcgcagg ggcgcccggt tctttttgtc aagaccgacc tgtccggtgc cctgaatgaa   4140
ctgcaggacg aggcagcgcg gctatcgtgg ctggccacga cgggcgttcc ttgcgcagct   4200
gtgctcgacg ttgtcactga agcgggaagg gactggctgc tattgggcga agtgccgggg   4260
caggatctcc tgtcatctca ccttgctcct gccgagaaag tatccatcat ggctgatgca   4320
atgcggcggc tgcatacgct tgatccggct acctgcccat tcgaccacca agcgaaacat   4380
cgcatcgagc gagcacgtac tcggatggaa gccggtcttg tcgatcagga tgatctggac   4440
gaagagcatc aggggctcgc gccagccgaa ctgttcgcca ggctcaaggc gcgcatgccc   4500
gacggcgagg atctcgtcgt gacccatggc gatgcctgct tgccgaatat catggtggaa   4560
aatggccgct tttctggatt catcgactgt ggccggctgg gtgtggcgga ccgctatcag   4620
gacatagcgt tggctacccg tgatattgct gaagagcttg gcggcgaatg ggctgaccgc   4680
ttcctcgtgc tttacggtat cgccgctccc gattcgcagc gcatcgcctt ctatcgcctt   4740
cttgacgagt tcttctgagc gggactctgg ggttcgcgaa atgaccgacc aagcgacgcc   4800
caacctgcca tcacgagatt tcgattccac cgccgccttc tatgaaaggt tgggcttcgg   4860
aatcgttttc cgggacgccg gctggatgat cctccagcgc ggggatctca tgctggagtt   4920
cttcgcccac cccaacttgt ttattgcagc ttataatggt tacaaataaa gcaatagcat   4980
cacaaatttc acaaataaag catttttttc actgcattct agttgtggtt tgtccaaact   5040
catcaatgta tcttatcatg tctgtatacc gtcgacctct agctagagct tggcgtaatc   5100
atggtcatag ctgtttcctg tgtgaaattg ttatccgctc acaattccac acaacatacg   5160
agccggaagc ataaagtgta aagcctgggg tgcctaatga gtgagctaac tcacattaat   5220
tgcgttgcgc tcactgcccg ctttccagtc gggaaacctg tcgtgccagc tgcattaatg   5280
aatcggccaa cgcgcgggga gaggcggttt gcgtattggg cgctcttccg cttcctcgct   5340
cactgactcg ctgcgctcgg tcgttcggct gcggcgagcg gtatcagctc actcaaaggc   5400
ggtaatacgg ttatccacag aatcagggga taacgcagga aagaacatgt gagcaaaagg   5460
ccagcaaaag gccaggaacc gtaaaaaggc cgcgttgctg gcgtttttcc ataggctccg   5520
```

-continued

```
ccccccctgac gagcatcaca aaaatcgacg ctcaagtcag aggtggcgaa acccgacagg   5580

actataaaga taccaggcgt ttccccctgg aagctccctc gtgcgctctc ctgttccgac   5640

cctgccgctt accggatacc tgtccgcctt tctcccttcg ggaagcgtgg cgctttctca   5700

atgctcacgc tgtaggtatc tcagttcggt gtaggtcgtt cgctccaagc tgggctgtgt   5760

gcacgaaccc cccgttcagc ccgaccgctg cgccttatcc ggtaactatc gtcttgagtc   5820

caacccggta agacacgact tatcgccact ggcagcagcc actggtaaca ggattagcag   5880

agcgaggtat gtaggcggtg ctacagagtt cttgaagtgg tggcctaact acggctacac   5940

tagaaggaca gtatttggta tctgcgctct gctgaagcca gttaccttcg gaaaaagagt   6000

tggtagctct tgatccggca aacaaaccac cgctggtagc ggtggttttt ttgtttgcaa   6060

gcagcagatt acgcgcagaa aaaaaggatc tcaagaagat cctttgatct tttctacggg   6120

gtctgacgct cagtggaacg aaaactcacg ttaagggatt ttggtcatga gattatcaaa   6180

aaggatcttc acctagatcc ttttaaatta aaaatgaagt tttaaatcaa tctaaagtat   6240

atatgagtaa acttggtctg acagttacca atgcttaatc agtgaggcac ctatctcagc   6300

gatctgtcta tttcgttcat ccatagttgc ctgactcccc gtcgtgtaga taactacgat   6360

acgggagggc ttaccatctg gccccagtgc tgcaatgata ccgcgagacc cacgctcacc   6420

ggctccagat ttatcagcaa taaaccagcc agccggaagg gccgagcgca gaagtggtcc   6480

tgcaacttta tccgcctcca tccagtctat taattgttgc cgggaagcta gagtaagtag   6540

ttcgccagtt aatagtttgc gcaacgttgt tgccattgct acaggcatcg tggtgtcacg   6600

ctcgtcgttt ggtatggctt cattcagctc cggttcccaa cgatcaaggc gagttacatg   6660

atcccccatg ttgtgcaaaa aagcggttag ctccttcggt cctccgatcg ttgtcagaag   6720

taagttggcc gcagtgttat cactcatggt tatggcagca ctgcataatt ctcttactgt   6780

catgccatcc gtaagatgct tttctgtgac tggtgagtac tcaaccaagt cattctgaga   6840

atagtgtatg cggcgaccga gttgctcttg cccggcgtca atacgggata ataccgcgcc   6900

acatagcaga actttaaaag tgctcatcat tggaaaacgt tcttcggggc gaaaactctc   6960

aaggatctta ccgctgttga gatccagttc gatgtaaccc actcgtgcac ccaactgatc   7020

ttcagcatct tttactttca ccagcgtttc tgggtgagca aaaacaggaa ggcaaaatgc   7080

cgcaaaaaag ggaataaggg cgacacggaa atgttgaata ctcatactct tcctttttca   7140

atattattga agcatttatc agggttattg tctcatgagc ggatacatat ttgaatgtat   7200

ttagaaaaat aaacaaatag gggttccgcg cacatttccc cgaaaagtgc cacctgacgt   7260

cgacggatcg ggagatctcc cgatccccta tggtcgactc tcagtacaat ctgctctgat   7320

gccgcatagt taagccagta tctgctccct gcttgtgtgt tggaggtcgc tgagtagtgc   7380

gcgagcaaaa tttaagctac aacaaggcaa ggcttgaccg acaattgcat gaagaatctg   7440

cttagg                                                               7446
```

<210> SEQ ID NO 101
<211> LENGTH: 6773
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 101

```
gttaggcgtt ttgcgctgct tcgcgatgta cgggccagat atacgcgttg acattgatta     60
```

-continued

```
ttgactagtt attaatagta atcaattacg gggtcattag ttcatagccc atatatggag    120
ttccgcgtta cataacttac ggtaaatggc ccgcctggct gaccgcccaa cgacccccgc    180
ccattgacgt caataatgac gtatgttccc atagtaacgc caatagggac tttccattga    240
cgtcaatggg tggagtattt acggtaaact gcccacttgg cagtacatca agtgtatcat    300
atgccaagta cgccccctat tgacgtcaat gacggtaaat ggcccgcctg gcattatgcc    360
cagtacatga ccttatggga ctttcctact tggcagtaca tctacgtatt agtcatcgct    420
attaccatgg tgatgcggtt ttggcagtac atcaatgggc gtggatagcg gtttgactca    480
cggggatttc caagtctcca ccccattgac gtcaatggga gtttgttttg gcaccaaaat    540
caacgggact ttccaaaatg tcgtaacaac tccgccccat tgacgcaaat gggcggtagg    600
cgtgtacggt gggaggtcta tataagcaga gctcgtttag tgaaccgtca gatcgcctgg    660
agacgccatc cacgctgttt tgacctccat agaagacacc gggaccgatc cagcctccgg    720
actctagagg atcgaaccct taagcttgcc accatgtaca ggatgcaact cctgtcttgc    780
attgcactaa gtcttgcact tgtcacgaat tcagacatcg tgctgacaca gagccctgcc    840
agcctggctg tttctctggg acagagagcc accatcagct gcaaggccag ccagagcgtt    900
gactacgacg gcgacagcta catgaactgg tatcagcaga agtccggcca gcctcctaag    960
ctgctgatct acgccgccag caatctggaa agcggcatcc ctgccagatt ttccggctct   1020
ggcagcggca ccgacttcac cctgaatatc catcctgtgg aagaagagga cgccgccacc   1080
tactactgcc agcagagcaa tgtggacccc tggacatttg gcggaggcac caagctggaa   1140
atcaagcgta cggtggctgc accatctgtc ttcatcttcc cgccatctga tgagcagttg   1200
aaatctggaa ctgcctctgt tgtgtgcctg ctgaataact tctatcccag agaggccaaa   1260
gtacagtgga aggtggataa cgccctccaa tcgggtaact cccaggagag tgtcacagag   1320
caggacagca aggacagcac ctacagcctc agcagcaccc tgacgctgag caaagcagac   1380
tacgagaaac acaaagtcta cgcctgcgaa gtcacccatc agggcctgag ctcgcccgtc   1440
acaaagagct tcaacagggg agagtgttag agggagctag cgtggcatct agacactctc   1500
gagaagggtt cgatccctac cggttagtaa tgagtttgat atctcgacaa tcaacctctg   1560
gattacaaaa tttgtgaaag attgactggt attcttaact atgttgctcc ttttacgcta   1620
tgtggatacg ctgctttaat gcctttgtat catgctattg cttcccgtat ggctttcatt   1680
ttctcctcct tgtataaatc ctggttgctg tctctttatg aggagttgtg gcccgttgtc   1740
aggcaacgtg gcgtggtgtg cactgtgttt gctgacgcaa cccccactgg ttggggcatt   1800
gccaccacct gtcagctcct ttccgggact ttcgctttcc ccctccctat tgccacggcg   1860
gaactcatcg ccgcctgcct tgcccgctgc tggacagggg ctcggctgtt gggcactgac   1920
aattccgtgg tgttgtcggg gaagctgacg tcctttccat ggctgctcgc ctgtgttgcc   1980
acctggattc tgcgcgggac gtccttctgc tacgtccctt cggccctcaa tccagcggac   2040
cttccttccc gcggcctgct gccggctctg cggcctcttc cgcgtcttcg ccttcgccct   2100
cagacgagtc ggatctccct ttgggccgcc tccccgcctg gaaacggggg aggctaactg   2160
aaacacggaa ggagacaata ccggaaggaa cccgcgctat gacggcaata aaaagacaga   2220
ataaaacgca cgggtgttgg gtcgtttgtt cataaacgcg gggttcggtc ccagggctgg   2280
cactctgtcg ataccccacc gagaccccat tggggccaat acgcccgcgt ttcttccttt   2340
tccccacccc accccccaag ttcgggtgaa ggcccagggc tcgcagccaa cgtcggggcg   2400
gcaggccctg ccatagcaga tctgcgcagc tggggctcta gggggtatcc ccacgcgccc   2460
```

```
tgtagcggcg cattaagcgc ggcgggtgtg gtggttacgc gcagcgtgac cgctacactt   2520
gccagcgccc tagcgcccgc tcctttcgct ttcttccctt cctttctcgc cacgttcgcc   2580
ggctttcccc gtcaagctct aaatcggggc atccctttag ggttccgatt tagtgcttta   2640
cggcacctcg accccaaaaa acttgattag ggtgatggtt cacgtagtgg gccatcgccc   2700
tgatagacgg tttttcgccc tttgacgttg gagtccacgt tctttaatag tggactcttg   2760
ttccaaactg gaacaacact caaccctatc tcggtctatt cttttgattt ataagggatt   2820
ttggggattt cggcctattg gttaaaaaat gagctgattt aacaaaaatt taacgcgaat   2880
taattctgtg gaatgtgtgt cagttagggt gtggaaagtc cccaggctcc ccagcaggca   2940
gaagtatgca aagcatgcat ctcaattagt cagcaaccag gtgtggaaag tccccaggct   3000
ccccagcagg cagaagtatg caaagcatgc atctcaatta gtcagcaacc atagtcccgc   3060
ccctaactcc gcccatcccg cccctaactc cgcccagttc cgcccattct ccgccccatg   3120
gctgactaat tttttttatt tatgcagagg ccgaggccgc ctctgcctct gagctattcc   3180
agaagtagtg aggaggcttt tttggaggcc taggcttttg caaaaagctc ccgggagctt   3240
gtatatccat tttcggatct gatcaagaga caggatgagg atcgtttcgc atgattgaac   3300
aagatggatt gcacgcaggt tctccggccg cttgggtgga gaggctattc ggctatgact   3360
gggcacaaca gacaatcggc tgctctgatg ccgccgtgtt ccggctgtca gcgcaggggc   3420
gcccggttct ttttgtcaag accgacctgt ccggtgccct gaatgaactg caggacgagg   3480
cagcgcggct atcgtggctg gccacgacgg gcgttccttg cgcagctgtg ctcgacgttg   3540
tcactgaagc gggaagggac tggctgctat tgggcgaagt gccggggcag gatctcctgt   3600
catctcacct tgctcctgcc gagaaagtat ccatcatggc tgatgcaatg cggcggctgc   3660
atacgcttga tccggctacc tgcccattcg accaccaagc gaaacatcgc atcgagcgag   3720
cacgtactcg gatggaagcc ggtcttgtcg atcaggatga tctggacgaa gagcatcagg   3780
ggctcgcgcc agccgaactg ttcgccaggc tcaaggcgcg catgcccgac ggcgaggatc   3840
tcgtcgtgac ccatggcgat gcctgcttgc cgaatatcat ggtggaaaat ggccgctttt   3900
ctggattcat cgactgtggc cggctgggtg tggcggaccg ctatcaggac atagcgttgg   3960
ctacccgtga tattgctgaa gagcttggcg gcgaatgggc tgaccgcttc ctcgtgcttt   4020
acggtatcgc cgctcccgat tcgcagcgca tcgccttcta tcgccttctt gacgagttct   4080
tctgagcggg actctggggt tcgcgaaatg accgaccaag cgacgcccaa cctgccatca   4140
cgagatttcg attccaccgc cgccttctat gaaaggttgg gcttcggaat cgttttccgg   4200
gacgccggct ggatgatcct ccagcgcggg gatctcatgc tggagttctt cgcccacccc   4260
aacttgttta ttgcagctta taatggttac aaataaagca atagcatcac aaatttcaca   4320
aataaagcat ttttttcact gcattctagt tgtggtttgt ccaaactcat caatgtatct   4380
tatcatgtct gtataccgtc gacctctagc tagagcttgg cgtaatcatg gtcatagctg   4440
tttcctgtgt gaaattgtta tccgctcaca attccacaca acatacgagc cggaagcata   4500
aagtgtaaag cctggggtgc ctaatgagtg agctaactca cattaattgc gttgcgctca   4560
ctgcccgctt tccagtcggg aaacctgtcg tgccagctgc attaatgaat cggccaacgc   4620
gcggggagag gcggtttgcg tattgggcgc tcttccgctt cctcgctcac tgactcgctg   4680
cgctcggtcg ttcggctgcg gcgagcggta tcagctcact caaaggcggt aatacggtta   4740
tccacagaat caggggataa cgcaggaaag aacatgtgag caaaaggcca gcaaaaggcc   4800
```

aggaaccgta aaaaggccgc gttgctggcg tttttccata ggctccgccc ccctgacgag 4860
catcacaaaa atcgacgctc aagtcagagg tggcgaaacc cgacaggact ataaagatac 4920
caggcgtttc cccctggaag ctccctcgtg cgctctcctg ttccgaccct gccgcttacc 4980
ggatacctgt ccgcctttct cccttcggga agcgtggcgc tttctcaatg ctcacgctgt 5040
aggtatctca gttcggtgta ggtcgttcgc tccaagctgg gctgtgtgca cgaacccccc 5100
gttcagcccg accgctgcgc cttatccggt aactatcgtc ttgagtccaa cccggtaaga 5160
cacgacttat cgccactggc agcagccact ggtaacagga ttagcagagc gaggtatgta 5220
ggcggtgcta cagagttctt gaagtggtgg cctaactacg gctacactag aaggacagta 5280
tttggtatct gcgctctgct gaagccagtt accttcggaa aaagagttgg tagctcttga 5340
tccggcaaac aaaccaccgc tggtagcggt ggtttttttg tttgcaagca gcagattacg 5400
cgcagaaaaa aaggatctca agaagatcct ttgatctttt ctacggggtc tgacgctcag 5460
tggaacgaaa actcacgtta agggattttg gtcatgagat tatcaaaaag gatcttcacc 5520
tagatccttt taaattaaaa atgaagtttt aaatcaatct aaagtatata tgagtaaact 5580
tggtctgaca gttaccaatg cttaatcagt gaggcaccta tctcagcgat ctgtctattt 5640
cgttcatcca tagttgcctg actccccgtc gtgtagataa ctacgatacg ggagggctta 5700
ccatctggcc ccagtgctgc aatgataccg cgagacccac gctcaccggc tccagattta 5760
tcagcaataa accagccagc cggaagggcc gagcgcagaa gtggtcctgc aactttatcc 5820
gcctccatcc agtctattaa ttgttgccgg gaagctagag taagtagttc gccagttaat 5880
agtttgcgca acgttgttgc cattgctaca ggcatcgtgg tgtcacgctc gtcgtttggt 5940
atggcttcat tcagctccgg ttcccaacga tcaaggcgag ttacatgatc ccccatgttg 6000
tgcaaaaaag cggttagctc cttcggtcct ccgatcgttg tcagaagtaa gttggccgca 6060
gtgttatcac tcatggttat ggcagcactg cataattctc ttactgtcat gccatccgta 6120
agatgctttt ctgtgactgg tgagtactca accaagtcat tctgagaata gtgtatgcgg 6180
cgaccgagtt gctcttgccc ggcgtcaata cgggataata ccgcgccaca tagcagaact 6240
ttaaaagtgc tcatcattgg aaaacgttct tcggggcgaa aactctcaag gatcttaccg 6300
ctgttgagat ccagttcgat gtaacccact cgtgcaccca actgatcttc agcatctttt 6360
actttcacca gcgtttctgg gtgagcaaaa acaggaaggc aaaatgccgc aaaaaaggga 6420
ataagggcga cacggaaatg ttgaatactc atactcttcc tttttcaata ttattgaagc 6480
atttatcagg gttattgtct catgagcgga tacatatttg aatgtattta gaaaaataaa 6540
caaatagggg ttccgcgcac atttccccga aaagtgccac ctgacgtcga cggatcggga 6600
gatctcccga tcccctatgg tcgactctca gtacaatctg ctctgatgcc gcatagttaa 6660
gccagtatct gctccctgct tgtgtgttgg aggtcgctga gtagtgcgcg agcaaaattt 6720
aagctacaac aaggcaaggc ttgaccgaca attgcatgaa gaatctgctt agg 6773

<210> SEQ ID NO 102
<211> LENGTH: 7449
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 102
gttaggcgtt ttgcgctgct tcgcgatgta cgggccagat atacgcgttg acattgatta 60

-continued

```
ttgactagtt attaatagta atcaattacg gggtcattag ttcatagccc atatatggag    120
ttccgcgtta cataacttac ggtaaatggc ccgcctggct gaccgcccaa cgacccccgc    180
ccattgacgt caataatgac gtatgttccc atagtaacgc caatagggac tttccattga    240
cgtcaatggg tggagtattt acggtaaact gcccacttgg cagtacatca agtgtatcat    300
atgccaagta cgccccctat tgacgtcaat gacggtaaat ggcccgcctg gcattatgcc    360
cagtacatga ccttatggga ctttcctact tggcagtaca tctacgtatt agtcatcgct    420
attaccatgg tgatgcggtt ttggcagtac atcaatgggc gtggatagcg gtttgactca    480
cggggatttc caagtctcca ccccattgac gtcaatggga gtttgttttg gcaccaaaat    540
caacgggact ttccaaaatg tcgtaacaac tccgccccat tgacgcaaat gggcggtagg    600
cgtgtacggt gggaggtcta tataagcaga gctcgtttag tgaaccgtca gatcgcctgg    660
agacgccatc cacgctgttt tgacctccat agaagacacc gggaccgatc cagcctccgg    720
actctagagg atcgaaccct taagcttgcc accatgtaca ggatgcaact cctgtcttgc    780
attgcactaa gtcttgcact tgtcacgaat tcggaggtcc agctgcagca gtctggcgcc    840
gaacttgtta gacctggcgc tctggtcaag ctgagctgta aagccagcgg cttcaacatc    900
aaggactacc acatgcactg ggtcaaagag cggcctgagc agggactcga gtggatcgga    960
tggatcgacc ccgagaacgg caacactatg tacgacccca agttccaggg caaagccagc   1020
atcaccgccg acacctctag caacacagcc tacctgcagc tgagcagcct gacctctgaa   1080
gataccgccg tgtactactg cgtgcgggga acagccagag ccagctttga ttattggggc   1140
cagggcacca cactgaccgt gtcatctgct agcaccaagg gcccatcggt cttccccctg   1200
gcgccctgct ccaggagcac ctccgagagc acagccgccc tgggctgcct ggtcaaggac   1260
tacttccccg aaccggtgac ggtgtcgtgg aactcaggcg ccctgaccag cggcgtgcac   1320
accttcccgg ctgtcctaca gtcctcagga ctctactccc tcagcagcgt ggtgaccgtg   1380
ccctccagca gcttgggcac gaagacctac acctgcaacg tagatcacaa gcccagcaac   1440
accaaggtgg acaagagagt tgagtccaaa tatggtcccc catgcccatc atgcccagca   1500
cctgagttcc tggggggacc atcagtcttc ctgttccccc caaaacccaa ggacactctc   1560
atgatctccc ggacccctga ggtcacgtgc gtggtggtgg acgtgagcca ggaagacccc   1620
gaggtccagt tcaactggta cgtggatggc gtggaggtgc ataatgccaa gacaaagccg   1680
cgggaggagc agttcaacag cacgtaccgt gtggtcagcg tcctcaccgt cctgcaccag   1740
gactggctga acggcaagga gtacaagtgc aaggtctcca acaaaggcct cccgtcctcc   1800
atcgagaaaa ccatctccaa agccaaaggg cagccccgag agccacaggt gtacaccctg   1860
cccccatccc aggaggagat gaccaagaac caggtcagcc tgacctgcct ggtcaaaggc   1920
ttctacccca gcgacatcgc cgtggagtgg gagagcaatg ggcagccgga gaacaactac   1980
aagaccacgc ctcccgtgct ggactccgac ggctccttct tcctctacag caggctaacc   2040
gtggacaaga gcaggtggca ggaggggaat gtcttctcat gctccgtgat gcatgaggct   2100
ctgcacaacc actacacaca gaagagcctc tccctgtctc tgggtaaata acctagcgtg   2160
gcatctagac actctcgaga agggttcgat ccctaccggt tagtaatgag tttgatatct   2220
cgacaatcaa cctctggatt acaaaatttg tgaaagattg actggtattc ttaactatgt   2280
tgctcctttt acgctatgtg gatacgctgc tttaatgcct ttgtatcatg ctattgcttc   2340
ccgtatggct ttcattttct cctccttgta taaatcctgg ttgctgtctc tttatgagga   2400
gttgtggccc gttgtcaggc aacgtggcgt ggtgtgcact gtgtttgctg acgcaacccc   2460
```

-continued

```
cactggttgg ggcattgcca ccacctgtca gctcctttcc gggactttcg ctttccccct   2520
ccctattgcc acggcggaac tcatcgccgc ctgccttgcc cgctgctgga caggggctcg   2580
gctgttgggc actgacaatt ccgtggtgtt gtcggggaag ctgacgtcct ttccatggct   2640
gctcgcctgt gttgccacct ggattctgcg cgggacgtcc ttctgctacg tcccttcggc   2700
cctcaatcca gcggaccttc cttcccgcgg cctgctgccg gctctgcggc ctcttccgcg   2760
tcttcgcctt cgccctcaga cgagtcggat ctccctttgg gccgcctccc cgcctggaaa   2820
cgggggaggc taactgaaac acggaaggag acaataccgg aaggaacccg cgctatgacg   2880
gcaataaaaa gacagaataa aacgcacggg tgttgggtcg tttgttcata aacgcggggt   2940
tcggtcccag ggctggcact ctgtcgatac cccaccgaga ccccattggg gccaatacgc   3000
ccgcgtttct tccttttccc caccccaccc cccaagttcg ggtgaaggcc cagggctcgc   3060
agccaacgtc ggggcggcag gccctgccat agcagatctg cgcagctggg gctctagggg   3120
gtatccccac gcgccctgta gcggcgcatt aagcgcggcg ggtgtggtgg ttacgcgcag   3180
cgtgaccgct acacttgcca gcgccctagc gcccgctcct ttcgctttct tcccttcctt   3240
tctcgccacg ttcgccggct ttccccgtca agctctaaat cggggcatcc ctttagggtt   3300
ccgatttagt gctttacggc acctcgaccc caaaaaactt gattagggtg atggttcacg   3360
tagtgggcca tcgccctgat agacggtttt tcgccctttg acgttggagt ccacgttctt   3420
taatagtgga ctcttgttcc aaactggaac aacactcaac cctatctcgg tctattcttt   3480
tgatttataa gggattttgg ggatttcggc ctattggtta aaaaatgagc tgatttaaca   3540
aaaatttaac gcgaattaat tctgtggaat gtgtgtcagt tagggtgtgg aaagtcccca   3600
ggctccccag caggcagaag tatgcaaagc atgcatctca attagtcagc aaccaggtgt   3660
ggaaagtccc caggctcccc agcaggcaga agtatgcaaa gcatgcatct caattagtca   3720
gcaaccatag tcccgcccct aactccgccc atcccgcccc taactccgcc cagttccgcc   3780
cattctccgc cccatggctg actaattttt tttatttatg cagaggccga ggccgcctct   3840
gcctctgagc tattccagaa gtagtgagga ggcttttttg gaggcctagg cttttgcaaa   3900
aagctcccgg gagcttgtat atccattttc ggatctgatc aagagacagg atgaggatcg   3960
tttcgcatga ttgaacaaga tggattgcac gcaggttctc cggccgcttg ggtggagagg   4020
ctattcggct atgactgggc acaacagaca atcggctgct ctgatgccgc cgtgttccgg   4080
ctgtcagcgc aggggcgccc ggttcttttt gtcaagaccg acctgtccgg tgccctgaat   4140
gaactgcagg acgaggcagc gcggctatcg tggctggcca cgacgggcgt tccttgcgca   4200
gctgtgctcg acgttgtcac tgaagcggga agggactggc tgctattggg cgaagtgccg   4260
gggcaggatc tcctgtcatc tcaccttgct cctgccgaga aagtatccat catggctgat   4320
gcaatgcggc ggctgcatac gcttgatccg gctacctgcc cattcgacca ccaagcgaaa   4380
catcgcatcg agcgagcacg tactcggatg gaagccggtc ttgtcgatca ggatgatctg   4440
gacgaagagc atcaggggct cgcgccagcc gaactgttcg ccaggctcaa ggcgcgcatg   4500
cccgacggcg aggatctcgt cgtgacccat ggcgatgcct gcttgccgaa tatcatggtg   4560
gaaaatggcc gcttttctgg attcatcgac tgtggccggc tgggtgtggc ggaccgctat   4620
caggacatag cgttggctac ccgtgatatt gctgaagagc ttggcggcga atgggctgac   4680
cgcttcctcg tgctttacgg tatcgccgct cccgattcgc agcgcatcgc cttctatcgc   4740
cttcttgacg agttcttctg agcgggactc tggggttcgc gaaatgaccg accaagcgac   4800
```

-continued

```
gcccaacctg ccatcacgag atttcgattc caccgccgcc ttctatgaaa ggttgggctt   4860
cggaatcgtt ttccgggacg ccggctggat gatcctccag cgcggggatc tcatgctgga   4920
gttcttcgcc caccccaact tgtttattgc agcttataat ggttacaaat aaagcaatag   4980
catcacaaat ttcacaaata aagcattttt ttcactgcat tctagttgtg gtttgtccaa   5040
actcatcaat gtatcttatc atgtctgtat accgtcgacc tctagctaga gcttggcgta   5100
atcatggtca tagctgtttc ctgtgtgaaa ttgttatccg ctcacaattc cacacaacat   5160
acgagccgga agcataaagt gtaaagcctg gggtgcctaa tgagtgagct aactcacatt   5220
aattgcgttg cgctcactgc ccgctttcca gtcgggaaac ctgtcgtgcc agctgcatta   5280
atgaatcggc caacgcgcgg ggagaggcgg tttgcgtatt gggcgctctt ccgcttcctc   5340
gctcactgac tcgctgcgct cggtcgttcg gctgcggcga gcggtatcag ctcactcaaa   5400
ggcggtaata cggttatcca cagaatcagg ggataacgca ggaaagaaca tgtgagcaaa   5460
aggccagcaa aaggccagga accgtaaaaa ggccgcgttg ctggcgtttt tccataggct   5520
ccgcccccct gacgagcatc acaaaaatcg acgctcaagt cagaggtggc gaaacccgac   5580
aggactataa agataccagg cgtttccccc tggaagctcc ctcgtgcgct ctcctgttcc   5640
gaccctgccg cttaccggat acctgtccgc ctttctccct tcgggaagcg tggcgctttc   5700
tcaatgctca cgctgtaggt atctcagttc ggtgtaggtc gttcgctcca agctgggctg   5760
tgtgcacgaa ccccccgttc agcccgaccg ctgcgcctta tccggtaact atcgtcttga   5820
gtccaacccg gtaagacacg acttatcgcc actggcagca gccactggta acaggattag   5880
cagagcgagg tatgtaggcg gtgctacaga gttcttgaag tggtggccta actacggcta   5940
cactagaagg acagtatttg gtatctgcgc tctgctgaag ccagttacct tcggaaaaag   6000
agttggtagc tcttgatccg gcaaacaaac caccgctggt agcggtggtt tttttgtttg   6060
caagcagcag attacgcgca gaaaaaaagg atctcaagaa gatcctttga tcttttctac   6120
ggggtctgac gctcagtgga acgaaaactc acgttaaggg attttggtca tgagattatc   6180
aaaaaggatc ttcacctaga tccttttaaa ttaaaaatga agttttaaat caatctaaag   6240
tatatatgag taaacttggt ctgacagtta ccaatgctta atcagtgagg cacctatctc   6300
agcgatctgt ctatttcgtt catccatagt tgcctgactc cccgtcgtgt agataactac   6360
gatacgggag ggcttaccat ctggccccag tgctgcaatg ataccgcgag acccacgctc   6420
accggctcca gatttatcag caataaacca gccagccgga agggccgagc gcagaagtgg   6480
tcctgcaact ttatccgcct ccatccagtc tattaattgt tgccgggaag ctagagtaag   6540
tagttcgcca gttaatagtt tgcgcaacgt tgttgccatt gctacaggca tcgtggtgtc   6600
acgctcgtcg tttggtatgg cttcattcag ctccggttcc caacgatcaa ggcgagttac   6660
atgatccccc atgttgtgca aaaaagcggt tagctccttc ggtcctccga tcgttgtcag   6720
aagtaagttg gccgcagtgt tatcactcat ggttatggca gcactgcata attctcttac   6780
tgtcatgcca tccgtaagat gcttttctgt gactggtgag tactcaacca agtcattctg   6840
agaatagtgt atgcggcgac cgagttgctc ttgcccggcg tcaatacggg ataataccgc   6900
gccacatagc agaactttaa aagtgctcat cattggaaaa cgttcttcgg ggcgaaaact   6960
ctcaaggatc ttaccgctgt tgagatccag ttcgatgtaa cccactcgtg cacccaactg   7020
atcttcagca tcttttactt tcaccagcgt ttctgggtga gcaaaaacag gaaggcaaaa   7080
tgccgcaaaa aagggaataa gggcgacacg gaaatgttga atactcatac tcttcctttt   7140
tcaatattat tgaagcattt atcagggtta ttgtctcatg agcggataca tatttgaatg   7200
```

tatttagaaa aataaacaaa taggggttcc gcgcacattt ccccgaaaag tgccacctga 7260
cgtcgacgga tcgggagatc tcccgatccc ctatggtcga ctctcagtac aatctgctct 7320
gatgccgcat agttaagcca gtatctgctc cctgcttgtg tgttggaggt cgctgagtag 7380
tgcgcgagca aaatttaagc tacaacaagg caaggcttga ccgacaattg catgaagaat 7440
ctgcttagg 7449

<210> SEQ ID NO 103
<211> LENGTH: 6773
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 103
gttaggcgtt ttgcgctgct tcgcgatgta cgggccagat atacgcgttg acattgatta 60
ttgactagtt attaatagta atcaattacg gggtcattag ttcatagccc atatatggag 120
ttccgcgtta cataacttac ggtaaatggc ccgcctggct gaccgcccaa cgacccccgc 180
ccattgacgt caataatgac gtatgttccc atagtaacgc caatagggac tttccattga 240
cgtcaatggg tggagtattt acggtaaact gcccacttgg cagtacatca agtgtatcat 300
atgccaagta cgccccctat tgacgtcaat gacggtaaat ggcccgcctg gcattatgcc 360
cagtacatga ccttatggga ctttcctact tggcagtaca tctacgtatt agtcatcgct 420
attaccatgg tgatgcggtt ttggcagtac atcaatgggc gtggatagcg gtttgactca 480
cggggatttc caagtctcca ccccattgac gtcaatggga gtttgttttg gcaccaaaat 540
caacgggact ttccaaaatg tcgtaacaac tccgccccat tgacgcaaat gggcggtagg 600
cgtgtacggt gggaggtcta tataagcaga gctcgtttag tgaaccgtca gatcgcctgg 660
agacgccatc cacgctgttt tgacctccat agaagacacc gggaccgatc cagcctccgg 720
actctagagg atcgaaccct taagcttgcc accatgtaca ggatgcaact cctgtcttgc 780
attgcactaa gtcttgcact tgtcacgaat tcagacatcg tgctgacaca gagccctgcc 840
agcctggctg tttctctggg acagagagcc accatcagct gcaaggccag ccagagcgtt 900
gactacgacg gcgacaccta catgaactgg tatcagcaga agcccggcca gccacctaag 960
ctgctgatct acacagccag caacctggaa agcggcatcc ccgccagatt ttctggcagc 1020
ggaagcggca ccgacttcac cctgaatatc catcctgtgg aagaggtgga cgccgccacc 1080
tactactgcc agcagagcaa tgaggacccc tggacatttg gcggaggcac caagctggaa 1140
atcaagcgta cggtggctgc accatctgtc ttcatcttcc cgccatctga tgagcagttg 1200
aaatctggaa ctgcctctgt tgtgtgcctg ctgaataact tctatcccag agaggccaaa 1260
gtacagtgga aggtggataa cgccctccaa tcgggtaact cccaggagag tgtcacagag 1320
caggacagca aggacagcac ctacagcctc agcagcaccc tgacgctgag caaagcagac 1380
tacgagaaac acaaagtcta cgcctgcgaa gtcacccatc agggcctgag ctcgcccgtc 1440
acaaagagct tcaacagggg agagtgttag agggagctag cgtggcatct agacactctc 1500
gagaagggtt cgatccctac cggttagtaa tgagtttgat atctcgacaa tcaacctctg 1560
gattacaaaa tttgtgaaag attgactggt attcttaact atgttgctcc ttttacgcta 1620
tgtggatacg ctgctttaat gcctttgtat catgctattg cttcccgtat ggctttcatt 1680
ttctcctcct tgtataaatc ctggttgctg tctctttatg aggagttgtg gcccgttgtc 1740
aggcaacgtg gcgtggtgtg cactgtgttt gctgacgcaa cccccactgg ttggggcatt 1800
gccaccacct gtcagctcct ttccgggact ttcgctttcc ccctccctat tgccacggcg 1860
gaactcatcg ccgcctgcct tgcccgctgc tggacagggg ctcggctgtt gggcactgac 1920
aattccgtgg tgttgtcggg gaagctgacg tcctttccat ggctgctcgc ctgtgttgcc 1980
acctggattc tgcgcgggac gtccttctgc tacgtccctt cggccctcaa tccagcggac 2040
cttccttccc gcggcctgct gccggctctg cggcctcttc cgcgtcttcg ccttcgccct 2100
cagacgagtc ggatctccct ttgggccgcc tccccgcctg gaaacggggg aggctaactg 2160
aaacacggaa ggagacaata ccggaaggaa cccgcgctat gacggcaata aaaagacaga 2220
ataaaacgca cgggtgttgg gtcgtttgtt cataaacgcg gggttcggtc ccagggctgg 2280
cactctgtcg ataccccacc gagaccccat tggggccaat acgcccgcgt ttcttccttt 2340
tccccacccc accccccaag ttcgggtgaa ggcccagggc tcgcagccaa cgtcggggcg 2400
gcaggccctg ccatagcaga tctgcgcagc tggggctcta gggggtatcc ccacgcgccc 2460
tgtagcggcg cattaagcgc ggcgggtgtg gtggttacgc gcagcgtgac cgctacactt 2520
gccagcgccc tagcgcccgc tcctttcgct ttcttccctt cctttctcgc cacgttcgcc 2580
ggctttcccc gtcaagctct aaatcggggc atccctttag ggttccgatt tagtgcttta 2640
cggcacctcg accccaaaaa acttgattag ggtgatggtt cacgtagtgg gccatcgccc 2700
tgatagacgg tttttcgccc tttgacgttg gagtccacgt tctttaatag tggactcttg 2760
ttccaaactg gaacaacact caaccctatc tcggtctatt cttttgattt ataagggatt 2820
ttggggattt cggcctattg gttaaaaaat gagctgattt aacaaaaatt taacgcgaat 2880
taattctgtg gaatgtgtgt cagttagggt gtggaaagtc cccaggctcc ccagcaggca 2940
gaagtatgca aagcatgcat ctcaattagt cagcaaccag gtgtggaaag tccccaggct 3000
ccccagcagg cagaagtatg caaagcatgc atctcaatta gtcagcaacc atagtcccgc 3060
ccctaactcc gcccatcccg cccctaactc cgcccagttc cgcccattct ccgccccatg 3120
gctgactaat tttttttatt tatgcagagg ccgaggccgc ctctgcctct gagctattcc 3180
agaagtagtg aggaggcttt tttggaggcc taggcttttg caaaaagctc ccgggagctt 3240
gtatatccat tttcggatct gatcaagaga caggatgagg atcgtttcgc atgattgaac 3300
aagatggatt gcacgcaggt tctccggccg cttgggtgga gaggctattc ggctatgact 3360
gggcacaaca gacaatcggc tgctctgatg ccgccgtgtt ccggctgtca gcgcaggggc 3420
gcccggttct ttttgtcaag accgacctgt ccggtgccct gaatgaactg caggacgagg 3480
cagcgcggct atcgtggctg gccacgacgg gcgttccttg cgcagctgtg ctcgacgttg 3540
tcactgaagc gggaagggac tggctgctat tgggcgaagt gccggggcag gatctcctgt 3600
catctcacct tgctcctgcc gagaaagtat ccatcatggc tgatgcaatg cggcggctgc 3660
atacgcttga tccggctacc tgcccattcg accaccaagc gaaacatcgc atcgagcgag 3720
cacgtactcg gatggaagcc ggtcttgtcg atcaggatga tctggacgaa gagcatcagg 3780
ggctcgcgcc agccgaactg ttcgccaggc tcaaggcgcg catgcccgac ggcgaggatc 3840
tcgtcgtgac ccatggcgat gcctgcttgc cgaatatcat ggtggaaaat ggccgctttt 3900
ctggattcat cgactgtggc cggctgggtg tggcggaccg ctatcaggac atagcgttgg 3960
ctacccgtga tattgctgaa gagcttggcg gcgaatgggc tgaccgcttc ctcgtgcttt 4020
acggtatcgc cgctcccgat tcgcagcgca tcgccttcta tcgccttctt gacgagttct 4080

-continued

```
tctgagcggg actctggggt tcgcgaaatg accgaccaag cgacgcccaa cctgccatca   4140
cgagatttcg attccaccgc cgccttctat gaaaggttgg gcttcggaat cgttttccgg   4200
gacgccggct ggatgatcct ccagcgcggg gatctcatgc tggagttctt cgcccacccc   4260
aacttgttta ttgcagctta taatggttac aaataaagca atagcatcac aaatttcaca   4320
aataaagcat ttttttcact gcattctagt tgtggtttgt ccaaactcat caatgtatct   4380
tatcatgtct gtataccgtc gacctctagc tagagcttgg cgtaatcatg gtcatagctg   4440
tttcctgtgt gaaattgtta tccgctcaca attccacaca acatacgagc cggaagcata   4500
aagtgtaaag cctggggtgc ctaatgagtg agctaactca cattaattgc gttgcgctca   4560
ctgcccgctt tccagtcggg aaacctgtcg tgccagctgc attaatgaat cggccaacgc   4620
gcggggagag gcggtttgcg tattgggcgc tcttccgctt cctcgctcac tgactcgctg   4680
cgctcggtcg ttcggctgcg gcgagcggta tcagctcact caaaggcggt aatacggtta   4740
tccacagaat caggggataa cgcaggaaag aacatgtgag caaaaggcca gcaaaaggcc   4800
aggaaccgta aaaaggccgc gttgctggcg tttttccata ggctccgccc ccctgacgag   4860
catcacaaaa atcgacgctc aagtcagagg tggcgaaacc cgacaggact ataaagatac   4920
caggcgtttc cccctggaag ctccctcgtg cgctctcctg ttccgaccct gccgcttacc   4980
ggatacctgt ccgcctttct cccttcggga agcgtggcgc tttctcaatg ctcacgctgt   5040
aggtatctca gttcggtgta ggtcgttcgc tccaagctgg gctgtgtgca cgaacccccc   5100
gttcagcccg accgctgcgc cttatccggt aactatcgtc ttgagtccaa cccggtaaga   5160
cacgacttat cgccactggc agcagccact ggtaacagga ttagcagagc gaggtatgta   5220
ggcggtgcta cagagttctt gaagtggtgg cctaactacg gctacactag aaggacagta   5280
tttggtatct gcgctctgct gaagccagtt accttcggaa aaagagttgg tagctcttga   5340
tccggcaaac aaaccaccgc tggtagcggt ggtttttttg tttgcaagca gcagattacg   5400
cgcagaaaaa aaggatctca agaagatcct ttgatctttt ctacggggtc tgacgctcag   5460
tggaacgaaa actcacgtta agggattttg gtcatgagat tatcaaaaag gatcttcacc   5520
tagatccttt taaattaaaa atgaagtttt aaatcaatct aaagtatata tgagtaaact   5580
tggtctgaca gttaccaatg cttaatcagt gaggcaccta tctcagcgat ctgtctattt   5640
cgttcatcca tagttgcctg actccccgtc gtgtagataa ctacgatacg ggagggctta   5700
ccatctggcc ccagtgctgc aatgataccg cgagacccac gctcaccggc tccagattta   5760
tcagcaataa accagccagc cggaagggcc gagcgcagaa gtggtcctgc aactttatcc   5820
gcctccatcc agtctattaa ttgttgccgg gaagctagag taagtagttc gccagttaat   5880
agtttgcgca acgttgttgc cattgctaca ggcatcgtgg tgtcacgctc gtcgtttggt   5940
atggcttcat tcagctccgg ttcccaacga tcaaggcgag ttacatgatc ccccatgttg   6000
tgcaaaaaag cggttagctc cttcggtcct ccgatcgttg tcagaagtaa gttggccgca   6060
gtgttatcac tcatggttat ggcagcactg cataattctc ttactgtcat gccatccgta   6120
agatgctttt ctgtgactgg tgagtactca accaagtcat tctgagaata gtgtatgcgg   6180
cgaccgagtt gctcttgccc ggcgtcaata cgggataata ccgcgccaca tagcagaact   6240
ttaaaagtgc tcatcattgg aaaacgttct tcggggcgaa aactctcaag gatcttaccg   6300
ctgttgagat ccagttcgat gtaacccact cgtgcaccca actgatcttc agcatctttt   6360
actttcacca gcgtttctgg gtgagcaaaa acaggaaggc aaaatgccgc aaaaaaggga   6420
ataagggcga cacggaaatg ttgaatactc atactcttcc tttttcaata ttattgaagc   6480
```

-continued

```
atttatcagg gttattgtct catgagcgga tacatatttg aatgtattta gaaaaataaa   6540

caaatagggg ttccgcgcac atttccccga aaagtgccac ctgacgtcga cggatcggga   6600

gatctcccga tcccctatgg tcgactctca gtacaatctg ctctgatgcc gcatagttaa   6660

gccagtatct gctccctgct tgtgtgttgg aggtcgctga gtagtgcgcg agcaaaattt   6720

aagctacaac aaggcaaggc ttgaccgaca attgcatgaa gaatctgctt agg          6773
```

<210> SEQ ID NO 104
<211> LENGTH: 7449
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104

```
gttaggcgtt ttgcgctgct tcgcgatgta cgggccagat atacgcgttg acattgatta     60

ttgactagtt attaatagta atcaattacg gggtcattag ttcatagccc atatatggag    120

ttccgcgtta cataacttac ggtaaatggc ccgcctggct gaccgcccaa cgacccccgc    180

ccattgacgt caataatgac gtatgttccc atagtaacgc caatagggac tttccattga    240

cgtcaatggg tggagtattt acggtaaact gcccacttgg cagtacatca agtgtatcat    300

atgccaagta cgccccctat tgacgtcaat gacggtaaat ggcccgcctg gcattatgcc    360

cagtacatga ccttatggga ctttcctact tggcagtaca tctacgtatt agtcatcgct    420

attaccatgg tgatgcggtt ttggcagtac atcaatgggc gtggatagcg gtttgactca    480

cggggatttc caagtctcca ccccattgac gtcaatggga gtttgttttg gcaccaaaat    540

caacgggact ttccaaaatg tcgtaacaac tccgccccat tgacgcaaat gggcggtagg    600

cgtgtacggt gggaggtcta tataagcaga gctcgtttag tgaaccgtca gatcgcctgg    660

agacgccatc cacgctgttt tgacctccat agaagacacc gggaccgatc cagcctccgg    720

actctagagg atcgaaccct taagcttgcc accatgtaca ggatgcaact cctgtcttgc    780

attgcactaa gtcttgcact tgtcacgaat tcggaggtcc agctgcagca gtctggcgcc    840

gaacttgtta gacctggcgc tctggtcaag tggtcctgta aagccagcgg cttcaacatc    900

aaggactacc acatccactg ggtcaagcag aggcctgagc agggcctcga ttggatcggc    960

tggatcgacc ccgagatcga caagaccctg tacgacccca agttccaggg caaagccaga   1020

atcaccgccg acaccagcag caacacagcc tacctgcaac tgagcagcct gaccagcgaa   1080

gataccgccg tgtactactg cgccagagga acagccagag ccagcttcga ttattggggc   1140

cagggcacca cactgaccgt gtcatctgct agcaccaagg gcccatcggt cttccccctg   1200

gcgccctgct ccaggagcac ctccgagagc acagccgccc tgggctgcct ggtcaaggac   1260

tacttccccg aaccggtgac ggtgtcgtgg aactcaggcg ccctgaccag cggcgtgcac   1320

accttcccgg ctgtcctaca gtcctcagga ctctactccc tcagcagcgt ggtgaccgtg   1380

ccctccagca gcttgggcac gaagacctac acctgcaacg tagatcacaa gcccagcaac   1440

accaaggtgg acaagagagt tgagtccaaa tatggtcccc catgcccatc atgcccagca   1500

cctgagttcc tggggggacc atcagtcttc ctgttccccc caaaacccaa ggacactctc   1560

atgatctccc ggacccctga ggtcacgtgc gtggtggtgg acgtgagcca ggaagacccc   1620

gaggtccagt tcaactggta cgtggatggc gtggaggtgc ataatgccaa gacaaagccg   1680

cgggaggagc agttcaacag cacgtaccgt gtggtcagcg tcctcaccgt cctgcaccag   1740
```

```
gactggctga acggcaagga gtacaagtgc aaggtctcca acaaaggcct cccgtcctcc   1800
atcgagaaaa ccatctccaa agccaaaggg cagccccgag agccacaggt gtacaccctg   1860
cccccatccc aggaggagat gaccaagaac caggtcagcc tgacctgcct ggtcaaaggc   1920
ttctacccca gcgacatcgc cgtggagtgg gagagcaatg ggcagccgga gaacaactac   1980
aagaccacgc ctcccgtgct ggactccgac ggctccttct tcctctacag caggctaacc   2040
gtggacaaga gcaggtggca ggaggggaat gtcttctcat gctccgtgat gcatgaggct   2100
ctgcacaacc actacacaca gaagagcctc tccctgtctc tgggtaaata acctagcgtg   2160
gcatctagac actctcgaga agggttcgat ccctaccggt tagtaatgag tttgatatct   2220
cgacaatcaa cctctggatt acaaaatttg tgaaagattg actggtattc ttaactatgt   2280
tgctcctttt acgctatgtg gatacgctgc tttaatgcct ttgtatcatg ctattgcttc   2340
ccgtatggct ttcattttct cctccttgta taaatcctgg ttgctgtctc tttatgagga   2400
gttgtggccc gttgtcaggc aacgtggcgt ggtgtgcact gtgtttgctg acgcaacccc   2460
cactggttgg ggcattgcca ccacctgtca gctcctttcc gggactttcg ctttccccct   2520
ccctattgcc acggcggaac tcatcgccgc ctgccttgcc cgctgctgga caggggctcg   2580
gctgttgggc actgacaatt ccgtggtgtt gtcggggaag ctgacgtcct ttccatggct   2640
gctcgcctgt gttgccacct ggattctgcg cgggacgtcc ttctgctacg tcccttcggc   2700
cctcaatcca gcggaccttc cttcccgcgg cctgctgccg gctctgcggc ctcttccgcg   2760
tcttcgcctt cgccctcaga cgagtcggat ctccctttgg gccgcctccc cgcctggaaa   2820
cgggggaggc taactgaaac acggaaggag acaataccgg aaggaacccg cgctatgacg   2880
gcaataaaaa gacagaataa aacgcacggg tgttgggtcg tttgttcata aacgcggggt   2940
tcggtcccag ggctggcact ctgtcgatac cccaccgaga ccccattggg gccaatacgc   3000
ccgcgtttct tccttttccc caccccaccc cccaagttcg ggtgaaggcc cagggctcgc   3060
agccaacgtc ggggcggcag gccctgccat agcagatctg cgcagctggg gctctagggg   3120
gtatccccac gcgccctgta gcggcgcatt aagcgcggcg ggtgtggtgg ttacgcgcag   3180
cgtgaccgct acacttgcca gcgccctagc gcccgctcct ttcgctttct tcccttcctt   3240
tctcgccacg ttcgccggct ttccccgtca agctctaaat cggggcatcc ctttagggtt   3300
ccgatttagt gctttacggc acctcgaccc caaaaaactt gattagggtg atggttcacg   3360
tagtgggcca tcgccctgat agacggtttt tcgccctttg acgttggagt ccacgttctt   3420
taatagtgga ctcttgttcc aaactggaac aacactcaac cctatctcgg tctattcttt   3480
tgatttataa gggattttgg ggatttcggc ctattggtta aaaaatgagc tgatttaaca   3540
aaaatttaac gcgaattaat tctgtggaat gtgtgtcagt tagggtgtgg aaagtcccca   3600
ggctccccag caggcagaag tatgcaaagc atgcatctca attagtcagc aaccaggtgt   3660
ggaaagtccc caggctcccc agcaggcaga agtatgcaaa gcatgcatct caattagtca   3720
gcaaccatag tcccgcccct aactccgccc atcccgcccc taactccgcc cagttccgcc   3780
cattctccgc cccatggctg actaattttt tttatttatg cagaggccga ggccgcctct   3840
gcctctgagc tattccagaa gtagtgagga ggcttttttg gaggcctagg cttttgcaaa   3900
aagctcccgg gagcttgtat atccattttc ggatctgatc aagagacagg atgaggatcg   3960
tttcgcatga ttgaacaaga tggattgcac gcaggttctc cggccgcttg ggtggagagg   4020
ctattcggct atgactgggc acaacagaca atcggctgct ctgatgccgc cgtgttccgg   4080
```

-continued

```
ctgtcagcgc aggggcgccc ggttcttttt gtcaagaccg acctgtccgg tgccctgaat   4140
gaactgcagg acgaggcagc gcggctatcg tggctggcca cgacgggcgt tccttgcgca   4200
gctgtgctcg acgttgtcac tgaagcggga agggactggc tgctattggg cgaagtgccg   4260
gggcaggatc tcctgtcatc tcaccttgct cctgccgaga aagtatccat catggctgat   4320
gcaatgcggc ggctgcatac gcttgatccg gctacctgcc cattcgacca ccaagcgaaa   4380
catcgcatcg agcgagcacg tactcggatg gaagccggtc ttgtcgatca ggatgatctg   4440
gacgaagagc atcaggggct cgcgccagcc gaactgttcg ccaggctcaa ggcgcgcatg   4500
cccgacggcg aggatctcgt cgtgacccat ggcgatgcct gcttgccgaa tatcatggtg   4560
gaaaatggcc gcttttctgg attcatcgac tgtggccggc tgggtgtggc ggaccgctat   4620
caggacatag cgttggctac ccgtgatatt gctgaagagc ttggcggcga atgggctgac   4680
cgcttcctcg tgctttacgg tatcgccgct cccgattcgc agcgcatcgc cttctatcgc   4740
cttcttgacg agttcttctg agcgggactc tggggttcgc gaaatgaccg accaagcgac   4800
gcccaacctg ccatcacgag atttcgattc caccgccgcc ttctatgaaa ggttgggctt   4860
cggaatcgtt ttccgggacg ccggctggat gatcctccag cgcggggatc tcatgctgga   4920
gttcttcgcc caccccaact tgtttattgc agcttataat ggttacaaat aaagcaatag   4980
catcacaaat ttcacaaata aagcattttt ttcactgcat tctagttgtg gtttgtccaa   5040
actcatcaat gtatcttatc atgtctgtat accgtcgacc tctagctaga gcttggcgta   5100
atcatggtca tagctgtttc ctgtgtgaaa ttgttatccg ctcacaattc cacacaacat   5160
acgagccgga agcataaagt gtaaagcctg gggtgcctaa tgagtgagct aactcacatt   5220
aattgcgttg cgctcactgc ccgctttcca gtcgggaaac ctgtcgtgcc agctgcatta   5280
atgaatcggc caacgcgcgg ggagaggcgg tttgcgtatt gggcgctctt ccgcttcctc   5340
gctcactgac tcgctgcgct cggtcgttcg gctgcggcga gcggtatcag ctcactcaaa   5400
ggcggtaata cggttatcca cagaatcagg ggataacgca ggaaagaaca tgtgagcaaa   5460
aggccagcaa aaggccagga accgtaaaaa ggccgcgttg ctggcgtttt tccataggct   5520
ccgcccccct gacgagcatc acaaaaatcg acgctcaagt cagaggtggc gaaacccgac   5580
aggactataa agataccagg cgtttccccc tggaagctcc ctcgtgcgct ctcctgttcc   5640
gaccctgccg cttaccggat acctgtccgc ctttctccct tcgggaagcg tggcgctttc   5700
tcaatgctca cgctgtaggt atctcagttc ggtgtaggtc gttcgctcca agctgggctg   5760
tgtgcacgaa ccccccgttc agcccgaccg ctgcgcctta tccggtaact atcgtcttga   5820
gtccaacccg gtaagacacg acttatcgcc actggcagca gccactggta acaggattag   5880
cagagcgagg tatgtaggcg gtgctacaga gttcttgaag tggtggccta actacggcta   5940
cactagaagg acagtatttg gtatctgcgc tctgctgaag ccagttacct tcggaaaaag   6000
agttggtagc tcttgatccg gcaaacaaac caccgctggt agcggtggtt tttttgtttg   6060
caagcagcag attacgcgca gaaaaaaagg atctcaagaa gatcctttga tcttttctac   6120
ggggtctgac gctcagtgga acgaaaactc acgttaaggg attttggtca tgagattatc   6180
aaaaaggatc ttcacctaga tccttttaaa ttaaaaatga agttttaaat caatctaaag   6240
tatatatgag taaacttggt ctgacagtta ccaatgctta atcagtgagg cacctatctc   6300
agcgatctgt ctatttcgtt catccatagt tgcctgactc cccgtcgtgt agataactac   6360
gatacgggag ggcttaccat ctggccccag tgctgcaatg ataccgcgag acccacgctc   6420
accggctcca gatttatcag caataaacca gccagccgga agggccgagc gcagaagtgg   6480
```

```
tcctgcaact ttatccgcct ccatccagtc tattaattgt tgccgggaag ctagagtaag   6540
tagttcgcca gttaatagtt tgcgcaacgt tgttgccatt gctacaggca tcgtggtgtc   6600
acgctcgtcg tttggtatgg cttcattcag ctccggttcc caacgatcaa ggcgagttac   6660
atgatccccc atgttgtgca aaaaagcggt tagctccttc ggtcctccga tcgttgtcag   6720
aagtaagttg gccgcagtgt tatcactcat ggttatggca gcactgcata attctcttac   6780
tgtcatgcca tccgtaagat gcttttctgt gactggtgag tactcaacca agtcattctg   6840
agaatagtgt atgcggcgac cgagttgctc ttgcccggcg tcaatacggg ataataccgc   6900
gccacatagc agaactttaa aagtgctcat cattggaaaa cgttcttcgg ggcgaaaact   6960
ctcaaggatc ttaccgctgt tgagatccag ttcgatgtaa cccactcgtg cacccaactg   7020
atcttcagca tcttttactt tcaccagcgt ttctgggtga gcaaaaacag gaaggcaaaa   7080
tgccgcaaaa aagggaataa gggcgacacg gaaatgttga atactcatac tcttcctttt   7140
tcaatattat tgaagcattt atcagggtta ttgtctcatg agcggataca tatttgaatg   7200
tatttagaaa aataaacaaa taggggttcc gcgcacattt ccccgaaaag tgccacctga   7260
cgtcgacgga tcgggagatc tcccgatccc ctatggtcga ctctcagtac aatctgctct   7320
gatgccgcat agttaagcca gtatctgctc cctgcttgtg tgttggaggt cgctgagtag   7380
tgcgcgagca aaatttaagc tacaacaagg caaggcttga ccgacaattg catgaagaat   7440
ctgcttagg                                                           7449
```

```
<210> SEQ ID NO 105
<211> LENGTH: 6773
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
```

```
gttaggcgtt ttgcgctgct tcgcgatgta cgggccagat atacgcgttg acattgatta     60
ttgactagtt attaatagta atcaattacg gggtcattag ttcatagccc atatatggag    120
ttccgcgtta cataacttac ggtaaatggc ccgcctggct gaccgcccaa cgacccccgc    180
ccattgacgt caataatgac gtatgttccc atagtaacgc caatagggac tttccattga    240
cgtcaatggg tggagtattt acggtaaact gcccacttgg cagtacatca agtgtatcat    300
atgccaagta cgccccctat tgacgtcaat gacggtaaat ggcccgcctg gcattatgcc    360
cagtacatga ccttatggga ctttcctact tggcagtaca tctacgtatt agtcatcgct    420
attaccatgg tgatgcggtt ttggcagtac atcaatgggc gtggatagcg gtttgactca    480
cggggatttc caagtctcca ccccattgac gtcaatggga gtttgttttg gcaccaaaat    540
caacgggact ttccaaaatg tcgtaacaac tccgccccat tgacgcaaat gggcggtagg    600
cgtgtacggt gggaggtcta tataagcaga gctcgtttag tgaaccgtca gatcgcctgg    660
agacgccatc cacgctgttt tgacctccat agaagacacc gggaccgatc cagcctccgg    720
actctagagg atcgaaccct taagcttgcc accatgtaca ggatgcaact cctgtcttgc    780
attgcactaa gtcttgcact tgtcacgaat tcagacaacg tgctgacaca gagccctgcc    840
agcctggctg tttctctggg acagagagcc accatcagct gcaaggccag ccagagcgtt    900
gactacgacg gcgacagcta catgaactgg tatcagcaga agcccggcca gccacctaag    960
gtgttcatct acgccgccag caacctggaa agcggcatcc ctgccagatt ttctggctct   1020
```

-continued

```
ggcagcggca ccaacttcac cctgaacatt caccccgtgg aagaagagga cgccgccacc   1080
tactactgcc agcagagcaa tgaggacccc tggacatttg gcggaggcac caagctggaa   1140
atcaagcgta cggtggctgc accatctgtc ttcatcttcc cgccatctga tgagcagttg   1200
aaatctggaa ctgcctctgt tgtgtgcctg ctgaataact tctatcccag agaggccaaa   1260
gtacagtgga aggtggataa cgccctccaa tcgggtaact cccaggagag tgtcacagag   1320
caggacagca aggacagcac ctacagcctc agcagcaccc tgacgctgag caaagcagac   1380
tacgagaaac acaaagtcta cgcctgcgaa gtcacccatc agggcctgag ctcgcccgtc   1440
acaaagagct tcaacagggg agagtgttag agggagctag cgtggcatct agacactctc   1500
gagaagggtt cgatccctac cggttagtaa tgagtttgat atctcgacaa tcaacctctg   1560
gattacaaaa tttgtgaaag attgactggt attcttaact atgttgctcc ttttacgcta   1620
tgtggatacg ctgctttaat gcctttgtat catgctattg cttcccgtat ggctttcatt   1680
ttctcctcct tgtataaatc ctggttgctg tctctttatg aggagttgtg gcccgttgtc   1740
aggcaacgtg gcgtggtgtg cactgtgttt gctgacgcaa cccccactgg ttggggcatt   1800
gccaccacct gtcagctcct ttccgggact ttcgctttcc ccctccctat tgccacggcg   1860
gaactcatcg ccgcctgcct tgcccgctgc tggacagggg ctcggctgtt gggcactgac   1920
aattccgtgg tgttgtcggg gaagctgacg tcctttccat ggctgctcgc ctgtgttgcc   1980
acctggattc tgcgcgggac gtccttctgc tacgtccctt cggccctcaa tccagcggac   2040
cttccttccc gcggcctgct gccggctctg cggcctcttc cgcgtcttcg ccttcgccct   2100
cagacgagtc ggatctccct ttgggccgcc tccccgcctg gaaacggggg aggctaactg   2160
aaacacggaa ggagacaata ccggaaggaa cccgcgctat gacggcaata aaaagacaga   2220
ataaaacgca cgggtgttgg gtcgtttgtt cataaacgcg ggttcggtc ccagggctgg    2280
cactctgtcg ataccccacc gagaccccat tggggccaat acgcccgcgt ttcttccttt   2340
tccccacccc acccccaag ttcgggtgaa ggcccagggc tcgcagccaa cgtcggggcg    2400
gcaggccctg ccatagcaga tctgcgcagc tggggctcta gggggtatcc ccacgcgccc   2460
tgtagcggcg cattaagcgc ggcgggtgtg gtggttacgc gcagcgtgac cgctacactt   2520
gccagcgccc tagcgcccgc tcctttcgct ttcttccctt cctttctcgc cacgttcgcc   2580
ggctttcccc gtcaagctct aaatcggggc atccctttag ggttccgatt tagtgcttta   2640
cggcacctcg accccaaaaa acttgattag ggtgatggtt cacgtagtgg gccatcgccc   2700
tgatagacgg tttttcgccc tttgacgttg gagtccacgt tctttaatag tggactcttg   2760
ttccaaactg gaacaacact caaccctatc tcggtctatt cttttgattt ataagggatt   2820
ttggggattt cggcctattg gttaaaaaat gagctgattt aacaaaaatt taacgcgaat   2880
taattctgtg gaatgtgtgt cagttagggt gtggaaagtc cccaggctcc ccagcaggca   2940
gaagtatgca aagcatgcat ctcaattagt cagcaaccag gtgtggaaag tccccaggct   3000
ccccagcagg cagaagtatg caaagcatgc atctcaatta gtcagcaacc atagtcccgc   3060
ccctaactcc gcccatcccg cccctaactc cgcccagttc cgcccattct ccgccccatg   3120
gctgactaat tttttttatt tatgcagagg ccgaggccgc ctctgcctct gagctattcc   3180
agaagtagtg aggaggcttt tttggaggcc taggcttttg caaaaagctc ccgggagctt   3240
gtatatccat tttcggatct gatcaagaga caggatgagg atcgtttcgc atgattgaac   3300
aagatggatt gcacgcaggt tctccggccg cttgggtgga gaggctattc ggctatgact   3360
```

-continued

```
gggcacaaca gacaatcggc tgctctgatg ccgccgtgtt ccggctgtca gcgcaggggc   3420
gcccggttct ttttgtcaag accgacctgt ccggtgccct gaatgaactg caggacgagg   3480
cagcgcggct atcgtggctg gccacgacgg gcgttccttg cgcagctgtg ctcgacgttg   3540
tcactgaagc gggaagggac tggctgctat tgggcgaagt gccggggcag gatctcctgt   3600
catctcacct tgctcctgcc gagaaagtat ccatcatggc tgatgcaatg cggcggctgc   3660
atacgcttga tccggctacc tgcccattcg accaccaagc gaaacatcgc atcgagcgag   3720
cacgtactcg gatggaagcc ggtcttgtcg atcaggatga tctggacgaa gagcatcagg   3780
ggctcgcgcc agccgaactg ttcgccaggc tcaaggcgcg catgcccgac ggcgaggatc   3840
tcgtcgtgac ccatggcgat gcctgcttgc cgaatatcat ggtggaaaat ggccgctttt   3900
ctggattcat cgactgtggc cggctgggtg tggcggaccg ctatcaggac atagcgttgg   3960
ctacccgtga tattgctgaa gagcttggcg gcgaatgggc tgaccgcttc ctcgtgcttt   4020
acggtatcgc cgctcccgat tcgcagcgca tcgccttcta tcgccttctt gacgagttct   4080
tctgagcggg actctggggt tcgcgaaatg accgaccaag cgacgcccaa cctgccatca   4140
cgagatttcg attccaccgc cgccttctat gaaaggttgg gcttcggaat cgttttccgg   4200
gacgccggct ggatgatcct ccagcgcggg gatctcatgc tggagttctt cgcccacccc   4260
aacttgttta ttgcagctta taatggttac aaataaagca atagcatcac aaatttcaca   4320
aataaagcat ttttttcact gcattctagt tgtggtttgt ccaaactcat caatgtatct   4380
tatcatgtct gtataccgtc gacctctagc tagagcttgg cgtaatcatg gtcatagctg   4440
tttcctgtgt gaaattgtta tccgctcaca attccacaca acatacgagc cggaagcata   4500
aagtgtaaag cctggggtgc ctaatgagtg agctaactca cattaattgc gttgcgctca   4560
ctgcccgctt tccagtcggg aaacctgtcg tgccagctgc attaatgaat cggccaacgc   4620
gcggggagag gcggtttgcg tattgggcgc tcttccgctt cctcgctcac tgactcgctg   4680
cgctcggtcg ttcggctgcg gcgagcggta tcagctcact caaaggcggt aatacggtta   4740
tccacagaat caggggataa cgcaggaaag aacatgtgag caaaaggcca gcaaaaggcc   4800
aggaaccgta aaaaggccgc gttgctggcg tttttccata ggctccgccc ccctgacgag   4860
catcacaaaa atcgacgctc aagtcagagg tggcgaaacc cgacaggact ataaagatac   4920
caggcgtttc cccctggaag ctccctcgtg cgctctcctg ttccgaccct gccgcttacc   4980
ggatacctgt ccgcctttct cccttcggga agcgtggcgc tttctcaatg ctcacgctgt   5040
aggtatctca gttcggtgta ggtcgttcgc tccaagctgg gctgtgtgca cgaacccccc   5100
gttcagcccg accgctgcgc cttatccggt aactatcgtc ttgagtccaa cccggtaaga   5160
cacgacttat cgccactggc agcagccact ggtaacagga ttagcagagc gaggtatgta   5220
ggcggtgcta cagagttctt gaagtggtgg cctaactacg gctacactag aaggacagta   5280
tttggtatct gcgctctgct gaagccagtt accttcggaa aaagagttgg tagctcttga   5340
tccggcaaac aaaccaccgc tggtagcggt ggtttttttg tttgcaagca gcagattacg   5400
cgcagaaaaa aaggatctca agaagatcct ttgatctttt ctacggggtc tgacgctcag   5460
tggaacgaaa actcacgtta agggattttg gtcatgagat tatcaaaaag gatcttcacc   5520
tagatccttt taaattaaaa atgaagtttt aaatcaatct aaagtatata tgagtaaact   5580
tggtctgaca gttaccaatg cttaatcagt gaggcaccta tctcagcgat ctgtctattt   5640
cgttcatcca tagttgcctg actccccgtc gtgtagataa ctacgatacg ggagggctta   5700
ccatctggcc ccagtgctgc aatgataccg cgagacccac gctcaccggc tccagattta   5760
```

```
tcagcaataa accagccagc cggaagggcc gagcgcagaa gtggtcctgc aactttatcc   5820

gcctccatcc agtctattaa ttgttgccgg gaagctagag taagtagttc gccagttaat   5880

agtttgcgca acgttgttgc cattgctaca ggcatcgtgg tgtcacgctc gtcgtttggt   5940

atggcttcat tcagctccgg ttcccaacga tcaaggcgag ttacatgatc ccccatgttg   6000

tgcaaaaaag cggttagctc cttcggtcct ccgatcgttg tcagaagtaa gttggccgca   6060

gtgttatcac tcatggttat ggcagcactg cataattctc ttactgtcat gccatccgta   6120

agatgctttt ctgtgactgg tgagtactca accaagtcat tctgagaata gtgtatgcgg   6180

cgaccgagtt gctcttgccc ggcgtcaata cgggataata ccgcgccaca tagcagaact   6240

ttaaaagtgc tcatcattgg aaaacgttct tcggggcgaa aactctcaag gatcttaccg   6300

ctgttgagat ccagttcgat gtaacccact cgtgcaccca actgatcttc agcatctttt   6360

actttcacca gcgtttctgg gtgagcaaaa acaggaaggc aaaatgccgc aaaaaaggga   6420

ataagggcga cacggaaatg ttgaatactc atactcttcc tttttcaata ttattgaagc   6480

atttatcagg gttattgtct catgagcgga tacatatttg aatgtattta gaaaaataaa   6540

caaatagggg ttccgcgcac atttccccga aaagtgccac ctgacgtcga cggatcggga   6600

gatctcccga tcccctatgg tcgactctca gtacaatctg ctctgatgcc gcatagttaa   6660

gccagtatct gctccctgct tgtgtgttgg aggtcgctga gtagtgcgcg agcaaaattt   6720

aagctacaac aaggcaaggc ttgaccgaca attgcatgaa gaatctgctt agg           6773
```

```
<210> SEQ ID NO 106
<211> LENGTH: 7452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
```

```
gttaggcgtt ttgcgctgct tcgcgatgta cgggccagat atacgcgttg acattgatta     60

ttgactagtt attaatagta atcaattacg gggtcattag ttcatagccc atatatggag    120

ttccgcgtta cataacttac ggtaaatggc ccgcctggct gaccgcccaa cgacccccgc    180

ccattgacgt caataatgac gtatgttccc atagtaacgc caatagggac tttccattga    240

cgtcaatggg tggagtattt acggtaaact gcccacttgg cagtacatca agtgtatcat    300

atgccaagta cgccccctat tgacgtcaat gacggtaaat ggcccgcctg gcattatgcc    360

cagtacatga ccttatggga ctttcctact tggcagtaca tctacgtatt agtcatcgct    420

attaccatgg tgatgcggtt ttggcagtac atcaatgggc gtggatagcg gtttgactca    480

cggggatttc caagtctcca ccccattgac gtcaatggga gtttgttttg gcaccaaaat    540

caacgggact ttccaaaatg tcgtaacaac tccgccccat tgacgcaaat gggcggtagg    600

cgtgtacggt gggaggtcta tataagcaga gctcgtttag tgaaccgtca gatcgcctgg    660

agacgccatc cacgctgttt tgacctccat agaagacacc gggaccgatc cagcctccgg    720

actctagagg atcgaaccct taagcttgcc accatgtaca ggatgcaact cctgtcttgc    780

attgcactaa gtcttgcact tgtcacgaat tcggaagtga agctggtgga aagcggcgga    840

ggactggttc aacctggcgg atctctgaag ctgagctgtg ccgccagcgg cttcaccttc    900

agcagataca caatgagctg ggtccgacag acccctgaga agagactgga atgggtcgcc    960

aagatcagaa acgtcggcgg catcacctac tatcccgaca ccgtgaaggg cagattcacc   1020
```

atctccagag acaacgccaa gaacaccctg tacctgcaga tgagcagcct gaagtccgag 1080
gacaccgcca tgtactactg cgccagacac tactacggca gcgaggacta cttcgactat 1140
tggggccagg gcaccacact gaccgttagc tctgctagca ccaagggccc atcggtcttc 1200
cccctggcgc cctgctccag gagcacctcc gagagcacag cggccctggg ctgcctggtc 1260
aaggactact tccccgaacc ggtgacggtg tcgtggaact caggcgctct gaccagcggc 1320
gtgcacacct tcccagctgt cctacagtcc tcaggactct actccctcag cagcgtggtg 1380
accgtgccct ccagcaactt cggcacccag acctacacct gcaacgtaga tcacaagccc 1440
agcaacacca aggtggacaa gacagttgag cgcaaatgtt gtgtcgagtg cccaccgtgc 1500
ccagcaccac ctgtggcagg accgtcagtc ttcctcttcc ccccaaaacc caaggacacc 1560
ctcatgatct cccggacccc tgaggtcacg tgcgtggtgg tggacgtgag ccacgaagac 1620
cccgaggtcc agttcaactg gtacgtggac ggcgtggagg tgcataatgc caagacaaag 1680
ccacgggagg agcagttcaa cagcacgttc cgtgtggtca gcgtcctcac cgttgtgcac 1740
caggactggc tgaacggcaa ggagtacaag tgcaaggtct ccaacaaagg cctcccagcc 1800
cccatcgaga aaaccatctc caaaaccaaa gggcagcccc gagaaccaca ggtgtacacc 1860
ctgcccccat cccgggagga gatgaccaag aaccaggtca gcctgacctg cctggtcaaa 1920
ggcttctacc ccagcgacat cgccgtggag tgggagagca atgggcagcc ggagaacaac 1980
tacaagacca cgcctcccat gctggactcc gacggctcct tcttcctcta cagcaagctc 2040
accgtggaca agagcaggtg gcagcagggg aacgtcttct catgctccgt gatgcatgag 2100
gctctgcaca accactacac gcagaagagc ctctccctgt ctccgggtaa atgacctagc 2160
gtggcatcta gacactctcg agaagggttc gatccctacc ggttagtaat gagtttgata 2220
tctcgacaat caacctctgg attacaaaat ttgtgaaaga ttgactggta ttcttaacta 2280
tgttgctcct tttacgctat gtggatacgc tgctttaatg cctttgtatc atgctattgc 2340
ttcccgtatg gctttcattt tctcctcctt gtataaatcc tggttgctgt ctctttatga 2400
ggagttgtgg cccgttgtca ggcaacgtgg cgtggtgtgc actgtgtttg ctgacgcaac 2460
ccccactggt tggggcattg ccaccacctg tcagctcctt tccgggactt tcgctttccc 2520
cctccctatt gccacggcgg aactcatcgc cgcctgcctt gcccgctgct ggacaggggc 2580
tcggctgttg ggcactgaca attccgtggt gttgtcgggg aagctgacgt cctttccatg 2640
gctgctcgcc tgtgttgcca cctggattct gcgcgggacg tccttctgct acgtcccttc 2700
ggccctcaat ccagcggacc ttccttcccg cggcctgctg ccggctctgc ggcctcttcc 2760
gcgtcttcgc cttcgccctc agacgagtcg gatctccctt tgggccgcct ccccgcctgg 2820
aaacggggga ggctaactga aacacggaag gagacaatac cggaaggaac ccgcgctatg 2880
acggcaataa aaagacagaa taaaacgcac gggtgttggg tcgtttgttc ataaacgcgg 2940
ggttcggtcc cagggctggc actctgtcga taccccaccg agaccccatt ggggccaata 3000
cgcccgcgtt tcttcctttt ccccacccca ccccccaagt tcgggtgaag gcccagggct 3060
cgcagccaac gtcggggcgg caggccctgc catagcagat ctgcgcagct ggggctctag 3120
ggggtatccc cacgcgccct gtagcggcgc attaagcgcg gcgggtgtgg tggttacgcg 3180
cagcgtgacc gctacacttg ccagcgccct agcgcccgct cctttcgctt tcttcccttc 3240
ctttctcgcc acgttcgccg gctttccccg tcaagctcta aatcggggca tccctttagg 3300
gttccgattt agtgctttac ggcacctcga ccccaaaaaa cttgattagg gtgatggttc 3360

-continued

```
acgtagtggg ccatcgccct gatagacggt ttttcgccct ttgacgttgg agtccacgtt   3420

ctttaatagt ggactcttgt tccaaactgg aacaacactc aaccctatct cggtctattc   3480

ttttgattta taagggattt tggggatttc ggcctattgg ttaaaaaatg agctgattta   3540

acaaaaattt aacgcgaatt aattctgtgg aatgtgtgtc agttagggtg tggaaagtcc   3600

ccaggctccc cagcaggcag aagtatgcaa agcatgcatc tcaattagtc agcaaccagg   3660

tgtggaaagt ccccaggctc cccagcaggc agaagtatgc aaagcatgca tctcaattag   3720

tcagcaacca tagtcccgcc cctaactccg cccatcccgc ccctaactcc gcccagttcc   3780

gcccattctc cgccccatgg ctgactaatt ttttttattt atgcagaggc cgaggccgcc   3840

tctgcctctg agctattcca gaagtagtga ggaggctttt ttggaggcct aggcttttgc   3900

aaaaagctcc cgggagcttg tatatccatt ttcggatctg atcaagagac aggatgagga   3960

tcgtttcgca tgattgaaca agatggattg cacgcaggtt ctccggccgc ttgggtggag   4020

aggctattcg gctatgactg ggcacaacag acaatcggct gctctgatgc cgccgtgttc   4080

cggctgtcag cgcaggggcg cccggttctt tttgtcaaga ccgacctgtc cggtgccctg   4140

aatgaactgc aggacgaggc agcgcggcta tcgtggctgg ccacgacggg cgttccttgc   4200

gcagctgtgc tcgacgttgt cactgaagcg ggaagggact ggctgctatt gggcgaagtg   4260

ccggggcagg atctcctgtc atctcacctt gctcctgccg agaaagtatc catcatggct   4320

gatgcaatgc ggcggctgca tacgcttgat ccggctacct gcccattcga ccaccaagcg   4380

aaacatcgca tcgagcgagc acgtactcgg atggaagccg gtcttgtcga tcaggatgat   4440

ctggacgaag agcatcaggg gctcgcgcca gccgaactgt tcgccaggct caaggcgcgc   4500

atgcccgacg gcgaggatct cgtcgtgacc catggcgatg cctgcttgcc gaatatcatg   4560

gtggaaaatg gccgcttttc tggattcatc gactgtggcc ggctgggtgt ggcggaccgc   4620

tatcaggaca tagcgttggc tacccgtgat attgctgaag agcttggcgg cgaatgggct   4680

gaccgcttcc tcgtgcttta cggtatcgcc gctcccgatt cgcagcgcat cgccttctat   4740

cgccttcttg acgagttctt ctgagcggga ctctggggtt cgcgaaatga ccgaccaagc   4800

gacgcccaac ctgccatcac gagatttcga ttccaccgcc gccttctatg aaaggttggg   4860

cttcggaatc gttttccggg acgccggctg gatgatcctc cagcgcgggg atctcatgct   4920

ggagttcttc gcccacccca acttgtttat tgcagcttat aatggttaca aataaagcaa   4980

tagcatcaca aatttcacaa ataaagcatt tttttcactg cattctagtt gtggtttgtc   5040

caaactcatc aatgtatctt atcatgtctg tataccgtcg acctctagct agagcttggc   5100

gtaatcatgg tcatagctgt ttcctgtgtg aaattgttat ccgctcacaa ttccacacaa   5160

catacgagcc ggaagcataa agtgtaaagc ctggggtgcc taatgagtga gctaactcac   5220

attaattgcg ttgcgctcac tgcccgcttt ccagtcggga aacctgtcgt gccagctgca   5280

ttaatgaatc ggccaacgcg cggggagagg cggtttgcgt attgggcgct cttccgcttc   5340

ctcgctcact gactcgctgc gctcggtcgt tcggctgcgg cgagcggtat cagctcactc   5400

aaaggcggta atacggttat ccacagaatc aggggataac gcaggaaaga acatgtgagc   5460

aaaaggccag caaaaggcca ggaaccgtaa aaaggccgcg ttgctggcgt ttttccatag   5520

gctccgcccc cctgacgagc atcacaaaaa tcgacgctca agtcagaggt ggcgaaaccc   5580

gacaggacta taaagatacc aggcgtttcc ccctggaagc tccctcgtgc gctctcctgt   5640

tccgaccctg ccgcttaccg gatacctgtc cgcctttctc ccttcgggaa gcgtggcgct   5700

ttctcaatgc tcacgctgta ggtatctcag ttcggtgtag gtcgttcgct ccaagctggg   5760
```

ctgtgtgcac gaacccccg ttcagcccga ccgctgcgcc ttatccggta actatcgtct 5820
tgagtccaac ccggtaagac acgacttatc gccactggca gcagccactg gtaacaggat 5880
tagcagagcg aggtatgtag gcggtgctac agagttcttg aagtggtggc ctaactacgg 5940
ctacactaga aggacagtat ttggtatctg cgctctgctg aagccagtta ccttcggaaa 6000
aagagttggt agctcttgat ccggcaaaca aaccaccgct ggtagcggtg gtttttttgt 6060
ttgcaagcag cagattacgc gcagaaaaaa aggatctcaa gaagatcctt tgatcttttc 6120
tacggggtct gacgctcagt ggaacgaaaa ctcacgttaa gggattttgg tcatgagatt 6180
atcaaaaagg atcttcacct agatcctttt aaattaaaaa tgaagtttta aatcaatcta 6240
aagtatatat gagtaaactt ggtctgacag ttaccaatgc ttaatcagtg aggcacctat 6300
ctcagcgatc tgtctatttc gttcatccat agttgcctga ctccccgtcg tgtagataac 6360
tacgatacgg gagggcttac catctggccc cagtgctgca atgataccgc gagacccacg 6420
ctcaccggct ccagatttat cagcaataaa ccagccagcc ggaagggccg agcgcagaag 6480
tggtcctgca actttatccg cctccatcca gtctattaat tgttgccggg aagctagagt 6540
aagtagttcg ccagttaata gtttgcgcaa cgttgttgcc attgctacag gcatcgtggt 6600
gtcacgctcg tcgtttggta tggcttcatt cagctccggt tcccaacgat caaggcgagt 6660
tacatgatcc cccatgttgt gcaaaaaagc ggttagctcc ttcggtcctc cgatcgttgt 6720
cagaagtaag ttggccgcag tgttatcact catggttatg gcagcactgc ataattctct 6780
tactgtcatg ccatccgtaa gatgcttttc tgtgactggt gagtactcaa ccaagtcatt 6840
ctgagaatag tgtatgcggc gaccgagttg ctcttgcccg gcgtcaatac gggataatac 6900
cgcgccacat agcagaactt taaaagtgct catcattgga aaacgttctt cggggcgaaa 6960
actctcaagg atcttaccgc tgttgagatc cagttcgatg taacccactc gtgcacccaa 7020
ctgatcttca gcatctttta ctttcaccag cgtttctggg tgagcaaaaa caggaaggca 7080
aaatgccgca aaaaagggaa taagggcgac acggaaatgt tgaatactca tactcttcct 7140
ttttcaatat tattgaagca tttatcaggg ttattgtctc atgagcggat acatatttga 7200
atgtatttag aaaaataaac aaataggggt tccgcgcaca tttccccgaa aagtgccacc 7260
tgacgtcgac ggatcgggag atctcccgat cccctatggt cgactctcag tacaatctgc 7320
tctgatgccg catagttaag ccagtatctg ctccctgctt gtgtgttgga ggtcgctgag 7380
tagtgcgcga gcaaaattta agctacaaca aggcaaggct tgaccgacaa ttgcatgaag 7440
aatctgctta gg 7452

<210> SEQ ID NO 107
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 107
atggaggacg tgtgc 15

<210> SEQ ID NO 108
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 108
atggaggacg tgtgc 15

<210> SEQ ID NO 109
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 109
atggaggacg tgtgc 15

<210> SEQ ID NO 110
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 110
gagctgcggg tgcgc 15

<210> SEQ ID NO 111
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 111
gagctgcggg tgagc 15

<210> SEQ ID NO 112
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 112
gagctgcggg tgagc 15

<210> SEQ ID NO 113
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 113
gacctgcaga agcgc 15

<210> SEQ ID NO 114
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide -continued

```
<400> SEQUENCE: 114

gacctgcaga agcgc                                                    15


<210> SEQ ID NO 115
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: a, c, t, g, unknown or other

<400> SEQUENCE: 115

gacctgcana agcgc                                                    15
```

ANTI-ApoE ANTIBODIES AND POLYNUCLEOTIDES THEREOF

CLAIM OF PRIORITY

This application is a § 371 National Stage Application of PCT/US2020/034978, filed May 28, 2020, which claims the benefit of U.S. Provisional Application No. 62/853,676, filed May 28, 2019, and U.S. Provisional Application No. 62/873,019, filed Jul. 11, 2019. The entire contents of the foregoing are incorporated by reference herein.

FEDERALLY SPONSORED RESEARCH OR DEVELOPMENT

This invention was made with Government support under Grant No. OD019833 awarded by the National Institutes of Health, Grant Nos. AG054671, AG031581, and AG19610 awarded by the National Institute on Aging, and Grant Nos. NS100121 and NS110048 awarded by the National Institute of Neurological Disorders and Stroke. The Government has certain rights in the invention.

SEQUENCE LISTING

This application contains a Sequence Listing that has been submitted electronically as an ASCII text file named '29539_0386US1_Sequence_Listing.txt'. The ASCII text file, created on Nov. 23, 2021, is 202 kilobytes in size. The material in the ASCII text filed is hereby incorporated by reference in its entirety.

TECHNICAL FIELD

Described herein are methods and compositions for preventing or treating cognitive decline associated with dementia and/or mild cognitive impairment by modulating the heparan sulfate proteoglycans (HSPG)/glycosaminoglycan (GAG) heparin-binding affinity of Apolipoprotein E (ApoE).

BACKGROUND

Alzheimer's disease (AD) is a chronic neurodegenerative disease that usually starts slowly and gradually worsens over time. It is the cause of 60-70% of cases of dementia. The disease process is associated with plaques and neurofibrillary tangles in the brain. There are presently no treatments to stop or reverse its progression, though some may temporarily improve symptoms. The accumulation, aggregation and deposition of amyloid-β (Aβ) peptides in the brain are central to the pathogenesis of Alzheimer's disease (AD). Growing evidence has demonstrated that ApoE strongly influences AD pathogenesis by controlling Aβ aggregation and metabolism (Fu et al., Mol Neurodegener 11:37, 2016). APOE impacts amyloid production, aggregation, and clearance, is a component of amyloid plaques, and exacerbates tau-mediated neurodegeneration. ApoE is 299 amino acids long and is polymorphic with three major alleles (epsilon 2, epsilon 3, and epsilon 4) which differ from each other by only one or two amino acids at positions 112 and 158: ApoE2 (cys112, cys158), ApoE3 (cys112, arg158), and ApoE4 (arg112, arg158). Accordingly, there is a need of therapeutics targeting and modulating the function of ApoE proteins for treating or preventing AD and cognitive decline associated with dementia or mild cognitive impairment.

SUMMARY

In one aspect, this disclosure features an isolated monoclonal antibody that specifically binds to one or more (e.g. 1, 2, 3 or 4) HSPG-binding sites or one or more (e.g. 1, 2, 3, or 4) sites of allosteric modulation of HSPG binding of a wild type or mutant Apolipoprotein E (ApoE). In some embodiments, the antibody binds to a polypeptide having an amino acid sequence at least 95% (e.g. 96%, 97%, 98%, 99% or 100%) identical to TEELRVRLASHLRK (SEQ ID NO:3). In some embodiments, the antibody binds to a polypeptide having an amino acid sequence at least 95% (e.g. 96%, 97%, 98%, 99% or 100%) identical to TEELRVSLASHLRK (SEQ ID NO:2). In some embodiments, the antibody binds to one or more (e.g. 1, 2, 3 or 4) HSPG-binding sites of a wild type or mutant ApoE2, ApoE3, or ApoE4.

In some embodiments, the antibody competes with and/or binds the same epitope as a reference anti-ApoE antibody comprising a heavy chain variable region (VH) and a light chain variable region (VL), wherein the VH and VL of the reference antibody comprise: (i) the amino acid sequence set forth in SEQ ID NO: 13 and the amino acid sequence set forth in SEQ ID NO:12, respectively; (ii) the amino acid sequence set forth in SEQ ID NO:23 and the amino acid sequence set forth in SEQ ID NO: 22, respectively; (iii) the amino acid sequence set forth in SEQ ID NO:33 and the amino acid sequence set forth in SEQ ID NO:32, respectively; or (iv) the amino acid sequence set forth in SEQ ID NO:43 and the amino acid sequence set forth in SEQ ID NO: 42, respectively. In some embodiments of any of the antibodies described herein, the antibody competes with and/or binds the same epitope as a reference anti-ApoE antibody comprising a heavy chain and a light chain, wherein the heavy chain and light chain of the reference antibody comprise the amino acid sequence set forth in SEQ ID NO: 53 and the amino acid sequence set forth in SEQ ID NO: 52.

In another aspect, provided herein are anti-ApoE antibodies comprising a VH comprising VHCDR1, VHCDR2, and VHCDR3, and a VL comprising VLCDR1, VLCDR2, and VLCDR3, wherein VHCDR1, VHCDR2, VHCDR3, VLCDR1, VLCDR2, and VLCDR3 comprise: (i) SEQ ID Nos: 7, 8, 9, 4, 5, 6, respectively; (ii) SEQ ID Nos: 17, 18, 19, 14, 15, 16, respectively; (iii) SEQ ID Nos: 27, 28, 29, 24, 25, 26, respectively; (iv) SEQ ID Nos: 37, 38, 39, 34, 35, 36, respectively; or (v) SEQ ID Nos: 47, 48, 49, 44, 45, 46, respectively. In some embodiments of any of the antibodies described herein, (i) the VH and the VL comprise an amino acid sequence that is at least 75%, 80%, 85%, 90%, 95%, or 100% identical to the amino acid sequences set forth in SEQ ID NOs: 13 and 12, respectively; (ii) the VH and the VL comprise an amino acid sequence that is at least 75%, 80%, 85%, 90%, 95%, or 100% identical to the amino acid sequences set forth in SEQ ID NOs: 23 and 22, respectively; (iii) the VH and the VL comprise an amino acid sequence that is at least 75%, 80%, 85%, 90%, 95%, or 100% identical to the amino acid sequences set forth in SEQ ID NOs: 33 and 32, respectively; or (iv) the VH and the VL comprise an amino acid sequence that is at least 75%, 80%, 85%, 90%, 95%, or 100% identical to the amino acid sequences set forth in SEQ ID NOs: 43 and 42, respectively. In some embodiments of any of the antibodies described herein, the antibody comprises a heavy chain and a light chain comprising an amino acid sequence that is at least 70%, 75%, 80%, 85%, 90%, 95%, or 100% identical to the amino acid sequence set forth in SEQ ID Nos: 53 and 52, respectively. In some embodiments, the antibody includes a mouse IgG1, IgG2a, IgG2b, IgG2c, or IgG3 heavy chain constant region. In some embodiments, the antibody includes a human IgG1, IgG2, IgG3, or IgG4 heavy chain constant region. In some embodiments, the antibody includes a human kappa or human lambda light chain constant region. In some embodiments, the antibody is a whole antibody, a single domain antibody, a humanized antibody, a chimeric antibody, a bispecific antibody, a Fv, a scFv, an sc(Fv)2, a diabody, an Fab, or an F(ab')2. In some embodiments, the antibody further includes a half-life extending moiety. In some embodiments, the antibody further includes a blood-brain barrier penetrating moiety. In some embodiments, the antibody further includes a detectable label. In some embodiments, provided herein are pharmaceutical compositions comprising any of the antibodies described herein. In some embodiments, provided herein are polynucleotide or polynucleotides encoding any of the antibodies described herein. In some embodiments, provided herein are vector or vectors comprising the polynucleotide or polynucleotides described herein. In some embodiments provided herein are host cells comprising the polynucleotide or polynucleotides described herein, or the vector or vectors described herein. In another aspect, provided herein are methods of making an anti-ApoE antibody, the methods include: (a) culturing any of the host cells described herein under conditions that permit expression of the antibody; and (b) isolating the antibody. In some embodiments, the methods further include formulating the antibody as a sterile formulation suitable for administration to a human.

In another aspect, provided herein is an Fc-fusion protein that includes: a HSPG-binding domain of a wild type ApoE or mutant ApoE comprising an amino acid sequence at least 95% identical to an amino acid sequence selected from the group consisting of STEELRVRLASHLRKLRKRLLRDADDLQK (SEQ ID NO:57), STEELRVSLASHLRKLRKRLLRDADDLQK (SEQ ID NO:58), RLVQYRGEVQAMLGQSTEELRVRLASHLRKL (SEQ ID NO:59), and RLVQYRGEVQAMLGQSTEELRVSLASHLRKL (SEQ ID NO:60). In some embodiments, the Fc-fusion protein includes an Fc region of a human antibody. In some embodiments, the human antibody is selected from the group consisting of a human IgG1, IgG2, IgG3 and IgG4 molecule. In some embodiments, provided herein are pharmaceutical compositions comprising any of the Fc-fusion proteins described herein. In some embodiments, provided herein are polynucleotide or polynucleotides encoding the Fc-fusion proteins described herein. In some embodiments, provided herein are vector or vectors comprising any of the polynucleotide or polynucleotides described herein. In some embodiments, provided herein are host cells comprising the polynucleotide or polynucleotides described herein, or the vector or vectors described herein.

In another aspect, provided herein are pharmaceutical composition for eliciting an immune response that include: (i) a HSPG-binding domain of a wild type ApoE or mutant ApoE comprising an amino acid sequence at least 95% identical to an amino acid sequence selected from the group consisting of STEELRVRLASHLRKLRKRLLRDADDLQK (SEQ ID NO:57), STEELRVSLASHLRKLRKRLLRDADDLQK (SEQ ID NO:58), RLVQYRGEVQAMLGQSTEELRVRLASHLRKL (SEQ ID NO:59), and RLVQYRGEVQAMLGQSTEELRVSLASHLRKL (SEQ ID NO:60); and (ii) a pharmaceutically acceptable adjuvant.

In another aspect, provided herein is a pharmaceutical composition comprising a human cell expressing any of the antibodies described herein or any of the Fc-fusion proteins described herein.

In another aspect, provided herein is a method of improving, slowing down, delaying the onset of, preventing or reversing cognitive decline associated with dementia and/or mild cognitive impairment and/or neurodegeneration in a human subject in need thereof, comprising administering to the human subject a therapeutically effective amount of any of the antibody, the Fc-fusion protein, or the pharmaceutical compositions described herein.

In another aspect, provided herein is a method of improving, slowing down, delaying the onset, preventing or reversing cognitive decline associated with dementia and/or mild cognitive impairment and/or neurodegeneration in a human subject in need thereof, the method comprising administering to said subject: (i) a viral vector comprising a nucleotide sequence encoding a gRNA molecule comprising a targeting domain complementary with a target domain from the APOE gene; (ii) a viral vector comprising a nucleotide sequence encoding a Cas9 molecule; and (iii) a viral vector comprising a template nucleic acid, wherein the template nucleic acid comprises an Adenine to replace the Cytosine at position 19:g.45412013C>A in the APOE gene, wherein said administration results in the generation of one or more ApoE R136S alleles in one or more cells of said subject. In some embodiments, the targeting domain of the gRNA molecule includes a sequence that is the same as, or differs by no more than 3 nucleotides from, a sequence from Table 7.

As used herein, "prevent" means to reduce risk of developing the disorder.

In some embodiments, the human subject is diagnosed with or is at risk for developing Alzheimer's disease. In some embodiments, the human subject carries one or more copies of the APOE4 allele. In some embodiments, the human subject carries one or more mutations in at least one gene selected from the group consisting of: APP, PSEN1, and PSEN2. In some embodiments, the human subject carries one or more mutations in additional genes that cause autosomal-dominant Alzheimer's disease (e.g. those described in Bateman et al., *Alzheimer's Research & Therapy* 3 (1): 1, 2011). In some embodiments, the human subject carries all or a portion of a third copy of chromosome 21. In some embodiments, the human subject is diagnosed with Alzheimer's disease by established biomarkers, such as those obtained via brain imaging, or blood or CSF samples. In some embodiments, the human subject is over the age of 50 (e.g. over the age of 55, 60, 65, 70, 75, 80, 85, 90, or 95).

In some embodiments, the human subject is diagnosed with or is at risk of developing a disorder selected from the group consisting of: vascular cognitive impairment, vascular dementia, cerebral autosomal dominant arteriopathy with subcortical infarcts and leukoencephalopathy (CADASIL), cerebral autosomal recessive arteriopathy with subcortical infarcts and leukoencephalopathy (CARASIL), Lewy body dementia, frontotemporal dementia, amyotrophic lateral sclerosis, multiple sclerosis, Parkinson's disease, Huntington's disease, neurodegenerative diseases, cerebrovascular diseases, brain injury, chronic traumatic encephalopathy, tauopathies, amyloidopathies, synucleinopathies, Creutzfeldt-Jakob disease, retinal degeneration, glaucoma, retinal injury, optic nerve degeneration, and aging.

In yet another aspect, provided herein is a method of identifying a human subject less susceptible to developing an early onset neurodegenerative disease, comprising: obtaining a biological sample from the subject; detecting the presence of at least one mutant allele of APOE3, or the presence of a mutant ApoE3 gene product, in the biological sample; and identifying a subject as being less susceptible to developing an early onset neurodegenerative disease, based on the presence of a mutant ApoE3 allele or gene product in the biological sample. In some embodiments, the biological sample is blood, cerebrospinal fluid, saliva, urine, tears, vitreous humor, aqueous humor, or a tissue specimen. In some embodiments, the neurodegenerative disease is Alzheimer's disease, Parkinson's disease, Huntington's disease, amyotrophic lateral sclerosis, retinal degeneration, or glaucoma. In some embodiments, the retinal degeneration is age-related macular degeneration. In some embodiments, the detecting comprises determining the sequence of an APOE3 allele in the subject. In some embodiments, the detecting comprises determining the presence or absence of an APOE3 sequence that encodes an ApoE3 protein with a mutation at R136 as compared to a wild type ApoE3 protein. In some embodiments, the mutation at R136 is R136S, R136H, or R136C. In some embodiments of any of the methods of identifying a human subject less susceptible to developing an early onset neurodegenerative disease described herein, the methods further include selecting a subject for inclusion in a clinical trial, and optionally administering an experimental treatment, or excluding the subject from the clinical trial, if the subject does not have a mutant APOE3 allele. In some embodiments of any of the methods of identifying a human subject less susceptible to developing an early onset neurodegenerative disease described herein, the methods further include selecting a subject for inclusion in a clinical trial, and optionally administering an experimental treatment, or excluding the subject from the clinical trial, if the subject has a mutant APOE3 allele.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 13A shows the amount of ApoE3 in various fractions in the absence of the ApoE3 antibody. FIG. 13B shows the amount of ApoE3 in various fractions in the presence of the ApoE3 antibody.

FIG. 17A shows a model of the wild type ApoE fragment containing amino acids 129-157 interacting with heparin. FIG. 17B shows a model of the fragment of ApoE R136S that contains amino acids 129-157 interacting with heparin. FIG. 17C shows a model of the wild type ApoE fragment containing amino acids 114-144 interacting with heparin. FIG. 17D shows a model of the fragment of ApoE R136S that contains amino acids 114-144 interacting with heparin.

DETAILED DESCRIPTION

Figure 1:
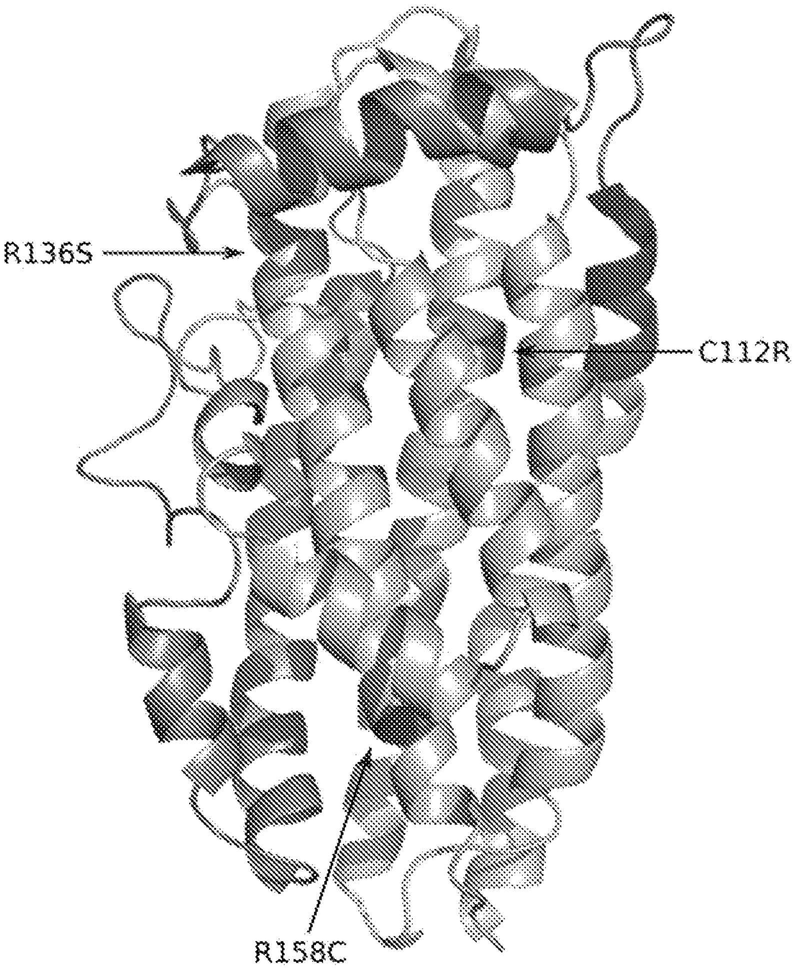
FIG. 1 shows a model of the structure of the wild-type APOE3 protein. N-terminal (residues 1-191) and C-terminal (residues 201-299) domains are shown. The amino acid positions for APOE4 (C112R), APOE3ch (R136S) and APOE2 (R158C) variants are shown.

The present disclosure uncovers that homozygosity for APOE3ch (having two copies of the APOE3 Christchurch (R136S) mutation) is associated with a profound resistance to the clinical onset of Alzheimer's disease, and that the R136S mutation significantly diminishes the ability of ApoE to bind heparan sulfate proteoglycans (HSPG)/heparin. Accordingly, the present disclosure is related to antibodies that bind to wild type ApoE and/or ApoE isoform(s) containing the R136S mutation (e.g. antibodies that block the interaction and/or reduces binding between ApoE and HSPG/GAG/heparin). Fusion proteins containing peptide fragments (e.g. HSPG/GAG/heparin-binding domain) of wild type and mutant ApoE containing the R136S mutation are also contemplated. These proteins may be administered via human cells expressing such compositions. The present disclosure is further related to small molecules that block the interaction between ApoE and HSPG/heparin, and methods of screening for small molecules of the same. Also provided are compositions and methods of editing the ApoE locus with a genome editing system. The antibodies, fusion proteins, small molecules, and genome editing systems described herein are useful in the treatment or prevention of cognitive decline associated with dementia and/or mild cognitive impairment (MCI) and/or neurodegeneration, e.g. Alzheimer's disease, vascular dementia, Lewy body dementia, frontotemporal dementia, Parkinson's disease, or Huntington's disease. The antibodies, fusion proteins, small molecules, and genome editing systems described herein are also useful in the treatment or prevention of neurodegenerative diseases, cerebrovascular conditions, brain injuries, retinal degeneration, optic nerve degeneration, or retinal injury.

Apolipoprotein E (ApoE)

Apolipoprotein E variants are the major genetic modifier of AD contributing to the susceptibility to late-onset AD. APOE4 allele leads to a change of cysteine to arginine at position 112 and is associated with a 5 fold increase in AD risk in single allele carriers, reaching a 20 fold increase in homozygote carriers. APOE2 leads to an amino acid change of arginine to cysteine at position 158 and is protective for AD whereas the APOE3 allele is thought to be neutral (Corder et al., Nat Genet (7) 180-184, 1994; Hauser et al., Cure Alzheimer Res (10); 808-817, 2013). APOE impacts amyloid production, aggregation, and clearance, is a component of amyloid plaques, and exacerbates tau-mediated neurodegeneration. APOE alleles also regulate lipid metabolism and cardiovascular risk. About 5-10% of APOE2 homozygote individuals develop hyperlipoproteinemia type III (HLP III), whereas other APOE rare variants are linked to autosomal dominant HLP III. HLP III is characterized by increased plasma cholesterol and triglycerides levels and by the presence of tuberous or striated palmar xanthomas. The mechanisms by which APOE alleles modify AD risk and cause HLP III are not completely understood. Salient APOE properties impacted by specific mutations include differences in 1) binding affinities to lipids and the LDL receptor; 2) nature of interdomain interactions between its N-terminus (amino acids 1 to 199) and C-terminus domains (216 to 299); and, 3) ability to form homo-oligomers mediated by the C-terminus domain (Frieden et al., PNAS (109):8913-8918, 2012; Georgiadou et al., PLOS One (6)e27037, 2011; Lalazar et al., J Biol Chem (263)3542-3545, 1988).

Heparan sulfate (HS) is a linear polysaccharide found in all animal tissues, which occurs as a proteoglycan (HSPG) in which two or three HS chains are attached in close proximity to cell surface or extracellular matrix proteins. HSPG moieties are present in hundreds of proteins located in the plasma membrane and in the extracellular matrix. Protein-protein interactions mediated via HSPG play a critical role in a multitude of processes relevant to Alzheimer's pathology including amyloid and tau pathology. Heparan sulfate is a member of the glycosaminoglycan family of carbohydrates and is very closely related in structure to heparin. Both consist of a variably sulfated repeating disaccharide unit. Heparan sulfate binds with a large number of extracellular proteins. These are often collectively called the "heparin interactome" or "heparin-binding proteins", because they are isolated by affinity chromatography on the related polysaccharide heparin.

An exemplary amino acid sequence of the human ApoE3 protein (Uniprot Accession No. P02649) is shown below:

(SEQ ID NO: 1)

KVEQAVETEPEPELRQQTEWQSGQRWELALGRFWDYLRWVQTLSEQVQEE

LLSSQVTQELRALMDETMKELKAYKSELEEQLTPVAEETRARLSKELQAA

QARLGADMEDVCGRLVQYRGEVQAMLGQSTEELRVRLASHLRKLRKRLLR

DADDLQKRLAVYQAGAREGAERGLSAIRERLGPLVEQGRVRAATVGSLAG

QPLQERAQAWGERLRARMEEMGSRTRDRLDEVKEQVAEVRAKLEEQAQQI

RLQAEAFQARLKSWEEPLVEDMQRQWAGLVEKVQAAVGTSAAPVPSDNH

At least two HSPG/heparin-binding domains have been identified in human ApoE, one located in the N-terminal domain and one in the C-terminal domain (Weisgraber et al. J Biol Chem, 261 (5): 2068-76, 1986; Saito et al., J Biol Chem, 278 (17): 14782-7, 2003). The HSPG/heparin-binding domain near arginine 136 (R136) (the N-terminal HSPG/heparin-binding domain) is functional in the full-length lipidated and delipidated ApoE, while the HSPG/heparin-binding domain in the C-terminal domain is functional only in the absence of the N-terminal domain and in delipidated ApoE. The N-terminal HSPG/heparin-binding domain is well-characterized, and comprises the amino acid residues 142 to 147 of SEQ ID NO: 1 (bolded). The C-terminal HSPG/heparin-binding domain is less well-characterized, and comprises the lysine (K) at position 233 and other charged amino acids in the vicinity including amino acid residues 211 to 218 and 243 to 272 of SEQ ID NO: 1. The present inventors show that the arginine at position 136 of ApoE plays a critical role in heparin binding of ApoE. Without wishing to be bound by theory, a potential mechanism is the allosteric modulation of heparin binding mediated by the arginine at position 136. Allosteric modulation as used herein is related to the modulation of ligand binding through the binding of allosteric modulators at one or more sites of allosteric modulation, which may be different from the binding site(s) of the ligand. In some embodiments, the one or more sites of allosteric modulation for ApoE and HSPG/heparin binding comprise the arginine at position 136 of ApoE as shown in SEQ ID NO: 1. "HSPG/heparin-binding domain(s)", "HSPG/heparin-binding site(s)", "HSPG-binding domain(s)", and "HSPG-binding site(s)" are used interchangeably herein.

Anti-ApoE Antibodies

Provided are anti-ApoE antibodies that bind to a wild type or a mutant ApoE protein (e.g., a human ApoE protein). In some instances, the antibodies described herein bind to a wild type ApoE protein (e.g. ApoE2, ApoE3 or ApoE4), but not to a mutant ApoE protein (e.g. ApoEch). In some instances, the antibodies described herein bind to a mutant ApoE protein (e.g. ApoEch), but not to a wild type ApoE protein (e.g. ApoE2, ApoE3 or ApoE4). In some instances, the antibodies described herein bind to both a mutant ApoE protein (e.g. ApoEch), and a wild type ApoE protein (e.g. ApoE2, ApoE3 or ApoE4).

In some instances, the antibodies provided herein block the interaction between a wild type ApoE protein (e.g. ApoE2, ApoE3 or ApoE4) and HSPG. The antibodies provided herein may reduce or modulate the binding affinity of an ApoE protein (e.g. ApoE2, ApoE3 or ApoE4) to HSPG. In some instances, the antibodies provided herein bind to the HSPG-binding domain of a wild type ApoE protein. In some instances, the antibodies provided herein bind to one or more sites of allosteric modulation of HSPG/ApoE binding (e.g., amino acid position 136 of ApoE). In some instances, the antibodies described herein reduces fibril formation and/or amyloid oligomerization.

In some instances, the antibodies provided herein bind to an amino acid sequence in a wild type or mutant ApoE that comprises or consists of TEELRVSLASHLRK (SEQ ID NO:2). In some instances, the antibodies provided herein bind to an amino acid sequence in a wild type or mutant ApoE that comprises or consists of TEELRVRLASHLRK (SEQ ID NO:3). In some instances, the amino acid sequence TEELRVSLASHLRK (SEQ ID NO:2) comprises or consists of an epitope for the antibodies provided herein. In some instances, the amino acid sequence TEELRVRLASHLRK (SEQ ID NO:3) comprises or consists of an epitope for the antibodies provided herein. Variants of these sequences can also be used, e.g., those that are at least 80%, 85%, 90%, or 95% identical to these sequences.

Calculations of "identity" between two sequences can be performed as follows. The sequences are aligned for optimal comparison purposes (e.g., gaps can be introduced in one or both of a first and a second nucleic acid sequence for optimal alignment and non-identical sequences can be disregarded for comparison purposes). The length of a sequence aligned for comparison purposes is at least 70% (e.g., at least 80%, 90% or 100%) of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two nucleotide sequences is determined using the Needleman and Wunsch ((1970) J. Mol. Biol. 48:444-453) algorithm, which has been incorporated into the GAP program in the GCG software package (available at gcg.com), using either a Blossum 62 matrix, a PAM250 matrix, a NWSgapdna.CMP matrix. In some embodiments, the percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

Usage of the term "antibody" in this disclosure is meant to cover a whole antibody (as opposed to a minibody or antibody fragment), a bispecific antibody, a tertravalent antibody, a multispecific antibody, a minibody, and antibody fragments. In some instances, the anti-ApoE antibody of this disclosure is a whole antibody. In some instances, the anti-ApoE antibody of this disclosure is a chimeric, human, or humanized antibody. In certain instances, the heavy chain constant region of the anti-ApoE antibody is a human IgG1, human IgG2, human IgG3, or human IgG4 constant region. In certain instances, the light constant region is a human kappa constant region. In other instances, the light constant region is a human lambda constant region. In some instances, the antibodies of this disclosure are designed to have low effector functionality (e.g., by Fc modifications such as N297Q, T299A, etc. See, also, Wang, X., Mathieu, M. & Brezski, R. J. *Protein Cell* (2018) 9: 63. doi.org/10.1007/s13238-017-0473-8 (incorporated by reference herein)). In some cases, the Fc moiety of the antibody is a hIgG1 Fc, a hIgG2 Fc, a hIgG3 Fc, a hIgG4 Fc, a hIgG1agly Fc, a hIgG2 SAA Fc, a hIgG4 (S228P) Fc, or a hIgG4 (S228P)/G1 agly Fc (in this format—that minimizes effector function—the CH1 and CH2 domains are IgG4 with a 'fixed' hinge (S228P) and is aglycosylated. The CH3 domain is hIgG1, or a hIgG4 (S228P) agly Fc). In one case, the antibody has one of the following three scaffolds with reduced effector function: hIgG1 agly (N297Q); hIgG2 SAA (see, Vafa et al. *Methods,* 65(1):114-26 (2014); and hIgG4P/G1 agly (see, US 2012/0100140 A1).

In some embodiments, an antibody or ApoE-binding fragment thereof described herein demonstrates the binding characteristics and/or biological properties as outlined for the antibodies 1H4-2, 7C11-1, 19G10-2, 23B2 (1343), 2H79-1, 30E1-2, 16H8, 25F1-2, and 29G10-1 illustrated in the Examples section below.

In some embodiments, the present disclosure provides an antibody that binds to wild type human ApoE or a portion thereof and has one or more of the following properties: (i) binds with high affinity of KD≤20 nM to wild type human ApoE; (ii) competes with wild type human ApoE for binding to heparin; and (iii) reduces Paired Helical Filament (PHF) Tau formation in retinal cells.

In some embodiments, the present disclosure provides an antibody that binds to a mutant human ApoE (e.g., those having a mutation at amino acid position 136 of the human ApoE, such as ApoEch) or a portion thereof and has one or more of the following properties: (i) binds with high affinity of KD≤20 nM to mutant human ApoE (e.g., mutation at amino acid position 136 of the human ApoE, such as ApoEch); (ii) competes with wild type human ApoE for binding to heparin; and (iii) reduces Paired Helical Filament (PHF) Tau formation in retinal cells.

Any of the anti-ApoE antibodies described herein are useful for treating or preventing disorders associated with dementia or mild cognitive impairment (MCI) (e.g. Alzheimer's disease, vascular dementia, Lewy body dementia, frontotemporal dementia, Parkinson's disease, or Huntington's disease), neurodegenerative diseases, cerebrovascular diseases, brain injury, retinal degeneration, or retinal injury.

Exemplary Antibody 1H4-2

Antibody 1H4-2 was generated by immunizing with APOE: KLH-CTEELRVRLASHLRK-CONH2 (SEQ ID NO: 54). The amino acid sequences of the complementarity determining regions (CDRs) and the heavy chain variable region and light chain variable regions of 1H4-2 are provided below.

| Variable region | Chain type | CDR-1 | CDR-2 | CDR-3 |
|---|---|---|---|---|
| 1H4-2 VL | Light chain | KASQSVDYDGDSYMN (SEQ ID NO: 4) | AASNLES (SEQ ID NO: 5) | QQSNEDPWT (SEQ ID NO: 6) |
| 1H4-2 VH | Heavy chain | SYTMS (SEQ ID NO: 7) | KIRNGGGITYYLDTLKG (SEQ ID NO: 8) | HYYGSEDYFDY (SEQ ID NO: 9) |

Variable Light Chain:

Nucleotide sequence:
Signal sequence-FR1-CDR1-FR2-CDR2-FR3-CDR3-FR4
(SEQ ID NO: 10)

ATGGAGACAGACACAATCCTGCTATGGGTGCTGCTGCTCTGGGTTCCAGG

CTCCACTGGTGACAATGTGCTGACCCAATCTCCAGCTTCTTTGGCTGTGT

CTCTAGGGCAGAGGGCCACCATCTCCTGCAAGGCCAGCCAAAGTGTTGAT

TATGATGGTGATAGTTATATGAACTGGTACCAACAGAAACCAGGACAGCC

ACCCAAAGTCTTCATCTATGCTGCATCCAATCTAGAATCTGGGATCCCAG

CCAGGTTTAGTGGCAGTGGGTCTGGGACAGACTTCACCCTCAACATCCAT

CCTGTGGAGGAGGAGGATGCTGCAACCTATTACTGTCAGCAAAGTAATGA

GGATCCGTGGACGTTCGGTGGAGGCACCAAGCTGG AAATCAAA

Amino acid sequence:
Signal peptide-FR1-CDR1-FR2-CDR2-FR3-CDR3-FR4
(SEQ ID NO: 12)

METDTILLWVLLLWVPGSTGDNVLTQSPASLAVSLGQRATISCKASQSVD

YDGDSYMNWYQQKPGQPPKVFIYAASNLESGIPARFSGSGSGTDFTLNIH

PVEEEDAATYYCQQSNEDPWTFGGGTKLEIK

Variable Heavy chain:
Nucleotide sequence
Signal sequence-FR1-CDR1-FR2-CDR2-FR3-CDR3-FR4
(SEQ ID NO: 11)

ATGAATTTCGGGCTCAGCTTGATTTTCCTTGTCCTTGTTTTAAAAGGTGT

CCTGTGTGAAGTGAAGCTGGTGGAATCTGGGGGAGGTGTGGTGCAGCCTG

GAGGGTCCCTGAAACTCTCCTGTGCAGCCTCTGGATTCACTTTCAGTAGC

TATACCATGTCTTGGGTTCGTCAGACTCCAGAGAAGAGGCTGGAGTGGGT

CGCAAAAATTCGTAATGGTGGTGGTATCACCTACTATTTAGACACTTTAA

-continued

AGGGCCGATTCACCATCTCCAGAGACAACGCCAAGAACACCCTATACCTG

CAAATGAGCAGTCTGAAGTCTGAAGACACGGCCATTTATTTCTGTGCAAG

ACATTACTACGGTAGCGAGGACTACTTTGACTACTGGGGCCAAGGCACCA

CTCTCACAGTCTCCTCA

Amino acid sequence:
Signal peptide-FR1-CDR1-FR2-CDR2-FR3-CDR3-FR4
(SEQ ID NO: 13)

MNFGLSLIFLVLVLKGVLCEVKLVESGGGVVQPGGSLKLSCAASGFTFSS

YTMSWVRQTPEKRLEWVAKIRNGGGITYYLDTLKGRFTISRDNAKNTLYL

QMSSLKSEDTAIYFCARHYYGSEDYFDYWGQGTTLTVSS

In some instances, the anti-ApoE antibody comprises a VH comprising the three VH CDRs and a VL comprising the three VL CDRs of antibody 1H4-2. The six CDRs can be based on any definition known in the art such as, but not limited to, Kabat, Chothia, enhanced Chothia, contact, IMGT, or Honegger definitions. These CDRs can be determined, e.g., by using the AbYsis database (bioinf.org.uk/abysis/sequence_input/key_annotation/key_annotation.cgi).

In one instance, an anti-ApoE antibody of this disclosure comprises (i) a VH comprising a VHCDR1 comprising the amino acid sequence set forth in SEQ ID NO: 7, a VHCDR2 comprising the amino acid sequence set forth in SEQ ID NO: 8, and a VHCDR3 comprising the amino acid sequence set forth in SEQ ID NO: 9; and (ii) a VL comprising a VLCDR1 comprising the amino acid sequence set forth in SEQ ID NO: 4, a VLCDR2 comprising the amino acid sequence set forth in SEQ ID NO: 5, and a VLCDR3 comprising the amino acid sequence set forth in SEQ ID NO: 6.

In some instances, the anti-ApoE antibody comprises a VH that is at least 75%, 80%, 85%, 90%, 91%, 92%, 93%, 94%, 95%, 96%, 97%, 98%, or 99% identical to the amino acid sequence set forth in SEQ ID NO: 13. In some instances, the anti-ApoE antibody comprises a VL that is at least 75%, 80%, 85%, 90%, 91%, 92%, 93%, 94%, 95%, 96%, 97%, 98%, or 99% identical to the amino acid sequence set forth in SEQ ID NO: 12. In one instance, the anti-ApoE antibody comprises a VH that is at least 85% identical to the amino acid sequence set forth in SEQ ID NO: 13 and a VL that is at least 85% identical to the amino acid sequence set forth in SEQ ID NO: 12. In another instance, the anti-ApoE antibody comprises a VH that is at least 90% identical to the amino acid sequence set forth in SEQ ID NO: 13 and a VL that is at least 90% identical to the amino acid sequence set forth in SEQ ID NO: 12. In yet another instance, the anti-ApoE antibody comprises a VH that is identical to the amino acid sequence set forth in SEQ ID NO: 13 and a VL that is identical to the amino acid sequence set forth in SEQ ID NO: 12.

In certain instances, an antibody of this disclosure that binds to ApoE is one that competes with or binds to the same epitope as a reference antibody with a VH having the amino acid sequence set forth in SEQ ID NO: 13 and a VL having the amino acid sequence set forth in SEQ ID NO: 12.

Exemplary Antibody 7C11-1

Antibody 7C11-1 generated by immunizing with APOE: KLH-CTEELRVRLASHLRK-CONH2 (SEQ ID NO: 54). The amino acid sequences of the complementarity determining regions (CDRs) and the heavy chain variable region and light chain variable regions of 7C11-1 are provided below.

| Variable region | Chain type | CDR-1 | CDR-2 | CDR-3 |
|---|---|---|---|---|
| 7C11-1 VL | Light chain | KASQSVDYDGDSYMN (SEQ ID NO: 14) | AASNLES (SEQ ID NO: 15) | QQSNEDPWT (SEQ ID NO: 16) |
| 7C11-1 VH | Heavy chain | RYTMS (SEQ ID NO: 17) | KIRNVGGITYYPD TVKG (SEQ ID NO: 18) | HYYGSEDYFDY (SEQ ID NO: 19) |

Variable Heavy Chain:

Nucleotide sequence
Signal sequence-FR1-CDR1-FR2-CDR2-FR3-CDR3-FR4
(SEQ ID NO: 20)

ATGAATTTCGGGCTCAGCGTGATTTTCCTTGTCCTTGTTTTAAAAGGTGT

CCTGTGTGAAGTGAAGCTGGTGGAGTCTGGGGGAGGTTTAGTGCAGCCTG

GAGGGTCCCTGAAACTCTCCTGTGCAGCCTCTGGATTCACTTTCAGTAGG

TATACCATGTCTTGGGTTCGGCAGACTCCAGAGAAGAGGCTGGAGTGGGT

CGCAAAAATTCGTAATGTTGGTGGTATCACCTACTATCCAGACACTGTAA

AGGGCCGATTCACCATCTCCAGAGACAACGCCAAGAACACCCTTTACCTG

CAAATGAGCAGTCTGAAGTCTGAAGACACGGCCATGTATTACTGTGCAAG

ACATTATTACGGTAGCGAGGACTACTTTGACTACTGGGGCCAAGGCACCA

CTCTCACAGTCTCCTCA

Amino acid sequence:
Signal peptide-FR1-CDR1-FR2-CDR2-FR3-CDR3-FR4
(SEQ ID NO: 22)

MNFGLSVIFLVLVLKGVLCEVKLVESGGGLVQPGGSLKLSCAASGFTFSR

YTMSWVRQTPEKRLEWVAKIRNVGGITYYPDTVKGRFTISRDNAKNTLYL

QMSSLKSEDTAMYYCARHYYGSEDYFDYWGQGTTLTVSS

Variable Light chain:
Nucleotide sequence:
Signal sequence-FR1-CDR1-FR2-CDR2-FR3-CDR3-FR4
(SEQ ID NO: 21)

ATGGAGACAGACACAATCCTGCTATGGGTGCTGCTGCTCTGGGTTCCAGG

CTCCACTGGTGACAATGTGCTGACCCAATCTCCAGCTTCTTTGGCTGTGT

CTCTAGGGCAGAGGGCCACCATCTCCTGCAAGGCCAGCCAAAGTGTTGAT

TATGATGGTGATAGTTATATGAACTGGTACCAACAGAAACCAGGACAGCC

ACCCAAAGTCTTCATCTATGCTGCATCCAATCTAGAATCTGGGATCCCAG

CCAGGTTTAGTGGCAGTGGGTCTGGGACAAACTTCACCCTCAACATCCAT

-continued

CCTGTGGAGGAGGAGGATGCTGCAACCTATTACTGTCAGCAAAGTAATGA

GGATCCGTGGACGTTCGGTGGA GGCACCAAGCTGGAAATCAAA

Amino acid sequence:

Signal sequence-FR1-CDR1-FR2-CDR2-FR3-CDR3-FR4

-continued (SEQ ID NO: 23)

METDTILLWVLLLWVPGSTGDNVLTQSPASLAVSLGQRATISCKASQSVD

YDGDSYMNWYQQKPGQPPKVFIYAASNLESGIPARFSGSGSGTNFTLNIH

PVEEEDAATYYCQQSNEDPWTFGG GTKLEIK

In some instances, the anti-ApoE antibody comprises a VH comprising the three VH CDRs and a VL comprising the three VL CDRs of antibody 7C11-1. The six CDRs can be based on any definition known in the art such as, but not limited to, Kabat, Chothia, enhanced Chothia, contact, IMGT, or Honegger definitions. These CDRs can be determined, e.g., by using the AbYsis database (bioinf.org.uk/abysis/sequence_input/key_annotation/key_annotation.cgi).

In one instance, an anti-ApoE antibody of this disclosure comprises (i) a VH comprising a VHCDR1 comprising the amino acid sequence set forth in SEQ ID NO: 17, a VHCDR2 comprising the amino acid sequence set forth in SEQ ID NO: 18, and a VHCDR3 comprising the amino acid sequence set forth in SEQ ID NO: 19; and (ii) a VL comprising a VLCDR1 comprising the amino acid sequence set forth in SEQ ID NO: 14, a VLCDR2 comprising the amino acid sequence set forth in SEQ ID NO: 15, and a VLCDR3 comprising the amino acid sequence set forth in SEQ ID NO: 16.

In some instances, the anti-ApoE antibody comprises a VH that is at least 75%, 80%, 85%, 90%, 91%, 92%, 93%, 94%, 95%, 96%, 97%, 98%, or 99% identical to the amino acid sequence set forth in SEQ ID NO: 22. In some instances, the anti-ApoE antibody comprises a VL that is at least 75%, 80%, 85%, 90%, 91%, 92%, 93%, 94%, 95%, 96%, 97%, 98%, or 99% identical to the amino acid sequence set forth in SEQ ID NO: 23. In one instance, the anti-ApoE antibody comprises a VH that is at least 85% identical to the amino acid sequence set forth in SEQ ID NO: 22 and a VL that is at least 85% identical to the amino acid sequence set forth in SEQ ID NO: 23. In another instance, the anti-ApoE antibody comprises a VH that is at least 90% identical to the amino acid sequence set forth in SEQ ID NO: 22 and a VL that is at least 90% identical to the amino acid sequence set forth in SEQ ID NO: 23. In yet another instance, the anti-ApoE antibody comprises a VH that is identical to the amino acid sequence set forth in SEQ ID NO: 22 and a VL that is identical to the amino acid sequence set forth in SEQ ID NO: 23.

In certain instances, an antibody of this disclosure that binds to ApoE is one that competes with or binds to the same epitope as a reference antibody with a VH having the amino acid sequence set forth in SEQ ID NO: 23 and a VL having the amino acid sequence set forth in SEQ ID NO: 22.

Exemplary Antibody 19G10-2

Antibody 19G10-2 generated by immunizing with KLH-CTEELRVSLASHLRK-CONH2 (SEQ ID NO: 55). The amino acid sequences of the complementarity determining regions (CDRs) and the heavy chain variable region and light chain variable regions of 19G10-2 are provided below.

| Variable region | Chain type | CDR-1 | CDR-2 | CDR-3 |
|---|---|---|---|---|
| 19G10-2 VL | Light chain | KASQSVDYDGDSYMN (SEQ ID NO: 24) | AASNLES (SEQ ID NO: 25) | QQSNVDPWT (SEQ ID NO: 26) |
| 19G10-2 VH | Heavy chain | DYHMH (SEQ ID NO: 27) | WIDPENGNTMYD PKFQG (SEQ ID NO: 28) | GTARASFDY (SEQ ID NO: 29) |

Variable Light Chain:

Nucleotide sequence:

Signal sequence-FR1-CDR1-FR2-CDR2-FR3-CDR3-FR4

(SEQ ID NO: 30)

ATGGAGACAGACACAATCCTGCTATGGGTGCTGCTGCTCTGGGTTCCAGG

CTCCACTGGTGACATTGTGCTGACCCAATCTCCAGCTTCTTTGGCTGTGT

CTCTAGGGCAGAGGGCCACCATCTCCTGCAAGGCCAGCCAAAGTGTTGAT

TATGATGGTGATAGTTATATGAATTGGTACCAACAGAAATCAGGACAGCC

ACCCAAACTCCTCATCTATGCTGCATCCAATCTAGAATCTGGGATCCCAG

CCAGGTTTAGTGGCAGTGGGTCTGGGACAGACTTCACCCTCAACATCCAT

CCTGTGGAGGAGGAGGATGCTGCAACCTATTACTGTCAGCAAAGTAATGT

GGATCCGTGGACGTTCGGTGGAGGCACCAAGCTGGAAATCAAA

Amino acid sequence:

Signal sequence-FR1-CDR1-FR2-CDR2-FR3-CDR3-FR4

(SEQ ID NO: 32)

METDTILLWVLLLWVPGSTGDIVLTQSPASLAVSLGQRATISCKASQSVD

YDGDSYMNWYQQKSGQPPKLLIYAASNLESGIPARFSGSGSGTDFTLNIH

PVEEEDAATYYCQQSNVDPWTFGGGTKLEIK

Variable Heavy chain analysis:

Nucleotide sequence

Signal sequence-FR1-CDR1-FR2-CDR2-FR3-CDR3-FR4

(SEQ ID NO: 31)

ATGAAATGCAGCTGGGTCATCTTCTTCCTGATGGCAGTGGTTACAGGGGT

CAATTCAGAGGTTCAGCTGCAGCAGTCTGGGGCTGAGCTTGTGAGGCCAG

GGGCCTTAGTCAAGTTGTCCTGCAAAGCTTCTGGCTTCAACATTAAAGAC

TACCATATGCACTGGGTGAAGGAGAGGCCTGAACAGGGCCTGGAGTGGAT

TGGATGGATTGATCCTGAGAATGGTAATACTATGTATGACCCGAAGTTCC

AGGGCAAGGCCAGTATAACAGCAGACACATCCTCCAACACAGCCTACCTG

CAGCTCAGCAGCCTGACATCTGAGGACACTGCCGTCTATTACTGTGTTAG

GGGGACAGCTCGGGCTTCCTTTGACTACTGGGGCCAAGGCACCACTCTCA

CAGTCTCCTCA

-continued

Amino acid sequence:
Signal sequence-FR1-CDR1-FR2-CDR2-FR3-CDR3-FR4
(SEQ ID NO: 33)

MKCSWVIFFLMAVVTGVNSEVQLQQSGAELVRPGALVKLSCKASGFNIKD

YHMHWVKERPEQGLEWIGWIDPENGNTMYDPKFQGKASITADTSSNTAYL

QLSSLTSEDTAVYYCVRGTARASFDYWGQGTTLTVSS

In some instances, the anti-ApoE antibody comprises a VH comprising the three VH CDRs and a VL comprising the three VL CDRs of antibody 19G10-2. The six CDRs can be based on any definition known in the art such as, but not limited to, Kabat, Chothia, enhanced Chothia, contact, IMGT, or Honegger definitions. These CDRs can be determined, e.g., by using the AbYsis database (bioinf.org.uk/abysis/sequence_input/key_annotation/key_annotation.cgi).

In one instance, an anti-ApoE antibody of this disclosure comprises (i) a VH comprising a VHCDR1 comprising the amino acid sequence set forth in SEQ ID NO: 27, a VHCDR2 comprising the amino acid sequence set forth in SEQ ID NO: 28, and a VHCDR3 comprising the amino acid sequence set forth in SEQ ID NO: 29; and (ii) a VL comprising a VLCDR1 comprising the amino acid sequence set forth in SEQ ID NO: 24, a VLCDR2 comprising the amino acid sequence set forth in SEQ ID NO: 25, and a VLCDR3 comprising the amino acid sequence set forth in SEQ ID NO: 26.

In some instances, the anti-ApoE antibody comprises a VH that is at least 75%, 80%, 85%, 90%, 91%, 92%, 93%, 94%, 95%, 96%, 97%, 98%, or 99% identical to the amino acid sequence set forth in SEQ ID NO: 33. In some instances, the anti-ApoE antibody comprises a VL that is at least 75%, 80%, 85%, 90%, 91%, 92%, 93%, 94%, 95%, 96%, 97%, 98%, or 99% identical to the amino acid sequence set forth in SEQ ID NO: 32. In one instance, the anti-ApoE antibody comprises a VH that is at least 85% identical to the amino acid sequence set forth in SEQ ID NO: 33 and a VL that is at least 85% identical to the amino acid sequence set forth in SEQ ID NO: 32. In another instance, the anti-ApoE antibody comprises a VH that is at least 90% identical to the amino acid sequence set forth in SEQ ID NO: 33 and a VL that is at least 90% identical to the amino acid sequence set forth in SEQ ID NO: 32. In yet another instance, the anti-ApoE antibody comprises a VH that is identical to the amino acid sequence set forth in SEQ ID NO: 33 and a VL that is identical to the amino acid sequence set forth in SEQ ID NO: 32.

In certain instances, an antibody of this disclosure that binds to ApoE is one that competes with or binds to the same epitope as a reference antibody with a VH having the amino acid sequence set forth in SEQ ID NO: 33 and a VL having the amino acid sequence set forth in SEQ ID NO: 32.

Exemplary Antibody 25F1-2

Antibody 25F1-2 was generated by immunizing with KLH-CTEELRVSLASHLRK-CONH2 (SEQ ID NO: 55). The amino acid sequences of the complementarity determining regions (CDRs) and the heavy chain variable region and light chain variable regions of 25F1-2 are provided below.

| Variable region | Chain type | CDR-1 | CDR-2 | CDR-3 |
|---|---|---|---|---|
| 25F1-2 VL | Light chain | KASQSVDYDGDTYMN (SEQ ID NO: 34) | TASNLES (SEQ ID NO: 35) | QQSNEDPWT (SEQ ID NO: 36) |
| 25F1-2 VH | Heavy chain | DYHIH (SEQ ID NO: 37) | WIDPEIDKTLYDP KFQG (SEQ ID NO: 38) | GTARASFDY (SEQ ID NO: 39) |

Variable Light Chain Analysis:

Nucleotide sequence:
Signal sequence-FR1-CDR1-FR2-CDR2-FR3-CDR3-FR4
(SEQ ID NO: 40)

ATGGAGACAGACACAATCCTGCTATGGGTGCTGCTGCTCTGGGTTCCAGG

CTCCACTGGTGACATTGTGCTGACCCAATCTCCAGCTTCTTTGGCTGTGT

CTCTAGGGCAGAGGGCCACCATCTCCTGCAAGGCCAGCCAAAGTGTTGAT

TATGATGGTGATACTTATATGAACTGGTACCAACAGAAACCAGGACAGCC

ACCCAAACTCCTCATCTATACTGCATCCAATCTAGAATCTGGGATCCCAG

CCAGGTTTAGTGGCAGTGGGTCTGGGACAGACTTCACCCTCAACATCCAT

CCTGTGGAGGAGGTGGATGCTGCAACCTATTACTGTCAGCAAAGTAATGA

GGATCCATGGACGTTCGGTGGAGGCACCAAGCTGG AAATCAAA

Amino acid sequence:
Signal sequence-FR1-CDR1-FR2-CDR2-FR3-CDR3-FR4
(SEQ ID NO: 42)

METDTILLWVLLLWVPGSTGDIVLTQSPASLAVSLGQRATISCKASQSVD

YDGDTYMNWYQQKPGQPPKLLIYTASNLESGIPARFSGSGSGTDFTLNIH

PVEEVDAATYYCQQSNEDPWTFGGGTKLEIK

Variable Heavy chain analysis:
Nucleotide sequence
Signal sequence-FR1-CDR1-FR2-CDR2-FR3-CDR3-FR4
(SEQ ID NO: 41)

ATGAAATGCAGCTGGGTCATCTTCTTCCTGATGGCAGTGGTTACAGGGGT

CAATTCAGAGGTTCAGCTGCAGCAGTCTGGGGCTGAGCTTGTGAGGCCAG

GGGCCTTAGTCAAGTGGTCCTGCAAAGCTTCTGGCTTCAACATTAAAGAC

TACCATATACACTGGGTGAAACAGAGGCCTGAACAGGGCCTGGACTGGAT

-continued

TGGATGGATTGATCCTGAGATTGATAAAACTCTATATGACCCGAAGTTTC

AGGGCAAGGCCAGAATAACAGCAGACACATCCTCCAATACAGCCTACCTG

CAGCTCAGCAGCCTGACATCTGAAGACACTGCCGTCTATTACTGTGCCAG

GGGGACAGCTCGGGCTTCCTTTGACTACTGGGGCCAAGGCACCACTCTCA

CAGTCTCCTCA

Amino acid sequence:
Signal sequence-FR1-CDR1-FR2-CDR2-FR3-CDR3-FR4
(SEQ ID NO: 43)

MKCSWVIFFLMAVVTGVNSEVQLQQSGAELVRPGALVKWSCKASGFNIKD

YHIHWVKQRPEQGLDWIGWIDPEIDKTLYDPKFQGKARITADTSSNTAYL

QLSSLTSEDTAVYYCARGTARASFDYWGQGTTLTVSS

In some instances, the anti-ApoE antibody comprises a VH comprising the three VH CDRs and a VL comprising the three VL CDRs of antibody 25F1-2. The six CDRs can be based on any definition known in the art such as, but not limited to, Kabat, Chothia, enhanced Chothia, contact, IMGT, or Honegger definitions. These CDRs can be determined, e.g., by using the AbYsis database (bioinf.org.uk/abysis/sequence_input/key_annotation/key_annotation.cgi).

In one instance, an anti-ApoE antibody of this disclosure comprises (i) a VH comprising a VHCDR1 comprising the amino acid sequence set forth in SEQ ID NO: 37, a VHCDR2 comprising the amino acid sequence set forth in SEQ ID NO: 38, and a VHCDR3 comprising the amino acid sequence set forth in SEQ ID NO: 39; and (ii) a VL comprising a VLCDR1 comprising the amino acid sequence set forth in SEQ ID NO: 34, a VLCDR2 comprising the amino acid sequence set forth in SEQ ID NO: 35, and a VLCDR3 comprising the amino acid sequence set forth in SEQ ID NO: 36.

In some instances, the anti-ApoE antibody comprises a VH that is at least 75%, 80%, 85%, 90%, 91%, 92%, 93%, 94%, 95%, 96%, 97%, 98%, or 99% identical to the amino acid sequence set forth in SEQ ID NO: 43. In some instances, the anti-ApoE antibody comprises a VL that is at least 75%, 80%, 85%, 90%, 91%, 92%, 93%, 94%, 95%, 96%, 97%, 98%, or 99% identical to the amino acid sequence set forth in SEQ ID NO: 42. In one instance, the anti-ApoE antibody comprises a VH that is at least 85% identical to the amino acid sequence set forth in SEQ ID NO: 43 and a VL that is at least 85% identical to the amino acid sequence set forth in SEQ ID NO: 42. In another instance, the anti-ApoE antibody comprises a VH that is at least 90% identical to the amino acid sequence set forth in SEQ ID NO: 43 and a VL that is at least 90% identical to the amino acid sequence set forth in SEQ ID NO: 42. In yet another instance, the anti-ApoE antibody comprises a VH that is identical to the amino acid sequence set forth in SEQ ID NO: 43 and a VL that is identical to the amino acid sequence set forth in SEQ ID NO: 42.

In certain instances, an antibody of this disclosure that binds to ApoE is one that competes with or binds to the same epitope as a reference antibody with a VH having the amino acid sequence set forth in SEQ ID NO: 43 and a VL having the amino acid sequence set forth in SEQ ID NO: 42.

Exemplary Antibody 1343ab

Antibody 1343ab was generated by immunizing with KLH-CTEELRVSLASHLRK-CONH2 (SEQ ID NO: 55). The amino acid sequences of the complementarity determining regions (CDRs) and the full length heavy and light chains are provided below.

| Variable region | Chain type | CDR-1 | CDR-2 | CDR-3 |
|---|---|---|---|---|
| 1343 VL | Light chain | KASQSVDYDGEN YMN (SEQ ID NO: 44) | VASNLES (SEQ ID NO: 45) | QQSNLDPWT (SEQ ID NO: 46) |
| 1343 VH | Heavy chain | GFNIKDY (SEQ ID NO: 47) | DPENGN (SEQ ID NO: 48) | GTARASFDY (SEQ ID NO: 49) |

Full length heavy chain
(SEQ ID NO: 53)

EVQLQQSGAELVRPGALVKLSCKASGFNIKDYHLHWVKQRPEQGLE

WIGWIDPENGNVIYDPKFQGKATMTV

VTSSNTAYLQLRSLTSEDTAVYFCTRGTARASFDYWGQGTSLTVSSAK

TTPPSVYPLAPGSAAQTNSMVTLG

CLVKGYFPEPVTVTWNSGSLSSGVHTFPAVLQSDLYTLSSSVTVPSST

WPSETVTCNVAHPASSTKVDKKIV

PRDCGCKPCICTVPEVSSVFIFPPKPKDVLTITLTPKVTCVVVDISKDD

PEVQFSWFVDDVEVHTAQTQPRE

EQFNSTFRSVSELPIMHQDWLNGKEFKCRVNSAAFPAPIEKTISKTKGR

PKAPQVYTIPPPKEQMAKDKVSL

TCMITDFFPEDITVEWQWNGQPAENYKNTQPIMDTDGSYFVYSKLNV

QKSNWEAGNTFTCSVLHEGLHNHHT

EKSLSHSPGK

Full length light chain
(SEQ ID NO: 52)

DIVLTQSPASLAVSLGQRATISCKASQSVDYDGENYMNWYQQKPGQS

PKLLIYVASNLESGIPARFSGSGSG

TDFTLNIHPVEEEDAATYYCQQSNLDPWTFGGGTKLEIKRADAAPTVS

IFPPSSEQLTSGGASVVCFLNNFY

PKDINVKWKIDGSERQNGVLNSWTDQDSKDSTYSMSSTLTLTKDEYE

RHNSYTCEATHKTSTSPIVKSFNRN

EC

N-linked glycosylation was detected on heavy chain constant region N at 292. Loss of C-terminal lysine observed on heavy chain.

In some instances, the anti-ApoE antibody comprises a VH comprising the three VH CDRs and a VL comprising the three VL CDRs of antibody 1343ab. The six CDRs can be based on any definition known in the art such as, but not limited to, Kabat, Chothia, enhanced Chothia, contact, IMGT, or Honegger definitions. These CDRs can be determined, e.g., by using the AbYsis database (bioinf.org.uk/abysis/sequence_input/key_annotation/key_annotation.cgi).

In one instance, an anti-ApoE antibody of this disclosure comprises (i) a VH comprising a VHCDR1 comprising the amino acid sequence set forth in SEQ ID NO: 47, a VHCDR2 comprising the amino acid sequence set forth in SEQ ID NO: 48, and a VHCDR3 comprising the amino acid sequence set forth in SEQ ID NO: 49; and (ii) a VL comprising a VLCDR1 comprising the amino acid sequence set forth in SEQ ID NO: 44, a VLCDR2 comprising the amino acid sequence set forth in SEQ ID NO: 45, and a VLCDR3 comprising the amino acid sequence set forth in SEQ ID NO: 46.

In some instances, the anti-ApoE antibody comprises a heavy chain that is at least 70%, 71%, 72%, 73%, 74%, 75%, 80%, 85%, 90%, 91%, 92%, 93%, 94%, 95%, 96%, 97%, 98%, or 99% identical to the amino acid sequence set forth in SEQ ID NO: 53. In some instances, the anti-ApoE antibody comprises a light chain that is at least 70%, 71%, 72%, 73%, 74%, 75%, 80%, 85%, 90%, 91%, 92%, 93%, 94%, 95%, 96%, 97%, 98%, or 99% identical to the amino acid sequence set forth in SEQ ID NO: 52. In one instance, the anti-ApoE antibody comprises a heavy chain that is at least 80% identical to the amino acid sequence set forth in SEQ ID NO: 53 and a light chain that is at least 80% identical to the amino acid sequence set forth in SEQ ID NO: 52. In another instance, the anti-ApoE antibody comprises a heavy chain that is at least 85% identical to the amino acid sequence set forth in SEQ ID NO: 53 and a light chain that is at least 85% identical to the amino acid sequence set forth in SEQ ID NO: 52. In yet another instance, the anti-ApoE antibody comprises a heavy chain that is identical to the amino acid sequence set forth in SEQ ID NO: 53 and a light chain that is identical to the amino acid sequence set forth in SEQ ID NO: 52.

In certain instances, an antibody of this disclosure that binds to ApoE is one that competes with or binds to the same epitope as a reference antibody with a heavy chain having the amino acid sequence set forth in SEQ ID NO: 53 and a light chain having the amino acid sequence set forth in SEQ ID NO: 52.

Chimeric, human, or humanized antibodies having the CDR sequences of any of the above antibodies can be generated based on methods described herein.

Antibody Fragments

Antibody fragments (e.g., Fab, Fab', F(ab')2, Facb, and Fv) can be prepared by proteolytic digestion of intact antibodies. For example, antibody fragments can be obtained by treating the whole antibody with an enzyme such as papain, pepsin, or plasmin. Papain digestion of whole antibodies produces F (ab) 2 or Fab fragments; pepsin digestion of whole antibodies yields F(ab')2 or Fab'; and plasmin digestion of whole antibodies yields Facb fragments.

Alternatively, antibody fragments can be produced recombinantly. For example, nucleic acids encoding the antibody fragments of interest can be constructed, introduced into an expression vector, and expressed in suitable host cells. See, e.g., Co, M. S. et al., *J. Immunol.,* 152:2968-2976 (1994); Better, M. and Horwitz, A. H., *Methods in Enzymology,* 178:476-496 (1989); Pluckthun, A. and Skerra, A., *Methods in Enzymology,* 178:476-496 (1989); Lamoyi, E., *Methods in Enzymology,* 121:652-663 (1989); Rousseaux, J. et al., *Methods in Enzymology,* (1989) 121:663-669 (1989); and Bird, R. E. et al., *TIBTECH,* 9:132-137 (1991)). Antibody fragments can be expressed in and secreted from *E. coli*, thus allowing the facile production of large amounts of these fragments. Antibody fragments can be isolated from the antibody phage libraries. Alternatively, Fab'-SH fragments can be directly recovered from *E. coli* and chemically coupled to form F (ab) 2 fragments (Carter et al., *Bio/Technology,* 10:163-167 (1992)). According to another approach, F(ab')2 fragments can be isolated directly from recombinant host cell culture. Fab and F(ab')2 fragment with increased in vivo half-life comprising a salvage receptor binding epitope residues are described in U.S. Pat. No. 5,869,046.

Conjugated Antibodies

The antibodies disclosed herein can be conjugated antibodies that are bound to various molecules including macromolecular substances such as polymers (e.g., polyethylene glycol (PEG), polyethylenimine (PEI) modified with PEG (PEI-PEG), polyglutamic acid (PGA) (N-(2-Hydroxypropyl) methacrylamide (HPMA) copolymers), hyaluronic acid, radioactive materials (e.g. $^{90}Y$, $^{131}I$), fluorescent substances, luminescent substances, haptens, enzymes, metal chelates, and drugs.

In some embodiments, the antibodies described herein are modified with a moiety that improves its stabilization and/or retention in circulation, e.g., in blood, serum, or other tissues, including the brain, e.g., by at least 1.5, 2, 5, 10, 15, 20, 25, 30, 40, or 50-fold. For example, the antibodies described herein can be associated with (e.g., conjugated to) a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used. For example, the antibodies described herein can be conjugated to a water soluble polymer, e.g., a hydrophilic polyvinyl polymer, e.g., polyvinylalcohol or polyvinylpyrrolidone. Examples of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene; polymethacrylates; carbomers; and branched or unbranched polysaccharides. In some embodiments, the antibodies described herein are modified with a moiety that improves its penetration of the blood-brain barrier (such as those described in Pardridge, J Cereb Blood Flow Metab 32 (11): 1959-1972, 2012). Exemplary blood-brain barrier penetrating moieties include, but are not limited to, glucose transporter type 1 (GLUT1), cationic amino-acid transporter type 1 (CAT1), monocarboxylic acid transporter type 1 (MCT1), concentrative nucleoside transporter type 2 (CNT2), active efflux transporter (AET) (e.g., p-glycoprotein, and those described in Pardridge, J Cereb Blood Flow Metab 32 (11): 1959-1972, 2012), Additional blood-brain barrier penetrating moieties are known in the art.

The above-described conjugated antibodies can be prepared by performing chemical modifications on the antibodies or the lower molecular weight forms thereof described herein. Methods for modifying antibodies are well known in the art (e.g., U.S. Pat. Nos. 5,057,313 and 5,156,840).

The anti-ApoE antibodies can be in the form of full length (or whole) antibodies, or in the form of low molecular weight forms (e.g., biologically active antibody fragments or minibodies) of the anti-ApoE antibodies, e.g., Fab, Fab', F(ab')2, Fv, Fd, dAb, scFv, and sc(Fv)2. Other anti-ApoE antibodies encompassed by this disclosure include single domain antibody (sdAb) containing a single variable chain such as, VH or VL, or a biologically active fragment thereof. See, e.g., Moller et al., *J. Biol. Chem.,* 285(49): 38348-38361 (2010); Harmsen et al., *Appl. Microbiol. Biotechnol.,* 77(1):13-22 (2007); U.S. 2005/0079574 and Davies et al. (1996) *Protein Eng.,* 9(6):531-7. Like a whole antibody, a sdAb is able to bind selectively to a specific antigen (e.g., ApoE2, ApoE3, ApoE4, or ApoEch). With a molecular weight of only 12-15 kDa, sdAbs are much smaller than common antibodies and even smaller than Fab fragments and single-chain variable fragments.

In certain embodiments, an anti-ApoE antibody or antigen-binding fragment thereof or low molecular weight antibodies thereof specifically binds to the HSPG/heparin-binding domain of ApoE and reduces the severity of symptoms when administered to human patients having one or more of, or animal models of: dementia and/or mild cognitive impairment (MCI) (e.g. those associated with Alzheimer's disease, vascular dementia, Lewy body dementia, frontotemporal dementia, Parkinson's disease, Huntington's disease, or neurodegeneration). In certain embodiments, an anti-ApoE antibody or antigen-binding fragment thereof or low molecular weight antibodies thereof specifically binds to the HSPG/heparin-binding domain of ApoE and reduces the severity of symptoms when administered to human patients having one or more of, or animal models of: neurodegenerative diseases, cerebrovascular diseases (e.g. stroke, carotid stenosis, vertebral stenosis, or aneurysms), brain injuries (e.g. traumatic brain injury, acquired brain injury), retinal degeneration, glaucoma, or retinal injury. These features of an anti-ApoE antibody or low molecular weight antibodies thereof can be measured according to methods known in the art.

Nucleic Acids, Vector, Host Cells

This disclosure also features nucleic acids encoding the antibodies disclosed herein. Provided herein are nucleic acids encoding the VH CDR1, VH CDR2, and VH CDR3 of the anti-ApoE antibodies described herein. Also provided are nucleic acids encoding the VL CDR1, VL CDR2, and VL CDR3 of the anti-ApoE antibodies described herein. Provided herein are nucleic acids encoding the VH CDR1, VH CDR2, VH CDR3, VL CDR1, VL CDR2, and VL CDR3 of the anti-ApoE antibodies described herein. Also provided are nucleic acids encoding the heavy chain variable region (VH) of the anti-ApoE antibodies described herein, and/or nucleic acids encoding the light chain variable region (VL) of the anti-ApoE antibodies described herein. In certain instances, provided herein are nucleic acids encoding the VH and/or VL of the anti-ApoE antibodies described herein, linked to human heavy and/or human light chain constant regions, respectively. Also provided herein are nucleic acids encoding both VH and VL of the anti-ApoE antibodies described herein. In some instances, the nucleic acids described herein include a nucleic acid encoding the Fc region of a human antibody (e.g., human IgG1, IgG2, IgG3, or IgG4). In certain instances, the nucleic acids include a nucleic acid encoding the Fc region of a human antibody that has been modified to reduce or eliminate effector function (e.g., a N297Q or T299A substitution in a human IgG1 Fc region (numbering according to EU numbering)). In some cases, the nucleic acids include a nucleic acid encoding an Fc moiety that is a hIgG1 Fc, a hIgG2 Fc, a hIgG3 Fc, a hIgG4 Fc, a hIgG1agly Fc, a hIgG2 SAA Fc, a hIgG4 (S228P) Fc, or a hIgG4 (S228P)/G1 agly Fc.

Also disclosed herein are vectors (e.g. expression vectors) containing any of the nucleic acids described above.

Furthermore, this disclosure relates to host cells (e.g. bacterial cells, yeast cells, insect cells, or mammalian cells) containing the vector(s) or the nucleic acid(s) described above.

Methods of Obtaining Anti-ApoE Antibodies

Also provided herein are methods for making anti-ApoE antibodies useful in the present methods. General methods for making antibodies, e.g., monospecific, polyclonal, or monoclonal antibodies, are known in the art. For monoclonal antibodies, the process involves obtaining antibody-secreting immune cells (lymphocytes) from the spleen of a mammal (e.g., mouse) that has been previously immunized with the antigen of interest (e.g., a peptide antigen as described herein) either in vivo or in vitro. The antibody-secreting lymphocytes are then fused with myeloma cells or transformed cells that are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, Nature 256:495 (1975).

Mammalian lymphocytes can be immunized by in vivo immunization of the animal (e.g., a mouse) with a peptide antigen, e.g., a peptide antigen that is at least 80%, 85%, 90%, or 95% identical to KLH-CTEELRVRLASHLRK-CONH2 (SEQ ID NO: 54) or KLH-CTEELRVSLASHLRK-CONH2 (SEQ ID NO:55), optionally with one or more substitutions or deletions, e.g., of up to 20% of the residues. For example, the methods can include immunizing the animal with a peptide comprising a sequence that is at least 80% identical to at least 10 consecutive amino acids from: the heparin-binding domain of APOE, e.g., a peptide comprising TEELRVRLASHLRK (SEQ ID NO: 3) or TEELRVSLASHLRK (SEQ ID NO: 2). Such immunizations are repeated as necessary at intervals of up to several weeks to obtain a sufficient titer of antibodies. Following the last antigen boost, the animals are sacrificed, and spleen cells removed.

Fusion with mammalian myeloma cells or other fusion partners capable of replicating indefinitely in cell culture is effected by known techniques, for example, using polyethylene glycol ("PEG") or other fusing agents (See Milstein and Kohler, Eur. J. Immunol. 6:511 (1976), which is hereby incorporated by reference). This immortal cell line, which is preferably murine, but can also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also known. Typically, such antibodies can be raised by administering the protein or polypeptide of the present invention subcutaneously to New Zealand white rabbits that have first been bled to obtain pre-immune serum. The antigens can be injected, e.g., at a total volume of 100 μl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthanized, e.g., with pentobarbital 150 mg/Kg IV. This and other procedures for raising polyclonal antibodies are disclosed in E. Harlow, et. al., editors, Antibodies: A Laboratory Manual (1988).

The method described herein comprises any one of the step(s) of producing a chimeric antibody, humanized antibody, single-chain antibody, Fab-fragment, bi-specific antibody, fusion antibody, labeled antibody or an analog of any one of those. Corresponding methods are known to the person skilled in the art and are described, e.g., in Harlow and Lane "Antibodies, A Laboratory Manual", CSH Press, Cold Spring Harbor (1988). When derivatives of said antibodies are obtained by the phage display technique, surface plasmon resonance as employed in the BIAcore system can be used to increase the efficiency of phage antibodies which bind to the same epitope as that of any one of the antibodies described herein (Schier, Human Antibodies Hybridomas 7 (1996), 97-105; Malmborg, J. Immunol. Methods 183 (1995), 7-13). The production of chimeric antibodies is described, for example, in international application WO89/09622. Methods for the production of humanized antibodies are described in, e.g., European application EP-A1 0 239 400 and international application WO90/07861. A further source of antibodies to be utilized in accordance with the present invention are so-called xenogeneic antibodies. The general principle for the production of xenogeneic antibodies such as human-like antibodies in mice is described in, e.g., international applications WO91/10741, WO94/02602, WO96/34096 and WO 96/33735. As discussed above, the antibody described herein may exist in a variety of forms besides complete antibodies; including, for example, Fv, Fab and F (ab) 2, as well as in single chains; see e.g. international application WO88/09344.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, Cold Spring Harbor Laboratory Press, 2nd ed. (1988); Hammerling et al., in: Monoclonal Antibodies and T-Cell Hybridomas Elsevier, N.Y., 563-681 (1981), said references incorporated by reference in their entireties. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology.

In the known hybridoma process (Kohler et al., Nature 256 (1975), 495) the relatively short-lived, or mortal, lymphocytes from a mammal, e.g., B cells derived from a murine subject as described herein, are fused with an immortal tumor cell line (e.g., a myeloma cell line), thus, producing hybrid cells or "hybridomas" which are both immortal and capable of producing the genetically coded antibody of the B cell. The resulting hybrids are segregated into single genetic strains by selection, dilution, and re-growth with each individual strain comprising specific genes for the formation of a single antibody. They produce antibodies, which are homogeneous against a desired antigen and, in reference to their pure genetic parentage, are termed "monoclonal".

Hybridoma cells thus prepared are seeded and grown in a suitable culture medium that contain one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. The binding specificity of the monoclonal antibodies produced by hybridoma cells is determined by in vitro assays such as immunoprecipitation, radioimmunoassay (RIA) or enzyme-linked immunoabsorbent assay (ELISA) as described herein. After hybridoma cells are identified that produce antibodies of the desired specificity, affinity and/or activity, the clones may be subcloned by limiting dilution procedures and grown by standard methods; see, e.g., Goding, Monoclonal Antibodies: Principles and Practice, Academic Press, pp 59-103 (1986). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

In another embodiment, lymphocytes can be selected by micromanipulation and the variable genes isolated. For example, peripheral blood mononuclear cells can be isolated from an immunized or naturally immune mammal, e.g., a human, and cultured for about 7 days in vitro. The cultures can be screened for specific immunoglobulins that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the VH and VL genes can be amplified using, e.g., RT-PCR. The VH and VL genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the invention as described below are described in Current Protocols in Immunology, Coligan et al., Eds., Green Publishing Associates and Wiley-Interscience, John Wiley and Sons, New York (1991) which is herein incorporated by reference in its entirety, including supplements.

Antibodies, such as those described above, can be made, for example, by preparing and expressing synthetic genes that encode the recited amino acid sequences. Methods of generating variants (e.g., comprising amino acid substitutions) of any of the anti-ApoE antibodies are well known in the art. These methods include, but are not limited to, preparation by site-directed (or oligonucleotide-mediated) mutagenesis, PCR mutagenesis, and cassette mutagenesis of a prepared DNA molecule encoding the antibody or any portion thereof (e.g., a framework region, a CDR, a constant region). Site-directed mutagenesis is well known in the art (see, e.g., Carter et al., *Nucl. Acids Res.,* 13:4431-4443 (1985) and Kunkel et al., *Proc. Natl. Acad. Sci. USA,* 82:488 (1987)). PCR mutagenesis is also suitable for making amino acid sequence variants of the starting polypeptide. See Higuchi, in *PCR Protocols, pp.* 177-183 (Academic Press, 1990); and Vallette et al., *Nucl. Acids Res.* 17:723-733 (1989). Another method for preparing sequence variants, cassette mutagenesis, is based on the technique described by Wells et al., *Gene,* 34:315-323 (1985).

Antibodies can be produced in bacterial or eukaryotic cells. Some antibodies, e.g., Fab's, can be produced in bacterial cells, e.g., *E. coli* cells. Antibodies can also be produced in eukaryotic cells such as transformed cell lines (e.g., CHO, 293E, COS, Hela). In addition, antibodies (e.g., scFv's) can be expressed in a yeast cell such as *Pichia* (see, e.g., Powers et al., *J Immunol Methods.* 251:123-35 (2001)), *Hanseula*, or *Saccharomyces*. To produce the antibody or antigen binding fragments thereof of interest, a polynucleotide encoding the antibody is constructed, introduced into an expression vector, and then expressed in suitable host cells. Standard molecular biology techniques are used to prepare the recombinant expression vector, transfect the host cells, select for transformants, culture the host cells and recover the antibody.

If the antibody is to be expressed in bacterial cells (e.g., *E. coli*), the expression vector should have characteristics that permit amplification of the vector in the bacterial cells. Additionally, when *E. coli* such as JM109, DH5α, HB101, or XL1-Blue is used as a host, the vector must have a promoter, for example, a lacZ promoter (Ward et al., 341: 544-546 (1989), araB promoter (Better et al., *Science,* 240:1041-1043 (1988)), or T7 promoter that can allow efficient expression in *E. coli*. Examples of such vectors include, for example, M13-series vectors, pUC-series vectors, pBR322, pBluescript, pCR-Script, pGEX-5X-1 (Pharmacia), "QIAexpress system" (QIAGEN), pEGFP, and pET (when this expression vector is used, the host is preferably BL21 expressing T7 RNA polymerase). The expression vector may contain a signal sequence for antibody secretion. For production into the periplasm of *E. coli*, the pelB signal sequence (Lei et al., J. Bacteriol., 169:4379 (1987)) may be used as the signal sequence for antibody secretion. For bacterial expression, calcium chloride methods or electroporation methods may be used to introduce the expression vector into the bacterial cell.

If the antibody is to be expressed in animal cells such as CHO, COS, and NIH3T3 cells, the expression vector includes a promoter necessary for expression in these cells, for example, an SV40 promoter (Mulligan et al., *Nature,* 277:108 (1979)), MMLV-LTR promoter, EF1α promoter (Mizushima et al., *Nucleic Acids Res.,* 18:5322 (1990)), or CMV promoter. In addition to the nucleic acid sequence encoding the immunoglobulin or domain thereof, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin, or methotrexate, on a host cell into which the vector has been introduced. Examples of vectors with selectable markers include pMAM, pDR2, pBK-RSV, pBK-CMV, pOPRSV, and pOP13.

In one embodiment, antibodies are produced in mammalian cells. Exemplary mammalian host cells for expressing an antibody include Chinese Hamster Ovary (CHO cells) (including $dhfr^-$ CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), human embryonic kidney 293 cells (e.g., 293, 293E, 293T), COS cells, NIH3T3 cells, lymphocytic cell lines, e.g., NSO myeloma cells and SP2 cells, and a cell from a transgenic animal, e.g., a transgenic mammal.

The antibodies of the present disclosure can be isolated from inside or outside (such as medium) of the host cell and purified as substantially pure and homogenous antibodies. Methods for isolation and purification commonly used for antibody purification may be used for the isolation and purification of antibodies, and are not limited to any particular method. Antibodies may be isolated and purified by appropriately selecting and combining, for example, column chromatography, filtration, ultrafiltration, salting out, solvent precipitation, solvent extraction, distillation, immunoprecipitation, SDS-polyacrylamide gel electrophoresis, isoelectric focusing, dialysis, and recrystallization. Chromatography includes, for example, affinity chromatography, ion exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., Cold Spring Harbor Laboratory Press, 1996). Chromatography can be carried out using liquid phase chromatography such as HPLC and FPLC. Columns used for affinity chromatography include protein A column and protein G column. Examples of columns using protein A column include Hyper D, POROS, and Sepharose FF (GE Healthcare Biosciences). The present disclosure also includes antibodies that are highly purified using these purification methods.

Characterization of the Antibodies

The ApoE-binding properties of the antibodies described herein may be measured by any standard method, e.g., one or more of the following methods: OCTET®, Surface Plasmon Resonance (SPR), BIACORE™ analysis, Enzyme Linked Immunosorbent Assay (ELISA), EIA (enzyme immunoassay), RIA (radioimmunoassay), and Fluorescence Resonance Energy Transfer (FRET).

Methods for using SPR are described, for example, in U.S. Pat. No. 5,641,640; Raether (1988) *Surface Plasmons* Springer Verlag; Sjolander and Urbaniczky (1991) *Anal. Chem.* 63:2338-2345; Szabo et al. (1995) *Curr. Opin. Struct. Biol.* 5:699-705 and on-line resources provide by BIAcore International AB (Uppsala, Sweden). Information from SPR can be used to provide an accurate and quantitative measure of the equilibrium dissociation constant ($K_d$), and kinetic parameters, including $K_{on}$ and $K_{off}$, for the binding of a biomolecule to a target.

Epitopes can also be directly mapped by assessing the ability of different antibodies to compete with each other for binding to wild type ApoE or mutant ApoE (e.g. ApoEch) using BIACORE chromatographic techniques (Pharmacia BIAtechnology Handbook, "Epitope Mapping", Section 6.3.2, (May 1994); see also Johne et al. (1993) *J. Immunol. Methods,* 160:191-198).

When employing an enzyme immunoassay, a sample containing an antibody, for example, a culture supernatant of antibody-producing cells or a purified antibody is added to an antigen-coated plate. A secondary antibody labeled with an enzyme such as alkaline phosphatase is added, the plate is incubated, and after washing, an enzyme substrate such as p-nitrophenylphosphate is added, and the absorbance is measured to evaluate the antigen binding activity.

Additional general guidance for evaluating antibodies, e.g., Western blots and immunoprecipitation assays, can be found in *Antibodies: A Laboratory Manual*, ed. by Harlow and Lane, Cold Spring Harbor press (1988)).

Mutant ApoE Proteins, Peptides and Fusion Proteins Thereof

The present disclosure provides mutant ApoE proteins or fragments thereof containing amino acid substitutions at one or more positions in the HSPG-binding domain as compared to a wild type ApoE protein. In some embodiments, the mutant ApoE protein or fragments thereof includes an amino acid other than Arginine at position 136. In some embodiments, the mutant ApoE protein or fragments thereof contains Serine, Histidine, or Cysteine at position 136. Also provided are nucleic acid (e.g., DNA or RNA) sequences encoding the mutant ApoE proteins or fragments thereof, and vectors containing the nucleic acid sequences. The mutant ApoE proteins or fragments thereof, nucleic acids encoding such proteins or fragments, and vectors containing the nucleic acid sequences are useful for treating or preventing disorders associated with dementia or mild cognitive impairment (MCI) (e.g. Alzheimer's disease, vascular dementia, Lewy body dementia, frontotemporal dementia, Parkinson's disease, or Huntington's disease), neurodegenerative diseases, cerebrovascular diseases, brain injury, retinal degeneration, or retinal injury.

In some embodiments, the mutant ApoE protein is an ApoEch protein (e.g. ApoE2ch, ApoE3ch, or ApoE4ch protein). Fragments of the ApoEch protein that includes the amino acid position 136 are also contemplated here. Exemplary sequence of a full-length ApoE3ch protein is shown below. The mutation from arginine to serine is bolded and double underlined.

(SEQ ID NO: 45)

MKVLWAALLVTFLAGCQAKVEQAVETEPEPELRQQTEWQSGQRWELALG

RFWDYLRWVQTLSEQVQEELLSSQVTQELRALMDETMKELKAYKSELEEQ

LTPVAEETRARLSKELQAAQARLGADMEDVCGRLVQYRGEVQAMLGQST

EELRVSLASHLRKLRKRLLRDADDLQKRLAVYQAGAREGAERGLSAIRER

LGPLVEQGRVRAATVGSLAGQPLQERAQAWGERLRARMEEMGSRTRDRLD

EVKEQVAEVRAKLEEQAQQIRLQAEAFQARLKSWFEPLVEDMQRQWAGL

VEKVQAAVGTSAAPVPSDNH

In some embodiments, the methods disclosed herein allows the mutant ApoE protein or fragments thereof to cross the blood-brain barrier. The mutant ApoE protein or fragments thereof may be delivered using nanocarriers, including but not limited to, polymeric nanoparticles, lipid based nanoparticles, liposome, micelle, dendrimer, a human cell expressing the protein, and nanotube (See, Dominguez et al. J Nanosci nanotechnol. 14(1):766-79, 2014). In some embodiments, the mutant ApoE protein or fragments thereof is delivered intranasally, via intracarotid or transmucosal delivery (e.g. intracarotid infusion of hypertonic solutions (arabinose or mannitol); see, Sanchez-Covarrubias et al., Curr Pharm Des. 20(10): 1422-49, 2014 and Miyake et al., World J Otorhinolaryngol Head Neck Surg. 1(1):11-16, 2015), or via the use of chlorotoxin (See, McCall et al., Tissue Barriers 2(4):e944449, 2014). Hypothermia techniques, receptor-mediated transport, cell-penetrating peptides, and cell-mediated delivery can also be used to facilitate the ApoE3ch protein to cross the blood brain barrier (See, Pandey et al., Tissue Barriers 4(1): e1129476, 2016). For example, immunocytes and stem cells (e.g., neural stem cells, induced pluripotent cells, and mesenchymal stem cells) can be used to carry therapeutic payloads across the BBB. Nanoparticle-loaded mesenchymal stem cells can be used for this purpose (See e.g., Roger et al. Biomaterials 31:8393-401, 2010). Genetically modified stem cells (e.g. genetically modified mesenchymal stem cells) can also be used (See e.g., Ebrahimi and Lalvand Hygeia. J. D. Med. vol. 5 (1): 90-104, 2013). Chemical drug delivery systems (CDDS), such as those described in He et al., Cells, 7(4):24, 2018, can also be used. Additional methods of transporting proteins across the blood-brain barrier are known in the art.

Nucleic acids (e.g., DNA or mRNA) encoding the mutant ApoE protein (e.g., any of the mutant ApoE proteins described herein, e.g. ApoEch) or fragments thereof are contemplated herein. In some embodiments, mRNA encoding the ApoEch protein may be modified to increase stability (such as those described in Zangi et al., Nat Biotechnol. 31(10):898-907, 2013 and developed by Moderna, Inc.; and those described in Alberer et al., Lancet 390(10101):1511-1520, 2017 and developed by Curevac and BioNTech).

Viral vectors containing DNA sequences encoding the mutant ApoE or fragments thereof are contemplated herein. An exemplary cDNA sequence encoding the full-length ApoE3ch protein (including the signal peptide region) is shown below. The mutation from Cytosine to Adenine is bolded and double underlined.

(SEQ ID NO: 56)

ATGAAGGTTCTGTGGGCTGCGTTGCTGGTCACATTCCTGGCAGGATGCCA

GGCCAAGGTGGAGCAAGCGGTGGAGACAGAGCCGGAGCCCGAGCTGCGCC

AGCAGACCGAGTGGCAGAGCGGCCAGCGCTGGGAACTGGCACTGGGTCGC

TTTTGGGATTACCTGCGCTGGGTGCAGACACTGTCTGAGCAGGTGCAGGA

GGAGCTGCTCAGCTCCCAGGTCACCCAGGAACTGAGGGCGCTGATGGACG

AGACCATGAAGGAGTTGAAGGCCTACAAATCGGAACTGGAGGAACAACTG

ACCCCGGTGGCGGAGGAGACGCGGGCACGGCTGTCCAAGGAGCTGCAGGC

GGCGCAGGCCCGGCTGGGCGCGGACATGGAGGACGTGTGCGGCCGCCTGG

TGCAGTACCGCGGCGAGGTGCAGGCCATGCTCGGCCAGAGCACCGAGGAG

CTGCGGGTGAGCCTCGCCTCCCACCTGCGCAAGCTGCGTAAGCGGCTCCT

CCGCGATGCCGATGACCTGCAGAAGCGCCTGGCAGTGTACCAGGCCGGGG

CCCGCGAGGGCGCCGAGCGCGGCCTCAGCGCCATCCGCGAGCGCCTGGGG

CCCCTGGTGGAACAGGGCCGCGTGCGGGCCGCCACTGTGGGCTCCCTGGC

CGGCCAGCCGCTACAGGAGCGGGCCCAGGCCTGGGGCGAGCGGCTGCGCG

CGCGGATGGAGGAGATGGGCAGCCGGACCCGCGACCGCCTGGACGAGGTG

AAGGAGCAGGTGGCGGAGGTGCGCGCCAAGCTGGAGGAGCAGGCCCAGCA

GATACGCCTGCAGGCCGAGGCCTTCCAGGCCCGCCTCAAGAGCTGGTTCG

AGCCCCTGGTGGAAGACATGCAGCGCCAGTGGGCCGGGCTGGTGGAGAAG

GTGCAGGCTGCCGTGGGCACCAGCGCCGCCCCTGTGCCCAGCGACAATCA

CTGA

Suitable vectors are known in the art. In some embodiments, the viral vector is an AAV vector (such as those described in Rosenberg et al., Hum Gene Ther Clin Dev 29 (1): 24-47, 2018). cDNA sequences encoding an ApoE protein containing a mutation at the R136 position other than R136S are also included. In some embodiments, the mutation is R136H or R136C.

Peptides and Fusion Proteins

In some embodiments, provided herein are peptides that comprise or consist of the HSPG/heparin-binding domain of a wild type or mutant ApoE (e.g., any of the mutant ApoE proteins described herein). In some instances, the amino acid sequence of the peptides provided herein comprise or consist of the sequences selected from the group consisting of (SEQ ID NO: 57)
STEELRVRLASHLRKLRKRLLRDADDLQK, (SEQ ID NO: 58)
STEELRVSLASHLRKLRKRLLRDADDLQK, (SEQ ID NO: 59)
RLVQYRGEVQAMLGQSTEELRVRLASHLRKL,
and (SEQ ID NO: 60)
RLVQYRGEVQAMLGQSTEELRVSLASHLRKL.

Variants having at least 80%, 85%, 90%, 95%, 96%, 97%, 98%, 99% or greater sequence identity with these sequences can also be used. Also disclosed are fusion proteins comprising the peptides provided above. In some embodiments, the fusion proteins further include an Fc region of a human antibody (e.g., human IgG1, IgG2, IgG3, or IgG4). In some instances, the fusion protein comprises an Fc region of a human antibody at the C-terminal of the HSPG/heparin-binding domain of a wild type or mutant ApoE. In some instances, the fusion protein comprises an Fc region of a human antibody at the N-terminal of the HSPG/heparin-binding domain of a wild type or mutant ApoE.

In some instances, the peptides and fusion proteins provided herein competes with a wild type ApoE protein for binding to HSPG/heparin. In some instances, the peptides and fusion proteins provided herein reduce or modulate the binding between a wild type ApoE protein and HSPG/heparin. In certain embodiments, the peptides and fusion proteins provided herein inhibits and/or reduces HSPG/heparin-binding of a wild type ApoE protein, and reduces the severity of symptoms when administered to human patients having one or more of, or animal models of: disorders associated with dementia or mild cognitive impairment (MCI) (e.g. Alzheimer's disease, vascular dementia, Lewy body dementia, frontotemporal dementia, Parkinson's disease, Huntington's disease), neurodegenerative diseases, cerebrovascular diseases, brain injury, retinal degeneration, or retinal injury. These features of the peptides and fusion proteins provided herein can be measured according to methods known in the art.

Also provided herein are anti-ApoE vaccines, which can be used to elicit a protective immune response against ApoE. In some embodiments, the anti-ApoE vaccines include one or more of the ApoE peptides provided herein (e.g., and a pharmaceutically acceptable adjuvant. Pharmaceutically acceptable adjuvants are known in the art.

Pharmaceutical Compositions and Methods of Administration

The methods described herein include the use of pharmaceutical compositions comprising any of the antibodies, peptides or fusion proteins described herein as an active ingredient.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intracranial, intranasal, intra-carotid, intravenous, intradermal, subcutaneous, oral (e.g., inhalation), and transmucosal.

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal. For transmucosal administration, penetrants appropriate to the barrier to be permeated are used in the formulation. Such penetrants are generally known in the art, and include, for example, detergents, bile salts, and fusidic acid derivatives. Transmucosal administration can be accomplished through the use of nasal sprays or suppositories or injection.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

CRISPR/Cas9-Mediated Gene Editing of APOE

Included herein are methods for treating or preventing disorders associated with dementia and/or mild cognitive impairment (MCI) (e.g. Alzheimer's disease, vascular dementia, Lewy body dementia, frontotemporal dementia, Parkinson's disease, or Huntington's disease), neurodegenerative diseases, cerebrovascular diseases, brain injury, retinal degeneration, or retinal injury, by editing the APOE gene using a genome editing system. Generally, the methods include administering a therapeutically effective amount of a genome editing system as described herein, to a subject who is in need of, or who has been determined to be in need of, such treatment. The term "genome editing system" refers to any system having RNA-guided DNA editing activity. Genome editing systems of the present disclosure include at least two components adapted from naturally occurring CRISPR systems: a gRNA and an RNA-guided nuclease. These two components form a complex that is capable of associating with a specific nucleic acid sequence in a cell and editing the DNA in or around that nucleic acid sequence, for example by making one or more of a single-strand break (an SSB or nick), a double-strand break (a DSB) and/or a base substitution. See, e.g., WO2018/026976 for a full description of genome editing systems. In certain aspects, the present disclosure provides AAV vectors encoding CRISPR/Cas9 genome editing systems, and on the use of such vectors to treat or prevent disorders as described herein.

RNA-Guided Nucleases/Cas9

Various RNA-guided nucleases can be used in the present methods, e.g., as described in WO 2018/026976. In some embodiments, the RNA-guided nuclease used in the present methods and compositions is a *S. aureus* Cas9 or a *S. pyogenes* cas9. Exemplary Cas9 proteins of the disclosure may be isolated or derived from any species, including, but not limited to, a bacteria or an archaea. In some embodiments of this disclosure a Cas9 sequence is modified to include two nuclear localization sequences (NLSs) (e.g., PKKKRKV (SEQ ID NO:61) at the C- and N-termini of the Cas9 protein, and a mini-polyadenylation signal (or Poly-A sequence). An exemplary NLS is SV40 large T antigen NLS (PKKKRRV (SEQ ID NO:62)) and nucleoplasmin NLS (KRPAATKKAGQAKKKK (SEQ ID NO:63)). Other NLSs are known in the art; see, e.g., Cokol et al., EMBO Rep. 2000 Nov. 15; 1(5):411-415; Freitas and Cunha, Curr Genomics. 2009 December; 10(8): 550-557. An exemplary polyadenylation signal is TAGCAATAAAGGATCGTTTATTTTCATTGGAAGCGTGTGTTGGTTTTTTGATCAGGCGCG (SEQ ID NO:64). In some embodiments, the RNA-guided nuclease is a nuclease-dead Cas protein (e.g., dCas9).

Guide RNAS

Provided herein are guide RNAs (gRNAs) designed to target one or more sites in the HSPG binding domain of a wild type ApoE. In some embodiments, the gRNAs are designed to introduce a mutation in the wild type ApoE that results in a mutation at amino acid position 136. In some embodiments, the guide RNAs provided herein are designed to introduce an R136S mutation in a wild type APOE gene (e.g. APOE2, APOE3, or APOE4), where exemplary guide RNAs can be found in Table 7. In some embodiments, also provided are templates for repairing the double stranded break and introducing an R136S mutation. An exemplary template sequence is as follows:

(SEQ ID NO: 65)

CGCCTGGTGCAGTACCGCGGCGAGGTGCAGGCCATGCTCGGCCAGAGCAC aGAGGAGCT*c*CGcGTGaGtCTCGCaagtCCACCTGCGCAAGCTGCGTAAG

CGGCTCCTCCGCGATGCCGATGACCTGC where silent mutations to abolish PAM motifs are double underlined, the codon corresponding to the R136S mutation is bolded, and silent mutation to generate SacI site for cleaving PCR products from clones that received the template is italicized.

In some embodiments, the guide RNAs provided herein are designed to target exon 3 (amino acids 1-61) of a wild type APOE gene, or of a variant present in a subject (the methods can thus include determining the sequence of the APOE gene in a subject, and using that sequence to determine the sequence of a suitable guideRNA for targeting exon 3 in that subject). In some embodiments, a double stranded break repair through non-homologous end joining (NHEJ) results in short insertions or deletions leading to ApoE knockout. Exemplary guide RNA sequences for ApoE knockout are shown in Table 8.

Base Editing

In some embodiments, the APOE gene is edited using the base editing technique (e.g. those described in Rees and Liu, Nature Reviews Genetics 19, 770-788, 2018; Komor et al., Nature 533, 420-424). In some embodiments, guide RNAs are designed to introduce an R136H mutation in a wild type APOE gene (e.g. APOE2, APOE3, or APOE4) using base editing, where exemplary guide RNAs can be found in Table 6. Base editors that convert C/G to A/T and adenine base editors that convert A/T to G/C can be used to introduce point mutations. Exemplary base editors include those described in Komor et al., Nature 533, 420-424 and Gaudelli et al., Nature 551, 464-471).

AAV Delivery Systems

The methods include delivery of a CRISPR/Cas9 genome editing system, including a Cas9 nuclease and one or two guide RNAs, to a subject in need thereof. The delivery methods can include, e.g., viral delivery, e.g., preferably using an adeno-associated virus (AAV) vector that comprises sequences encoding the Cas9 and guide RNA(s). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro and Immunol. 158:97-129 (1992)). AAV vectors efficiently transduce various cell types and can produce long-term expression of transgenes in vivo. AAV vectors have been extensively used for gene augmentation or replacement and have shown therapeutic efficacy in a range of animal models as well as in the clinic; see, e.g., Mingozzi and High, Nature Reviews Genetics 12, 341-355 (2011); Deyle and Russell, Curr Opin Mol Ther. 2009 August; 11(4): 442-447; Asokan et al., Mol Ther. 2012 April; 20(4): 699-708. AAV vectors containing as little as 300 base pairs of AAV can be packaged and can produce recombinant protein expression. For example, AAV2, AAV5, AAV2/5, AAV2/8 and AAV2/7 vectors have been used to introduce DNA into photoreceptor cells (see, e.g., Pang et al., Vision Research 2008, 48 (3): 377-385; Khani et al., Invest Ophthalmol Vis Sci. 2007 September; 48(9):3954-61; Allocca et al., J. Virol. 2007 81(20):11372-11380). In some embodiments, the AAV vector can include (or include a sequence encoding) an AAV capsid polypeptide described in PCT/US2014/060163; for example, a virus particle comprising an AAV capsid polypeptide having an amino acid sequence selected from the group consisting of SEQ ID NOs: 1, 3, 5, 7, 9, 11, 13, 15, and 17 of PCT/US2014/060163, and a Cas9 sequence and guide RNA sequence as described herein. In some embodiments, the AAV capsid polypeptide is an Anc80 polypeptide, e.g., Anc80L27; Anc80L59; Anc80L60; Anc80L62; Anc80L65; Anc80L33; Anc80L36; or Anc80L44. In some embodiments, the AAV incorporates inverted terminal repeats (ITRs) derived from the AAV2 serotype. Exemplary left and right ITRs are presented in Table 6 of WO 2018/026976. It should be noted, however, that numerous modified versions of the AAV2 ITRs are used in the field, and the ITR sequences shown below are exemplary and are not intended to be limiting. Modifications of these sequences are known in the art, or will be evident to skilled artisans, and are thus included in the scope of this disclosure.

Cas9 expression is driven by a promoter known in the art. In some embodiments, expression is driven by one of three promoters: cytomegalovirus (CMV), elongation factor-1 (EFS), or human g-protein receptor coupled kinase-1 (hGRK1), which is specifically expressed in retinal photoreceptor cells. Nucleotide sequences for each of these promoters are provided in Table 5 of WO 2018/026976. Modifications of these sequences may be possible or desirable in certain applications, and such modifications are within the scope of this disclosure.

Expression of the gRNAs in the AAV vector is driven by a promoter known in the art. In some embodiments, a polymerase III promoter, such as a human U6 promoter. An exemplary U6 promoter sequence is presented below:

```
                                          (SEQ ID NO: 66)
AAGGTCGGGCAGGAAGAGGGCCTATTTCCCATGATTCCTTCATATTTGCA

TATACGATACAAGGCTGTTAGAGAGATAATTAGAATTAATTTGACTGTAA

ACACAAAGATATTAGTACAAAATACGTGACGTAGAAAGTAATAATTTCTT

GGGTAGTTTGCAGTTTTAAAATTATGTTTTAAAATGGACTATCATATGCT

TACCGTAACTTGAAAGTATTTCGATTTCTTGGCTTTATATATCTTGTGGA

AAGGACGAAACACC.
```

In some embodiments, the nucleic acid or AAV vector shares at least 80%, 85%, 90%, 95%, 96%, 97%, 98%, 99% or greater sequence identity with one of the nucleic acids or AAV vectors recited above.

The AAV genomes described above can be packaged into AAV capsids (for example, AAV5 capsids), which capsids can be included in compositions (such as pharmaceutical compositions) and/or administered to subjects. An exemplary pharmaceutical composition comprising an AAV capsid according to this disclosure can include a pharmaceutically acceptable carrier such as balanced saline solution (BSS) and one or more surfactants (e.g., Tween 20) and/or a thermosensitive or reverse-thermosensitive polymer (e.g., pluronic). Other pharmaceutical formulation elements known in the art may also be suitable for use in the compositions described here.

Compositions comprising AAV vectors according to this disclosure can be administered to subjects by any suitable means, including without limitation injection (e.g., intracranial injection) and intranasal delivery. The concentration of AAV vector within the composition is selected to ensure, among other things, that a sufficient AAV dose is administered to the brain of the subject, taking account of dead volume within the injection apparatus and the relatively limited volume that can be safely administered. Suitable doses may include, for example, $1\times10^{11}$ viral genomes (vg)/mL, $2\times10^{11}$ viral genomes (vg)/mL, $3\times10^{11}$ viral genomes (vg)/mL, $4\times10^{11}$ viral genomes (vg)/mL, $5\times10^{11}$ viral genomes (vg)/mL, $6\times10^{11}$ viral genomes (vg)/mL, $7\times10^{11}$ viral genomes (vg)/mL, $8\times10^{11}$ viral genomes (vg)/mL, $9\times10^{11}$ viral genomes (vg)/mL, $1\times10^{12}$ vg/mL, $2\times10^{12}$ viral genomes (vg)/mL, $3\times10^{12}$ viral genomes (vg)/mL, $4\times10^{12}$ viral genomes (vg)/mL, $5\times10^{12}$ viral genomes (vg)/mL, $6\times10^{12}$ viral genomes (vg)/mL, $7\times10^{12}$ viral genomes (vg)/mL, $8\times10^{12}$ viral genomes (vg)/mL, $9\times10^{12}$ viral genomes (vg)/mL, $1\times10^{13}$ vg/mL, $2\times10^{13}$ viral genomes (vg)/mL, $3\times10^{13}$ viral genomes (vg)/mL, $4\times10^{13}$ viral genomes (vg)/mL, $5\times10^{13}$ viral genomes (vg)/mL, $6\times10^{13}$ viral genomes (vg)/mL, $7\times10^{13}$ viral genomes (vg)/mL, $8\times10^{13}$ viral genomes (vg)/mL, or $9\times10^{13}$ viral genomes (vg)/mL. Any suitable volume of the composition may be delivered to the subretinal or cochlear space. In some instances, the volume is selected to form a bleb in the subretinal space, for example 1 microliter, 10 microliters, 50 microliters, 100 microliters, 150 microliters, 200 microliters, 250 microliters, 300 microliters, etc.

Explants are particularly useful for studying the expression of gRNAs and/or Cas9 following viral transduction, and for studying genome editing over comparatively short intervals. These models also permit higher throughput than may be possible in animal models, and can be predictive of expression and genome editing in animal models and subjects. Small (mouse, rat) and large animal models (such as rabbit, pig, nonhuman primate) can be used for pharmacological and/or toxicological studies and for testing the systems, nucleotides, vectors and compositions of this disclosure under conditions and at volumes that approximate those that will be used in clinic. Because model systems are selected to recapitulate relevant aspects of human anatomy and/or physiology, the data obtained in these systems will generally (though not necessarily) be predictive of the behavior of AAV vectors and compositions according to this disclosure in human and animal subjects.

Methods of Screening (Test Compounds)

Included herein are methods for screening test compounds, e.g., polypeptides, polynucleotides, inorganic or organic large or small molecule test compounds, to identify agents useful in the treatment or prevention of disorders associated with dementia and/or mild cognitive impairment (e.g., Alzheimer's disease, vascular dementia, Lewy body dementia, frontotemporal dementia, Parkinson's disease, or Huntington's disease), neurodegenerative diseases, cerebrovascular diseases, brain injury, retinal degeneration, or retinal injury. In some embodiments, the test compounds modulate the HSPG/heparin-binding properties of an ApoE protein (e.g. a wild type ApoE protein). In some embodiments, the test compounds reduce the HSPG/heparin-binding properties of an ApoE protein (e.g. a wild type ApoE protein).

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample, e.g., a sample containing one or more ApoE protein(s), and one or more effects of the test compound (e.g. HSPG/heparin binding affinity of the ApoE protein(s)) is evaluated. The ability of test compounds to modify the HSPG/heparin binding affinity of the ApoE protein(s) can be evaluated, e.g. using heparin sepharose columns, or antibodies that specifically recognize the HSPG-binding domain of ApoE as described herein. In some embodiments, methods for screening test compounds as described herein include evaluating the ability of a test compound to modify (e.g. inhibit or reduce) binding of antibodies as described herein that bind to one or more HSPG-binding sites or one or more sites of allosteric modulation of HSPG binding of a wild type or mutant ApoE. In some embodiments, a test compound competes with the antibodies as described herein for ApoE binding.

In some embodiments, the test sample is, or is derived from (e.g., a sample taken from) an in vivo model of a disorder as described herein. For example, an animal model, e.g., a rodent such as a rat, can be used.

A test compound that has been screened by a method described herein and determined to reduce or modify ApoE and HSPG/heparin binding, can be considered a candidate compound. A candidate compound that has been screened, e.g., in an in vivo model of a disorder, e.g., dementia and/or mild cognitive impairment (such as those associated with Alzheimer's disease, vascular dementia, Lewy body dementia, frontotemporal dementia, Parkinson's disease or Huntington's disease), neurodegenerative diseases, cerebrovascular diseases, brain injury, retinal degeneration, or retinal injury, and determined to have a desirable effect on the disorder, e.g., on one or more symptoms of the disorder, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that have a desirable effect on the disorder) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating, preventing, or delaying of development or progression of disorders associated with dementia and/or mild cognitive impairment, as described herein, e.g., Alzheimer's disease, vascular dementia, Lewy body dementia, frontotemporal dementia, Parkinson's disease or Huntington's disease, and useful in treating, preventing, or delaying of development or progression of neurodegenerative diseases, cerebrovascular diseases, brain injury, retinal degeneration, or retinal injury. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of a disorder associated with any of the disorders as described herein. The animal can be monitored for a change in the disorder, e.g., for an improvement in a parameter of the disorder, e.g., a parameter related to clinical outcome.

Methods of Treatment

The methods described herein include methods for the treatment, prevention, or delay of development or progression of disorders associated with dementia and/or mild cognitive impairments, neurodegenerative diseases, cerebrovascular diseases, brain injury, retinal degeneration, or retinal injury. In some embodiments, the disorder associated with dementia and/or mild cognitive impairments is Alzheimer's disease, vascular dementia, Lewy body dementia, frontotemporal dementia, Parkinson's disease, or Huntington's disease. Additional non-limiting examples of neurodegenerative diseases include prion disease, motor neuron disease, and amyotrophic lateral sclerosis (ALS). Non-limiting examples of cerebrovascular diseases include stroke, carotid stenosis, vertebral stenosis, and aneurysms. Non-limiting examples of brain injuries include traumatic brain injury and acquired brain injury. Retinal degeneration such as glaucoma, age-related macular degeneration, may involve amyloid-beta and neurofibrillary tangle toxicity, establishing a link between retinal degeneration and neurodegeneration (e.g., Alzheimer's disease) (See, e.g. Mckinnon, Frontiers in Bioscience 8, s1140-1156, 2003; Johnson et al. PNAS 99 (18) 11830-11835, 2002; and Sivak, Investigative Ophthalmology &Visual Science, 54 (1) 871-880, 2013). Accordingly, treatments for neurodegeneration can be used to treat retinal or optic nerve degeneration.

The methods include administering a therapeutically effective amount of any of the antibodies, peptides, fusion proteins, or genome editing system as described herein, to a subject who is in need of, or who has been determined to be in need of, such treatment.

The methods described herein are also useful for subjects at risk for developing any of the disorders described herein. Subjects at risk for developing Alzheimer's disease may include those that are homozygous or heterozygous for the APOE4 allele, carriers of autosomal dominant Alzheimer's disease-causing mutations (e.g. mutations in the amyloid beta precursor (APP) gene, PSEN1 gene, or PSEN2 gene), trisomy 21 (e.g. subjects whose cognitive impairment is developmental only). Subjects at risk for developing Alzheimer's disease may also include those that have polygenic risk scores associated with increased risk of developing the disease, and those with brain imaging or other biomarker (e.g. biomarker in the body fluids) evidence of Alzheimer's disease. The methods for preventing or delaying the development of disorders described herein may also be useful for subjects that are not at risk for developing the above disorders, such as any subjects over the age of 50 (e.g. over the age of 55, 60, 65, 70, 75, 80, 85, 90, or 95).

As used in this context, to "treat" means to ameliorate at least one symptom of the disorder associated with the disorders as described herein. Often, Alzheimer's disease results in fibril formation, amyloid aggregation, and reduced cognitive performance; thus, a treatment can result in a reduction in fibril formation and/or amyloid aggregation in the brain, reduced tau formation of tangles, improved brain metabolism, improved neurocognitive functions and/or cognitive performance.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art can develop equivalent means or reactants without the exercise of inventive capacity and without departing from the scope of the invention.

Example 1: Identification of the APOE3 Christchurch R136S Mutation in a PSEN1 Mutation Carrier Materials and Methods:

Clinical assessments: Institutional review boards from the University of Antioquia, Massachusetts General Hospital, and the Schepens Eye Research Institute of Massachusetts Eye and Ear approved this study. Like all of the research participants, the proband case provided her written informed consent. Clinical ratings and neuropsychological tests were performed as noted in Table 1. PSEN1 E280A genotyping was conducted as previously described.[1]

All clinical measures were undertaken at the University of Antioquia (Medellín, Colombia) and were conducted in Spanish by physicians and psychologists trained in assessment. Neurocognitive testing included a comprehensive multi-domain assessment. Some of the test administered were the Spanish versions of the Mini-Mental State Examination (MMSE), the Clinical Dementia Rating (CDR), and the Consortium to Establish a Registry for Alzheimer's disease battery, which have been adapted to this Colombian population.[2] Additional testing consisted of the Yesavage Geriatric Depression Scale[3] and the Functional Assessment Staging test[4], which were done within six months of brain imaging.

A detailed ophthalmic evaluation was performed. It included visual acuity assessment, slit-lamp and indirect ophthalmoscopy examination. Ultra-widefield fundus and fundus autofluorescence images using Optos Panoramic 200Tx imaging system (Optos PLC, Dunfermline, Scotland, UK) were obtained. Additionally, Spectralis SD-OCT (Heidelberg Engineering, Heidelberg, Germany) and OCT angiography with Cirrus HD-OCT with AngioPlex (Carl Zeiss Meditec, Dublin, CA) were also done.

Additional studies were conducted after the PSEN1 E280A mutation carrier was discovered to have two copies of the APOE3ch variant. A fasting serum lipid panel was performed to explore the possibility of hyperliproteinemia type III, a condition found in 5-10% of persons homozygous for the relatively AD protective APOE2 allele and in most but not all APOE3ch carriers.[5]

Finally, an analysis of data from clinically and neuropathologically verified AD cases and controls from the AD Genetics Consortium was used to clarify whether homozygosity for the APOE2 allele was associated with an exceptionally low risk of late-onset AD dementia.

Whole exome sequencing: Whole-exome capture and sequencing were performed using Illumina chemistry for variant discovery; rare variants with less than 1% frequency in genes previously associated with AD were considered in the search for candidate risk modifiers. Specifically, rare DNA variants (minor allele frequency <1%) within exonic regions and splice-site junctions (5 bp into introns) of genes were identified using bioinformatics tools. Whole exome libraries were constructed and sequenced on an Illumina HiSeq 4000 sequencer with the use of 151 bp paired-end reads. Library construction was performed using a previously described protocol[6] modified as follows. Genomic DNA input was reduced from 3 μg to 50 ng in 10 μL of solution and enzymatically sheared. Dual-indexed Illumina paired end adapters were replaced with palindromic forked adapters with unique 8 base index sequences embedded within the adapter and added to each end for adapter ligation. In-solution hybrid selection was performed using the Illumina Rapid Capture Exome enrichment kit with 38 Mb target territory (29 Mb baited). The targeted region included 98.3% of the intervals in the Refseq exome database. Dual-indexed libraries were pooled into groups of up to 96 samples prior to hybridization. The enriched library pools were quantified via PicoGreen after elution from streptavadin beads and then normalized. For cluster amplification and sequencing, the libraries prepared using forked, indexed adapters were quantified using quantitative PCR (KAPA biosystems), normalized to 2 nM using Hamilton Starlet Liquid Handling system, and pooled with equal volume using the Hamilton Starlet Liquid Handling system. Pools were then denatured in 0.1 N NaOH. Denatured samples were diluted into strip tubes using the Hamilton Starlet Liquid Handling system. Cluster amplification of the templates was performed according to the manufacturer's protocol (Illumina) using the Illumina cBot. Flowcells were sequenced on HiSeq 4000 Sequencing-by-Synthesis Kits, then analyzed using RTA2.7.3.

Exome sequencing data was processed and analyzed with the bioinformatics pipeline of the Center's Clinical Exome Sequencing of the Center for Personalized Medicine (CPM) Clinical Genomics Laboratory and the Translational Genomics Research Institute. Briefly, Edico Genome's Dragen Genome Pipeline with default parameters was used to perform sequence alignment and variant calling. The open source software samtools and bcftools (samtools.github.io/) were used along with a set of custom scripts to perform coverage determination and initial variant filtering based on ExAC (Exome Aggregation Consortium, exac. broadinstitute.org/) allele frequencies.[7] Sequence alignment was done against the Human hs37d5 decoy genome.[8] To identify the potential modifier variants, a primary gene list of 15 genes was generated based on two HPO terms: HP: 0002511, Alzheimer disease; HP: 0003584, Late onset. These genes were AAGAB, ABCC8, AKT2, APOE, APP, BEAN1, GATA1, GCK, HMGA1, HNF1B, HNF4A, LDB3, PAX4, PSEN1, and PSEN2.[9] Rare DNA variants (minor allele frequency <1%) within exonic regions and splice-site junctions (5 bp into introns) of these genes were further annotated and analyzed using a commercial tool (Cartagenia v5.0). Sequence alterations were reported according to the Human Genome Variation Society (HGVS v2.0) nomenclature guidelines.

Whole genome sequencing: Whole-genome sequencing (WGS) and a Genomizer analysis (v 10.1.0) were used to conduct a comprehensive and unbiased ranking of other potential genetic risk modifiers, including those associated with a lower risk of Alzheimer's dementia, helping to exclude other potentially protective genetic factors.[10] For processing the WGS data, the same dragen pipeline described above was used. The data was aligned to the GRCh37 decoy genome (hs37d5). Variants that were called at a depth of <10× were filtered out and then were annotated using Ensembl's Variant Effect Predictor (VEP) tool. The version of VEP using was v93. The filtered and annotated set of variants was then compiled for Genomizer analysis.

APOE structure display: Image was obtained and modified from the RCSB PDB (rcsb.org) of PDB 2L7B a previously published structure[11] using NGL Viewer[12].

APOE Genotyping by Sanger sequencing: Reaction mixture for the amplification process was performed in a 50 μL volume that included the following components: 1×PfuUltra II Hostart Master Mix, 1 μL of each primer (10 μmol/L) (Forward primer: 5'-AGCCCTTCTCCCCGCCTCCCACTGT-3' (SEQ ID NO: 67) and Reverse primer: 5'-CTCCGCCACCTGCTCCTTCACCTCG-3' (SEQ ID NO: 68)), 5% DMSO and 1 μL of genomic DNA (100 ng/μL).[13] PCR cycling was run with initial denaturation at 95° C. for 2 min followed by 35 cycles with denaturation at 95° C. for 20 seconds, annealing at 60° C. for 30 seconds, extension at 72° C. for 40 seconds, and a final extension at 72° C. for 5 min. PCR products were purified using QIAquick Gel Extraction kit from Qiagen and sequenced by MGH CCIB DNA core using the 3730xl sequencer from Applied Biosystems.

MRI and PET imaging: Pittsburgh Compound B (PiB), flortaucipir (FTP) positron emission tomography (PET) and structural magnetic resonance imaging (MRI) measurements were acquired at Massachusetts General Hospital and analyzed at Massachusetts General Hospital and Banner Alzheimer's Institute as previously described.[14] Fluorodeoxyglucose PET images were acquired at the University of Antioquia, Colombia, and analyzed as previously described[15]. Imaging data from the case were compared to those from younger PSEN1 E280A mutation carriers who developed MCI at the kindred's expected age at clinical onset, and from mutation carriers who were cognitively unimpaired.

MRI was performed on a 3T Tim Trio (Siemens) and included a magnetization-prepared rapid gradient-echo (MPRAGE) processed with Freesurfer (FS) to identify grey white and pial surfaces to permit regions of interest (ROI) parcellation as follows: cerebellar grey, hippocampus, and the following Braak Stage related cortices: entorhinal, parahippocampal, inferior temporal, fusiform, posterior cingulate, as described previously[16-19].

18F-Flortaucipir (FTP) was prepared at MGH with a radiochemical yield of 14±3% and specific activity of 216±60 GBq/μmol at the end of synthesis (60 min), and validated for human use (Shoup et al., 2013). 11C-Pittsburgh Compound B was prepared and PET images were acquired as previously described.[16] All PET images were acquired using a Siemens/CTI (Knoxville, TN) ECAT HR+ scanner (3D mode; 63 image planes; 15.2 cm axial field of view; 5.6 mm transaxial resolution and 2.4 mm slice interval. 11C PiB PET was acquired with a 8.5 to 15 mCi bolus injection followed immediately by a 60-minute dynamic acquisition in 69 frames (12×15 seconds, 57×60 seconds)). 18F FTP was acquired from 80-100 minutes after a 9.0 to 11.0 mCi bolus injection in 4×5-minute frames. PET images were reconstructed and attenuation-corrected, and each frame was evaluated to verify adequate count statistics and absence of head motion.

18F FTP specific binding was expressed in FS ROIs as the standardized uptake value ratio (SUVR) to cerebellum, similar to a previous report[19], using the FS cerebellar grey ROI as reference. For voxelwise analyses, each subject's MPRAGE was registered to the template MR in SPM8 (SPM), and the spatially transformed SUVR PET data was smoothed with a 8 mm Gaussian kernel to account for individual anatomic differences[20]. To account for possible 18F FTP off-target binding in choroid plexus, which may confound hippocampal signal, we used a linear regression to regress the choroid plexus, as previously reported[21].

11C PiB PET data were expressed as the distribution volume ratio (DVR) with cerebellar grey as reference tissue; regional time-activity curves were used to compute regional DVRs for each ROI using the Logan graphical method applied to data from 40 to 60 minutes after injection[16,22]. 11C PiB retention was assessed using a large cortical ROI aggregate that included frontal, lateral temporal and retrosplenial cortices (FLR) as described previously[23,24]

18F-fludeoxyglucose PET was performed on a 64-section PET/computed tomography imaging system (Biograph mCT; Siemens) using intravenous administration of 5 mCi (185 million Bq) of 18F-fludeoxyglucose after a 30-minute radiotracer uptake period when resting in a darkened room, followed by a 30-minute dynamic emission scan (six 5-minute frames). Images were reconstructed with computed tomographic attenuation correction. Precuneus to whole-brain cerebral metabolic rate for glucose (CMRgl) ratios were characterized from a bilateral region of interest (ROI) in each participant's 18F-fludeoxyglucose PET image using an automated brain mapping algorithm (SPM8; fil.ion.ucl.ac.uk/spm/software/spm8). Hippocampal to total intracranial volume ratios were characterized from bilateral ROIs in each participant's T1-weighted MR image using FreeSurfer (surfer.nmr.mgh.harvard.edu). All images were visually inspected to verify ROI characterization.

Amyloid aggregation studies: Human ApoE3 protein fragments (including the carboxyl-terminus domain plus a histidine tag) with and without the Christchurch variant were synthesized in bacteria, purified (Innovagen), and used to assess the differential effects of these proteins on $A\beta_{42}$ aggregation in vitro using Thioflavin T (SensoLyte® ThT β-Amyloid (1-42) Aggregation kit, cat. #AS-72214). For this assay, 55 μM of $A\beta_{42}$ was added to solutions of either 10 μM Wild Type apoE3 protein or Mutant 136 Arg→Ser ApoE3 protein in a transparent, no-binding 96-well plate. Samples were then mixed with 2 mM Thioflavin T dye and fluorescence was read at Ex/Em=440/484 at intermittent time intervals over 2 hours. The plate was kept at 37° C. with 15 seconds shaking between reads.

Full-length ApoE3 proteins with and without the Christchurch mutation were also expressed in Flp-In™ T-REX™ 293 (Thermo Fisher Scientific) mammalian cells via transient transfection to confirm the impact of these proteins on Aβ42 aggregation using a previously published split-luciferase complementation assay.[26] The latter analysis were conducted using the human APOE3 expression from Addgene (Plasmid #8708627) as the WT or APOE3 with the Christchurch variant introduced via site-directed mutagenesis. Reagents for luciferase assay were purchased from Promega.

Results

About 1,200 Colombian Presenilin 1 (PSEN1) E280A mutation carriers and 4,600 non-carriers were identified, who together compose the world's largest known kindred with autosomal dominant Alzheimer's disease (ADAD).[28,29] The mutation carriers usually develop mild cognitive impairment (MCI) and dementia at the respective median ages of 44 (95% CI, 43-45) and 49 (95% CI, 49-50) years.[30,31] Studying autosomal dominant AD (ADAD) mutation carriers who remain cognitively unimpaired until older ages could help in the discovery of risk-reducing gene variants.[32] Characterizing AD biomarkers in these individuals could help inform the potentially targetable mechanisms by which these genes exert their relative protective effects. We identified a PSEN1 E280A mutation carrier who did not develop MCI until her seventies, nearly three decades after the median age at onset.

This study was conducted with the participant's written informed consent following Institutional Review Board guidelines (her exact age and other identifying information are omitted to protect her anonymity and confidentiality). The participant was confirmed to carry the amyloid-$\beta_{42}$ ($A\beta_{42}$)-overproducing PSEN1 E280A mutation, confirmed by report of family informants to be cognitively unimpaired until her seventies, and subsequently met criteria for MCI[33] during a 24-month period of annual assessments. She remained fully independent for basic and instrumental activities of daily living, without evident signs of worsening of her abilities to perform these activities. At intake assessment, her memory deficits were limited to recent events and her neurological exams were normal. Her age and education-adjusted neuropsychological test scores indicated a preferential impairment in recall memory, relatively preserved recognition memory, initial learning, naming, visuospatial abilities and verbal fluency skills, and relatively stable cognitive performance during the 24-month assessment period (Table 1).

TABLE 1

Cognitive Test Scores and Percentiles

| Cognitive Tests | Raw Scores (Percentiles**) | | | Mean (SD)** |
|---|---|---|---|---|
| MMSE/30* | 18 ($1^{st}$) | 16 (<$1^{st}$) | 19 ($4^{th}$) | 22 (1.7) |
| Naming/15 | 9 ($7^{th}$) | 9 ($7^{th}$) | 8 ($3^{rd}$) | 12.03 (2.1) |
| CERAD Word List Learning/30 | 10 ($5^{th}$) | 6 (<$1^{st}$) | 8 ($1^{st}$) | 15.64 (3.44) |
| CERAD Word List Delayed Recall/10 | 0 (<$1^{st}$) | 0 (<$1^{st}$) | 0 (<$1^{st}$) | 5.77 (1.98) |
| CERAD Word List Recognition/10 | 9 ($27^{th}$) | 8 ($5^{th}$) | 7 ($1^{st}$) | 9.58 (0.98) |
| CERAD Praxis-Copy/11 | 8 ($18^{th}$) | 9 ($39^{th}$) | 6 ($1^{st}$) | 9.42 (1.57) |
| CERAD Praxis-Recall/11 | 0 (<$1^{st}$) | 2 ($3^{rd}$) | 0 (<$1^{st}$) | 7.52 (2.84) |
| Semantic Fluency (Animals) | 12 ($13^{th}$) | 12 ($13^{th}$) | 12 ($13^{th}$) | 16.97 (4.3) |
| Phonemic Fluency ("F" Words) | 10 ($13^{th}$) | 11($14^{th}$) | 10 ($13^{th}$) | 23.75 (11.89) |

TABLE 1-continued

| Cognitive Test Scores and Percentiles | | | | |
|---|---|---|---|---|
| Cognitive Tests | Raw Scores (Percentiles**) | | | Mean (SD)** |
| Raven's Matrices Test, Form A/12 | 7 ($27^{th}$) | 7 ($27^{th}$) | 8 ($47^{th}$) | 8.21 (2.13) |
| GDS/15 | 9 | 2 | 9 | |
| EDG/7 | 3 | 3 | 4 | |

MMSE: Mini-Mental State Examination
CERAD: Consortium to Establish a Registry for Alzheimer's Disease Test Battery.
GDS: Geriatric Depression Scale
EDG: Global Deterioration Scale
*MMSE subtests that require reading and writing skills were not administered due to her limited literacy skills. Her maximum possible score was 23 (instead of 30).
**Percentiles were calculated using norms for this Colombian population.
Percentiles between 25 and 75 place her performance in the average range for her age and education.
Percentiles between 9 and 25 classify her performance as below average. Percentiles between 2 and 8 classify her performance as low. Percentiles below 1 classify her performance as extremely low.
#Brain imaging described in this report was acquired three months after the initial cognitive testing.

Whole exome sequencing corroborated her PSEN1 E280A mutation and discovered that she also had two copies of the rare APOE3 Christchurch R136S (APOEch) mutation. Sanger sequencing confirmed the latter finding. Whole genome sequencing and a Genomizer analysis were used to comprehensibly identify and rank all potentially significant rare and common variants.[34] Using this approach, the PSEN1 E280A mutation was confirmed to be the participant's primary risk factor and APOE3ch homozygosity was confirmed to be her primary resistance factor.

APOE, the major susceptibility gene for late-onset AD, has three common alleles (APOE2, 3, and 4). Compared to the most common APOE3/3 genotype, APOE2 is associated with a lower AD risk and older age at dementia onset,[35] and each additional copy of APOE4 is associated with a higher risk and younger age at onset.[36,37] The APOEch variant, an arginine-to-serine substitution at amino acid 136 (136Arg→Ser), corresponding to codon 154,[38] can reside on any of the common APOE alleles,[39] including this participant's two APOE3 alleles. FIG. 1 shows a model of the structure of the wild type ApoE3 protein. N-terminal (residues 1-191) and C-terminal (residues 201-299) domains are highlighted. The amino acid positions for APOE4 (C112R), APOE3ch (R136S) and APOE2 (R158C) variants are shown.

The APOE3ch variant was absent from AlzAD or ExAC databases reporting on about 180,000 exomes. The R136S was previously identified in APOE2 individuals with HLP III but its potential effect in the progression of AD has not been previously reported.[40] We sequenced DNA samples from two other PSEN1 E280A carriers with delayed age-at-onset (age at onset 62 and 70 years) via whole genome sequencing. None of these individuals had the APOE3 R136S variant nor APOE2; the latter was previously shown to delay disease onset in this kindred.[41]

Figure 2:
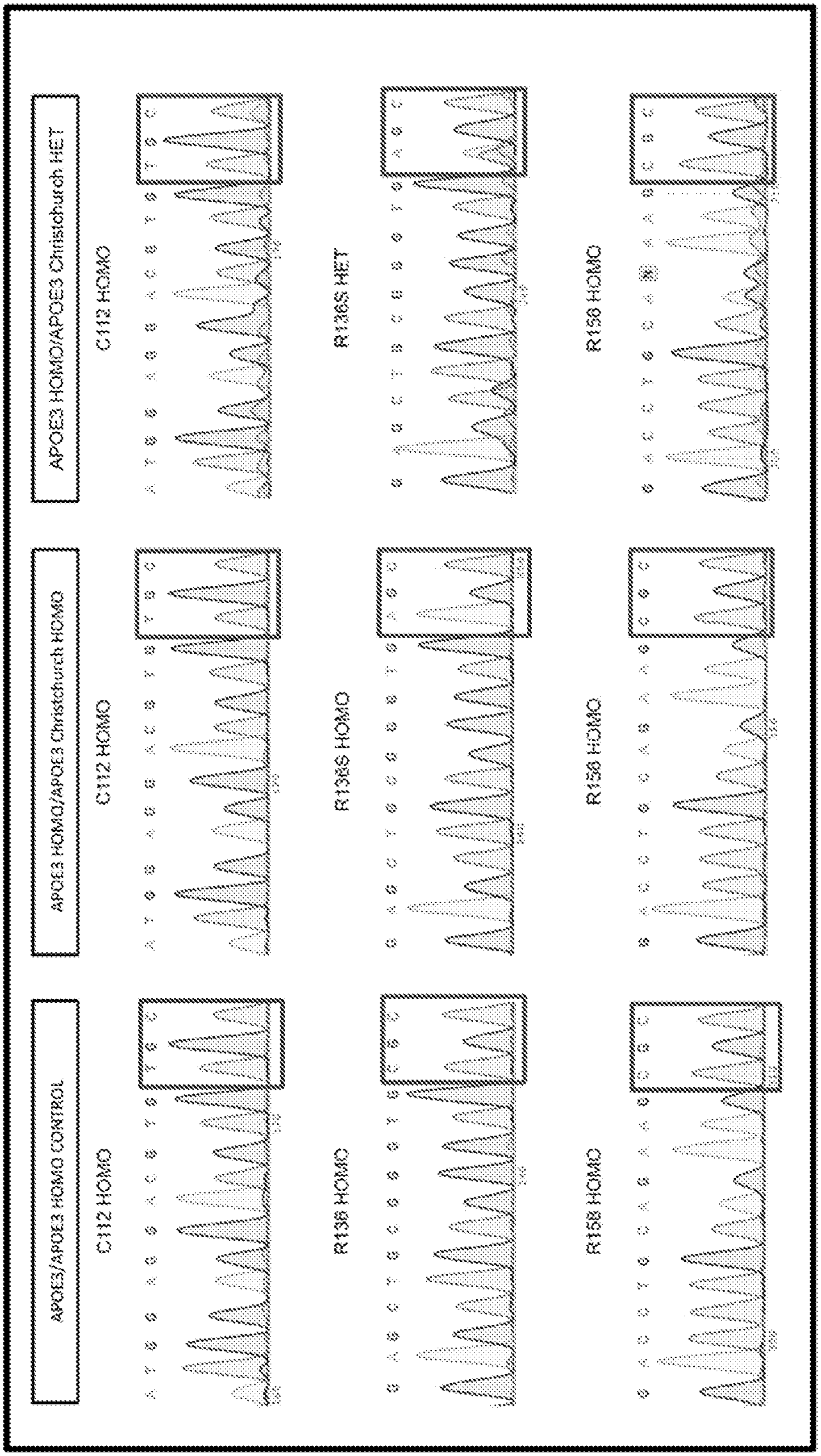
FIG. 2 shows representative Sanger sequencing results of APOE from control, proband and descendant's samples.
Figure 3:
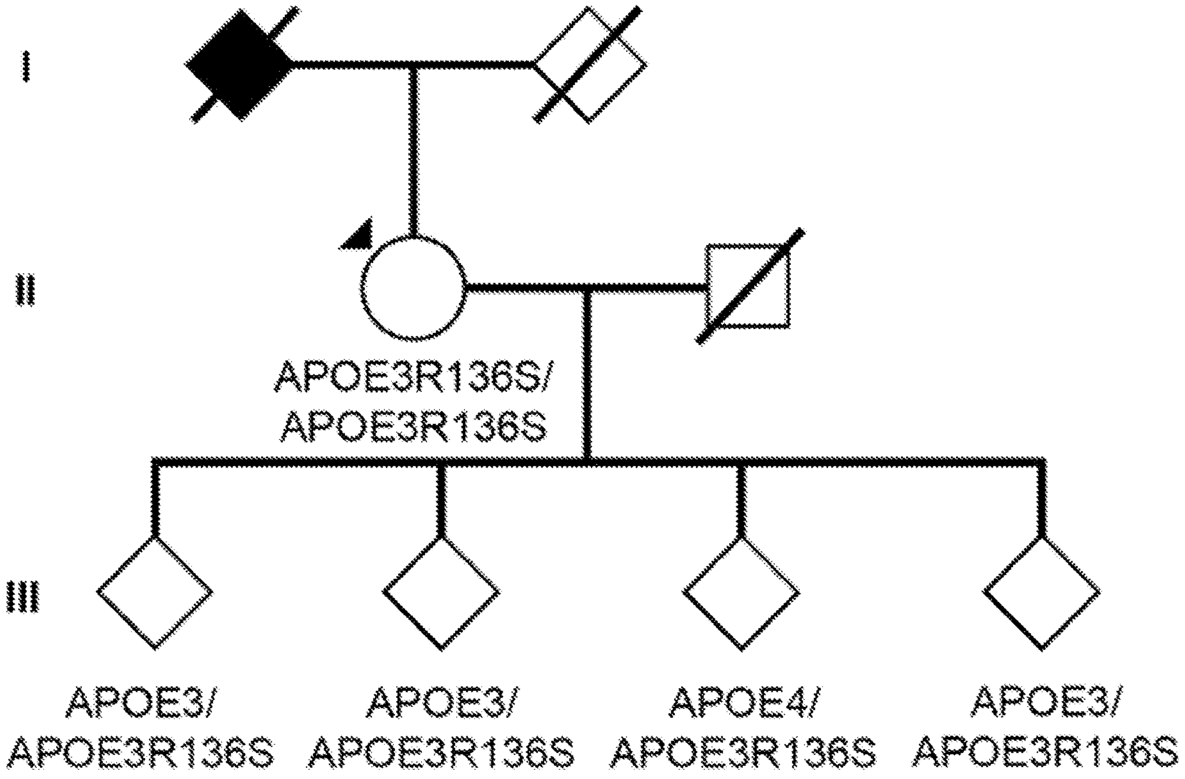
FIG. 3 depicts the subject's genealogy, with circles representing females, squares representing males, diamonds representing individuals whose gender has been masked for privacy, arrowhead depicts proband individual with MCI, and shading indicates individual with history of dementia. Deceased individuals are marked with a crossed bar. The individual APOE and PSEN1 genotypes are indicated as appropriate to preserve anonymity.

To confirm a potential association between the APOE3 R136S mutation and delayed age at onset of AD, we conducted whole genome sequencing, neurological, and neuropsychological testing in the four descendants of the proband case, which were all older than fifty years, and expected to carry the APOE3 R136S. FIG. 2 shows representative Sanger sequencing results of APOE from control, proband and descendant's samples. Upper row: C112 homozygous sequences are shown in all cases. Middle row: R136 homozygous sequence is shown in left panel from a control individual. Middle panel shows homozygous change resulting in R136S mutation. Right panel shows a R136S heterozygous mutation example of a descendant of the proband. Low row: R158 homozygous sequences are shown in all cases. FIG. 3 shows the proband's genealogy, with circles representing females, squares representing males, diamonds representing individuals whose gender has been masked for privacy, arrowhead depicts proband individual with MCI, and shading indicates individual with history of dementia. Deceased individuals are marked with a crossed bar. The individual APOE and PSEN1 genotypes are indicated as appropriate to preserve anonymity. Although other unknown genetic or epigenetic factors may have contributed to late age at onset of cognitive impairment in these two related PSEN1 E280A carriers, we suggest that the APOE3 R136S variant modifies the AD phenotype by buffering the effects of amyloid-β accumulation in the brain and subsequently delaying the emergence of tau pathology, neurodegeneration (i.e. brain atrophy), and symptoms onset.

Carriers of APOEch and other rare mutations in APOE's low density lipoprotein receptor (LDLR) binding region commonly have hyperlipoproteinemia type III (HLP-III), similar to that observed in 5-10% of APOE2 homozygotes.[43,44] The participant in this report was confirmed to have HLP-III, including APOEch and elevated triglyceride and total cholesterol levels (See, Table 2).

TABLE 2

| Dyslipidemia workup | | |
|---|---|---|
| Test Lipid panel | Subject | Normal range* |
| Triglycerides (mg/dl) | 691.88 | <250 |
| Total Cholesterol (mg/dl) | 511.76 | 150-199 |
| VLDL-C (mg/dl) | (–) | <30 |
| LDL-C (mg/dl) | (–) | ≤130 |
| Direct LDL-C (mg/dl) | 147 | ≤130 |
| HDL-C (mg/dl) | 55.74 | ≥40 |
| Cholesterol/HDL ratio | 9.18 | <5 |
| Apolipoprotein A-I (mg/dl) | 177 | F: 98-210 |
| Apolipoprotein B (mg/dl) | 217 | F: 44-148 |
| Apo B/Apo-I ratio | 1.23 | F: 0.35-1.15 |
| Lipoprotein A (mg/dl) | 86.6 | ≤30 |

HDL-C: High-density lipoprotein cholesterol,
VLDL-C: Very low-density lipoprotein cholesterol,
LDL-C: Low-density lipoprotein cholesterol.
*Normal range according to Merck Manual and Laboratory values.

Detailed laboratory workup showed abnormal lipid profile in our proband individual and three of the four descendants carrying the APOE3 R136S (Table 3). These four subjects had high level of total cholesterol and triglycerides. Very low-density lipoprotein (VLDL) and low-density lipoprotein (LDL) were higher in two of the descendants and not measurable in the proband individual and one of the descendants, which had triglyceride levels higher 400 mg/dL (the threshold for accuracy of the indirect method of lipid profiling) (Table 3). Further analyses using direct enzymatic tests showed higher than normal LDL in these two individuals. One of the descendants had a lipid profile within normal limits despite carrying the APOE3 R136S and the APOE4. Incomplete penetrance of HLP III has been previously reported for APOE2 and for R136S mutation carriers.[45] We ruled out secondary causes of lipid disorders as diabetes, obesity, alcoholism, renal disorders or thyroid diseases in these subjects. None of the mutation carrier individuals had xanthomas, which are diagnostic of HLP III, or cardiovascular diseases. The combination of the abnormal lipid profile and APOE3 R136S mutation in these subjects is consistent with a diagnosis of familial HLP III.

TABLE 3

Dementia and dyslipidemia workup in study population

| Test | Patient No. (Sex-Age) 1 (F-75) | 2 (F-51) | 3 (F-53) | 4 (M-49) | 5 (M-54) | Normal range* |
|---|---|---|---|---|---|---|
| CBC | | | | | | |
| RBC count (×$10^6$ $mm^3$) | 4.7 | 4.73 | 4.47 | 5.26 | 5.37 | 4.2-5.9 |
| Hemoglobin (g/dl) | 13 | 14.1 | 12.9 | 15.1 | 15.1 | M: 14-17 F: 12-16 |
| Hematocrit (%) | 38.5 | 42.3 | 39.2 | 46.3 | 45.7 | M: 41-51 F: 36-47 |
| MCV (fL) | 81.9 | 89.4 | 87.8 | 88.1 | 85 | 80-100 |
| MCH (pg) | 27.6 | 29.8 | 28.8 | 28.6 | 28.1 | 28-32 |
| MCHC (g/dl) | 33.7 | 33.4 | 32.8 | 32.5 | 33 | 32-36 |
| RDW (%) | 13.7 | 12.5 | 13 | 13.3 | 13.5 | 11.5-14.5 |
| WBC count (×$10^3$ $mm^3$) | 5.51 | 10.45 | 9.61 | 12.78 | 20.18 | 4.5-11 |
| Platelets (×$10^3$ $mm^3$) | 264 | 289 | 334 | 256 | 295 | 150-350 |
| MPV (fL) | 7 | 8.2 | 8.8 | 8.3 | 7.8 | 6.5-13.5 |
| ESR (mm/h) | 30 | 20 | 51 | 18 | 2 | M: 0-15 F: 0-20 |
| BMP | | | | | | |
| Glucose (mg/dl) | 107.1 | 128.28 | 107.82 | 112.15 | 131.19 | 70-105 |
| BUN (mg/dl) | 11.98 | 13.03 | 9.71 | 15.65 | 14.39 | 8-20 |
| Creatinine (mg/dl) | 0.57 | 0.59 | 0.67 | 1.04 | 0.95 | 0.7-1.3 |
| Sodium (mmol/l) | 139.3 | 141.4 | 140 | 137.3 | 136.6 | 136-145 |
| Potassium (mmol/l) | 3.79 | 4.03 | 4.92 | 4.76 | 4.29 | 3.5-5 |
| Chloride (mmol/l) | 102 | 106.5 | 108.3 | 106.6 | 107.1 | 98-106 |
| LPP | | | | | | |
| Total Cholesterol (mg/dl) | 511.76 | 192.6 | 434.25 | 336.21 | 323.2 | 150-199 |
| HDL-C (mg/dl) | 55.74 | 60.52 | 60.56 | 53.76 | 33.78 | ≥40 |
| Cholesterol/HDL ratio | 9.18 | 3.18 | 7.17 | 6.25 | 9.57 | <5 |
| Triglycerides (mg/dl) | 691.88 | 50.32 | 321.3 | 282.49 | 437.92 | <250 |
| VLDL-C (mg/dl) | (—) | 10.06 | 64.26 | 56.5 | (—) | <30 |
| LDL-C (mg/dl) | (—) | 122.02 | 309.43 | 225.95 | (—) | ≤130 |
| Additional tests | | | | | | |
| Apolipoprotein A-I (mg/dl) | 177 | 106 | 150 | 126 | 133 | M: 88-180 F: 98-210 |
| Apolipoprotein B (mg/dl) | 217 | 75 | 179 | 173 | 160 | M: 55-151 F: 44-148 |
| Apo B/Apo-I ratio | 1.23 | 0.71 | 1.19 | 1.37 | 1.2 | M: 0.45-1.25 F: 0.35-1.15 |
| Hemolytic Complement 50% (U/ml) | 50.8 | 58 | 58.6 | 56.1 | 68.8 | 31.6-57.6 |
| Plasmatic homocysteine (μmol/l) | 9.54 | 6.47 | 7.48 | 15.34 | 13.55 | M: 4-16 F: 3-14 |
| Lipoprotein A (mg/dl) | 86.6 | 6 | 86.1 | 6.5 | 62 | ≤30 |
| Serum complement C3 (mg/dl) | 130.1 | 1202.6 | 1314.5 | 1281.9 | 1292.6 | 55-120 |
| Serum complement C4 (mg/dl) | 20.6 | 177.9 | 131.7 | 146.5 | 245.5 | 20-59 |
| Complement Clq (mg/dl) | 24 | 23 | 28 | 28 | 33 | 10-25 |
| Free thyroxine (ng/dl) | 1.38 | 1.13 | 1.12 | 1.26 | 1.09 | 0.9-2.4 |
| TSH (μIU/ml) | 4.5 | 0.78 | 4.08 | 3.56 | 3.72 | 0.50-5.0 |
| Vitamin B12 (pg/ml) | 517 | 382 | 294 | 263 | 352 | 200-800 |
| Folate (ng/ml) | 16.14 | 7.52 | 8.38 | 2.14 | 6.6 | 2.5-20 |

Figure 4B:
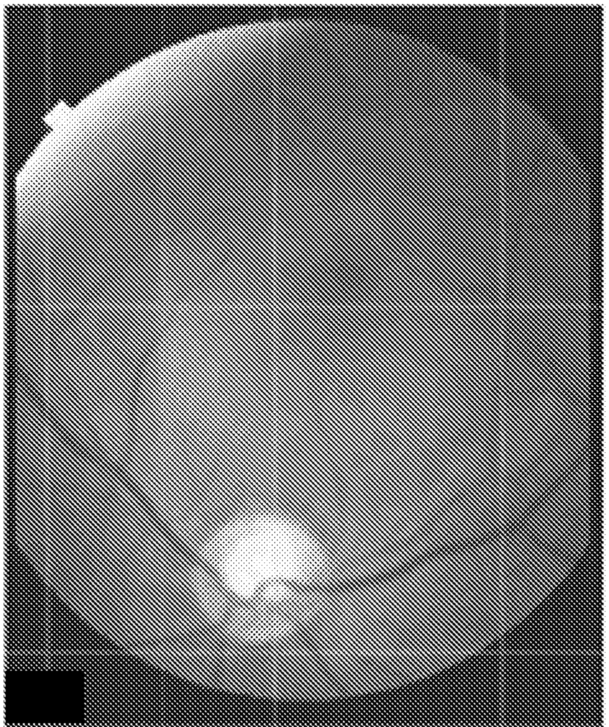
FIGS. 4A and 4B are fundus photographs of the right and left eyes, respectively.
Figure 4A:
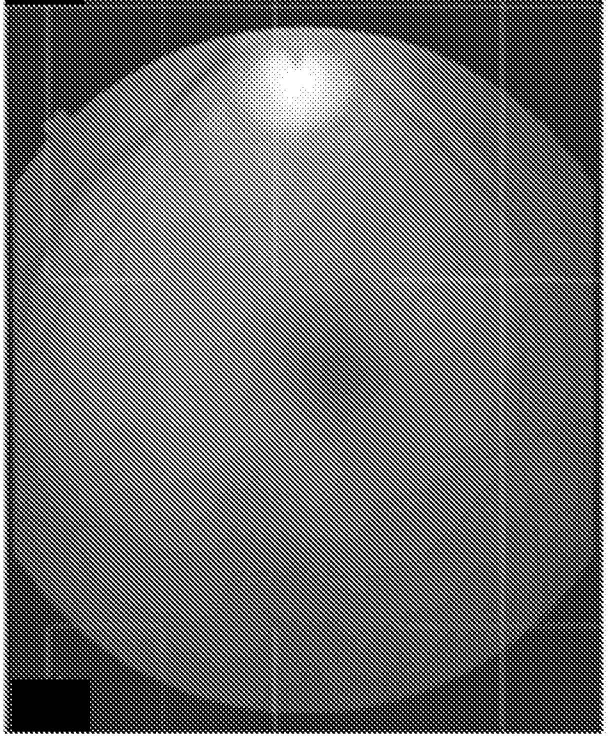
Figure 4C:
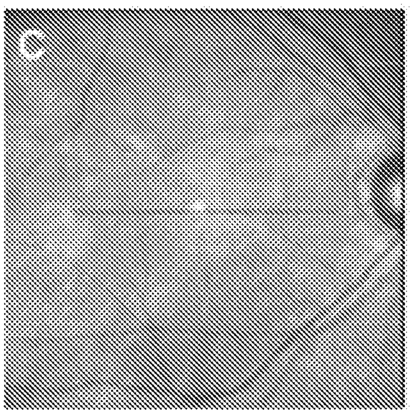
FIG. 4C shows an infrared image of the right eye that depicts the cross section of the retina (line) seen in FIG. 4D.
Figure 4D:
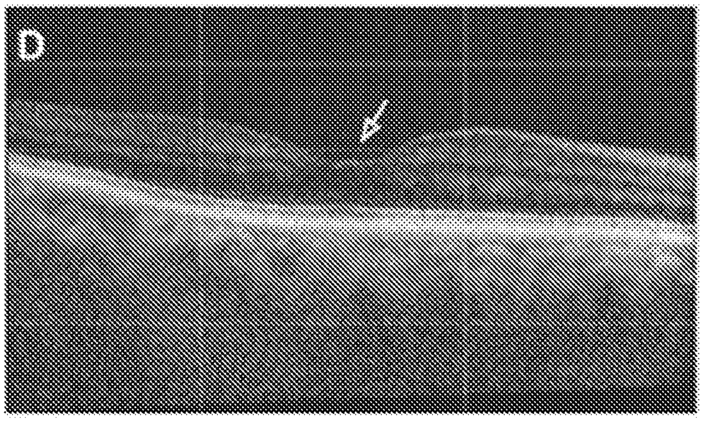
FIG. 4D shows results of optical coherence tomography (OCT) of the right eye.
Figure 4E:
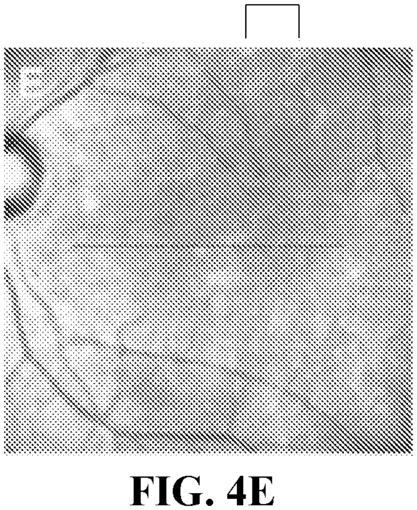
FIG. 4E shows an infrared image of the left eye.
Figure 4F:
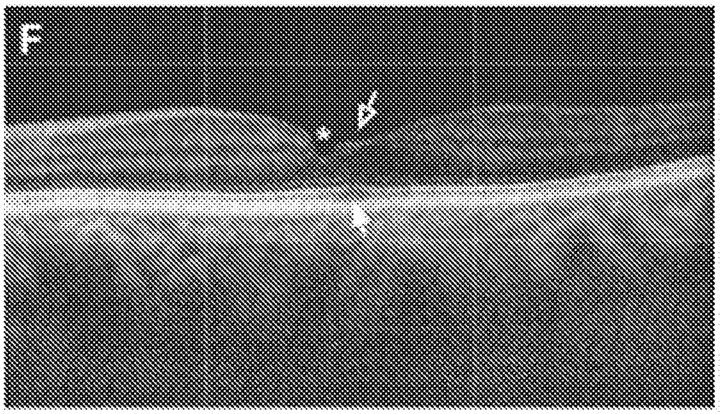
FIG. 4F shows results of OCT imaging of the left eye.

A detailed ophthalmic evaluation of the PSEN1 E280A mutation carrier with two APOE3ch alleles was performed. This carrier had a vision of 20/70 in the right eye and 20/40 in the left eye. The anterior segment exam was notable for a posterior chamber intraocular lens in the right eye with a dense posterior capsular opacification. Anterior segment of the left eye was notable for a nuclear sclerotic cataract (FIGS. 4A and 4B). The posterior segment examination of both eyes was normal, with a clear vitreous cavity, normal appearing optic nerve, macula, and peripheral retina. Further testing via optical coherence tomography (OCT) of the right eye was normal except for a small area of hyper-reflectivity overlying the fovea (FIG. 4D). FIG. 4C shows an infrared image of the right eye that depicts the cross section of the retina (line) seen in FIG. 4D. Further, OCT imaging of the left eye revealed a degenerative lamellar hole (denoted by the * in FIG. 4F) with a small defect in the external limiting membrane and ellipsoid layer (arrow in FIG. 4F).

While several mechanisms have been proposed to account for the impact of APOE variants on AD risk, most studies have focused on their differential effects (APOE2<3<4) on $A\beta_{42}$ aggregation and plaque burden.[47] In the present study, neuroimaging measurements were used to clarify whether the participant's resistance to the clinical onset of AD was associated with a) relatively little Aβ plaque burden despite more than seventy years of $A\beta_{42}$ overproduction or with b) relatively high Aβ plaque burden but limited downstream measurements of paired helical filament (PHF) tau (neurofibrillary tangle burden) and neurodegeneration.

Figure 5:
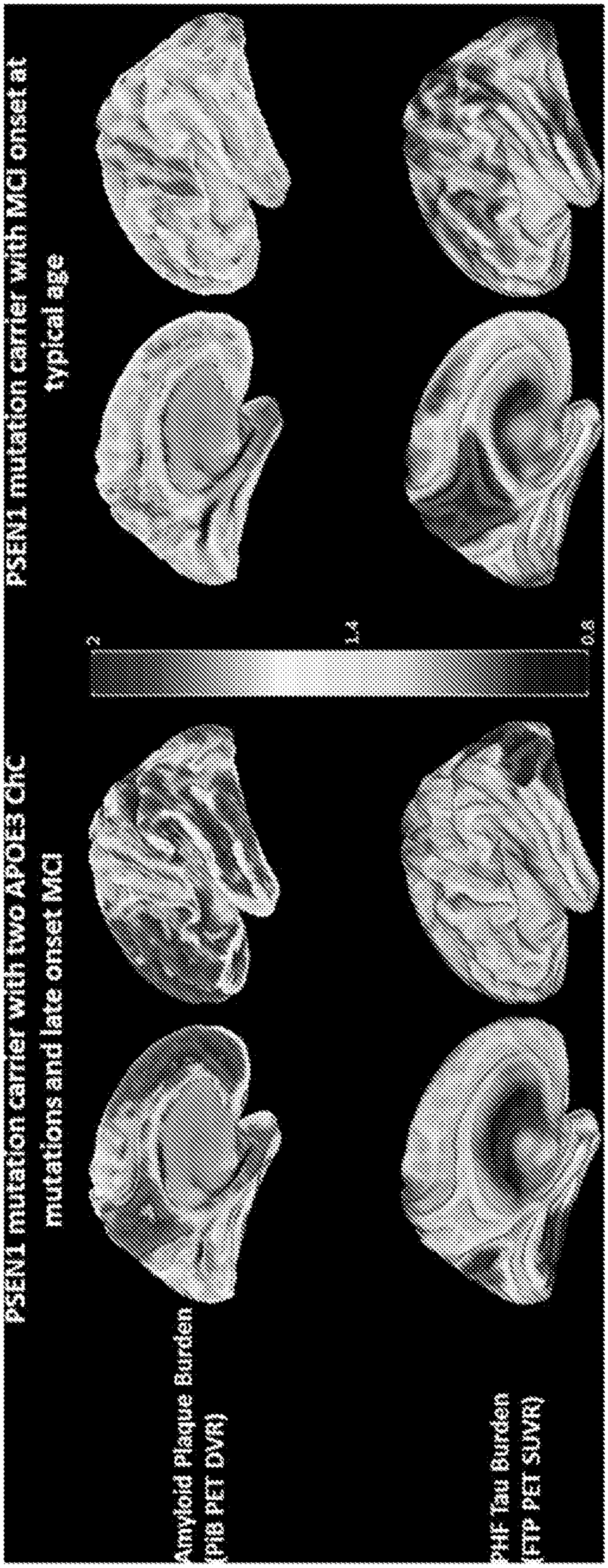
FIG. 5 shows brain imaging results showing the amyloid plaque burden and PHF Tau burden in the brains of the PSEN1 mutation carrier with late onset MCI (mild cognitive impairment) and a PSEN1 mutation carrier with MCI onset at a typical age for this mutation (44 years).

The participant's neuroimaging findings are shown in FIG. 5. The positron emission tomography (PET) images are superimposed onto the medial and lateral surfaces of the left hemisphere. The top row shows PET measurements of amyloid plaque burden (PiB DVRs). The bottom row shows PET measurements of paired helical filament (PHF) tau (i.e., neurofibrillary tangle) burden. The person with late-onset of MCI is in her seventies, and the person with the typical age at MCI onset is 44 years old.

As shown in FIG. 5, the person with late onset of MCI had unusually high PET measurements of Aβ plaque burden, as indicated by a higher mean cortical-to-cerebellar Pittsburgh Compound B (PiB) distribution volume ratio (DVR=1.96) than in PSEN1 E280A carriers who developed MCI in their forties (DVRs of 1.49-1.60). Despite her high Aβ plaque burden, the magnitude and/or spatial extent of her PHF tau burden and neurodegeneration were relatively limited: Her flortaucipir (tau) PET measurements were restricted to medial temporal and less commonly affected occipital regions with relative sparing of other regions that are characteristically affected in the clinical stages of AD (FIG. 5). Her fluorodeoxyglucose PET measurements of the cerebral metabolic rate for glucose were preserved in brain regions that are known to be preferentially affected by AD, including higher precuneus-to-whole brain measurements than in PSEN1 E280A mutation carriers who developed MCI at younger ages and many younger, cognitively unimpaired mutation carriers.

Figure 6:
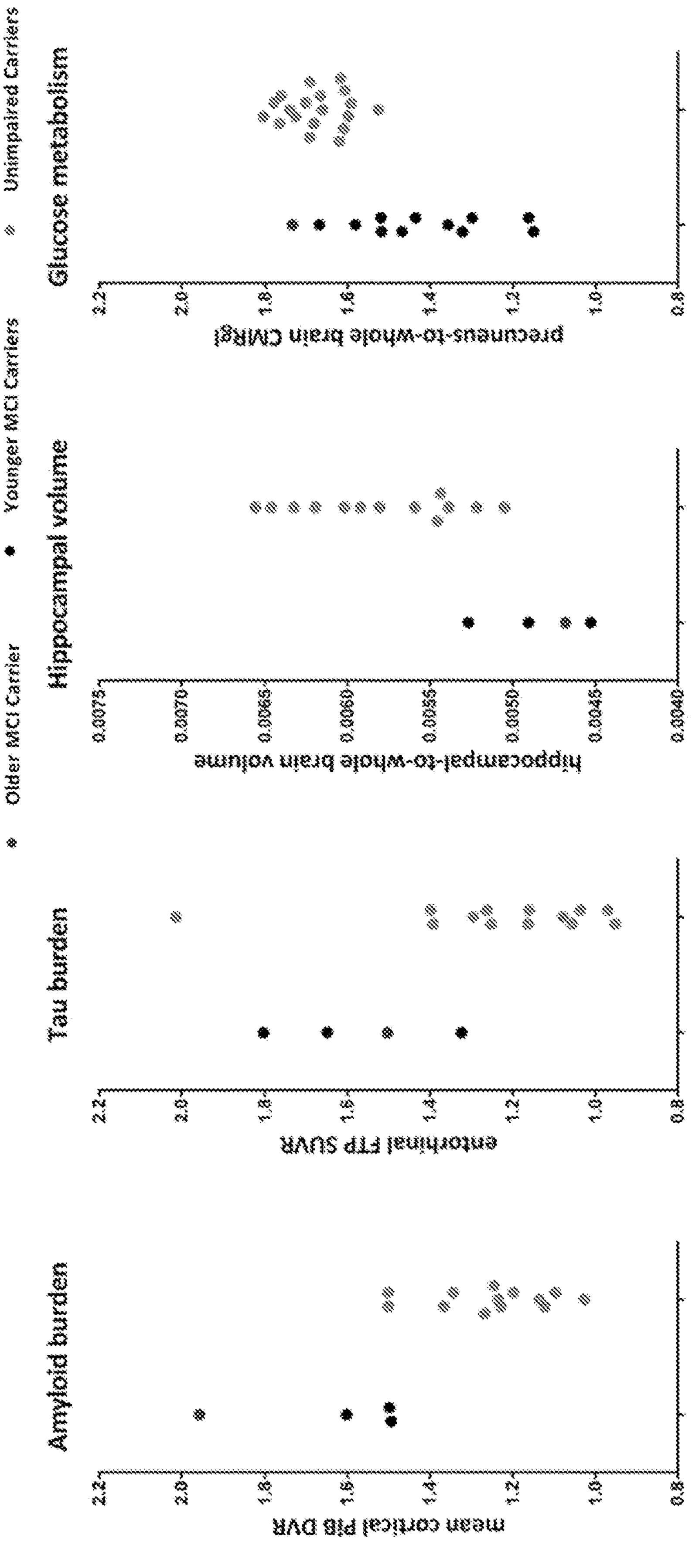
FIG. 6 shows measurements of amyloid burden, tau burden, hippocampal volume, and the levels of glucose metabolism in PSEN1 E280A mutation carriers. Red dots represent the measurements for the carrier with two APOE3ch alleles and an exceptionally late onset of MCI. Black dots represent PSEN1 E280A mutation carriers with MCI at the kindred's typical, younger age at MCI onset. Gray dots represent PSEN1 E280A mutation carriers who have not yet developed MCI.

FIG. 6 shows measurements of mean cortical amyloid plaque burden, entorhinal cortex PHF tau burden, hippocampal volume, and precuneus glucose metabolism. These measurements were based on brain imaging results obtain from the PSEN1 E280A mutation carrier with two APOE3ch alleles and exceptionally late-onset of MCI (red dots), PSEN1 E280A mutation carriers with MCI at the kindred's typical, younger age at MCI onset (black dots), and PSEN1 E280A mutation carriers who have not yet developed MCI (gray dots). Amyloid plaque burden is expressed as mean cortical-to-cerebellar distribution volume ratios (DVRs). Paired helical filament (PHF) tau burden is expressed as entorhinal cortex-to-cerebellar flortaucipir (FTP) standard uptake value ratios (SUVRs). Hippocampal volumes, which may be reduced by hippocampal atrophy, are expressed as hippocampal-to-whole brain volume ratios. Cerebral glucose metabolism, which is reduced in AD-affected brain regions with synaptic dysfunction and loss, is reflected as precuneus-to-whole brain cerebral metabolic rate for glucose (CMRgl) ratios. As shown FIG. 6, while the PSEN1 E280A mutation carrier with two APOE3ch alleles had by far the highest amyloid plaque burden, she did not have comparably severe PHF tau burden or hippocampal atrophy, and she had no evidence of precuneus glucose hypometabolism. Her MRI-based hippocampal-to-whole brain volume, a hippocampal atrophy measurement that can be affected by AD and/or normal aging, was within the range of mutation carriers who developed MCI in their forties. Without wishing to be bound by theory, these results suggest that this APOE3ch homozygote's resistance to the clinical onset of AD is mediated through a mechanism that limits tau pathology and neurodegeneration even in the face of high Aβ plaque burden.

Figure 7:
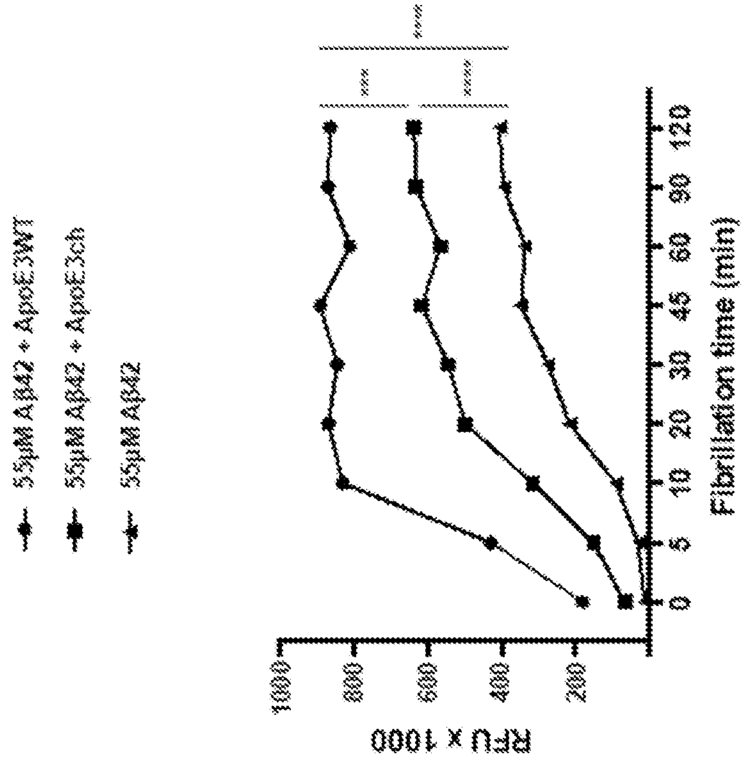
FIG. 7 shows the rate of Aβ42 fibril formation in the presence of APOE3 wild-type, APOE3ch, or in the absence of APOE as detected by Thioflavin T fluorescence. Changes in relative fluorescence units (RFU) were plotted for time in minutes (min). (* $P<0.001$, ** $P<0.0001$)

To study functional consequences of the APOE3ch variant, $A\beta_{42}$ aggregation in vitro in the presence of the bacteria-derived wild type human ApoE3 protein, presence of the mutant ApoE3ch protein, or in the absence of any ApoE protein were compared. The rate of Aβ42 fibril formation was detected by Thioflavin T fluorescence. $A\beta_{42}$ aggregation was highest in the presence of wild type human ApoE3 protein (C-terminus domain), lower in the presence of human ApoE3ch (similar to that observed in the presence of ApoE2[48]), and lowest in the absence of any ApoE (FIG. 7).

Figure 8:
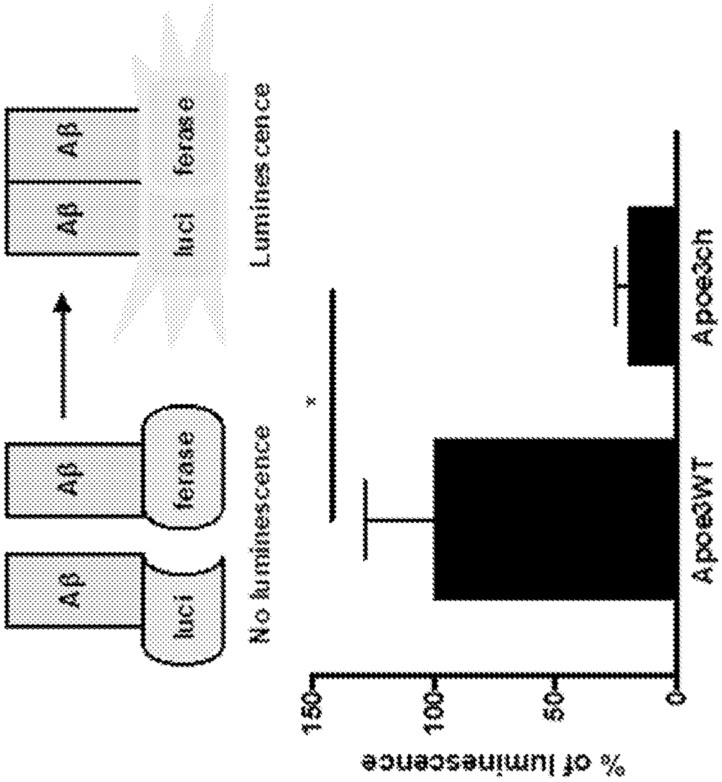
FIG. 8 shows schematic of the split-luciferase complementation triggered by amyloid oligomerization (top) and percentage of luminescence obtained by split-luciferase complementation assay after 24 hours in culture medium from 293T cells transfected with ApoE3ch or ApoE3 wild type.

This finding was confirmed using a sensitive split-luciferase complementation assay in which luciferase signal is reconstituted once amyloid forms oligomers,[48] some of the most toxic amyloid species.[49] Full-length ApoE3ch expression in mammalian cells triggered significantly less oligomerization of $A\beta_{42}$ compared to wild type ApoE3, as luciferase luminescence by oligomer formation was significantly reduced in ApoE3ch compared to wild type ApoE3 (FIG. 8). These results provide validation of the genetic analysis and suggest that the protective effects of the ApoEch protein may result, at least in part, from its limited ability to promote $A\beta_{42}$ aggregation. It remains possible that the research participant may have had even greater Aβ plaque deposition had she survived to her seventies without the APOEch/3ch genotype and that the ApoE3ch protein altered the morphology of Aβ aggregates in ways that limited downstream neuroinflammation, tau pathology, neurodegeneration and cognitive decline.

A small percentage of Colombian kindred members were found to carry one copy of the APOE3ch mutation,[50] including four PSEN1 E280A mutation carriers who progressed to MCI at the median age of 45. For this reason, it was postulated that APOE3ch homozygosity may be required to dramatically lower the risk and postpone the clinical onset of autosomal dominant AD. Because the sample size was small, it remains possible that APOEch heterozygote individuals may have partial protection against autosomal dominant AD-related cognitive decline and substantial protection against sporadic late onset AD and/or neurodegeneration.

These results suggest that APOE variants differ in the extent of their pathogenic functions (APOEch and APOE2<3<4) and APOE3ch/3ch and APOE2/2 are associated with greatest functional loss. Interventions that safely and sufficiently edit APOE, lower its expression, or inhibit its pathogenic functions could have a profound impact on the treatment and prevention of AD. Interestingly, suppression of APOE expression in brain using an anti-sense oligonucleotide in Aβ-overproducing mice led to altered Aβ plaque morphology and fewer dystrophic neurites.[51] This approach may be feasible because absence of APOE expression was tolerated in a middle-aged man who was homozygous for a frame-shift variant[52] and availability of statins to treat HPL-III support the potential tolerability of ApoE-lowering treatments. See, e.g. Reiman et al. Nat Commun 1191): 667, 2020.

Without wishing to be bound by theory, these results further suggest that homozygosity for APOE3ch—and APOE2—is associated with a profound resistance to the clinical onset of AD; that these genotypes exert their beneficial effects by directly or indirectly limiting downstream tau pathology and neurodegeneration; and that these effects are not based solely on the magnitude of Aβ plaque burden despite relative reductions in ApoE-mediated Aβ aggregation. These findings have implications for APOE's roles in the understanding, treatment, and prevention of AD, and may galvanize interest in developing APOE-modifying genetic and drug therapies for this disorder.

Example 2: Heparin Binding Properties of the APOE3ch Mutant Protein

Materials and Methods

Heparin column protocol: The heparin binding affinity of ApoE2, ApoE3, ApoE3ch and ApoE4 protein isoforms were compared using 1 ml Heparin Columns (BioVision-6554-1). The columns were acclimatized to room temperature for 1 hour prior to use. The columns were washed with 5 mL of 20 mM TRIS-HCL (pH7.5). 1 mL sample containing 50 μg/mL of APOE recombinant protein in 20 mM TRIS-HCL (pH7.5) was then recycled through the column 5 times. The column was then washed through 5 times with 20 mM TRIS-HCL (pH7.5). An increasing NaCl gradient (0.025-1M) in 20 mM TRIS-HCL was passed through the column and 1 mL fractions were collected and subsequently prepared for western blotting.

Western blotting: Western Blotting confirmed the elution of ApoE isoforms within fractions collected from the heparin binding columns. Fractions were diluted in 10 μl RIPA buffer (Cell Signaling Technology), 4 μl DTT (1M) and 10 μl Laemmli buffer to a final volume of 40 μl. Samples were separated on a 4-20% Mini-PROTEAN® TGX™ Precast Protein Gels (Bio-Rad), transferred to nitrocellulose membranes (VWR; 27376-991), blocked with Odyssey Blocking Buffer (LI-COR Biosciences, Lincoln, NE), and probed with mouse anti-his tag (Novus biologicals), and IRDye 800CW donkey anti-rabbit (LI-COR Biosciences) antibodies. Immunoreactive bands were visualized using the Odyssey Infrared Imaging System and visualized on the Image Studio version 2.1 (LI-COR Biosciences). Individual gels were stitched together to generate FIG. 10.

Heparin plate ELISA protocol: An ELISA was carried out using heparin microplates (Bioworld; 50-197-531). These were blocked for one hour using sample preparation reagent (DY008). Heparin plates were incubated with 0.1 μg/well of each of the recombinant ApoE protein isoforms (ApoE2, ApoE3, ApoE3ch and ApoE4) for 2 hours, the plate was then washed five times in PBS containing a gradient of NaCl (0-0.5M) and then washed three times in the Wash Buffer (DY008). Anti-His tag antibody was incubated overnight at 1:10,000 (Novus biologicals; NBP2-61482). The plate was then washed five times to ensure removal of unbound primary antibody, incubated with donkey anti-rabbit-HRP (1:10000) for 45 minutes, and then washed five times to ensure removal of secondary antibody. Sulfuric acid from the ELISA reagent kit (DY008) was warmed to 37° C. prior to addition of 100 μl of tetramethylbenzidine (Millipore) initiating the detection phase of the reaction. After a 5-mins incubation, sulfuric acid was added to terminate the reaction. The plate was then read using a SPECTRAmax plus 384 (Molecular Devices). The wavelength of the read was 450 nm. For calculating the amount of antigen present in the samples, a standard curve was plotted using Prism 6 (GraphPad Software) based on the serial diluted recombinant Notch3 protein.

Results

Figure 9:
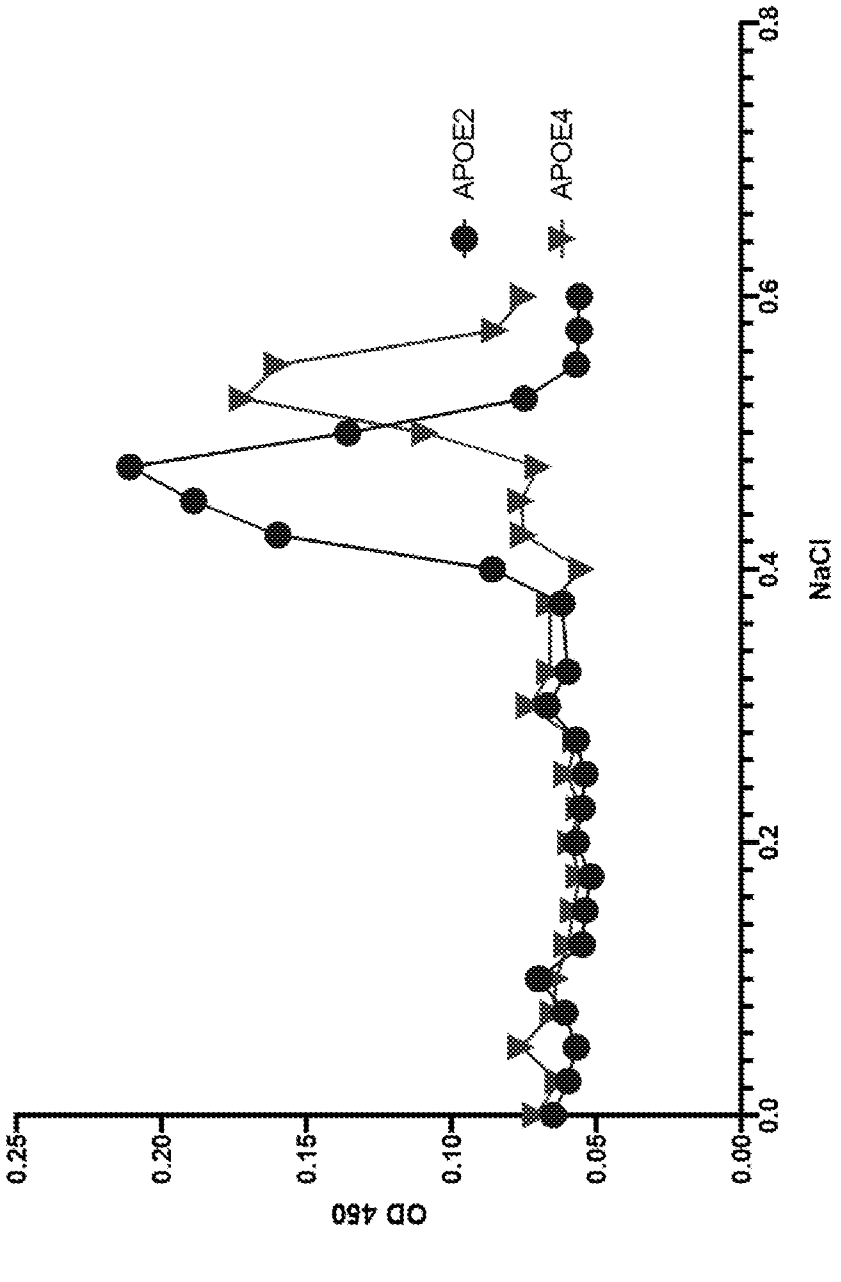
FIG. 9 shows ELISA results of APOE2 and APOE4 heparin-binding affinity.
Figure 10:
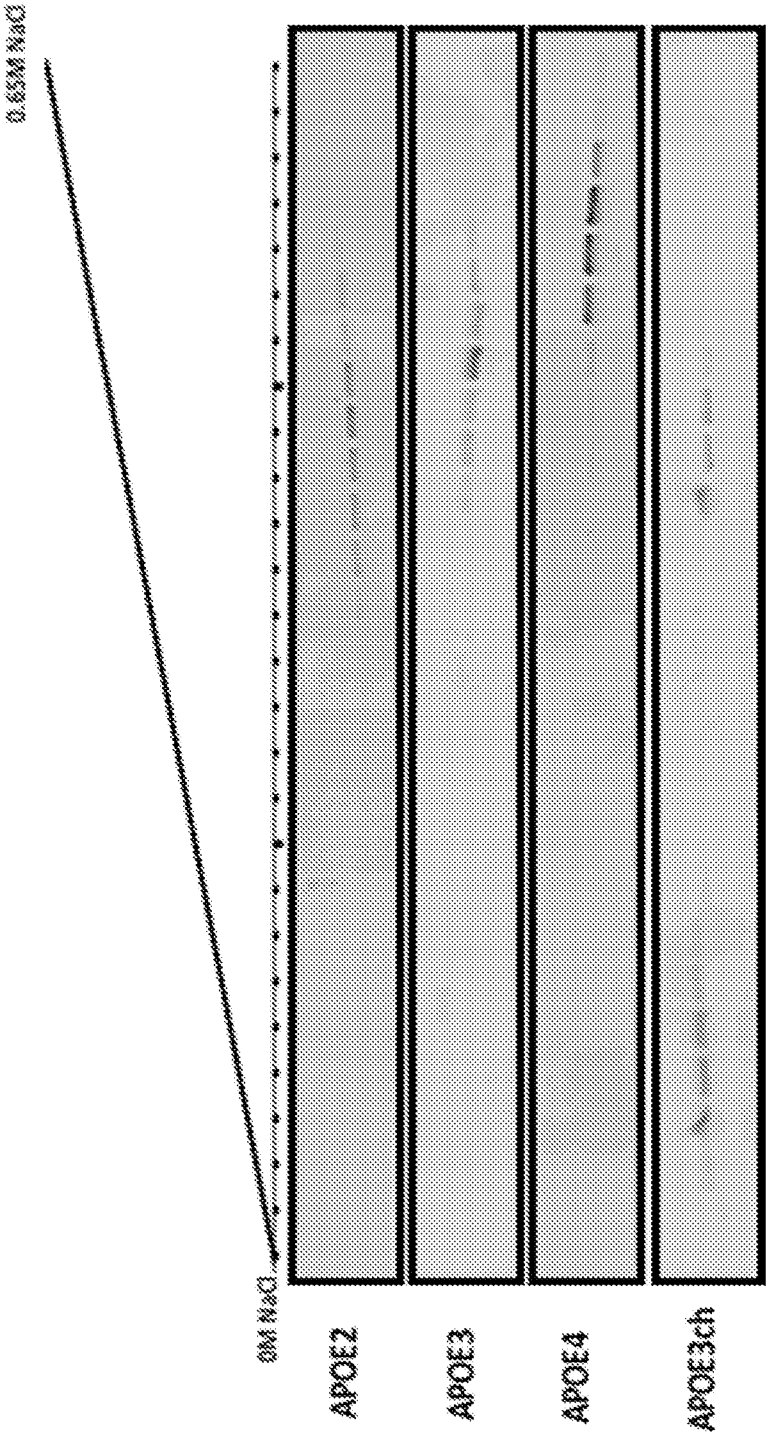
FIG. 10 shows western blot analysis of the heparin-binding affinity of ApoE2, ApoE3, ApoE4 and ApoE3ch.
Figure 11A:
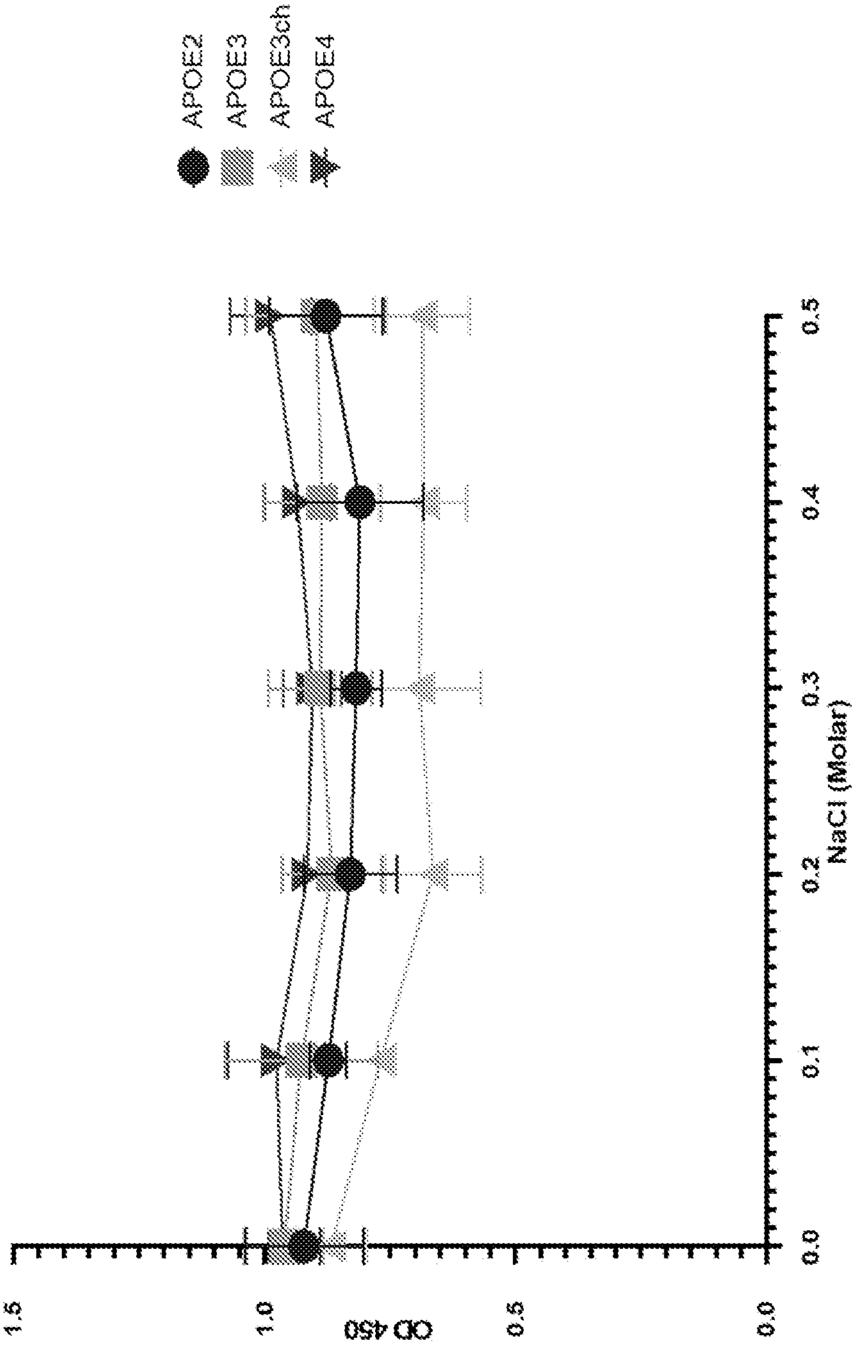
FIGS. 11A and 11B show ELISA results of the heparin-binding affinity of ApoE2, ApoE3, ApoE4 and ApoE3ch.
Figure 11B:
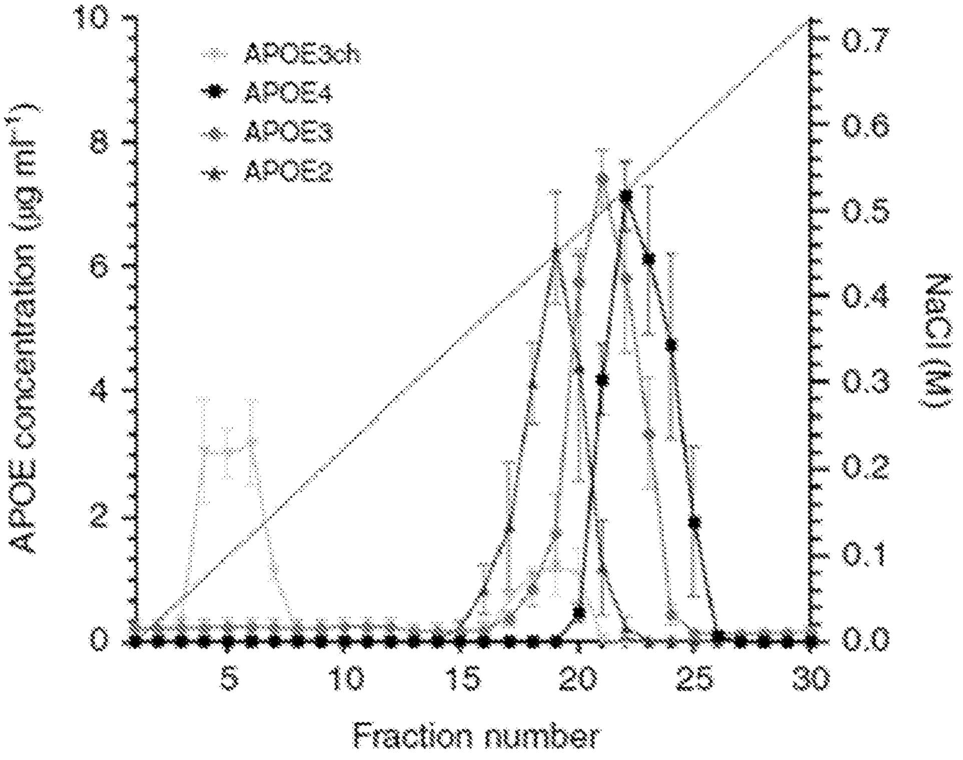

Heparin sulfate proteoglycans (HSPG) moieties are a type of glycosaminoglycans present in hundreds of proteins located in the plasma membrane and in the extracellular matrix. Protein-protein interactions mediated via HSPG play a critical role in a multitude of processes relevant to Alzheimer's pathology including amyloid and tau pathology and neurodegeneration. The ability of various ApoE isoforms, including ApoEch, to bind to heparin, a glycosaminoglycan commonly used to model HSPG-protein interactions, was investigated. Briefly, fractions containing ApoE isoforms ApoE2 and ApoE4 eluted from heparin columns under an increasing NaCl gradient (0-0.65M) were analyzed using ELISA. As shown in FIG. 9, the ApoE variant associated with higher risk of Alzheimer's disease, ApoE4, has higher affinity for heparin compared to the variant ApoE2, which is known to be protective. Next, fractions that contain His-tagged ApoE2, ApoE3, ApoE4 and ApoE3ch which were eluted from heparin columns under an increasing NaCl gradient (0-0.65M) were analyzed using western blot. As shown in FIG. 10, ApoE3ch had impaired heparin binding, which is much lower than that of ApoE2. The affinity of the ApoE isoforms for heparin were also analyzed using the heparin plate ELISA protocol as described in Materials and Methods. As shown in FIGS. 11A-11B, ApoE3ch showed remarkably low level of heparin binding, as ApoE3ch was released from the heparin column at much lower concentrations of NaCl compared to those required for ApoE4 release.

Example 3: Generation of Antibodies Against Wild Type ApoE and ApoEch Mutant Protein Materials and Methods Antibody competition assay: Antibodies were incubated with an ApoE3 recombinant protein (50 μg/ml in 20 mM Tris-HCL) at a 1:10 ratio and incubated for 3 hours at room temperature. A negative control containing the media only, and a positive control containing the recombinant protein ApoE3 only were used. The antibody/ApoE3 recombinant protein solution and controls were passed through heparin columns and exposed to an increasing NaCl gradient (as described in Example 2 above). Fractions were collected and assessed by ELISA and western blotting.

BCA Assay: Fractions collected from the heparin columns were first screened using the bicinchoninic acid assay (BCA assay) (Pierce BCA Protein Assay Kit). The assay was preformed using 200 μl of Reagent A and B Mix and 25 μl of each fraction. The 96 well plate was incubated for 30 minutes at 37° C., and read at 562 nm. The plate was read using Synery 2 microplate reader (BioTek Instrument. Inc) and the Gen5 version1.11 software).

Western Blotting: Western Blotting confirmed the elution of ApoE3 recombinant protein within fractions collected from the heparin binding columns. Fractions were diluted in 10 μl using RIPA buffer (Cell Signaling Technology), 10× (DTT 1M) and 4× Laemmli buffer for a final volume of 40 μl. Samples were separated on a 4-20% Mini-PROTEAN® TGX™ Precast Protein Gels (Bio-Rad), transferred to nitrocellulose membranes (VWR; 27376-991), blocked with Odyssey Blocking Buffer (LI-COR Biosciences, Lincoln, NE), and probed with mouse anti-his tag (Novus biologicals) and IRDye 800CW donkey anti-rabbit (LI-COR Biosciences) antibodies. Immunoreactive bands were visualized using the Odyssey Infrared Imaging System and visualized on the Image Studio version 2.1 (LI-COR Biosciences).

ELISA: Antibodies designed against the heparin-binding domain of ApoE were tested for their affinity to ApoE3 and ApoEch mutant recombinant proteins using ELISA. The Ni-NTA HisSorb Plates (Qiagen) were washed 3 times with wash buffer 1 (DY008). The ApoE recombinant proteins were suspended in buffer (DY008) to give a final concentration of 0.5 μg/ml. The plates were incubated with 200 μl of ApoE recombinant proteins for 2 hours, and washed 5 times with 1× wash buffer (DY008). The plates were then incubated with antibodies at a serial dilution of from 1:1,000 to 1:32,000 for overnight at 4° C. The plate was then washed 5 times in 1× wash buffer (DY008), and incubated with anti-mouse HRP (Abcam; ab97046, 1:10,000) for 45 minutes, followed by 5 washes in 1× wash buffer to ensure complete removal of unbound secondary antibody. The sulfuric acid from the ELISA reagent kit (DY008) was warmed to 37° C. 100 μl of tetramethylbenzidine (Millipore) was added to initiate the detection phase of the reaction. After a 5-min incubation, sulfuric acid was added to terminate the reaction. The plate was then read using Synery 2 microplate reader (BioTek Instrument. Inc) and the Gen5 version1.11 software).

Results

Figure 12A:
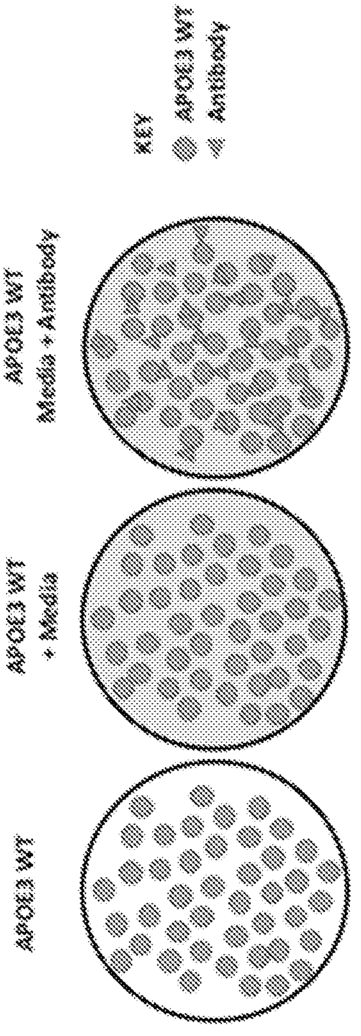
FIG. 12A is a schematic showing the experimental setup for testing the specificity of the monoclonal ApoE3 antibody in blocking ApoE3/heparin binding.
Figure 12B:
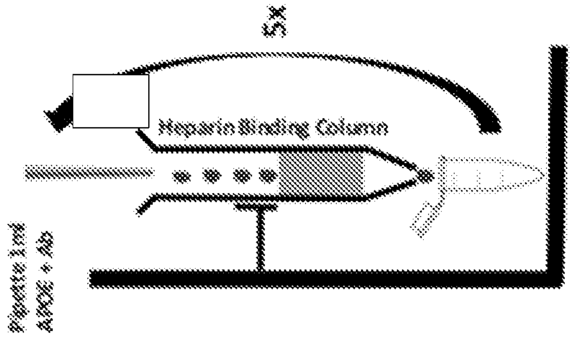
FIGS. 12B and 12C are schematics showing the process of passing the ApoE3 protein pre-incubated with the monoclonal antibody through a heparin binding column followed by washing and eluting.
Figure 12C:
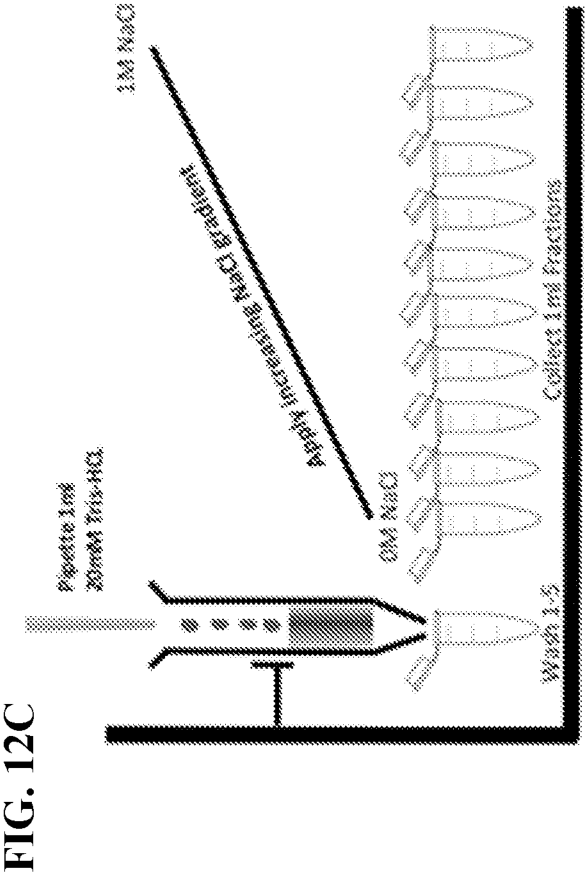

A monoclonal antibody against amino acids 130 to 143 of ApoE was generated and tested for its effect on the binding between full-length ApoE3 protein and heparin. Briefly, full-length wild type ApoE3 protein or those pre-incubated with the monoclonal antibody was passed through a heparin column and recycled five times to ensure maximal ApoE3 binding. The column was then washed five times with 20 mM Tris-HCl (pH=7.5) and exposed to an increasing gradient of NaCl (0 to 1M) in 20 mM Tris-HCl (pH=7.5). The elution from the Tris-HCl washes and from various NaCl concentrations were collected (FIGS. 12A-12C).

Figure 13B:
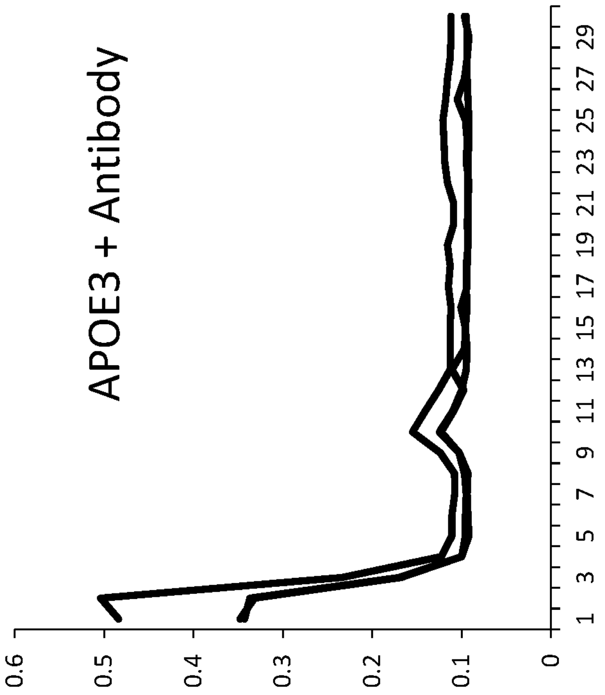
FIGS. 13A-13B show results from BCA assays performed on various fractions from the heparin binding column.
Figure 13A:
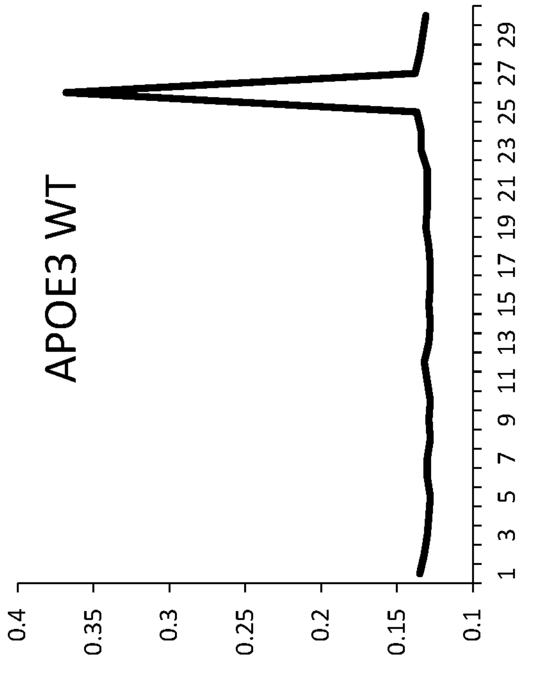
Figure 14:
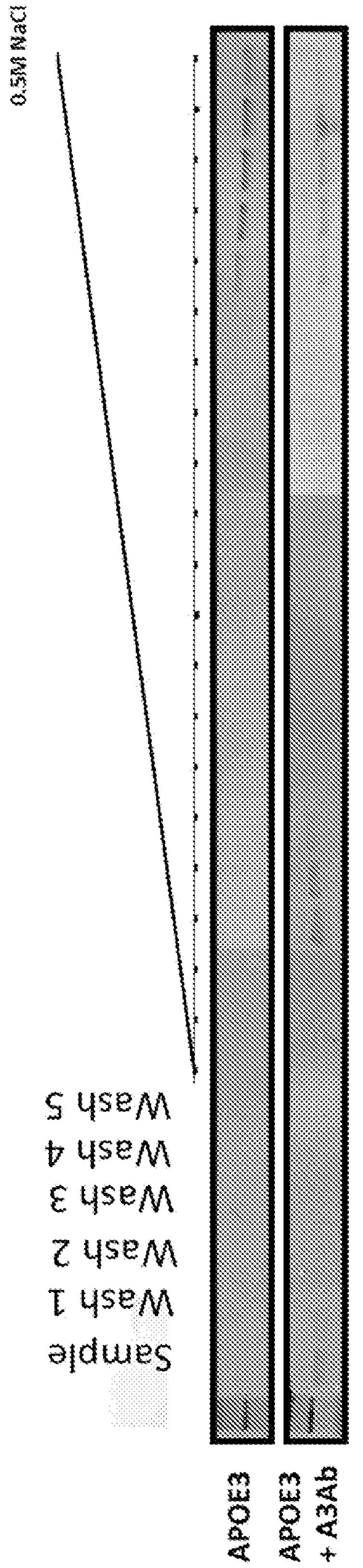
FIG. 14 shows western blot results showing the amount of ApoE3 in various fractions with or without pre-incubation with the monoclonal ApoE3 antibody.

The fractions collected from the column were first screened by the bicinchoninic acid (BCA) assay. As shown in FIG. 13A, protein signal was detected for wild type ApoE3 in fractions to the right of the curve, indicating strong binding of ApoE3 to heparin. In contrast, strong signal was observed in early fractions with low ionic strength when ApoE3 was pre-incubated with the monoclonal antibody (FIG. 13B). To verify the results, western blotting was used to analyze the column washes and NaCl gradient fractions collected from the heparin column. As shown in FIG. 14, pre-incubation of wild type ApoE3 with the monoclonal antibody (A3Ab) (this antibody was named 1343 in Arboleda-Velasquez et al., Nature Medicine, 25, pages 1680-1683 (2019)) reduced its ability to bind to heparin, to a level similar to that of an ApoE3ch mutant protein. Individual gels were stitched together to generate FIG. 14. These results suggest that an antibody may be used to modify the binding properties of ApoE to heparin, thereby preventing or treating Alzheimer's disease or related dementias or neurodegeneration.

Figure 15A:
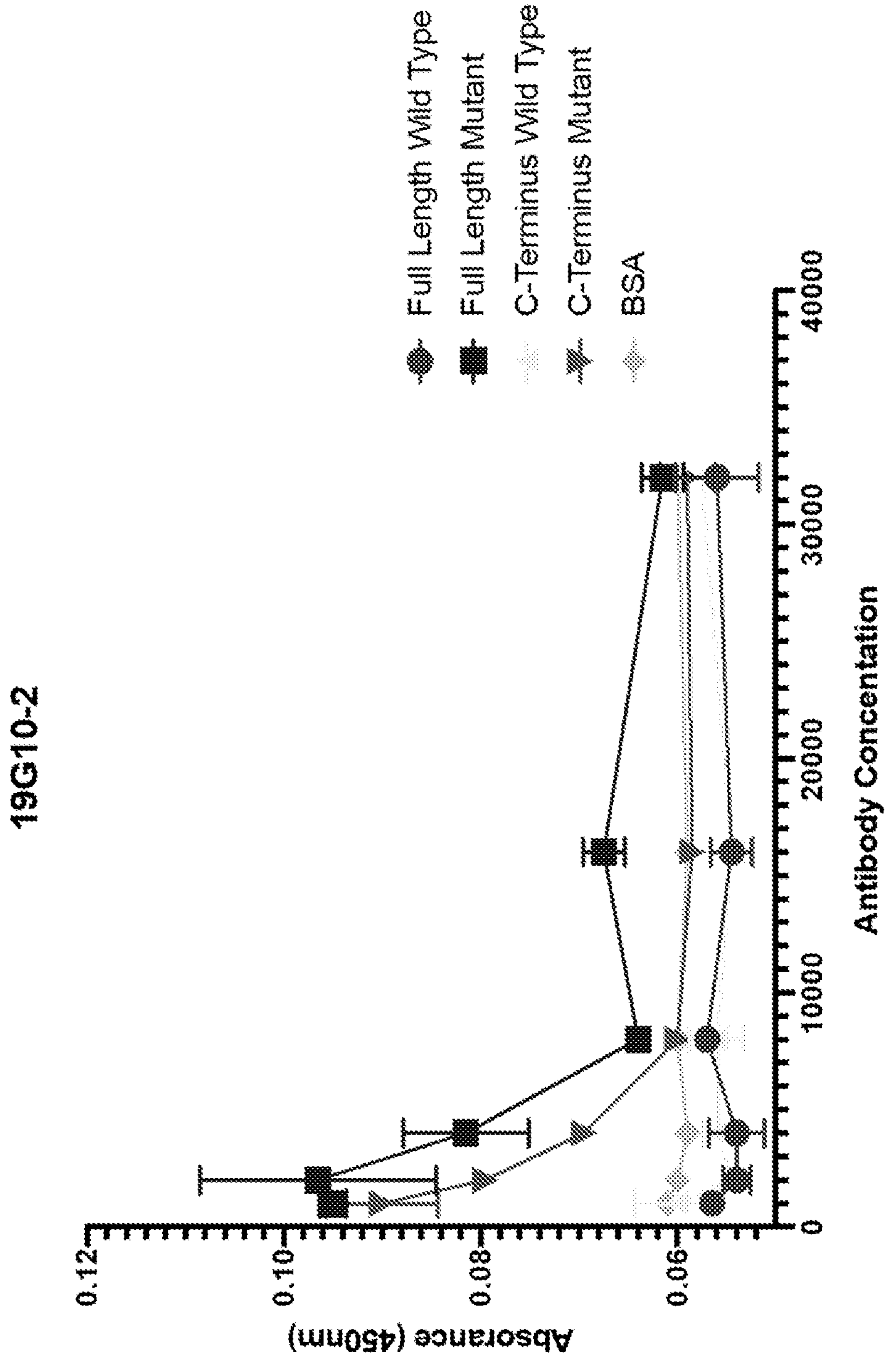
FIGS. 15A-15G show ELISA analysis of the 19G10-2, 23B2, 2H79-1, 30E1-2, 16H8, 25F1-2, and 29G10-1 antibody, respectively.
Figure 15B:
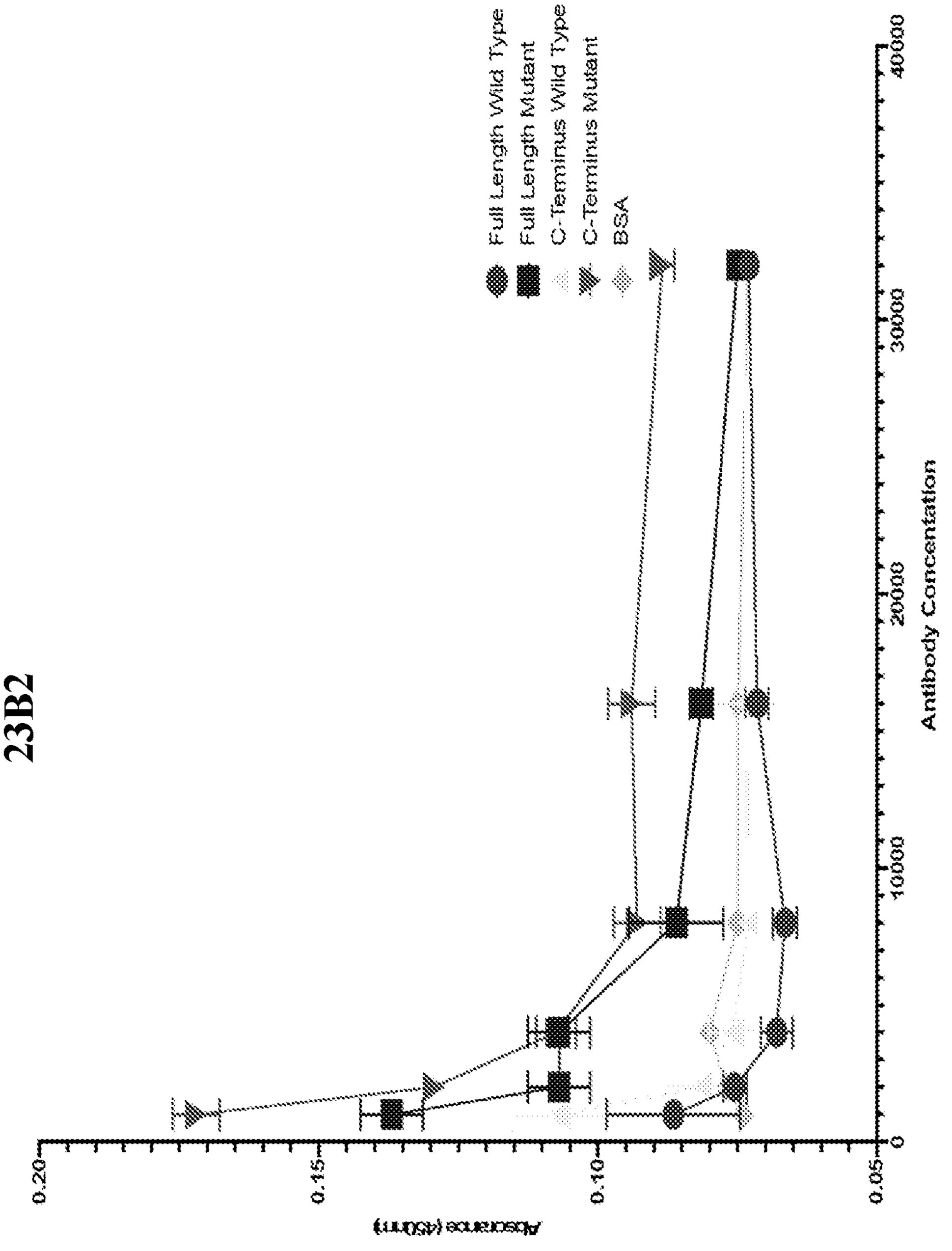
Figure 15C:
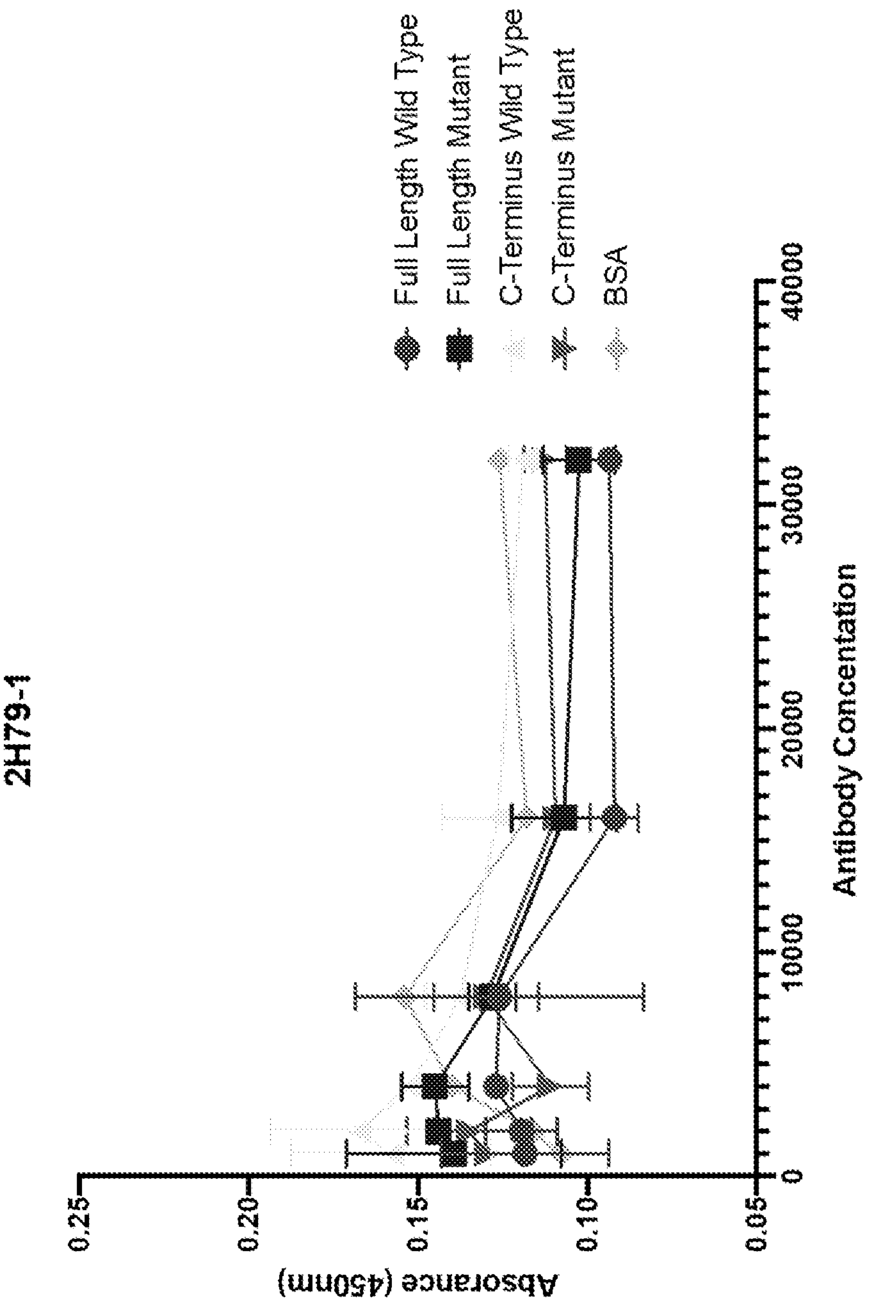
Figure 15D:
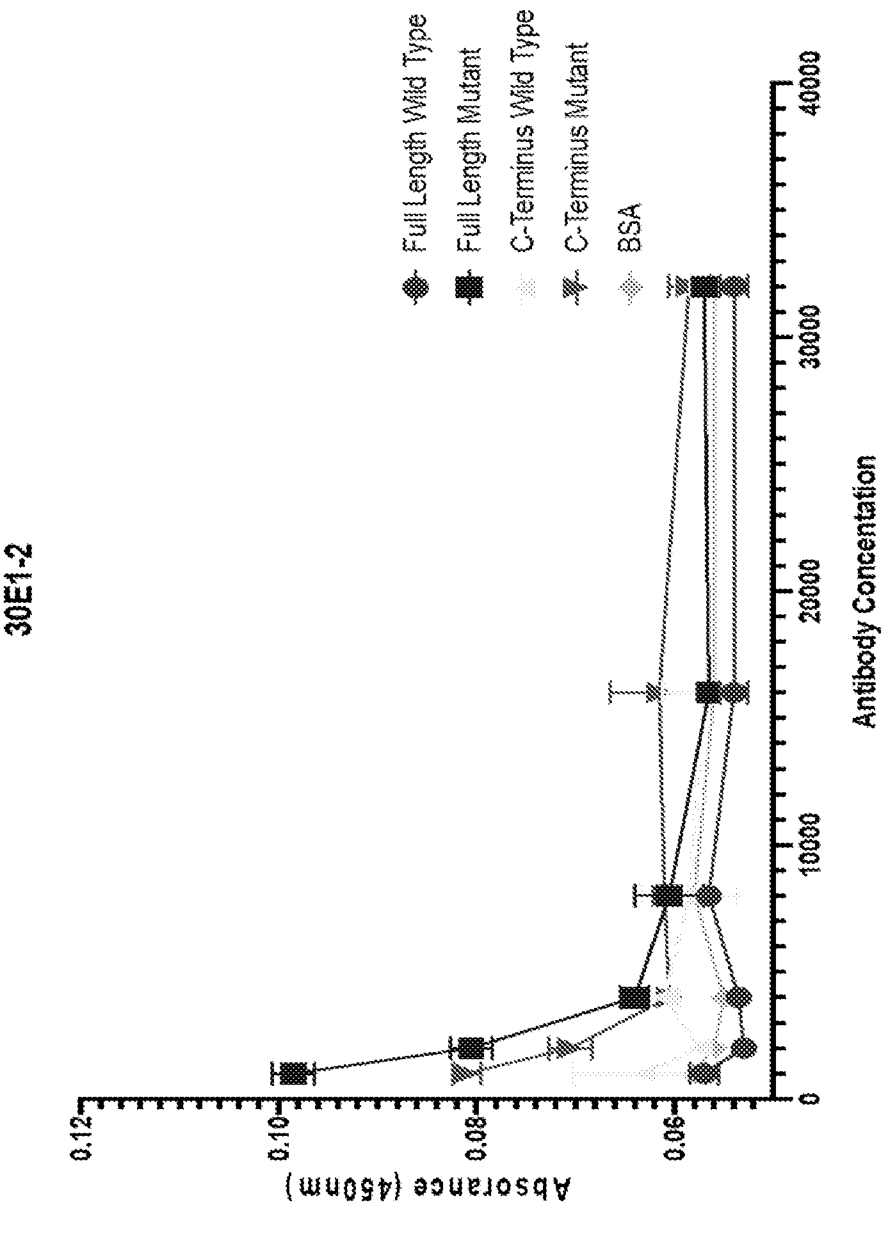
Figure 15E:
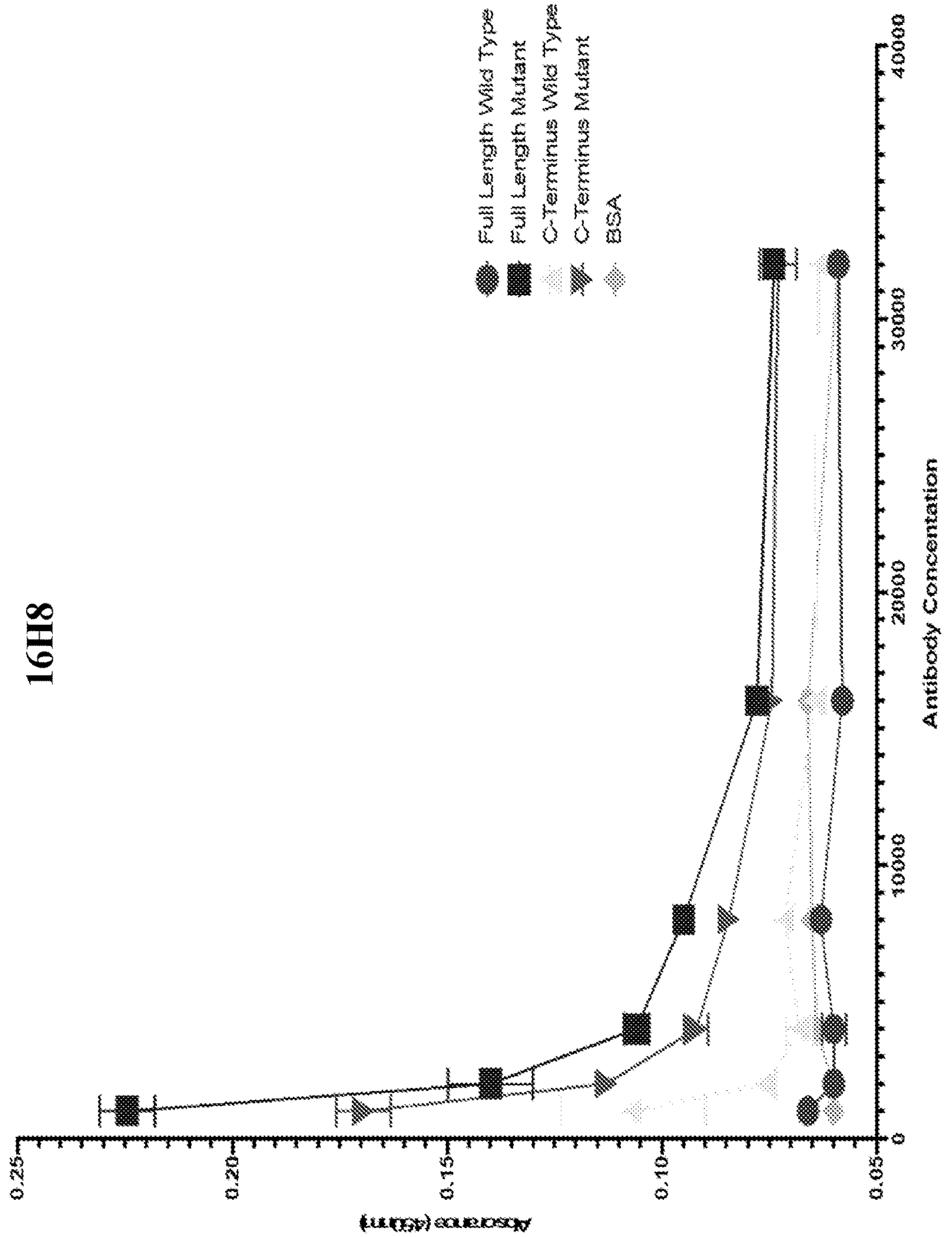
Figure 15F:
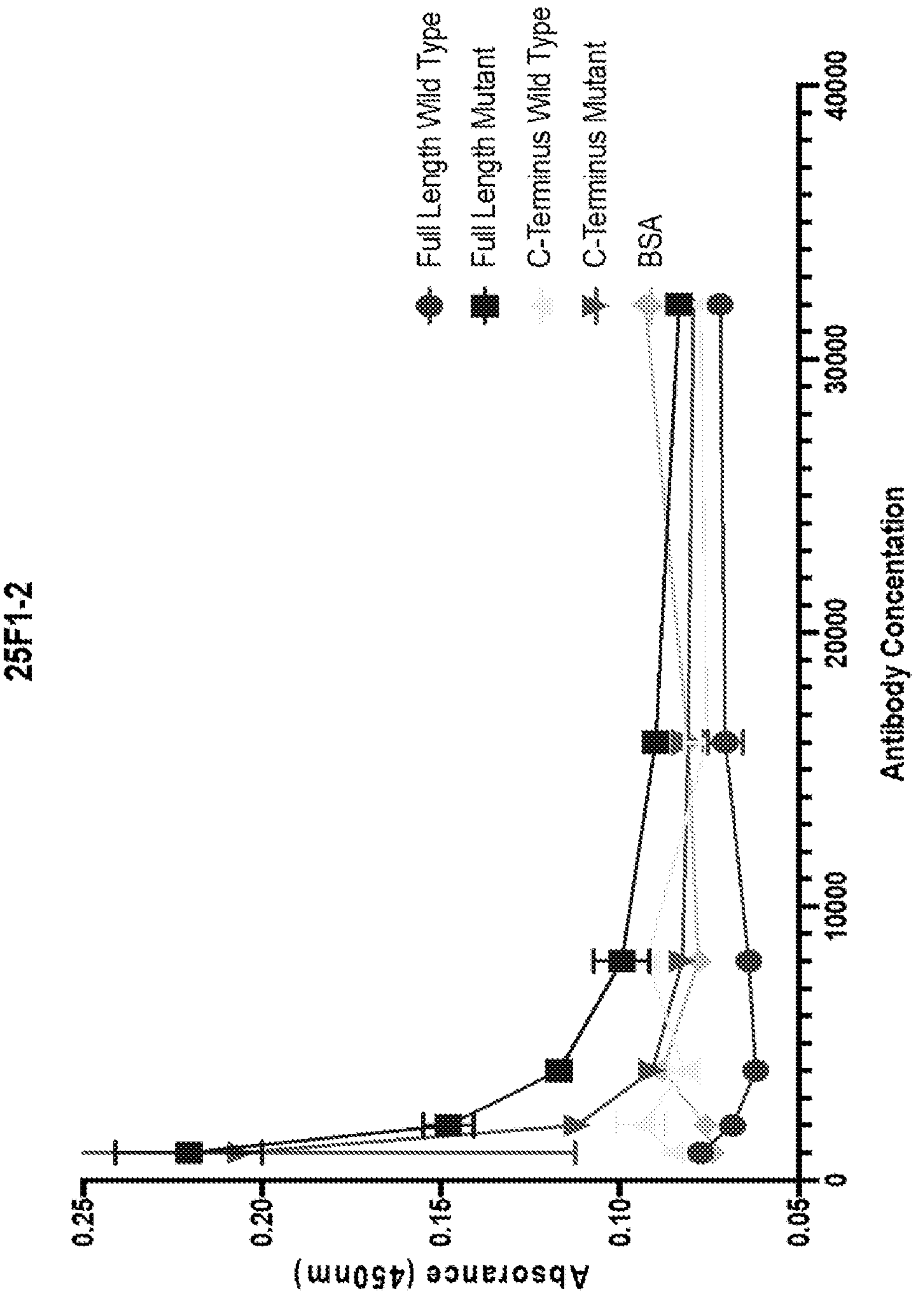
Figure 15G:
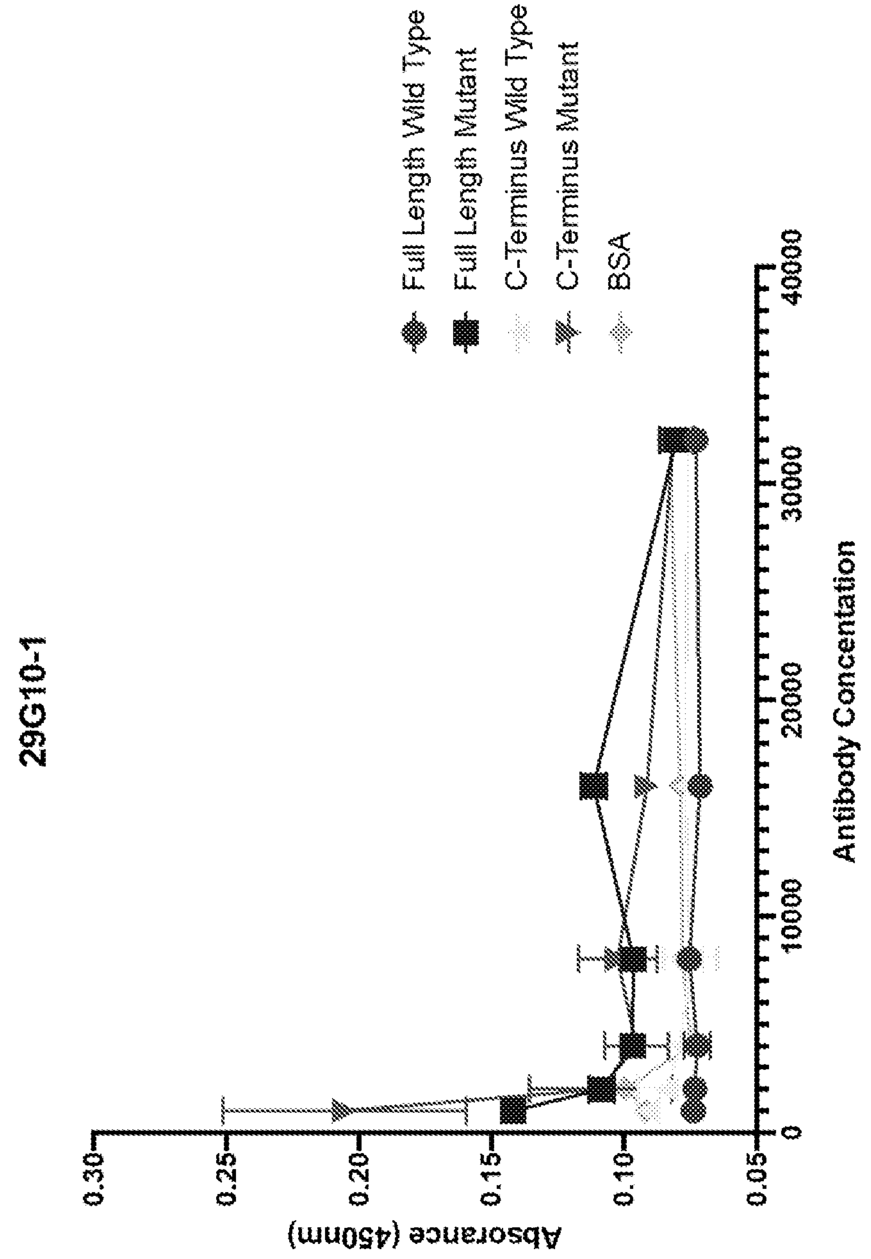

To generate monoclonal antibodies against the heparin-binding domain of ApoE, mice were immunized using the wild type ApoE peptide: KLH-CTEELRVRLASHLRK-CONH2 (SEQ ID NO:54), and the ApoEch peptide: KLH-CTEELRVSLASHLRK-CONH2 (SEQ ID NO:55). A cysteine residue was added at the N-terminus to facilitate conjugation of the peptides. Cell fusions were obtained from positive clones and cell supernatants tested for activity against the wild type and mutant peptides and proteins. Seven antibodies generated were analyzed by ELISA as examples, as described in the materials and methods section. The 19G10-2 antibody serum displayed specificity towards both the full-length and C-terminal of the APOE3ch mutant protein and some interaction with the wild type APOE3 protein (FIG. 15A). The 23B2 antibody displayed reactivity to both the wild type ApoE3 and ApoE3ch mutant C-terminal and full-length recombinant proteins (FIG. 15B). The 2H79-1 antibody displayed non-specific binding to bovine serum albumin (BSA) and showed no affinity for either wild type ApoE3 or ApoE3ch mutant (FIG. 15C). Both the 30E1-2 and 16H8 antibodies showed reactivity to the full-length and C-terminal ApoE3ch mutant proteins and the C-terminal form of wild type ApoE3, but did not react with the full-length wild type APOE3 protein (FIGS. 15D and 15E). The 25F1-2 antibody serum showed high affinity for the full-length and C-terminal ApoE3ch mutant proteins, and appeared to have variable binding to the C-terminus of the wild type ApoE3 protein and some interaction with the full-length wild type ApoE3 protein (FIG. 15F). The 29G10-2 antibody showed high affinity for both the full-length and C-terminal of the ApoE3ch mutant proteins, and also showed reactivity to the C-terminal wild type ApoE3 and BSA. Lastly, the 29G10-2 antibody did not interact with the full-length wild type ApoE3 protein (FIG. 15G).

The variable heavy chain (VH), variable light chain (VL) and complementarity determining region (CDR) sequences of 25F1-2 and 19G10-2 are described herein.

Further, the following parental clones with specificity for wild type ApoE were generated, and the specificity for the wild type ApoE peptide (WT peptide), the wild type ApoE protein (WT protein), the mutant ApoE peptide (ApoEch; Mut peptide) and the mutant ApoE3ch protein (Mut protein) were tested as shown in Table 6. The values indicate levels of absorbance as detected by ELISA. The bolded clones showed specificity for the wild type ApoE peptide (KLH-CTEELRVRLASHLRK-CONH2 (SEQ ID NO:54) and the wild type ApoE protein).

TABLE 6

| | WT peptide | WT protein | Mut peptide | Mut protein |
|---|---|---|---|---|
| 1D5 | 1.742 | 1.086 | 0.060 | 0.062 |
| 1H4 | 2.578 | 2.113 | 0.070 | 0.056 |
| 3A6 | 2.412 | 0.733 | 0.059 | 0.056 |
| 7C3 | 1.698 | 1.245 | 0.064 | 0.051 |
| 7C4 | 2.097 | 0.586 | 0.057 | 0.056 |
| 7C11 | 1.282 | 0.689 | 0.058 | 0.055 |
| 16G6 | 0.739 | 0.449 | 0.076 | 0.067 |
| Pos. ctrl | 1.980 | 1.171 | 0.254 | 0.144 |
| Neg. ctrl | 0.068 | 0.051 | 0.056 | 0.048 |

Example 4: Generation of Fusion Proteins Containing the Heparin-Binding Domain of APOE Materials and Methods Peptide Competition Assay: Wild type ApoE3 and ApoE3ch mutant peptides (50 μg/ml) were incubated with ApoE3 recombinant protein (50 μg/ml prepared in 20 mM Tris-HCL) for 3 hours at room temperature. The peptide/ApoE3 recombinant protein solution were then passed through heparin columns and exposed to an increasing NaCl gradient (as described in Example 2 and 3 above). Fractions were collected and assessed by western blotting.

Western Blotting: Western blotting confirmed the elution of ApoE3 within fractions collected from the heparin binding columns. Fractions were diluted in 10 μl RIPA buffer (Cell Signaling Technology), 10× (DTT 1M) and 4× Laemmli buffer to a final volume of 40 μl. Samples were separated on a 4-20% Mini-PROTEAN® TGX™ Precast Protein Gels (Bio-Rad), transferred to nitrocellulose membranes (VWR; 27376-991), blocked with Odyssey Blocking Buffer (LI-COR Biosciences, Lincoln, NE), and probed with mouse anti-his tag (Novus biologicals) and IRDye 800CW donkey anti-rabbit (LI-COR Biosciences) antibodies. Immunoreactive bands were visualized using the Odyssey Infrared Imaging System and visualized on the Image Studio version 2.1 (LI-COR Biosciences).

Results

Figure 16:
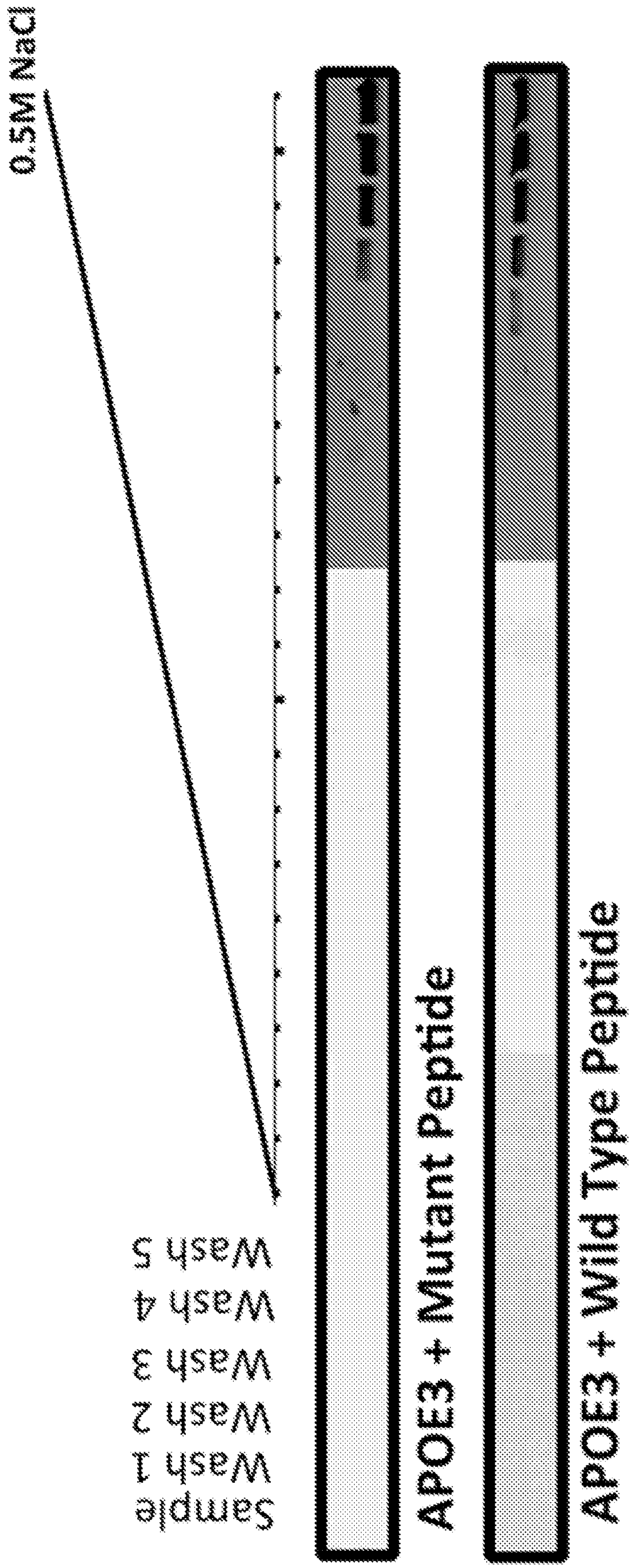
FIG. 16 shows western blot analysis of the heparin-binding affinity of ApoE3 treated with the wild type ApoE3 peptide and the ApoE3ch mutant peptide.

Peptides containing amino acids 130-143 of the wild type ApoE protein and ApoEch mutant protein, respectively, were generated. To examine the effect of these peptides on the binding between wild type ApoE3 recombinant protein and heparin sepharose, a peptide competition assay was carried out as described in materials and methods. As shown in FIG. 16, the wild type ApoE peptide resulted in a one-fraction shift of wild type ApoE3 recombinant protein binding, suggesting that this peptide can compete with wild type full-length ApoE3 for binding to heparin. These results suggest that ApoE fragments containing amino acids 130-

143 of the wild type ApoE protein may be used to change the binding properties of ApoE to heparin, thereby preventing or treating Alzheimer's disease or related dementias or neurodegeneration.

To increase protein stability of the peptides, C-terminal and N-terminal fusion proteins containing the heparin-binding domain of human ApoE (wild type and the R136S mutant version) or a site of allosteric modulation of the heparin-binding domain were generated using the backbone Fc IgG2 constructs pfuse-hfc1 and pfcn-hg2 (Invivogen). The human ApoE fragments excluded the sites for APOE2 and APOE4 variants. Administration of ApoE fragments with an R at position 136 may compete with endogenous ApoE for interaction with binding partners including HSPG leading to protection against neurodegeneration. Administration of ApoE fragments with an S at position 136 may bind molecules that do not bind to the wild type ApoE, leading to protection against neurodegeneration. The amino acid sequences for the fragments from the wild type and the R136S mutant ApoE used to generate the fusion proteins are shown below (the R136 position is bolded and double underlined).

Downstream of R136 Fragment

WT (SEQ ID NO: 57)

STEELRVRLASHLRKLRKRLLRDADDLQK

-continued

Mutant (SEQ ID NO: 58)

STEELRVSLASHLRKLRKRLLRDADDLQK

Upstream of R136 Fragment

WT (SEQ ID NO: 59)

RLVQYRGEVQAMLGQSTEELRVRLASHLRKL

Mutant (SEQ ID NO: 60)

RLVQYRGEVQAMLGQSTEELRVSLASHLRKL

Figure 17A:
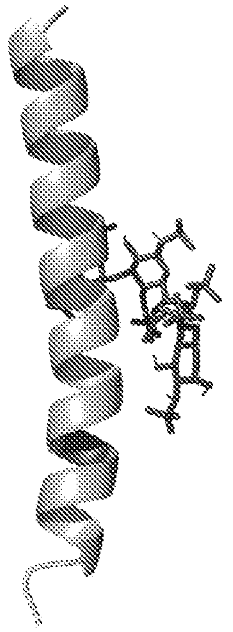
FIGS. 17A-17D show modeling of the interaction of ApoE fragments with heparin.
Figure 17B:
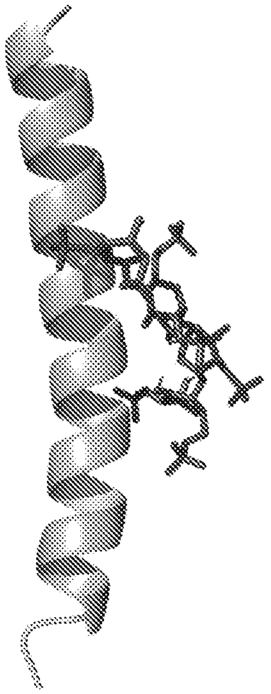
Figure 17C:
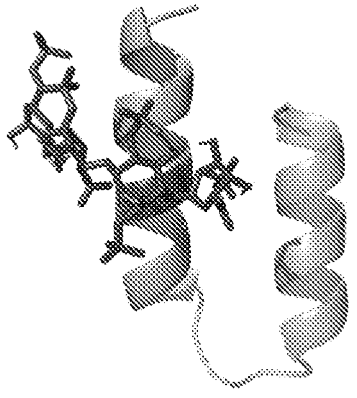
Figure 17D:
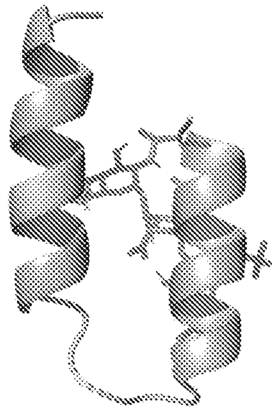

FIGS. 17A-17D show models of the interaction of ApoE fragments with heparin. FIG. 17A shows a model of the wild type ApoE fragment (downstream of R136 fragment, helix) interacting with heparin. FIG. 17B shows a model of the fragment of ApoE R136S (downstream of R136 fragment, helix) interacting with heparin. FIG. 17C shows a model of the wild type ApoE fragment (upstream of R136 fragment, helix) interacting with heparin. FIG. 17D shows a model of the fragment of ApoE R136S (upstream of R136 fragment, helix) interacting with heparin.

The nucleic acid and amino acid sequences for exemplary fusion protein constructs containing either the downstream of R136 fragment or the upstream of R136 fragment are shown below.

184Q pfcn-hg2 ApoE 114-144
Nucleic acid sequence (SEQ ID NO: 81)

```
   1 GGATCTGCGA TCGCTCCGGT GCCCGTCAGT GGGCAGAGCG CACATCGCCC ACAGTCCCCG

  61 AGAAGTTGGG GGGAGGGGTC GGCAATTGAA CGGGTGCCTA GAGAAGGTGG CGCGGGGTAA

 121 ACTGGGAAAG TGATGTCGTG TACTGGCTCC GCCTTTTTCC CGAGGGTGGG GGAGAACCGT

 181 ATATAAGTGC AGTAGTCGCC GTGAACGTTC TTTTTCGCAA CGGGTTTGCC GCCAGAACAC

 241 AGCTGAAGCT TCGAGGGGCT CGCATCTCTC CTTCACGCGC CCGCCGCCCT ACCTGAGGCC

 301 GCCATCCACG CCGGTTGAGT CGCGTTCTGC CGCCTCCCGC CTGTGGTGCC TCCTGAACTG

 361 CGTCCGCCGT CTAGGTAAGT TTAAAGCTCA GGTCGAGACC GGGCCTTTGT CCGGCGCTCC

 421 CTTGGAGCCT ACCTAGACTC AGCCGGCTCT CCACGCTTTG CCTGACCCtg cttgctcaac

 481 tctacgTCTT TGTTTCGTTT TCTGTTCTGC GCCGTTACAG ATCCAAGCTG TGACCGGCGC

 541 CTACCTGAGA TCACCGGCGA AGGAGGGCCA CCATGTACAG GATGCAACTC CTGTCTTGCA

 601 TTGCACTAAG TCTTGCACTT GTCACGAATT CGGCACCTCT CGAGCGCAAA TCTAGTGTCG

 661 AGTGCCCACC GTGCCCAGCA CCACCTGTGG CAGGACCGTC AGTCTTCCTC TTCCCCCCAA

 721 AACCCAAGGA CACCCTCATG ATCTCCCGGA CCCCTGAGGT CACGTGCGTG GTGGTGGACG

 781 TGAGCCACGA AGACCCCGAG GTCCAGTTCA ACTGGTACGT GGACGGCGTG GAGGTGCATA

 841 ATGCCAAGAC AAAGCCACGG GAGGAGCAGT TCAACAGCAC GTTCCGTGTG GTCAGCGTCC

 901 TCACCGTTGT GCACCAGGAC TGGCTGAACG GCAAGGAGTA CAAGTGCAAG GTCTCCAACA

 961 AAGGCCTCCC AGCCCCCATC GAGAAAACCA TCTCCAAAAC CAAAGGGCAG CCCCGAGAAC

1021 CACAGGTGTA CACCCTGCCC CCATCCCGGG AGGAGATGAC CAAGAACCAG GTCAGCCTGA

1081 CCTGCCTGGT CAAAGGCTTC TACCCCAGCG ACATCGCCGT GGAGTGGGAG AGCAATGGGC

1141 AGCCGGAGAA CAACTACAAG ACCACGCCTC CCATGCTGGA CTCCGACGGC TCCTTCTTCC

1201 TCTACAGCAA GCTCACCGTG GACAAGAGCA GGTGGCAGCA GGGGAACGTC TTCTCATGCT
```

-continued

1261 CCGTGATGCA TGAGGCTCTG CACAACCACT ACACGCAGAA GAGCCTCTCC CTGTCTCCGG

1321 GTGCACGTAC GCGCCTGGTG CAGTACCGCG GCGAGGTGCA GGCCATGCTC GGCCAGAGCA

1381 CCGAGGAGCT GCGGGTGCGC CTCGCCTCCC ACCTGCGCAA GCTGtgaTAT CTCGAGCTAG

1441 CTGGCCAGAC ATGATAAGAT ACATTGATGA GTTTGGACAA ACCACAACTA GAATGCAGTG

1501 AAAAAAATGC TTTATTTGTG AAATTTGTGA TGCTATTGCT TTATTTGTAA CCATTATAAG

1561 CTGCAATAAA CAAGTTAACA ACAACAATTG CATTCATTTT ATGTTTCAGG TTCAGGGGGA

1621 GGTGTGGGAG GTTTTTTAAA GCAAGTAAAA CCTCTACAAA TGTGGTATGG AATTAATTCT

1681 AAAATACAGC ATAGCAAAAC TTTAACCTCC AAATCAAGCC TCTACTTGAA TCCTTTTCTG

1741 AGGGATGAAT AAGGCATAGG CATCAGGGGC TGTTGCCAAT GTGCATTAGC TGTTTGCAGC

1801 CTCACCTTCT TTCATGGAGT TTAAGATATA GTGTATTTTC CCAAGGTTTG AACTAGCTCT

1861 TCATTTCTTT ATGTTTTAAA TGCACTGACC TCCCACATTC CCTTTTTAGT AAAATATTCA

1921 GAAATAATTT AAATACATCA TTGCAATGAA AATAAATGTT TTTTATTAGG CAGAATCCAG

1981 ATGCTCAAGG CCCTTCATAA TATCCCCCAG TTTAGTAGTT GGACTTAGGG AACAAAGGAA

2041 CCTTTAATAG AAATTGGACA GCAAGAAAGC GAGCTTCTAG CTTATCCTCA GTCCTGCTCC

2101 TCTGCCACAA AGTGCACGCA GTTGCCGGCC GGGTCGCGCA GGGCGAACTC CCGCCCCCAC

2161 GGCTGCTCGC CGATCTCGGT CATGGCCGGC CCGGAGGCGT CCCGGAAGTT CGTGGACACG

2221 ACCTCCGACC ACTCGGCGTA CAGCTCGTCC AGGCCGCGCA CCCACACCCA GGCCAGGGTG

2281 TTGTCCGGCA CCACCTGGTC CTGGACCGCG CTGATGAACA GGGTCACGTC GTCCCGGACC

2341 ACACCGGCGA AGTCGTCCTC CACGAAGTCC CGGGAGAACC CGAGCCGGTC GGTCCAGAAC

2401 TCGACCGCTC CGGCGACGTC GCGCGCGGTG AGCACCGGAA CGGCACTGGT CAACTTGGCC

2461 ATGATGGCTC CTCctgtcag gagaggaaag agaagaaggt tagtacaatt gCTATAGTGA

2521 GTTGTATTAT ACTATGCAGA TATACTATGC CAATGATTAA TTGTCAAACT AGGGCTGCAg 2581 ggttcatagt gccacttttc ctgcactgcc ccatctcctg cccacccttt cccaggcata 2641 gacagtcagt gacttacCAA ACTCACAGGA GGGAGAAGGC AGAAGCTTGA GACAGACCCG

2701 CGGGACCGCC GAACTGCGAG GGGACGTGGC TAGGGCGGCT TCTTTTATGG TGCGCCGGCC

2761 CTCGGAGGCA GGGCGCTCGG GGAGGCCTAG CGGCCAATCT GCGGTGGCAG GAGGCGGGGC

2821 CGAAGGCCGT GCCTGACCAA TCCGGAGCAC ATAGGAGTCT CAGCCCCCCG CCCCAAAGCA

2881 AGGGGAAGTC ACGCGCCTGT AGCGCCAGCG TGTTGTGAAA TGGGGGCTTG GGGGGGTTGG

2941 GGCCCTGACT AGTCAAAACA AACTCCCATT GACGTCAATG GGGTGGAGAC TTGGAAATCC

3001 CCGTGAGTCA AACCGCTATC CACGCCCATT GATGTACTGC CAAAACCGCA TCATCATGGT

3061 AATAGCGATG ACTAATACGT AGATGTACTG CCAAGTAGGA AAGTCCCATA AGGTCATGTA

3121 CTGGGCATAA TGCCAGGCGG GCCATTTACC GTCATTGACG TCAATAGGGG GCGTACTTGG

3181 CATATGATAC ACTTGATGTA CTGCCAAGTG GGCAGTTTAC CGTAAATACT CCACCCATTG

3241 ACGTCAATGG AAAGTCCCTA TTGGCGTTAC TATGGGAACA TACGTCATTA TTGACGTCAA

3301 TGGGCGGGGG TCGTTGGGCG GTCAGCCAGG CGGGCCATTT ACCGTAAGTT ATGTAACGCC

3361 TGCAGGTTAA TTAAGAACAT GTGAGCAAAA GGCCAGCAAA AGGCCAGGAA CCGTAAAAAG

3421 GCCGCGTTGC TGGCGTTTTT CCATAGGCTC CGCCCCCCTG ACGAGCATCA CAAAAATCGA

3481 CGCTCAAGTC AGAGGTGGCG AAACCCGACA GGACTATAAA GATACCAGGC GTTTCCCCCT

3541 GGAAGCTCCC TCGTGCGCTC TCCTGTTCCG ACCCTGCCGC TTACCGGATA CCTGTCCGCC

3601 TTTCTCCCTT CGGGAAGCGT GGCGCTTTCT CATAGCTCAC GCTGTAGGTA TCTCAGTTCG

3661 GTGTAGGTCG TTCGCTCCAA GCTGGGCTGT GTGCACGAAC CCCCCGTTCA GCCCGACCGC

-continued

3721 TGCGCCTTAT CCGGTAACTA TCGTCTTGAG TCCAACCCGG TAAGACACGA CTTATCGCCA

3781 CTGGCAGCAG CCACTGGTAA CAGGATTAGC AGAGCGAGGT ATGTAGGCGG TGCTACAGAG

3841 TTCTTGAAGT GGTGGCCTAA CTACGGCTAC ACTAGAAGAA CAGTATTTGG TATCTGCGCT

3901 CTGCTGAAGC CAGTTACCTT CGGAAAAAGA GTTGGTAGCT CTTGATCCGG CAAACAAACC

3961 ACCGCTGGTA GCGGTGGTTT TTTTGTTTGC AAGCAGCAGA TTACGCGCAG AAAAAAAGGA

4021 TCTCAAGAAG ATCCTTTGAT CTTTTCTACG GGGTCTGACG CTCAGTGGAA CGAAAACTCA

4081 CGTTAAGGGA TTTTGGTCAT GGCTAGTTAA TTAACATTTA AATCAGCGGC CGCAATAAAA

4141 TATCTTTATT TTCATTACAT CTGTGTGTTG GTTTTTTGTG TGAATCGTAA CTAACATACG

4201 CTCTCCATCA AAACAAAACG AAACAAAACA AACTAGCAAA ATAGGCTGTC CCCAGTGCAA

4261 GTGCAGGTGC CAGAACATTT CTCTATCGAA

Amino acid sequence (SEQ ID NO: 82)

MYRMQLLSCIALSLALVTNSAPLERKSSVECPPCPAPPVAGPSVFLFPP

KPKDTLMISRTPEVTCVVVDVSHEDPEVQFNWYVDGVEVEINAKTKPREEQF

NSTFRVVSVLTVVHQDWLNGKEYKCKVSNKGLPAPIEKTISKTKGQPREPQV

YTLPPSREEMTKNQVSLTCLVKGFYPSDIAVEWESNGQPENNYKTTPPMLDS

DGSFFLYSKLTVDKSRWQQGNVFSCSVMHEALHNHYTQKSLSLSPGARTRL

VQYRGEVQAMLGQSTEELRVRLASHLRKL 184R pfcn-hg2 ApoE 114-144 R1365
Nucleic acid sequence (SEQ ID NO: 83)

1 GGATCTGCGA TCGCTCCGGT GCCCGTCAGT GGGCAGAGCG CACATCGCCC ACAGTCCCCG

61 AGAAGTTGGG GGGAGGGGTC GGCAATTGAA CGGGTGCCTA GAGAAGGTGG CGCGGGGTAA

121 ACTGGGAAAG TGATGTCGTG TACTGGCTCC GCCTTTTTCC CGAGGGTGGG GGAGAACCGT

181 ATATAAGTGC AGTAGTCGCC GTGAACGTTC TTTTTCGCAA CGGGTTTGCC GCCAGAACAC

241 AGCTGAAGCT TCGAGGGGCT CGCATCTCTC CTTCACGCGC CCGCCGCCCT ACCTGAGGCC

301 GCCATCCACG CCGGTTGAGT CGCGTTCTGC CGCCTCCCGC CTGTGGTGCC TCCTGAACTG

361 CGTCCGCCGT CTAGGTAAGT TTAAAGCTCA GGTCGAGACC GGGCCTTTGT CCGGCGCTCC

421 CTTGGAGCCT ACCTAGACTC AGCCGGCTCT CCACGCTTTG CCTGACCCtg cttgctcaac 481 tctacgTCTT TGTTTCGTTT TCTGTTCTGC GCCGTTACAG ATCCAAGCTG TGACCGGCGC

541 CTACCTGAGA TCACCGGCGA AGGAGGGCCA CCATGTACAG GATGCAACTC CTGTCTTGCA

601 TTGCACTAAG TCTTGCACTT GTCACGAATT CGGCACCTCT CGAGCGCAAA TCTAGTGTCG

661 AGTGCCCACC GTGCCCAGCA CCACCTGTGG CAGGACCGTC AGTCTTCCTC TTCCCCCCAA

721 AACCCAAGGA CACCCTCATG ATCTCCCGGA CCCCTGAGGT CACGTGCGTG GTGGTGGACG

781 TGAGCCACGA AGACCCCGAG GTCCAGTTCA ACTGGTACGT GGACGGCGTG GAGGTGCATA

841 ATGCCAAGAC AAAGCCACGG GAGGAGCAGT TCAACAGCAC GTTCCGTGTG GTCAGCGTCC

901 TCACCGTTGT GCACCAGGAC TGGCTGAACG GCAAGGAGTA CAAGTGCAAG GTCTCCAACA

961 AAGGCCTCCC AGCCCCCATC GAGAAAACCA TCTCCAAAAC CAAAGGGCAG CCCCGAGAAC

1021 CACAGGTGTA CACCCTGCCC CCATCCCGGG AGGAGATGAC CAAGAACCAG GTCAGCCTGA

1081 CCTGCCTGGT CAAAGGCTTC TACCCCAGCG ACATCGCCGT GGAGTGGGAG AGCAATGGGC

1141 AGCCGGAGAA CAACTACAAG ACCACGCCTC CCATGCTGGA CTCCGACGGC TCCTTCTTCC

1201 TCTACAGCAA GCTCACCGTG GACAAGAGCA GGTGGCAGCA GGGGAACGTC TTCTCATGCT

1261 CCGTGATGCA TGAGGCTCTG CACAACCACT ACACGCAGAA GAGCCTCTCC CTGTCTCCGG

-continued

```
1321 GTGCACGTAC GCGCCTGGTG CAGTACCGCG GCGAGGTGCA GGCCATGCTC GGCCAGAGCA
1381 CCGAGGAGCT GCGGGTGaGC CTCGCCTCCC ACCTGCGCAA GCTGtgaTAT CTCGAGCTAG
1441 CTGGCCAGAC ATGATAAGAT ACATTGATGA GTTTGGACAA ACCACAACTA GAATGCAGTG
1501 AAAAAAATGC TTTATTTGTG AAATTTGTGA TGCTATTGCT TTATTTGTAA CCATTATAAG
1561 CTGCAATAAA CAAGTTAACA ACAACAATTG CATTCATTTT ATGTTTCAGG TTCAGGGGGA
1621 GGTGTGGGAG GTTTTTTAAA GCAAGTAAAA CCTCTACAAA TGTGGTATGG AATTAATTCT
1681 AAAATACAGC ATAGCAAAAC TTTAACCTCC AAATCAAGCC TCTACTTGAA TCCTTTTCTG
1741 AGGGATGAAT AAGGCATAGG CATCAGGGGC TGTTGCCAAT GTGCATTAGC TGTTTGCAGC
1801 CTCACCTTCT TTCATGGAGT TTAAGATATA GTGTATTTTC CCAAGGTTTG AACTAGCTCT
1861 TCATTTCTTT ATGTTTTAAA TGCACTGACC TCCCACATTC CCTTTTTAGT AAAATATTCA
1921 GAAATAATTT AAATACATCA TTGCAATGAA AATAAATGTT TTTTATTAGG CAGAATCCAG
1981 ATGCTCAAGG CCCTTCATAA TATCCCCCAG TTTAGTAGTT GGACTTAGGG AACAAAGGAA
2041 CCTTTAATAG AAATTGGACA GCAAGAAAGC GAGCTTCTAG CTTATCCTCA GTCCTGCTCC
2101 TCTGCCACAA AGTGCACGCA GTTGCCGGCC GGGTCGCGCA GGGCGAACTC CCGCCCCCAC
2161 GGCTGCTCGC CGATCTCGGT CATGGCCGGC CCGGAGGCGT CCCGGAAGTT CGTGGACACG
2221 ACCTCCGACC ACTCGGCGTA CAGCTCGTCC AGGCCGCGCA CCCACACCCA GGCCAGGGTG
2281 TTGTCCGGCA CCACCTGGTC CTGGACCGCG CTGATGAACA GGGTCACGTC GTCCCGGACC
2341 ACACCGGCGA AGTCGTCCTC CACGAAGTCC CGGGAGAACC CGAGCCGGTC GGTCCAGAAC
2401 TCGACCGCTC CGGCGACGTC GCGCGCGGTG AGCACCGGAA CGGCACTGGT CAACTTGGCC
2461 ATGATGGCTC CTCctgtcag gagaggaaag agaagaaggt tagtacaatt gCTATAGTGA
2521 GTTGTATTAT ACTATGCAGA TATACTATGC CAATGATTAA TTGTCAAACT AGGGCTGCAg
2581 ggttcatagt gccacttttc ctgcactgcc ccatctcctg cccacccttt cccaggcata
2641 gacagtcagt gacttacCAA ACTCACAGGA GGGAGAAGGC AGAAGCTTGA GACAGACCCG
2701 CGGGACCGCC GAACTGCGAG GGGACGTGGC TAGGGCGGCT TCTTTTATGG TGCGCCGGCC
2761 CTCGGAGGCA GGGCGCTCGG GGAGGCCTAG CGGCCAATCT GCGGTGGCAG GAGGCGGGGC
2821 CGAAGGCCGT GCCTGACCAA TCCGGAGCAC ATAGGAGTCT CAGCCCCCCG CCCCAAAGCA
2881 AGGGGAAGTC ACGCGCCTGT AGCGCCAGCG TGTTGTGAAA TGGGGGCTTG GGGGGGTTGG
2941 GGCCCTGACT AGTCAAAACA AACTCCCATT GACGTCAATG GGGTGGAGAC TTGGAAATCC
3001 CCGTGAGTCA AACCGCTATC CACGCCCATT GATGTACTGC CAAAACCGCA TCATCATGGT
3061 AATAGCGATG ACTAATACGT AGATGTACTG CCAAGTAGGA AAGTCCCATA AGGTCATGTA
3121 CTGGGCATAA TGCCAGGCGG GCCATTTACC GTCATTGACG TCAATAGGGG GCGTACTTGG
3181 CATATGATAC ACTTGATGTA CTGCCAAGTG GGCAGTTTAC CGTAAATACT CCACCCATTG
3241 ACGTCAATGG AAAGTCCCTA TTGGCGTTAC TATGGGAACA TACGTCATTA TTGACGTCAA
3301 TGGGCGGGGG TCGTTGGGCG GTCAGCCAGG CGGGCCATTT ACCGTAAGTT ATGTAACGCC
3361 TGCAGGTTAA TTAAGAACAT GTGAGCAAAA GGCCAGCAAA AGGCCAGGAA CCGTAAAAAG
3421 GCCGCGTTGC TGGCGTTTTT CCATAGGCTC CGCCCCCCTG ACGAGCATCA CAAAAATCGA
3481 CGCTCAAGTC AGAGGTGGCG AAACCCGACA GGACTATAAA GATACCAGGC GTTTCCCCCT
3541 GGAAGCTCCC TCGTGCGCTC TCCTGTTCCG ACCCTGCCGC TTACCGGATA CCTGTCCGCC
3601 TTTCTCCCTT CGGGAAGCGT GGCGCTTTCT CATAGCTCAC GCTGTAGGTA TCTCAGTTCG
3661 GTGTAGGTCG TTCGCTCCAA GCTGGGCTGT GTGCACGAAC CCCCCGTTCA GCCCGACCGC
```

-continued

3721 TGCGCCTTAT CCGGTAACTA TCGTCTTGAG TCCAACCCGG TAAGACACGA CTTATCGCCA

3781 CTGGCAGCAG CCACTGGTAA CAGGATTAGC AGAGCGAGGT ATGTAGGCGG TGCTACAGAG

3841 TTCTTGAAGT GGTGGCCTAA CTACGGCTAC ACTAGAAGAA CAGTATTTGG TATCTGCGCT

3901 CTGCTGAAGC CAGTTACCTT CGGAAAAAGA GTTGGTAGCT CTTGATCCGG CAAACAAACC

3961 ACCGCTGGTA GCGGTGGTTT TTTTGTTTGC AAGCAGCAGA TTACGCGCAG AAAAAAAGGA

4021 TCTCAAGAAG ATCCTTTGAT CTTTTCTACG GGGTCTGACG CTCAGTGGAA CGAAAACTCA

4081 CGTTAAGGGA TTTTGGTCAT GGCTAGTTAA TTAACATTTA AATCAGCGGC CGCAATAAAA

4141 TATCTTTATT TTCATTACAT CTGTGTGTTG GTTTTTTGTG TGAATCGTAA CTAACATACG

4201 CTCTCCATCA AAACAAAACG AAACAAAACA AACTAGCAAA ATAGGCTGTC CCCAGTGCAA

4261 GTGCAGGTGC CAGAACATTT CTCTATCGAA

Amino acid sequence (SEQ ID NO: 84)

MYRMQLLSCIALSLALVTNSAPLERKSSVECPPCPAPPVAGPSVFLFPP

KPKDTLMISRTPEVTCVVVDVSHEDPEVQFNWYVDGVEVEINAKTKPREEQF

NSTFRVVSVLTVVHQDWLNGKEYKCKVSNKGLPAPIEKTISKTKGQPREPQV

YTLPPSREEMTKNQVSLTCLVKGFYPSDIAVEWESNGQPENNYKTTPPMLDS

DGSFFLYSKLTVDKSRWQQGNVFSCSVMHEALHNHYTQKSLSLSPGARTRL

VQYRGEVQAMLGQSTEELRVSLASHLRKL 197F pfuse hfc2 ApoE 114-144
Nucleic acid sequence (SEQ ID NO: 85)

1 GGATCTGCGA TCGCTCCGGT GCCCGTCAGT GGGCAGAGCG CACATCGCCC ACAGTCCCCG

61 AGAAGTTGGG GGGAGGGGTC GGCAATTGAA CGGGTGCCTA GAGAAGGTGG CGCGGGGTAA

121 ACTGGGAAAG TGATGTCGTG TACTGGCTCC GCCTTTTTCC CGAGGGTGGG GGAGAACCGT

181 ATATAAGTGC AGTAGTCGCC GTGAACGTTC TTTTTCGCAA CGGGTTTGCC GCCAGAACAC

241 AGCTGAAGCT TCGAGGGGCT CGCATCTCTC CTTCACGCGC CCGCCGCCCT ACCTGAGGCC

301 GCCATCCACG CCGGTTGAGT CGCGTTCTGC CGCCTCCCGC CTGTGGTGCC TCCTGAACTG

361 CGTCCGCCGT CTAGGTAAGT TTAAAGCTCA GGTCGAGACC GGGCCTTTGT CCGGCGCTCC

421 CTTGGAGCCT ACCTAGACTC AGCCGGCTCT CCACGCTTTG CCTGACCCTG CTTGCTCAAC

481 TCTACGTCTT TGTTTCGTTT TCTGTTCTGC GCCGTTACAG ATCCAAGCTG TGACCGGCGC

541 CTACCTGAGA TCAccggcGA AGGAGGGCCA CCATGTACAG GATGCAACTC CTGTCTTGCA

601 TTGCACTAAG TCTTGCACTT GTCACGAATT CGATaCGCCT GGTGCAGTAC CGCGGCGAGG

661 TGCAGGCCAT GCTCGGCCAG AGtACtGAGG AGCTGCGGGT GCGCCTCGCC TCCCACCTGC

721 GCAAGCTGat ATCGGCCATG GTTAGATCTG TGGAGTGCCC ACCTTGCCCA GCACCACCTG

781 TGGCAGGACC TTCAGTCTTC CTCTTCCCCC CAAAACCCAA GGACACCCTG ATGATCTCCA

841 GAACCCCTGA GGTCACGTGC GTGGTGGTGG ACGTGAGCCA CGAAGACCCC GAGGTCCAGT

901 TCAACTGGTA CGTGGACGGC ATGGAGGTGC ATAATGCCAA GACAAAGCCA CGGGAGGAGC

961 AGTTCAACAG CACGTTCCGT GTGGTCAGCG TCCTCACCGT CGTGCACCAG GACTGGCTGA

1021 ACGGCAAGGA GTACAAGTGC AAGGTCTCCA ACAAAGGCCT CCCAGCCCCC ATCGAGAAAA

1081 CCATCTCCAA AACCAAAGGG CAGCCCCGAG AACCACAGGT GTACACCCTG CCCCCATCCC

1141 GGGAGGAGAT GACCAAGAAC CAGGTCAGCC TGACCTGCCT GGTCAAAGGC TTCTACCCCA

1201 GCGACATCGC CGTGGAGTGG GAGAGCAATG GGCAGCCGGA GAACAACTAC AAGACCACAC

1261 CTCCCATGCT GGACTCCGAC GGCTCCTTCT TCCTCTACAG CAAGCTCACC GTGGACAAGA

-continued

1321 GCAGGTGGCA GCAGGGGAAC GTCTTCTCAT GCTCCGTGAT GCATGAGGCT CTGCACAACC

1381 ACTACACACA GAAGAGCCTC TCCCTGTCTC CGGGTAAATG AgtgccacgG CTAGCTGGCC

1441 AGACATGATA AGATACATTG ATGAGTTTGG ACAAACCACA ACTAGAATGC AGTGAAAAAA

1501 ATGCTTTATT TGTGAAATTT GTGATGCTAT TGCTTTATTT GTAACCATTA TAAGCTGCAA

1561 TAAACAAGTT AACAACAACA ATTGCATTCA TTTTATGTTT CAGGTTCAGG GGGAGGTGTG

1621 GGAGGTTTTT TAAAGCAAGT AAAACCTCTA CAAATGTGGT ATGGAATTAA TTCTAAAATA

1681 CAGCATAGCA AAACTTTAAC CTCCAAATCA AGCCTCTACT TGAATCCTTT TCTGAGGGAT

1741 GAATAAGGCA TAGGCATCAG GGGCTGTTGC CAATGTGCAT TAGCTGTTTG CAGCCTCACC

1801 TTCTTTCATG GAGTTTAAGA TATAGTGTAT TTTCCCAAGG TTTGAACTAG CTCTTCATTT

1861 CTTTATGTTT TAAATGCACT GACCTCCCAC ATTCCCTTTT TAGTAAAATA TTCAGAAATA

1921 ATTTAAATAC ATCATTGCAA TGAAAATAAA TGTTTTTTAT TAGGCAGAAT CCAGATGCTC

1981 AAGGCCCTTC ATAATATCCC CCAGTTTAGT AGTTGGACTT AGGGAACAAA GGAACCTTTA

2041 ATAGAAATTG GACAGCAAGA AAGCGAGCTT CTAGCTTATC CTCAGTCCTG CTCCTCTGCC

2101 ACAAAGTGCA CGCAGTTGCC GGCCGGGTCG CGCAGGGCGA ACTCCCGCCC CCACGGCTGC

2161 TCGCCGATCT CGGTCATGGC CGGCCCGGAG GCGTCCCGGA AGTTCGTGGA CACGACCTCC

2221 GACCACTCGG CGTACAGCTC GTCCAGGCCG CGCACCCACA CCCAGGCCAG GGTGTTGTCC

2281 GGCACCACCT GGTCCTGGAC CGCGCTGATG AACAGGGTCA CGTCGTCCCG GACCACACCG

2341 GCGAAGTCGT CCTCCACGAA GTCCCGGGAG AACCCGAGCC GGTCGGTCCA GAACTCGACC

2401 GCTCCGGCGA CGTCGCGCGC GGTGAGCACC GGAACGGCAC TGGTCAACTT GGCCATGATG

2461 GCTCCTCctg tcaggagagg aaagagaaga aggttagtac aattgCTATA GTGAGTTGTA

2521 TTATACTATG CAGATATACT ATGCCAATGA TTAATTGTCA AACTAGGGCT GCAgggttca 2581 tagtgccact tttcctgcac tgccccatct cctgccccacc ctttcccagg catagacagt 2641 cagtgactta cCAAACTCAC AGGAGGGAGA AGGCAGAAGC TTGAGACAGA CCCGCGGGAC

2701 CGCCGAACTG CGAGGGGACG TGGCTAGGGC GGCTTCTTTT ATGGTGCGCC GGCCCTCGGA

2761 GGCAGGGCGC TCGGGGAGGC CTAGCGGCCA ATCTGCGGTG GCAGGAGGCG GGGCCGAAGG

2821 CCGTGCCTGA CCAATCCGGA GCACATAGGA GTCTCAGCCC CCCGCCCCAA AGCAAGGGGA

2881 AGTCACGCGC CTGTAGCGCC AGCGTGTTGT GAAATGGGGG CTTGGGGGGG TTGGGGCCCT

2941 GACTAGTCAA AACAAACTCC CATTGACGTC AATGGGGTGG AGACTTGGAA ATCCCCGTGA

3001 GTCAAACCGC TATCCACGCC CATTGATGTA CTGCCAAAAC CGCATCATCA TGGTAATAGC

3061 GATGACTAAT ACGTAGATGT ACTGCCAAGT AGGAAAGTCC CATAAGGTCA TGTACTGGGC

3121 ATAATGCCAG GCGGGCCATT TACCGTCATT GACGTCAATA GGGGGCGTAC TTGGCATATG

3181 ATACACTTGA TGTACTGCCA AGTGGGCAGT TTACCGTAAA TACTCCACCC ATTGACGTCA

3241 ATGGAAAGTC CCTATTGGCG TTACTATGGG AACATACGTC ATTATTGACG TCAATGGGCG

3301 GGGGTCGTTG GGCGGTCAGC CAGGCGGGCC ATTTACCGTA AGTTATGTAA CGCCTGCAGG

3361 TTAATTAAGA ACATGTGAGC AAAAGGCCAG CAAAAGGCCA GGAACCGTAA AAAGGCCGCG

3421 TTGCTGGCGT TTTTCCATAG GCTCCGCCCC CCTGACGAGC ATCACAAAAA TCGACGCTCA

3481 AGTCAGAGGT GGCGAAACCC GACAGGACTA TAAAGATACC AGGCGTTTCC CCCTGGAAGC

3541 TCCCTCGTGC GCTCTCCTGT TCCGACCCTG CCGCTTACCG GATACCTGTC CGCCTTTCTC

3601 CCTTCGGGAA GCGTGGCGCT TTCTCATAGC TCACGCTGTA GGTATCTCAG TTCGGTGTAG

3661 GTCGTTCGCT CCAAGCTGGG CTGTGTGCAC GAACCCCCCG TTCAGCCCGA CCGCTGCGCC

3721 TTATCCGGTA ACTATCGTCT TGAGTCCAAC CCGGTAAGAC ACGACTTATC GCCACTGGCA

-continued

3781 GCAGCCACTG GTAACAGGAT TAGCAGAGCG AGGTATGTAG GCGGTGCTAC AGAGTTCTTG

3841 AAGTGGTGGC CTAACTACGG CTACACTAGA AGAACAGTAT TTGGTATCTG CGCTCTGCTG

3901 AAGCCAGTTA CCTTCGGAAA AAGAGTTGGT AGCTCTTGAT CCGGCAAACA AACCACCGCT

3961 GGTAGCGGTG GTTTTTTTGT TTGCAAGCAG CAGATTACGC GCAGAAAAAA AGGATCTCAA

4021 GAAGATCCTT TGATCTTTTC TACGGGGTCT GACGCTCAGT GGAACGAAAA CTCACGTTAA

4081 GGGATTTTGG TCATGGCTAG TTAATTAACA TTTAAATCAG CGGCCGCAAT AAAATATCTT

4141 TATTTTCATT ACATCTGTGT GTTGGTTTTT TGTGTGAATC GTAACTAACA TACGCTCTCC

4201 ATCAAAACAA AACGAAACAA AACAAACTAG CAAAATAGGC TGTCCCCAGT GCAAGTGCAG

4261 GTGCCAGAAC ATTTCTCTAT CGAA

Amino acid sequence (SEQ ID NO: 86)

MYRMQLLSCIALSLALVTNSIRLVQYRGEVQAMLGQSTEELRVRLAS

HLRKLISAMVRSVECPPCPAPPVAGPSVFLFPPKPKDTLMISRTPEVTCVVVDV

SHEDPEVQFNWYVDGMEVEINAKTKPREEQFNSTFRVVSVLTVVHQDWLNG

KEYKCKVSNKGLPAPIEKTISKTKGQPREPQVYTLPPSREEMTKNQVSLTCLV

KGFYPSDIAVEWESNGQPENNYKTTPPMLDSDGSFFLYSKLTVDKSRWQQGN

VFSCSVMHEALHNHYTQKSLSLSPGK 197G pfuse-hfc2 ApoE 114-144 R136S
Nucleic acid sequence (SEQ ID NO: 87)

1 GGATCTGCGA TCGCTCCGGT GCCCGTCAGT GGGCAGAGCG CACATCGCCC ACAGTCCCCG

61 AGAAGTTGGG GGGAGGGGTC GGCAATTGAA CGGGTGCCTA GAGAAGGTGG CGCGGGGTAA

121 ACTGGGAAAG TGATGTCGTG TACTGGCTCC GCCTTTTTCC CGAGGGTGGG GGAGAACCGT

181 ATATAAGTGC AGTAGTCGCC GTGAACGTTC TTTTTCGCAA CGGGTTTGCC GCCAGAACAC

241 AGCTGAAGCT TCGAGGGGCT CGCATCTCTC CTTCACGCGC CCGCCGCCCT ACCTGAGGCC

301 GCCATCCACG CCGGTTGAGT CGCGTTCTGC CGCCTCCCGC CTGTGGTGCC TCCTGAACTG

361 CGTCCGCCGT CTAGGTAAGT TTAAAGCTCA GGTCGAGACC GGGCCTTTGT CCGGCGCTCC

421 CTTGGAGCCT ACCTAGACTC AGCCGGCTCT CCACGCTTTG CCTGACCCTG CTTGCTCAAC

481 TCTACGTCTT TGTTTCGTTT TCTGTTCTGC GCCGTTACAG ATCCAAGCTG TGACCGGCGC

541 CTACCTGAGA TCAccggcGA AGGAGGGCCA CCATGTACAG GATGCAACTC CTGTCTTGCA

601 TTGCACTAAG TCTTGCACTT GTCACGAATT CGATaCGCCT GGTGCAGTAC CGCGGCGAGG

661 TGCAGGCCAT GCTCGGCCAG AGtActGAGG AGCTGCGGGT GaGCCTCGCC TCCCACCTGC

721 GCAAGCTGat ATCGGCCATG GTTAGATCTG TGGAGTGCCC ACCTTGCCCA GCACCACCTG

781 TGGCAGGACC TTCAGTCTTC CTCTTCCCCC CAAAACCCAA GGACACCCTG ATGATCTCCA

841 GAACCCCTGA GGTCACGTGC GTGGTGGTGG ACGTGAGCCA CGAAGACCCC GAGGTCCAGT

901 TCAACTGGTA CGTGGACGGC ATGGAGGTGC ATAATGCCAA GACAAAGCCA CGGGAGGAGC

961 AGTTCAACAG CACGTTCCGT GTGGTCAGCG TCCTCACCGT CGTGCACCAG GACTGGCTGA

1021 ACGGCAAGGA GTACAAGTGC AAGGTCTCCA ACAAAGGCCT CCCAGCCCCC ATCGAGAAAA

1081 CCATCTCCAA AACCAAAGGG CAGCCCCGAG AACCACAGGT GTACACCCTG CCCCCATCCC

1141 GGGAGGAGAT GACCAAGAAC CAGGTCAGCC TGACCTGCCT GGTCAAAGGC TTCTACCCCA

1201 GCGACATCGC CGTGGAGTGG GAGAGCAATG GGCAGCCGGA GAACAACTAC AAGACCACAC

1261 CTCCCATGCT GGACTCCGAC GGCTCCTTCT TCCTCTACAG CAAGCTCACC GTGGACAAGA

1321 GCAGGTGGCA GCAGGGGAAC GTCTTCTCAT GCTCCGTGAT GCATGAGGCT CTGCACAACC

-continued

1381 ACTACACACA GAAGAGCCTC TCCCTGTCTC CGGGTAAATG AgtgccacgG CTAGCTGGCC

1441 AGACATGATA AGATACATTG ATGAGTTTGG ACAAACCACA ACTAGAATGC AGTGAAAAAA

1501 ATGCTTTATT TGTGAAATTT GTGATGCTAT TGCTTTATTT GTAACCATTA TAAGCTGCAA

1561 TAAACAAGTT AACAACAACA ATTGCATTCA TTTTATGTTT CAGGTTCAGG GGGAGGTGTG

1621 GGAGGTTTTT TAAAGCAAGT AAAACCTCTA CAAATGTGGT ATGGAATTAA TTCTAAAATA

1681 CAGCATAGCA AAACTTTAAC CTCCAAATCA AGCCTCTACT TGAATCCTTT TCTGAGGGAT

1741 GAATAAGGCA TAGGCATCAG GGGCTGTTGC CAATGTGCAT TAGCTGTTTG CAGCCTCACC

1801 TTCTTTCATG GAGTTTAAGA TATAGTGTAT TTTCCCAAGG TTTGAACTAG CTCTTCATTT

1861 CTTTATGTTT TAAATGCACT GACCTCCCAC ATTCCCTTTT TAGTAAAATA TTCAGAAATA

1921 ATTTAAATAC ATCATTGCAA TGAAAATAAA TGTTTTTTAT TAGGCAGAAT CCAGATGCTC

1981 AAGGCCCTTC ATAATATCCC CCAGTTTAGT AGTTGGACTT AGGGAACAAA GGAACCTTTA

2041 ATAGAAATTG GACAGCAAGA AAGCGAGCTT CTAGCTTATC CTCAGTCCTG CTCCTCTGCC

2101 ACAAAGTGCA CGCAGTTGCC GGCCGGGTCG CGCAGGGCGA ACTCCCGCCC CCACGGCTGC

2161 TCGCCGATCT CGGTCATGGC CGGCCCGGAG GCGTCCCGGA AGTTCGTGGA CACGACCTCC

2221 GACCACTCGG CGTACAGCTC GTCCAGGCCG CGCACCCACA CCCAGGCCAG GGTGTTGTCC

2281 GGCACCACCT GGTCCTGGAC CGCGCTGATG AACAGGGTCA CGTCGTCCCG GACCACACCG

2341 GCGAAGTCGT CCTCCACGAA GTCCCGGGAG AACCCGAGCC GGTCGGTCCA GAACTCGACC

2401 GCTCCGGCGA CGTCGCGCGC GGTGAGCACC GGAACGGCAC TGGTCAACTT GGCCATGATG

2461 GCTCCTCctg tcaggagagg aaagagaaga aggttagtac aattgCTATA GTGAGTTGTA

2521 TTATACTATG CAGATATACT ATGCCAATGA TTAATTGTCA AACTAGGGCT GCAgggttca 2581 tagtgccact tttcctgcac tgccccatct cctgcccacc ctttcccagg catagacagt 2641 cagtgactta cCAAACTCAC AGGAGGGAGA AGGCAGAAGC TTGAGACAGA CCCGCGGGAC

2701 CGCCGAACTG CGAGGGGACG TGGCTAGGGC GGCTTCTTTT ATGGTGCGCC GGCCCTCGGA

2761 GGCAGGGCGC TCGGGGAGGC CTAGCGGCCA ATCTGCGGTG GCAGGAGGCG GGGCCGAAGG

2821 CCGTGCCTGA CCAATCCGGA GCACATAGGA GTCTCAGCCC CCCGCCCCAA AGCAAGGGGA

2881 AGTCACGCGC CTGTAGCGCC AGCGTGTTGT GAAATGGGGG CTTGGGGGGG TTGGGGCCCT

2941 GACTAGTCAA AACAAACTCC CATTGACGTC AATGGGGTGG AGACTTGGAA ATCCCCGTGA

3001 GTCAAACCGC TATCCACGCC CATTGATGTA CTGCCAAAAC CGCATCATCA TGGTAATAGC

3061 GATGACTAAT ACGTAGATGT ACTGCCAAGT AGGAAAGTCC CATAAGGTCA TGTACTGGGC

3121 ATAATGCCAG GCGGGCCATT TACCGTCATT GACGTCAATA GGGGGCGTAC TTGGCATATG

3181 ATACACTTGA TGTACTGCCA AGTGGGCAGT TTACCGTAAA TACTCCACCC ATTGACGTCA

3241 ATGGAAAGTC CCTATTGGCG TTACTATGGG AACATACGTC ATTATTGACG TCAATGGGCG

3301 GGGGTCGTTG GGCGGTCAGC CAGGCGGGCC ATTTACCGTA AGTTATGTAA CGCCTGCAGG

3361 TTAATTAAGA ACATGTGAGC AAAAGGCCAG CAAAAGGCCA GGAACCGTAA AAAGGCCGCG

3421 TTGCTGGCGT TTTTCCATAG GCTCCGCCCC CCTGACGAGC ATCACAAAAA TCGACGCTCA

3481 AGTCAGAGGT GGCGAAACCC GACAGGACTA TAAAGATACC AGGCGTTTCC CCCTGGAAGC

3541 TCCCTCGTGC GCTCTCCTGT TCCGACCCTG CCGCTTACCG GATACCTGTC CGCCTTTCTC

3601 CCTTCGGGAA GCGTGGCGCT TTCTCATAGC TCACGCTGTA GGTATCTCAG TTCGGTGTAG

3661 GTCGTTCGCT CCAAGCTGGG CTGTGTGCAC GAACCCCCCG TTCAGCCCGA CCGCTGCGCC

3721 TTATCCGGTA ACTATCGTCT TGAGTCCAAC CCGGTAAGAC ACGACTTATC GCCACTGGCA

-continued

3781 GCAGCCACTG GTAACAGGAT TAGCAGAGCG AGGTATGTAG GCGGTGCTAC AGAGTTCTTG

3841 AAGTGGTGGC CTAACTACGG CTACACTAGA AGAACAGTAT TTGGTATCTG CGCTCTGCTG

3901 AAGCCAGTTA CCTTCGGAAA AAGAGTTGGT AGCTCTTGAT CCGGCAAACA AACCACCGCT

3961 GGTAGCGGTG GTTTTTTTGT TTGCAAGCAG CAGATTACGC GCAGAAAAAA AGGATCTCAA

4021 GAAGATCCTT TGATCTTTTC TACGGGGTCT GACGCTCAGT GGAACGAAAA CTCACGTTAA

4081 GGGATTTTGG TCATGGCTAG TTAATTAACA TTTAAATCAG CGGCCGCAAT AAAATATCTT

4141 TATTTTCATT ACATCTGTGT GTTGGTTTTT TGTGTGAATC GTAACTAACA TACGCTCTCC

4201 ATCAAAACAA AACGAAACAA AACAAACTAG CAAAATAGGC TGTCCCCAGT GCAAGTGCAG

4261 GTGCCAGAAC ATTTCTCTAT CGAA

Amino acid sequence (SEQ ID NO: 88)

MYRMQLLSCIALSLALVTNSIRLVQYRGEVQAMLGQSTEELRVSLASH

LRKLISAMVRSVECPPCPAPPVAGPSVFLFPPKPKDTLMISRTPEVTCVVVDVS

HEDPEVQFNWYVDGMEVEINAKTKPREEQFNSTFRVVSVLTVVEIQDWLNGK

EYKCKVSNKGLPAPIEKTISKTKGQPREPQVYTLPPSREEMTKNQVSLTCLVK

GFYPSDIAVEWESNGQPENNYKTTPPMLDSDGSFFLYSKLTVDKSRWQQGNV

FSCSVMHEALHNHYTQKSLSLSPGK 184U pfcn hg2 ApoE 129-157
Nucleic acid sequence (SEQ ID NO: 89)

1 GGATCTGCGA TCGCTCCGGT GCCCGTCAGT GGGCAGAGCG CACATCGCCC ACAGTCCCCG

61 AGAAGTTGGG GGGAGGGGTC GGCAATTGAA CGGGTGCCTA GAGAAGGTGG CGCGGGGTAA

121 ACTGGGAAAG TGATGTCGTG TACTGGCTCC GCCTTTTTCC CGAGGGTGGG GGAGAACCGT

181 ATATAAGTGC AGTAGTCGCC GTGAACGTTC TTTTTCGCAA CGGGTTTGCC GCCAGAACAC

241 AGCTGAAGCT TCGAGGGGCT CGCATCTCTC CTTCACGCGC CCGCCGCCCT ACCTGAGGCC

301 GCCATCCACG CCGGTTGAGT CGCGTTCTGC CGCCTCCCGC CTGTGGTGCC TCCTGAACTG

361 CGTCCGCCGT CTAGGTAAGT TTAAAGCTCA GGTCGAGACC GGGCCTTTGT CCGGCGCTCC

421 CTTGGAGCCT ACCTAGACTC AGCCGGCTCT CCACGCTTTG CCTGACCCtg cttgctcaac 481 tctacgTCTT TGTTTCGTTT TCTGTTCTGC GCCGTTACAG ATCCAAGCTG TGACCGGCGC

541 CTACCTGAGA TCACCGGCGA AGGAGGGCCA CCATGTACAG GATGCAACTC CTGTCTTGCA

601 TTGCACTAAG TCTTGCACTT GTCACGAATT CGGCACCTCT CGAGCGCAAA TCTAGTGTCG

661 AGTGCCCACC GTGCCCAGCA CCACCTGTGG CAGGACCGTC AGTCTTCCTC TTCCCCCCAA

721 AACCCAAGGA CACCCTCATG ATCTCCCGGA CCCCTGAGGT CACGTGCGTG GTGGTGGACG

781 TGAGCCACGA AGACCCCGAG GTCCAGTTCA ACTGGTACGT GGACGGCGTG GAGGTGCATA

841 ATGCCAAGAC AAAGCCACGG GAGGAGCAGT TCAACAGCAC GTTCCGTGTG GTCAGCGTCC

901 TCACCGTTGT GCACCAGGAC TGGCTGAACG GCAAGGAGTA CAAGTGCAAG GTCTCCAACA

961 AAGGCCTCCC AGCCCCCATC GAGAAAACCA TCTCCAAAAC CAAAGGGCAG CCCCGAGAAC

1021 CACAGGTGTA CACCCTGCCC CCATCCCGGG AGGAGATGAC CAAGAACCAG GTCAGCCTGA

1081 CCTGCCTGGT CAAAGGCTTC TACCCCAGCG ACATCGCCGT GGAGTGGGAG AGCAATGGGC

1141 AGCCGGAGAA CAACTACAAG ACCACGCCTC CCATGCTGGA CTCCGACGGC TCCTTCTTCC

1201 TCTACAGCAA GCTCACCGTG GACAAGAGCA GGTGGCAGCA GGGGAACGTC TTCTCATGCT

1261 CCGTGATGCA TGAGGCTCTG CACAACCACT ACACGCAGAA GAGCCTCTCC CTGTCTCCGG

1321 GTGCACGTAC GAGCACCGAG GAGCTGCGGG TGCGCCTCGC CTCCCACCTG CGCAAGCTGC

-continued

1381 GTAAGCGGCT CCTCCGCGAT GCCGATGACC TGCAGAAGtg aTATCTCGAG CTAGCTGGCC

1441 AGACATGATA AGATACATTG ATGAGTTTGG ACAAACCACA ACTAGAATGC AGTGAAAAAA

1501 ATGCTTTATT TGTGAAATTT GTGATGCTAT TGCTTTATTT GTAACCATTA TAAGCTGCAA

1561 TAAACAAGTT AACAACAACA ATTGCATTCA TTTTATGTTT CAGGTTCAGG GGGAGGTGTG

1621 GGAGGTTTTT TAAAGCAAGT AAAACCTCTA CAAATGTGGT ATGGAATTAA TTCTAAAATA

1681 CAGCATAGCA AAACTTTAAC CTCCAAATCA AGCCTCTACT TGAATCCTTT TCTGAGGGAT

1741 GAATAAGGCA TAGGCATCAG GGGCTGTTGC CAATGTGCAT TAGCTGTTTG CAGCCTCACC

1801 TTCTTTCATG GAGTTTAAGA TATAGTGTAT TTTCCCAAGG TTTGAACTAG CTCTTCATTT

1861 CTTTATGTTT TAAATGCACT GACCTCCCAC ATTCCCTTTT TAGTAAAATA TTCAGAAATA

1921 ATTTAAATAC ATCATTGCAA TGAAAATAAA TGTTTTTTAT TAGGCAGAAT CCAGATGCTC

1981 AAGGCCCTTC ATAATATCCC CCAGTTTAGT AGTTGGACTT AGGGAACAAA GGAACCTTTA

2041 ATAGAAATTG GACAGCAAGA AAGCGAGCTT CTAGCTTATC CTCAGTCCTG CTCCTCTGCC

2101 ACAAAGTGCA CGCAGTTGCC GGCCGGGTCG CGCAGGGCGA ACTCCCGCCC CCACGGCTGC

2161 TCGCCGATCT CGGTCATGGC CGGCCCGGAG GCGTCCCGGA AGTTCGTGGA CACGACCTCC

2221 GACCACTCGG CGTACAGCTC GTCCAGGCCG CGCACCCACA CCCAGGCCAG GGTGTTGTCC

2281 GGCACCACCT GGTCCTGGAC CGCGCTGATG AACAGGGTCA CGTCGTCCCG GACCACACCG

2341 GCGAAGTCGT CCTCCACGAA GTCCCGGGAG AACCCGAGCC GGTCGGTCCA GAACTCGACC

2401 GCTCCGGCGA CGTCGCGCGC GGTGAGCACC GGAACGGCAC TGGTCAACTT GGCCATGATG

2461 GCTCCTCctg tcaggagagg aaagagaaga aggttagtac aattgCTATA GTGAGTTGTA

2521 TTATACTATG CAGATATACT ATGCCAATGA TTAATTGTCA AACTAGGGCT GCAgggttca 2581 tagtgccact tttcctgcac tgccccatct cctgcccacc ctttcccagg catagacagt 2641 cagtgactta cCAAACTCAC AGGAGGGAGA AGGCAGAAGC TTGAGACAGA CCCGCGGGAC

2701 CGCCGAACTG CGAGGGGACG TGGCTAGGGC GGCTTCTTTT ATGGTGCGCC GGCCCTCGGA

2761 GGCAGGGCGC TCGGGGAGGC CTAGCGGCCA ATCTGCGGTG GCAGGAGGCG GGGCCGAAGG

2821 CCGTGCCTGA CCAATCCGGA GCACATAGGA GTCTCAGCCC CCCGCCCCAA AGCAAGGGGA

2881 AGTCACGCGC CTGTAGCGCC AGCGTGTTGT GAAATGGGGG CTTGGGGGGG TTGGGGCCCT

2941 GACTAGTCAA AACAAACTCC CATTGACGTC AATGGGGTGG AGACTTGGAA ATCCCCGTGA

3001 GTCAAACCGC TATCCACGCC CATTGATGTA CTGCCAAAAC CGCATCATCA TGGTAATAGC

3061 GATGACTAAT ACGTAGATGT ACTGCCAAGT AGGAAAGTCC CATAAGGTCA TGTACTGGGC

3121 ATAATGCCAG GCGGGCCATT TACCGTCATT GACGTCAATA GGGGGCGTAC TTGGCATATG

3181 ATACACTTGA TGTACTGCCA AGTGGGCAGT TTACCGTAAA TACTCCACCC ATTGACGTCA

3241 ATGGAAAGTC CCTATTGGCG TTACTATGGG AACATACGTC ATTATTGACG TCAATGGGCG

3301 GGGGTCGTTG GGCGGTCAGC CAGGCGGGCC ATTTACCGTA AGTTATGTAA CGCCTGCAGG

3361 TTAATTAAGA ACATGTGAGC AAAAGGCCAG CAAAAGGCCA GGAACCGTAA AAAGGCCGCG

3421 TTGCTGGCGT TTTTCCATAG GCTCCGCCCC CCTGACGAGC ATCACAAAAA TCGACGCTCA

3481 AGTCAGAGGT GGCGAAACCC GACAGGACTA TAAAGATACC AGGCGTTTCC CCCTGGAAGC

3541 TCCCTCGTGC GCTCTCCTGT TCCGACCCTG CCGCTTACCG GATACCTGTC CGCCTTTCTC

3601 CCTTCGGGAA GCGTGGCGCT TTCTCATAGC TCACGCTGTA GGTATCTCAG TTCGGTGTAG

3661 GTCGTTCGCT CCAAGCTGGG CTGTGTGCAC GAACCCCCCG TTCAGCCCGA CCGCTGCGCC

3721 TTATCCGGTA ACTATCGTCT TGAGTCCAAC CCGGTAAGAC ACGACTTATC GCCACTGGCA

3781 GCAGCCACTG GTAACAGGAT TAGCAGAGCG AGGTATGTAG GCGGTGCTAC AGAGTTCTTG

-continued

3841 AAGTGGTGGC CTAACTACGG CTACACTAGA AGAACAGTAT TTGGTATCTG CGCTCTGCTG

3901 AAGCCAGTTA CCTTCGGAAA AAGAGTTGGT AGCTCTTGAT CCGGCAAACA AACCACCGCT

3961 GGTAGCGGTG GTTTTTTTGT TTGCAAGCAG CAGATTACGC GCAGAAAAAA AGGATCTCAA

4021 GAAGATCCTT TGATCTTTTC TACGGGGTCT GACGCTCAGT GGAACGAAAA CTCACGTTAA

4081 GGGATTTTGG TCATGGCTAG TTAATTAACA TTTAAATCAG CGGCCGCAAT AAAATATCTT

4141 TATTTTCATT ACATCTGTGT GTTGGTTTTT TGTGTGAATC GTAACTAACA TACGCTCTCC

4201 ATCAAAACAA AACGAAACAA AACAAACTAG CAAAATAGGC TGTCCCCAGT GCAAGTGCAG

4261 GTGCCAGAAC ATTTCTCTAT CGAA

Amino acid sequence (SEQ ID NO: 90)

MYRMQLLSCIALSLALVTNSAPLERKSSVECPPCPAPPVAGPSVFLFPP

KPKDTLMISRTPEVTCVVVDVSHEDPEVQFNWYVDGVEVEINAKTKPREEQF

NSTFRVVSVLTVVHQDWLNGKEYKCKVSNKGLPAPIEKTISKTKGQPREPQV

YTLPPSREEMTKNQVSLTCLVKGFYPSDIAVEWESNGQPENNYKTTPPMLDS

DGSFFLYSKLTVDKSRWQQGNVFSCSVMHEALHNHYTQKSLSLSPGARTSTE

ELRVRLASHLRKLRKRLLRDADDLQK 184V pfcn hg2 129-157 R136S
Nucleic acid sequence (SEQ ID NO: 91)

1 GGATCTGCGA TCGCTCCGGT GCCCGTCAGT GGGCAGAGCG CACATCGCCC ACAGTCCCCG

61 AGAAGTTGGG GGGAGGGGTC GGCAATTGAA CGGGTGCCTA GAGAAGGTGG CGCGGGGTAA

121 ACTGGGAAAG TGATGTCGTG TACTGGCTCC GCCTTTTTCC CGAGGGTGGG GGAGAACCGT

181 ATATAAGTGC AGTAGTCGCC GTGAACGTTC TTTTTCGCAA CGGGTTTGCC GCCAGAACAC

241 AGCTGAAGCT TCGAGGGGCT CGCATCTCTC CTTCACGCGC CCGCCGCCCT ACCTGAGGCC

301 GCCATCCACG CCGGTTGAGT CGCGTTCTGC CGCCTCCCGC CTGTGGTGCC TCCTGAACTG

361 CGTCCGCCGT CTAGGTAAGT TTAAAGCTCA GGTCGAGACC GGGCCTTTGT CCGGCGCTCC

421 CTTGGAGCCT ACCTAGACTC AGCCGGCTCT CCACGCTTTG CCTGACCCtg cttgctcaac 481 tctacgTCTT TGTTTCGTTT TCTGTTCTGC GCCGTTACAG ATCCAAGCTG TGACCGGCGC

541 CTACCTGAGA TCACCGGCGA AGGAGGGCCA CCATGTACAG GATGCAACTC CTGTCTTGCA

601 TTGCACTAAG TCTTGCACTT GTCACGAATT CGGCACCTCT CGAGCGCAAA TCTAGTGTCG

661 AGTGCCCACC GTGCCCAGCA CCACCTGTGG CAGGACCGTC AGTCTTCCTC TTCCCCCCAA

721 AACCCAAGGA CACCCTCATG ATCTCCCGGA CCCCTGAGGT CACGTGCGTG GTGGTGGACG

781 TGAGCCACGA AGACCCCGAG GTCCAGTTCA ACTGGTACGT GGACGGCGTG GAGGTGCATA

841 ATGCCAAGAC AAAGCCACGG GAGGAGCAGT TCAACAGCAC GTTCCGTGTG GTCAGCGTCC

901 TCACCGTTGT GCACCAGGAC TGGCTGAACG GCAAGGAGTA CAAGTGCAAG GTCTCCAACA

961 AAGGCCTCCC AGCCCCCATC GAGAAAACCA TCTCCAAAAC CAAAGGGCAG CCCCGAGAAC

1021 CACAGGTGTA CACCCTGCCC CCATCCCGGG AGGAGATGAC CAAGAACCAG GTCAGCCTGA

1081 CCTGCCTGGT CAAAGGCTTC TACCCCAGCG ACATCGCCGT GGAGTGGGAG AGCAATGGGC

1141 AGCCGGAGAA CAACTACAAG ACCACGCCTC CCATGCTGGA CTCCGACGGC TCCTTCTTCC

1201 TCTACAGCAA GCTCACCGTG GACAAGAGCA GGTGGCAGCA GGGGAACGTC TTCTCATGCT

1261 CCGTGATGCA TGAGGCTCTG CACAACCACT ACACGCAGAA GAGCCTCTCC CTGTCTCCGG

1321 GTGCACGTAC GAGCACCGAG GAGCTGCGGG TGaGCCTCGC CTCCCACCTG CGCAAGCTGC

1381 GTAAGCGGCT CCTCCGCGAT GCCGATGACC TGCAGAAGtg aTATCTCGAG CTAGCTGGCC

-continued

1441 AGACATGATA AGATACATTG ATGAGTTTGG ACAAACCACA ACTAGAATGC AGTGAAAAAA
1501 ATGCTTTATT TGTGAAATTT GTGATGCTAT TGCTTTATTT GTAACCATTA TAAGCTGCAA
1561 TAAACAAGTT AACAACAACA ATTGCATTCA TTTTATGTTT CAGGTTCAGG GGGAGGTGTG
1621 GGAGGTTTTT TAAAGCAAGT AAAACCTCTA CAAATGTGGT ATGGAATTAA TTCTAAAATA
1681 CAGCATAGCA AAACTTTAAC CTCCAAATCA AGCCTCTACT TGAATCCTTT TCTGAGGGAT
1741 GAATAAGGCA TAGGCATCAG GGGCTGTTGC CAATGTGCAT TAGCTGTTTG CAGCCTCACC
1801 TTCTTTCATG GAGTTTAAGA TATAGTGTAT TTTCCCAAGG TTTGAACTAG CTCTTCATTT
1861 CTTTATGTTT TAAATGCACT GACCTCCCAC ATTCCCTTTT TAGTAAAATA TTCAGAAATA
1921 ATTTAAATAC ATCATTGCAA TGAAAATAAA TGTTTTTTAT TAGGCAGAAT CCAGATGCTC
1981 AAGGCCCTTC ATAATATCCC CCAGTTTAGT AGTTGGACTT AGGGAACAAA GGAACCTTTA
2041 ATAGAAATTG GACAGCAAGA AAGCGAGCTT CTAGCTTATC CTCAGTCCTG CTCCTCTGCC
2101 ACAAAGTGCA CGCAGTTGCC GGCCGGGTCG CGCAGGGCGA ACTCCCGCCC CCACGGCTGC
2161 TCGCCGATCT CGGTCATGGC CGGCCCGGAG GCGTCCCGGA AGTTCGTGGA CACGACCTCC
2221 GACCACTCGG CGTACAGCTC GTCCAGGCCG CGCACCCACA CCCAGGCCAG GGTGTTGTCC
2281 GGCACCACCT GGTCCTGGAC CGCGCTGATG AACAGGGTCA CGTCGTCCCG GACCACACCG
2341 GCGAAGTCGT CCTCCACGAA GTCCCGGGAG AACCCGAGCC GGTCGGTCCA GAACTCGACC
2401 GCTCCGGCGA CGTCGCGCGC GGTGAGCACC GGAACGGCAC TGGTCAACTT GGCCATGATG
2461 GCTCCTCctg tcaggagagg aaagagaaga aggttagtac aattgCTATA GTGAGTTGTA
2521 TTATACTATG CAGATATACT ATGCCAATGA TTAATTGTCA AACTAGGGCT GCAgggttca
2581 tagtgccact tttcctgcac tgccccatct cctgcccacc ctttcccagg catagacagt
2641 cagtgactta cCAAACTCAC AGGAGGGAGA AGGCAGAAGC TTGAGACAGA CCCGCGGGAC
2701 CGCCGAACTG CGAGGGGACG TGGCTAGGGC GGCTTCTTTT ATGGTGCGCC GGCCCTCGGA
2761 GGCAGGGCGC TCGGGGAGGC CTAGCGGCCA ATCTGCGGTG GCAGGAGGCG GGGCCGAAGG
2821 CCGTGCCTGA CCAATCCGGA GCACATAGGA GTCTCAGCCC CCCGCCCCAA AGCAAGGGGA
2881 AGTCACGCGC CTGTAGCGCC AGCGTGTTGT GAAATGGGGG CTTGGGGGGG TTGGGGCCCT
2941 GACTAGTCAA AACAAACTCC CATTGACGTC AATGGGGTGG AGACTTGGAA ATCCCCGTGA
3001 GTCAAACCGC TATCCACGCC CATTGATGTA CTGCCAAAAC CGCATCATCA TGGTAATAGC
3061 GATGACTAAT ACGTAGATGT ACTGCCAAGT AGGAAAGTCC CATAAGGTCA TGTACTGGGC
3121 ATAATGCCAG GCGGGCCATT TACCGTCATT GACGTCAATA GGGGGCGTAC TTGGCATATG
3181 ATACACTTGA TGTACTGCCA AGTGGGCAGT TTACCGTAAA TACTCCACCC ATTGACGTCA
3241 ATGGAAAGTC CCTATTGGCG TTACTATGGG AACATACGTC ATTATTGACG TCAATGGGCG
3301 GGGGTCGTTG GGCGGTCAGC CAGGCGGGCC ATTTACCGTA AGTTATGTAA CGCCTGCAGG
3361 TTAATTAAGA ACATGTGAGC AAAAGGCCAG CAAAAGGCCA GGAACCGTAA AAAGGCCGCG
3421 TTGCTGGCGT TTTTCCATAG GCTCCGCCCC CCTGACGAGC ATCACAAAAA TCGACGCTCA
3481 AGTCAGAGGT GGCGAAACCC GACAGGACTA TAAAGATACC AGGCGTTTCC CCCTGGAAGC
3541 TCCCTCGTGC GCTCTCCTGT TCCGACCCTG CCGCTTACCG GATACCTGTC CGCCTTTCTC
3601 CCTTCGGGAA GCGTGGCGCT TTCTCATAGC TCACGCTGTA GGTATCTCAG TTCGGTGTAG
3661 GTCGTTCGCT CCAAGCTGGG CTGTGTGCAC GAACCCCCCG TTCAGCCCGA CCGCTGCGCC
3721 TTATCCGGTA ACTATCGTCT TGAGTCCAAC CCGGTAAGAC ACGACTTATC GCCACTGGCA
3781 GCAGCCACTG GTAACAGGAT TAGCAGAGCG AGGTATGTAG GCGGTGCTAC AGAGTTCTTG -continued

3841 AAGTGGTGGC CTAACTACGG CTACACTAGA AGAACAGTAT TTGGTATCTG CGCTCTGCTG

3901 AAGCCAGTTA CCTTCGGAAA AAGAGTTGGT AGCTCTTGAT CCGGCAAACA AACCACCGCT

3961 GGTAGCGGTG GTTTTTTTGT TTGCAAGCAG CAGATTACGC GCAGAAAAAA AGGATCTCAA

4021 GAAGATCCTT TGATCTTTTC TACGGGGTCT GACGCTCAGT GGAACGAAAA CTCACGTTAA

4081 GGGATTTTGG TCATGGCTAG TTAATTAACA TTTAAATCAG CGGCCGCAAT AAAATATCTT

4141 TATTTTCATT ACATCTGTGT GTTGGTTTTT TGTGTGAATC GTAACTAACA TACGCTCTCC

4201 ATCAAAACAA AACGAAACAA AACAAACTAG CAAAATAGGC TGTCCCCAGT GCAAGTGCAG

4261 GTGCCAGAAC ATTTCTCTAT CGAA

Amino acid sequence (SEQ ID NO: 92)

MYRMQLLSCIALSLALVTNSAPLERKSSVECPPCPAPPVAGPSVFLFPP

KPKDTLMISRTPEVTCVVVDVSHEDPEVQFNWYVDGVEVEINAKTKPREEQF

NSTFRVVSVLTVVHQDWLNGKEYKCKVSNKGLPAPIEKTISKTKGQPREPQV

YTLPPSREEMTKNQVSLTCLVKGFYPSDIAVEWESNGQPENNYKTTPPMLDS

DGSFFLYSKLTVDKSRWQQGNVFSCSVMHEALHNHYTQKSLSLSPGARTSTE

ELRVSLASHLRKLRKRLLRDADDLQK 197H pfuse hfc2 ApoE 129-157
Nucleic acid sequence (SEQ ID NO: 93)

1 GGATCTGCGA TCGCTCCGGT GCCCGTCAGT GGGCAGAGCG CACATCGCCC ACAGTCCCCG

61 AGAAGTTGGG GGGAGGGGTC GGCAATTGAA CGGGTGCCTA GAGAAGGTGG CGCGGGGTAA

121 ACTGGGAAAG TGATGTCGTG TACTGGCTCC GCCTTTTTCC CGAGGGTGGG GGAGAACCGT

181 ATATAAGTGC AGTAGTCGCC GTGAACGTTC TTTTTCGCAA CGGGTTTGCC GCCAGAACAC

241 AGCTGAAGCT TCGAGGGGCT CGCATCTCTC CTTCACGCGC CCGCCGCCCT ACCTGAGGCC

301 GCCATCCACG CCGGTTGAGT CGCGTTCTGC CGCCTCCCGC CTGTGGTGCC TCCTGAACTG

361 CGTCCGCCGT CTAGGTAAGT TTAAAGCTCA GGTCGAGACC GGGCCTTTGT CCGGCGCTCC

421 CTTGGAGCCT ACCTAGACTC AGCCGGCTCT CCACGCTTTG CCTGACCCtg cttgctcaac 481 tctacgTCTT TGTTTCGTTT TCTGTTCTGC GCCGTTACAG ATCCAAGCTG TGACCGGCGC 541 CTACCTGAGA TCAccggcGA AGGAGGGCCA CCATGTACAG GATGCAACTC CTGTCTTGCA

601 TTGCACTAAG TCTTGCACTT GTCACGAATT CGATAAGCAC CGAGGAGCTG CGGGTGCGCC

661 TCGCCTCCCA CCTGCGCAAG CTGCGTAAGC GGCTCCTCCG CGATGCCGAT GACCTGCAGA

721 AGatatcgGC CATGGTTAGA TCTGTGGAGT GCCCACCTTG CCCAGCACCA CCTGTGGCAG

781 GACCTTCAGT CTTCCTCTTC CCCCCAAAAC CCAAGGACAC CCTGATGATC TCCAGAACCC

841 CTGAGGTCAC GTGCGTGGTG GTGGACGTGA GCCACGAAGA CCCCGAGGTC CAGTTCAACT

901 GGTACGTGGA CGGCATGGAG GTGCATAATG CCAAGACAAA GCCACGGGAG GAGCAGTTCA

961 ACAGCACGTT CCGTGTGGTC AGCGTCCTCA CCGTCGTGCA CCAGGACTGG CTGAACGGCA

1021 AGGAGTACAA GTGCAAGGTC TCCAACAAAG GCCTCCCAGC CCCCATCGAG AAAACCATCT

1081 CCAAAACCAA AGGGCAGCCC CGAGAACCAC AGGTGTACAC CCTGCCCCCA TCCCGGGAGG

1141 AGATGACCAA GAACCAGGTC AGCCTGACCT GCCTGGTCAA AGGCTTCTAC CCCAGCGACA

1201 TCGCCGTGGA GTGGGAGAGC AATGGGCAGC CGGAGAACAA CTACAAGACC ACACCTCCCA

1261 TGCTGGACTC CGACGGCTCC TTCTTCCTCT ACAGCAAGCT CACCGTGGAC AAGAGCAGGT

1321 GGCAGCAGGG GAACGTCTTC TCATGCTCCG TGATGCATGA GGCTCTGCAC AACCACTACA

1381 CACAGAAGAG CCTCTCCCTG TCTCCGGGTA AATGAgtgcc acgGCTAGCT GGCCAGACAT

-continued

```
1441 GATAAGATAC ATTGATGAGT TTGGACAAAC CACAACTAGA ATGCAGTGAA AAAAATGCTT
1501 TATTTGTGAA ATTTGTGATG CTATTGCTTT ATTTGTAACC ATTATAAGCT GCAATAAACA
1561 AGTTAACAAC AACAATTGCA TTCATTTTAT GTTTCAGGTT CAGGGGGAGG TGTGGGAGGT
1621 TTTTTAAAGC AAGTAAAACC TCTACAAATG TGGTATGGAA TTAATTCTAA AATACAGCAT
1681 AGCAAAACTT TAACCTCCAA ATCAAGCCTC TACTTGAATC CTTTTCTGAG GGATGAATAA
1741 GGCATAGGCA TCAGGGGCTG TTGCCAATGT GCATTAGCTG TTTGCAGCCT CACCTTCTTT
1801 CATGGAGTTT AAGATATAGT GTATTTTCCC AAGGTTTGAA CTAGCTCTTC ATTTCTTTAT
1861 GTTTTAAATG CACTGACCTC CCACATTCCC TTTTTAGTAA AATATTCAGA AATAATTTAA
1921 ATACATCATT GCAATGAAAA TAAATGTTTT TTATTAGGCA GAATCCAGAT GCTCAAGGCC
1981 CTTCATAATA TCCCCCAGTT TAGTAGTTGG ACTTAGGGAA CAAAGGAACC TTTAATAGAA
2041 ATTGGACAGC AAGAAAGCGA GCTTCTAGCT TATCCTCAGT CCTGCTCCTC TGCCACAAAG
2101 TGCACGCAGT TGCCGGCCGG GTCGCGCAGG GCGAACTCCC GCCCCCACGG CTGCTCGCCG
2161 ATCTCGGTCA TGGCCGGCCC GGAGGCGTCC CGGAAGTTCG TGGACACGAC CTCCGACCAC
2221 TCGGCGTACA GCTCGTCCAG GCCGCGCACC CACACCCAGG CCAGGGTGTT GTCCGGCACC
2281 ACCTGGTCCT GGACCGCGCT GATGAACAGG GTCACGTCGT CCCGGACCAC ACCGGCGAAG
2341 TCGTCCTCCA CGAAGTCCCG GGAGAACCCG AGCCGGTCGG TCCAGAACTC GACCGCTCCG
2401 GCGACGTCGC GCGCGGTGAG CACCGGAACG GCACTGGTCA ACTTGGCCAT GATGGCTCCT
2461 Cctgtcagga gaggaaagag aagaaggtta gtacaattgC TATAGTGAGT TGTATTATAC
2521 TATGCAGATA TACTATGCCA ATGATTAATT GTCAAACTAG GGCTGCAggg ttcatagtgc
2581 cacttttcct gcactgcccc atctcctgcc cacccctttcc caggcataga cagtcagtga
2641 cttacCAAAC TCACAGGAGG GAGAAGGCAG AAGCTTGAGA CAGACCCGCG GGACCGCCGA
2701 ACTGCGAGGG GACGTGGCTA GGGCGGCTTC TTTTATGGTG CGCCGGCCCT CGGAGGCAGG
2761 GCGCTCGGGG AGGCCTAGCG GCCAATCTGC GGTGGCAGGA GGCGGGGCCG AAGGCCGTGC
2821 CTGACCAATC CGGAGCACAT AGGAGTCTCA GCCCCCCGCC CCAAAGCAAG GGGAAGTCAC
2881 GCGCCTGTAG CGCCAGCGTG TTGTGAAATG GGGGCTTGGG GGGGTTGGGG CCCTGACTAG
2941 TCAAAACAAA CTCCCATTGA CGTCAATGGG GTGGAGACTT GGAAATCCCC GTGAGTCAAA
3001 CCGCTATCCA CGCCCATTGA TGTACTGCCA AAACCGCATC ATCATGGTAA TAGCGATGAC
3061 TAATACGTAG ATGTACTGCC AAGTAGGAAA GTCCCATAAG GTCATGTACT GGGCATAATG
3121 CCAGGCGGGC CATTTACCGT CATTGACGTC AATAGGGGGC GTACTTGGCA TATGATACAC
3181 TTGATGTACT GCCAAGTGGG CAGTTTACCG TAAATACTCC ACCCATTGAC GTCAATGGAA
3241 AGTCCCTATT GGCGTTACTA TGGGAACATA CGTCATTATT GACGTCAATG GGCGGGGGTC
3301 GTTGGGCGGT CAGCCAGGCG GGCCATTTAC CGTAAGTTAT GTAACGCCTG CAGGTTAATT
3361 AAGAACATGT GAGCAAAAGG CCAGCAAAAG GCCAGGAACC GTAAAAAGGC CGCGTTGCTG
3421 GCGTTTTTCC ATAGGCTCCG CCCCCCTGAC GAGCATCACA AAAATCGACG CTCAAGTCAG
3481 AGGTGGCGAA ACCCGACAGG ACTATAAAGA TACCAGGCGT TTCCCCCTGG AAGCTCCCTC
3541 GTGCGCTCTC CTGTTCCGAC CCTGCCGCTT ACCGGATACC TGTCCGCCTT TCTCCCTTCG
3601 GGAAGCGTGG CGCTTTCTCA TAGCTCACGC TGTAGGTATC TCAGTTCGGT GTAGGTCGTT
3661 CGCTCCAAGC TGGGCTGTGT GCACGAACCC CCCGTTCAGC CCGACCGCTG CGCCTTATCC
3721 GGTAACTATC GTCTTGAGTC CAACCCGGTA AGACACGACT TATCGCCACT GGCAGCAGCC
3781 ACTGGTAACA GGATTAGCAG AGCGAGGTAT GTAGGCGGTG CTACAGAGTT CTTGAAGTGG
3841 TGGCCTAACT ACGGCTACAC TAGAAGAACA GTATTTGGTA TCTGCGCTCT GCTGAAGCCA
```

-continued

3901 GTTACCTTCG GAAAAAGAGT TGGTAGCTCT TGATCCGGCA AACAAACCAC CGCTGGTAGC

3961 GGTGGTTTTT TTGTTTGCAA GCAGCAGATT ACGCGCAGAA AAAAAGGATC TCAAGAAGAT

4021 CCTTTGATCT TTTCTACGGG GTCTGACGCT CAGTGGAACG AAAACTCACG TTAAGGGATT

4081 TTGGTCATGG CTAGTTAATT AACATTTAAA TCAGCGGCCG CAATAAAATA TCTTTATTTT

4141 CATTACATCT GTGTGTTGGT TTTTTGTGTG AATCGTAACT AACATACGCT CTCCATCAAA

4201 ACAAAACGAA ACAAAACAAA CTAGCAAAAT AGGCTGTCCC CAGTGCAAGT GCAGGTGCCA

4261 GAACATTTCT CTATCGAA

Amino acid sequence (SEQ ID NO: 94)

MYRMQLLSCIALSLALVTNSISTEELRVRLASHLRKLRKRLLRDADDL

QKISAMVRSVECPPCPAPPVAGPSVFLFPPKPKDTLMISRTPEVTCVVVDVSHE

DPEVQFNWYVDGMEVHNAKTKPREEQFNSTFRVVSVLTVVEIQDWLNGKEY

KCKVSNKGLPAPIEKTISKTKGQPREPQVYTLPPSREEMTKNQVSLTCLVKGF

YPSDIAVEWESNGQPENNYKTTPPMLDSDGSFFLYSKLTVDKSRWQQGNVFS

CSVMHEALHNHYTQKSLSLSPGK 1971 pfuse hfc2 ApoE 129-157 R136S
Nucleic acid sequence (SEQ ID NO: 95)

1 GGATCTGCGA TCGCTCCGGT GCCCGTCAGT GGGCAGAGCG CACATCGCCC ACAGTCCCCG

61 AGAAGTTGGG GGGAGGGGTC GGCAATTGAA CGGGTGCCTA GAGAAGGTGG CGCGGGGTAA

121 ACTGGGAAAG TGATGTCGTG TACTGGCTCC GCCTTTTTCC CGAGGGTGGG GGAGAACCGT

181 ATATAAGTGC AGTAGTCGCC GTGAACGTTC TTTTTCGCAA CGGGTTTGCC GCCAGAACAC

241 AGCTGAAGCT TCGAGGGGCT CGCATCTCTC CTTCACGCGC CCGCCGCCCT ACCTGAGGCC

301 GCCATCCACG CCGGTTGAGT CGCGTTCTGC CGCCTCCCGC CTGTGGTGCC TCCTGAACTG

361 CGTCCGCCGT CTAGGTAAGT TTAAAGCTCA GGTCGAGACC GGGCCTTTGT CCGGCGCTCC

421 CTTGGAGCCT ACCTAGACTC AGCCGGCTCT CCACGCTTTG CCTGACCCtg cttgctcaac 481 tctacgTCTT TGTTTCGTTT TCTGTTCTGC GCCGTTACAG ATCCAAGCTG TGACCGGCGC 541 CTACCTGAGA TCAccggcGA AGGAGGGCCA CCATGTACAG GATGCAACTC CTGTCTTGCA 601 TTGCACTAAG TCTTGCACTT GTCACGAATT CGATAAGCAC CGAGGAGCTG CGGGTGaGCC

661 TCGCCTCCCA CCTGCGCAAG CTGCGTAAGC GGCTCCTCCG CGATGCCGAT GACCTGCAGA

721 AGatatcgGC CATGGTTAGA TCTGTGGAGT GCCCACCTTG CCCAGCACCA CCTGTGGCAG

781 GACCTTCAGT CTTCCTCTTC CCCCCAAAAC CCAAGGACAC CCTGATGATC TCCAGAACCC

841 CTGAGGTCAC GTGCGTGGTG GTGGACGTGA GCCACGAAGA CCCCGAGGTC CAGTTCAACT

901 GGTACGTGGA CGGCATGGAG GTGCATAATG CCAAGACAAA GCCACGGGAG GAGCAGTTCA

961 ACAGCACGTT CCGTGTGGTC AGCGTCCTCA CCGTCGTGCA CCAGGACTGG CTGAACGGCA

1021 AGGAGTACAA GTGCAAGGTC TCCAACAAAG GCCTCCCAGC CCCCATCGAG AAAACCATCT

1081 CCAAAACCAA AGGGCAGCCC CGAGAACCAC AGGTGTACAC CCTGCCCCCA TCCCGGGAGG

1141 AGATGACCAA GAACCAGGTC AGCCTGACCT GCCTGGTCAA AGGCTTCTAC CCCAGCGACA

1201 TCGCCGTGGA GTGGGAGAGC AATGGGCAGC CGGAGAACAA CTACAAGACC ACACCTCCCA

1261 TGCTGGACTC CGACGGCTCC TTCTTCCTCT ACAGCAAGCT CACCGTGGAC AAGAGCAGGT

1321 GGCAGCAGGG GAACGTCTTC TCATGCTCCG TGATGCATGA GGCTCTGCAC AACCACTACA

1381 CACAGAAGAG CCTCTCCCTG TCTCCGGGTA AATGAgtgcc acgGCTAGCT GGCCAGACAT

1441 GATAAGATAC ATTGATGAGT TTGGACAAAC CACAACTAGA ATGCAGTGAA AAAAATGCTT

-continued

1501 TATTTGTGAA ATTTGTGATG CTATTGCTTT ATTTGTAACC ATTATAAGCT GCAATAAACA

1561 AGTTAACAAC AACAATTGCA TTCATTTTAT GTTTCAGGTT CAGGGGGAGG TGTGGGAGGT

1621 TTTTTAAAGC AAGTAAAACC TCTACAAATG TGGTATGGAA TTAATTCTAA AATACAGCAT

1681 AGCAAAACTT TAACCTCCAA ATCAAGCCTC TACTTGAATC CTTTTCTGAG GGATGAATAA

1741 GGCATAGGCA TCAGGGGCTG TTGCCAATGT GCATTAGCTG TTTGCAGCCT CACCTTCTTT

1801 CATGGAGTTT AAGATATAGT GTATTTTCCC AAGGTTTGAA CTAGCTCTTC ATTTCTTTAT

1861 GTTTTAAATG CACTGACCTC CCACATTCCC TTTTTAGTAA AATATTCAGA AATAATTTAA

1921 ATACATCATT GCAATGAAAA TAAATGTTTT TTATTAGGCA GAATCCAGAT GCTCAAGGCC

1981 CTTCATAATA TCCCCCAGTT TAGTAGTTGG ACTTAGGGAA CAAAGGAACC TTTAATAGAA

2041 ATTGGACAGC AAGAAAGCGA GCTTCTAGCT TATCCTCAGT CCTGCTCCTC TGCCACAAAG

2101 TGCACGCAGT TGCCGGCCGG GTCGCGCAGG GCGAACTCCC GCCCCCACGG CTGCTCGCCG

2161 ATCTCGGTCA TGGCCGGCCC GGAGGCGTCC CGGAAGTTCG TGGACACGAC CTCCGACCAC

2221 TCGGCGTACA GCTCGTCCAG GCCGCGCACC CACACCCAGG CCAGGGTGTT GTCCGGCACC

2281 ACCTGGTCCT GGACCGCGCT GATGAACAGG GTCACGTCGT CCCGGACCAC ACCGGCGAAG

2341 TCGTCCTCCA CGAAGTCCCG GGAGAACCCG AGCCGGTCGG TCCAGAACTC GACCGCTCCG

2401 GCGACGTCGC GCGCGGTGAG CACCGGAACG GCACTGGTCA ACTTGGCCAT GATGGCTCCT

2461 Cctgtcagga gaggaaagag aagaaggtta gtacaattgC TATAGTGAGT TGTATTATAC

2521 TATGCAGATA TACTATGCCA ATGATTAATT GTCAAACTAG GGCTGCAggg ttcatagtgc 2581 cacttttcct gcactgcccc atctcctgcc caccctttcc caggcataga cagtcagtga 2641 cttacCAAAC TCACAGGAGG GAGAAGGCAG AAGCTTGAGA CAGACCCGCG GGACCGCCGA

2701 ACTGCGAGGG GACGTGGCTA GGGCGGCTTC TTTTATGGTG CGCCGGCCCT CGGAGGCAGG

2761 GCGCTCGGGG AGGCCTAGCG GCCAATCTGC GGTGGCAGGA GGCGGGGCCG AAGGCCGTGC

2821 CTGACCAATC CGGAGCACAT AGGAGTCTCA GCCCCCCGCC CCAAAGCAAG GGGAAGTCAC

2881 GCGCCTGTAG CGCCAGCGTG TTGTGAAATG GGGGCTTGGG GGGGTTGGGG CCCTGACTAG

2941 TCAAAACAAA CTCCCATTGA CGTCAATGGG GTGGAGACTT GGAAATCCCC GTGAGTCAAA

3001 CCGCTATCCA CGCCCATTGA TGTACTGCCA AAACCGCATC ATCATGGTAA TAGCGATGAC

3061 TAATACGTAG ATGTACTGCC AAGTAGGAAA GTCCCATAAG GTCATGTACT GGGCATAATG

3121 CCAGGCGGGC CATTTACCGT CATTGACGTC AATAGGGGGC GTACTTGGCA TATGATACAC

3181 TTGATGTACT GCCAAGTGGG CAGTTTACCG TAAATACTCC ACCCATTGAC GTCAATGGAA

3241 AGTCCCTATT GGCGTTACTA TGGGAACATA CGTCATTATT GACGTCAATG GGCGGGGGTC

3301 GTTGGGCGGT CAGCCAGGCG GGCCATTTAC CGTAAGTTAT GTAACGCCTG CAGGTTAATT

3361 AAGAACATGT GAGCAAAAGG CCAGCAAAAG GCCAGGAACC GTAAAAAGGC CGCGTTGCTG

3421 GCGTTTTTCC ATAGGCTCCG CCCCCCTGAC GAGCATCACA AAAATCGACG CTCAAGTCAG

3481 AGGTGGCGAA ACCCGACAGG ACTATAAAGA TACCAGGCGT TTCCCCCTGG AAGCTCCCTC

3541 GTGCGCTCTC CTGTTCCGAC CCTGCCGCTT ACCGGATACC TGTCCGCCTT TCTCCCTTCG

3601 GGAAGCGTGG CGCTTTCTCA TAGCTCACGC TGTAGGTATC TCAGTTCGGT GTAGGTCGTT

3661 CGCTCCAAGC TGGGCTGTGT GCACGAACCC CCCGTTCAGC CCGACCGCTG CGCCTTATCC

3721 GGTAACTATC GTCTTGAGTC CAACCCGGTA AGACACGACT TATCGCCACT GGCAGCAGCC

3781 ACTGGTAACA GGATTAGCAG AGCGAGGTAT GTAGGCGGTG CTACAGAGTT CTTGAAGTGG

3841 TGGCCTAACT ACGGCTACAC TAGAAGAACA GTATTTGGTA TCTGCGCTCT GCTGAAGCCA

-continued

```
3901 GTTACCTTCG GAAAAAGAGT TGGTAGCTCT TGATCCGGCA AACAAACCAC CGCTGGTAGC
3961 GGTGGTTTTT TTGTTTGCAA GCAGCAGATT ACGCGCAGAA AAAAAGGATC TCAAGAAGAT
4021 CCTTTGATCT TTTCTACGGG GTCTGACGCT CAGTGGAACG AAAACTCACG TTAAGGGATT
4081 TTGGTCATGG CTAGTTAATT AACATTTAAA TCAGCGGCCG CAATAAAATA TCTTTATTTT
4141 CATTACATCT GTGTGTTGGT TTTTTGTGTG AATCGTAACT AACATACGCT CTCCATCAAA
4201 ACAAAACGAA ACAAAACAAA CTAGCAAAAT AGGCTGTCCC CAGTGCAAGT GCAGGTGCCA
4261 GAACATTTCT CTATCGAA
```

Amino acid sequence (SEQ ID NO: 96)

MYRMQLLSCIALSLALVTNSISTEELRVSLASHLRKLRKRLLRDADDL

QKISAMVRSVECPPCPAPPVAGPSVFLFPPKPKDTLMISRTPEVTCVVVDVSHE

DPEVQFNWYVDGMEVHNAKTKPREEQFNSTFRVVSVLTVVHQDWLNGKEY

KCKVSNKGLPAPIEKTISKTKGQPREPQVYTLPPSREEMTKNQVSLTCLVKGF

YPSDIAVEWESNGQPENNYKTTPPMLDSDGSFFLYSKLTVDKSRWQQGNVFS

CSVMHEALHNHYTQKSLSLSPGK

Example 5: CRISPR-Cas9 Mediated Editing and Base Editing of APOE

To introduce the R136S mutation in APOE using CRISPR-Cas9, gRNA sequences were designed (Table 7). In one example, a gRNA sequence is cloned into lentiCRISPR v2 using 2 oligos to form a linker containing the 20 base sequence that is cloned into the BsmB1 site downstream of the U6 promoter. To support repair, a template was designed with 2 additional silent mutations. The template has 50 bases flanking the area with the mutations. An exemplary template sequence is as follows:

(SEQ ID NO: 65)

CGCCTGGTGCAGTACCGCGGCGAGGTGCAGGCCATGCTCGGCCAGAGCAC aGAGGAGCT*c*CGcGTGaGtCTCGCaagCCACCTGCGCAAGCTGCGTAAGC

GGCTCCTCCGCGATGCCGATGACCTGC where silent mutations to abolish PAM motifs are double underlined, the codon corresponding to the R136S mutation is bolded, and silent mutation to generate SacI site for cleaving PCR products from clones that received the template is italicized.

TABLE 7 gRNA designs for introducing R136S mutation

| Plasmid | gRNA | SEQ ID NO: | Distance From DSB | ON target score | OFF target score |
|---|---|---|---|---|---|
| 18401 | CTTACGCAGCTTGCGCAGGT | 69 | 16 | 61.2 | 90.5 |
| 18402 | GCTTGCGCAGGTGGGAGGCG | 70 | 6 | 59.5 | 53.9 |
| 18403 | ACGCAGCTTGCGCAGGTGGG | 71 | 13 | 59.4 | 62.9 |
| 18404 | CCAGAGCACCGAGGAGCTGC | 72 | 9 | 49.3 | 42.7 |
| Optional 18405 | GCCAGAGCACCGAGGAGCTG | 73 | 10 | 52.8 | 33.7 |
| Optional 18406 | GAGGCGCACCCGCAGCTCCT | 74 | 11 | 51.1 | 60.5 |

Without wishing to be bound by theory, a proposed mechanism for the APOE3ch mutation is loss of function (e.g. in binding to HSPG). Accordingly, gRNA sequences were designed to "knockout" APOE using CRISPR-Cas9 (Table 8). The gRNAs are designed to target exon 3 (amino acids 1-61) of ApoE. In an example, a gRNA sequence is cloned into lentiCRISPR v2 by ordering 2 oligos to form a linker containing the 20 base sequence that is cloned into BsmB1 site downstream of the U6 promoter. Repair is done by non-homologous end joining (NHEJ), which is an error-prone process and often results in short insertions or deletions leading to APOE knockout.

TABLE 8 gRNA designs for APOE knockout

| Plasmid | gRNA | SEQ ID NO: | Break at amino acid | ON target score | OFF target score |
|---|---|---|---|---|---|
| 184Q1 | AGCTGCGCCAGCAGACCGAG | 75 | 18 | 66.3 | 74.4 |
| 184Q2 | CCAGGCCAAGGTGGAGCAAG | 76 | 3 | 65.6 | 49.3 |
| 184Q3 | CACAGGATGCCAGGCCAAGG | 77 | 1 | 65.4 | 44.5 |
| 184Q4 | ACAGTGTCTGCACCCAGCGC | 78 | 38 | 60.6 | 71.4 |
| 184Q5 | GGCCAAGGTGGAGCAAGCGG | 79 | 5 | 59.3 | 71.3 |

A R136H mutation in APOE is predicted to have a similar effect as the R136S mutation. Accordingly, to introduce a R136H mutation in APOE using base editing techniques, the following gRNA was designed (Table 9). The gRNA sequence GAGGCGCACCCGCAGCTCCT (SEQ ID NO: 74) is cloned into pLenti sgRNA (addgene 71409), using 2 oligos to form a linker containing the 20 base sequence that is cloned into BsmB1 site downstream of the U6 promoter. Plasmid Addgene base editor plasmid pCMV-BE3 (#73021) is used to produce base editing.

TABLE 9 gRNA design for APOE base editing

| gRNA | SEQ ID NO: | R136H change | Base editing score | OFF target score |
|---|---|---|---|---|
| GAGGCGCACCCGCAGCTCCT | 80 | CGC→CAC | 4.6 | 60.5 |

Example 6: High-Throughput Screening of Molecules that Modify ApoE and Heparin Binding To screen for molecules that affect ApoE and heparin binding, ApoE proteins are pre-incubated with candidate polypeptides, small molecules, nucleic acids, lipids or carbohydrates. The pre-incubated ApoE proteins are introduced to heparin-coated surfaces (such as plates or columns), allowed to bind to heparin/HSPG/GAG, and unbound ApoE and candidate molecules are washed off. Alternatively, heparin-coated surfaces (such as plates) can be pre-incubated with candidate molecules, before applying ApoE proteins. The levels of ApoE bound to heparin are detected using antibodies, protein assays, or fluorescence, and the effect of the candidate molecules on ApoE/heparin binding are assessed. Candidate molecules that reduce ApoE/heparin binding may represent novel therapeutics for prevention or treatment of cognitive decline associated with dementia and/or mild cognitive impairment in a human subject in need of such treatments. An example of such molecules include EZ-482 (See, e.g. Mondal et al. Biochemistry 55 (18): 2613-21, 2016. The structure of EZ-482 is shown below).

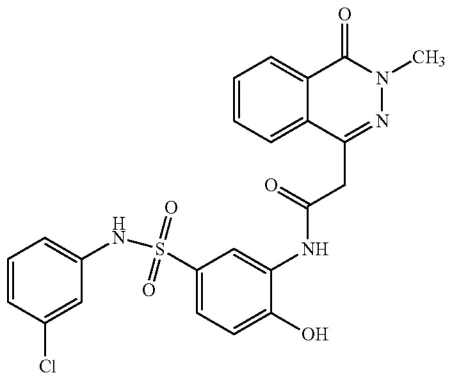 [SMILES: Cn1nc(CC(=O)Nc2cc(S(=O)(=O)Nc3cccc(Cl)c3)ccc2O)c2ccccc2c1=O]

Example 7: High-Throughput Screening of Molecules that Modify ApoE and Anti-ApoE Antibody Binding To screen for molecules that affect ApoE and anti-ApoE antibody binding, ApoE proteins are pre-incubated with candidate polypeptides, small molecules, nucleic acids, lipids or carbohydrates. The pre-incubated ApoE proteins are introduced to surfaces (such as plates or columns) coated with antibodies that bind to the HSPG-binding sites of ApoE (any of the anti-ApoE antibodies as described herein), allowed to bind to the antibodies, and unbound ApoE and candidate molecules are washed off. Alternatively, heparin-coated surfaces (such as plates) can be pre-incubated with candidate molecules, before applying ApoE proteins. The levels of ApoE bound to anti-ApoE antibodies are detected using antibodies, protein assays, or fluorescence, and the effect of the candidate molecules on the binding are assessed. Candidate molecules that increase or reduce ApoE/heparin binding may represent novel therapeutics for prevention or treatment of cognitive decline associated with dementia and/or mild cognitive impairment in a human subject in need of such treatments.

Example 8: Antibody Characterization

Antibodies that bind to wild type ApoE and ApoEch mutant were further evaluated using heparin-affinity chromatography, western blotting, subclones analysis, monoclonal antibody screening, screening for selectivity between huApoE3 and msApoE, and in vivo subretinal injections.

Methods

Chromatography Experiments

His-tagged recombinant ApoE peptide (50 μg/mL) was incubated 3 h R.T. with each antibody individually at 1:10 dilution in 20 mM Tris HCl buffer (pH 7.5). Samples were tested for heparin binding using the heparin sepharose column. Briefly, the column was allowed to reach R.T. and washed 5 times with 20 mM Tris-HCL. Protein input was loaded onto the column upon collecting 10 μL for WB experiments. Input was recycled through the column 5 times. Flow-through was collected and the column was subsequently washed 5 times and recovered fractions were labeled as "washes". 1 mL fractions were retrieved for each 0.05 M step of the NaCl salt gradient from 0 to 1 M. 5 M fraction was also tested to ensure complete release of the protein from the column. WB or ELISA were used to test changes in ApoE binding to heparin.

Western Blotting

Samples for WB analyses were prepared by diluting 10 μL of each fraction in 4× sample buffer (Laemmli's SDS-Sample buffer, BP-110R, Boston bioproducts), 4 μL DTT (Sigma Aldrich), and 16 μL 1×RIPA buffer. Electrophoresis was performed under denaturing conditions, using a vertical electrophoretic chamber (Biorad). Bands separated on 4-20% precast gels (Biorad) using constant voltage (15' 70V, 1 h 100V). Transfer of the proteins was performed on nitrocellulose membranes (Millipore) at 70 V constant voltage for 1 h. Membranes were blocked 1 h R.T. using Odyssey blocking buffer (Licor) and membranes were washed 3×10' with TBS-0.05% Tween 20 (Thermo fisher) prior incubation with primary antibody (Anti-His, rb, 1:5000, Novus biological) and secondary antibody (Donkey anti-rb-800, 1:10000, Licor). Image acquisition was done using Odyssey scanner. Data was analyzed using Image J. Data was normalized by the input and expressed normalized intensities over fraction number (0=input, 1-27=increasing 0.05 M NaCl step gradient in 20 mM Tris HCl pH 7.5, 28=5 M NaCl in 20 mM Tris HCl pH 7.5).

ELISA

To test selectivity of the antibodies for huApoE3WT, huApoE3ch or msApoE, anti-his ELISA coated plates were incubated with 0.0025 μg/μL of the target protein for 2 h at R.T. under gentle shaking. Wells were washed 5 times with 1× wash buffer (R&D) and subsequently incubated with serial dilutions of Innovagen antibody of interest over night at 4° C. on a shaker (100 μL/well). The following day, wells were washed 5 times with sample buffer and incubated for 45 minutes using Rabbit-anti-mouse HRP-conjugated buffer (1:10,000; 100 μL/well; Abcam). After 5 more washes, plates were incubated with chromogen A+B 1:1 to initiate the colorimetric reaction (100 μL/well). The reaction was stopped with 2 N sulfidric acid (R&D stop solution, 50 μL/well) and absorbance detected at 450 nm spectroscopically.

Antibodies designed against the heparin binding domain of APOE were tested for affinity to APOE3 and APOEch mutant recombinant protein using an ELISA. The Ni-NTA HisSorb Plates (Qiagen) plates were washed 3 times with wash buffer 1 (DY008), the APOE recombinant proteins were suspended in buffer (DY008) to give a final concentration of 0.5 ug/ml. The plates were incubated with 200 ul for 2 hours. The plate was then washed 5 times with 1× wash buffer (DY008), the plates were then incubated with antibodies in a serial dilution series from 1:1000 to 1:32000 and incubated overnight at 4° C. The plate is then washed 5 times in 1× wash buffer (DY008). The plates were then incubated with Anti-mouse HRP (Abcam; ab97046) (1:10000) for 45 minutes. The plate was then washed 5 times in 1× wash buffer to ensure complete removal of unbound secondary antibody. The Sulfuric acid from the ELISA reagent kit (DY008) was warmed to 37° C. prior to addition of 100 μl of tetramethylbenzidine (Millipore) initiating the detection phase of the reaction. After a 5-mins incubation, sulfuric acid was added to terminate the reaction. The plate was then read using Synery 2 microplate reader (BioTek Instrument. Inc) and the Gen5 version1.11 software).

Results

Figure 18A:
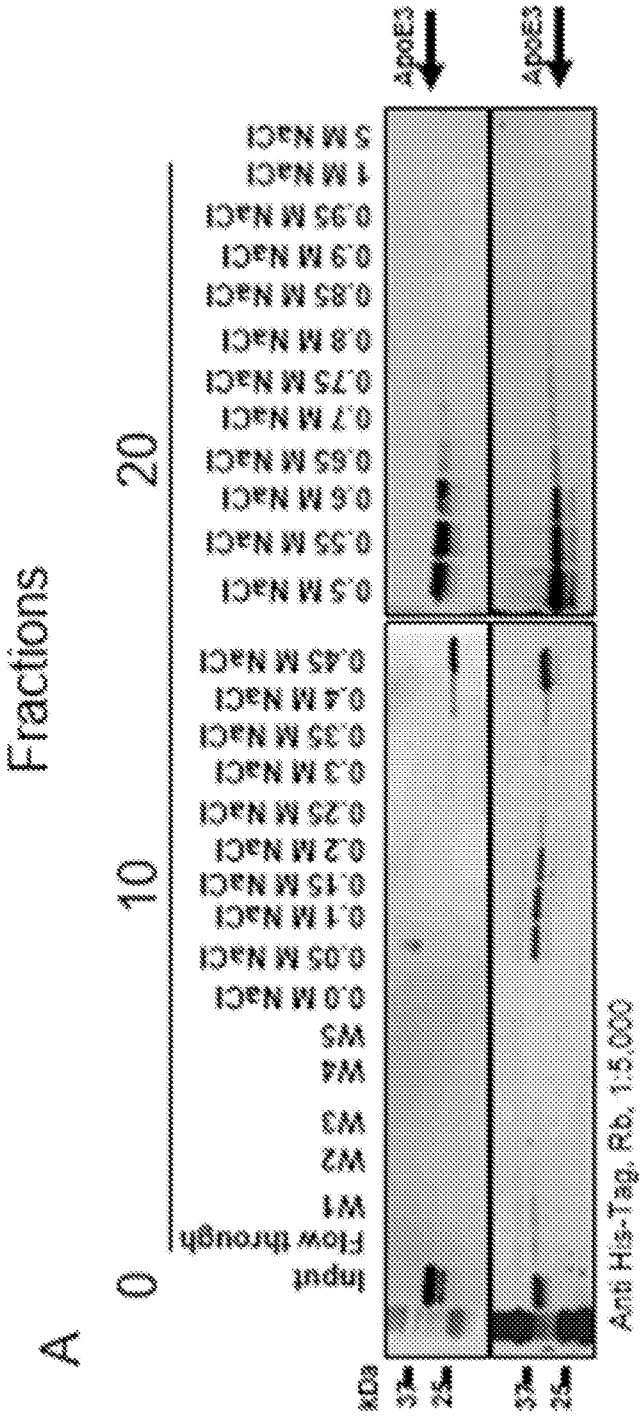
FIGS. 18A-18B show heparin-affinity chromatography and western blot analysis of antibody 1H4.
Figure 18B:
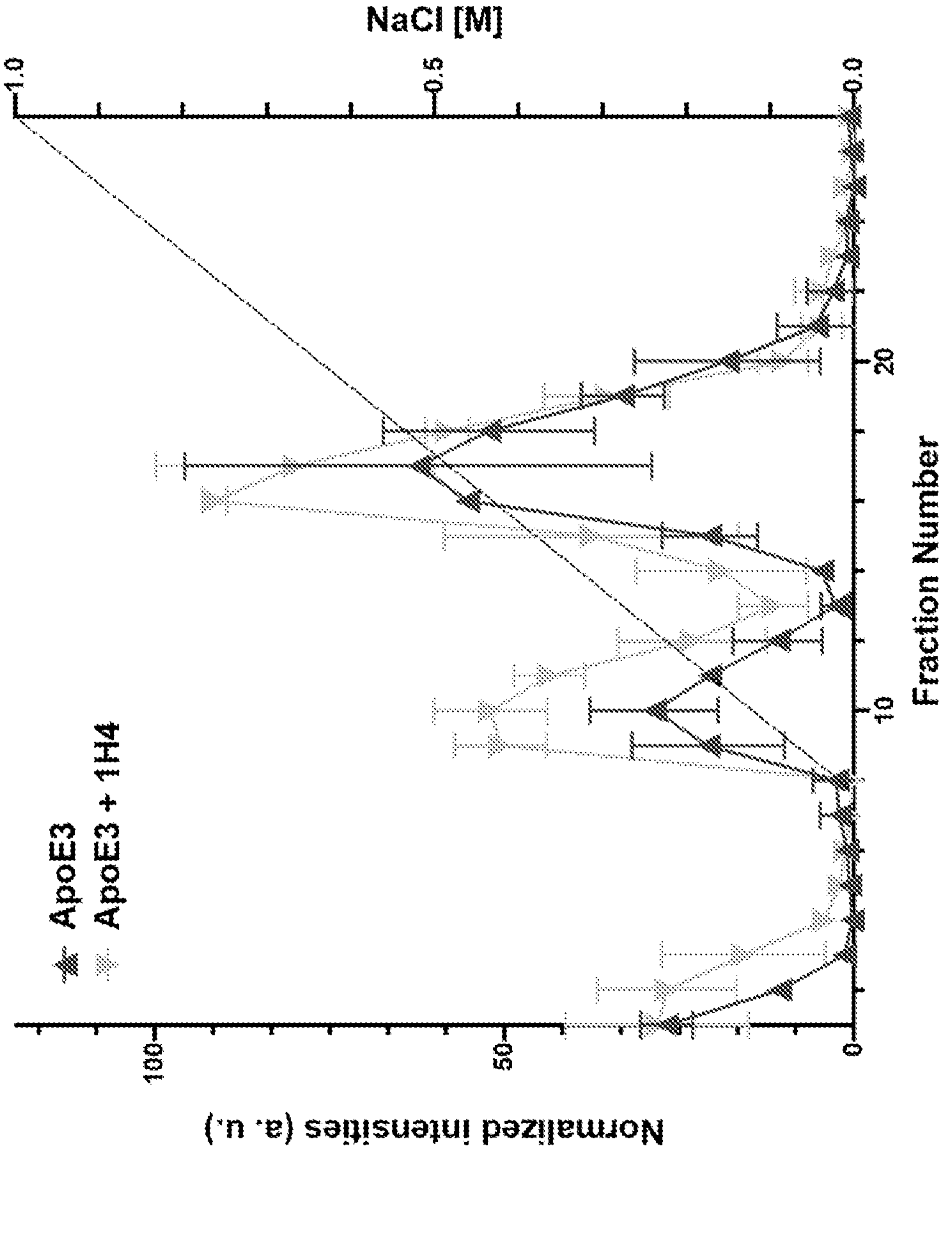
Figure 19:
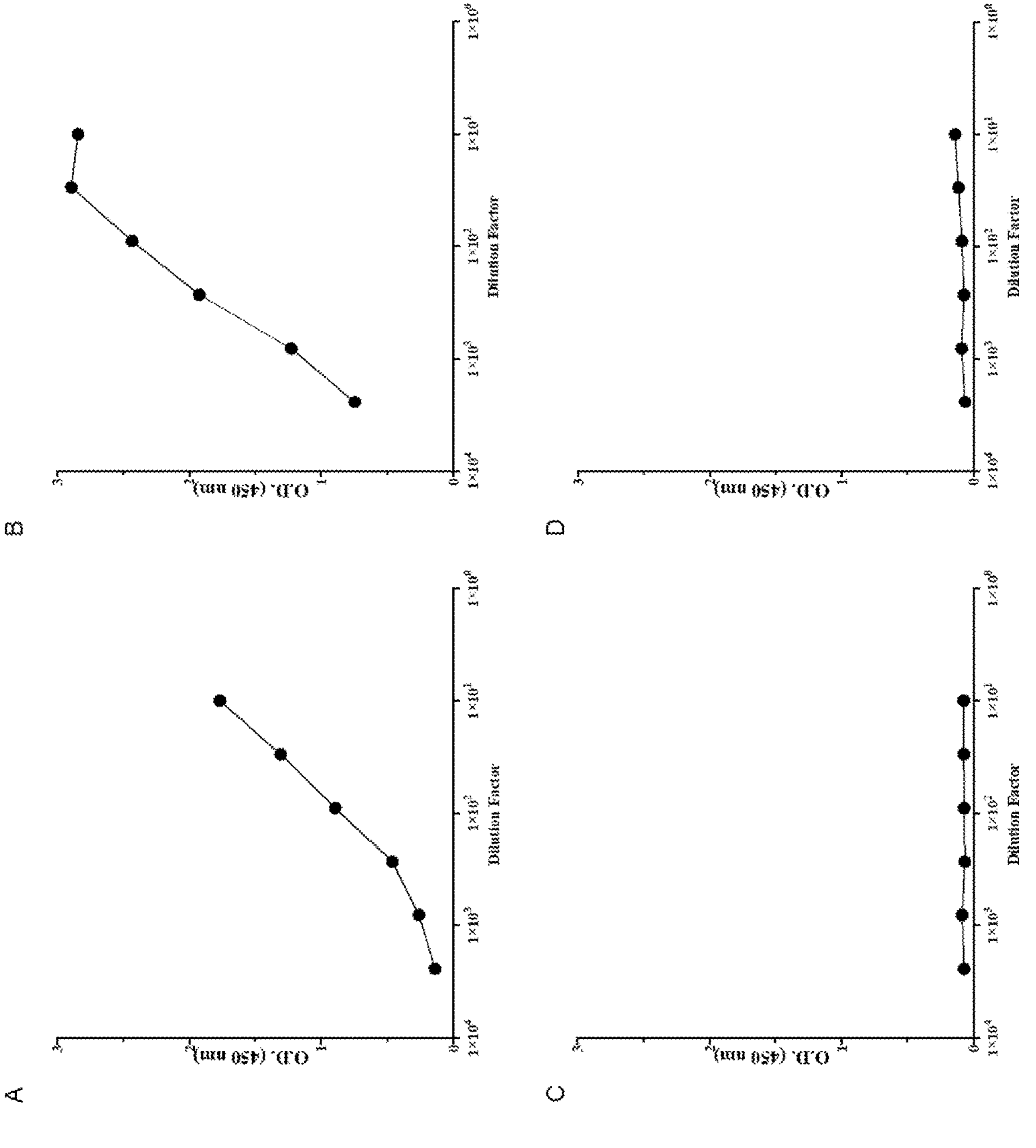
FIGS. 19A-19D show ELISA results of 1H4-2 serum tested with ApoE3 WT full-length protein (A), ApoE3 WT peptide (B), ApoE3ch full length protein (C), and ApoE3ch peptide (D).

Antibody 1H4 was evaluated using heparin-affinity chromatography and western blotting. ApoE3 was incubated either with negative control (vehicle, top blots) or 1H4 (bottom blots) and each fraction was subjected to heparin-affinity chromatography and western blotting (FIG. 18A). ApoE3 positive bands are indicated by the arrows and detected using the antibody anti his-tag (rb, 1:5,000) that specifically detects the his-tag of the recombinant human APOE. FIG. 18B shows quantification of WB blotting bands detected by the antibody anti hi-tag as shown in FIG. 18A. Intensities were normalized to the input. These results show that ApoE3 binding to heparin was reduced in the presence of the antibody, and that antibody 1H4 competes with ApoE for heparin binding. N=2 independent experiments.

Figure 20:
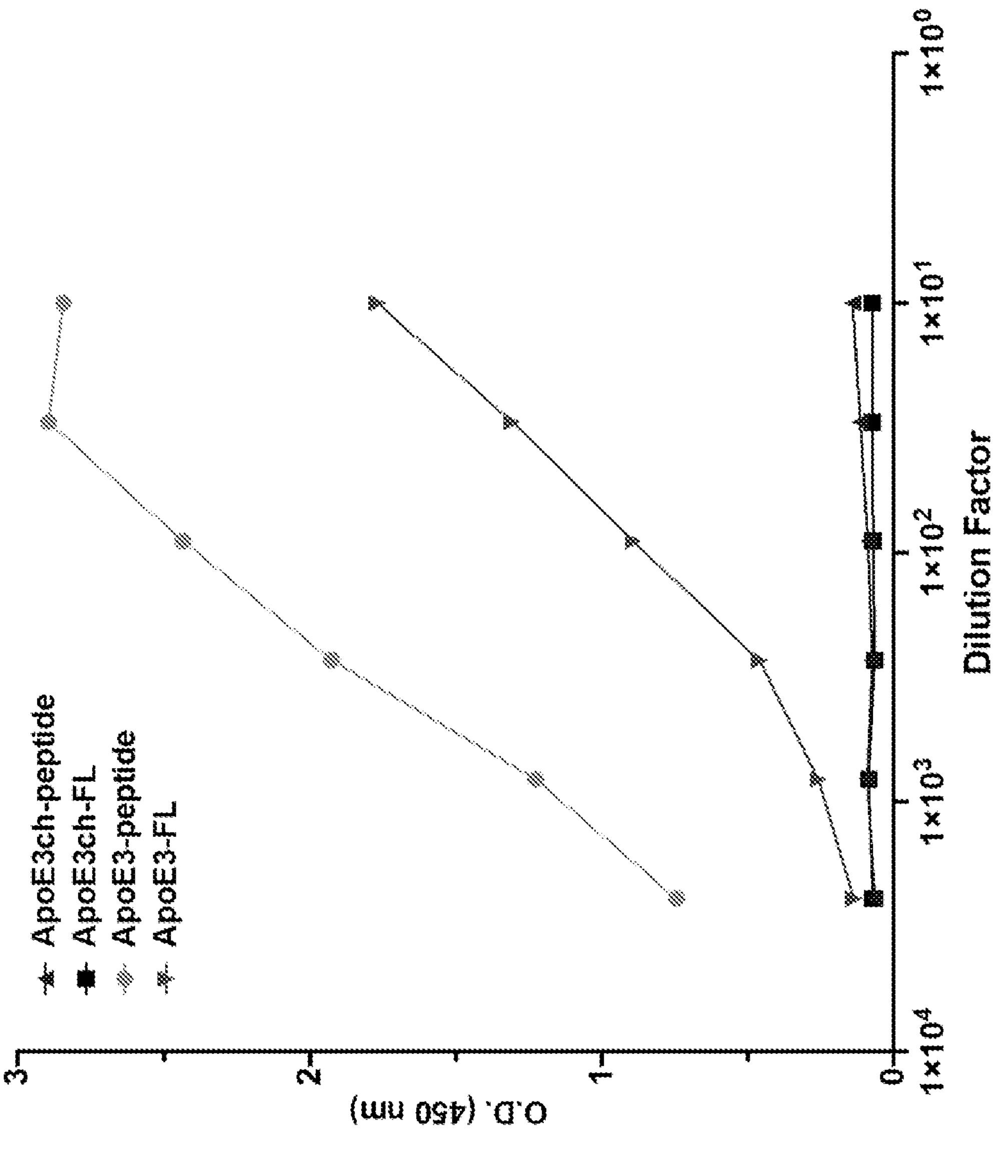
FIG. 20 shows ELISA results of 1H4-2 serum tested with ApoE3 WT full-length protein, ApoE3 WT peptide, ApoE3ch full length protein, and ApoE3ch peptide.

Next, subclone analysis of 1H4 serum was carried out. FIGS. 19A-19D show ELISA results of 1H4-2 serum tested with ApoE3 WT full-length protein (A), ApoE3 WT peptide (B), ApoE3ch full length protein (C), and ApoE3ch peptide (D). The results are expressed as optical density at 450 nm over dilution factor of the serum tested. FIG. 20 is a diagram comparing the results shown in FIGS. 19A-19D.

Figure 21:
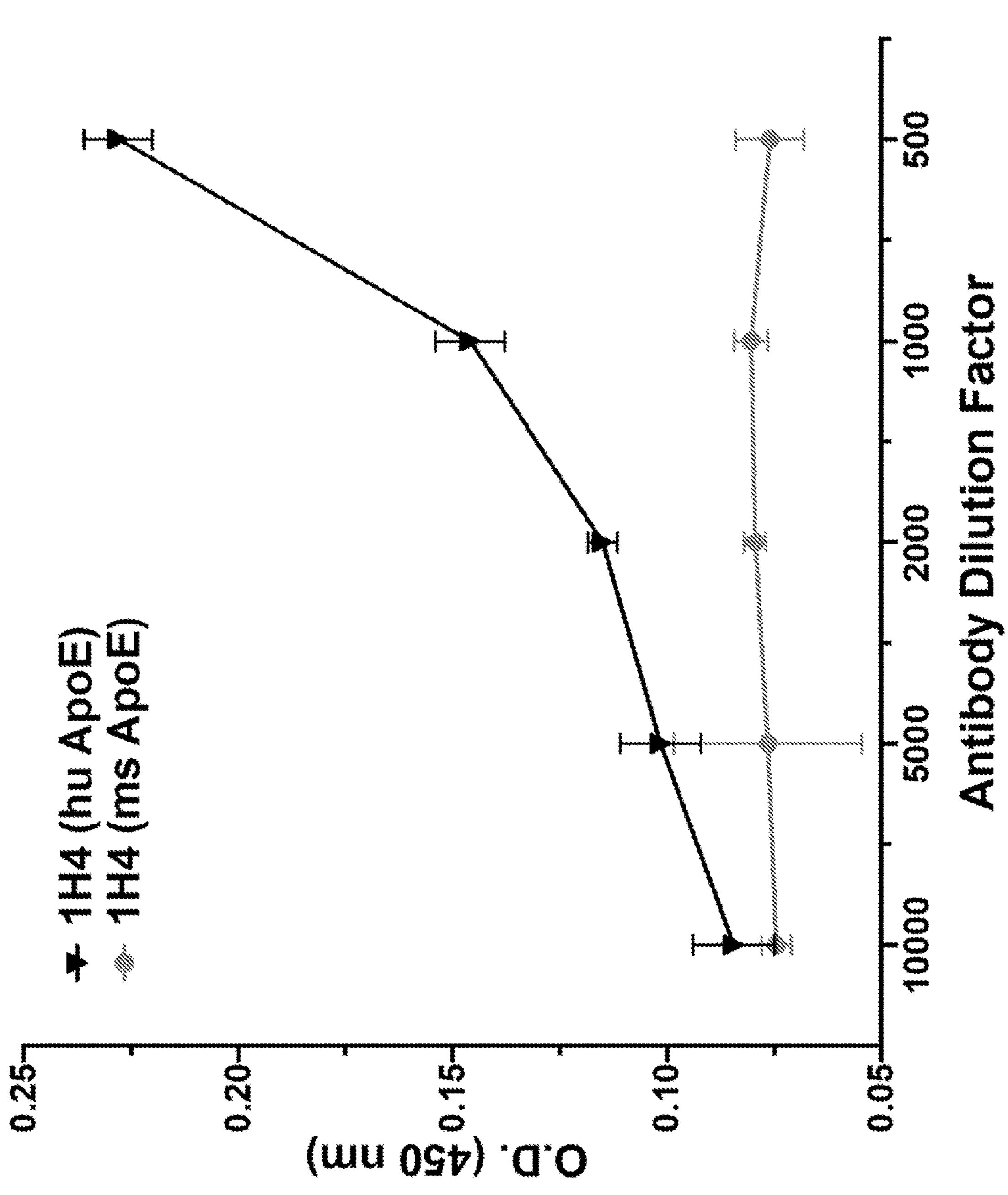
FIG. 21 shows representative ELISA profiles of serial dilutions of the antibody 1H4 incubated either with human recombinant ApoE3 or mouse recombinant ApoE3.

FIG. 21 shows representative ELISA profiles of serial dilutions of the antibody 1H4 incubated either with human recombinant ApoE3 or mouse recombinant ApoE3. The results show that the antibody preferentially binds to the human protein and not to the mouse, and that antibody 1H4 is selective for human ApoE. The results are shown as averaged optical densities detected at 450 nm±s.e.m. (n=2).

Figure 22:
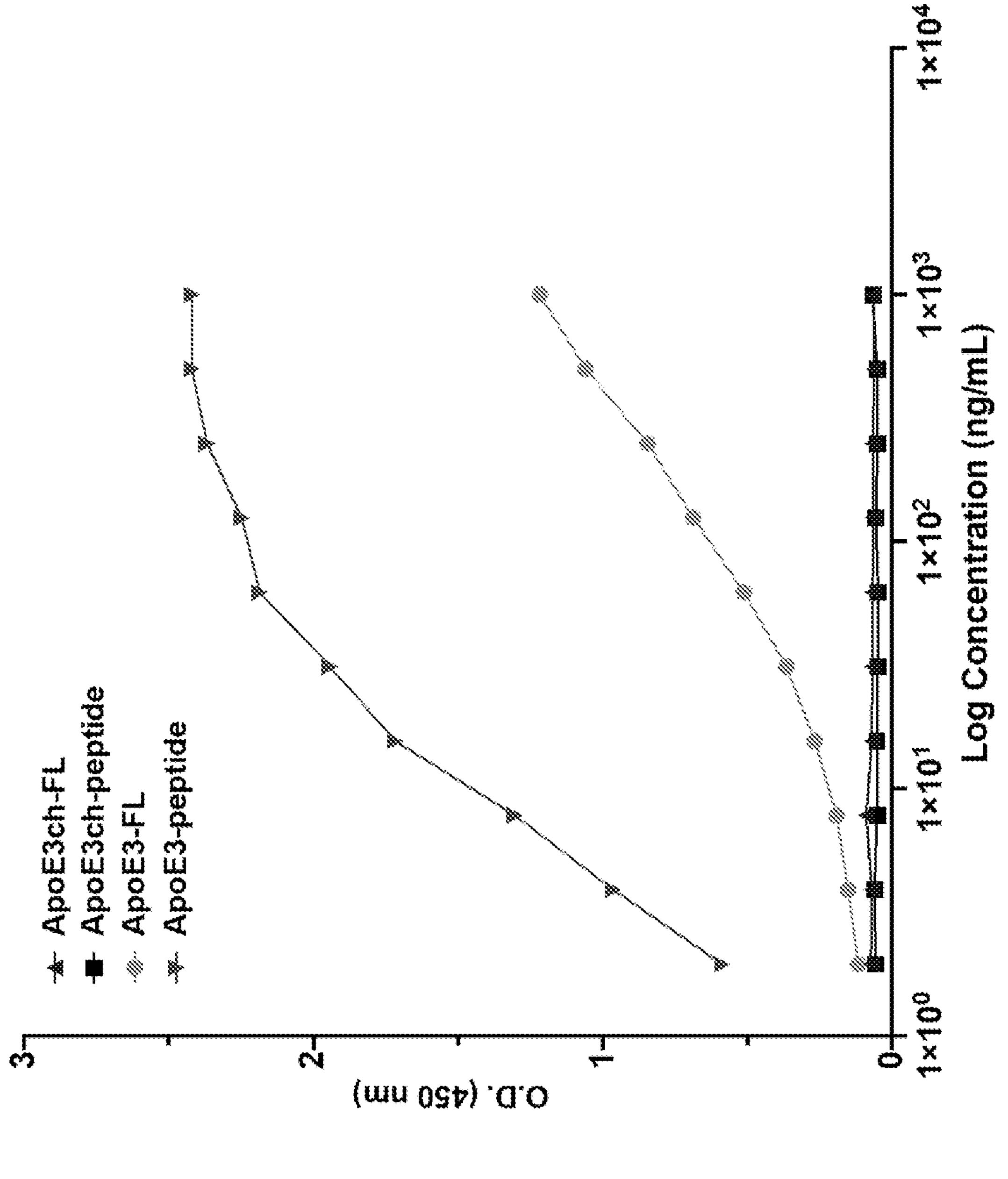
FIG. 22 shows ELISA results for the monoclonal 1H4 antibody purified from cloned hybridoma.

Next, monoclonal 1H4 antibody was purified from cloned hybridoma, and subjected to ELISA evaluation. FIG. 22 shows results from the ELISA experiments.

Antibody 7C11 was evaluated using heparin-affinity chromatography, western blotting, quantitative ELISA for chromatography fractions, and competitive ELISA for binding analyses.

Figure 23A:
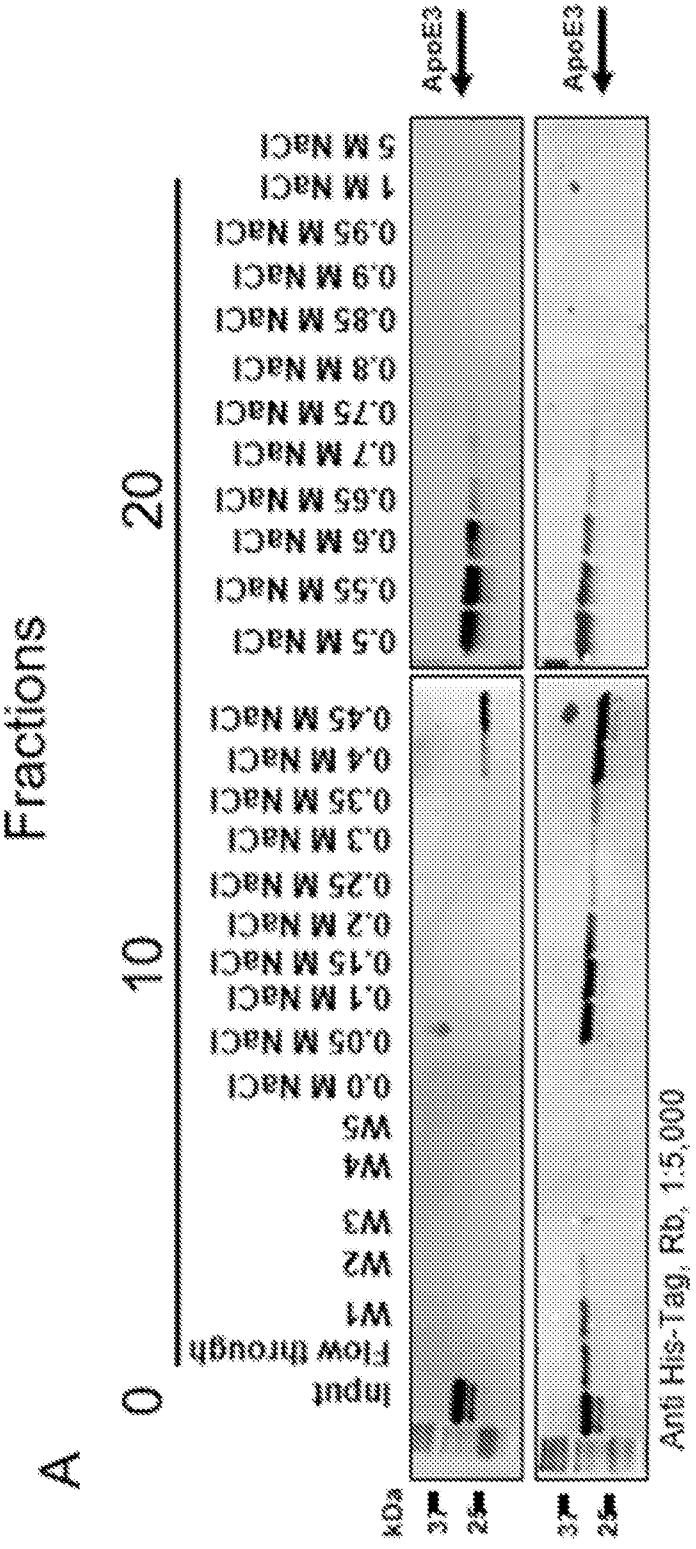
FIGS. 23A and 23B show heparin-affinity chromatography and western blot analysis of antibody 7C11.
Figure 23B:
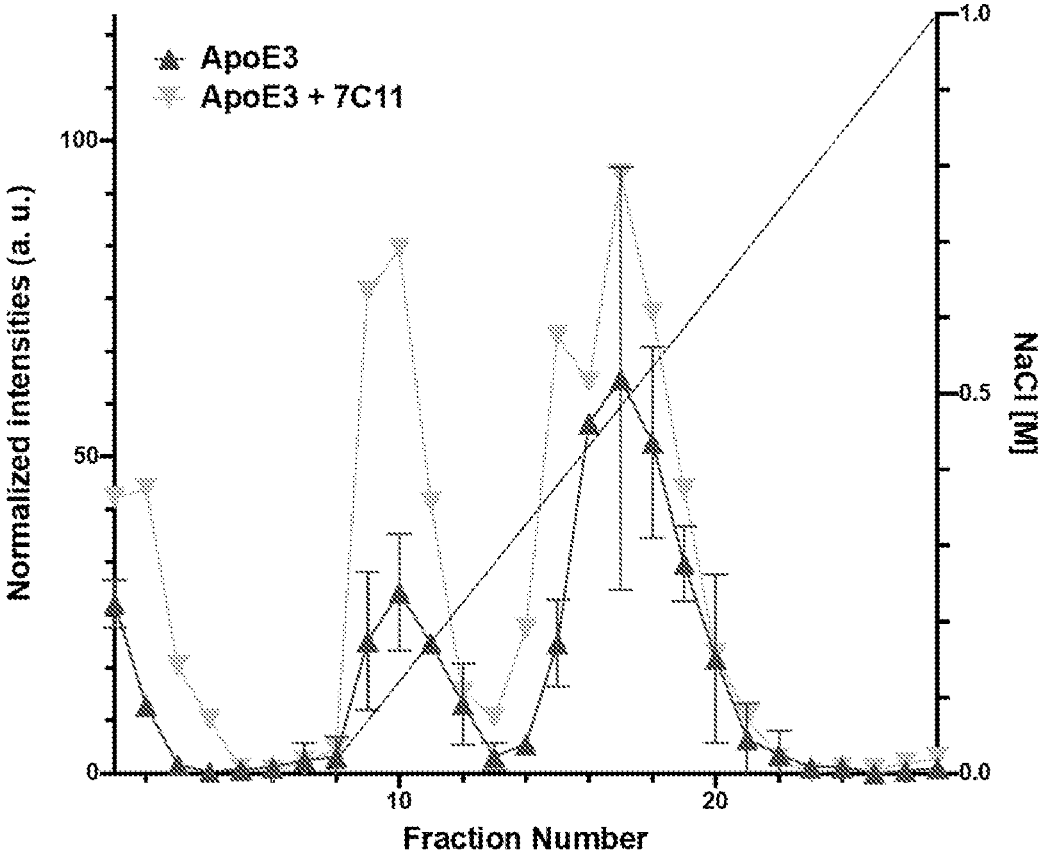
Figure 24:
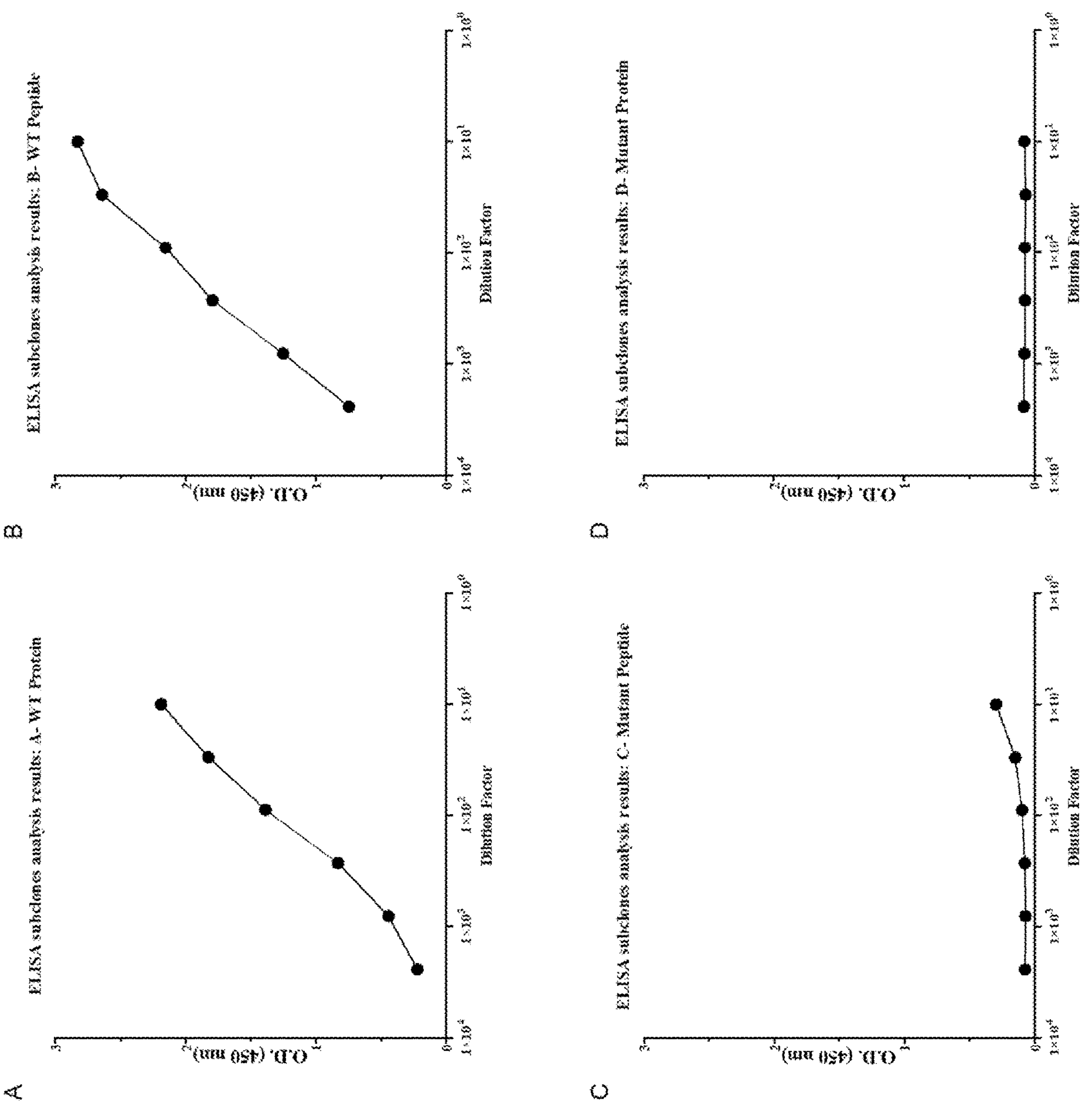
FIGS. 24A-24D show ELISA results from testing the 7C11-1 serum with ApoE3 WT full-length protein (A), ApoE3 WT peptide (B), ApoE3ch full length protein (C), or ApoE3ch peptide (D).

Heparin affinity chromatography fractions of ApoE3 incubated either with negative control (vehicle, top blots) or the antibody 7C11 (bottom blots) and subjected to western blotting (FIG. 23A). ApoE3 positive bands are indicated by the arrows and detected using the antibody anti his-tag (rb, 1:5,000) that specifically detects the his-tag of the recombinant peptide. FIG. 23B shows quantification of the WB blotting bands detected by the antibody anti hi-tag as shown in FIG. 23A. Intensities were normalized to the input. These results show that ApoE3 binding to heparin was reduced in the presence of the antibody, and that 7C11 competes with ApoE for heparin binding.

Figure 25:
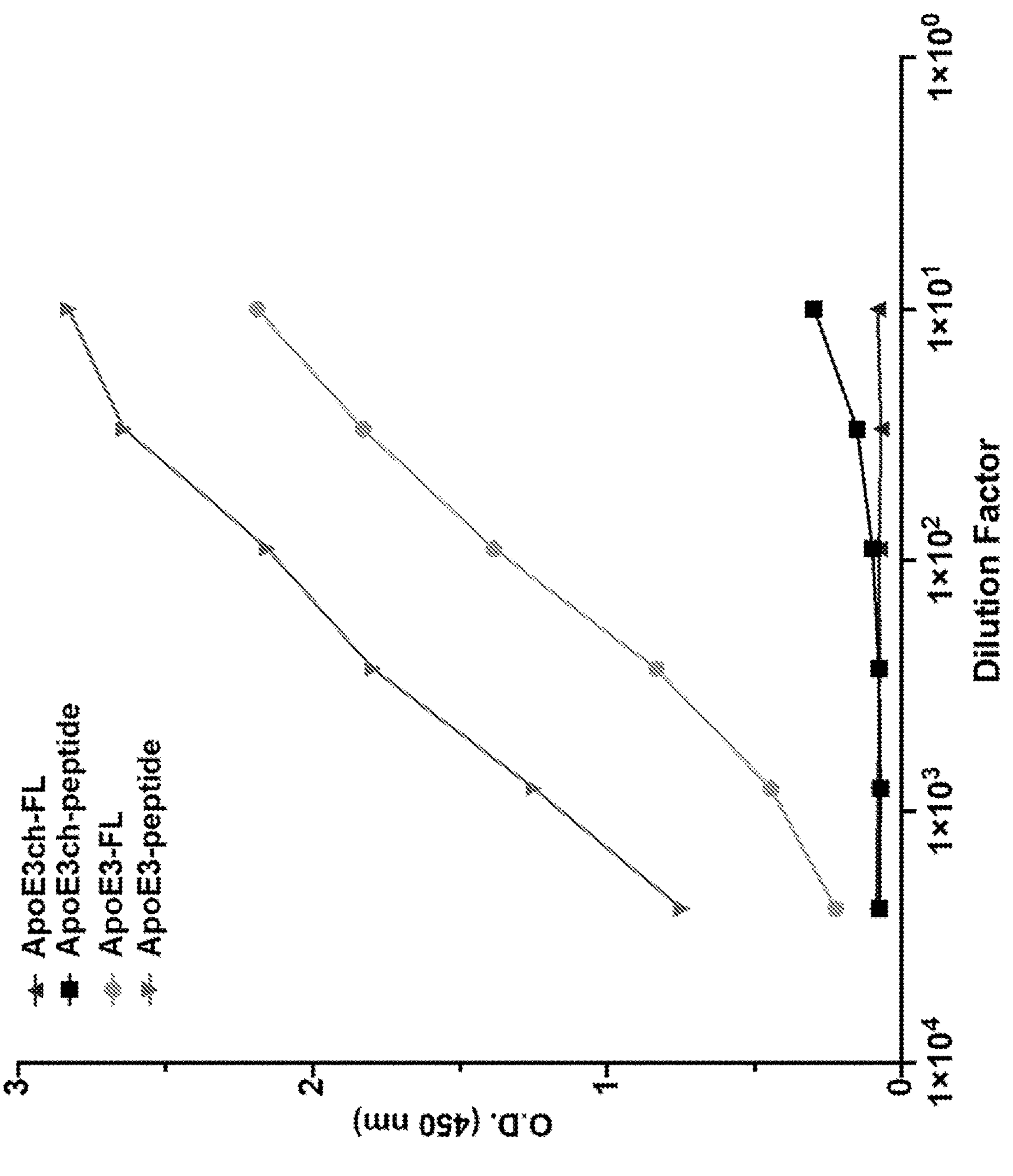
FIG. 25 shows ELISA results from testing the 7C11-1 serum with ApoE3 WT full-length protein, ApoE3 WT peptide, ApoE3ch full length protein, or ApoE3ch peptide.
Figure 26:
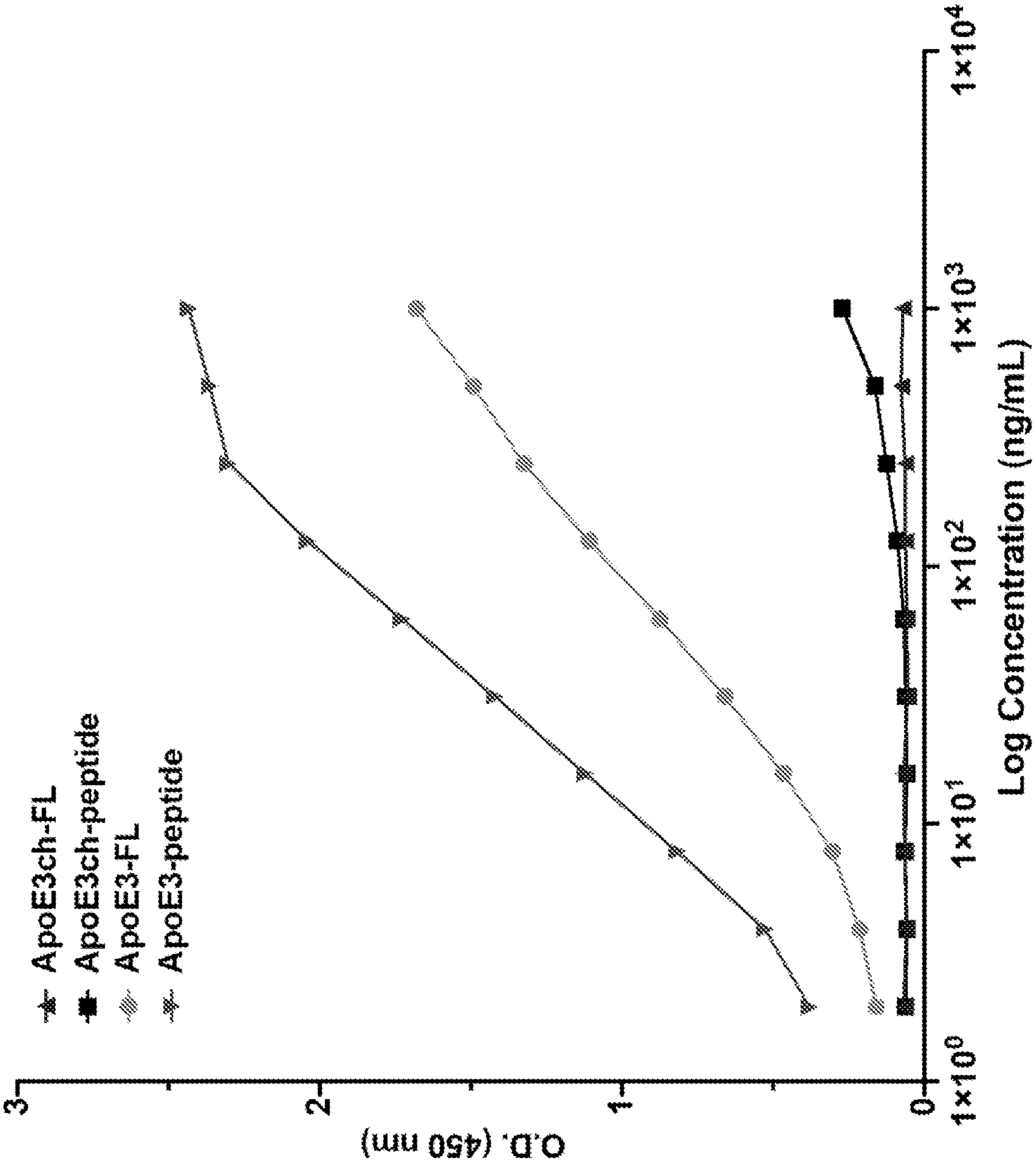
FIG. 26 shows ELISA results for the monoclonal 7C11-1 antibody purified from cloned hybridoma.

Next, subclone analysis of 7C11-1 serum was carried out. FIGS. 24A-24D show ELISA results from testing the 7C11-1 serum with ApoE3 WT full-length protein (A), ApoE3 WT peptide (B), ApoE3ch full length protein (C), or ApoE3ch peptide (D). The results are shown as optical density at 450 nm over dilution factor of the serum tested. FIG. 25 is a diagram comparing the results shown in FIGS. 19A-19D. Next, monoclonal 7C11-1 antibody was purified from cloned hybridoma, and subjected to ELISA evaluation. FIG. 26 shows results from the ELISA experiments.

Figure 27:
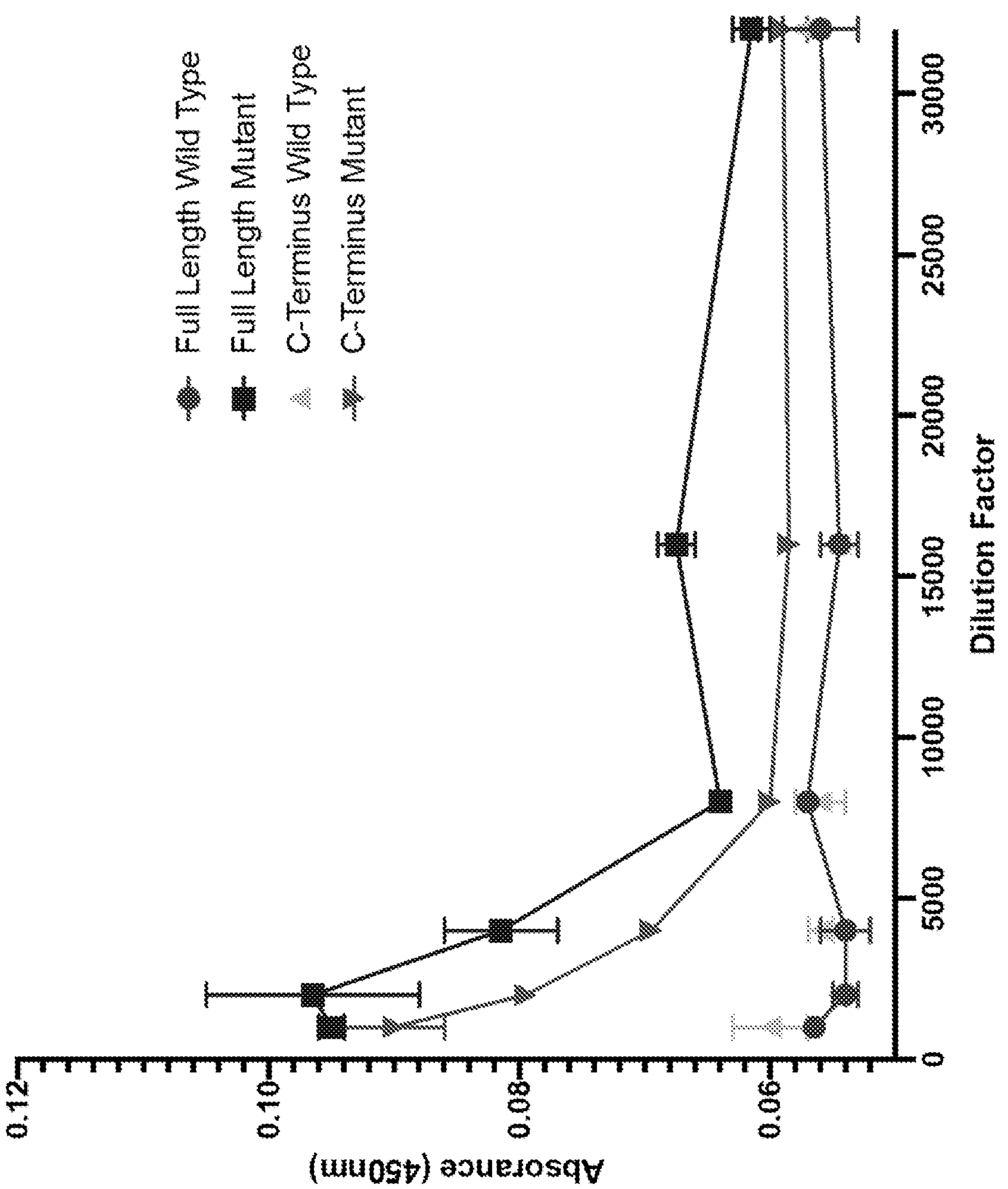
FIG. 27 shows results from ELISA screening of the 19G10-2 antibody against the heparin binding domain of APOE3 Wild Type (WT) and APOE3ch Mutant recombinant protein.

The 19G10-2 antibody was further evaluated using Heparin-Affinity chromatography, Western Blotting, Quantitative ELISA for chromatography fractions, and ELISA for binding analyses. ELISA screening of the 19G10-2 antibody was performed against the heparin binding domain of APOE3 Wild Type (WT) and APOE3ch Mutant recombinant protein. As shown in FIG. 27, the 19G10-2 antibody displays specificity towards both the full length and c-terminal domain of the APOE3ch (amino acids 125 to 299) mutant recombinant protein and some interaction with APOE3 WT.

Figure 28A:
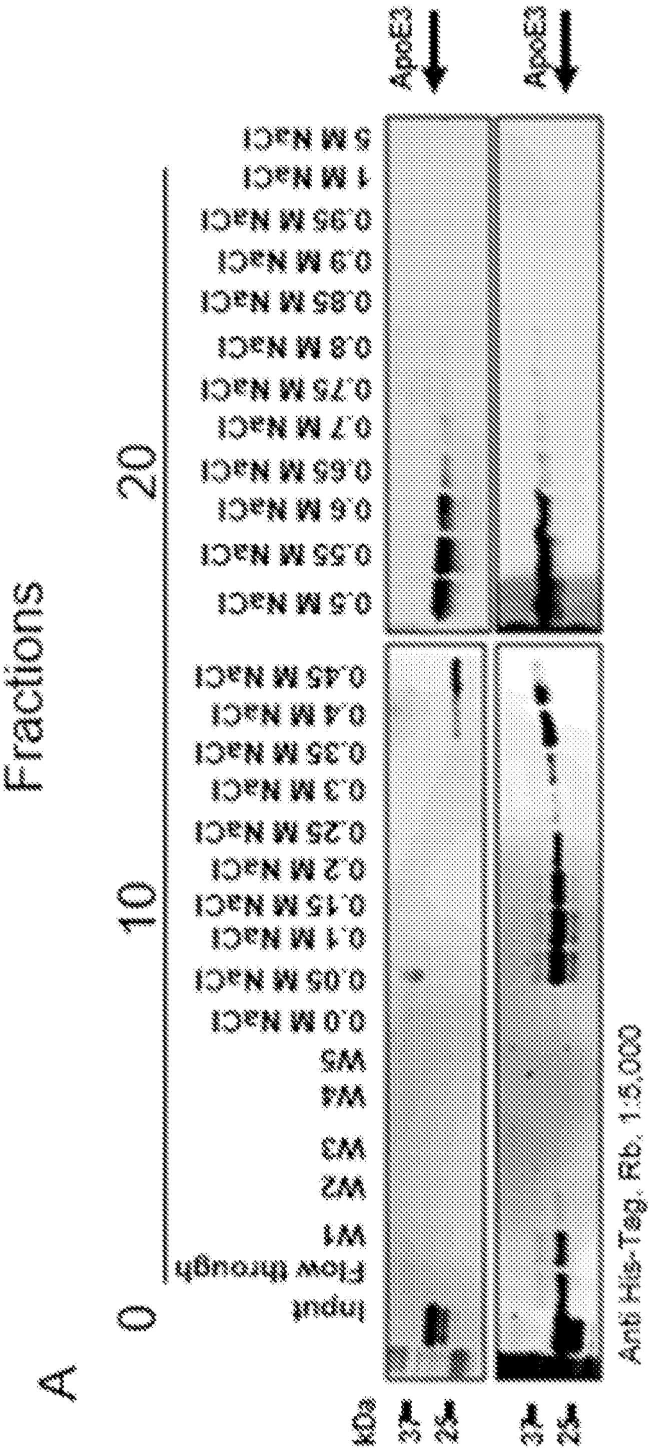
FIGS. 28A and 28B show heparin-affinity chromatography and western blot analysis of antibody 19G10-2.
Figure 28B:
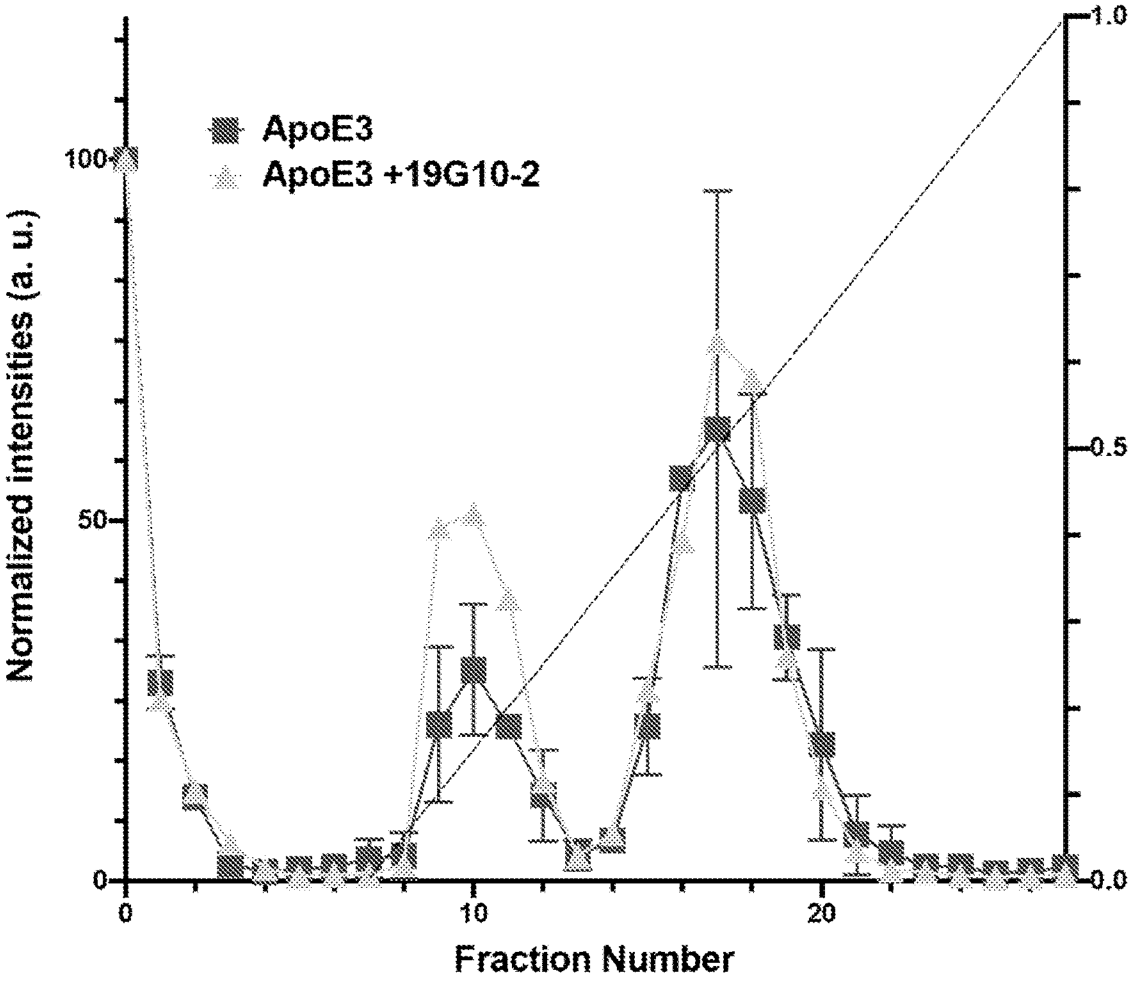

Heparin affinity chromatography fractions of ApoE3 incubated either with negative control (vehicle, top blots) or the antibody 19G10-2 (bottom blots) were subjected to ELISA analysis (FIG. 28A). ApoE3 positive bands are indicated by the arrows and detected using the antibody anti his-tag (rb, 1:5,000) that specifically detects the his-tag of the recombinant peptide. FIG. 28B shows quantification of WB blotting bands detected by the antibody anti hi-tag as shown in FIG. 28A. Intensities were normalized to the input. These results show that despite being designed against the ApoE3ch-HSPG domain, 19G10-2 competes with wild type ApoE for heparin binding and resulted in reduced ApoE3 binding to heparin. Without wishing to be bound by theory, antibody 19G10-2 may recognize and/or stabilize a conformation specific feature of APOE (e.g. an APOE polymer or aggregate) that is less likely to bind heparin/HSPG/GAG.

Figure 29:
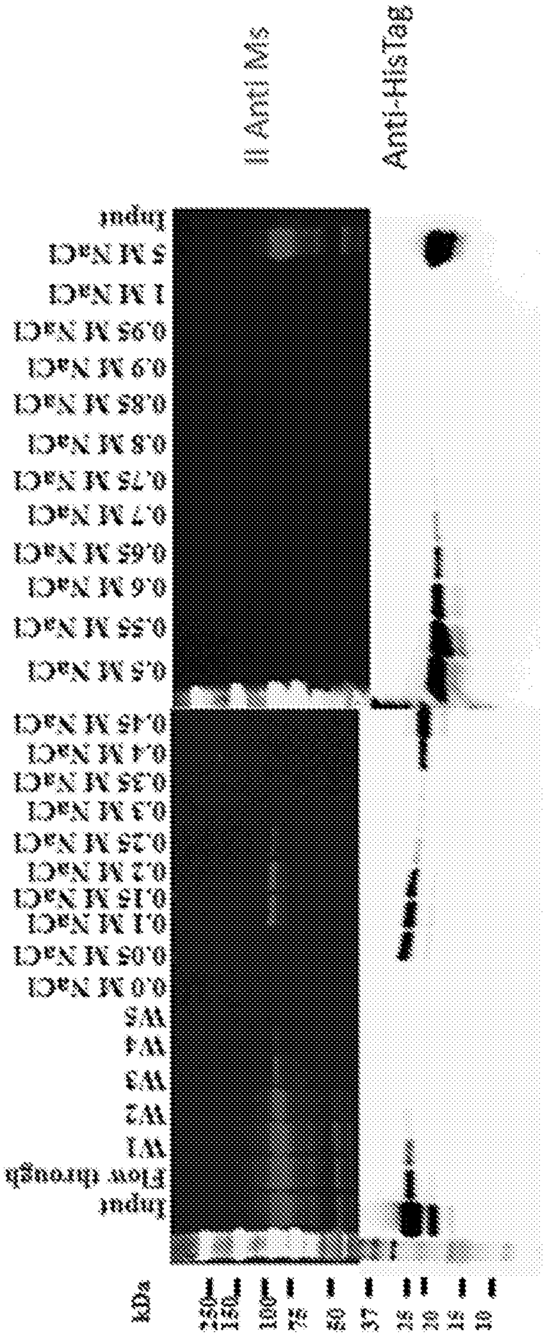
FIG. 29 shows western blotting of ApoE3 WT incubated with 19G10-2 serum antibody.

FIG. 29 shows western blotting of ApoE3 WT incubated with 19G10-2 serum antibody. Top blots: membranes probed with secondary anti-mouse to detect 19G10-2 antibody. Bottom membranes were incubated with anti his-tag as described previously to detect ApoE3 positive fractions. This analysis demonstrates that antibody-APOE complexes (left side of the blots; top and bottom) do not bind to heparin, while free APOE bind to heparin with high affinity (right side of the blot; bottom).

Figure 30:
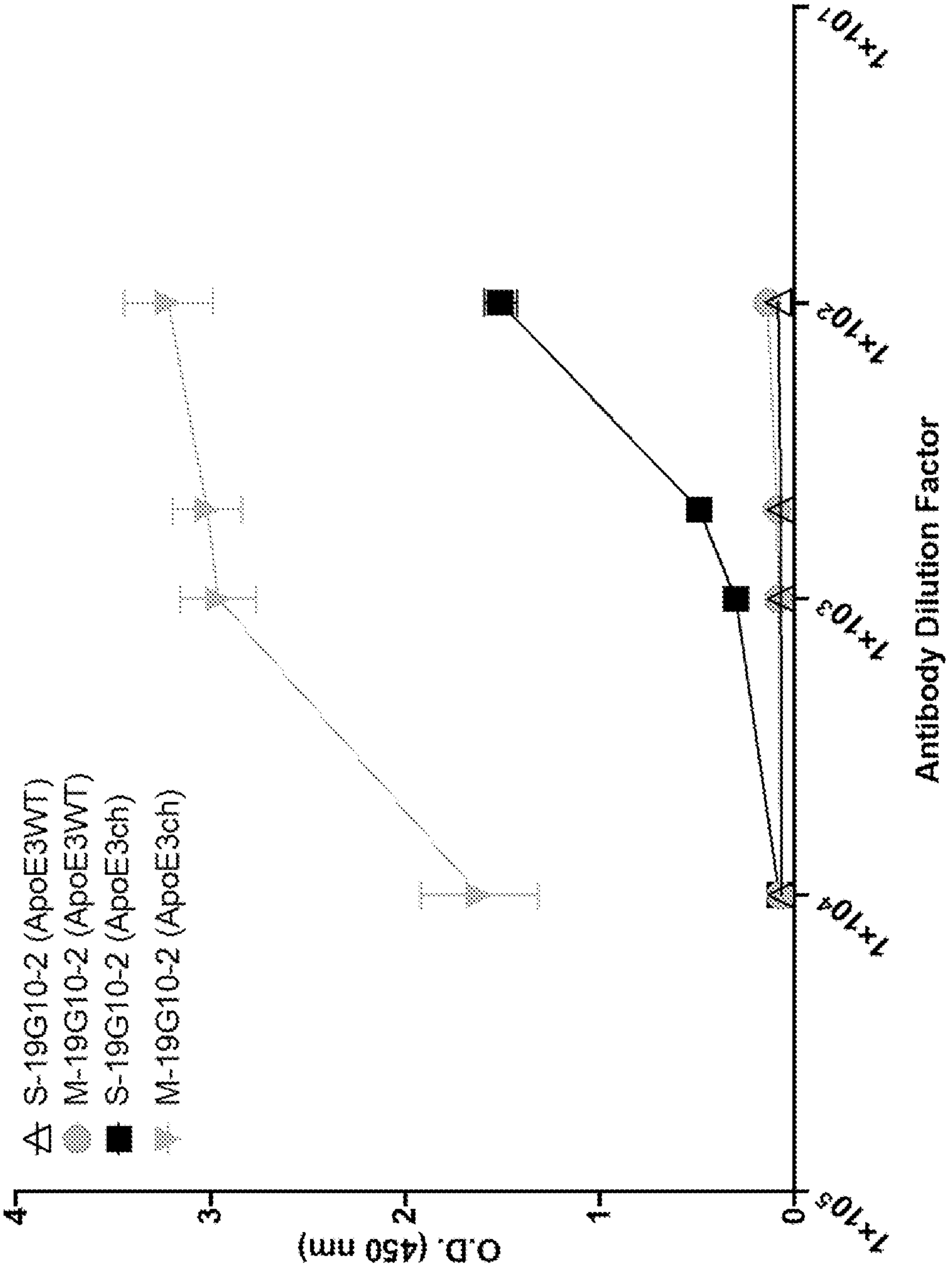
FIG. 30 is representative ELISA showing the differences in binding of both serum and monoclonal antibody hybridoma supernatant 19G10-2 for ApoE3WT or ApoE3ch.
Figure 31:
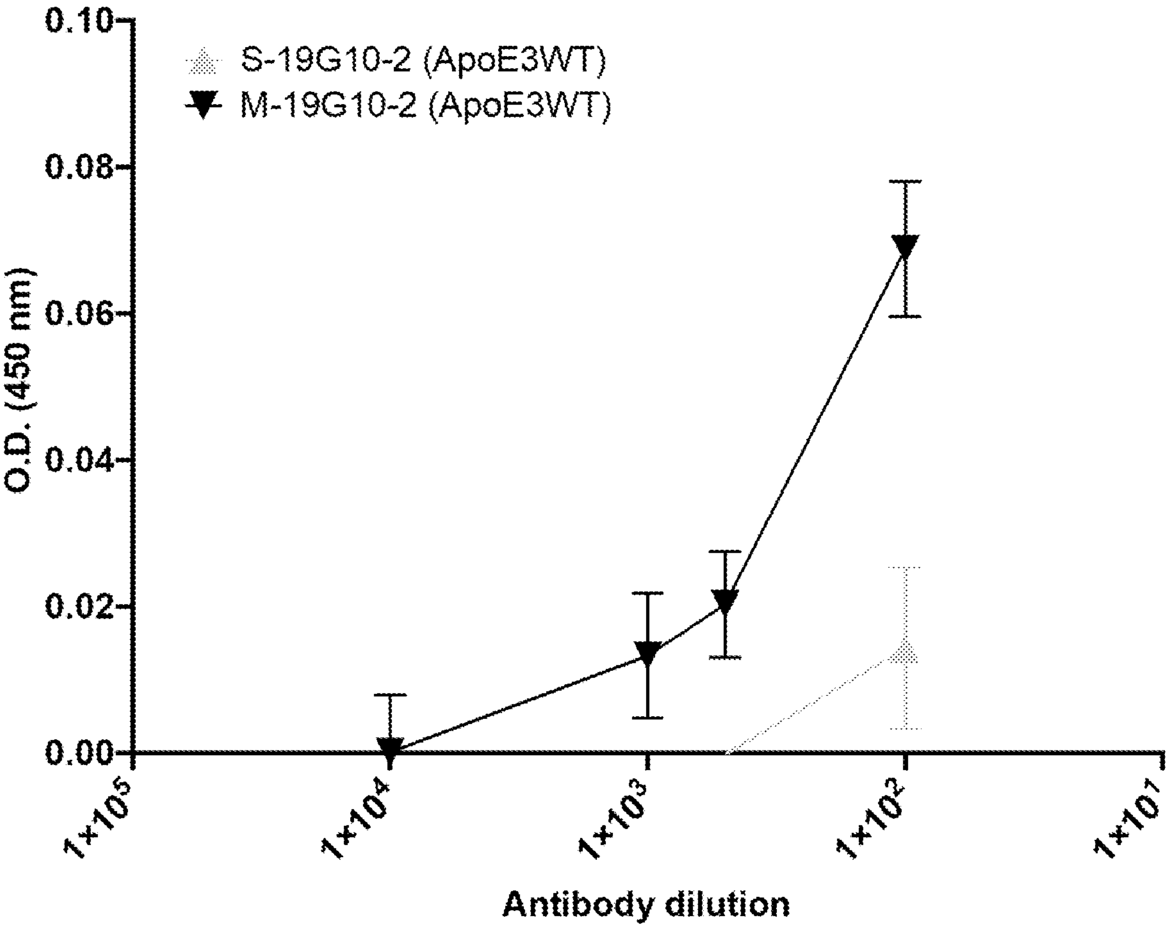
FIG. 31 is an enlargement of the Y axes in FIG. 30.
Figure 32:
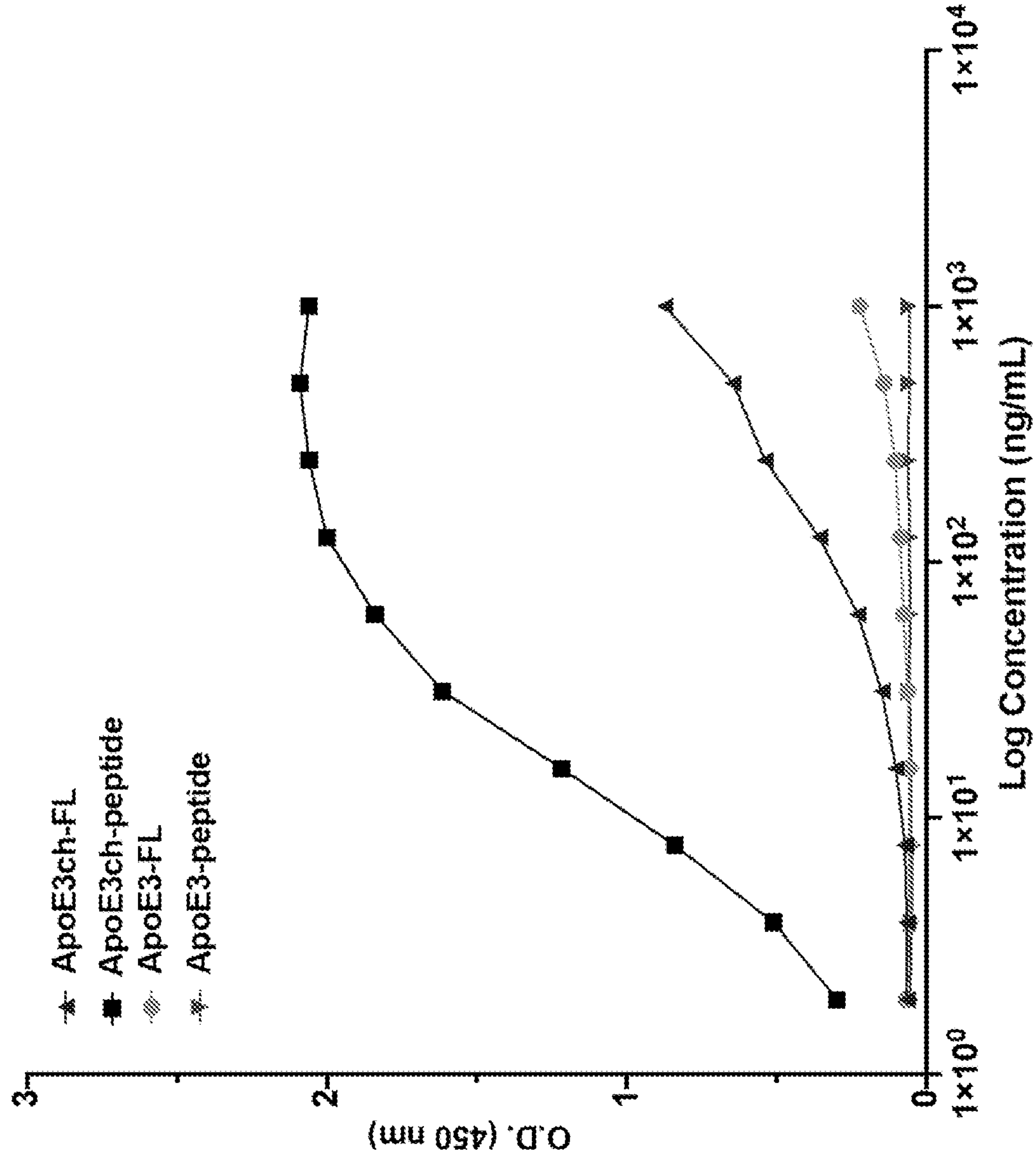
FIG. 32 shows ELISA results for the monoclonal 19G10-2 antibody purified from cloned hybridoma.

FIG. 30 is representative ELISA showing the differences in binding of both serum and monoclonal antibody hybridoma supernatant 19G10-2 for ApoE3WT or ApoE3ch. Data confirms the preponderant selectivity of this antibody for the ApoE3ch variant. FIG. 31 is an enlargement of the Y axes showing some limited binding profiles of the antibody 19G10-2 (serum, grey profile; monoclonal, black binding profile) in the presence of ApoE3WT. Next, monoclonal 19G10-2 antibody was purified from cloned hybridoma, and subjected to ELISA evaluation. FIG. 32 shows results from the ELISA experiments. A signal of recognition of the full-length WT APOE higher than that of the WT ApoE peptide suggest binding of a conformation-specific feature.

Figure 33:
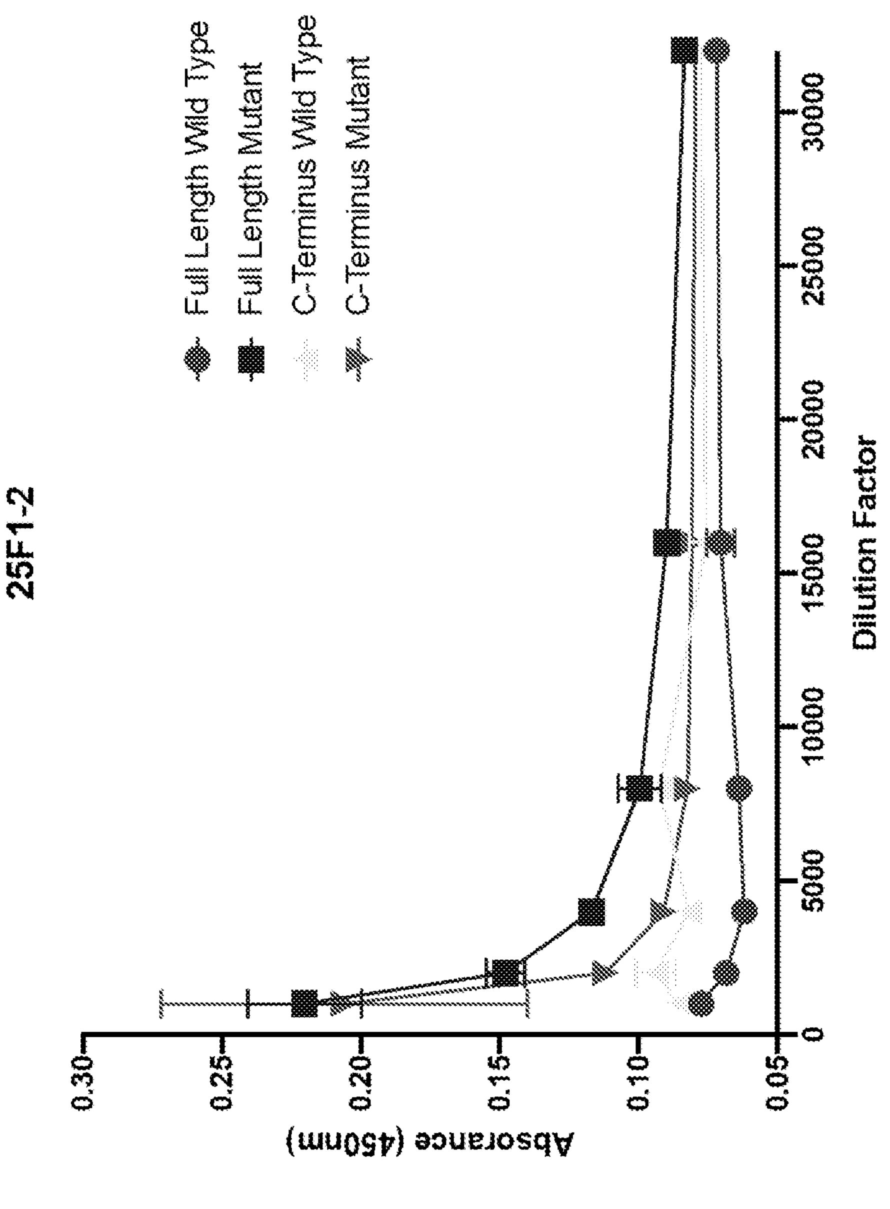
FIG. 33 shows results from ELISA screening of the 25F1-2 antibody against the heparin binding domain of APOE3 Wild Type (WT) and APOE3ch Mutant recombinant protein.

The 25F1-2 antibody was further evaluated using Heparin-Affinity chromatography, Western Blotting, Quantitative ELISA for chromatography fractions, and ELISA for binding analyses. FIG. 33 shows ELISA screening of the 25F1-2 antibody against the heparin binding domain of APOE3 Wild Type (WT) and APOE3ch Mutant recombinant protein. As shown in FIG. 33, the 25F1-2 antibody shows high affinity for the APOE3 mutant full length and c terminal protein, however, it does not appear to have strong binding to the c-terminus of the APOE3WT protein and showed limited interaction with APOE3 WT full length protein. The results are displayed as optical density at 450 nm over dilution factor of the serum tested.

Figure 34A:
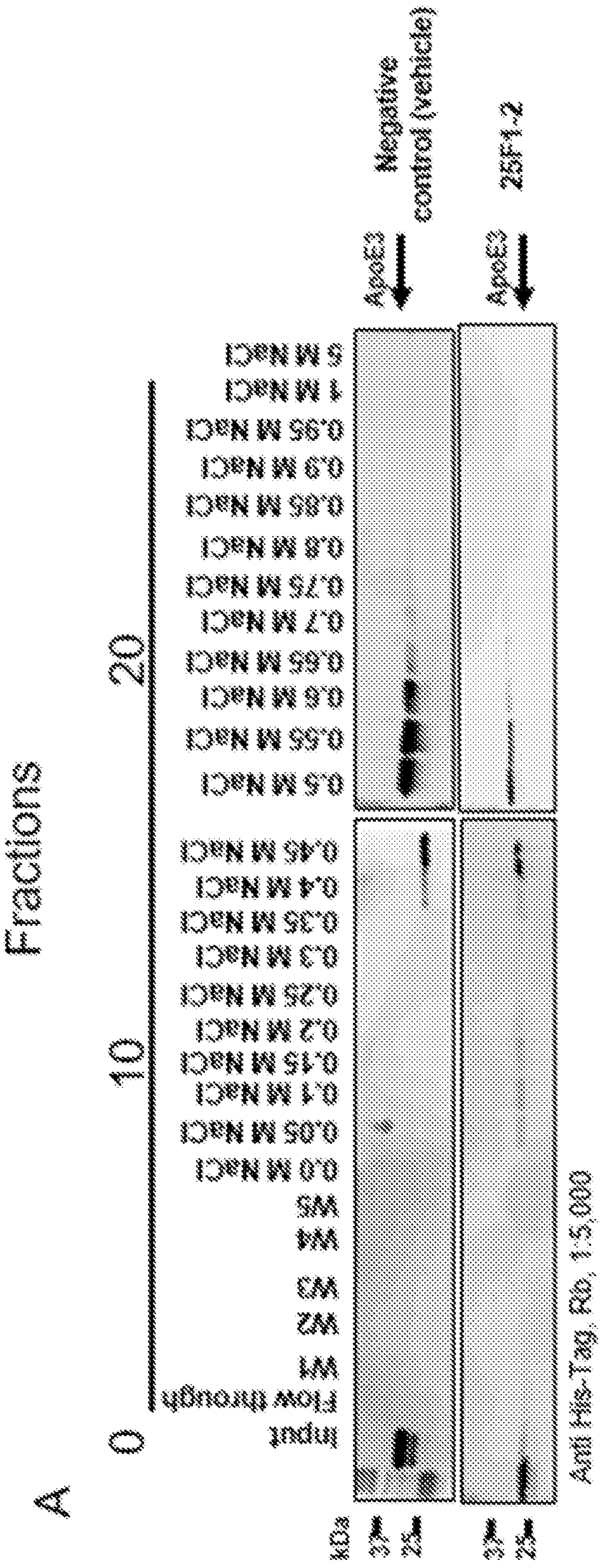
FIGS. 34A and 34B show heparin-affinity chromatography and western blot analysis of antibody 25F1-2.
Figure 34B:
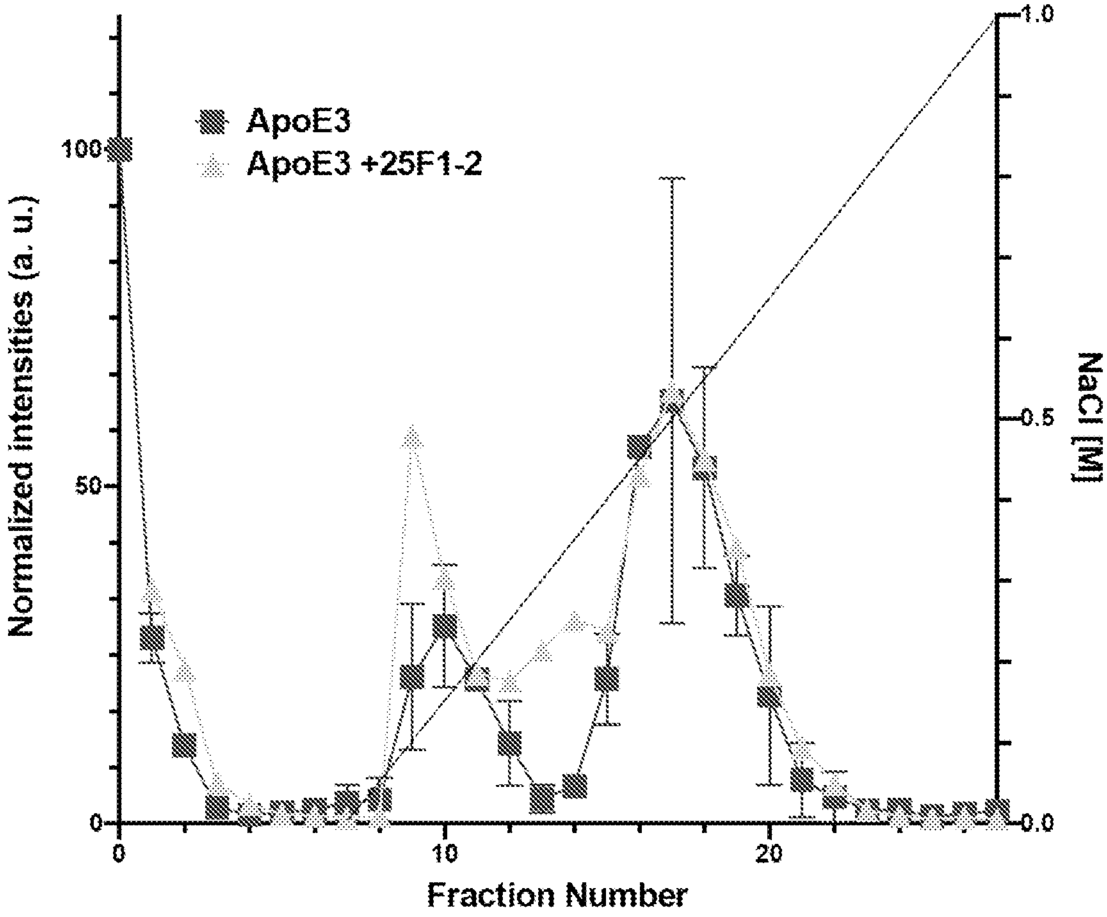

Heparin affinity chromatography fractions of ApoE3 incubated either with negative control (vehicle, top blots) or the antibody 25F1-2 (bottom blots) were subjected to western blotting (FIG. 34A). ApoE3 positive bands are indicated by the arrows and detected using the antibody anti his-tag (rb, 1:5,000) that specifically detects the his-tag of the recombinant peptide. FIG. 34B shows quantification of WB blotting bands detected by the antibody anti hi-tag as shown in FIG. 34A. Intensities were normalized to the input. These results show that despite being designed against the ApoE3ch-HSPG domain, 25F1-2 competes with wild type ApoE for heparin binding and resulted in reduced ApoE3 binding to heparin.

Figure 35:
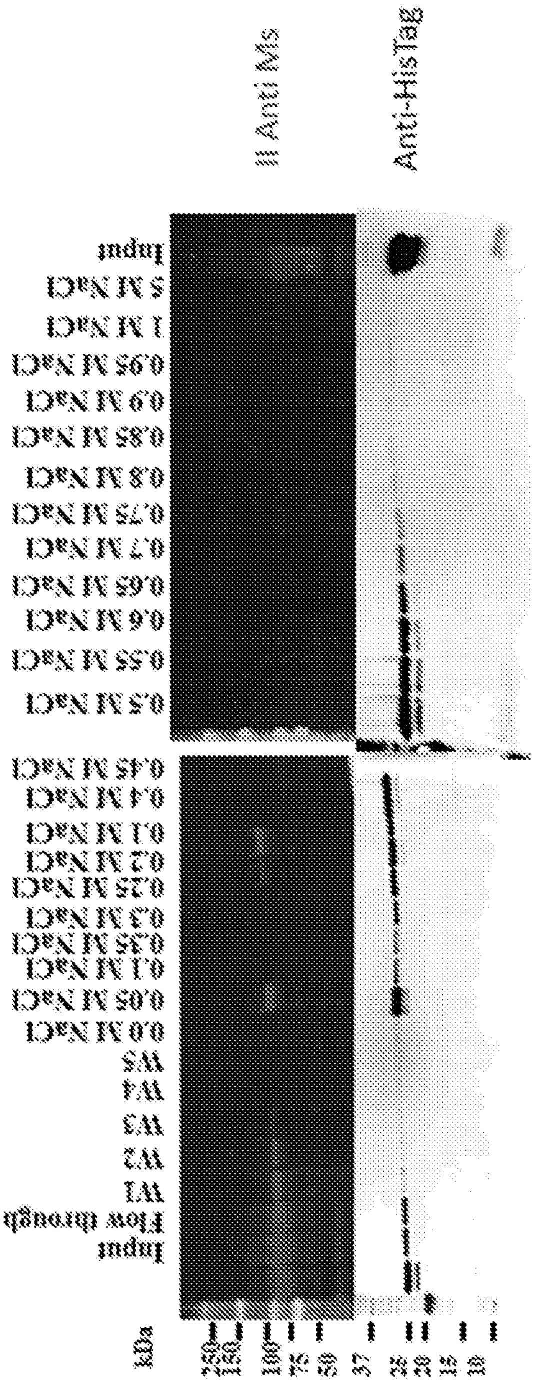
FIG. 35 shows western blotting of ApoE3 WT incubated with the 25F1-2 monoclonal antibody.

FIG. 35 shows western blotting of ApoE3 WT incubated with the 25F1-2 monoclonal antibody. Top blots: membranes probed with secondary anti-mouse to detect 25F1-2. Bottom membranes were incubated with anti his-tag as described previously to detect ApoE3 positive fractions. This analysis demonstrates that antibody-APOE complexes (left blots; top and bottom) do not bind to heparin, while free ApoE bind to heparin with high affinity (right blot, bottom).

Figure 36:
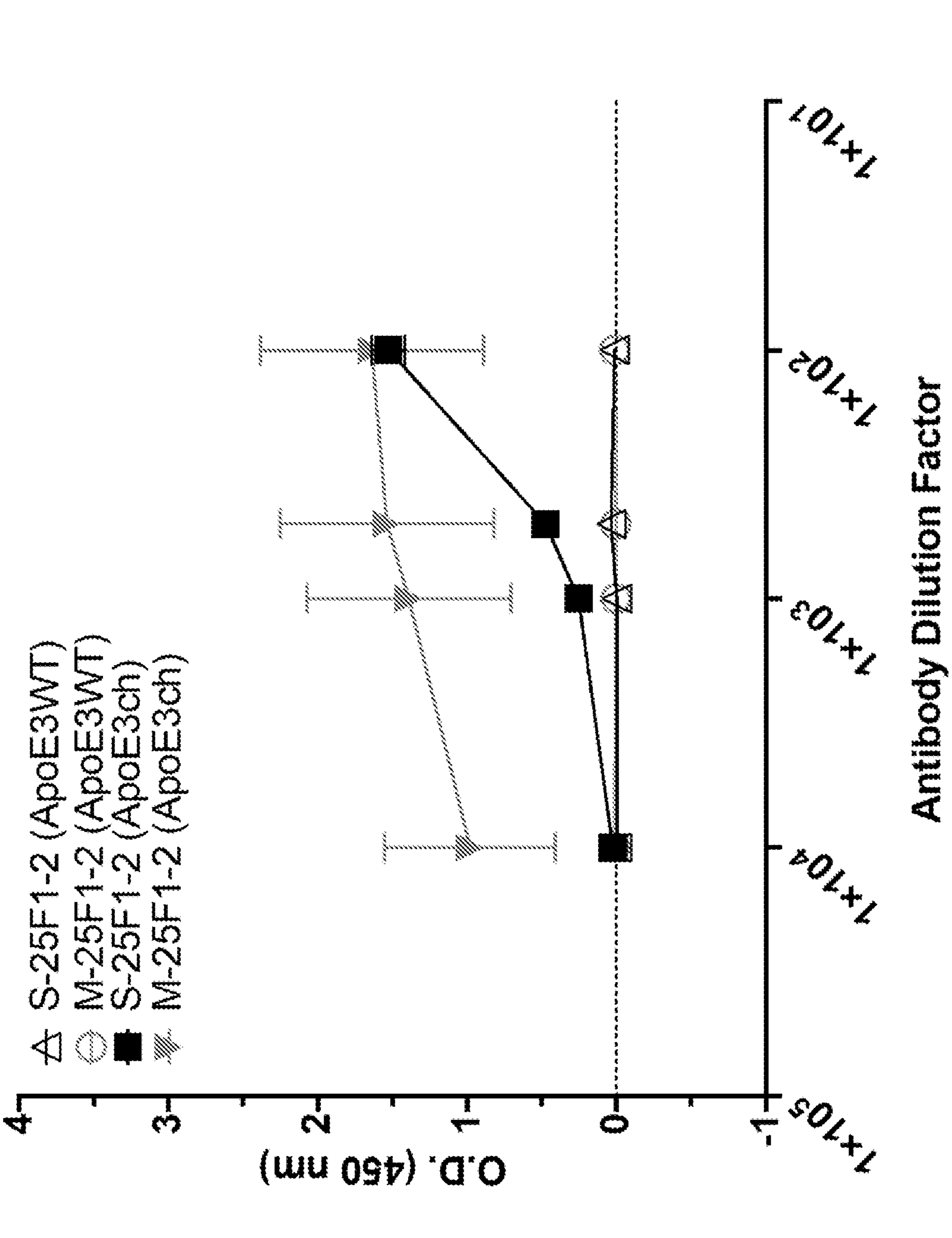
FIG. 36 is representative ELISA showing the differences in binding of both 25F1-2 serum and monoclonal antibody hybridoma supernatant 25F1-2 for ApoE3WT or ApoE3ch.
Figure 37:
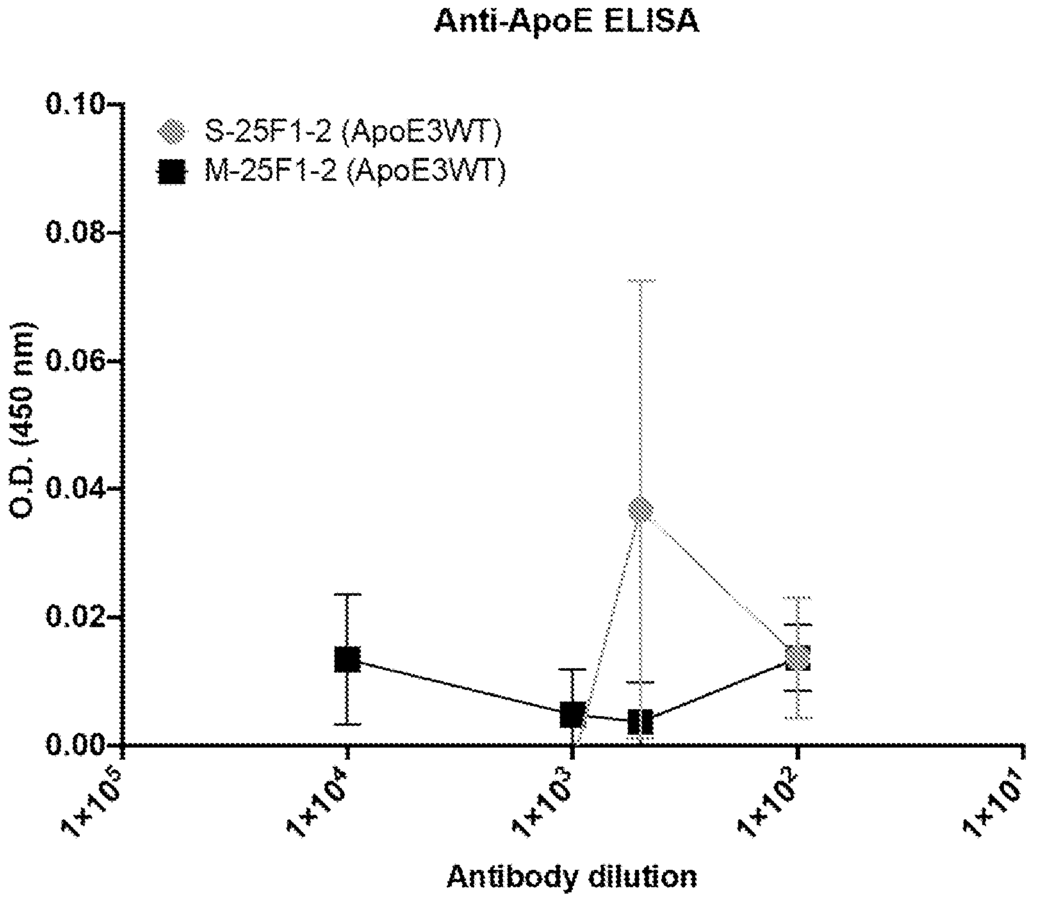
FIG. 37 is an enlargement of the Y axes of FIG. 36.
Figure 38:
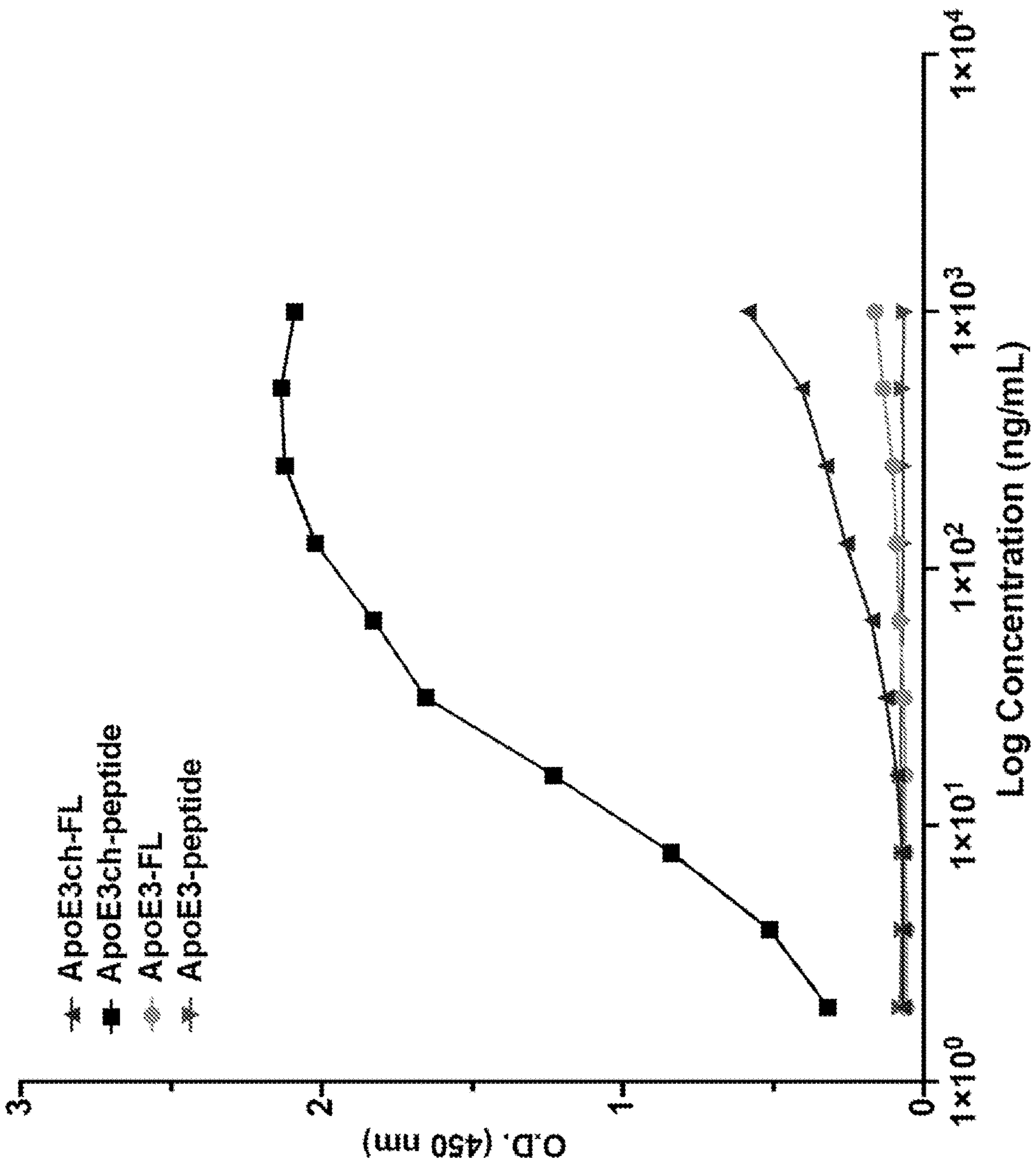
FIG. 38 shows ELISA results for the monoclonal 25F1-2 antibody purified from cloned hybridoma.

FIG. 36 is representative ELISA showing the differences in binding of both 25F1-2 serum and monoclonal antibody hybridoma supernatant 25F1-2 for ApoE3WT or ApoE3ch. These results confirms the preponderant selectivity of this antibody for the ApoE3ch variant. FIG. 37 is an enlargement of the Y axes of FIG. 36, showing the binding profiles of the antibody 25F1-2 in the presence of ApoE3WT. Next, monoclonal 25F1-2 antibody was purified from cloned hybridoma, and subjected to ELISA evaluation. FIG. 38 shows results from the ELISA experiments. A signal of some recognition of the full-length WT APOE higher than that of the WT ApoE peptide suggest binding of a conformation-specific feature.

Figure 39:
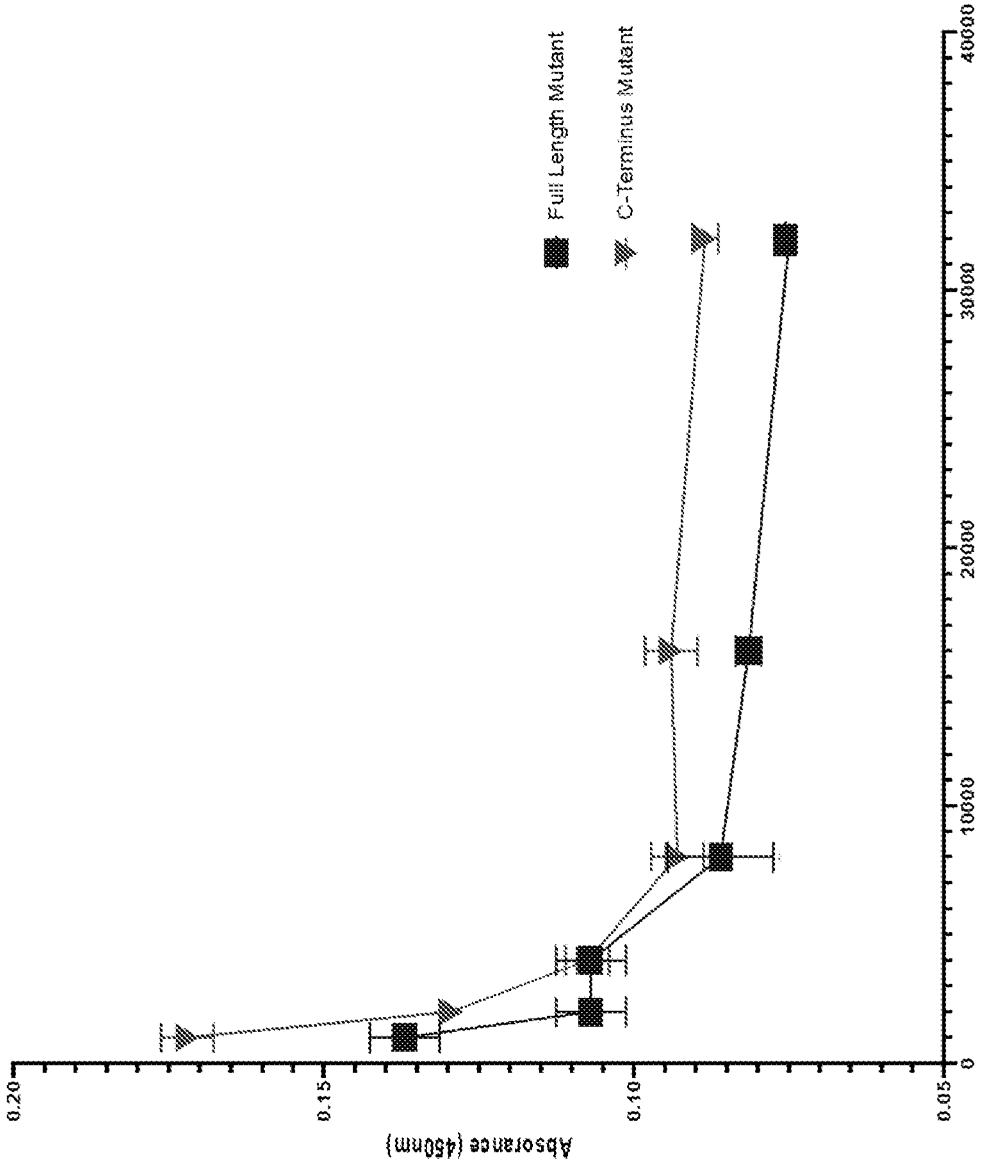
FIG. 39 shows ELISA screening of the 1343 antibody against the heparin binding domain of APOE3 Wild Type (WT) and APOE3ch Mutant recombinant protein.
Figure 40:
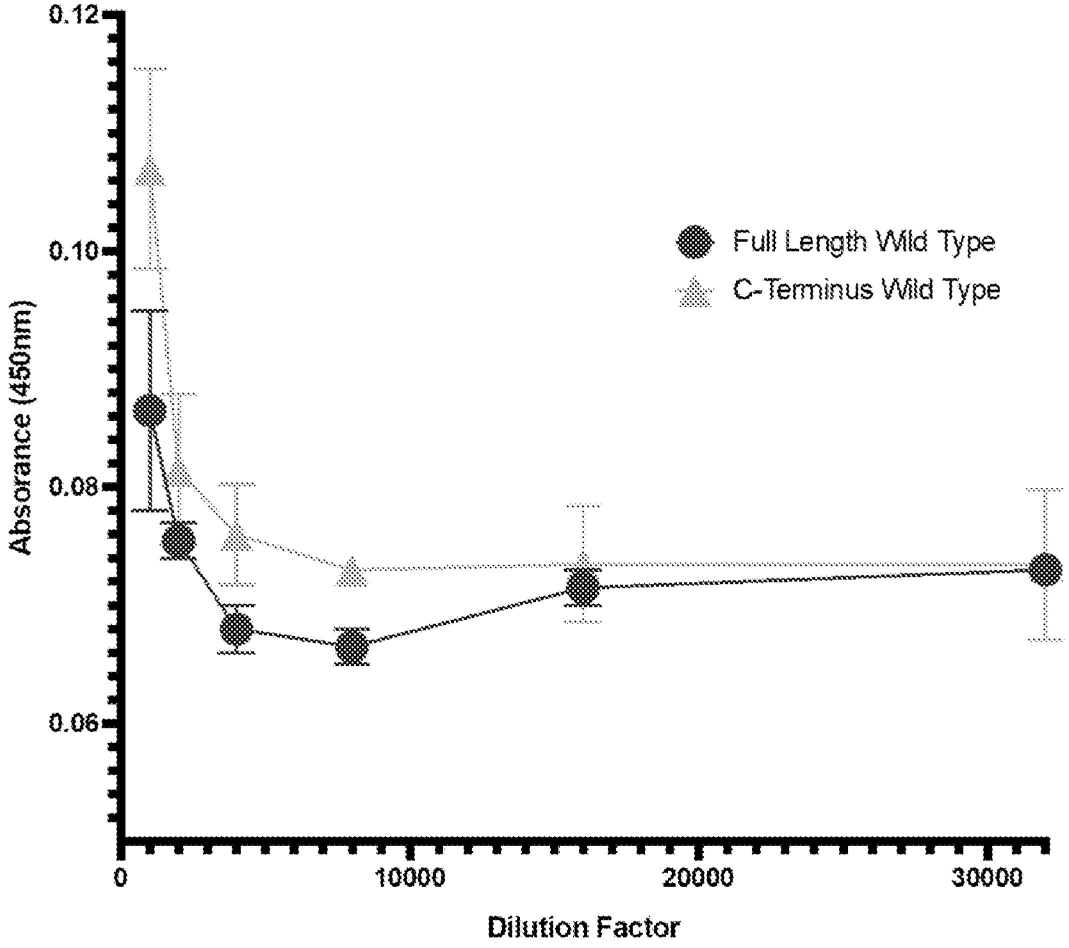
FIG. 40 shows ELISA screening of the 1343 antibody against the heparin binding domain of APOE3 Wild Type (WT) and APOE3ch Mutant recombinant protein.

The mouse antibody 1343ab (renamed from 23B2) was evaluated using heparin-affinity chromatography and western blotting, and quantitative ELISA for chromatography fractions. FIGS. 39 and 40 show ELISA screening of the 1343 antibody against the heparin binding domain of APOE3 Wild Type (WT) and APOE3ch Mutant recombinant protein. 1343 displayed reactivity to both the APOE3 WT and APOE3ch mutant C-Terminus and full-length recombinant APOE proteins (mutant refers to Christchurch mutant).

Figure 41A:
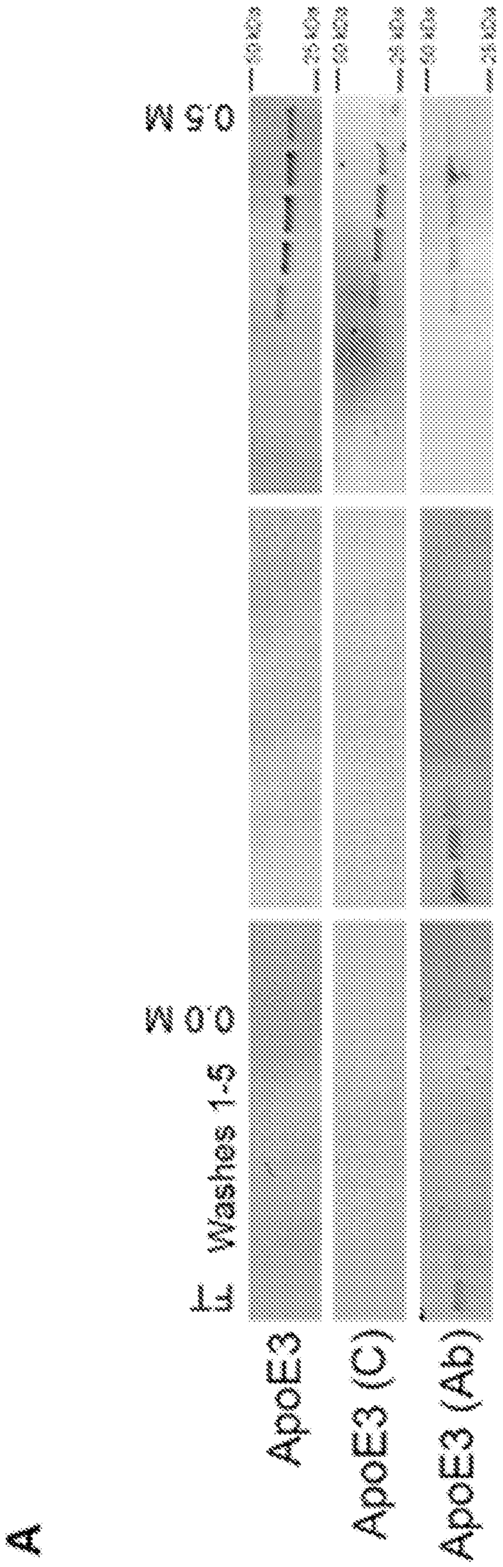
FIG. 41A shows western blot analysis of ApoE in protein fractions eluted from heparin columns in the presence or absence of the 1343 antibody.
Figure 41B:
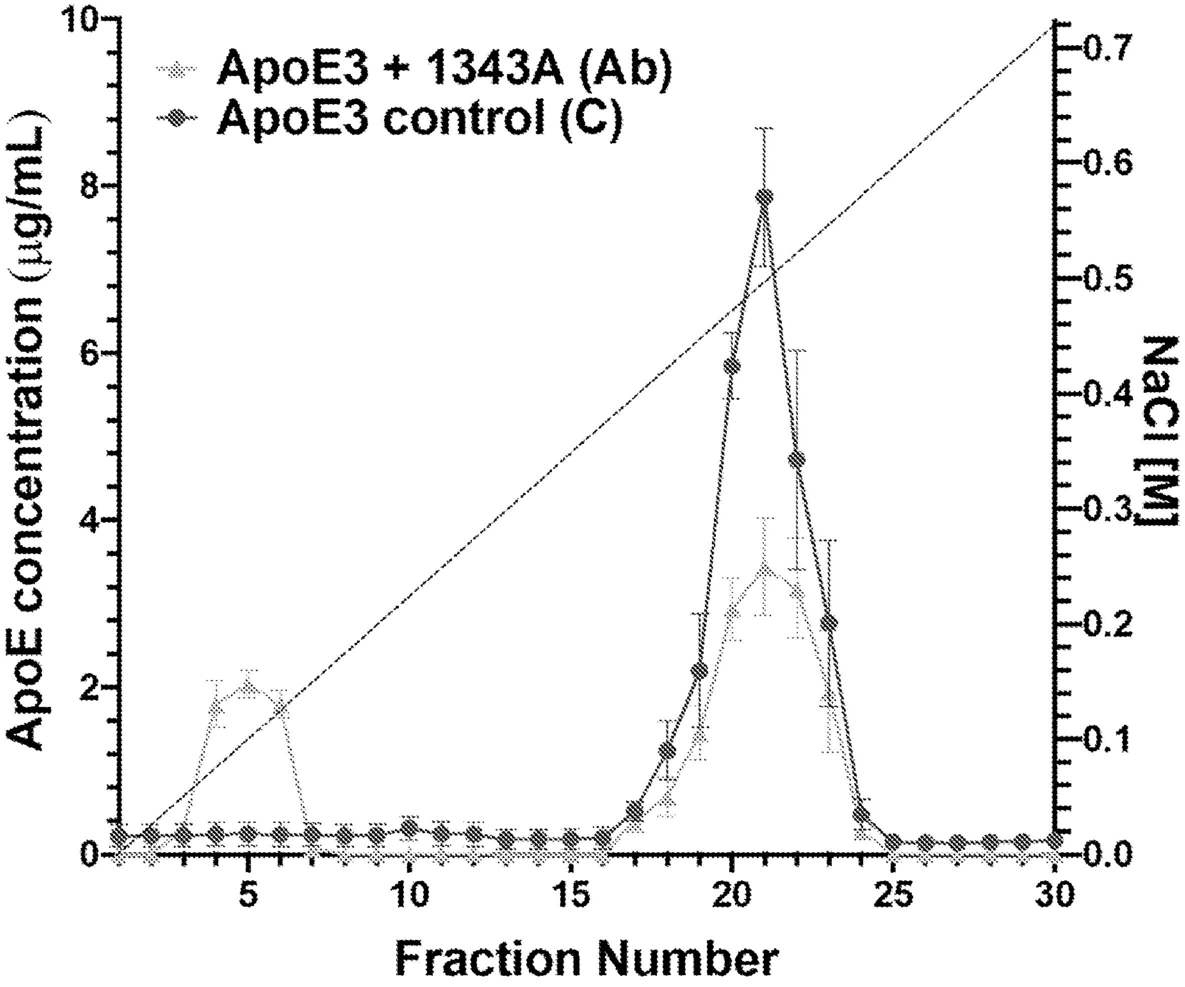
FIG. 41B shows ELISA analysis of the fractions.

ApoE in protein fractions eluted from heparin columns using an increasing NaCl gradient in the presence or absence of the 1343 was subjected to western blotting (FIG. 41A). Individual blots were cropped between 25 to 50 kDa. Blank spaces separate individual blots. FT=flow through. An ELISA was carried out to quantify differences in the NaCl elution patterns of different ApoE in the presence and absence of 1343 (FIG. 41B). N=3 columns per isoform in independent experiments were analyzed side-by-side twice on different days to quantify differences. Error bars depict standard error of mean.

Upon validation, CDR sequences from mouse antibodies 1H4-2, 7C11-1, 19G10-2, 25F1-2, and 1343ab were grafted into human IgG backbones (IgG2 or IgG4) to generate humanized counterparts.

Example 9: In Vivo Validation of ApoE Antibodies

Figure 42A:
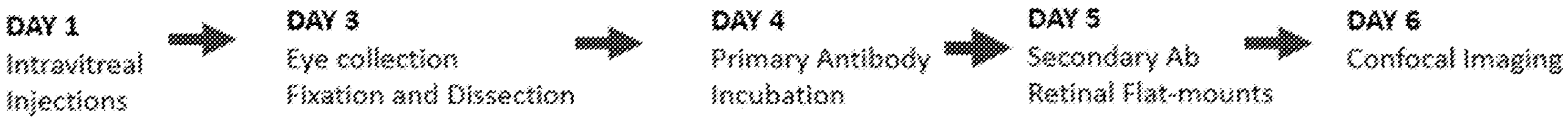
FIG. 42A shows an exemplary experimental outline for an intraocular model of inducible APOE-dependent Tau hyperphosphorylation.

An intraocular model of inducible APOE-dependent Tau hyperphosphorylation (paired helical filament formation) was generated. This model was used to test the ability for the ApoE antibodies to inhibit Tau pathology, which is a marker of neurodegeneration. FIG. 42A shows an exemplary experimental outline.

Briefly, his-tagged recombinant human APOE3 was injected intravitreally into a B6;C3-Tg (Prnp-MAPT*P301S) PS19Vle/J mouse (Jackson lab 008169) (Yoshiyama et al. 53 (3): 337-51, 2007). This mouse model contains a human tau P301S mutation and is a validated animal model for Alzheimer's disease and other tauopathies such as frontotemporal dementia (See e.g. Bugiani et al. 58 (6): 667-77, 1999). Mice injected with PBS were used as control.

Figure 42B:
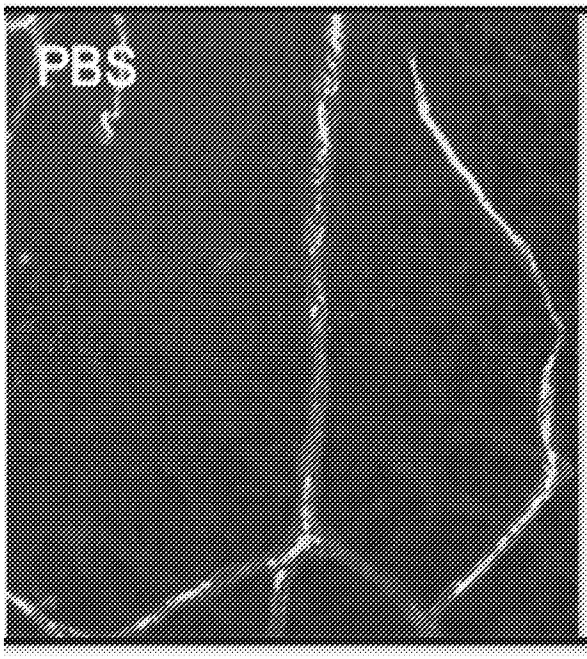
FIG. 42B shows PHF tau in control retina injected with PBS.
Figure 42C:
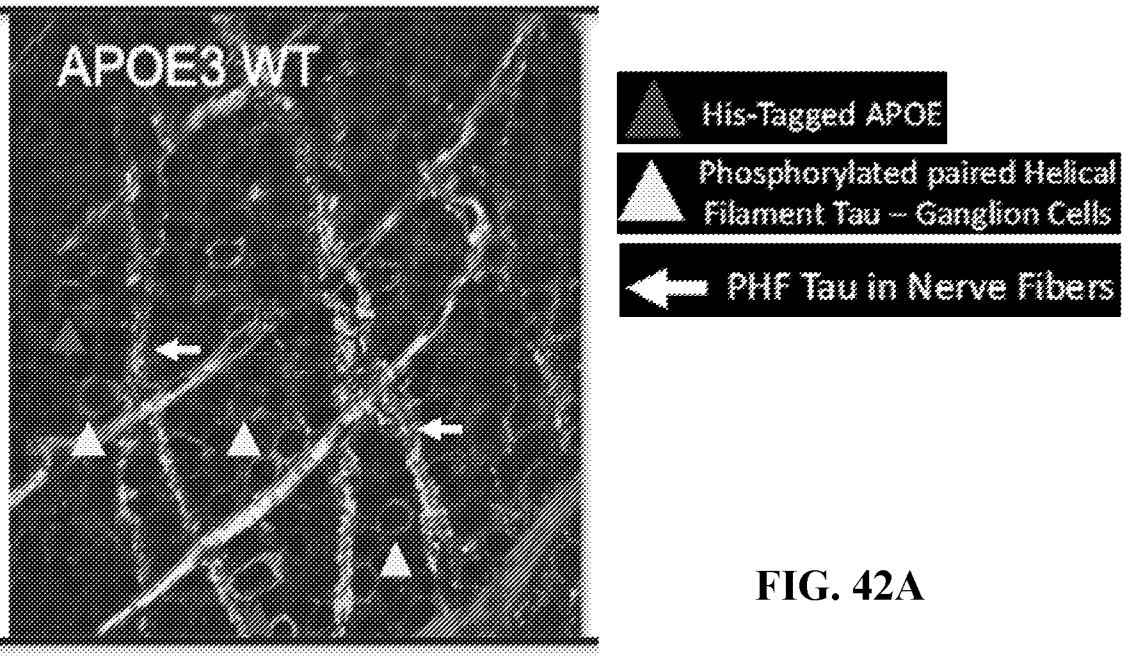
FIG. 42C shows retina injected with recombinant human APOE3.

As shown in FIG. 42B, in the control retina of 6-week old mice, paired helical filaments of phosphorylated tau (PHF) are absent from ganglion cells and their axon fibers (signal inside vessels labeled with isolectin B4 are background signal). In contrast, administration of recombinant human APOE3 (his tagged) triggered robust formation of PHF detected with the AT8 antibody. PHF are robust in ganglion cell axons (arrows) and in the ganglion cell bodies. Human APOE was detected around the ganglion cell bodies using anti-His antibody.

Figure 43A:
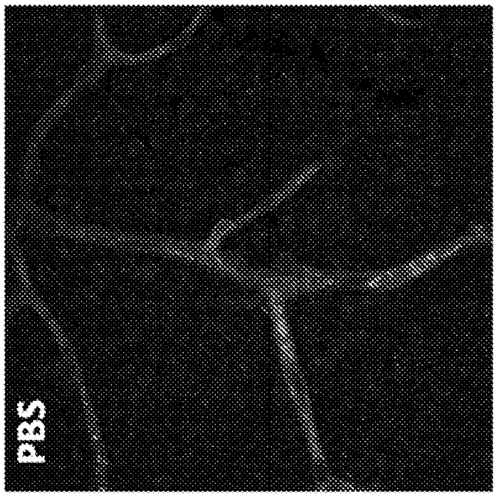
FIGS. 43A-43I show PHF tau in control retina as compared to retina injected with either the mouse 1H4-2 antibody or the humanized 1343Ah antibody.
Figure 43B:
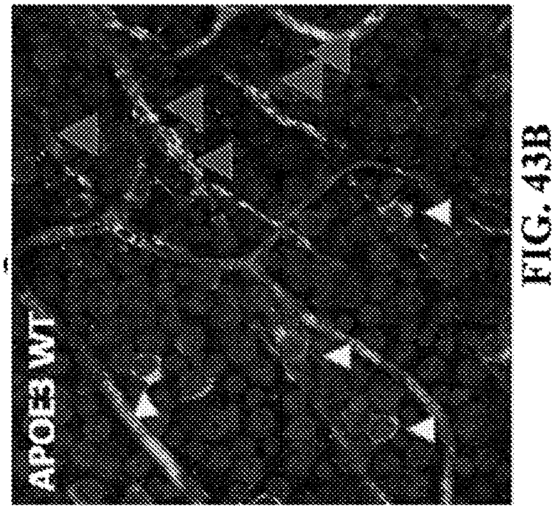
Figure 43C:
Figure 43D:
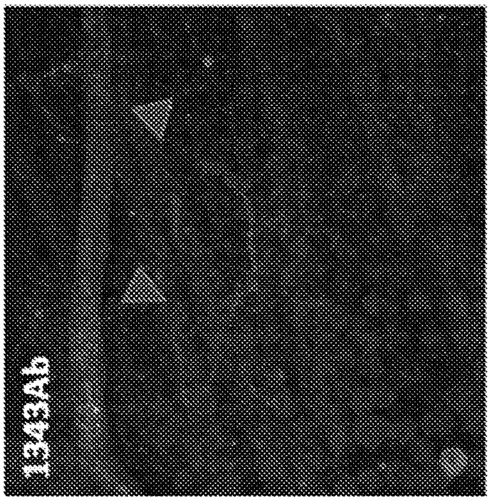
Figure 43E:
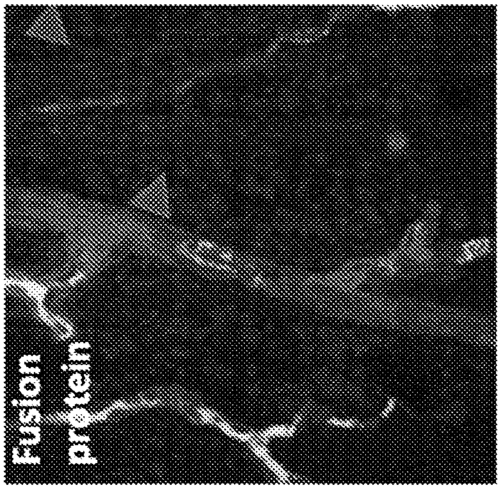
Figure 43F:
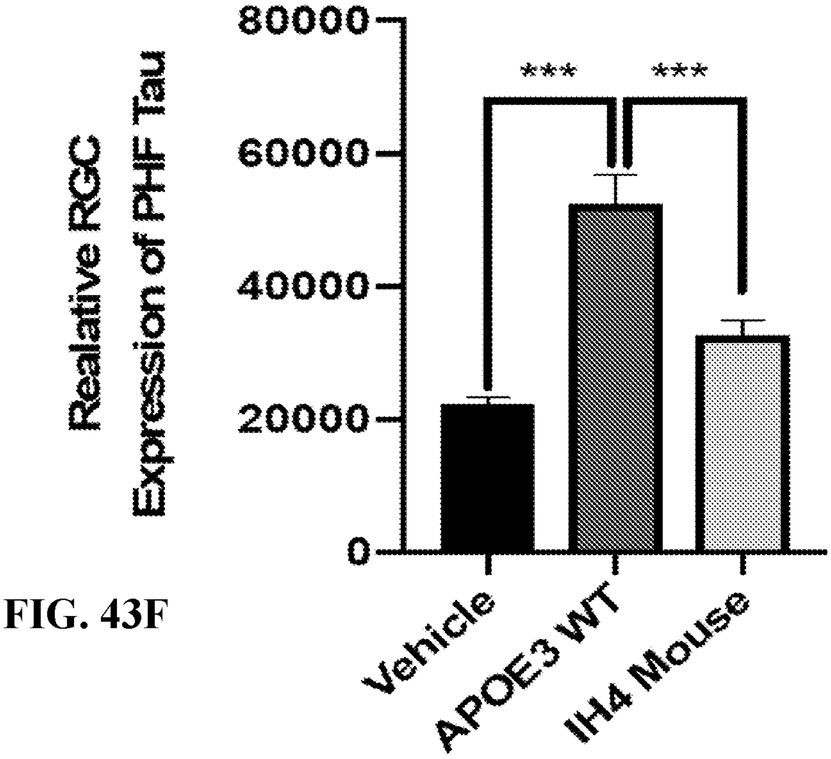
Figure 43G:
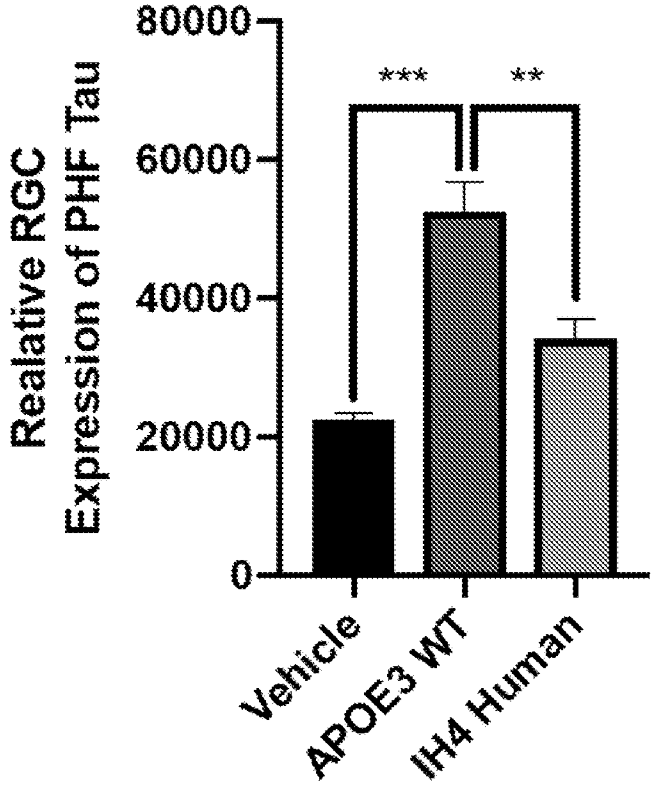
Figure 43I:
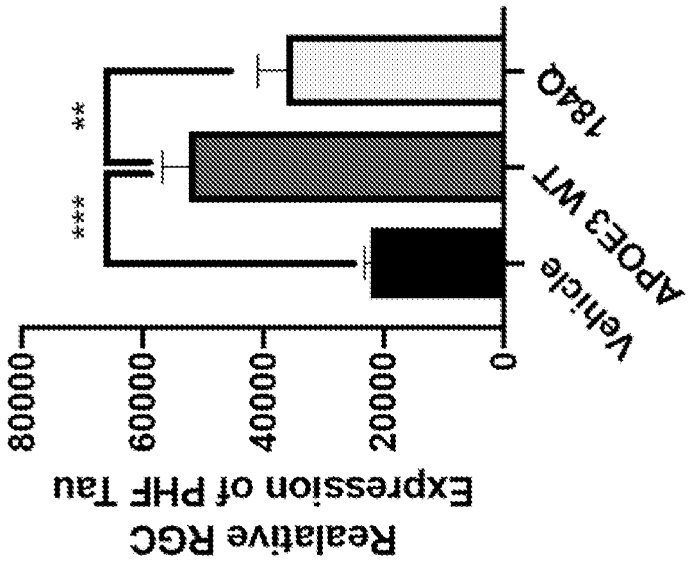
Figure 43H:
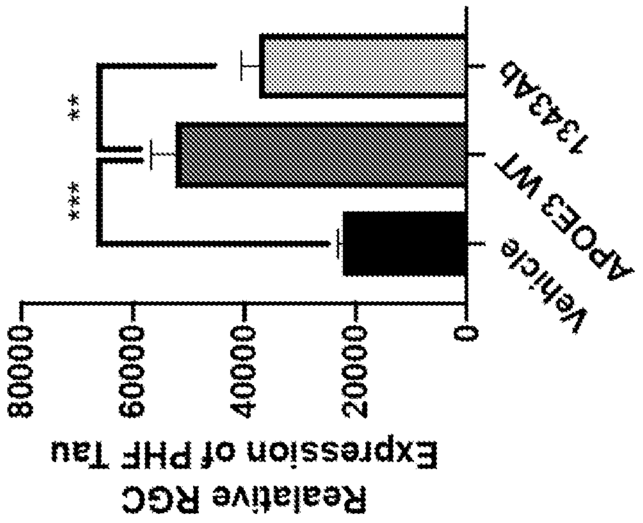

The mouse 1H4-2 antibody and the humanized 1343Ah antibody were injected intravitreally into the eye of mice from the above mouse model (final volume 2 μL). The animals were sacrificed on day 3 post injection and retinas were dissected and immunolabeled. Retinas were stained with DAPI, Isolectin, and AT8 (pTAU), which recognizes phosphorylated paired helical filament tau (PHF tau). Retinas were imaged using the SP8 confocal microscope. As shown in FIGS. 43B, 43C, 43F and 43G, APOE3 WT resulted in a significant increase in PHF Tau, which is significantly reduced by 1H4-2 (*p<0.001). Similarly, administration of the humanized 1H4-2 IgG2/kappa recombinant monoclonal antibody effectively reduced APOE-dependent induction of PHF tau pathology in vivo (FIG. 43H; p<0.01, *p<0.001). As shown in FIGS. 43D and 43H, PHF Tau level was significantly reduced by the humanized 1343Ah (p<0.01, ***p<0.001).

The similarity of the efficacy between the mouse monoclonal antibody and the corresponding humanized antibody confirms the affinity of the binding domain for ApoE or ApoEch, and that the binding property is retained during humanization. This shows the binding properties of the CDRs are transferable from the original mouse IgG1 to other proteins including human IgG2.

Figure 44:
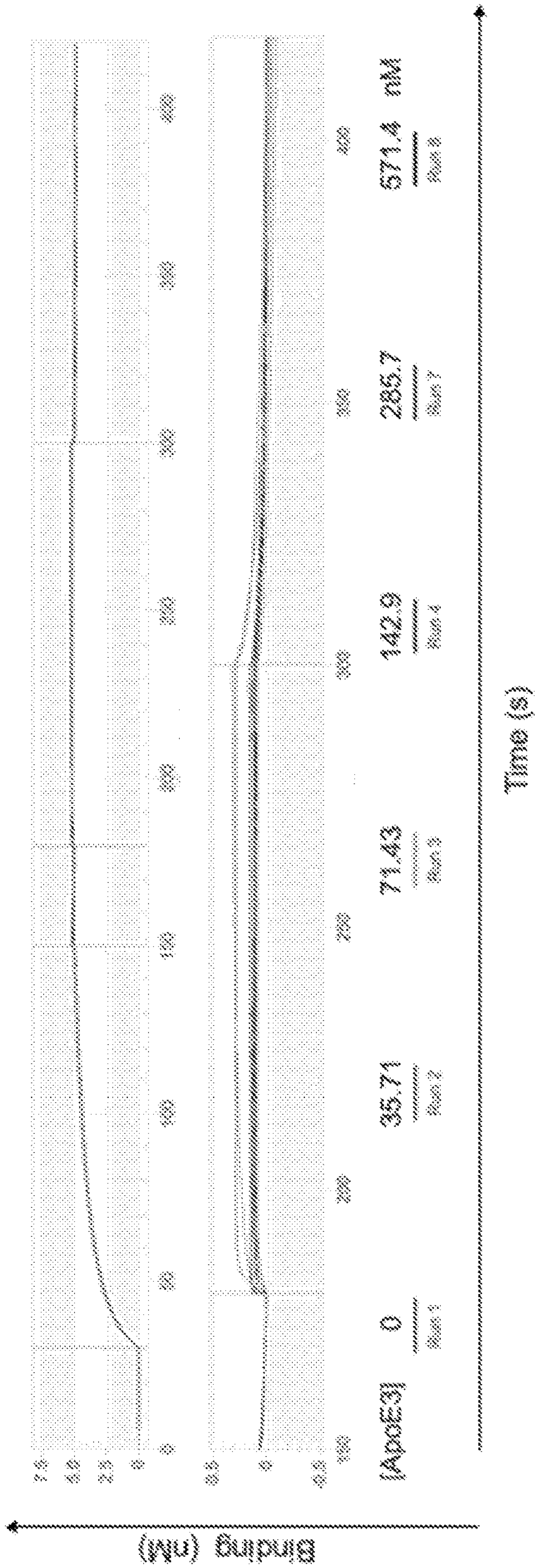
FIG. 44 shows representative binding measurements of increasing concentrations (nM) of ApoE3 protein to 1H4 on the protein A biosensor.

The binding affinity between ApoE3 and the monoclonal antibody 1H4 (mAb 1H4) was determined using the advanced kinetic module of the BLItz system (Blitz Pro, FB-609928, ver. 1.3.1.3). Briefly, a protein A biosensor was loaded with mAb 1H4 and both association and dissociation constants were determined at increasing concentrations of the full length ApoE3 protein (Innovagen) from 0 to 571.4 nM. The following running settings were used: 30 s initial baseline in the experimental media, 120 s loading of the ligand (mAb 1H4) on the biosensors, 30 s new baseline before association (120 s) and dissociation (120 s) steps. A total of 6 runs of 420 s at 2200 rpm and room temperature were conducted to determine the binding parameters of ApoE3. Global fitting and step corrections of the dissociation experiments were performed using the BLItz software (ver. 1.1.0.7). FIG. 44 shows representative binding measurements of increasing concentrations (nM) of ApoE3 protein to 1H4 on protein A biosensor. KD, Ka and Kd were measured (table 10) and calculated using the BLItz system. Top panel is representative of the association steps, the bottom panel is representative of the dissociation steps of the binding kinetic. The X and Y axes depicts time in second and binding in nM, respectively.

| Run Index | Con. ApoE3 (nM) | KD (nM) | ka (1/Ms) | Ka Error | kd (1/s) | kd Error |
|---|---|---|---|---|---|---|
| 1 | 0 | | | | | |
| 2 | 35.71 | 14.28 | 2900000 | 0.04142 | 0.001119 | 0.1543 |
| 3 | 71.43 | 14.28 | 2900000 | 0.04142 | 0.001119 | 0.1425 |
| 4 | 142.9 | 14.28 | 2900000 | 0.04142 | 0.001119 | 0.3063 |
| 7 | 285.7 | 14.28 | 2900000 | 0.04142 | 0.001119 | 0.09633 |
| 8 | 571.4 | 14.28 | 2900000 | 0.04142 | 0.001119 | 0.146 |

| Run Index | Con. ApoE3 (nM) | Rmax | Rmax Error | R Equilibrium |
|---|---|---|---|---|
| 1 | 0 | | | |
| 2 | 35.71 | 0.1543 | 0.005199 | 0.1102 |
| 3 | 71.43 | 0.1425 | 0.003305 | 0.1187 |
| 4 | 142.9 | 0.3063 | 0.003587 | 0.2785 |
| 7 | 285.7 | 0.09633 | 0.001949 | 0.09174 |
| 8 | 571.4 | 0.146 | 0.001883 | 0.1425 |

Example 10: In Vivo Validation of APOE Fragment Fusion Proteins

Next, a fusion protein containing an APOE fragment that includes the HSPG-binding domain, and the Fc region of a human IgG was tested using a similar in vivo model. Briefly, 0.78 μg of recombinant full-length APOE was used to induce tau pathology. 0.14 μg of the fusion protein was injected intravitreally in to the mice. As shown in FIGS. 43E and 43I, the fusion protein diminished APOE-dependent tau pathology in neurons.

Example 11: Sequences of Chimeric Antibodies

The sequences of the chimeric antibodies where CDRs were transferred from mouse to human IgG2 or IgG4 are shown below:

```
Normal font = vector
Italicized = Signal peptide
underlined = VL/VH
double underlined = Constant part (human Kappa/IgG4/IgG2)
Sequences of expression vectors for mAb 1H4 IgG2/kappa:
>p1H4.VL.hk
GTTAGGCGTTTTGCGCTGCTTCGCGATGTACGGGCCAGATATACGCGTTGACATTGATTATT

GACTAGTTATTAATAGTAATCAATTACGGGGTCATTAGTTCATAGCCCATATATGGAGTTCC

GCGTTACATAACTTACGGTAAATGGCCCGCCTGGCTGACCGCCCAACGACCCCCGCCCATTG

ACGTCAATAATGACGTATGTTCCCATAGTAACGCCAATAGGGACTTTCCATTGACGTCAATG

GGTGGAGTATTTACGGTAAACTGCCCACTTGGCAGTACATCAAGTGTATCATATGCCAAGTA

CGCCCCCTATTGACGTCAATGACGGTAAATGGCCCGCCTGGCATTATGCCCAGTACATGACC
```

-continued

TTATGGGACTTTCCTACTTGGCAGTACATCTACGTATTAGTCATCGCTATTACCATGGTGAT

GCGGTTTTGGCAGTACATCAATGGGCGTGGATAGCGGTTTGACTCACGGGGATTTCCAAGTC

TCCACCCCATTGACGTCAATGGGAGTTTGTTTTGGCACCAAAATCAACGGGACTTTCCAAAA

TGTCGTAACAACTCCGCCCCATTGACGCAAATGGGCGGTAGGCGTGTACGGTGGGAGGTCTA

TATAAGCAGAGCTCGTTTAGTGAACCGTCAGATCGCCTGGAGACGCCATCCACGCTGTTTTG

ACCTCCATAGAAGACACCGGGACCGATCCAGCCTCCGGACTCTAGAGGATCGAACCCTTAAG

CTTGCCACCA*TGTACAGGATGCAACTCCTGTCTTGCATTGCACTAAGTCTTGCACTTGTCAC*

*GAATTCA*GACAACGTGCTGACACAGAGCCCTGCCAGCCTGGCTGTTTCTCTGGGACAGAGAG

CCACCATCAGCTGCAAGGCCAGCCAGAGCGTTGACTACGACGGCGACAGCTACATGAACTGG

TATCAGCAGAAGCCCGGCCAGCCACCTAAGGTGTTCATCTACGCCGCCAGCAACCTGGAAAG

CGGCATCCCTGCCAGATTTTCTGGCTCTGGCAGCGGCACCGACTTCACCCTGAATATCCATC

CTGTGGAAGAAGAGGACGCCGCCACCTACTACTGCCAGCAGAGCAATGAGGACCCCTGGACA

TTTGGCGGAGGCACCAAGCTGGAAATCAAGCGTACGGTGGCTGCACCATCTGTCTTCATCTT

CCCGCCATCTGATGAGCAGTTGAAATCTGGAACTGCCTCTGTTGTGTGCCTGCTGAATAACT

TCTATCCCAGAGAGGCCAAAGTACAGTGGAAGGTGGATAACGCCCTCCAATCGGGTAACTCC

CAGGAGAGTGTCACAGAGCAGGACAGCAAGGACAGCACCTACAGCCTCAGCAGCACCCTGAC

GCTGAGCAAAGCAGACTACGAGAAACACAAAGTCTACGCCTGCGAAGTCACCCATCAGGGCC

TGAGCTCGCCCGTCACAAAGAGCTTCAACAGGGGAGAGTGTTAGAGGGAGCTAGCGTGGCAT

CTAGACACTCTCGAGAAGGGTTCGATCCCTACCGGTTAGTAATGAGTTTGATATCTCGACAA

TCAACCTCTGGATTACAAAATTTGTGAAAGATTGACTGGTATTCTTAACTATGTTGCTCCTT

TTACGCTATGTGGATACGCTGCTTTAATGCCTTTGTATCATGCTATTGCTTCCCGTATGGCT

TTCATTTTCTCCTCCTTGTATAAATCCTGGTTGCTGTCTCTTTATGAGGAGTTGTGGCCCGT

TGTCAGGCAACGTGGCGTGGTGTGCACTGTGTTTGCTGACGCAACCCCCACTGGTTGGGGCA

TTGCCACCACCTGTCAGCTCCTTTCCGGGACTTTCGCTTTCCCCCTCCCTATTGCCACGGCG

GAACTCATCGCCGCCTGCCTTGCCCGCTGCTGGACAGGGGCTCGGCTGTTGGGCACTGACAA

TTCCGTGGTGTTGTCGGGGAAGCTGACGTCCTTTCCATGGCTGCTCGCCTGTGTTGCCACCT

GGATTCTGCGCGGGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCGCCCTCAGACGAG

TCGGATCTCCCTTTGGGCCGCCTCCCCGCCTGGAAACGGGGGAGGCTAACTGAAACACGGAA

GGAGACAATACCGGAAGGAACCCGCGCTATGACGGCAATAAAAAGACAGAATAAAACGCACG

GGTGTTGGGTCGTTTGTTCATAAACGCGGGGTTCGGTCCCAGGGCTGGCACTCTGTCGATAC

CCCACCGAGACCCCATTGGGGCCAATACGCCCGCGTTTCTTCCTTTTCCCCACCCCACCCCC

CAAGTTCGGGTGAAGGCCCAGGGCTCGCAGCCAACGTCGGGGCGGCAGGCCCTGCCATAGCA

GATCTGCGCAGCTGGGGCTCTAGGGGGTATCCCCACGCGCCCTGTAGCGGCGCATTAAGCGC

GGCGGGTGTGGTGGTTACGCGCAGCGTGACCGCTACACTTGCCAGCGCCCTAGCGCCCGCTC

CTTTCGCTTTCTTCCCTTCCTTTCTCGCCACGTTCGCCGGCTTTCCCCGTCAAGCTCTAAAT

CGGGGCATCCCTTTAGGGTTCCGATTTAGTGCTTTACGGCACCTCGACCCCAAAAAACTTGA

TTAGGGTGATGGTTCACGTAGTGGGCCATCGCCCTGATAGACGGTTTTTCGCCCTTTGACGT

TGGAGTCCACGTTCTTTAATAGTGGACTCTTGTTCCAAACTGGAACAACACTCAACCCTATC

TCGGTCTATTCTTTTGATTTATAAGGGATTTTGGGGATTTCGGCCTATTGGTTAAAAAATGA

-continued

GCTGATTTAACAAAAATTTAACGCGAATTAATTCTGTGGAATGTGTGTCAGTTAGGGTGTGG

AAAGTCCCCAGGCTCCCCAGCAGGCAGAAGTATGCAAAGCATGCATCTCAATTAGTCAGCAA

CCAGGTGTGGAAAGTCCCCAGGCTCCCCAGCAGGCAGAAGTATGCAAAGCATGCATCTCAAT

TAGTCAGCAACCATAGTCCCGCCCCTAACTCCGCCCATCCCGCCCCTAACTCCGCCCAGTTC

CGCCCATTCTCCGCCCCATGGCTGACTAATTTTTTTTATTTATGCAGAGGCCGAGGCCGCCT

CTGCCTCTGAGCTATTCCAGAAGTAGTGAGGAGGCTTTTTTGGAGGCCTAGGCTTTTGCAAA

AAGCTCCCGGGAGCTTGTATATCCATTTTCGGATCTGATCAAGAGACAGGATGAGGATCGTT

TCGCATGATTGAACAAGATGGATTGCACGCAGGTTCTCCGGCCGCTTGGGTGGAGAGGCTAT

TCGGCTATGACTGGGCACAACAGACAATCGGCTGCTCTGATGCCGCCGTGTTCCGGCTGTCA

GCGCAGGGGCGCCCGGTTCTTTTTGTCAAGACCGACCTGTCCGGTGCCCTGAATGAACTGCA

GGACGAGGCAGCGCGGCTATCGTGGCTGGCCACGACGGGCGTTCCTTGCGCAGCTGTGCTCG

ACGTTGTCACTGAAGCGGGAAGGGACTGGCTGCTATTGGGCGAAGTGCCGGGGCAGGATCTC

CTGTCATCTCACCTTGCTCCTGCCGAGAAAGTATCCATCATGGCTGATGCAATGCGGCGGCT

GCATACGCTTGATCCGGCTACCTGCCCATTCGACCACCAAGCGAAACATCGCATCGAGCGAG

CACGTACTCGGATGGAAGCCGGTCTTGTCGATCAGGATGATCTGGACGAAGAGCATCAGGGG

CTCGCGCCAGCCGAACTGTTCGCCAGGCTCAAGGCGCGCATGCCCGACGGCGAGGATCTCGT

CGTGACCCATGGCGATGCCTGCTTGCCGAATATCATGGTGGAAAATGGCCGCTTTTCTGGAT

TCATCGACTGTGGCCGGCTGGGTGTGGCGGACCGCTATCAGGACATAGCGTTGGCTACCCGT

GATATTGCTGAAGAGCTTGGCGGCGAATGGGCTGACCGCTTCCTCGTGCTTTACGGTATCGC

CGCTCCCGATTCGCAGCGCATCGCCTTCTATCGCCTTCTTGACGAGTTCTTCTGAGCGGGAC

TCTGGGGTTCGCGAAATGACCGACCAAGCGACGCCCAACCTGCCATCACGAGATTTCGATTC

CACCGCCGCCTTCTATGAAAGGTTGGGCTTCGGAATCGTTTTCCGGGACGCCGGCTGGATGA

TCCTCCAGCGCGGGGATCTCATGCTGGAGTTCTTCGCCCACCCCAACTTGTTTATTGCAGCT

TATAATGGTTACAAATAAAGCAATAGCATCACAAATTTCACAAATAAAGCATTTTTTTCACT

GCATTCTAGTTGTGGTTTGTCCAAACTCATCAATGTATCTTATCATGTCTGTATACCGTCGA

CCTCTAGCTAGAGCTTGGCGTAATCATGGTCATAGCTGTTTCCTGTGTGAAATTGTTATCCG

CTCACAATTCCACACAACATACGAGCCGGAAGCATAAAGTGTAAAGCCTGGGGTGCCTAATG

AGTGAGCTAACTCACATTAATTGCGTTGCGCTCACTGCCCGCTTTCCAGTCGGGAAACCTGT

CGTGCCAGCTGCATTAATGAATCGGCCAACGCGCGGGGAGAGGCGGTTTGCGTATTGGGCGC

TCTTCCGCTTCCTCGCTCACTGACTCGCTGCGCTCGGTCGTTCGGCTGCGGCGAGCGGTATC

AGCTCACTCAAAGGCGGTAATACGGTTATCCACAGAATCAGGGGATAACGCAGGAAAGAACA

TGTGAGCAAAAGGCCAGCAAAAGGCCAGGAACCGTAAAAAGGCCGCGTTGCTGGCGTTTTTC

CATAGGCTCCGCCCCCCTGACGAGCATCACAAAAATCGACGCTCAAGTCAGAGGTGGCGAAA

CCCGACAGGACTATAAAGATACCAGGCGTTTCCCCCTGGAAGCTCCCTCGTGCGCTCTCCTG

TTCCGACCCTGCCGCTTACCGGATACCTGTCCGCCTTTCTCCCTTCGGGAAGCGTGGCGCTT

TCTCAATGCTCACGCTGTAGGTATCTCAGTTCGGTGTAGGTCGTTCGCTCCAAGCTGGGCTG

TGTGCACGAACCCCCCGTTCAGCCCGACCGCTGCGCCTTATCCGGTAACTATCGTCTTGAGT

CCAACCCGGTAAGACACGACTTATCGCCACTGGCAGCAGCCACTGGTAACAGGATTAGCAGA

GCGAGGTATGTAGGCGGTGCTACAGAGTTCTTGAAGTGGTGGCCTAACTACGGCTACACTAG

AAGGACAGTATTTGGTATCTGCGCTCTGCTGAAGCCAGTTACCTTCGGAAAAAGAGTTGGTA

GCTCTTGATCCGGCAAACAAACCACCGCTGGTAGCGGTGGTTTTTTTGTTTGCAAGCAGCAG

-continued

ATTACGCGCAGAAAAAAAGGATCTCAAGAAGATCCTTTGATCTTTTCTACGGGGTCTGACGC

TCAGTGGAACGAAAACTCACGTTAAGGGATTTTGGTCATGAGATTATCAAAAAGGATCTTCA

CCTAGATCCTTTTAAATTAAAAATGAAGTTTTAAATCAATCTAAAGTATATATGAGTAAACT

TGGTCTGACAGTTACCAATGCTTAATCAGTGAGGCACCTATCTCAGCGATCTGTCTATTTCG

TTCATCCATAGTTGCCTGACTCCCCGTCGTGTAGATAACTACGATACGGGAGGGCTTACCAT

CTGGCCCCAGTGCTGCAATGATACCGCGAGACCCACGCTCACCGGCTCCAGATTTATCAGCA

ATAAACCAGCCAGCCGGAAGGGCCGAGCGCAGAAGTGGTCCTGCAACTTTATCCGCCTCCAT

CCAGTCTATTAATTGTTGCCGGGAAGCTAGAGTAAGTAGTTCGCCAGTTAATAGTTTGCGCA

ACGTTGTTGCCATTGCTACAGGCATCGTGGTGTCACGCTCGTCGTTTGGTATGGCTTCATTC

AGCTCCGGTTCCCAACGATCAAGGCGAGTTACATGATCCCCCATGTTGTGCAAAAAAGCGGT

TAGCTCCTTCGGTCCTCCGATCGTTGTCAGAAGTAAGTTGGCCGCAGTGTTATCACTCATGG

TTATGGCAGCACTGCATAATTCTCTTACTGTCATGCCATCCGTAAGATGCTTTTCTGTGACT

GGTGAGTACTCAACCAAGTCATTCTGAGAATAGTGTATGCGGCGACCGAGTTGCTCTTGCCC

GGCGTCAATACGGGATAATACCGCGCCACATAGCAGAACTTTAAAAGTGCTCATCATTGGAA

AACGTTCTTCGGGGCGAAAACTCTCAAGGATCTTACCGCTGTTGAGATCCAGTTCGATGTAA

CCCACTCGTGCACCCAACTGATCTTCAGCATCTTTTACTTTCACCAGCGTTTCTGGGTGAGC

AAAAACAGGAAGGCAAAATGCCGCAAAAAAGGGAATAAGGGCGACACGGAAATGTTGAATAC

TCATACTCTTCCTTTTTCAATATTATTGAAGCATTTATCAGGGTTATTGTCTCATGAGCGGA

TACATATTTGAATGTATTTAGAAAAATAAACAAATAGGGGTTCCGCGCACATTTCCCCGAAA

AGTGCCACCTGACGTCGACGGATCGGGAGATCTCCCGATCCCCTATGGTCGACTCTCAGTAC

AATCTGCTCTGATGCCGCATAGTTAAGCCAGTATCTGCTCCCTGCTTGTGTGTTGGAGGTCG

CTGAGTAGTGCGCGAGCAAAATTTAAGCTACAACAAGGCAAGGCTTGACCGACAATTGCATG

AAGAATCTGCTTAGG (SEQ ID NO: 97)

>p1H4.VE.hIgG2
GTTAGGCGTTTTGCGCTGCTTCGCGATGTACGGGCCAGATATACGCGTTGACATTGATTATT

GACTAGTTATTAATAGTAATCAATTACGGGGTCATTAGTTCATAGCCCATATATGGAGTTCC

GCGTTACATAACTTACGGTAAATGGCCCGCCTGGCTGACCGCCCAACGACCCCCGCCCATTG

ACGTCAATAATGACGTATGTTCCCATAGTAACGCCAATAGGGACTTTCCATTGACGTCAATG

GGTGGAGTATTTACGGTAAACTGCCCACTTGGCAGTACATCAAGTGTATCATATGCCAAGTA

CGCCCCCTATTGACGTCAATGACGGTAAATGGCCCGCCTGGCATTATGCCCAGTACATGACC

TTATGGGACTTTCCTACTTGGCAGTACATCTACGTATTAGTCATCGCTATTACCATGGTGAT

GCGGTTTTGGCAGTACATCAATGGGCGTGGATAGCGGTTTGACTCACGGGGATTTCCAAGTC

TCCACCCCATTGACGTCAATGGGAGTTTGTTTTGGCACCAAAATCAACGGGACTTTCCAAAA

TGTCGTAACAACTCCGCCCCATTGACGCAAATGGGCGGTAGGCGTGTACGGTGGGAGGTCTA

TATAAGCAGAGCTCGTTTAGTGAACCGTCAGATCGCCTGGAGACGCCATCCACGCTGTTTTG

ACCTCCATAGAAGACACCGGGACCGATCCAGCCTCCGGACTCTAGAGGATCGAACCCTTAAG

CTTGCCACC*ATGTACAGGATGCAACTCCTGTCTTGCATTGCACTAAGTCTTGCACTTGTCAC*

*GAATTC*GGAAGTGAAGCTGGTGGAAAGCGGCGGAGGTGTTGTTCAGCCTGGCGGATCTCTGA

AGCTGAGCTGTGCCGCCAGCGGCTTCACCTTTAGCAGCTACACAATGAGCTGGGTCCGACAG

ACCCCTGAGAAGAGACTGGAATGGGTCGCCAAGATCCGGAACGGCGGAGGCATCACCTACTA

CCTGGATACCCTGAAGGGCAGATTCACCATCAGCCGGGACAACGCCAAGAACACCCTGTACC

-continued

TGCAGATGAGCAGCCTGAAGTCCGAGGACACCGCCATCTACTTTTGCGCCAGACACTACTAC
GGCAGCGAGGACTACTTCGACTATTGGGGCCAGGGCACCACACTGACCGTTAGCTCTGCTAG
CACCAAGGGCCCATCGGTCTTCCCCCTGGCGCCCTGCTCCAGGAGCACCTCCGAGAGCACAG
CGGCCCTGGGCTGCCTGGTCAAGGACTACTTCCCCGAACCGGTGACGGTGTCGTGGAACTCA
GGCGCTCTGACCAGCGGCGTGCACACCTTCCCAGCTGTCCTACAGTCCTCAGGACTCTACTC
CCTCAGCAGCGTGGTGACCGTGCCCTCCAGCAACTTCGGCACCCAGACCTACACCTGCAACG
TAGATCACAAGCCCAGCAACACCAAGGTGGACAAGACAGTTGAGCGCAAATGTTGTGTCGAG
TGCCCACCGTGCCCAGCACCACCTGTGGCAGGACCGTCAGTCTTCCTCTTCCCCCCAAAACC
CAAGGACACCCTCATGATCTCCCGGACCCCTGAGGTCACGTGCGTGGTGGTGGACGTGAGCC
ACGAAGACCCCGAGGTCCAGTTCAACTGGTACGTGGACGGCGTGGAGGTGCATAATGCCAAG
ACAAAGCCACGGGAGGAGCAGTTCAACAGCACGTTCCGTGTGGTCAGCGTCCTCACCGTTGT
GCACCAGGACTGGCTGAACGGCAAGGAGTACAAGTGCAAGGTCTCCAACAAAGGCCTCCCAG
CCCCCATCGAGAAAACCATCTCCAAAACCAAAGGGCAGCCCCGAGAACCACAGGTGTACACC
CTGCCCCCATCCCGGGAGGAGATGACCAAGAACCAGGTCAGCCTGACCTGCCTGGTCAAAGG
CTTCTACCCCAGCGACATCGCCGTGGAGTGGGAGAGCAATGGGCAGCCGGAGAACAACTACA
AGACCACGCCTCCCATGCTGGACTCCGACGGCTCCTTCTTCCTCTACAGCAAGCTCACCGTG
GACAAGAGCAGGTGGCAGCAGGGGAACGTCTTCTCATGCTCCGTGATGCATGAGGCTCTGCA
CAACCACTACACGCAGAAGAGCCTCTCCCTGTCTCCGGGTAAATGACCTAGCGTGGCATCTA
GACACTCTCGAGAAGGGTTCGATCCCTACCGGTTAGTAATGAGTTTGATATCTCGACAATCA
ACCTCTGGATTACAAAATTTGTGAAAGATTGACTGGTATTCTTAACTATGTTGCTCCTTTTA
CGCTATGTGGATACGCTGCTTTAATGCCTTTGTATCATGCTATTGCTTCCCGTATGGCTTTC
ATTTTCTCCTCCTTGTATAAATCCTGGTTGCTGTCTCTTTATGAGGAGTTGTGGCCCGTTGT
CAGGCAACGTGGCGTGGTGTGCACTGTGTTTGCTGACGCAACCCCCACTGGTTGGGGCATTG
CCACCACCTGTCAGCTCCTTTCCGGGACTTTCGCTTTCCCCCTCCCTATTGCCACGGCGGAA
CTCATCGCCGCCTGCCTTGCCCGCTGCTGGACAGGGGCTCGGCTGTTGGGCACTGACAATTC
CGTGGTGTTGTCGGGGAAGCTGACGTCCTTTCCATGGCTGCTCGCCTGTGTTGCCACCTGGA
TTCTGCGCGGGACGTCCTTCTGCTACGTCCCTTCGGCCCTCAATCCAGCGGACCTTCCTTCC
CGCGGCCTGCTGCCGGCTCTGCGGCCTCTTCCGCGTCTTCGCCTTCGCCCTCAGACGAGTCG
GATCTCCCTTTGGGCCGCCTCCCCGCCTGGAAACGGGGGAGGCTAACTGAAACACGGAAGGA
GACAATACCGGAAGGAACCCGCGCTATGACGGCAATAAAAAGACAGAATAAAACGCACGGGT
GTTGGGTCGTTTGTTCATAAACGCGGGGTTCGGTCCCAGGGCTGGCACTCTGTCGATACCCC
ACCGAGACCCCATTGGGGCCAATACGCCCGCGTTTCTTCCTTTTCCCCACCCCACCCCCCAA
GTTCGGGTGAAGGCCCAGGGCTCGCAGCCAACGTCGGGGCGGCAGGCCCTGCCATAGCAGAT
CTGCGCAGCTGGGGCTCTAGGGGGTATCCCCACGCGCCCTGTAGCGGCGCATTAAGCGCGGC
GGGTGTGGTGGTTACGCGCAGCGTGACCGCTACACTTGCCAGCGCCCTAGCGCCCGCTCCTT
TCGCTTTCTTCCCTTCCTTTCTCGCCACGTTCGCCGGCTTTCCCCGTCAAGCTCTAAATCGG
GGCATCCCTTTAGGGTTCCGATTTAGTGCTTTACGGCACCTCGACCCCAAAAAACTTGATTA
GGGTGATGGTTCACGTAGTGGGCCATCGCCCTGATAGACGGTTTTTCGCCCTTTGACGTTGG
AGTCCACGTTCTTTAATAGTGGACTCTTGTTCCAAACTGGAACAACACTCAACCCTATCTCG
GTCTATTCTTTTGATTTATAAGGGATTTTGGGGATTTCGGCCTATTGGTTAAAAAATGAGCT

-continued

GATTTAACAAAAATTTAACGCGAATTAATTCTGTGGAATGTGTGTCAGTTAGGGTGTGGAAA

GTCCCCAGGCTCCCCAGCAGGCAGAAGTATGCAAAGCATGCATCTCAATTAGTCAGCAACCA

GGTGTGGAAAGTCCCCAGGCTCCCCAGCAGGCAGAAGTATGCAAAGCATGCATCTCAATTAG

TCAGCAACCATAGTCCCGCCCCTAACTCCGCCCATCCCGCCCCTAACTCCGCCCAGTTCCGC

CCATTCTCCGCCCCATGGCTGACTAATTTTTTTTATTTATGCAGAGGCCGAGGCCGCCTCTG

CCTCTGAGCTATTCCAGAAGTAGTGAGGAGGCTTTTTTGGAGGCCTAGGCTTTTGCAAAAAG

CTCCCGGGAGCTTGTATATCCATTTTCGGATCTGATCAAGAGACAGGATGAGGATCGTTTCG

CATGATTGAACAAGATGGATTGCACGCAGGTTCTCCGGCCGCTTGGGTGGAGAGGCTATTCG

GCTATGACTGGGCACAACAGACAATCGGCTGCTCTGATGCCGCCGTGTTCCGGCTGTCAGCG

CAGGGGCGCCCGGTTCTTTTTGTCAAGACCGACCTGTCCGGTGCCCTGAATGAACTGCAGGA

CGAGGCAGCGCGGCTATCGTGGCTGGCCACGACGGGCGTTCCTTGCGCAGCTGTGCTCGACG

TTGTCACTGAAGCGGGAAGGGACTGGCTGCTATTGGGCGAAGTGCCGGGGCAGGATCTCCTG

TCATCTCACCTTGCTCCTGCCGAGAAAGTATCCATCATGGCTGATGCAATGCGGCGGCTGCA

TACGCTTGATCCGGCTACCTGCCCATTCGACCACCAAGCGAAACATCGCATCGAGCGAGCAC

GTACTCGGATGGAAGCCGGTCTTGTCGATCAGGATGATCTGGACGAAGAGCATCAGGGGCTC

GCGCCAGCCGAACTGTTCGCCAGGCTCAAGGCGCGCATGCCCGACGGCGAGGATCTCGTCGT

GACCCATGGCGATGCCTGCTTGCCGAATATCATGGTGGAAAATGGCCGCTTTTCTGGATTCA

TCGACTGTGGCCGGCTGGGTGTGGCGGACCGCTATCAGGACATAGCGTTGGCTACCCGTGAT

ATTGCTGAAGAGCTTGGCGGCGAATGGGCTGACCGCTTCCTCGTGCTTTACGGTATCGCCGC

TCCCGATTCGCAGCGCATCGCCTTCTATCGCCTTCTTGACGAGTTCTTCTGAGCGGGACTCT

GGGGTTCGCGAAATGACCGACCAAGCGACGCCCAACCTGCCATCACGAGATTTCGATTCCAC

CGCCGCCTTCTATGAAAGGTTGGGCTTCGGAATCGTTTTCCGGGACGCCGGCTGGATGATCC

TCCAGCGCGGGGATCTCATGCTGGAGTTCTTCGCCCACCCCAACTTGTTTATTGCAGCTTAT

AATGGTTACAAATAAAGCAATAGCATCACAAATTTCACAAATAAAGCATTTTTTTCACTGCA

TTCTAGTTGTGGTTTGTCCAAACTCATCAATGTATCTTATCATGTCTGTATACCGTCGACCT

CTAGCTAGAGCTTGGCGTAATCATGGTCATAGCTGTTTCCTGTGTGAAATTGTTATCCGCTC

ACAATTCCACACAACATACGAGCCGGAAGCATAAAGTGTAAAGCCTGGGGTGCCTAATGAGT

GAGCTAACTCACATTAATTGCGTTGCGCTCACTGCCCGCTTTCCAGTCGGGAAACCTGTCGT

GCCAGCTGCATTAATGAATCGGCCAACGCGCGGGGAGAGGCGGTTTGCGTATTGGGCGCTCT

TCCGCTTCCTCGCTCACTGACTCGCTGCGCTCGGTCGTTCGGCTGCGGCGAGCGGTATCAGC

TCACTCAAAGGCGGTAATACGGTTATCCACAGAATCAGGGGATAACGCAGGAAAGAACATGT

GAGCAAAAGGCCAGCAAAAGGCCAGGAACCGTAAAAAGGCCGCGTTGCTGGCGTTTTTCCAT

AGGCTCCGCCCCCCTGACGAGCATCACAAAAATCGACGCTCAAGTCAGAGGTGGCGAAACCC

GACAGGACTATAAAGATACCAGGCGTTTCCCCCTGGAAGCTCCCTCGTGCGCTCTCCTGTTC

CGACCCTGCCGCTTACCGGATACCTGTCCGCCTTTCTCCCTTCGGGAAGCGTGGCGCTTTCT

CAATGCTCACGCTGTAGGTATCTCAGTTCGGTGTAGGTCGTTCGCTCCAAGCTGGGCTGTGT

GCACGAACCCCCCGTTCAGCCCGACCGCTGCGCCTTATCCGGTAACTATCGTCTTGAGTCCA

ACCCGGTAAGACACGACTTATCGCCACTGGCAGCAGCCACTGGTAACAGGATTAGCAGAGCG

AGGTATGTAGGCGGTGCTACAGAGTTCTTGAAGTGGTGGCCTAACTACGGCTACACTAGAAG

GACAGTATTTGGTATCTGCGCTCTGCTGAAGCCAGTTACCTTCGGAAAAAGAGTTGGTAGCT

CTTGATCCGGCAAACAAACCACCGCTGGTAGCGGTGGTTTTTTTGTTTGCAAGCAGCAGATT

-continued

ACGCGCAGAAAAAAAGGATCTCAAGAAGATCCTTTGATCTTTTCTACGGGGTCTGACGCTCA

GTGGAACGAAAACTCACGTTAAGGGATTTTGGTCATGAGATTATCAAAAAGGATCTTCACCT

AGATCCTTTTAAATTAAAAATGAAGTTTTAAATCAATCTAAAGTATATATGAGTAAACTTGG

TCTGACAGTTACCAATGCTTAATCAGTGAGGCACCTATCTCAGCGATCTGTCTATTTCGTTC

ATCCATAGTTGCCTGACTCCCCGTCGTGTAGATAACTACGATACGGGAGGGCTTACCATCTG

GCCCCAGTGCTGCAATGATACCGCGAGACCCACGCTCACCGGCTCCAGATTTATCAGCAATA

AACCAGCCAGCCGGAAGGGCCGAGCGCAGAAGTGGTCCTGCAACTTTATCCGCCTCCATCCA

GTCTATTAATTGTTGCCGGGAAGCTAGAGTAAGTAGTTCGCCAGTTAATAGTTTGCGCAACG

TTGTTGCCATTGCTACAGGCATCGTGGTGTCACGCTCGTCGTTTGGTATGGCTTCATTCAGC

TCCGGTTCCCAACGATCAAGGCGAGTTACATGATCCCCCATGTTGTGCAAAAAAGCGGTTAG

CTCCTTCGGTCCTCCGATCGTTGTCAGAAGTAAGTTGGCCGCAGTGTTATCACTCATGGTTA

TGGCAGCACTGCATAATTCTCTTACTGTCATGCCATCCGTAAGATGCTTTTCTGTGACTGGT

GAGTACTCAACCAAGTCATTCTGAGAATAGTGTATGCGGCGACCGAGTTGCTCTTGCCCGGC

GTCAATACGGGATAATACCGCGCCACATAGCAGAACTTTAAAAGTGCTCATCATTGGAAAAC

GTTCTTCGGGGCGAAAACTCTCAAGGATCTTACCGCTGTTGAGATCCAGTTCGATGTAACCC

ACTCGTGCACCCAACTGATCTTCAGCATCTTTTACTTTCACCAGCGTTTCTGGGTGAGCAAA

AACAGGAAGGCAAAATGCCGCAAAAAAGGGAATAAGGGCGACACGGAAATGTTGAATACTCA

TACTCTTCCTTTTTCAATATTATTGAAGCATTTATCAGGGTTATTGTCTCATGAGCGGATAC

ATATTTGAATGTATTTAGAAAAATAAACAAATAGGGGTTCCGCGCACATTTCCCCGAAAAGT

GCCACCTGACGTCGACGGATCGGGAGATCTCCCGATCCCCTATGGTCGACTCTCAGTACAAT

CTGCTCTGATGCCGCATAGTTAAGCCAGTATCTGCTCCCTGCTTGTGTGTTGGAGGTCGCTG

AGTAGTGCGCGAGCAAAATTTAAGCTACAACAAGGCAAGGCTTGACCGACAATTGCATGAAG

AATCTGCTTAGG (SEQ ID NO: 98)

Sequences of expression vectors for mAb 1343Ah IgG2/kappa:
>p1343Ah.VL.hk
GTTAGGCGTTTTGCGCTGCTTCGCGATGTACGGGCCAGATATACGCGTTGACATTGATTATT

GACTAGTTATTAATAGTAATCAATTACGGGGTCATTAGTTCATAGCCCATATATGGAGTTCC

GCGTTACATAACTTACGGTAAATGGCCCGCCTGGCTGACCGCCCAACGACCCCCGCCCATTG

ACGTCAATAATGACGTATGTTCCCATAGTAACGCCAATAGGGACTTTCCATTGACGTCAATG

GGTGGAGTATTTACGGTAAACTGCCCACTTGGCAGTACATCAAGTGTATCATATGCCAAGTA

CGCCCCCTATTGACGTCAATGACGGTAAATGGCCCGCCTGGCATTATGCCCAGTACATGACC

TTATGGGACTTTCCTACTTGGCAGTACATCTACGTATTAGTCATCGCTATTACCATGGTGAT

GCGGTTTTGGCAGTACATCAATGGGCGTGGATAGCGGTTTGACTCACGGGGATTTCCAAGTC

TCCACCCCATTGACGTCAATGGGAGTTTGTTTTGGCACCAAAATCAACGGGACTTTCCAAAA

TGTCGTAACAACTCCGCCCCATTGACGCAAATGGGCGGTAGGCGTGTACGGTGGGAGGTCTA

TATAAGCAGAGCTCGTTTAGTGAACCGTCAGATCGCCTGGAGACGCCATCCACGCTGTTTTG

ACCTCCATAGAAGACACCGGGACCGATCCAGCCTCCGGACTCTAGAGGATCGAACCCTTAAG

CTTGCCACC*ATGTACAGGATGCAACTCCTGTCTTGCATTGCACTAAGTCTTGCACTTGTCAC*

*GAATTCA*GACATCGTGCTGACACAGAGCCCTGCCAGCCTGGCTGTTTCTCTGGGACAGAGAG

CCACCATCAGCTGCAAGGCCAGCCAGAGCGTTGACTACGACGGCGAGAACTACATGAACTGG

TATCAGCAGAAGCCCGGACAGAGCCCCAAGCTGCTGATCTACGTGGCCAGCAATCTGGAAAG

-continued

CGGCATCCCCGCCAGATTTTCTGGCAGCGGAAGCGGCACCGACTTCACCCTGAATATCCATC
CTGTGGAAGAAGAGGACGCCGCCACCTACTACTGCCAGCAGTCCAATCTGGACCCCTGGACA
TTTGGCGGAGGCACCAAGCTGGAAATCAAGCGTACGGTGGCTGCACCATCTGTCTTCATCTT
CCCGCCATCTGATGAGCAGTTGAAATCTGGAACTGCCTCTGTTGTGTGCCTGCTGAATAACT
TCTATCCCAGAGAGGCCAAAGTACAGTGGAAGGTGGATAACGCCCTCCAATCGGGTAACTCC
CAGGAGAGTGTCACAGAGCAGGACAGCAAGGACAGCACCTACAGCCTCAGCAGCACCCTGAC
GCTGAGCAAAGCAGACTACGAGAAACACAAAGTCTACGCCTGCGAAGTCACCCATCAGGGCC
TGAGCTCGCCCGTCACAAAGAGCTTCAACAGGGGAGAGTGTTAGAGGGAGCTAGCGTGGCAT
CTAGACACTCTCGAGAAGGGTTCGATCCCTACCGGTTAGTAATGAGTTTGATATCTCGACAA
TCAACCTCTGGATTACAAAATTTGTGAAAGATTGACTGGTATTCTTAACTATGTTGCTCCTT
TTACGCTATGTGGATACGCTGCTTTAATGCCTTTGTATCATGCTATTGCTTCCCGTATGGCT
TTCATTTTCTCCTCCTTGTATAAATCCTGGTTGCTGTCTCTTTATGAGGAGTTGTGGCCCGT
TGTCAGGCAACGTGGCGTGGTGTGCACTGTGTTTGCTGACGCAACCCCCACTGGTTGGGGCA
TTGCCACCACCTGTCAGCTCCTTTCCGGGACTTTCGCTTTCCCCCTCCCTATTGCCACGGCG
GAACTCATCGCCGCCTGCCTTGCCCGCTGCTGGACAGGGGCTCGGCTGTTGGGCACTGACAA
TTCCGTGGTGTTGTCGGGGAAGCTGACGTCCTTTCCATGGCTGCTCGCCTGTGTTGCCACCT
GGATTCTGCGCGGGACGTCCTTCTGCTACGTCCCTTCGGCCCTCAATCCAGCGGACCTTCCT
TCCCGCGGCCTGCTGCCGGCTCTGCGGCCTCTTCCGCGTCTTCGCCTTCGCCCTCAGACGAG
TCGGATCTCCCTTTGGGCCGCCTCCCCGCCTGGAAACGGGGGAGGCTAACTGAAACACGGAA
GGAGACAATACCGGAAGGAACCCGCGCTATGACGGCAATAAAAAGACAGAATAAAACGCACG
GGTGTTGGGTCGTTTGTTCATAAACGCGGGGTTCGGTCCCAGGGCTGGCACTCTGTCGATAC
CCCACCGAGACCCCATTGGGGCCAATACGCCCGCGTTTCTTCCTTTTCCCCACCCCACCCCC
CAAGTTCGGGTGAAGGCCCAGGGCTCGCAGCCAACGTCGGGGCGGCAGGCCCTGCCATAGCA
GATCTGCGCAGCTGGGGCTCTAGGGGGTATCCCCACGCGCCCTGTAGCGGCGCATTAAGCGC
GGCGGGTGTGGTGGTTACGCGCAGCGTGACCGCTACACTTGCCAGCGCCCTAGCGCCCGCTC
CTTTCGCTTTCTTCCCTTCCTTTCTCGCCACGTTCGCCGGCTTTCCCCGTCAAGCTCTAAAT
CGGGGCATCCCTTTAGGGTTCCGATTTAGTGCTTTACGGCACCTCGACCCCAAAAAACTTGA
TTAGGGTGATGGTTCACGTAGTGGGCCATCGCCCTGATAGACGGTTTTTCGCCCTTTGACGT
TGGAGTCCACGTTCTTTAATAGTGGACTCTTGTTCCAAACTGGAACAACACTCAACCCTATC
TCGGTCTATTCTTTTGATTTATAAGGGATTTTGGGGATTTCGGCCTATTGGTTAAAAAATGA
GCTGATTTAACAAAAATTTAACGCGAATTAATTCTGTGGAATGTGTGTCAGTTAGGGTGTGG
AAAGTCCCCAGGCTCCCCAGCAGGCAGAAGTATGCAAAGCATGCATCTCAATTAGTCAGCAA
CCAGGTGTGGAAAGTCCCCAGGCTCCCCAGCAGGCAGAAGTATGCAAAGCATGCATCTCAAT
TAGTCAGCAACCATAGTCCCGCCCCTAACTCCGCCCATCCCGCCCCTAACTCCGCCCAGTTC
CGCCCATTCTCCGCCCCATGGCTGACTAATTTTTTTTATTTATGCAGAGGCCGAGGCCGCCT
CTGCCTCTGAGCTATTCCAGAAGTAGTGAGGAGGCTTTTTTGGAGGCCTAGGCTTTTGCAAA
AAGCTCCCGGGAGCTTGTATATCCATTTTCGGATCTGATCAAGAGACAGGATGAGGATCGTT
TCGCATGATTGAACAAGATGGATTGCACGCAGGTTCTCCGGCCGCTTGGGTGGAGAGGCTAT
TCGGCTATGACTGGGCACAACAGACAATCGGCTGCTCTGATGCCGCCGTGTTCCGGCTGTCA
GCGCAGGGGCGCCCGGTTCTTTTTGTCAAGACCGACCTGTCCGGTGCCCTGAATGAACTGCA
GGACGAGGCAGCGCGGCTATCGTGGCTGGCCACGACGGGCGTTCCTTGCGCAGCTGTGCTCG

-continued

ACGTTGTCACTGAAGCGGGAAGGGACTGGCTGCTATTGGGCGAAGTGCCGGGGCAGGATCTC

CTGTCATCTCACCTTGCTCCTGCCGAGAAAGTATCCATCATGGCTGATGCAATGCGGCGGCT

GCATACGCTTGATCCGGCTACCTGCCCATTCGACCACCAAGCGAAACATCGCATCGAGCGAG

CACGTACTCGGATGGAAGCCGGTCTTGTCGATCAGGATGATCTGGACGAAGAGCATCAGGGG

CTCGCGCCAGCCGAACTGTTCGCCAGGCTCAAGGCGCGCATGCCCGACGGCGAGGATCTCGT

CGTGACCCATGGCGATGCCTGCTTGCCGAATATCATGGTGGAAAATGGCCGCTTTTCTGGAT

TCATCGACTGTGGCCGGCTGGGTGTGGCGGACCGCTATCAGGACATAGCGTTGGCTACCCGT

GATATTGCTGAAGAGCTTGGCGGCGAATGGGCTGACCGCTTCCTCGTGCTTTACGGTATCGC

CGCTCCCGATTCGCAGCGCATCGCCTTCTATCGCCTTCTTGACGAGTTCTTCTGAGCGGGAC

TCTGGGGTTCGCGAAATGACCGACCAAGCGACGCCCAACCTGCCATCACGAGATTTCGATTC

CACCGCCGCCTTCTATGAAAGGTTGGGCTTCGGAATCGTTTTCCGGGACGCCGGCTGGATGA

TCCTCCAGCGCGGGGATCTCATGCTGGAGTTCTTCGCCCACCCCAACTTGTTTATTGCAGCT

TATAATGGTTACAAATAAAGCAATAGCATCACAAATTTCACAAATAAAGCATTTTTTTCACT

GCATTCTAGTTGTGGTTTGTCCAAACTCATCAATGTATCTTATCATGTCTGTATACCGTCGA

CCTCTAGCTAGAGCTTGGCGTAATCATGGTCATAGCTGTTTCCTGTGTGAAATTGTTATCCG

CTCACAATTCCACACAACATACGAGCCGGAAGCATAAAGTGTAAAGCCTGGGGTGCCTAATG

AGTGAGCTAACTCACATTAATTGCGTTGCGCTCACTGCCCGCTTTCCAGTCGGGAAACCTGT

CGTGCCAGCTGCATTAATGAATCGGCCAACGCGCGGGGAGAGGCGGTTTGCGTATTGGGCGC

TCTTCCGCTTCCTCGCTCACTGACTCGCTGCGCTCGGTCGTTCGGCTGCGGCGAGCGGTATC

AGCTCACTCAAAGGCGGTAATACGGTTATCCACAGAATCAGGGGATAACGCAGGAAAGAACA

TGTGAGCAAAAGGCCAGCAAAAGGCCAGGAACCGTAAAAAGGCCGCGTTGCTGGCGTTTTTC

CATAGGCTCCGCCCCCCTGACGAGCATCACAAAAATCGACGCTCAAGTCAGAGGTGGCGAAA

CCCGACAGGACTATAAAGATACCAGGCGTTTCCCCCTGGAAGCTCCCTCGTGCGCTCTCCTG

TTCCGACCCTGCCGCTTACCGGATACCTGTCCGCCTTTCTCCCTTCGGGAAGCGTGGCGCTT

TCTCAATGCTCACGCTGTAGGTATCTCAGTTCGGTGTAGGTCGTTCGCTCCAAGCTGGGCTG

TGTGCACGAACCCCCCGTTCAGCCCGACCGCTGCGCCTTATCCGGTAACTATCGTCTTGAGT

CCAACCCGGTAAGACACGACTTATCGCCACTGGCAGCAGCCACTGGTAACAGGATTAGCAGA

GCGAGGTATGTAGGCGGTGCTACAGAGTTCTTGAAGTGGTGGCCTAACTACGGCTACACTAG

AAGGACAGTATTTGGTATCTGCGCTCTGCTGAAGCCAGTTACCTTCGGAAAAAGAGTTGGTA

GCTCTTGATCCGGCAAACAAACCACCGCTGGTAGCGGTGGTTTTTTTGTTTGCAAGCAGCAG

ATTACGCGCAGAAAAAAAGGATCTCAAGAAGATCCTTTGATCTTTTCTACGGGGTCTGACGC

TCAGTGGAACGAAAACTCACGTTAAGGGATTTTGGTCATGAGATTATCAAAAAGGATCTTCA

CCTAGATCCTTTTAAATTAAAAATGAAGTTTTAAATCAATCTAAAGTATATATGAGTAAACT

TGGTCTGACAGTTACCAATGCTTAATCAGTGAGGCACCTATCTCAGCGATCTGTCTATTTCG

TTCATCCATAGTTGCCTGACTCCCCGTCGTGTAGATAACTACGATACGGGAGGGCTTACCAT

CTGGCCCCAGTGCTGCAATGATACCGCGAGACCCACGCTCACCGGCTCCAGATTTATCAGCA

ATAAACCAGCCAGCCGGAAGGGCCGAGCGCAGAAGTGGTCCTGCAACTTTATCCGCCTCCAT

CCAGTCTATTAATTGTTGCCGGGAAGCTAGAGTAAGTAGTTCGCCAGTTAATAGTTTGCGCA

ACGTTGTTGCCATTGCTACAGGCATCGTGGTGTCACGCTCGTCGTTTGGTATGGCTTCATTC

AGCTCCGGTTCCCAACGATCAAGGCGAGTTACATGATCCCCCATGTTGTGCAAAAAAGCGGT

-continued

TAGCTCCTTCGGTCCTCCGATCGTTGTCAGAAGTAAGTTGGCCGCAGTGTTATCACTCATGG

TTATGGCAGCACTGCATAATTCTCTTACTGTCATGCCATCCGTAAGATGCTTTTCTGTGACT

GGTGAGTACTCAACCAAGTCATTCTGAGAATAGTGTATGCGGCGACCGAGTTGCTCTTGCCC

GGCGTCAATACGGGATAATACCGCGCCACATAGCAGAACTTTAAAAGTGCTCATCATTGGAA

AACGTTCTTCGGGGCGAAAACTCTCAAGGATCTTACCGCTGTTGAGATCCAGTTCGATGTAA

CCCACTCGTGCACCCAACTGATCTTCAGCATCTTTTACTTTCACCAGCGTTTCTGGGTGAGC

AAAAACAGGAAGGCAAAATGCCGCAAAAAAGGGAATAAGGGCGACACGGAAATGTTGAATAC

TCATACTCTTCCTTTTTCAATATTATTGAAGCATTTATCAGGGTTATTGTCTCATGAGCGGA

TACATATTTGAATGTATTTAGAAAAATAAACAAATAGGGGTTCCGCGCACATTTCCCCGAAA

AGTGCCACCTGACGTCGACGGATCGGGAGATCTCCCGATCCCCTATGGTCGACTCTCAGTAC

AATCTGCTCTGATGCCGCATAGTTAAGCCAGTATCTGCTCCCTGCTTGTGTGTTGGAGGTCG

CTGAGTAGTGCGCGAGCAAAATTTAAGCTACAACAAGGCAAGGCTTGACCGACAATTGCATG

AAGAATCTGCTTAGG (SEQ ID NO: 99)

>p1343Ah.VH.hIgG2
GTTAGGCGTTTTGCGCTGCTTCGCGATGTACGGGCCAGATATACGCGTTGACATTGATTATT

GACTAGTTATTAATAGTAATCAATTACGGGGTCATTAGTTCATAGCCCATATATGGAGTTCC

GCGTTACATAACTTACGGTAAATGGCCCGCCTGGCTGACCGCCCAACGACCCCCGCCCATTG

ACGTCAATAATGACGTATGTTCCCATAGTAACGCCAATAGGGACTTTCCATTGACGTCAATG

GGTGGAGTATTTACGGTAAACTGCCCACTTGGCAGTACATCAAGTGTATCATATGCCAAGTA

CGCCCCCTATTGACGTCAATGACGGTAAATGGCCCGCCTGGCATTATGCCCAGTACATGACC

TTATGGGACTTTCCTACTTGGCAGTACATCTACGTATTAGTCATCGCTATTACCATGGTGAT

GCGGTTTTGGCAGTACATCAATGGGCGTGGATAGCGGTTTGACTCACGGGGATTTCCAAGTC

TCCACCCCATTGACGTCAATGGGAGTTTGTTTTGGCACCAAAATCAACGGGACTTTCCAAAA

TGTCGTAACAACTCCGCCCCATTGACGCAAATGGGCGGTAGGCGTGTACGGTGGGAGGTCTA

TATAAGCAGAGCTCGTTTAGTGAACCGTCAGATCGCCTGGAGACGCCATCCACGCTGTTTTG

ACCTCCATAGAAGACACCGGGACCGATCCAGCCTCCGGACTCTAGAGGATCGAACCCTTAAG

CTTGCCACC*ATGTACAGGATGCAACTCCTGTCTTGCATTGCACTAAGTCTTGCACTTGTCAC*

*GAATTC*GGAGGTCCAGCTGCAGCAGTCTGGCGCCGAACTTGTTAGACCTGGCGCTCTGGTCA

AGCTGAGCTGTAAAGCCAGCGGCTTCAACATCAAGGACTACCATCTGCACTGGGTCAAGCAG

AGGCCTGAGCAGGGACTCGAGTGGATCGGCTGGATCGACCCCGAGAACGGCAACGTGATCTA

CGACCCCAAGTTCCAGGGCAAAGCCACCATGACCGTGGTCACCAGCAGCAACACAGCCTACC

TGCAGCTGAGAAGCCTGACCAGCGAAGATACCGCCGTGTACTTCTGCACCAGAGGCACAGCC

AGAGCCAGCTTCGATTATTGGGGCCAGGGCACCAGCCTGACCGTTTCTTCTGCTAGCACCAA

GGGCCCATCGGTCTTCCCCCTGGCGCCCTGCTCCAGGAGCACCTCCGAGAGCACAGCGGCCC

TGGGCTGCCTGGTCAAGGACTACTTCCCCGAACCGGTGACGGTGTCGTGGAACTCAGGCGCT

CTGACCAGCGGCGTGCACACCTTCCCAGCTGTCCTACAGTCCTCAGGACTCTACTCCCTCAG

CAGCGTGGTGACCGTGCCCTCCAGCAACTTCGGCACCCAGACCTACACCTGCAACGTAGATC

ACAAGCCCAGCAACACCAAGGTGGACAAGACAGTTGAGCGCAAATGTTGTGTCGAGTGCCCA

CCGTGCCCAGCACCACCTGTGGCAGGACCGTCAGTCTTCCTCTTCCCCCCAAAACCCAAGGA

CACCCTCATGATCTCCCGGACCCCTGAGGTCACGTGCGTGGTGGTGGACGTGAGCCACGAAG

ACCCCGAGGTCCAGTTCAACTGGTACGTGGACGGCGTGGAGGTGCATAATGCCAAGACAAAG

-continued

CCACGGGAGGAGCAGTTCAACAGCACGTTCCGTGTGGTCAGCGTCCTCACCGTTGTGCACCA
GGACTGGCTGAACGGCAAGGAGTACAAGTGCAAGGTCTCCAACAAAGGCCTCCCAGCCCCCA
TCGAGAAAACCATCTCCAAAACCAAAGGGCAGCCCCGAGAACCACAGGTGTACACCCTGCCC
CCATCCCGGGAGGAGATGACCAAGAACCAGGTCAGCCTGACCTGCCTGGTCAAAGGCTTCTA
CCCCAGCGACATCGCCGTGGAGTGGGAGAGCAATGGGCAGCCGGAGAACAACTACAAGACCA
CGCCTCCCATGCTGGACTCCGACGGCTCCTTCTTCCTCTACAGCAAGCTCACCGTGGACAAG
AGCAGGTGGCAGCAGGGGAACGTCTTCTCATGCTCCGTGATGCATGAGGCTCTGCACAACCA
CTACACGCAGAAGAGCCTCTCCCTGTCTCCGGGTAAATGACCTAGCGTGGCATCTAGACACT
CTCGAGAAGGGTTCGATCCCTACCGGTTAGTAATGAGTTTGATATCTCGACAATCAACCTCT
GGATTACAAAATTTGTGAAAGATTGACTGGTATTCTTAACTATGTTGCTCCTTTTACGCTAT
GTGGATACGCTGCTTTAATGCCTTTGTATCATGCTATTGCTTCCCGTATGGCTTTCATTTTC
TCCTCCTTGTATAAATCCTGGTTGCTGTCTCTTTATGAGGAGTTGTGGCCCGTTGTCAGGCA
ACGTGGCGTGGTGTGCACTGTGTTTGCTGACGCAACCCCCACTGGTTGGGGCATTGCCACCA
CCTGTCAGCTCCTTTCCGGGACTTTCGCTTTCCCCCTCCCTATTGCCACGGCGGAACTCATC
GCCGCCTGCCTTGCCCGCTGCTGGACAGGGGCTCGGCTGTTGGGCACTGACAATTCCGTGGT
GTTGTCGGGGAAGCTGACGTCCTTTCCATGGCTGCTCGCCTGTGTTGCCACCTGGATTCTGC
GCGGGACGTCCTTCTGCTACGTCCCTTCGGCCCTCAATCCAGCGGACCTTCCTTCCCGCGGC
CTGCTGCCGGCTCTGCGGCCTCTTCCGCGTCTTCGCCTTCGCCCTCAGACGAGTCGGATCTC
CCTTTGGGCCGCCTCCCCGCCTGGAAACGGGGGAGGCTAACTGAAACACGGAAGGAGACAAT
ACCGGAAGGAACCCGCGCTATGACGGCAATAAAAAGACAGAATAAAACGCACGGGTGTTGGG
TCGTTTGTTCATAAACGCGGGGTTCGGTCCCAGGGCTGGCACTCTGTCGATACCCCACCGAG
ACCCCATTGGGGCCAATACGCCCGCGTTTCTTCCTTTTCCCCACCCCACCCCCCAAGTTCGG
GTGAAGGCCCAGGGCTCGCAGCCAACGTCGGGGCGGCAGGCCCTGCCATAGCAGATCTGCGC
AGCTGGGGCTCTAGGGGGTATCCCCACGCGCCCTGTAGCGGCGCATTAAGCGCGGCGGGTGT
GGTGGTTACGCGCAGCGTGACCGCTACACTTGCCAGCGCCCTAGCGCCCGCTCCTTTCGCTT
TCTTCCCTTCCTTTCTCGCCACGTTCGCCGGCTTTCCCCGTCAAGCTCTAAATCGGGGCATC
CCTTTAGGGTTCCGATTTAGTGCTTTACGGCACCTCGACCCCAAAAAACTTGATTAGGGTGA
TGGTTCACGTAGTGGGCCATCGCCCTGATAGACGGTTTTTCGCCCTTTGACGTTGGAGTCCA
CGTTCTTTAATAGTGGACTCTTGTTCCAAACTGGAACAACACTCAACCCTATCTCGGTCTAT
TCTTTTGATTTATAAGGGATTTTGGGGATTTCGGCCTATTGGTTAAAAAATGAGCTGATTTA
ACAAAAATTTAACGCGAATTAATTCTGTGGAATGTGTGTCAGTTAGGGTGTGGAAAGTCCCC
AGGCTCCCCAGCAGGCAGAAGTATGCAAAGCATGCATCTCAATTAGTCAGCAACCAGGTGTG
GAAAGTCCCCAGGCTCCCCAGCAGGCAGAAGTATGCAAAGCATGCATCTCAATTAGTCAGCA
ACCATAGTCCCGCCCCTAACTCCGCCCATCCCGCCCCTAACTCCGCCCAGTTCCGCCCATTC
TCCGCCCCATGGCTGACTAATTTTTTTTATTTATGCAGAGGCCGAGGCCGCCTCTGCCTCTG
AGCTATTCCAGAAGTAGTGAGGAGGCTTTTTTGGAGGCCTAGGCTTTTGCAAAAAGCTCCCG
GGAGCTTGTATATCCATTTTCGGATCTGATCAAGAGACAGGATGAGGATCGTTTCGCATGAT
TGAACAAGATGGATTGCACGCAGGTTCTCCGGCCGCTTGGGTGGAGAGGCTATTCGGCTATG
ACTGGGCACAACAGACAATCGGCTGCTCTGATGCCGCCGTGTTCCGGCTGTCAGCGCAGGGG
CGCCCGGTTCTTTTTGTCAAGACCGACCTGTCCGGTGCCCTGAATGAACTGCAGGACGAGGC
AGCGCGGCTATCGTGGCTGGCCACGACGGGCGTTCCTTGCGCAGCTGTGCTCGACGTTGTCA

-continued

CTGAAGCGGGAAGGGACTGGCTGCTATTGGGCGAAGTGCCGGGGCAGGATCTCCTGTCATCT

CACCTTGCTCCTGCCGAGAAAGTATCCATCATGGCTGATGCAATGCGGCGGCTGCATACGCT

TGATCCGGCTACCTGCCCATTCGACCACCAAGCGAAACATCGCATCGAGCGAGCACGTACTC

GGATGGAAGCCGGTCTTGTCGATCAGGATGATCTGGACGAAGAGCATCAGGGGCTCGCGCCA

GCCGAACTGTTCGCCAGGCTCAAGGCGCGCATGCCCGACGGCGAGGATCTCGTCGTGACCCA

TGGCGATGCCTGCTTGCCGAATATCATGGTGGAAAATGGCCGCTTTTCTGGATTCATCGACT

GTGGCCGGCTGGGTGTGGCGGACCGCTATCAGGACATAGCGTTGGCTACCCGTGATATTGCT

GAAGAGCTTGGCGGCGAATGGGCTGACCGCTTCCTCGTGCTTTACGGTATCGCCGCTCCCGA

TTCGCAGCGCATCGCCTTCTATCGCCTTCTTGACGAGTTCTTCTGAGCGGGACTCTGGGGTT

CGCGAAATGACCGACCAAGCGACGCCCAACCTGCCATCACGAGATTTCGATTCCACCGCCGC

CTTCTATGAAAGGTTGGGCTTCGGAATCGTTTTCCGGGACGCCGGCTGGATGATCCTCCAGC

GCGGGGATCTCATGCTGGAGTTCTTCGCCCACCCCAACTTGTTTATTGCAGCTTATAATGGT

TACAAATAAAGCAATAGCATCACAAATTTCACAAATAAAGCATTTTTTTCACTGCATTCTAG

TTGTGGTTTGTCCAAACTCATCAATGTATCTTATCATGTCTGTATACCGTCGACCTCTAGCT

AGAGCTTGGCGTAATCATGGTCATAGCTGTTTCCTGTGTGAAATTGTTATCCGCTCACAATT

CCACACAACATACGAGCCGGAAGCATAAAGTGTAAAGCCTGGGGTGCCTAATGAGTGAGCTA

ACTCACATTAATTGCGTTGCGCTCACTGCCCGCTTTCCAGTCGGGAAACCTGTCGTGCCAGC

TGCATTAATGAATCGGCCAACGCGCGGGGAGAGGCGGTTTGCGTATTGGGCGCTCTTCCGCT

TCCTCGCTCACTGACTCGCTGCGCTCGGTCGTTCGGCTGCGGCGAGCGGTATCAGCTCACTC

AAAGGCGGTAATACGGTTATCCACAGAATCAGGGGATAACGCAGGAAAGAACATGTGAGCAA

AAGGCCAGCAAAAGGCCAGGAACCGTAAAAAGGCCGCGTTGCTGGCGTTTTTCCATAGGCTC

CGCCCCCCTGACGAGCATCACAAAAATCGACGCTCAAGTCAGAGGTGGCGAAACCCGACAGG

ACTATAAAGATACCAGGCGTTTCCCCCTGGAAGCTCCCTCGTGCGCTCTCCTGTTCCGACCC

TGCCGCTTACCGGATACCTGTCCGCCTTTCTCCCTTCGGGAAGCGTGGCGCTTTCTCAATGC

TCACGCTGTAGGTATCTCAGTTCGGTGTAGGTCGTTCGCTCCAAGCTGGGCTGTGTGCACGA

ACCCCCCGTTCAGCCCGACCGCTGCGCCTTATCCGGTAACTATCGTCTTGAGTCCAACCCGG

TAAGACACGACTTATCGCCACTGGCAGCAGCCACTGGTAACAGGATTAGCAGAGCGAGGTAT

GTAGGCGGTGCTACAGAGTTCTTGAAGTGGTGGCCTAACTACGGCTACACTAGAAGGACAGT

ATTTGGTATCTGCGCTCTGCTGAAGCCAGTTACCTTCGGAAAAAGAGTTGGTAGCTCTTGAT

CCGGCAAACAAACCACCGCTGGTAGCGGTGGTTTTTTTGTTTGCAAGCAGCAGATTACGCGC

AGAAAAAAAGGATCTCAAGAAGATCCTTTGATCTTTTCTACGGGGTCTGACGCTCAGTGGAA

CGAAAACTCACGTTAAGGGATTTTGGTCATGAGATTATCAAAAAGGATCTTCACCTAGATCC

TTTTAAATTAAAAATGAAGTTTTAAATCAATCTAAAGTATATATGAGTAAACTTGGTCTGAC

AGTTACCAATGCTTAATCAGTGAGGCACCTATCTCAGCGATCTGTCTATTTCGTTCATCCAT

AGTTGCCTGACTCCCCGTCGTGTAGATAACTACGATACGGGAGGGCTTACCATCTGGCCCCA

GTGCTGCAATGATACCGCGAGACCCACGCTCACCGGCTCCAGATTTATCAGCAATAAACCAG

CCAGCCGGAAGGGCCGAGCGCAGAAGTGGTCCTGCAACTTTATCCGCCTCCATCCAGTCTAT

TAATTGTTGCCGGGAAGCTAGAGTAAGTAGTTCGCCAGTTAATAGTTTGCGCAACGTTGTTG

CCATTGCTACAGGCATCGTGGTGTCACGCTCGTCGTTTGGTATGGCTTCATTCAGCTCCGGT

TCCCAACGATCAAGGCGAGTTACATGATCCCCCATGTTGTGCAAAAAAGCGGTTAGCTCCTT

-continued

CGGTCCTCCGATCGTTGTCAGAAGTAAGTTGGCCGCAGTGTTATCACTCATGGTTATGGCAG

CACTGCATAATTCTCTTACTGTCATGCCATCCGTAAGATGCTTTTCTGTGACTGGTGAGTAC

TCAACCAAGTCATTCTGAGAATAGTGTATGCGGCGACCGAGTTGCTCTTGCCCGGCGTCAAT

ACGGGATAATACCGCGCCACATAGCAGAACTTTAAAAGTGCTCATCATTGGAAAACGTTCTT

CGGGGCGAAAACTCTCAAGGATCTTACCGCTGTTGAGATCCAGTTCGATGTAACCCACTCGT

GCACCCAACTGATCTTCAGCATCTTTTACTTTCACCAGCGTTTCTGGGTGAGCAAAAACAGG

AAGGCAAAATGCCGCAAAAAAGGGAATAAGGGCGACACGGAAATGTTGAATACTCATACTCT

TCCTTTTTCAATATTATTGAAGCATTTATCAGGGTTATTGTCTCATGAGCGGATACATATTT

GAATGTATTTAGAAAAATAAACAAATAGGGGTTCCGCGCACATTTCCCCGAAAAGTGCCACC

TGACGTCGACGGATCGGGAGATCTCCCGATCCCCTATGGTCGACTCTCAGTACAATCTGCTC

TGATGCCGCATAGTTAAGCCAGTATCTGCTCCCTGCTTGTGTGTTGGAGGTCGCTGAGTAGT

GCGCGAGCAAAATTTAAGCTACAACAAGGCAAGGCTTGACCGACAATTGCATGAAGAATCTG

CTTAGG (SEQ ID NO: 100)

Sequences of expression vectors for mAb 19G10 IgG4/kappa:
>p19G10.VL.hk
GTTAGGCGTTTTGCGCTGCTTCGCGATGTACGGGCCAGATATACGCGTTGACATTGATTATT

GACTAGTTATTAATAGTAATCAATTACGGGGTCATTAGTTCATAGCCCATATATGGAGTTCC

GCGTTACATAACTTACGGTAAATGGCCCGCCTGGCTGACCGCCCAACGACCCCCGCCCATTG

ACGTCAATAATGACGTATGTTCCCATAGTAACGCCAATAGGGACTTTCCATTGACGTCAATG

GGTGGAGTATTTACGGTAAACTGCCCACTTGGCAGTACATCAAGTGTATCATATGCCAAGTA

CGCCCCCTATTGACGTCAATGACGGTAAATGGCCCGCCTGGCATTATGCCCAGTACATGACC

TTATGGGACTTTCCTACTTGGCAGTACATCTACGTATTAGTCATCGCTATTACCATGGTGAT

GCGGTTTTGGCAGTACATCAATGGGCGTGGATAGCGGTTTGACTCACGGGGATTTCCAAGTC

TCCACCCCATTGACGTCAATGGGAGTTTGTTTTGGCACCAAAATCAACGGGACTTTCCAAAA

TGTCGTAACAACTCCGCCCCATTGACGCAAATGGGCGGTAGGCGTGTACGGTGGGAGGTCTA

TATAAGCAGAGCTCGTTTAGTGAACCGTCAGATCGCCTGGAGACGCCATCCACGCTGTTTTG

ACCTCCATAGAAGACACCGGGACCGATCCAGCCTCCGGACTCTAGAGGATCGAACCCTTAAG

CTTGCCACC*ATGTACAGGATGCAACTCCTGTCTTGCATTGCACTAAGTCTTGCACTTGTCAC*

*GAATTCA*GACATCGTGCTGACACAGAGCCCTGCCAGCCTGGCTGTTTCTCTGGGACAGAGAG

CCACCATCAGCTGCAAGGCCAGCCAGAGCGTTGACTACGACGGCGACAGCTACATGAACTGG

TATCAGCAGAAGTCCGGCCAGCCTCCTAAGCTGCTGATCTACGCCGCCAGCAATCTGGAAAG

CGGCATCCCTGCCAGATTTTCCGGCTCTGGCAGCGGCACCGACTTCACCCTGAATATCCATC

CTGTGGAAGAAGAGGACGCCGCCACCTACTACTGCCAGCAGAGCAATGTGGACCCCTGGACA

TTTGGCGGAGGCACCAAGCTGGAAATCAAGCGTACGGTGGCTGCACCATCTGTCTTCATCTT

CCCGCCATCTGATGAGCAGTTGAAATCTGGAACTGCCTCTGTTGTGTGCCTGCTGAATAACT

TCTATCCCAGAGAGGCCAAAGTACAGTGGAAGGTGGATAACGCCCTCCAATCGGGTAACTCC

CAGGAGAGTGTCACAGAGCAGGACAGCAAGGACAGCACCTACAGCCTCAGCAGCACCCTGAC

GCTGAGCAAAGCAGACTACGAGAAACACAAAGTCTACGCCTGCGAAGTCACCCATCAGGGCC

TGAGCTCGCCCGTCACAAAGAGCTTCAACAGGGGAGAGTGTTAGAGGGAGCTAGCGTGGCAT

CTAGACACTCTCGAGAAGGGTTCGATCCCTACCGGTTAGTAATGAGTTTGATATCTCGACAA

TCAACCTCTGGATTACAAAATTTGTGAAAGATTGACTGGTATTCTTAACTATGTTGCTCCTT

TTACGCTATGTGGATACGCTGCTTTAATGCCTTTGTATCATGCTATTGCTTCCCGTATGGCT

-continued

TTCATTTTCTCCTCCTTGTATAAATCCTGGTTGCTGTCTCTTTATGAGGAGTTGTGGCCCGT

TGTCAGGCAACGTGGCGTGGTGTGCACTGTGTTTGCTGACGCAACCCCCACTGGTTGGGGCA

TTGCCACCACCTGTCAGCTCCTTTCCGGGACTTTCGCTTTCCCCCTCCCTATTGCCACGGCG

GAACTCATCGCCGCCTGCCTTGCCCGCTGCTGGACAGGGGCTCGGCTGTTGGGCACTGACAA

TTCCGTGGTGTTGTCGGGGAAGCTGACGTCCTTTCCATGGCTGCTCGCCTGTGTTGCCACCT

GGATTCTGCGCGGGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCGCCCTCAGACGAG

TCGGATCTCCCTTTGGGCCGCCTCCCCGCCTGGAAACGGGGGAGGCTAACTGAAACACGGAA

GGAGACAATACCGGAAGGAACCCGCGCTATGACGGCAATAAAAAGACAGAATAAAACGCACG

GGTGTTGGGTCGTTTGTTCATAAACGCGGGGTTCGGTCCCAGGGCTGGCACTCTGTCGATAC

CCCACCGAGACCCCATTGGGGCCAATACGCCCGCGTTTCTTCCTTTTCCCCACCCCACCCCC

CAAGTTCGGGTGAAGGCCCAGGGCTCGCAGCCAACGTCGGGGCGGCAGGCCCTGCCATAGCA

GATCTGCGCAGCTGGGGCTCTAGGGGGTATCCCCACGCGCCCTGTAGCGGCGCATTAAGCGC

GGCGGGTGTGGTGGTTACGCGCAGCGTGACCGCTACACTTGCCAGCGCCCTAGCGCCCGCTC

CTTTCGCTTTCTTCCCTTCCTTTCTCGCCACGTTCGCCGGCTTTCCCCGTCAAGCTCTAAAT

CGGGGCATCCCTTTAGGGTTCCGATTTAGTGCTTTACGGCACCTCGACCCCAAAAAACTTGA

TTAGGGTGATGGTTCACGTAGTGGGCCATCGCCCTGATAGACGGTTTTTCGCCCTTTGACGT

TGGAGTCCACGTTCTTTAATAGTGGACTCTTGTTCCAAACTGGAACAACACTCAACCCTATC

TCGGTCTATTCTTTTGATTTATAAGGGATTTTGGGGATTTCGGCCTATTGGTTAAAAAATGA

GCTGATTTAACAAAAATTTAACGCGAATTAATTCTGTGGAATGTGTGTCAGTTAGGGTGTGG

AAAGTCCCCAGGCTCCCCAGCAGGCAGAAGTATGCAAAGCATGCATCTCAATTAGTCAGCAA

CCAGGTGTGGAAAGTCCCCAGGCTCCCCAGCAGGCAGAAGTATGCAAAGCATGCATCTCAAT

TAGTCAGCAACCATAGTCCCGCCCCTAACTCCGCCCATCCCGCCCCTAACTCCGCCCAGTTC

CGCCCATTCTCCGCCCCATGGCTGACTAATTTTTTTTATTTATGCAGAGGCCGAGGCCGCCT

CTGCCTCTGAGCTATTCCAGAAGTAGTGAGGAGGCTTTTTTGGAGGCCTAGGCTTTTGCAAA

AAGCTCCCGGGAGCTTGTATATCCATTTTCGGATCTGATCAAGAGACAGGATGAGGATCGTT

TCGCATGATTGAACAAGATGGATTGCACGCAGGTTCTCCGGCCGCTTGGGTGGAGAGGCTAT

TCGGCTATGACTGGGCACAACAGACAATCGGCTGCTCTGATGCCGCCGTGTTCCGGCTGTCA

GCGCAGGGGCGCCCGGTTCTTTTTGTCAAGACCGACCTGTCCGGTGCCCTGAATGAACTGCA

GGACGAGGCAGCGCGGCTATCGTGGCTGGCCACGACGGGCGTTCCTTGCGCAGCTGTGCTCG

ACGTTGTCACTGAAGCGGGAAGGGACTGGCTGCTATTGGGCGAAGTGCCGGGGCAGGATCTC

CTGTCATCTCACCTTGCTCCTGCCGAGAAAGTATCCATCATGGCTGATGCAATGCGGCGGCT

GCATACGCTTGATCCGGCTACCTGCCCATTCGACCACCAAGCGAAACATCGCATCGAGCGAG

CACGTACTCGGATGGAAGCCGGTCTTGTCGATCAGGATGATCTGGACGAAGAGCATCAGGGG

CTCGCGCCAGCCGAACTGTTCGCCAGGCTCAAGGCGCGCATGCCCGACGGCGAGGATCTCGT

CGTGACCCATGGCGATGCCTGCTTGCCGAATATCATGGTGGAAAATGGCCGCTTTTCTGGAT

TCATCGACTGTGGCCGGCTGGGTGTGGCGGACCGCTATCAGGACATAGCGTTGGCTACCCGT

GATATTGCTGAAGAGCTTGGCGGCGAATGGGCTGACCGCTTCCTCGTGCTTTACGGTATCGC

CGCTCCCGATTCGCAGCGCATCGCCTTCTATCGCCTTCTTGACGAGTTCTTCTGAGCGGGAC

TCTGGGGTTCGCGAAATGACCGACCAAGCGACGCCCAACCTGCCATCACGAGATTTCGATTC

-continued

CACCGCCGCCTTCTATGAAAGGTTGGGCTTCGGAATCGTTTTCCGGGACGCCGGCTGGATGA

TCCTCCAGCGCGGGGATCTCATGCTGGAGTTCTTCGCCCACCCCAACTTGTTTATTGCAGCT

TATAATGGTTACAAATAAAGCAATAGCATCACAAATTTCACAAATAAAGCATTTTTTTCACT

GCATTCTAGTTGTGGTTTGTCCAAACTCATCAATGTATCTTATCATGTCTGTATACCGTCGA

CCTCTAGCTAGAGCTTGGCGTAATCATGGTCATAGCTGTTTCCTGTGTGAAATTGTTATCCG

CTCACAATTCCACACAACATACGAGCCGGAAGCATAAAGTGTAAAGCCTGGGGTGCCTAATG

AGTGAGCTAACTCACATTAATTGCGTTGCGCTCACTGCCCGCTTTCCAGTCGGGAAACCTGT

CGTGCCAGCTGCATTAATGAATCGGCCAACGCGCGGGGAGAGGCGGTTTGCGTATTGGGCGC

TCTTCCGCTTCCTCGCTCACTGACTCGCTGCGCTCGGTCGTTCGGCTGCGGCGAGCGGTATC

AGCTCACTCAAAGGCGGTAATACGGTTATCCACAGAATCAGGGGATAACGCAGGAAAGAACA

TGTGAGCAAAAGGCCAGCAAAAGGCCAGGAACCGTAAAAAGGCCGCGTTGCTGGCGTTTTTC

CATAGGCTCCGCCCCCCTGACGAGCATCACAAAAATCGACGCTCAAGTCAGAGGTGGCGAAA

CCCGACAGGACTATAAAGATACCAGGCGTTTCCCCCTGGAAGCTCCCTCGTGCGCTCTCCTG

TTCCGACCCTGCCGCTTACCGGATACCTGTCCGCCTTTCTCCCTTCGGGAAGCGTGGCGCTT

TCTCAATGCTCACGCTGTAGGTATCTCAGTTCGGTGTAGGTCGTTCGCTCCAAGCTGGGCTG

TGTGCACGAACCCCCCGTTCAGCCCGACCGCTGCGCCTTATCCGGTAACTATCGTCTTGAGT

CCAACCCGGTAAGACACGACTTATCGCCACTGGCAGCAGCCACTGGTAACAGGATTAGCAGA

GCGAGGTATGTAGGCGGTGCTACAGAGTTCTTGAAGTGGTGGCCTAACTACGGCTACACTAG

AAGGACAGTATTTGGTATCTGCGCTCTGCTGAAGCCAGTTACCTTCGGAAAAAGAGTTGGTA

GCTCTTGATCCGGCAAACAAACCACCGCTGGTAGCGGTGGTTTTTTTGTTTGCAAGCAGCAG

ATTACGCGCAGAAAAAAAGGATCTCAAGAAGATCCTTTGATCTTTTCTACGGGGTCTGACGC

TCAGTGGAACGAAAACTCACGTTAAGGGATTTTGGTCATGAGATTATCAAAAAGGATCTTCA

CCTAGATCCTTTTAAATTAAAAATGAAGTTTTAAATCAATCTAAAGTATATATGAGTAAACT

TGGTCTGACAGTTACCAATGCTTAATCAGTGAGGCACCTATCTCAGCGATCTGTCTATTTCG

TTCATCCATAGTTGCCTGACTCCCCGTCGTGTAGATAACTACGATACGGGAGGGCTTACCAT

CTGGCCCCAGTGCTGCAATGATACCGCGAGACCCACGCTCACCGGCTCCAGATTTATCAGCA

ATAAACCAGCCAGCCGGAAGGGCCGAGCGCAGAAGTGGTCCTGCAACTTTATCCGCCTCCAT

CCAGTCTATTAATTGTTGCCGGGAAGCTAGAGTAAGTAGTTCGCCAGTTAATAGTTTGCGCA

ACGTTGTTGCCATTGCTACAGGCATCGTGGTGTCACGCTCGTCGTTTGGTATGGCTTCATTC

AGCTCCGGTTCCCAACGATCAAGGCGAGTTACATGATCCCCCATGTTGTGCAAAAAAGCGGT

TAGCTCCTTCGGTCCTCCGATCGTTGTCAGAAGTAAGTTGGCCGCAGTGTTATCACTCATGG

TTATGGCAGCACTGCATAATTCTCTTACTGTCATGCCATCCGTAAGATGCTTTTCTGTGACT

GGTGAGTACTCAACCAAGTCATTCTGAGAATAGTGTATGCGGCGACCGAGTTGCTCTTGCCC

GGCGTCAATACGGGATAATACCGCGCCACATAGCAGAACTTTAAAAGTGCTCATCATTGGAA

AACGTTCTTCGGGGCGAAAACTCTCAAGGATCTTACCGCTGTTGAGATCCAGTTCGATGTAA

CCCACTCGTGCACCCAACTGATCTTCAGCATCTTTTACTTTCACCAGCGTTTCTGGGTGAGC

AAAAACAGGAAGGCAAAATGCCGCAAAAAAGGGAATAAGGGCGACACGGAAATGTTGAATAC

TCATACTCTTCCTTTTTCAATATTATTGAAGCATTTATCAGGGTTATTGTCTCATGAGCGGA

TACATATTTGAATGTATTTAGAAAAATAAACAAATAGGGGTTCCGCGCACATTTCCCCGAAA

AGTGCCACCTGACGTCGACGGATCGGGAGATCTCCCGATCCCCTATGGTCGACTCTCAGTAC

AATCTGCTCTGATGCCGCATAGTTAAGCCAGTATCTGCTCCCTGCTTGTGTGTTGGAGGTCG

-continued

CTGAGTAGTGCGCGAGCAAAATTTAAGCTACAACAAGGCAAGGCTTGACCGACAATTGCATG

AAGAATCTGCTTAGG (SEQ ID NO: 101)

>p19G10.VH.hIgG4
GTTAGGCGTTTTGCGCTGCTTCGCGATGTACGGGCCAGATATACGCGTTGACATTGATTATT

GACTAGTTATTAATAGTAATCAATTACGGGGTCATTAGTTCATAGCCCATATATGGAGTTCC

GCGTTACATAACTTACGGTAAATGGCCCGCCTGGCTGACCGCCCAACGACCCCCGCCCATTG

ACGTCAATAATGACGTATGTTCCCATAGTAACGCCAATAGGGACTTTCCATTGACGTCAATG

GGTGGAGTATTTACGGTAAACTGCCCACTTGGCAGTACATCAAGTGTATCATATGCCAAGTA

CGCCCCCTATTGACGTCAATGACGGTAAATGGCCCGCCTGGCATTATGCCCAGTACATGACC

TTATGGGACTTTCCTACTTGGCAGTACATCTACGTATTAGTCATCGCTATTACCATGGTGAT

GCGGTTTTGGCAGTACATCAATGGGCGTGGATAGCGGTTTGACTCACGGGGATTTCCAAGTC

TCCACCCCATTGACGTCAATGGGAGTTTGTTTTGGCACCAAAATCAACGGGACTTTCCAAAA

TGTCGTAACAACTCCGCCCCATTGACGCAAATGGGCGGTAGGCGTGTACGGTGGGAGGTCTA

TATAAGCAGAGCTCGTTTAGTGAACCGTCAGATCGCCTGGAGACGCCATCCACGCTGTTTTG

ACCTCCATAGAAGACACCGGGACCGATCCAGCCTCCGGACTCTAGAGGATCGAACCCTTAAG

CTTGCCACC*ATGTACAGGATGCAACTCCTGTCTTGCATTGCACTAAGTCTTGCACTTGTCAC*

*GAATTC*GGAGGTCCAGCTGCAGCAGTCTGGCGCCGAACTTGTTAGACCTGGCGCTCTGGTCA

AGCTGAGCTGTAAAGCCAGCGGCTTCAACATCAAGGACTACCACATGCACTGGGTCAAAGAG

CGGCCTGAGCAGGGACTCGAGTGGATCGGATGGATCGACCCCGAGAACGGCAACACTATGTA

CGACCCCAAGTTCCAGGGCAAAGCCAGCATCACCGCCGACACCTCTAGCAACACAGCCTACC

TGCAGCTGAGCAGCCTGACCTCTGAAGATACCGCCGTGTACTACTGCGTGCGGGGAACAGCC

AGAGCCAGCTTTGATTATTGGGGCCAGGGCACCACACTGACCGTGTCATCTGCTAGCACCAA

GGGCCCATCGGTCTTCCCCCTGGCGCCCTGCTCCAGGAGCACCTCCGAGAGCACAGCCGCCC

TGGGCTGCCTGGTCAAGGACTACTTCCCCGAACCGGTGACGGTGTCGTGGAACTCAGGCGCC

CTGACCAGCGGCGTGCACACCTTCCCGGCTGTCCTACAGTCCTCAGGACTCTACTCCCTCAG

CAGCGTGGTGACCGTGCCCTCCAGCAGCTTGGGCACGAAGACCTACACCTGCAACGTAGATC

ACAAGCCCAGCAACACCAAGGTGGACAAGAGAGTTGAGTCCAAATATGGTCCCCCATGCCCA

TCATGCCCAGCACCTGAGTTCCTGGGGGGACCATCAGTCTTCCTGTTCCCCCCAAAACCCAA

GGACACTCTCATGATCTCCCGGACCCCTGAGGTCACGTGCGTGGTGGTGGACGTGAGCCAGG

AAGACCCCGAGGTCCAGTTCAACTGGTACGTGGATGGCGTGGAGGTGCATAATGCCAAGACA

AAGCCGCGGGAGGAGCAGTTCAACAGCACGTACCGTGTGGTCAGCGTCCTCACCGTCCTGCA

CCAGGACTGGCTGAACGGCAAGGAGTACAAGTGCAAGGTCTCCAACAAAGGCCTCCCGTCCT

CCATCGAGAAAACCATCTCCAAAGCCAAAGGGCAGCCCCGAGAGCCACAGGTGTACACCCTG

CCCCCATCCCAGGAGGAGATGACCAAGAACCAGGTCAGCCTGACCTGCCTGGTCAAAGGCTT

CTACCCCAGCGACATCGCCGTGGAGTGGGAGAGCAATGGGCAGCCGGAGAACAACTACAAGA

CCACGCCTCCCGTGCTGGACTCCGACGGCTCCTTCTTCCTCTACAGCAGGCTAACCGTGGAC

AAGAGCAGGTGGCAGGAGGGGAATGTCTTCTCATGCTCCGTGATGCATGAGGCTCTGCACAA

CCACTACACACAGAAGAGCCTCTCCCTGTCTCTGGGTAAATAACCTAGCGTGGCATCTAGAC

ACTCTCGAGAAGGGTTCGATCCCTACCGGTTAGTAATGAGTTTGATATCTCGACAATCAACC

TCTGGATTACAAAATTTGTGAAAGATTGACTGGTATTCTTAACTATGTTGCTCCTTTTACGC

TATGTGGATACGCTGCTTTAATGCCTTTGTATCATGCTATTGCTTCCCGTATGGCTTTCATT

-continued

TTCTCCTCCTTGTATAAATCCTGGTTGCTGTCTCTTTATGAGGAGTTGTGGCCCGTTGTCAG
GCAACGTGGCGTGGTGTGCACTGTGTTTGCTGACGCAACCCCCACTGGTTGGGGCATTGCCA
CCACCTGTCAGCTCCTTTCCGGGACTTTCGCTTTCCCCCTCCCTATTGCCACGGCGGAACTC
ATCGCCGCCTGCCTTGCCCGCTGCTGGACAGGGGCTCGGCTGTTGGGCACTGACAATTCCGT
GGTGTTGTCGGGGAAGCTGACGTCCTTTCCATGGCTGCTCGCCTGTGTTGCCACCTGGATTC
TGCGCGGGACGTCCTTCTGCTACGTCCCTTCGGCCCTCAATCCAGCGGACCTTCCTTCCCGC
GGCCTGCTGCCGGCTCTGCGGCCTCTTCCGCGTCTTCGCCTTCGCCCTCAGACGAGTCGGAT
CTCCCTTTGGGCCGCCTCCCCGCCTGGAAACGGGGGAGGCTAACTGAAACACGGAAGGAGAC
AATACCGGAAGGAACCCGCGCTATGACGGCAATAAAAAGACAGAATAAAACGCACGGGTGTT
GGGTCGTTTGTTCATAAACGCGGGGTTCGGTCCCAGGGCTGGCACTCTGTCGATACCCCACC
GAGACCCCATTGGGGCCAATACGCCCGCGTTTCTTCCTTTTCCCCACCCCACCCCCCAAGTT
CGGGTGAAGGCCCAGGGCTCGCAGCCAACGTCGGGGCGGCAGGCCCTGCCATAGCAGATCTG
CGCAGCTGGGGCTCTAGGGGGTATCCCCACGCGCCCTGTAGCGGCGCATTAAGCGCGGCGGG
TGTGGTGGTTACGCGCAGCGTGACCGCTACACTTGCCAGCGCCCTAGCGCCCGCTCCTTTCG
CTTTCTTCCCTTCCTTTCTCGCCACGTTCGCCGGCTTTCCCCGTCAAGCTCTAAATCGGGGC
ATCCCTTTAGGGTTCCGATTTAGTGCTTTACGGCACCTCGACCCCAAAAAACTTGATTAGGG
TGATGGTTCACGTAGTGGGCCATCGCCCTGATAGACGGTTTTTCGCCCTTTGACGTTGGAGT
CCACGTTCTTTAATAGTGGACTCTTGTTCCAAACTGGAACAACACTCAACCCTATCTCGGTC
TATTCTTTTGATTTATAAGGGATTTTGGGGATTTCGGCCTATTGGTTAAAAAATGAGCTGAT
TTAACAAAAATTTAACGCGAATTAATTCTGTGGAATGTGTGTCAGTTAGGGTGTGGAAAGTC
CCCAGGCTCCCCAGCAGGCAGAAGTATGCAAAGCATGCATCTCAATTAGTCAGCAACCAGGT
GTGGAAAGTCCCCAGGCTCCCCAGCAGGCAGAAGTATGCAAAGCATGCATCTCAATTAGTCA
GCAACCATAGTCCCGCCCCTAACTCCGCCCATCCCGCCCCTAACTCCGCCCAGTTCCGCCCA
TTCTCCGCCCCATGGCTGACTAATTTTTTTTATTTATGCAGAGGCCGAGGCCGCCTCTGCCT
CTGAGCTATTCCAGAAGTAGTGAGGAGGCTTTTTTGGAGGCCTAGGCTTTTGCAAAAAGCTC
CCGGGAGCTTGTATATCCATTTTCGGATCTGATCAAGAGACAGGATGAGGATCGTTTCGCAT
GATTGAACAAGATGGATTGCACGCAGGTTCTCCGGCCGCTTGGGTGGAGAGGCTATTCGGCT
ATGACTGGGCACAACAGACAATCGGCTGCTCTGATGCCGCCGTGTTCCGGCTGTCAGCGCAG
GGGCGCCCGGTTCTTTTTGTCAAGACCGACCTGTCCGGTGCCCTGAATGAACTGCAGGACGA
GGCAGCGCGGCTATCGTGGCTGGCCACGACGGGCGTTCCTTGCGCAGCTGTGCTCGACGTTG
TCACTGAAGCGGGAAGGGACTGGCTGCTATTGGGCGAAGTGCCGGGGCAGGATCTCCTGTCA
TCTCACCTTGCTCCTGCCGAGAAAGTATCCATCATGGCTGATGCAATGCGGCGGCTGCATAC
GCTTGATCCGGCTACCTGCCCATTCGACCACCAAGCGAAACATCGCATCGAGCGAGCACGTA
CTCGGATGGAAGCCGGTCTTGTCGATCAGGATGATCTGGACGAAGAGCATCAGGGGCTCGCG
CCAGCCGAACTGTTCGCCAGGCTCAAGGCGCGCATGCCCGACGGCGAGGATCTCGTCGTGAC
CCATGGCGATGCCTGCTTGCCGAATATCATGGTGGAAAATGGCCGCTTTTCTGGATTCATCG
ACTGTGGCCGGCTGGGTGTGGCGGACCGCTATCAGGACATAGCGTTGGCTACCCGTGATATT
GCTGAAGAGCTTGGCGGCGAATGGGCTGACCGCTTCCTCGTGCTTTACGGTATCGCCGCTCC
CGATTCGCAGCGCATCGCCTTCTATCGCCTTCTTGACGAGTTCTTCTGAGCGGGACTCTGGG
GTTCGCGAAATGACCGACCAAGCGACGCCCAACCTGCCATCACGAGATTTCGATTCCACCGC

-continued

CGCCTTCTATGAAAGGTTGGGCTTCGGAATCGTTTTCCGGGACGCCGGCTGGATGATCCTCC

AGCGCGGGGATCTCATGCTGGAGTTCTTCGCCCACCCCAACTTGTTTATTGCAGCTTATAAT

GGTTACAAATAAAGCAATAGCATCACAAATTTCACAAATAAAGCATTTTTTTCACTGCATTC

TAGTTGTGGTTTGTCCAAACTCATCAATGTATCTTATCATGTCTGTATACCGTCGACCTCTA

GCTAGAGCTTGGCGTAATCATGGTCATAGCTGTTTCCTGTGTGAAATTGTTATCCGCTCACA

ATTCCACACAACATACGAGCCGGAAGCATAAAGTGTAAAGCCTGGGGTGCCTAATGAGTGAG

CTAACTCACATTAATTGCGTTGCGCTCACTGCCCGCTTTCCAGTCGGGAAACCTGTCGTGCC

AGCTGCATTAATGAATCGGCCAACGCGCGGGGAGAGGCGGTTTGCGTATTGGGCGCTCTTCC

GCTTCCTCGCTCACTGACTCGCTGCGCTCGGTCGTTCGGCTGCGGCGAGCGGTATCAGCTCA

CTCAAAGGCGGTAATACGGTTATCCACAGAATCAGGGGATAACGCAGGAAAGAACATGTGAG

CAAAAGGCCAGCAAAAGGCCAGGAACCGTAAAAAGGCCGCGTTGCTGGCGTTTTTCCATAGG

CTCCGCCCCCCTGACGAGCATCACAAAAATCGACGCTCAAGTCAGAGGTGGCGAAACCCGAC

AGGACTATAAAGATACCAGGCGTTTCCCCCTGGAAGCTCCCTCGTGCGCTCTCCTGTTCCGA

CCCTGCCGCTTACCGGATACCTGTCCGCCTTTCTCCCTTCGGGAAGCGTGGCGCTTTCTCAA

TGCTCACGCTGTAGGTATCTCAGTTCGGTGTAGGTCGTTCGCTCCAAGCTGGGCTGTGTGCA

CGAACCCCCCGTTCAGCCCGACCGCTGCGCCTTATCCGGTAACTATCGTCTTGAGTCCAACC

CGGTAAGACACGACTTATCGCCACTGGCAGCAGCCACTGGTAACAGGATTAGCAGAGCGAGG

TATGTAGGCGGTGCTACAGAGTTCTTGAAGTGGTGGCCTAACTACGGCTACACTAGAAGGAC

AGTATTTGGTATCTGCGCTCTGCTGAAGCCAGTTACCTTCGGAAAAAGAGTTGGTAGCTCTT

GATCCGGCAAACAAACCACCGCTGGTAGCGGTGGTTTTTTTGTTTGCAAGCAGCAGATTACG

CGCAGAAAAAAAGGATCTCAAGAAGATCCTTTGATCTTTTCTACGGGGTCTGACGCTCAGTG

GAACGAAAACTCACGTTAAGGGATTTTGGTCATGAGATTATCAAAAAGGATCTTCACCTAGA

TCCTTTTAAATTAAAAATGAAGTTTTAAATCAATCTAAAGTATATATGAGTAAACTTGGTCT

GACAGTTACCAATGCTTAATCAGTGAGGCACCTATCTCAGCGATCTGTCTATTTCGTTCATC

CATAGTTGCCTGACTCCCCGTCGTGTAGATAACTACGATACGGGAGGGCTTACCATCTGGCC

CCAGTGCTGCAATGATACCGCGAGACCCACGCTCACCGGCTCCAGATTTATCAGCAATAAAC

CAGCCAGCCGGAAGGGCCGAGCGCAGAAGTGGTCCTGCAACTTTATCCGCCTCCATCCAGTC

TATTAATTGTTGCCGGGAAGCTAGAGTAAGTAGTTCGCCAGTTAATAGTTTGCGCAACGTTG

TTGCCATTGCTACAGGCATCGTGGTGTCACGCTCGTCGTTTGGTATGGCTTCATTCAGCTCC

GGTTCCCAACGATCAAGGCGAGTTACATGATCCCCCATGTTGTGCAAAAAAGCGGTTAGCTC

CTTCGGTCCTCCGATCGTTGTCAGAAGTAAGTTGGCCGCAGTGTTATCACTCATGGTTATGG

CAGCACTGCATAATTCTCTTACTGTCATGCCATCCGTAAGATGCTTTTCTGTGACTGGTGAG

TACTCAACCAAGTCATTCTGAGAATAGTGTATGCGGCGACCGAGTTGCTCTTGCCCGGCGTC

AATACGGGATAATACCGCGCCACATAGCAGAACTTTAAAAGTGCTCATCATTGGAAAACGTT

CTTCGGGGCGAAAACTCTCAAGGATCTTACCGCTGTTGAGATCCAGTTCGATGTAACCCACT

CGTGCACCCAACTGATCTTCAGCATCTTTTACTTTCACCAGCGTTTCTGGGTGAGCAAAAAC

AGGAAGGCAAAATGCCGCAAAAAAGGGAATAAGGGCGACACGGAAATGTTGAATACTCATAC

TCTTCCTTTTTCAATATTATTGAAGCATTTATCAGGGTTATTGTCTCATGAGCGGATACATA

TTTGAATGTATTTAGAAAAATAAACAAATAGGGGTTCCGCGCACATTTCCCCGAAAAGTGCC

ACCTGACGTCGACGGATCGGGAGATCTCCCGATCCCCTATGGTCGACTCTCAGTACAATCTG

CTCTGATGCCGCATAGTTAAGCCAGTATCTGCTCCCTGCTTGTGTGTTGGAGGTCGCTGAGT

-continued

AGTGCGCGAGCAAAATTTAAGCTACAACAAGGCAAGGCTTGACCGACAATTGCATGAAGAAT

CTGCTTAGG (SEQ ID NO: 102)

Sequences of expression vectors for mAb 25F1 IgG4/kappa:
>p25F1.VL.hk
GTTAGGCGTTTTGCGCTGCTTCGCGATGTACGGGCCAGATATACGCGTTGACATTGATTATT

GACTAGTTATTAATAGTAATCAATTACGGGGTCATTAGTTCATAGCCCATATATGGAGTTCC

GCGTTACATAACTTACGGTAAATGGCCCGCCTGGCTGACCGCCCAACGACCCCCGCCCATTG

ACGTCAATAATGACGTATGTTCCCATAGTAACGCCAATAGGGACTTTCCATTGACGTCAATG

GGTGGAGTATTTACGGTAAACTGCCCACTTGGCAGTACATCAAGTGTATCATATGCCAAGTA

CGCCCCCTATTGACGTCAATGACGGTAAATGGCCCGCCTGGCATTATGCCCAGTACATGACC

TTATGGGACTTTCCTACTTGGCAGTACATCTACGTATTAGTCATCGCTATTACCATGGTGAT

GCGGTTTTGGCAGTACATCAATGGGCGTGGATAGCGGTTTGACTCACGGGGATTTCCAAGTC

TCCACCCCATTGACGTCAATGGGAGTTTGTTTTGGCACCAAAATCAACGGGACTTTCCAAAA

TGTCGTAACAACTCCGCCCCATTGACGCAAATGGGCGGTAGGCGTGTACGGTGGGAGGTCTA

TATAAGCAGAGCTCGTTTAGTGAACCGTCAGATCGCCTGGAGACGCCATCCACGCTGTTTTG

ACCTCCATAGAAGACACCGGGACCGATCCAGCCTCCGGACTCTAGAGGATCGAACCCTTAAG

CTTGCCACC*ATGTACAGGATGCAACTCCTGTCTTGCATTGCACTAAGTCTTGCACTTGTCAC*

*GAATTCA*GACATCGTGCTGACACAGAGCCCTGCCAGCCTGGCTGTTTCTCTGGGACAGAGAG

CCACCATCAGCTGCAAGGCCAGCCAGAGCGTTGACTACGACGGCGACACCTACATGAACTGG

TATCAGCAGAAGCCCGGCCAGCCACCTAAGCTGCTGATCTACACAGCCAGCAACCTGGAAAG

CGGCATCCCCGCCAGATTTTCTGGCAGCGGAAGCGGCACCGACTTCACCCTGAATATCCATC

CTGTGGAAGAGGTGGACGCCGCCACCTACTACTGCCAGCAGAGCAATGAGGACCCCTGGACA

TTTGGCGGAGGCACCAAGCTGGAAATCAAGCGTACGGTGGCTGCACCATCTGTCTTCATCTT

CCCGCCATCTGATGAGCAGTTGAAATCTGGAACTGCCTCTGTTGTGTGCCTGCTGAATAACT

TCTATCCCAGAGAGGCCAAAGTACAGTGGAAGGTGGATAACGCCCTCCAATCGGGTAACTCC

CAGGAGAGTGTCACAGAGCAGGACAGCAAGGACAGCACCTACAGCCTCAGCAGCACCCTGAC

GCTGAGCAAAGCAGACTACGAGAAACACAAAGTCTACGCCTGCGAAGTCACCCATCAGGGCC

TGAGCTCGCCCGTCACAAAGAGCTTCAACAGGGGAGAGTGTTAGAGGGAGCTAGCGTGGCAT

CTAGACACTCTCGAGAAGGGTTCGATCCCTACCGGTTAGTAATGAGTTTGATATCTCGACAA

TCAACCTCTGGATTACAAAATTTGTGAAAGATTGACTGGTATTCTTAACTATGTTGCTCCTT

TTACGCTATGTGGATACGCTGCTTTAATGCCTTTGTATCATGCTATTGCTTCCCGTATGGCT

TTCATTTTCTCCTCCTTGTATAAATCCTGGTTGCTGTCTCTTTATGAGGAGTTGTGGCCCGT

TGTCAGGCAACGTGGCGTGGTGTGCACTGTGTTTGCTGACGCAACCCCCACTGGTTGGGGCA

TTGCCACCACCTGTCAGCTCCTTTCCGGGACTTTCGCTTTCCCCCTCCCTATTGCCACGGCG

GAACTCATCGCCGCCTGCCTTGCCCGCTGCTGGACAGGGGCTCGGCTGTTGGGCACTGACAA

TTCCGTGGTGTTGTCGGGGAAGCTGACGTCCTTTCCATGGCTGCTCGCCTGTGTTGCCACCT

GGATTCTGCGCGGGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCGCCCTCAGACGAG

TCGGATCTCCCTTTGGGCCGCCTCCCCGCCTGGAAACGGGGGAGGCTAACTGAAACACGGAA

GGAGACAATACCGGAAGGAACCCGCGCTATGACGGCAATAAAAAGACAGAATAAAACGCACG

GGTGTTGGGTCGTTTGTTCATAAACGCGGGGTTCGGTCCCAGGGCTGGCACTCTGTCGATAC

-continued

CCCACCGAGACCCCATTGGGGCCAATACGCCCGCGTTTCTTCCTTTTCCCCACCCCACCCCC

CAAGTTCGGGTGAAGGCCCAGGGCTCGCAGCCAACGTCGGGGCGGCAGGCCCTGCCATAGCA

GATCTGCGCAGCTGGGGCTCTAGGGGGTATCCCCACGCGCCCTGTAGCGGCGCATTAAGCGC

GGCGGGTGTGGTGGTTACGCGCAGCGTGACCGCTACACTTGCCAGCGCCCTAGCGCCCGCTC

CTTTCGCTTTCTTCCCTTCCTTTCTCGCCACGTTCGCCGGCTTTCCCCGTCAAGCTCTAAAT

CGGGGCATCCCTTTAGGGTTCCGATTTAGTGCTTTACGGCACCTCGACCCCAAAAAACTTGA

TTAGGGTGATGGTTCACGTAGTGGGCCATCGCCCTGATAGACGGTTTTTCGCCCTTTGACGT

TGGAGTCCACGTTCTTTAATAGTGGACTCTTGTTCCAAACTGGAACAACACTCAACCCTATC

TCGGTCTATTCTTTTGATTTATAAGGGATTTTGGGGATTTCGGCCTATTGGTTAAAAAATGA

GCTGATTTAACAAAAATTTAACGCGAATTAATTCTGTGGAATGTGTGTCAGTTAGGGTGTGG

AAAGTCCCCAGGCTCCCCAGCAGGCAGAAGTATGCAAAGCATGCATCTCAATTAGTCAGCAA

CCAGGTGTGGAAAGTCCCCAGGCTCCCCAGCAGGCAGAAGTATGCAAAGCATGCATCTCAAT

TAGTCAGCAACCATAGTCCCGCCCCTAACTCCGCCCATCCCGCCCCTAACTCCGCCCAGTTC

CGCCCATTCTCCGCCCCATGGCTGACTAATTTTTTTTATTTATGCAGAGGCCGAGGCCGCCT

CTGCCTCTGAGCTATTCCAGAAGTAGTGAGGAGGCTTTTTTGGAGGCCTAGGCTTTTGCAAA

AAGCTCCCGGGAGCTTGTATATCCATTTTCGGATCTGATCAAGAGACAGGATGAGGATCGTT

TCGCATGATTGAACAAGATGGATTGCACGCAGGTTCTCCGGCCGCTTGGGTGGAGAGGCTAT

TCGGCTATGACTGGGCACAACAGACAATCGGCTGCTCTGATGCCGCCGTGTTCCGGCTGTCA

GCGCAGGGGCGCCCGGTTCTTTTTGTCAAGACCGACCTGTCCGGTGCCCTGAATGAACTGCA

GGACGAGGCAGCGCGGCTATCGTGGCTGGCCACGACGGGCGTTCCTTGCGCAGCTGTGCTCG

ACGTTGTCACTGAAGCGGGAAGGGACTGGCTGCTATTGGGCGAAGTGCCGGGGCAGGATCTC

CTGTCATCTCACCTTGCTCCTGCCGAGAAAGTATCCATCATGGCTGATGCAATGCGGCGGCT

GCATACGCTTGATCCGGCTACCTGCCCATTCGACCACCAAGCGAAACATCGCATCGAGCGAG

CACGTACTCGGATGGAAGCCGGTCTTGTCGATCAGGATGATCTGGACGAAGAGCATCAGGGG

CTCGCGCCAGCCGAACTGTTCGCCAGGCTCAAGGCGCGCATGCCCGACGGCGAGGATCTCGT

CGTGACCCATGGCGATGCCTGCTTGCCGAATATCATGGTGGAAAATGGCCGCTTTTCTGGAT

TCATCGACTGTGGCCGGCTGGGTGTGGCGGACCGCTATCAGGACATAGCGTTGGCTACCCGT

GATATTGCTGAAGAGCTTGGCGGCGAATGGGCTGACCGCTTCCTCGTGCTTTACGGTATCGC

CGCTCCCGATTCGCAGCGCATCGCCTTCTATCGCCTTCTTGACGAGTTCTTCTGAGCGGGAC

TCTGGGGTTCGCGAAATGACCGACCAAGCGACGCCCAACCTGCCATCACGAGATTTCGATTC

CACCGCCGCCTTCTATGAAAGGTTGGGCTTCGGAATCGTTTTCCGGGACGCCGGCTGGATGA

TCCTCCAGCGCGGGGATCTCATGCTGGAGTTCTTCGCCCACCCCAACTTGTTTATTGCAGCT

TATAATGGTTACAAATAAAGCAATAGCATCACAAATTTCACAAATAAAGCATTTTTTTCACT

GCATTCTAGTTGTGGTTTGTCCAAACTCATCAATGTATCTTATCATGTCTGTATACCGTCGA

CCTCTAGCTAGAGCTTGGCGTAATCATGGTCATAGCTGTTTCCTGTGTGAAATTGTTATCCG

CTCACAATTCCACACAACATACGAGCCGGAAGCATAAAGTGTAAAGCCTGGGGTGCCTAATG

AGTGAGCTAACTCACATTAATTGCGTTGCGCTCACTGCCCGCTTTCCAGTCGGGAAACCTGT

CGTGCCAGCTGCATTAATGAATCGGCCAACGCGCGGGGAGAGGCGGTTTGCGTATTGGGCGC

TCTTCCGCTTCCTCGCTCACTGACTCGCTGCGCTCGGTCGTTCGGCTGCGGCGAGCGGTATC

AGCTCACTCAAAGGCGGTAATACGGTTATCCACAGAATCAGGGGATAACGCAGGAAAGAACA

TGTGAGCAAAAGGCCAGCAAAAGGCCAGGAACCGTAAAAAGGCCGCGTTGCTGGCGTTTTTC

-continued

CATAGGCTCCGCCCCCCTGACGAGCATCACAAAAATCGACGCTCAAGTCAGAGGTGGCGAAA

CCCGACAGGACTATAAAGATACCAGGCGTTTCCCCCTGGAAGCTCCCTCGTGCGCTCTCCTG

TTCCGACCCTGCCGCTTACCGGATACCTGTCCGCCTTTCTCCCTTCGGGAAGCGTGGCGCTT

TCTCAATGCTCACGCTGTAGGTATCTCAGTTCGGTGTAGGTCGTTCGCTCCAAGCTGGGCTG

TGTGCACGAACCCCCCGTTCAGCCCGACCGCTGCGCCTTATCCGGTAACTATCGTCTTGAGT

CCAACCCGGTAAGACACGACTTATCGCCACTGGCAGCAGCCACTGGTAACAGGATTAGCAGA

GCGAGGTATGTAGGCGGTGCTACAGAGTTCTTGAAGTGGTGGCCTAACTACGGCTACACTAG

AAGGACAGTATTTGGTATCTGCGCTCTGCTGAAGCCAGTTACCTTCGGAAAAAGAGTTGGTA

GCTCTTGATCCGGCAAACAAACCACCGCTGGTAGCGGTGGTTTTTTTGTTTGCAAGCAGCAG

ATTACGCGCAGAAAAAAAGGATCTCAAGAAGATCCTTTGATCTTTTCTACGGGGTCTGACGC

TCAGTGGAACGAAAACTCACGTTAAGGGATTTTGGTCATGAGATTATCAAAAAGGATCTTCA

CCTAGATCCTTTTAAATTAAAAATGAAGTTTTAAATCAATCTAAAGTATATATGAGTAAACT

TGGTCTGACAGTTACCAATGCTTAATCAGTGAGGCACCTATCTCAGCGATCTGTCTATTTCG

TTCATCCATAGTTGCCTGACTCCCCGTCGTGTAGATAACTACGATACGGGAGGGCTTACCAT

CTGGCCCCAGTGCTGCAATGATACCGCGAGACCCACGCTCACCGGCTCCAGATTTATCAGCA

ATAAACCAGCCAGCCGGAAGGGCCGAGCGCAGAAGTGGTCCTGCAACTTTATCCGCCTCCAT

CCAGTCTATTAATTGTTGCCGGGAAGCTAGAGTAAGTAGTTCGCCAGTTAATAGTTTGCGCA

ACGTTGTTGCCATTGCTACAGGCATCGTGGTGTCACGCTCGTCGTTTGGTATGGCTTCATTC

AGCTCCGGTTCCCAACGATCAAGGCGAGTTACATGATCCCCCATGTTGTGCAAAAAAGCGGT

TAGCTCCTTCGGTCCTCCGATCGTTGTCAGAAGTAAGTTGGCCGCAGTGTTATCACTCATGG

TTATGGCAGCACTGCATAATTCTCTTACTGTCATGCCATCCGTAAGATGCTTTTCTGTGACT

GGTGAGTACTCAACCAAGTCATTCTGAGAATAGTGTATGCGGCGACCGAGTTGCTCTTGCCC

GGCGTCAATACGGGATAATACCGCGCCACATAGCAGAACTTTAAAAGTGCTCATCATTGGAA

AACGTTCTTCGGGGCGAAAACTCTCAAGGATCTTACCGCTGTTGAGATCCAGTTCGATGTAA

CCCACTCGTGCACCCAACTGATCTTCAGCATCTTTTACTTTCACCAGCGTTTCTGGGTGAGC

AAAAACAGGAAGGCAAAATGCCGCAAAAAAGGGAATAAGGGCGACACGGAAATGTTGAATAC

TCATACTCTTCCTTTTTCAATATTATTGAAGCATTTATCAGGGTTATTGTCTCATGAGCGGA

TACATATTTGAATGTATTTAGAAAAATAAACAAATAGGGGTTCCGCGCACATTTCCCCGAAA

AGTGCCACCTGACGTCGACGGATCGGGAGATCTCCCGATCCCCTATGGTCGACTCTCAGTAC

AATCTGCTCTGATGCCGCATAGTTAAGCCAGTATCTGCTCCCTGCTTGTGTGTTGGAGGTCG

CTGAGTAGTGCGCGAGCAAAATTTAAGCTACAACAAGGCAAGGCTTGACCGACAATTGCATG

AAGAATCTGCTTAGG (SEQ ID NO: 103)

>p20F1.VE.hIgG4
GTTAGGCGTTTTGCGCTGCTTCGCGATGTACGGGCCAGATATACGCGTTGACATTGATTATT

GACTAGTTATTAATAGTAATCAATTACGGGGTCATTAGTTCATAGCCCATATATGGAGTTCC

GCGTTACATAACTTACGGTAAATGGCCCGCCTGGCTGACCGCCCAACGACCCCCGCCCATTG

ACGTCAATAATGACGTATGTTCCCATAGTAACGCCAATAGGGACTTTCCATTGACGTCAATG

GGTGGAGTATTTACGGTAAACTGCCCACTTGGCAGTACATCAAGTGTATCATATGCCAAGTA

CGCCCCCTATTGACGTCAATGACGGTAAATGGCCCGCCTGGCATTATGCCCAGTACATGACC

TTATGGGACTTTCCTACTTGGCAGTACATCTACGTATTAGTCATCGCTATTACCATGGTGAT

GCGGTTTTGGCAGTACATCAATGGGCGTGGATAGCGGTTTGACTCACGGGGATTTCCAAGTC

-continued

TCCACCCCATTGACGTCAATGGGAGTTTGTTTTGGCACCAAAATCAACGGGACTTTCCAAAA

TGTCGTAACAACTCCGCCCCATTGACGCAAATGGGCGGTAGGCGTGTACGGTGGGAGGTCTA

TATAAGCAGAGCTCGTTTAGTGAACCGTCAGATCGCCTGGAGACGCCATCCACGCTGTTTTG

ACCTCCATAGAAGACACCGGGACCGATCCAGCCTCCGGACTCTAGAGGATCGAACCCTTAAG

CTTGCCACC*ATGTACAGGATGCAACTCCTGTCTTGCATTGCACTAAGTCTTGCACTTGTCAC*

*GAATTC*GGAGGTCCAGCTGCAGCAGTCTGGCGCCGAACTTGTTAGACCTGGCGCTCTGGTCA

AGTGGTCCTGTAAAGCCAGCGGCTTCAACATCAAGGACTACCACATCCACTGGGTCAAGCAG

AGGCCTGAGCAGGGCCTCGATTGGATCGGCTGGATCGACCCCGAGATCGACAAGACCCTGTA

CGACCCCAAGTTCCAGGGCAAAGCCAGAATCACCGCCGACACCAGCAGCAACACAGCCTACC

TGCAACTGAGCAGCCTGACCAGCGAAGATACCGCCGTGTACTACTGCGCCAGAGGAACAGCC

AGAGCCAGCTTCGATTATTGGGGCCAGGGCACCACACTGACCGTGTCATCTGCTAGCACCAA

GGGCCCATCGGTCTTCCCCCTGGCGCCCTGCTCCAGGAGCACCTCCGAGAGCACAGCCGCCC

TGGGCTGCCTGGTCAAGGACTACTTCCCCGAACCGGTGACGGTGTCGTGGAACTCAGGCGCC

CTGACCAGCGGCGTGCACACCTTCCCGGCTGTCCTACAGTCCTCAGGACTCTACTCCCTCAG

CAGCGTGGTGACCGTGCCCTCCAGCAGCTTGGGCACGAAGACCTACACCTGCAACGTAGATC

ACAAGCCCAGCAACACCAAGGTGGACAAGAGAGTTGAGTCCAAATATGGTCCCCCATGCCCA

TCATGCCCAGCACCTGAGTTCCTGGGGGGACCATCAGTCTTCCTGTTCCCCCCAAAACCCAA

GGACACTCTCATGATCTCCCGGACCCCTGAGGTCACGTGCGTGGTGGTGGACGTGAGCCAGG

AAGACCCCGAGGTCCAGTTCAACTGGTACGTGGATGGCGTGGAGGTGCATAATGCCAAGACA

AAGCCGCGGGAGGAGCAGTTCAACAGCACGTACCGTGTGGTCAGCGTCCTCACCGTCCTGCA

CCAGGACTGGCTGAACGGCAAGGAGTACAAGTGCAAGGTCTCCAACAAAGGCCTCCCGTCCT

CCATCGAGAAAACCATCTCCAAAGCCAAAGGGCAGCCCCGAGAGCCACAGGTGTACACCCTG

CCCCCATCCCAGGAGGAGATGACCAAGAACCAGGTCAGCCTGACCTGCCTGGTCAAAGGCTT

CTACCCCAGCGACATCGCCGTGGAGTGGGAGAGCAATGGGCAGCCGGAGAACAACTACAAGA

CCACGCCTCCCGTGCTGGACTCCGACGGCTCCTTCTTCCTCTACAGCAGGCTAACCGTGGAC

AAGAGCAGGTGGCAGGAGGGGAATGTCTTCTCATGCTCCGTGATGCATGAGGCTCTGCACAA

CCACTACACACAGAAGAGCCTCTCCCTGTCTCTGGGTAAATAACCTAGCGTGGCATCTAGAC

ACTCTCGAGAAGGGTTCGATCCCTACCGGTTAGTAATGAGTTTGATATCTCGACAATCAACC

TCTGGATTACAAAATTTGTGAAAGATTGACTGGTATTCTTAACTATGTTGCTCCTTTTACGC

TATGTGGATACGCTGCTTTAATGCCTTTGTATCATGCTATTGCTTCCCGTATGGCTTTCATT

TTCTCCTCCTTGTATAAATCCTGGTTGCTGTCTCTTTATGAGGAGTTGTGGCCCGTTGTCAG

GCAACGTGGCGTGGTGTGCACTGTGTTTGCTGACGCAACCCCCACTGGTTGGGGCATTGCCA

CCACCTGTCAGCTCCTTTCCGGGACTTTCGCTTTCCCCCTCCCTATTGCCACGGCGGAACTC

ATCGCCGCCTGCCTTGCCCGCTGCTGGACAGGGGCTCGGCTGTTGGGCACTGACAATTCCGT

GGTGTTGTCGGGGAAGCTGACGTCCTTTCCATGGCTGCTCGCCTGTGTTGCCACCTGGATTC

TGCGCGGGACGTCCTTCTGCTACGTCCCTTCGGCCCTCAATCCAGCGGACCTTCCTTCCCGC

GGCCTGCTGCCGGCTCTGCGGCCTCTTCCGCGTCTTCGCCTTCGCCCTCAGACGAGTCGGAT

CTCCCTTTGGGCCGCCTCCCCGCCTGGAAACGGGGGAGGCTAACTGAAACACGGAAGGAGAC

AATACCGGAAGGAACCCGCGCTATGACGGCAATAAAAAGACAGAATAAAACGCACGGGTGTT

GGGTCGTTTGTTCATAAACGCGGGGTTCGGTCCCAGGGCTGGCACTCTGTCGATACCCCACC

-continued

GAGACCCCATTGGGGCCAATACGCCCGCGTTTCTTCCTTTTCCCCACCCCACCCCCCAAGTT

CGGGTGAAGGCCCAGGGCTCGCAGCCAACGTCGGGGCGGCAGGCCCTGCCATAGCAGATCTG

CGCAGCTGGGGCTCTAGGGGGTATCCCCACGCGCCCTGTAGCGGCGCATTAAGCGCGGCGGG

TGTGGTGGTTACGCGCAGCGTGACCGCTACACTTGCCAGCGCCCTAGCGCCCGCTCCTTTCG

CTTTCTTCCCTTCCTTTCTCGCCACGTTCGCCGGCTTTCCCCGTCAAGCTCTAAATCGGGGC

ATCCCTTTAGGGTTCCGATTTAGTGCTTTACGGCACCTCGACCCCAAAAAACTTGATTAGGG

TGATGGTTCACGTAGTGGGCCATCGCCCTGATAGACGGTTTTTCGCCCTTTGACGTTGGAGT

CCACGTTCTTTAATAGTGGACTCTTGTTCCAAACTGGAACAACACTCAACCCTATCTCGGTC

TATTCTTTTGATTTATAAGGGATTTTGGGGATTTCGGCCTATTGGTTAAAAAATGAGCTGAT

TTAACAAAAATTTAACGCGAATTAATTCTGTGGAATGTGTGTCAGTTAGGGTGTGGAAAGTC

CCCAGGCTCCCCAGCAGGCAGAAGTATGCAAAGCATGCATCTCAATTAGTCAGCAACCAGGT

GTGGAAAGTCCCCAGGCTCCCCAGCAGGCAGAAGTATGCAAAGCATGCATCTCAATTAGTCA

GCAACCATAGTCCCGCCCCTAACTCCGCCCATCCCGCCCCTAACTCCGCCCAGTTCCGCCCA

TTCTCCGCCCCATGGCTGACTAATTTTTTTTATTTATGCAGAGGCCGAGGCCGCCTCTGCCT

CTGAGCTATTCCAGAAGTAGTGAGGAGGCTTTTTTGGAGGCCTAGGCTTTTGCAAAAAGCTC

CCGGGAGCTTGTATATCCATTTTCGGATCTGATCAAGAGACAGGATGAGGATCGTTTCGCAT

GATTGAACAAGATGGATTGCACGCAGGTTCTCCGGCCGCTTGGGTGGAGAGGCTATTCGGCT

ATGACTGGGCACAACAGACAATCGGCTGCTCTGATGCCGCCGTGTTCCGGCTGTCAGCGCAG

GGGCGCCCGGTTCTTTTTGTCAAGACCGACCTGTCCGGTGCCCTGAATGAACTGCAGGACGA

GGCAGCGCGGCTATCGTGGCTGGCCACGACGGGCGTTCCTTGCGCAGCTGTGCTCGACGTTG

TCACTGAAGCGGGAAGGGACTGGCTGCTATTGGGCGAAGTGCCGGGGCAGGATCTCCTGTCA

TCTCACCTTGCTCCTGCCGAGAAAGTATCCATCATGGCTGATGCAATGCGGCGGCTGCATAC

GCTTGATCCGGCTACCTGCCCATTCGACCACCAAGCGAAACATCGCATCGAGCGAGCACGTA

CTCGGATGGAAGCCGGTCTTGTCGATCAGGATGATCTGGACGAAGAGCATCAGGGGCTCGCG

CCAGCCGAACTGTTCGCCAGGCTCAAGGCGCGCATGCCCGACGGCGAGGATCTCGTCGTGAC

CCATGGCGATGCCTGCTTGCCGAATATCATGGTGGAAAATGGCCGCTTTTCTGGATTCATCG

ACTGTGGCCGGCTGGGTGTGGCGGACCGCTATCAGGACATAGCGTTGGCTACCCGTGATATT

GCTGAAGAGCTTGGCGGCGAATGGGCTGACCGCTTCCTCGTGCTTTACGGTATCGCCGCTCC

CGATTCGCAGCGCATCGCCTTCTATCGCCTTCTTGACGAGTTCTTCTGAGCGGGACTCTGGG

GTTCGCGAAATGACCGACCAAGCGACGCCCAACCTGCCATCACGAGATTTCGATTCCACCGC

CGCCTTCTATGAAAGGTTGGGCTTCGGAATCGTTTTCCGGGACGCCGGCTGGATGATCCTCC

AGCGCGGGGATCTCATGCTGGAGTTCTTCGCCCACCCCAACTTGTTTATTGCAGCTTATAAT

GGTTACAAATAAAGCAATAGCATCACAAATTTCACAAATAAAGCATTTTTTTCACTGCATTC

TAGTTGTGGTTTGTCCAAACTCATCAATGTATCTTATCATGTCTGTATACCGTCGACCTCTA

GCTAGAGCTTGGCGTAATCATGGTCATAGCTGTTTCCTGTGTGAAATTGTTATCCGCTCACA

ATTCCACACAACATACGAGCCGGAAGCATAAAGTGTAAAGCCTGGGGTGCCTAATGAGTGAG

CTAACTCACATTAATTGCGTTGCGCTCACTGCCCGCTTTCCAGTCGGGAAACCTGTCGTGCC

AGCTGCATTAATGAATCGGCCAACGCGCGGGGAGAGGCGGTTTGCGTATTGGGCGCTCTTCC

GCTTCCTCGCTCACTGACTCGCTGCGCTCGGTCGTTCGGCTGCGGCGAGCGGTATCAGCTCA

CTCAAAGGCGGTAATACGGTTATCCACAGAATCAGGGGATAACGCAGGAAAGAACATGTGAG

CAAAAGGCCAGCAAAAGGCCAGGAACCGTAAAAAGGCCGCGTTGCTGGCGTTTTTCCATAGG

-continued

CTCCGCCCCCCTGACGAGCATCACAAAAATCGACGCTCAAGTCAGAGGTGGCGAAACCCGAC

AGGACTATAAAGATACCAGGCGTTTCCCCCTGGAAGCTCCCTCGTGCGCTCTCCTGTTCCGA

CCCTGCCGCTTACCGGATACCTGTCCGCCTTTCTCCCTTCGGGAAGCGTGGCGCTTTCTCAA

TGCTCACGCTGTAGGTATCTCAGTTCGGTGTAGGTCGTTCGCTCCAAGCTGGGCTGTGTGCA

CGAACCCCCCGTTCAGCCCGACCGCTGCGCCTTATCCGGTAACTATCGTCTTGAGTCCAACC

CGGTAAGACACGACTTATCGCCACTGGCAGCAGCCACTGGTAACAGGATTAGCAGAGCGAGG

TATGTAGGCGGTGCTACAGAGTTCTTGAAGTGGTGGCCTAACTACGGCTACACTAGAAGGAC

AGTATTTGGTATCTGCGCTCTGCTGAAGCCAGTTACCTTCGGAAAAAGAGTTGGTAGCTCTT

GATCCGGCAAACAAACCACCGCTGGTAGCGGTGGTTTTTTTGTTTGCAAGCAGCAGATTACG

CGCAGAAAAAAAGGATCTCAAGAAGATCCTTTGATCTTTTCTACGGGGTCTGACGCTCAGTG

GAACGAAAACTCACGTTAAGGGATTTTGGTCATGAGATTATCAAAAAGGATCTTCACCTAGA

TCCTTTTAAATTAAAAATGAAGTTTTAAATCAATCTAAAGTATATATGAGTAAACTTGGTCT

GACAGTTACCAATGCTTAATCAGTGAGGCACCTATCTCAGCGATCTGTCTATTTCGTTCATC

CATAGTTGCCTGACTCCCCGTCGTGTAGATAACTACGATACGGGAGGGCTTACCATCTGGCC

CCAGTGCTGCAATGATACCGCGAGACCCACGCTCACCGGCTCCAGATTTATCAGCAATAAAC

CAGCCAGCCGGAAGGGCCGAGCGCAGAAGTGGTCCTGCAACTTTATCCGCCTCCATCCAGTC

TATTAATTGTTGCCGGGAAGCTAGAGTAAGTAGTTCGCCAGTTAATAGTTTGCGCAACGTTG

TTGCCATTGCTACAGGCATCGTGGTGTCACGCTCGTCGTTTGGTATGGCTTCATTCAGCTCC

GGTTCCCAACGATCAAGGCGAGTTACATGATCCCCCATGTTGTGCAAAAAAGCGGTTAGCTC

CTTCGGTCCTCCGATCGTTGTCAGAAGTAAGTTGGCCGCAGTGTTATCACTCATGGTTATGG

CAGCACTGCATAATTCTCTTACTGTCATGCCATCCGTAAGATGCTTTTCTGTGACTGGTGAG

TACTCAACCAAGTCATTCTGAGAATAGTGTATGCGGCGACCGAGTTGCTCTTGCCCGGCGTC

AATACGGGATAATACCGCGCCACATAGCAGAACTTTAAAAGTGCTCATCATTGGAAAACGTT

CTTCGGGGCGAAAACTCTCAAGGATCTTACCGCTGTTGAGATCCAGTTCGATGTAACCCACT

CGTGCACCCAACTGATCTTCAGCATCTTTTACTTTCACCAGCGTTTCTGGGTGAGCAAAAAC

AGGAAGGCAAAATGCCGCAAAAAAGGGAATAAGGGCGACACGGAAATGTTGAATACTCATAC

TCTTCCTTTTTCAATATTATTGAAGCATTTATCAGGGTTATTGTCTCATGAGCGGATACATA

TTTGAATGTATTTAGAAAAATAAACAAATAGGGGTTCCGCGCACATTTCCCCGAAAAGTGCC

ACCTGACGTCGACGGATCGGGAGATCTCCCGATCCCCTATGGTCGACTCTCAGTACAATCTG

CTCTGATGCCGCATAGTTAAGCCAGTATCTGCTCCCTGCTTGTGTGTTGGAGGTCGCTGAGT

AGTGCGCGAGCAAAATTTAAGCTACAACAAGGCAAGGCTTGACCGACAATTGCATGAAGAAT

CTGCTTAGG (SEQ ID NO: 104)

Sequences of expression vectors for mAb 7C11.1 IgG2/kappa:
>p7C11.1.VL.hk
GTTAGGCGTTTTGCGCTGCTTCGCGATGTACGGGCCAGATATACGCGTTGACATTGATTATT

GACTAGTTATTAATAGTAATCAATTACGGGGTCATTAGTTCATAGCCCATATATGGAGTTCC

GCGTTACATAACTTACGGTAAATGGCCCGCCTGGCTGACCGCCCAACGACCCCCGCCCATTG

ACGTCAATAATGACGTATGTTCCCATAGTAACGCCAATAGGGACTTTCCATTGACGTCAATG

GGTGGAGTATTTACGGTAAACTGCCCACTTGGCAGTACATCAAGTGTATCATATGCCAAGTA

CGCCCCCTATTGACGTCAATGACGGTAAATGGCCCGCCTGGCATTATGCCCAGTACATGACC

TTATGGGACTTTCCTACTTGGCAGTACATCTACGTATTAGTCATCGCTATTACCATGGTGAT

-continued

GCGGTTTTGGCAGTACATCAATGGGCGTGGATAGCGGTTTGACTCACGGGGATTTCCAAGTC

TCCACCCCATTGACGTCAATGGGAGTTTGTTTTGGCACCAAAATCAACGGGACTTTCCAAAA

TGTCGTAACAACTCCGCCCCATTGACGCAAATGGGCGGTAGGCGTGTACGGTGGGAGGTCTA

TATAAGCAGAGCTCGTTTAGTGAACCGTCAGATCGCCTGGAGACGCCATCCACGCTGTTTTG

ACCTCCATAGAAGACACCGGGACCGATCCAGCCTCCGGACTCTAGAGGATCGAACCCTTAAG

CTTGCCACC*ATGTACAGGATGCAACTCCTGTCTTGCATTGCACTAAGTCTTGCACTTGTCAC*

*GAATTCA*GACAACGTGCTGACACAGAGCCCTGCCAGCCTGGCTGTTTCTCTGGGACAGAGAG

CCACCATCAGCTGCAAGGCCAGCCAGAGCGTTGACTACGACGGCGACAGCTACATGAACTGG

TATCAGCAGAAGCCCGGCCAGCCACCTAAGGTGTTCATCTACGCCGCCAGCAACCTGGAAAG

CGGCATCCCTGCCAGATTTTCTGGCTCTGGCAGCGGCACCAACTTCACCCTGAACATTCACC

CCGTGGAAGAAGAGGACGCCGCCACCTACTACTGCCAGCAGAGCAATGAGGACCCCTGGACA

TTTGGCGGAGGCACCAAGCTGGAAATCAAGCGTACGGTGGCTGCACCATCTGTCTTCATCTT

CCCGCCATCTGATGAGCAGTTGAAATCTGGAACTGCCTCTGTTGTGTGCCTGCTGAATAACT

TCTATCCCAGAGAGGCCAAAGTACAGTGGAAGGTGGATAACGCCCTCCAATCGGGTAACTCC

CAGGAGAGTGTCACAGAGCAGGACAGCAAGGACAGCACCTACAGCCTCAGCAGCACCCTGAC

GCTGAGCAAAGCAGACTACGAGAAACACAAAGTCTACGCCTGCGAAGTCACCCATCAGGGCC

TGAGCTCGCCCGTCACAAAGAGCTTCAACAGGGGAGAGTGTTAGAGGGAGCTAGCGTGGCAT

CTAGACACTCTCGAGAAGGGTTCGATCCCTACCGGTTAGTAATGAGTTTGATATCTCGACAA

TCAACCTCTGGATTACAAAATTTGTGAAAGATTGACTGGTATTCTTAACTATGTTGCTCCTT

TTACGCTATGTGGATACGCTGCTTTAATGCCTTTGTATCATGCTATTGCTTCCCGTATGGCT

TTCATTTTCTCCTCCTTGTATAAATCCTGGTTGCTGTCTCTTTATGAGGAGTTGTGGCCCGT

TGTCAGGCAACGTGGCGTGGTGTGCACTGTGTTTGCTGACGCAACCCCCACTGGTTGGGGCA

TTGCCACCACCTGTCAGCTCCTTTCCGGGACTTTCGCTTTCCCCCTCCCTATTGCCACGGCG

GAACTCATCGCCGCCTGCCTTGCCCGCTGCTGGACAGGGGCTCGGCTGTTGGGCACTGACAA

TTCCGTGGTGTTGTCGGGGAAGCTGACGTCCTTTCCATGGCTGCTCGCCTGTGTTGCCACCT

GGATTCTGCGCGGGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCGCCCTCAGACGAG

TCGGATCTCCCTTTGGGCCGCCTCCCCGCCTGGAAACGGGGGAGGCTAACTGAAACACGGAA

GGAGACAATACCGGAAGGAACCCGCGCTATGACGGCAATAAAAAGACAGAATAAAACGCACG

GGTGTTGGGTCGTTTGTTCATAAACGCGGGGTTCGGTCCCAGGGCTGGCACTCTGTCGATAC

CCCACCGAGACCCCATTGGGGCCAATACGCCCGCGTTTCTTCCTTTTCCCCACCCCACCCCC

CAAGTTCGGGTGAAGGCCCAGGGCTCGCAGCCAACGTCGGGGCGGCAGGCCCTGCCATAGCA

GATCTGCGCAGCTGGGGCTCTAGGGGGTATCCCCACGCGCCCTGTAGCGGCGCATTAAGCGC

GGCGGGTGTGGTGGTTACGCGCAGCGTGACCGCTACACTTGCCAGCGCCCTAGCGCCCGCTC

CTTTCGCTTTCTTCCCTTCCTTTCTCGCCACGTTCGCCGGCTTTCCCCGTCAAGCTCTAAAT

CGGGGCATCCCTTTAGGGTTCCGATTTAGTGCTTTACGGCACCTCGACCCCAAAAAACTTGA

TTAGGGTGATGGTTCACGTAGTGGGCCATCGCCCTGATAGACGGTTTTTCGCCCTTTGACGT

TGGAGTCCACGTTCTTTAATAGTGGACTCTTGTTCCAAACTGGAACAACACTCAACCCTATC

TCGGTCTATTCTTTTGATTTATAAGGGATTTGGGGATTTCGGCCTATTGGTTAAAAAATGA

GCTGATTTAACAAAAATTTAACGCGAATTAATTCTGTGGAATGTGTGTCAGTTAGGGTGTGG

AAAGTCCCCAGGCTCCCCAGCAGGCAGAAGTATGCAAAGCATGCATCTCAATTAGTCAGCAA

-continued

CCAGGTGTGGAAAGTCCCCAGGCTCCCCAGCAGGCAGAAGTATGCAAAGCATGCATCTCAAT

TAGTCAGCAACCATAGTCCCGCCCCTAACTCCGCCCATCCCGCCCCTAACTCCGCCCAGTTC

CGCCCATTCTCCGCCCCATGGCTGACTAATTTTTTTTATTTATGCAGAGGCCGAGGCCGCCT

CTGCCTCTGAGCTATTCCAGAAGTAGTGAGGAGGCTTTTTTGGAGGCCTAGGCTTTTGCAAA

AAGCTCCCGGGAGCTTGTATATCCATTTTCGGATCTGATCAAGAGACAGGATGAGGATCGTT

TCGCATGATTGAACAAGATGGATTGCACGCAGGTTCTCCGGCCGCTTGGGTGGAGAGGCTAT

TCGGCTATGACTGGGCACAACAGACAATCGGCTGCTCTGATGCCGCCGTGTTCCGGCTGTCA

GCGCAGGGGCGCCCGGTTCTTTTTGTCAAGACCGACCTGTCCGGTGCCCTGAATGAACTGCA

GGACGAGGCAGCGCGGCTATCGTGGCTGGCCACGACGGGCGTTCCTTGCGCAGCTGTGCTCG

ACGTTGTCACTGAAGCGGGAAGGGACTGGCTGCTATTGGGCGAAGTGCCGGGGCAGGATCTC

CTGTCATCTCACCTTGCTCCTGCCGAGAAAGTATCCATCATGGCTGATGCAATGCGGCGGCT

GCATACGCTTGATCCGGCTACCTGCCCATTCGACCACCAAGCGAAACATCGCATCGAGCGAG

CACGTACTCGGATGGAAGCCGGTCTTGTCGATCAGGATGATCTGGACGAAGAGCATCAGGGG

CTCGCGCCAGCCGAACTGTTCGCCAGGCTCAAGGCGCGCATGCCCGACGGCGAGGATCTCGT

CGTGACCCATGGCGATGCCTGCTTGCCGAATATCATGGTGGAAAATGGCCGCTTTTCTGGAT

TCATCGACTGTGGCCGGCTGGGTGTGGCGGACCGCTATCAGGACATAGCGTTGGCTACCCGT

GATATTGCTGAAGAGCTTGGCGGCGAATGGGCTGACCGCTTCCTCGTGCTTTACGGTATCGC

CGCTCCCGATTCGCAGCGCATCGCCTTCTATCGCCTTCTTGACGAGTTCTTCTGAGCGGGAC

TCTGGGGTTCGCGAAATGACCGACCAAGCGACGCCCAACCTGCCATCACGAGATTTCGATTC

CACCGCCGCCTTCTATGAAAGGTTGGGCTTCGGAATCGTTTTCCGGGACGCCGGCTGGATGA

TCCTCCAGCGCGGGGATCTCATGCTGGAGTTCTTCGCCCACCCCAACTTGTTTATTGCAGCT

TATAATGGTTACAAATAAAGCAATAGCATCACAAATTTCACAAATAAAGCATTTTTTTCACT

GCATTCTAGTTGTGGTTTGTCCAAACTCATCAATGTATCTTATCATGTCTGTATACCGTCGA

CCTCTAGCTAGAGCTTGGCGTAATCATGGTCATAGCTGTTTCCTGTGTGAAATTGTTATCCG

CTCACAATTCCACACAACATACGAGCCGGAAGCATAAAGTGTAAAGCCTGGGGTGCCTAATG

AGTGAGCTAACTCACATTAATTGCGTTGCGCTCACTGCCCGCTTTCCAGTCGGGAAACCTGT

CGTGCCAGCTGCATTAATGAATCGGCCAACGCGCGGGGAGAGGCGGTTTGCGTATTGGGCGC

TCTTCCGCTTCCTCGCTCACTGACTCGCTGCGCTCGGTCGTTCGGCTGCGGCGAGCGGTATC

AGCTCACTCAAAGGCGGTAATACGGTTATCCACAGAATCAGGGGATAACGCAGGAAAGAACA

TGTGAGCAAAAGGCCAGCAAAAGGCCAGGAACCGTAAAAAGGCCGCGTTGCTGGCGTTTTTC

CATAGGCTCCGCCCCCCTGACGAGCATCACAAAAATCGACGCTCAAGTCAGAGGTGGCGAAA

CCCGACAGGACTATAAAGATACCAGGCGTTTCCCCCTGGAAGCTCCCTCGTGCGCTCTCCTG

TTCCGACCCTGCCGCTTACCGGATACCTGTCCGCCTTTCTCCCTTCGGGAAGCGTGGCGCTT

TCTCAATGCTCACGCTGTAGGTATCTCAGTTCGGTGTAGGTCGTTCGCTCCAAGCTGGGCTG

TGTGCACGAACCCCCCGTTCAGCCCGACCGCTGCGCCTTATCCGGTAACTATCGTCTTGAGT

CCAACCCGGTAAGACACGACTTATCGCCACTGGCAGCAGCCACTGGTAACAGGATTAGCAGA

GCGAGGTATGTAGGCGGTGCTACAGAGTTCTTGAAGTGGTGGCCTAACTACGGCTACACTAG

AAGGACAGTATTTGGTATCTGCGCTCTGCTGAAGCCAGTTACCTTCGGAAAAAGAGTTGGTA

GCTCTTGATCCGGCAAACAAACCACCGCTGGTAGCGGTGGTTTTTTTGTTTGCAAGCAGCAG

ATTACGCGCAGAAAAAAAGGATCTCAAGAAGATCCTTTGATCTTTTCTACGGGGTCTGACGC

-continued

TCAGTGGAACGAAAACTCACGTTAAGGGATTTTGGTCATGAGATTATCAAAAAGGATCTTCA

CCTAGATCCTTTTAAATTAAAAATGAAGTTTTAAATCAATCTAAAGTATATATGAGTAAACT

TGGTCTGACAGTTACCAATGCTTAATCAGTGAGGCACCTATCTCAGCGATCTGTCTATTTCG

TTCATCCATAGTTGCCTGACTCCCCGTCGTGTAGATAACTACGATACGGGAGGGCTTACCAT

CTGGCCCCAGTGCTGCAATGATACCGCGAGACCCACGCTCACCGGCTCCAGATTTATCAGCA

ATAAACCAGCCAGCCGGAAGGGCCGAGCGCAGAAGTGGTCCTGCAACTTTATCCGCCTCCAT

CCAGTCTATTAATTGTTGCCGGGAAGCTAGAGTAAGTAGTTCGCCAGTTAATAGTTTGCGCA

ACGTTGTTGCCATTGCTACAGGCATCGTGGTGTCACGCTCGTCGTTTGGTATGGCTTCATTC

AGCTCCGGTTCCCAACGATCAAGGCGAGTTACATGATCCCCCATGTTGTGCAAAAAAGCGGT

TAGCTCCTTCGGTCCTCCGATCGTTGTCAGAAGTAAGTTGGCCGCAGTGTTATCACTCATGG

TTATGGCAGCACTGCATAATTCTCTTACTGTCATGCCATCCGTAAGATGCTTTTCTGTGACT

GGTGAGTACTCAACCAAGTCATTCTGAGAATAGTGTATGCGGCGACCGAGTTGCTCTTGCCC

GGCGTCAATACGGGATAATACCGCGCCACATAGCAGAACTTTAAAAGTGCTCATCATTGGAA

AACGTTCTTCGGGGCGAAAACTCTCAAGGATCTTACCGCTGTTGAGATCCAGTTCGATGTAA

CCCACTCGTGCACCCAACTGATCTTCAGCATCTTTTACTTTCACCAGCGTTTCTGGGTGAGC

AAAAACAGGAAGGCAAAATGCCGCAAAAAAGGGAATAAGGGCGACACGGAAATGTTGAATAC

TCATACTCTTCCTTTTTCAATATTATTGAAGCATTTATCAGGGTTATTGTCTCATGAGCGGA

TACATATTTGAATGTATTTAGAAAAATAAACAAATAGGGGTTCCGCGCACATTTCCCCGAAA

AGTGCCACCTGACGTCGACGGATCGGGAGATCTCCCGATCCCCTATGGTCGACTCTCAGTAC

AATCTGCTCTGATGCCGCATAGTTAAGCCAGTATCTGCTCCCTGCTTGTGTGTTGGAGGTCG

CTGAGTAGTGCGCGAGCAAAATTTAAGCTACAACAAGGCAAGGCTTGACCGACAATTGCATG

AAGAATCTGCTTAGG (SEQ ID NO: 105)

>p7C11.1.VH.hIgG2

GTTAGGCGTTTTGCGCTGCTTCGCGATGTACGGGCCAGATATACGCGTTGACATTGATTATT

GACTAGTTATTAATAGTAATCAATTACGGGGTCATTAGTTCATAGCCCATATATGGAGTTCC

GCGTTACATAACTTACGGTAAATGGCCCGCCTGGCTGACCGCCCAACGACCCCCGCCCATTG

ACGTCAATAATGACGTATGTTCCCATAGTAACGCCAATAGGGACTTTCCATTGACGTCAATG

GGTGGAGTATTTACGGTAAACTGCCCACTTGGCAGTACATCAAGTGTATCATATGCCAAGTA

CGCCCCCTATTGACGTCAATGACGGTAAATGGCCCGCCTGGCATTATGCCCAGTACATGACC

TTATGGGACTTTCCTACTTGGCAGTACATCTACGTATTAGTCATCGCTATTACCATGGTGAT

GCGGTTTTGGCAGTACATCAATGGGCGTGGATAGCGGTTTGACTCACGGGGATTTCCAAGTC

TCCACCCCATTGACGTCAATGGGAGTTTGTTTTGGCACCAAAATCAACGGGACTTTCCAAAA

TGTCGTAACAACTCCGCCCCATTGACGCAAATGGGCGGTAGGCGTGTACGGTGGGAGGTCTA

TATAAGCAGAGCTCGTTTAGTGAACCGTCAGATCGCCTGGAGACGCCATCCACGCTGTTTTG

ACCTCCATAGAAGACACCGGGACCGATCCAGCCTCCGGACTCTAGAGGATCGAACCCTTAAG

CTTGCCACC*ATGTACAGGATGCAACTCCTGTCTTGCATTGCACTAAGTCTTGCACTTGTCAC*

*GAATTC*GGAAGTGAAGCTGGTGGAAAGCGGCGGAGGACTGGTTCAACCTGGCGGATCTCTGA

AGCTGAGCTGTGCCGCCAGCGGCTTCACCTTCAGCAGATACACAATGAGCTGGGTCCGACAG

ACCCCTGAGAAGAGACTGGAATGGGTCGCCAAGATCAGAAACGTCGGCGGCATCACCTACTA

TCCCGACACCGTGAAGGGCAGATTCACCATCTCCAGAGACAACGCCAAGAACACCCTGTACC

TGCAGATGAGCAGCCTGAAGTCCGAGGACACCGCCATGTACTACTGCGCCAGACACTACTAC

-continued

GGCAGCGAGGACTACTTCGACTATTGGGGCCAGGGCACCACACTGACCGTTAGCTCTGCTAG

CACCAAGGGCCCATCGGTCTTCCCCCTGGCGCCCTGCTCCAGGAGCACCTCCGAGAGCACAG

CGGCCCTGGGCTGCCTGGTCAAGGACTACTTCCCCGAACCGGTGACGGTGTCGTGGAACTCA

GGCGCTCTGACCAGCGGCGTGCACACCTTCCCAGCTGTCCTACAGTCCTCAGGACTCTACTC

CCTCAGCAGCGTGGTGACCGTGCCCTCCAGCAACTTCGGCACCCAGACCTACACCTGCAACG

TAGATCACAAGCCCAGCAACACCAAGGTGGACAAGACAGTTGAGCGCAAATGTTGTGTCGAG

TGCCCACCGTGCCCAGCACCACCTGTGGCAGGACCGTCAGTCTTCCTCTTCCCCCCAAAACC

CAAGGACACCCTCATGATCTCCCGGACCCCTGAGGTCACGTGCGTGGTGGTGGACGTGAGCC

ACGAAGACCCCGAGGTCCAGTTCAACTGGTACGTGGACGGCGTGGAGGTGCATAATGCCAAG

ACAAAGCCACGGGAGGAGCAGTTCAACAGCACGTTCCGTGTGGTCAGCGTCCTCACCGTTGT

GCACCAGGACTGGCTGAACGGCAAGGAGTACAAGTGCAAGGTCTCCAACAAAGGCCTCCCAG

CCCCCATCGAGAAAACCATCTCCAAAACCAAAGGGCAGCCCCGAGAACCACAGGTGTACACC

CTGCCCCCATCCCGGGAGGAGATGACCAAGAACCAGGTCAGCCTGACCTGCCTGGTCAAAGG

CTTCTACCCCAGCGACATCGCCGTGGAGTGGGAGAGCAATGGGCAGCCGGAGAACAACTACA

AGACCACGCCTCCCATGCTGGACTCCGACGGCTCCTTCTTCCTCTACAGCAAGCTCACCGTG

GACAAGAGCAGGTGGCAGCAGGGGAACGTCTTCTCATGCTCCGTGATGCATGAGGCTCTGCA

CAACCACTACACGCAGAAGAGCCTCTCCCTGTCTCCGGGTAAATGACCTAGCGTGGCATCTA

GACACTCTCGAGAAGGGTTCGATCCCTACCGGTTAGTAATGAGTTTGATATCTCGACAATCA

ACCTCTGGATTACAAAATTTGTGAAAGATTGACTGGTATTCTTAACTATGTTGCTCCTTTTA

CGCTATGTGGATACGCTGCTTTAATGCCTTTGTATCATGCTATTGCTTCCCGTATGGCTTTC

ATTTTCTCCTCCTTGTATAAATCCTGGTTGCTGTCTCTTTATGAGGAGTTGTGGCCCGTTGT

CAGGCAACGTGGCGTGGTGTGCACTGTGTTTGCTGACGCAACCCCCACTGGTTGGGGCATTG

CCACCACCTGTCAGCTCCTTTCCGGGACTTTCGCTTTCCCCCTCCCTATTGCCACGGCGGAA

CTCATCGCCGCCTGCCTTGCCCGCTGCTGGACAGGGGCTCGGCTGTTGGGCACTGACAATTC

CGTGGTGTTGTCGGGGAAGCTGACGTCCTTTCCATGGCTGCTCGCCTGTGTTGCCACCTGGA

TTCTGCGCGGGACGTCCTTCTGCTACGTCCCTTCGGCCCTCAATCCAGCGGACCTTCCTTCC

CGCGGCCTGCTGCCGGCTCTGCGGCCTCTTCCGCGTCTTCGCCTTCGCCCTCAGACGAGTCG

GATCTCCCTTTGGGCCGCCTCCCCGCCTGGAAACGGGGGAGGCTAACTGAAACACGGAAGGA

GACAATACCGGAAGGAACCCGCGCTATGACGGCAATAAAAAGACAGAATAAAACGCACGGGT

GTTGGGTCGTTTGTTCATAAACGCGGGGTTCGGTCCCAGGGCTGGCACTCTGTCGATACCCC

ACCGAGACCCCATTGGGGCCAATACGCCCGCGTTTCTTCCTTTTCCCCACCCCACCCCCCAA

GTTCGGGTGAAGGCCCAGGGCTCGCAGCCAACGTCGGGGCGGCAGGCCCTGCCATAGCAGAT

CTGCGCAGCTGGGGCTCTAGGGGGTATCCCCACGCGCCCTGTAGCGGCGCATTAAGCGCGGC

GGGTGTGGTGGTTACGCGCAGCGTGACCGCTACACTTGCCAGCGCCCTAGCGCCCGCTCCTT

TCGCTTTCTTCCCTTCCTTTCTCGCCACGTTCGCCGGCTTTCCCCGTCAAGCTCTAAATCGG

GGCATCCCTTTAGGGTTCCGATTTAGTGCTTTACGGCACCTCGACCCCAAAAAACTTGATTA

GGGTGATGGTTCACGTAGTGGGCCATCGCCCTGATAGACGGTTTTTCGCCCTTTGACGTTGG

AGTCCACGTTCTTTAATAGTGGACTCTTGTTCCAAACTGGAACAACACTCAACCCTATCTCG

GTCTATTCTTTTGATTTATAAGGGATTTTGGGGATTTCGGCCTATTGGTTAAAAAATGAGCT

GATTTAACAAAAATTTAACGCGAATTAATTCTGTGGAATGTGTGTCAGTTAGGGTGTGGAAA

GTCCCCAGGCTCCCCAGCAGGCAGAAGTATGCAAAGCATGCATCTCAATTAGTCAGCAACCA

-continued

GGTGTGGAAAGTCCCCAGGCTCCCCAGCAGGCAGAAGTATGCAAAGCATGCATCTCAATTAG

TCAGCAACCATAGTCCCGCCCCTAACTCCGCCCATCCCGCCCCTAACTCCGCCCAGTTCCGC

CCATTCTCCGCCCCATGGCTGACTAATTTTTTTTATTTATGCAGAGGCCGAGGCCGCCTCTG

CCTCTGAGCTATTCCAGAAGTAGTGAGGAGGCTTTTTTGGAGGCCTAGGCTTTTGCAAAAAG

CTCCCGGGAGCTTGTATATCCATTTTCGGATCTGATCAAGAGACAGGATGAGGATCGTTTCG

CATGATTGAACAAGATGGATTGCACGCAGGTTCTCCGGCCGCTTGGGTGGAGAGGCTATTCG

GCTATGACTGGGCACAACAGACAATCGGCTGCTCTGATGCCGCCGTGTTCCGGCTGTCAGCG

CAGGGGCGCCCGGTTCTTTTTGTCAAGACCGACCTGTCCGGTGCCCTGAATGAACTGCAGGA

CGAGGCAGCGCGGCTATCGTGGCTGGCCACGACGGGCGTTCCTTGCGCAGCTGTGCTCGACG

TTGTCACTGAAGCGGGAAGGGACTGGCTGCTATTGGGCGAAGTGCCGGGGCAGGATCTCCTG

TCATCTCACCTTGCTCCTGCCGAGAAAGTATCCATCATGGCTGATGCAATGCGGCGGCTGCA

TACGCTTGATCCGGCTACCTGCCCATTCGACCACCAAGCGAAACATCGCATCGAGCGAGCAC

GTACTCGGATGGAAGCCGGTCTTGTCGATCAGGATGATCTGGACGAAGAGCATCAGGGGCTC

GCGCCAGCCGAACTGTTCGCCAGGCTCAAGGCGCGCATGCCCGACGGCGAGGATCTCGTCGT

GACCCATGGCGATGCCTGCTTGCCGAATATCATGGTGGAAAATGGCCGCTTTTCTGGATTCA

TCGACTGTGGCCGGCTGGGTGTGGCGGACCGCTATCAGGACATAGCGTTGGCTACCCGTGAT

ATTGCTGAAGAGCTTGGCGGCGAATGGGCTGACCGCTTCCTCGTGCTTTACGGTATCGCCGC

TCCCGATTCGCAGCGCATCGCCTTCTATCGCCTTCTTGACGAGTTCTTCTGAGCGGGACTCT

GGGGTTCGCGAAATGACCGACCAAGCGACGCCCAACCTGCCATCACGAGATTTCGATTCCAC

CGCCGCCTTCTATGAAAGGTTGGGCTTCGGAATCGTTTTCCGGGACGCCGGCTGGATGATCC

TCCAGCGCGGGGATCTCATGCTGGAGTTCTTCGCCCACCCCAACTTGTTTATTGCAGCTTAT

AATGGTTACAAATAAAGCAATAGCATCACAAATTTCACAAATAAAGCATTTTTTTCACTGCA

TTCTAGTTGTGGTTTGTCCAAACTCATCAATGTATCTTATCATGTCTGTATACCGTCGACCT

CTAGCTAGAGCTTGGCGTAATCATGGTCATAGCTGTTTCCTGTGTGAAATTGTTATCCGCTC

ACAATTCCACACAACATACGAGCCGGAAGCATAAAGTGTAAAGCCTGGGGTGCCTAATGAGT

GAGCTAACTCACATTAATTGCGTTGCGCTCACTGCCCGCTTTCCAGTCGGGAAACCTGTCGT

GCCAGCTGCATTAATGAATCGGCCAACGCGCGGGGAGAGGCGGTTTGCGTATTGGGCGCTCT

TCCGCTTCCTCGCTCACTGACTCGCTGCGCTCGGTCGTTCGGCTGCGGCGAGCGGTATCAGC

TCACTCAAAGGCGGTAATACGGTTATCCACAGAATCAGGGGATAACGCAGGAAAGAACATGT

GAGCAAAAGGCCAGCAAAAGGCCAGGAACCGTAAAAAGGCCGCGTTGCTGGCGTTTTTCCAT

AGGCTCCGCCCCCCTGACGAGCATCACAAAAATCGACGCTCAAGTCAGAGGTGGCGAAACCC

GACAGGACTATAAAGATACCAGGCGTTTCCCCCTGGAAGCTCCCTCGTGCGCTCTCCTGTTC

CGACCCTGCCGCTTACCGGATACCTGTCCGCCTTTCTCCCTTCGGGAAGCGTGGCGCTTTCT

CAATGCTCACGCTGTAGGTATCTCAGTTCGGTGTAGGTCGTTCGCTCCAAGCTGGGCTGTGT

GCACGAACCCCCCGTTCAGCCCGACCGCTGCGCCTTATCCGGTAACTATCGTCTTGAGTCCA

ACCCGGTAAGACACGACTTATCGCCACTGGCAGCAGCCACTGGTAACAGGATTAGCAGAGCG

AGGTATGTAGGCGGTGCTACAGAGTTCTTGAAGTGGTGGCCTAACTACGGCTACACTAGAAG

GACAGTATTTGGTATCTGCGCTCTGCTGAAGCCAGTTACCTTCGGAAAAAGAGTTGGTAGCT

CTTGATCCGGCAAACAAACCACCGCTGGTAGCGGTGGTTTTTTTGTTTGCAAGCAGCAGATT

ACGCGCAGAAAAAAAGGATCTCAAGAAGATCCTTTGATCTTTTCTACGGGGTCTGACGCTCA

-continued

GTGGAACGAAAACTCACGTTAAGGGATTTTGGTCATGAGATTATCAAAAAGGATCTTCACCT

AGATCCTTTTAAATTAAAAATGAAGTTTTAAATCAATCTAAAGTATATATGAGTAAACTTGG

TCTGACAGTTACCAATGCTTAATCAGTGAGGCACCTATCTCAGCGATCTGTCTATTTCGTTC

ATCCATAGTTGCCTGACTCCCCGTCGTGTAGATAACTACGATACGGGAGGGCTTACCATCTG

GCCCCAGTGCTGCAATGATACCGCGAGACCCACGCTCACCGGCTCCAGATTTATCAGCAATA

AACCAGCCAGCCGGAAGGGCCGAGCGCAGAAGTGGTCCTGCAACTTTATCCGCCTCCATCCA

GTCTATTAATTGTTGCCGGGAAGCTAGAGTAAGTAGTTCGCCAGTTAATAGTTTGCGCAACG

TTGTTGCCATTGCTACAGGCATCGTGGTGTCACGCTCGTCGTTTGGTATGGCTTCATTCAGC

TCCGGTTCCCAACGATCAAGGCGAGTTACATGATCCCCCATGTTGTGCAAAAAAGCGGTTAG

CTCCTTCGGTCCTCCGATCGTTGTCAGAAGTAAGTTGGCCGCAGTGTTATCACTCATGGTTA

TGGCAGCACTGCATAATTCTCTTACTGTCATGCCATCCGTAAGATGCTTTTCTGTGACTGGT

GAGTACTCAACCAAGTCATTCTGAGAATAGTGTATGCGGCGACCGAGTTGCTCTTGCCCGGC

GTCAATACGGGATAATACCGCGCCACATAGCAGAACTTTAAAAGTGCTCATCATTGGAAAAC

GTTCTTCGGGGCGAAAACTCTCAAGGATCTTACCGCTGTTGAGATCCAGTTCGATGTAACCC

ACTCGTGCACCCAACTGATCTTCAGCATCTTTTACTTTCACCAGCGTTTCTGGGTGAGCAAA

AACAGGAAGGCAAAATGCCGCAAAAAAGGGAATAAGGGCGACACGGAAATGTTGAATACTCA

TACTCTTCCTTTTTCAATATTATTGAAGCATTTATCAGGGTTATTGTCTCATGAGCGGATAC

ATATTTGAATGTATTTAGAAAAATAAACAAATAGGGGTTCCGCGCACATTTCCCCGAAAAGT

GCCACCTGACGTCGACGGATCGGGAGATCTCCCGATCCCCTATGGTCGACTCTCAGTACAAT

CTGCTCTGATGCCGCATAGTTAAGCCAGTATCTGCTCCCTGCTTGTGTGTTGGAGGTCGCTG

AGTAGTGCGCGAGCAAAATTTAAGCTACAACAAGGCAAGGCTTGACCGACAATTGCATGAAG

AATCTGCTTAGG (SEQ ID NO: 106)

REFERENCES

1. Lendon, C. L., et al. E280A PS-1 mutation causes Alzheimer's disease but age of onset is not modified by ApoE alleles. Hum Mutat 10, 186-195 (1997).
2. Aguirre-Acevedo, D. C., et al. [Validity and reliability of the CERAD-Col neuropsychological battery]. Rev Neurol 45, 655-660 (2007).
3. Yesavage, J. A. Opportunities for and obstacles to treatments for dementias. J Am Geriatr Soc 31, 59-60 (1983).
4. Reisberg, B. Functional assessment staging (FAST). Psychopharmacol Bull 24, 653-659 (1988).
5. Mahley, R. W., Huang, Y. & Rall, S. C., Jr. Pathogenesis of type III hyperlipoproteinemia (dysbetalipoproteinemia). Questions, quandaries, and paradoxes. J Lipid Res 40, 1933-1949 (1999).
6. Fisher, S., et al. A scalable, fully automated process for construction of sequence-ready human exome targeted capture libraries. Genome Biol 12, R1 (2011).
7. Lek, M., et al. Analysis of protein-coding genetic variation in 60,706 humans. Nature 536, 285-291 (2016).
8. Li, H. Aligning sequence reads, clone sequences and assembly contigs with BWA-MEM . . . arXiv: 1303.3997v1 [q-bio.GN] (2013).
9. Kohler, S., et al. The Human Phenotype Ontology project: linking molecular biology and disease through phenotype data. Nucleic Acids Res 42, D966-974 (2014).
10. Smedley, D., et al. A Whole-Genome Analysis Framework for Effective Identification of Pathogenic Regulatory Variants in Mendelian Disease. Am J Hum Genet 99, 595-606 (2016).
11. Chen, J., Li, Q. & Wang, J. Topology of human apolipoprotein E3 uniquely regulates its diverse biological functions. Proc Natl Acad Sci USA 108, 14813-14818 (2011).
12. Rose, A. S., et al. NGL viewer: web-based molecular graphics for large complexes. Bioinformatics 34, 3755-3758 (2018).
13. Zhong, L., et al. A rapid and cost-effective method for genotyping apolipoprotein E gene polymorphism. Mol Neurodegener 11, 2 (2016).
14. Quiroz, Y. T., et al. Association Between Amyloid and Tau Accumulation in Young Adults With Autosomal Dominant Alzheimer Disease. JAMA Neurol (2018).
15. Fleisher, A. S., et al. Associations between biomarkers and age in the presenilin 1 E280A autosomal dominant Alzheimer disease kindred: a cross-sectional study. JAMA Neurol 72, 316-324 (2015).
16. Becker, J. A., et al. Amyloid-β associated cortical thinning in clinically normal elderly. Ann Neurol 69, 1032-1042 (2011).
17. Braak, H., Rüb, U., Schultz, C. & Del Tredici, K. Vulnerability of cortical neurons to Alzheimer's and Parkinson's diseases. J Alzheimers Dis 9, 35-44 (2006).
18. Braak, H. & Braak, E. Diagnostic criteria for neuropathologic assessment of Alzheimer's disease. Neurobiol Aging 18, S85-88 (1997).
19. Johnson, K. A., et al. Tau positron emission tomographic imaging in aging and early Alzheimer disease. Ann Neurol 79, 110-119 (2016).

20. Chien, D. T., et al. Early clinical PET imaging results with the novel PHF-tau radioligand [F-18]-T807. J Alzheimers Dis 34, 457-468 (2013).
21. Wang, L., et al. Evaluation of Tau Imaging in Staging Alzheimer Disease and Revealing Interactions Between beta-Amyloid and Tauopathy. JAMA Neurol 73, 1070-1077 (2016).
22. Logan, J., et al. Graphical analysis of reversible radioligand binding from time-activity measurements applied to [N-11C-methyl]-(−)-cocaine PET studies in human subjects. J Cereb Blood Flow Metab 10, 740-747 (1990).
23. Amariglio, R. E., et al. Subjective cognitive concerns, amyloid-β, and neurodegeneration in clinically normal elderly. Neurology 85, 56-62 (2015).
24. Hedden, T., et al. Disruption of functional connectivity in clinically normal older adults harboring amyloid burden. J Neurosci 29, 12686-12694 (2009).
25. Beecham, G. W., et al. Genome-wide association meta-analysis of neuropathologic features of Alzheimer's disease and related dementias. PLOS Genet 10, e1004606 (2014).
26. Hashimoto, T., et al. Apolipoprotein E, especially apolipoprotein E4, increases the oligomerization of amyloid beta peptide. J Neurosci 32, 15181-15192 (2012).
27. Hudry, E., et al. Gene transfer of human Apoe isoforms results in differential modulation of amyloid deposition and neurotoxicity in mouse brain. Sci Transl Med 5, 212ra161 (2013).
28. Lemere, C. A., et al. The E280A presenilin 1 Alzheimer mutation produces increased A beta 42 deposition and severe cerebellar pathology. Nat Med 2, 1146-1150 (1996).
29. Quiroz, Y. T., et al. Association Between Amyloid and Tau Accumulation in Young Adults With Autosomal Dominant Alzheimer Disease. JAMA Neurol (2018).
30. Acosta-Baena, N., et al. Pre-dementia clinical stages in presenilin 1 E280A familial early-onset Alzheimer's disease: a retrospective cohort study. Lancet Neurol 10, 213-220 (2011).
31. Lopera, F., et al. Clinical features of early-onset Alzheimer disease in a large kindred with an E280A presenilin-1 mutation. JAMA 277, 793-799 (1997).
32. Cacace, R., Sleegers, K. & Van Broeckhoven, C. Molecular genetics of early-onset Alzheimer's disease revisited. Alzheimers Dement 12, 733-748 (2016).
33. Albert, M. S., et al. The diagnosis of mild cognitive impairment due to Alzheimer's disease: recommendations from the National Institute on Aging-Alzheimer's Association workgroups on diagnostic guidelines for Alzheimer's disease. Alzheimers Dement 7, 270-279 (2011).
34. Smedley, D., et al. A Whole-Genome Analysis Framework for Effective Identification of Pathogenic Regulatory Variants in Mendelian Disease. Am J Hum Genet 99, 595-606 (2016).
35. Corder, E. H., et al. Protective effect of apolipoprotein E type 2 allele for late onset Alzheimer disease. Nat Genet 7, 180-184 (1994).
36. Corder, E. H., et al. Gene dose of apolipoprotein E type 4 allele and the risk of Alzheimer's disease in late onset families. Science 261, 921-923 (1993).
37. Farrer, L. A., et al. Effects of age, sex, and ethnicity on the association between apolipoprotein E genotype and Alzheimer disease. A meta-analysis. APOE and Alzheimer Disease Meta Analysis Consortium. JAMA 278, 1349-1356 (1997).
38. Wardell, M. R., Brennan, S. O., Janus, E. D., Fraser, R. & Carrell, R. W. Apolipoprotein E2-Christchurch (136 Arg-Ser). New variant of human apolipoprotein E in a patient with type III hyperlipoproteinemia. J Clin Invest 80, 483-490 (1987).
39. Candas-Estebanez, B., et al. APOE Variants E2, E3, and E4 Can Be Miscalled By Classical PCR-RFLP When The Christchurch Variant Is Also Present. J Clin Lab Anal 31 (2017).
40. Wardell M R, Brennan S O, Janus E D, Fraser R, Carrell R W. Apolipoprotein E2-Christchurch (136 Arg-Ser). New variant of human apolipoprotein E in a patient with type III hyperlipoproteinemia. J Clin Invest 1987; 80:483-90.
41. Velez J I, Lopera F, Sepulveda-Falla D, et al. APOE*E2 allele delays age of onset in PSEN1 E280A Alzheimer's disease. Mol Psychiatry 2016; 21:916-24.
42. Hollingworth P, Harold D, Sims R, et al. Common variants at ABCA7, MS4A6A/MS4A4E, EPHA1, CD33 and CD2AP are associated with Alzheimer's disease. Nat Genet 2011; 43:429-35.
43. Wardell, M. R., Brennan, S. O., Janus, E. D., Fraser, R. & Carrell, R. W. Apolipoprotein E2-Christchurch (136 Arg-Ser). New variant of human apolipoprotein E in a patient with type III hyperlipoproteinemia. J Clin Invest 80, 483-490 (1987).
44. Mahley, R. W., Huang, Y. & Rall, S. C., Jr. Pathogenesis of type III hyperlipoproteinemia (dysbetalipoproteinemia). Questions, quandaries, and paradoxes. J Lipid Res 40, 1933-1949 (1999).
45. Mahley R W. Apolipoprotein E: from cardiovascular disease to neurodegenerative disorders. J Mol Med (Berl) 2016; 94:739-46.
46. Romeo S, Pennacchio L A, Fu Y, et al. Population-based resequencing of ANGPTL4 uncovers variations that reduce triglycerides and increase HDL. Nat Genet 2007; 39:513-6.
47. Mahley, R. W. Apolipoprotein E: from cardiovascular disease to neurodegenerative disorders. J Mol Med (Berl) 94, 739-746 (2016).
48. Hashimoto, T., et al. Apolipoprotein E, especially apolipoprotein E4, increases the oligomerization of amyloid beta peptide. J Neurosci 32, 15181-15192 (2012).
49. Walsh, D. M., et al. Naturally secreted oligomers of amyloid beta protein potently inhibit hippocampal long-term potentiation in vivo. Nature 416, 535-539 (2002).
50. Lalli, M. A., et al. Whole-genome sequencing suggests a chemokine gene cluster that modifies age at onset in familial Alzheimer's disease. Mol Psychiatry 20, 1294-1300 (2015).
51. Huynh, T. V., et al. Age-Dependent Effects of apoE Reduction Using Antisense Oligonucleotides in a Model of beta-amyloidosis. Neuron 96, 1013-1023 e1014 (2017).
52. Huynh, T. V., et al. Age-Dependent Effects of apoE Reduction Using Antisense Oligonucleotides in a Model of beta-amyloidosis. Neuron 96, 1013-1023 e1014 (2017).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated antibody or antigen binding domain thereof that binds to Apolipoprotein E (ApoE), wherein the antibody or antigen binding domain thereof comprises a heavy chain variable region (VH) comprising a VHCDR1, a VHCDR2, and a VHCDR3; and a light chain variable region (VL) comprising a VLCDR1, a VLCDR2, and a VLCDR3, wherein the VHCDR1, the VHCDR2, the VHCDR3, the VLCDR1, the VLCDR2, and the VLCDR3 comprise the amino acid sequences of SEQ ID NOs: 17, 18, 19, 14, 15, and 16, respectively.

2. The antibody or antigen binding domain thereof of claim 1, wherein the antibody or antigen binding domain thereof binds to an epitope that comprises or consists of the amino acid sequence TEELRVRLASHLRK (SEQ ID NO:3).

3. The antibody or antigen binding domain thereof of claim 1, wherein the antibody or antigen binding domain thereof binds to one or more HSPG-binding sites of ApoE2, ApoE3, or ApoE4.

4. The antibody or antigen binding domain thereof of claim 1, wherein the antibody or antigen binding domain thereof does not bind to a mutant ApoE protein comprising the amino acid sequence TEELRVSLASHLRK (SEQ ID NO: 2).

5. The antibody or antigen binding domain thereof of claim 4, wherein the antibody or antigen binding domain thereof binds to an epitope that comprises or consists of the amino acid sequence TEELRVRLASHLRK (SEQ ID NO:3).

6. The antibody or antigen binding domain thereof of claim 1, wherein the antibody or antigen binding domain thereof competes with and/or binds a same epitope as a reference anti-ApoE antibody comprising a heavy chain variable region (VH) and a light chain variable region (VL), wherein the VH and VL of the reference antibody comprise: (i) the amino acid sequence of SEQ ID NO: 13 and the amino acid sequence of SEQ ID NO:12, respectively; (ii) the amino acid sequence of SEQ ID NO:22 and the amino acid sequence of SEQ ID NO:23, respectively; (iii) the amino acid sequence of SEQ ID NO:33 and the amino acid sequence of SEQ ID NO:32, respectively; or (iv) the amino acid sequence of SEQ ID NO:43 and the amino acid sequence of SEQ ID NO:42, respectively.

7. The antibody or antigen binding domain thereof of claim 1, wherein the antibody or antigen binding domain thereof comprises a mouse IgG1, IgG2a, IgG2b, IgG2c, or IgG3 heavy chain constant region.

8. The antibody or antigen binding domain thereof of claim 1, wherein the antibody or antigen binding domain thereof is an antibody and comprises a human IgG1, IgG2, IgG3, or IgG4 heavy chain constant region.

9. The antibody or antigen binding domain thereof of claim 1, wherein the antibody or antigen binding domain thereof comprises a human kappa or human lambda light chain constant region.

10. The antibody or antigen binding domain thereof of claim 1, wherein the antibody is a whole antibody, a monoclonal antibody, a humanized antibody, or a chimeric antibody, and wherein the antigen-binding domain is a Fv, a scFv, an sc(Fv)2, an Fab, or an F(ab')2.

11. The antibody or antigen binding domain thereof of claim 1, further comprising one or more of: a half-life extending moiety, a blood-brain barrier penetrating moiety, or a detectable label.

12. A pharmaceutical composition comprising the antibody or antigen binding domain thereof of claim 1.

13. An anti-ApoE antibody or antigen binding domain thereof comprising a VH comprising VHCDR1, VHCDR2, and VHCDR3, and a VL comprising VLCDR1, VLCDR2, and VLCDR3, wherein the VHCDR1, VHCDR2, VHCDR3, VLCDR1, VLCDR2, and VLCDR3 comprise the amino acid sequences of SEQ ID NOS: 17, 18, 19, 14, 15, and 16, respectively.

14. The antibody or antigen binding domain thereof of claim 13, wherein the VH comprises the amino acid sequence that is at least 80% identical to the amino acid sequences of SEQ ID NO: 22 and comprises VHCDR1, VHCDR2 and VHCDR3 having the amino acid sequences of SEQ ID NOs: 17, 18 and 19, respectively; and the VL comprises the amino acid sequence that is at least 80% identical to the amino acid sequence of SEQ ID NO:23 and comprises VLCDR1, VLCDR2 and VLCDR3 having the amino acid sequences of SEQ ID NOs: 14, 15 and 16, respectively.

15. The antibody of claim 14, wherein the VH comprises the amino acid sequence with at least 90% sequence identity to the amino acid sequences of SEQ ID NO: 22 and comprises VHCDR1, VHCDR2 and VHCDR3 having the amino acid sequences of SEQ ID NOs: 17, 18 and 19, respectively; and the VL comprises the amino acid sequence with at least 90% sequence identity to the amino acid sequence of SEQ ID NO:23 and comprises VLCDR1, VLCDR2 and VLCDR3 having the amino acid sequences of SEQ ID NOs: 14, 15 and 16, respectively.

16. The antibody or antigen binding domain thereof of claim 13, wherein (i) the VH comprises the amino acid sequence with at least 80% sequence identity to amino acids 20-139 of the amino acid sequence of SEQ ID NO: 22 and comprises VHCDR1, VHCDR2 and VHCDR3 having the amino acid sequences of SEQ ID NOs: 17, 18 and 19, respectively; and (ii) the VL comprise the amino acid sequence with at least 80% sequence identity to amino acids 21-131 of the amino acid sequence of SEQ ID NO: 23 and comprises VLCDR1, VLCDR2, and VLCDR3 having the amino acid sequences of SEQ ID NOs: 14, 15 and 16, respectively.

17. The antibody or antigen binding domain thereof of claim 16, wherein (i) the VH comprises the amino acid sequence with at least 90% sequence identity to amino acids 20-139 of the amino acid sequence of SEQ ID NO: 22 and comprises VHCDR1, VHCDR2 and VHCDR3 having the amino acid sequences of SEQ ID NOs: 17, 18 and 19, respectively; and (ii) the VL comprise the amino acid sequence with at least 90% sequence identity to amino acids 21-131 of the amino acid sequence of SEQ ID NO: 23 and comprises VLCDR1, VLCDR2, and VLCDR3 having the amino acid sequences of SEQ ID NOs: 14, 15 and 16, respectively.

18. The antibody or antigen binding domain thereof of claim 17, wherein (i) the VH comprises the amino acid sequence with at least 95% sequence identity to amino acids 20-139 of the amino acid sequence of SEQ ID NO: 22 and comprises VHCDR1, VHCDR2 and VHCDR3 having the amino acid sequences of SEQ ID NOs: 17, 18 and 19, respectively; and (ii) the VL comprise the amino acid sequence with at least 95% sequence identity to amino acids 21-131 of the amino acid sequence of SEQ ID NO: 23 and comprises VLCDR1, VLCDR2 and VLCDR3 having the amino acid sequences of SEQ ID NOs: 14, 15 and 16, respectively.

19. The antibody or antigen binding domain thereof of claim 18, wherein (i) the VH comprises the amino acid sequence of amino acids 20-139 of the amino acid sequence of SEQ ID NO: 22, and (ii) the VL comprise the amino acid sequence of amino acids 21-131 of the amino acid sequence of SEQ ID NO: 23.

20. An isolated polynucleotide or polynucleotides encoding the antibody or antigen binding domain thereof of claim 1.

21. A vector or vectors comprising the polynucleotide or polynucleotides of claim 20.

22. An isolated host cell comprising the vector or vectors of claim 21.

* * * * *